United States Patent
Anthony et al.

(10) Patent No.: US 9,771,602 B2
(45) Date of Patent: Sep. 26, 2017

(54) COMPETITIVE GROWTH AND/OR PRODUCTION ADVANTAGE FOR BUTANOLOGEN MICROORGANISM

(71) Applicant: BUTAMAX ADVANCED BIOFUELS LLC, Wilmington, DE (US)

(72) Inventors: Larry Cameron Anthony, Aston, PA (US); Michael Dauner, Wilmington, DE (US)

(73) Assignee: Butamax Advanced Biofuels LLC, Wilmington, DE (US)

( * ) Notice: Subject to any disclaimer, the term of this patent is extended or adjusted under 35 U.S.C. 154(b) by 0 days.

(21) Appl. No.: 14/213,274

(22) Filed: Mar. 14, 2014

(65) Prior Publication Data

US 2014/0273130 A1    Sep. 18, 2014

Related U.S. Application Data

(60) Provisional application No. 61/801,239, filed on Mar. 15, 2013.

(51) Int. Cl.
| | | |
|---|---|---|
| C12P 7/16 | (2006.01) | |
| C12N 1/00 | (2006.01) | |
| C12P 7/10 | (2006.01) | |

(52) U.S. Cl.
CPC ...... *C12P 7/16* (2013.01); *C12P 7/10* (2013.01); Y02E 50/10 (2013.01); Y02E 50/16 (2013.01)

(58) Field of Classification Search
CPC .... C12P 7/16; C12P 7/10; Y02E 50/16; Y02E 50/10
USPC ............................................ 435/160, 254.11
See application file for complete search history.

(56) References Cited

U.S. PATENT DOCUMENTS

| | | | |
|---|---|---|---|
| 4,034,091 A | 7/1977 | Powell et al. | |
| 4,626,505 A * | 12/1986 | Falco ................... | C12N 15/81 435/254.21 |
| 5,686,276 A | 11/1997 | Laffend et al. | |
| 6,432,688 B1 | 8/2002 | Ito et al. | |
| 7,541,173 B2 | 6/2009 | Bramucci et al. | |
| 7,574,601 B2 | 8/2009 | Jahromi et al. | |
| 7,659,104 B2 | 2/2010 | Bramucci et al. | |
| 7,666,644 B2 | 2/2010 | Castle et al. | |
| 7,851,188 B2 | 12/2010 | Donaldson et al. | |
| 7,863,503 B2 | 1/2011 | Castle et al. | |
| 7,910,342 B2 | 3/2011 | Liao et al. | |
| 7,993,889 B1 | 8/2011 | Donaldson et al. | |
| 8,017,364 B2 | 9/2011 | Bramucci et al. | |
| 8,017,376 B2 * | 9/2011 | Dundon ................. | C12N 9/88 435/254.2 |
| 8,101,808 B2 | 1/2012 | Evanko et al. | |
| 8,129,162 B2 | 3/2012 | Li et al. | |
| 8,178,328 B2 | 5/2012 | Donaldson et al. | |
| 8,188,250 B2 | 5/2012 | Bramucci et al. | |
| 8,206,970 B2 | 6/2012 | Eliot et al. | |
| 8,222,017 B2 | 7/2012 | Li et al. | |
| 8,241,878 B2 | 8/2012 | Anthony et al. | |
| 8,273,558 B2 | 9/2012 | Donaldson et al. | |
| 8,283,144 B2 | 10/2012 | Donaldson et al. | |
| 8,372,612 B2 | 2/2013 | Larossa et al. | |
| 8,389,252 B2 | 3/2013 | Larossa | |
| 8,409,834 B2 | 4/2013 | Burlew et al. | |
| 8,426,173 B2 | 4/2013 | Bramucci et al. | |
| 8,426,174 B2 | 4/2013 | Bramucci et al. | |
| 8,455,224 B2 | 6/2013 | Paul | |
| 8,455,225 B2 | 6/2013 | Bramucci et al. | |
| 8,465,964 B2 | 6/2013 | Anthony et al. | |
| 8,476,047 B2 | 7/2013 | Burlew et al. | |
| 8,518,678 B2 | 8/2013 | Flint et al. | |
| 8,530,226 B2 * | 9/2013 | Festel ................... | C12N 9/0006 435/160 |
| 8,557,562 B2 | 10/2013 | Bramucci et al. | |
| 8,614,085 B2 | 12/2013 | Van Dyk et al. | |
| 8,617,861 B2 | 12/2013 | Grady et al. | |
| 8,637,281 B2 | 1/2014 | Paul et al. | |
| 8,637,289 B2 | 1/2014 | Anthony et al. | |
| 8,652,823 B2 | 2/2014 | Flint et al. | |
| 8,669,094 B2 | 3/2014 | Anthony et al. | |
| 8,691,540 B2 | 4/2014 | Bramucci et al. | |
| 8,697,404 B2 | 4/2014 | Anton et al. | |
| 8,735,114 B2 | 5/2014 | Donaldson et al. | |
| 8,759,044 B2 | 6/2014 | DiCosimo et al. | |
| 8,765,425 B2 | 7/2014 | DiCosimo et al. | |
| 8,765,433 B2 | 7/2014 | Satagopan et al. | |
| 8,785,166 B2 | 7/2014 | Anthony et al. | |
| 8,795,992 B2 | 8/2014 | Bramucci et al. | |
| 8,828,694 B2 | 9/2014 | Anthony et al. | |
| 8,828,695 B2 | 9/2014 | Grady et al. | |

(Continued)

FOREIGN PATENT DOCUMENTS

| | | |
|---|---|---|
| BR | 8903744 | 1/1991 |
| EP | 0147198 | 7/1987 |

(Continued)

OTHER PUBLICATIONS

Akada et al., Genetically modified industrial yeast ready for application. J. Biosci. Bioeng., 2002, vol. 94 (6): 536-544.*
Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*

(Continued)

*Primary Examiner* — Ganapathirama Raghu

(57) ABSTRACT

Provided herein are recombinant yeast host cells and methods for their use for production of fermentation products. Host cells provided herein comprise a pyruvate-utilizing pathway and a competitive growth advantage over other microorganisms in solution.

10 Claims, 19 Drawing Sheets

(56) References Cited

U.S. PATENT DOCUMENTS

| | | |
|---|---|---|
| 8,828,704 B2 | 9/2014 | Donaldson et al. |
| 8,865,443 B2 | 10/2014 | Burlew et al. |
| 8,871,488 B2 | 10/2014 | Dauner et al. |
| 8,889,385 B2 | 11/2014 | Donaldson et al. |
| 8,895,307 B2 | 11/2014 | Li et al. |
| 8,906,666 B2 | 12/2014 | Alsaker |
| 8,911,981 B2 | 12/2014 | Li et al. |
| 8,940,511 B2 | 1/2015 | Larossa |
| 8,945,859 B2 | 2/2015 | Donaldson et al. |
| 8,945,899 B2 | 2/2015 | Li et al. |
| 8,951,774 B2 | 2/2015 | Donaldson et al. |
| 8,951,937 B2 | 2/2015 | Flint et al. |
| 8,956,850 B2 | 2/2015 | Anthony et al. |
| 8,962,298 B2 | 2/2015 | Donaldson et al. |
| 8,969,055 B2 | 3/2015 | Grady et al. |
| 8,969,065 B2 | 3/2015 | Anthony et al. |
| 8,975,049 B2 * | 3/2015 | Liao ................ C12N 15/52 435/157 |
| 8,980,612 B2 | 3/2015 | Donaldson et al. |
| 9,012,190 B2 | 4/2015 | Dauner et al. |
| 9,040,263 B2 | 5/2015 | Anton et al. |
| 9,267,157 B2 * | 2/2016 | Anthony ............ C12N 9/0006 |
| 2007/0031918 A1 | 2/2007 | Dunson et al. |
| 2008/0182308 A1 | 7/2008 | Donaldson et al. |
| 2008/0274526 A1 | 11/2008 | Bramucci et al. |
| 2009/0305370 A1 | 12/2009 | Grady et al. |
| 2010/0081154 A1 | 4/2010 | Flint et al. |
| 2010/0081179 A1 | 4/2010 | Anthony et al. |
| 2010/0081182 A1 | 4/2010 | Paul et al. |
| 2010/0093020 A1 | 4/2010 | Bramucci et al. |
| 2010/0120105 A1 | 5/2010 | Anthony et al. |
| 2011/0097773 A1 | 4/2011 | Grady et al. |
| 2011/0124060 A1 | 5/2011 | Anthony et al. |
| 2011/0136192 A1 | 6/2011 | Paul et al. |
| 2011/0136193 A1 | 6/2011 | Grady et al. |
| 2011/0195505 A1 | 8/2011 | Euler et al. |
| 2011/0244536 A1 | 10/2011 | Nagarajan et al. |
| 2011/0250610 A1 | 10/2011 | Liao et al. |
| 2011/0312044 A1 | 12/2011 | Anton et al. |
| 2011/0312053 A1 | 12/2011 | Burlew et al. |
| 2012/0058541 A1 | 3/2012 | Alsaker et al. |
| 2012/0064561 A1 | 3/2012 | Flint et al. |
| 2012/0149080 A1 | 6/2012 | Nagarajan et al. |
| 2012/0196341 A1 | 8/2012 | Donaldson et al. |
| 2012/0237988 A1 | 9/2012 | Anthony et al. |
| 2012/0258873 A1 | 10/2012 | Gibson et al. |
| 2013/0035515 A1 | 2/2013 | Dobson et al. |
| 2013/0071898 A1 | 3/2013 | Anthony et al. |
| 2013/0171706 A1 | 7/2013 | Donaldson et al. |
| 2013/0203138 A1 | 8/2013 | McElvain et al. |
| 2013/0252296 A1 | 9/2013 | Maggio-Hall et al. |
| 2013/0316414 A1 | 11/2013 | Paul et al. |
| 2014/0004526 A1 | 1/2014 | Dauner et al. |
| 2014/0030782 A1 | 1/2014 | Anthony et al. |
| 2014/0030783 A1 | 1/2014 | Anthony et al. |
| 2014/0038263 A1 | 2/2014 | Flint et al. |
| 2014/0038268 A1 | 2/2014 | Flint et al. |
| 2014/0051133 A1 | 2/2014 | Govindarajan et al. |
| 2014/0051137 A1 | 2/2014 | Flint et al. |
| 2014/0057329 A1 | 2/2014 | Li et al. |
| 2014/0093930 A1 | 4/2014 | Li et al. |
| 2014/0093931 A1 | 4/2014 | Dauner et al. |
| 2014/0094630 A1 | 4/2014 | Anton et al. |
| 2014/0096439 A1 | 4/2014 | Bramucci et al. |
| 2014/0141479 A1 | 5/2014 | Anthony et al. |
| 2014/0170732 A1 | 6/2014 | Bramucci et al. |
| 2014/0186910 A1 | 7/2014 | Rothman et al. |
| 2014/0186911 A1 | 7/2014 | Anthony et al. |
| 2014/0273116 A1 | 9/2014 | Kelly et al. |
| 2014/0273129 A1 | 9/2014 | Bhalla et al. |
| 2014/0308735 A1 | 10/2014 | Anthony et al. |
| 2014/0335582 A1 | 11/2014 | Donaldson et al. |
| 2014/0349349 A1 | 11/2014 | Dauner et al. |
| 2014/0377824 A1 | 12/2014 | Satagopan et al. |
| 2015/0037855 A1 | 2/2015 | Bhadra et al. |
| 2015/0111269 A1 | 4/2015 | Li et al. |
| 2015/0119608 A1 | 4/2015 | Donaldson et al. |
| 2015/0125920 A1 | 5/2015 | Anthony et al. |

FOREIGN PATENT DOCUMENTS

| | | |
|---|---|---|
| WO | 2006013736 | 2/2006 |
| WO | 2009086423 | 7/2009 |

OTHER PUBLICATIONS

Seffernick et al., Melamine deaminase and Atrazine chlorohydrolase: 98 percent identical but functionally different. J. Bacteriol., 2001, vol. 183 (8): 2405-2410.*

Sen et al., Developments in directed evolution for improving enzyme functions. Appl. Biochem. Biotechnol., 2007, vol. 143: 212-223.*

Whisstock et al., Prediction of protein function from protein sequence. Q. Rev. Biophysics., 2003, vol. 36 (3): 307-340.*

Wishart et al., A single mutation converts a novel phosphotyrosine binding domain into a dual-specificity phosphatase. J. Biol. Chem., 1995, vol. 270(45): 26782-26785.*

Witkowski et al., Conversion of b-ketoacyl synthase to a Malonyl Decarboxylase by replacement of the active cysteine with glutamine. Biochemistry, 1999, vol. 38: 11643-11650.*

Bajaj et al., "Construction of Killer Industrial Yeast *Saccharomyces cerevisiae* HAU-1 and its Fermentation Performance", Brazilian Journal of Microbiology, vol. 41(2):477-485 (2010).

Brachmann et al., "Designer deletion strains derived from *Saccharomyces cerevisiae* S288C: a useful set of strains plasmids for PCR-mediated gene disruption and other applications," Yeast 14:115-132 (1998).

Cao et al., "A novel 5-enolpyruvylshikimate-3-phosphate synthase shows high glyphosphate tolerance in *Escherichia coli* and Tobacco plants," PLoS ONE 7(6): e38718 (2012).

Chianelli et al., "Isolation of a trifluoroleucine-resistant mutant of *Saccharomyces cerevisiae* deficient in both high- and low-affinity L-leucine transport," Cell. Mol. Biol. 42(6):847-57 (1996) (Abstract).

Dickinson et al., "An investigation of the metabolism of valine to isobutyl alcohol in *Saccharomyces cerevisiae*," J. Biol. Chem. 273:25752-6 (1998).

Domenico et al., "Resistance to bismuth among gram-negative bacteria is dependent upon iron and its uptake", Journal of Antimicrobial Chemotherapy, vol. 38(6):1031-1040 (1996).

Fukuda et al., "Altered regulation of aromatic amino acid biosynthesis in B-phenylmethyl-alcohol-overproducing mutants of Sake yeast *Saccharomyces cerevisiae*," Agric. Biol. Chem. 54:3151-6 (1990).

Gharieb et al., "Role of glutathione in detoxification of metal(loid)s by *Saccharomyces cerevisiae*", Biometals, vol. 17 (2):183-8 (2004).

LaRossa and Smul, "ilvB-encoded acetolactate synthase is resistant to the herbicide sulfometuron methyl," J. Bacteriol. 160(1):391-4 (1984).

Meuris, "Feedback-insensitive mutants of the gene for the tyrosine-inhibited DAHP synthetase in yeast," Genetics 76:735-44 (1974).

Oba et al., "Properties of a trifluoroleucine-resistant mutant of *Saccharomyces cerevisiae*," Biosci. Biotechnol. Biochem. 70(7):1776-9 (2006).

Park et al., "Use of sulfite resistance in *Saccharomyces cerevisiae* as a dominant selectable marker," Curr Genet 36(6): 339-44 (1999).

Penninckx, "An overview on glutathione in *Saccharomyces* versus non-conventional yeasts", FEMS Yeast Research, Wiley-Blackwell Publishing Ltd. GB, NL, vol. 2(3):295-305 (2002).

Shimura et al., "Genetic transformation of industrial yeasts using an amino acid analog resistance gene as a directly selectable marker," Enzyme Microbiol. Technol. 15:874-6 (1993).

Siehl et al., "Evolution of a microbial acetyltransferase for modification of glyphosphate: a novel tolerance strategy," Pest Manag Sci. 61(3):235-40 (2005).

(56) References Cited

OTHER PUBLICATIONS

Stalker et al., "A single amino acid substitution in the enzyme 5-enolpyruvylshikimate-3-phosphate synthase confers resistance to the herbicide glyphosphate," J Biol Chem 260(8): 4724-8 (1985).
Vande Berg et al., "Characterization and plant expression of a glyphospate-tolerant enolpyruvyishikimate phosphate synthase," Pest Manag Sci. 64(4):340-5 (2008).
Vido et al., "A Proteome Analysis of the Cadmium Response in *Saccharomyces cerevisiae*," J Biol Chem. 276(11): 8469-74 (2001).
Yadav et al., "Single amino acid substitutions in the enzyme acetolactate synthase confer resistance to the herbicide sulfometuron methyl," Proc Natl Acad Sci USA 83(12):4418-22 (1986).
Falco and Dumas, "Genetic Analysis of mutants of *Saccharomyces cerevisiae* resistant to the herbicide sulfometuron methyl," Genetics 109:21-35 (1985).
Xiao and Rank, "The construction of recombinant industrial yeasts free of bacterial sequences by directed gene replacement into a nonessential region of the genome," Gene 76:99-107 (1989).
International Search Report and Written Opinion, mailed on Oct. 15, 2014, in International Patent Application No. PCT/US2014/028519, filed on Mar. 14, 2014.

\* cited by examiner

COMPETITIVE GROWTH AND/OR PRODUCTION ADVANTAGE FOR BUTANOLOGEN MICROORGANISM

CROSS-REFERENCE TO RELATED APPLICATIONS

This application claims benefit of priority from U.S. Provisional Application No. 61/801,239, filed Mar. 15, 2013, which is hereby incorporated by reference in its entirety.

REFERENCE TO A SEQUENCE LISTING SUBMITTED ELECTRONICALLY VIA EFS-WEB

The content of the electronically submitted sequence listing (Name: 20140314_CL5075USNP_SequenceListing.txt; Size: 498,298 bytes; and Date of Creation: Mar. 14, 2014) is herein incorporated by reference in its entirety.

FIELD OF THE INVENTION

The invention relates to the fields of industrial microbiology and alcohol production. The invention also relates to the development of an industrial microorganism capable of producing fermentation products via an engineered pyruvate-utilizing pathway in the microorganism. The invention also relates to the development and use of a butanologen. The invention also relates to the use of inhibitors, antibiotics, and mixtures thereof to give the butanologen a competitive growth and/or production advantage over other organisms in culture in order to increase the yield of fermentation products.

BACKGROUND OF THE INVENTION

Butanol is an important industrial chemical, useful as a fuel additive, as a feedstock chemical in the plastics industry, and as a food grade extractant in the food and flavor industry. Each year 10 to 12 billion pounds of butanol are produced by petrochemical means.

Methods for the chemical synthesis of the butanol isomer, isobutanol, are known, such as oxo synthesis, catalytic hydrogenation of carbon monoxide (Ullmann's Encyclopedia of Industrial Chemistry, 6th edition, 2003, Wiley-VCH Verlag GmbH and Co., Weinheim, Germany, Vol. 5, pp. 716-719) and Guerbet condensation of methanol with n-propanol (Carlini et al., *J. Molec. Catal. A. Chem.* 220:215-220, 2004). These processes use starting materials derived from petrochemicals. The production of isobutanol from plant-derived raw materials could minimize the use of fossil fuels and would represent an advance in the art. Microorganisms capable of fermentative production of isobutanol have been described (for example, in U.S. Pat. Nos. 7,851,188 and 7,993,889).

Isobutanol is produced biologically as a by-product of yeast fermentation. It is a component of "fusel oil" that forms as a result of the incomplete metabolism of amino acids by this group of fungi. Isobutanol may be produced from catabolism of L-valine. After the amine group of L-valine is harvested as a nitrogen source, the resulting α-keto acid is decarboxylated and reduced to isobutanol by enzymes of the so-called Ehrlich pathway (Dickinson et al., *J. Biol. Chem.* 273:25752-25756, 1998). Microorganisms expressing engineered biosynthetic pathways for producing butanol isomers, including isobutanol, are also described (see U.S. Pat. Nos. 7,851,188 and 7,993,889, which are incorporated herein by reference).

SUMMARY OF THE INVENTION

In some embodiments, the invention is directed to a method for production of a fermentation product in a fermentation process comprising contacting a fermentation mix comprising a recombinant production microorganism which comprises a pyruvate-utilizing pathway with at least one compound which preferentially inhibits at least one contaminant yeast microorganism.

In some embodiments, the specific growth rate of the at least one contaminant microorganism is reduced more than the specific growth rate of the recombinant production microorganism.

In some embodiments, production of the fermentation product of the at least one contaminant microorganism is reduced more than production of the fermentation product of the recombinant production microorganism.

In some embodiments, both the production microorganism and the at least one contaminant microorganism are yeast microorganisms. In some embodiments, the contaminant yeast microorganism is *S. cerevisiae*.

In some embodiments, the pyruvate utilizing pathway is a butanol biosynthetic pathway. In some embodiments, the pyruvate utilizing pathway is an isobutanol biosynthetic pathway. In some embodiments, the fermentation product of the at least one contaminant microorganism is ethanol.

In some embodiments, the mechanism of action of the compound that inhibits is heavy metal toxicity, inhibition of amino acid biosynthesis, sulfitolysis, cross-linking, inhibition of ethanol dehydrogenase or inhibition of pyruvate decarboxylase.

In some embodiments, the inhibitor is an inhibitor of an ethanol biosynthesis pathway. In some embodiments, the inhibitor inhibits pyruvate decarboxylase and/or ethanol dehydrogenase. In some embodiments, the inhibitor comprises a member of the XC6H4CH=CHCOCOOH class of inhibitors/substrate analogues, cinnamaldehydes, glyoxalic acid, ketomalonate, regulatory site inhibitors, p chloromercuribenzoic acid, 5,5'-dithiobis(2-nitrobenzoic acid), pyrazole, 4-pyrazolecarboxylic acid, 1-H-pyrazole-1-carboxamidine-HCl, 4-methylpyrazole, 1-bromo-2-butanone, pyrazole-3,5-dicarboxylic acid monohydrate and mixtures thereof. In some embodiments, the inhibitor is selected from the group consisting of fluoroacetate, formaldehyde, sulfite, and mixtures thereof. In some embodiments, the inhibitor is an inhibitor of an amino acid biosynthesis pathway. In some embodiments, the inhibitor is inhibiting at least one enzyme selected from the group consisting of 5-enolpyruvoyl-shikimate-3-phosphate synthetase, α-isopropyl malate synthase, 3-deoxy-D-arabino-heptolusonate-7-phosphate synthase and mixtures thereof. In some embodiments, the inhibitor is selected from the group consisting of imidazolinone, triazolopyrimidine, pyrimidinyl oxybenzoate, sulfonylurea, sulfonylamino carbonyl triazolinone, glyphosate, trifluoroleucine, fluorophenyalanine and mixtures thereof. In some embodiments, the inhibitor is glyphosate. In some embodiments, the inhibitor is selected from a group consisting of nicosulfuron methyl, metsulfuron methyl, chlorimuron ethyl, sulfometuron methyl, chlorsulfuron, thifensulfuron methyl, and mixtures thereof. In some embodiments, the inhibitor is selected from a group consisting of aureobasidin A, bialaphos, cerulenin, chloramphenicol, cyclohexamide, geneticin, hygromycin B, methotrexate, nourseothricin, phleomycin, triazole, and mixtures thereof. In some embodiments, the inhibitor is selected from a group consisting of bismuth (III), copper (II), and mixtures thereof.

In some embodiments, the recombinant production microorganism is engineered to express a polypeptide that increases tolerance of the host cell to the at least one compound which preferentially inhibits at least one contaminant microorganism. In some embodiments, the polypeptide comprises an amino acid sequence of at least about 80% identity to SEQ ID NO:9, or an active variant, fragment or derivative of SEQ ID NO:9. In some embodiments, the polypeptide comprises an amino acid sequence of at least about 80% identity to formaldehyde dehydrogenase (SEQ ID NO:7). In some embodiments, the polypeptide is selected from a group consisting of an amino acid sequence of at least about 80% identity to SEQ ID NO:6, an amino acid sequence of at least about 80% identity to SEQ ID NO:7, and mixtures thereof. In some embodiments, the polypeptide is selected from a group consisting of an amino acid sequence of at least about 80% identity to SEQ ID NO:11, an amino acid sequence of at least about 80% identity to SEQ ID NO:12, and mixtures thereof. In some embodiments, the polypeptide has 3-phosphoshikimate 1-carboxylvinyltransferase activity. In some embodiments, the polypeptide comprises an amino acid sequence of at least about 80% identity to 3-phosphoshikimate 1-carboxylvinyltransferase. In some embodiments, the polypeptide comprises an amino acid sequence of at least about 80% identity to SEQ ID NO:13. In some embodiments, the polypeptide is selected from a group consisting of a polypeptide that has 5-enolpyruvoylshikimate-3-phosphate synthetase (ESPS) activity and confers resistance to glyphosate, a polypeptide that has glyphosate N-acetyltransferase activity and confers resistance to glyphosate, and mixtures thereof.

In some embodiments, the polypeptide is from a bacteria of the family Enterobacteriaceae. In some embodiments, the polypeptide is from a bacterial genus selected from the group consisting of: *Alishewanella, Alterococcus, Aquamonas, Aranicola, Arsenophonus, Azotivirga, Blochmannia, Brenneria, Buchnera, Budvicia, Buttiauxella, Cedecea, Citrobacter, Cronobacter, Dickeya, Edwardsiella, Enterobacter, Erwinia, Escherichia, Ewingella, Grimontella, Hafnia, Klebsiella, Kluyvera, Leclercia, Leminorella, Moellerella, Morganella, Obesumbacterium, Pantoea, Candidatus Phlomobacter, Photorhabdus, Poodoomaamaana, Plesiomonas, Pragia, Proteus, Providencia, Rahnella, Raoultella, Salmonella, Samsonia, Serratia, Shigella, Sodalis, Tatumella, Trabulsiella, Wigglesworthia, Xenorhabdus, Yersinia*, and *Yokenella*. In some embodiments, the polypeptide is from a microorganism of the genus *Saccharomyces*.

In some embodiments, the polypeptide is selected from a group consisting of: a polypeptide that has 5-enolpyruvoylshikimate-3-phosphate synthetase (ESPS) activity and confers resistance to glyphosate and a polypeptide that has glyphosate N-acetyltransferase activity and confers resistance to glyphosate. In some embodiments, the polypeptide is encoded by a heterologous polynucleotide.

In some embodiments, the invention is directed to a genetically modified recombinant production microorganism comprising an engineered pyruvate-utilizing pathway; and a polypeptide that increases tolerance of the host cell to inhibitors, antibiotics, or a combination thereof, wherein the production microorganism has a growth advantage over contaminant microorganisms that do not produce a desired fermentation product and do not contain said polypeptide.

In some embodiments, the recombinant production microorganism is selected from the group consisting of bacteria, cyanobacteria, filamentous fungi and yeasts. In some embodiments, the microorganism is a bacterial or cyanobacterial cell. In some embodiments, the genus of the microorganism is selected from the group consisting of *Salmonella, Arthrobacter, Bacillus, Brevibacterium, Clostridium, Corynebacterium, Gluconobacter, Nocardia, Pseudomonas, Rhodococcus, Streptomyces, Zymomonas, Escherichia, Lactobacillus, Lactococcus, Enterococcus, Alcaligenes, Klebsiella, Paenibacillus, Xanthomonas, Saccharomyces, Pichia, Hansenula, Yarrowia, Aspergillus, Kluyveromyces, Pachysolen, Rhodotorula, Zygosaccharomyces, Galactomyces, Schizosaccharomyces, Torulaspora, Debayomyces, Williopsis, Dekkera, Kloeckera, Metschnikowia,* and *Candida*.

In some embodiments, the recombinant production microorganism further comprises one or more polynucleotides that encode one or more enzymes having the following Enzyme Commission Numbers: EC 2.2.1.6, EC 1.1.1.86, EC 4.2.1.9, EC 4.1.1.72, EC 1.1.1.1, EC 1.1.1.265, EC 1.1.1.2, EC 1.2.4.4, EC 1.3.99.2, EC 1.2.1.57, EC 1.2.1.10, EC 2.6.1.66, EC 2.6.1.42, EC 1.4.1.9, EC 1.4.1.8, EC 4.1.1.14, EC 2.6.1.18, EC 2.3.1.9, EC 2.3.1.16, EC 1.1.130, EC 1.1.1.35, EC 1.1.1.157, EC 1.1.1.36, EC 4.2.1.17, EC 4.2.1.55, EC 1.3.1.44, EC 1.3.1.38, EC 5.4.99.13, EC 4.1.1.5, EC 2.7.1.29, EC 1.1.1.76, EC 1.2.1.57, and EC 4.2.1.28.

In some embodiments, the recombinant production microorganism has reduced expression of an enzyme having the following Enzyme Commission Number: EC 4.1.1.1 (pyruvate decarboxylase). In some embodiments, microorganism has reduced expression of an enzyme having the following Enzyme Commission Number: EC 1.1.1.1 (ethanol dehydrogenase).

Some embodiments are directed to a method for the production of a C3-C6 alcohol comprising the recombinant production microorganisms described herein, wherein said engineered pyruvate-utilizing pathway is a C3-C6 alcohol biosynthetic pathway; contacting said recombinant microorganism with a fermentable carbon substrate in a fermentation medium under conditions whereby a C3-C6 alcohol is produced; and recovering said C3-C6 alcohol.

In some embodiments, the C3-C6 alcohol is produced at a titer from about 5 g/L to about 100 g/L. In some embodiments, the C3-C6 alcohol is produced at a titer of at least 20 g/L. In some embodiments, the C3-C6 alcohol is selected from the group consisting of butanol, isobutanol, propanol, isopropanol, and mixtures thereof.

Some embodiments are directed to a method for the production of ethanol comprising: providing any recombinant microorganism described herein, wherein said pyruvate-utilizing pathway is an ethanol producing pathway; contacting said recombinant microorganism with a fermentable carbon substrate in a fermentation medium under conditions whereby the ethanol is produced; and recovering said ethanol.

In some embodiments, the fermentation medium comprises one or more inhibitors, antibiotics, or combinations thereof.

In some embodiments, the ethanol is produced at a titer from about 80 g/L to about 120 g/L. In some embodiments, the ethanol is produced at a titer of about 120 g/L.

Some embodiments are directed to a composition comprising any genetically modified recombinant microorganism of the invention, a fermentation medium, and one or more inhibitors, antibiotics or combinations thereof.

Some embodiments are directed to a method for reducing microbial contamination in a fermentation mix, wherein said method comprises contacting any genetically modified recombinant microorganism of the invention and a fermentation medium with one or more inhibitors, antibiotics, or mixtures thereof, and wherein the addition of more inhibitors, antibiotics, or mixtures thereof results in from about 1 log to about 10 log reduction in contamination. In some embodiments, the fermentation mix is in a propagation tank. In some embodiments, the fermentation mix is in a fermenter.

In some embodiments, reduction in contamination is measured by standard plating assays, qPCR/RT-PCR, or by measuring improved fermentation yields of desired product.

Some embodiments are directed to a method for reducing microbial contamination in a fermentation mix, wherein said method comprises contacting any genetically modified recombinant microorganism of the invention and a fermentation medium with one or more inhibitors, antibiotics, or combinations thereof, and wherein the addition of inhibitors, antibiotics, or combinations thereof results in from about 1 log to about 10 log reduction in contamination.

In some embodiments, the addition of inhibitors, antibiotics, or combinations thereof results in the death of between about 10% and about 100% of the microbial contaminants in the fermentation mix.

Some embodiments of the invention are directed to a method for reducing microbial contamination in a fermentation mix, wherein said method comprises contacting any genetically modified recombinant microorganism of the invention and a fermentation medium comprising one or more inhibitors, antibiotics, or combinations thereof, and wherein the reduction in contamination is associated with a decrease in ethanol production. Some embodiments are directed to any composition of the invention, wherein the ethanol titer is less than about 5 g/L, or less than about 1 g/L.

Some embodiments of the invention are directed to a method for reducing microbial contamination in a fermentation mix, wherein said method comprises contacting any genetically modified recombinant microorganism of the invention and a fermentation medium comprising one or more inhibitors, antibiotics, or combinations thereof, and wherein the reduction in contamination is associated with an increase in ethanol production.

Some embodiments are directed to a method for reducing microbial contamination in a fermentation mix, wherein said method comprises contacting any genetically modified recombinant microorganism of the invention and a fermentation medium comprising one or more inhibitors, antibiotics, or combinations thereof, and wherein the addition of said one or more inhibitors, antibiotics, or combinations thereof results in less than an about 20% loss in the yield of a lower alkyl alcohol produced by said host cell due to the presence of microbial contaminants.

In some embodiments, the addition of said one or more inhibitors, antibiotics, or combinations thereof results in less than an about 10% loss in the yield of a lower alkyl alcohol produced by said host cell due to the presence of microbial contaminants. In some embodiments, the C3-C6 alcohol or ethanol produced is a gasoline fuel component.

Some embodiments are directed to a gasoline blend comprising about 5 to about 20% of the C3-C6 alcohol produced by the recombinant microorganisms described herein.

DETAILED DESCRIPTION

Figure 1:
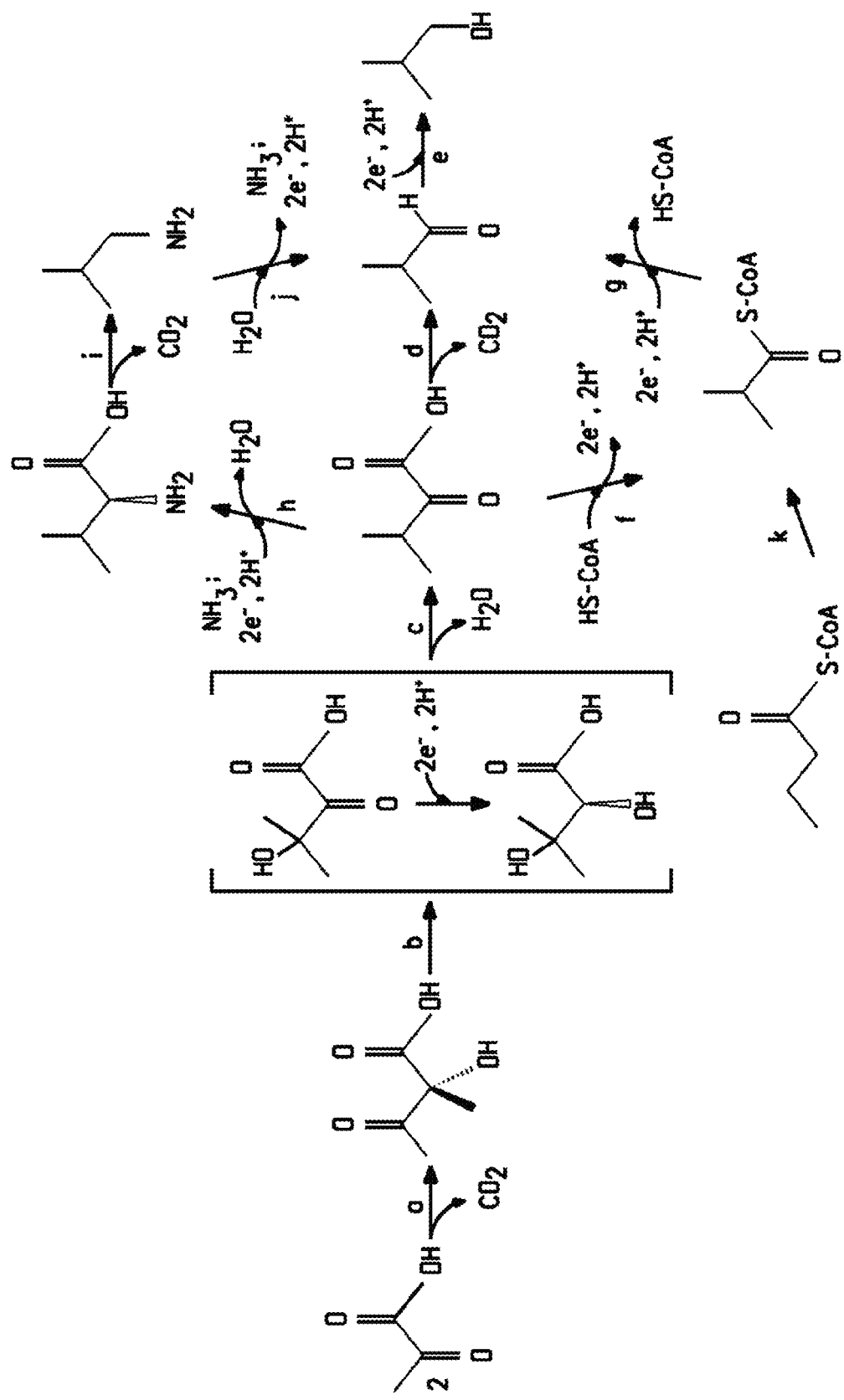
FIG. 1 depicts different isobutanol biosynthetic pathways. The steps labeled "a", "b", "c", "d", "e", "f", "g", "h", "i", "j", and "k" represent substrate to product conversions described below. "a" may be catalyzed, for example, by acetolactate synthase. "b" may be catalyzed, for example, by ketol-acid reductoisomerase. "c" may be catalyzed, for example, by acetohydroxy acid dehydratase. "d" may be catalyzed, for example, by branched-chain keto acid decarboxylase. "e" may be catalyzed, for example, by branched chain alcohol dehydrogenase. "f" may be catalyzed, for example, by branched chain keto acid dehydrogenase. "g" may be catalyzed, for example, by acetylating aldehyde dehydrogenase. "h" may be catalyzed, for example, by transaminase or valine dehydrogenase. "i" may be catalyzed, for example, by valine decarboxylase. "j" may be catalyzed, for example, by omega transaminase. "k" may be catalyzed, for example by isobutyryl-CoA mutase.

Competition for carbon substrates in a butanologen fermentation process between the butanologen and contaminant microorganisms, such as, for example ethanol-producing yeast strains. A competitive advantage and/or selective pressure in favor of the butanologen could thus favor high yields of butanol. Such an advantage for a butanologen system may be extended to any organisms competing for the carbon substrate. The same competitive advantage may be desirable for any other recombinant production microorganism, particularly yeast competing with wildtype, ethanologen yeast and/or other microbial communities.

This invention is directed to methods employing engineered microorganisms that produce fermentation products for industrial uses, and to optimizations for producing such fermentation products at high rates and titers with advantaged economic process conditions.

Contamination by ethanologen yeast and other microbes can be problematic and can quickly lead to takeover of the fermentation, particularly when the butanologen has a slower growth rate or is otherwise less fit than the ethanologen yeast or microbe.

Applicants have solved the problem of microbial contamination by ethanologen yeast and other microbes through the use of inhibitors, antibiotics, and mixtures thereof. Butanologen yeasts either have resistance to the inhibitors, antibiotics and mixtures thereof employed, or are engineered to have resistance to the inhibitors, antibiotics, and mixtures thereof employed. The yield of the butanol process when contacted with a carbon substrate may be increased without a buildup of microbial contamination.

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents and other references mentioned herein are incorporated by reference in their entireties for all purposes.

In order to further define this invention, the following terms and definitions are herein provided.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers. For example, a composition, a mixture, a process, a method, an article, or an apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the term "consists of," or variations such as "consist of" or "consisting of," as used throughout the specification and claims, indicate the inclusion of any recited integer or group of integers, but that no additional integer or group of integers may be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. §2111.03.

Also, the indefinite articles "a" and "an" preceding an element or component of the invention are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the application.

As used herein, the term "about" modifying the quantity of an ingredient or reactant of the invention employed refers to variation in the numerical quantity that can occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about", the claims include equivalents to the quantities. In embodiments, the term "about" means within 10% of the reported numerical value, preferably within 5% of the reported numerical value.

In some instances, "biomass" as used herein refers to the cell biomass of the fermentation product-producing microorganism, typically provided in units g/L dry cell weight (dcw).

The term "fermentation product" includes any desired product of interest, including, but not limited to lactic acid, 3-hydroxy-propionic acid, acrylic acid, acetic acid, succinic acid, citric acid, fumaric acid, malic acid, itaconic acid, 1,3-propane-diol, ethylene, glycerol, isobutyrate, butanol and other lower alkyl alcohols etc.

The term "fermentation process" refers to any process by which a desired fermentation product is produced.

The term "specific growth rate", often also referred to as "μ" or "mu", is defined as μ=1/cx*dcx/dt, representing the change of the biomass concentration cx in an infinitesimal short time interval dt, divided by the biomass concentration at this time.

The term "maximum specific growth rate", often also referred to as "$\mu_{max}$" or "mumax", refers to the "specific growth rate" ("mu") during the exponential growth phase of a culture. Usually during the exponential growth phase, mu is approximately constant as the substrates are not limiting as well as the produced by-products are still not exerting a significant inhibition on growth.

The term "lower alkyl alcohol" refers to any straight-chain or branched, saturated or unsaturated, alcohol molecule with 3-6 carbon atoms.

The term "butanol" refers to 1-butanol, 2-butanol, 2-butanone, isobutanol, or mixtures thereof. Isobutanol is also known as 2-methyl-1-propanol.

The term "C3-C6 alcohol" refers to any alcohol with 3, 4, 5 or 6 carbons.

The term "butanol biosynthetic pathway" as used herein refers to an enzyme pathway to produce 1-butanol, 2-butanol, 2-butanone or isobutanol. For example, isobutanol biosynthetic pathways are disclosed in U.S. Pat. No. 7,851,188, which is incorporated by reference herein.

The term "isobutanol biosynthetic pathway" refers to the enzymatic pathway to produce isobutanol. From time to time "isobutanol biosynthetic pathway" is used synonymously with "isobutanol production pathway" (see U.S. Pat. Nos. 7,851,188 and 7,993,889, which are herein incorporated herein by reference).

The term "1-butanol biosynthetic pathway" refers to an enzymatic pathway to produce 1-butanol. A "1-butanol biosynthetic pathway" can refer to an enzyme pathway to produce 1-butanol from acetyl-coenzyme A (acetyl-CoA). For example, 1-butanol biosynthetic pathways are disclosed in U.S. Patent Application Publication No. 2008/0182308 and International Publication No. WO 2007/041269, which are herein incorporated by reference in their entireties.

The term "2-butanol biosynthetic pathway" refers to an enzymatic pathway to produce 2-butanol. A "2-butanol biosynthetic pathway" can refer to an enzyme pathway to produce 2-butanol from pyruvate. For example, 2-butanol biosynthetic pathways are disclosed in U.S. Pat. No. 8,206,970, U.S. Patent Application Publication No. 2007/0292927, International Publication Nos. WO 2007/130518 and WO 2007/130521, which are herein incorporated by reference in their entireties.

The term "2-butanone biosynthetic pathway" as used herein refers to an enzymatic pathway to produce 2-butanone (see U.S. Appl. Pub. No. 2007/0259410 and U.S. Appl. Pub. No. 2009/0155870, which are incorporated herein by reference).

The term "engineered" as used herein refers to an enzymatic pathway that is not present endogenously in a microorganism and is deliberately constructed to produce a fermentation product from a starting substrate through a series of specific substrate to product conversions.

A "recombinant microbial host cell" or a "recombinant microorganism" is defined as a host cell that has been genetically manipulated to express a biosynthetic production pathway, wherein the host cell either produces a biosynthetic product in greater quantities relative to an unmodified host cell or produces a biosynthetic product that is not ordinarily produced by an unmodified host cell. A "production microorganism" is any microorganism that produces a desired fermentation product. A "contaminant microorganism" is any microorganism that either does not produce a desired fermentation product or does produce a desired fermentation product, but at lower efficiency (for example, with lower specific productivity, rate, titer or yield) than a production microorganism. It will be appreciated that microorganisms may produce measureable amounts of more than one product, however, for the purposes herein, "product" typically refers to the major product produced by a microorganism.

The term "fermentable carbon substrate" refers to a carbon source capable of being metabolized by the microorganisms such as those disclosed herein. Suitable fermentable carbon substrates include, but are not limited to, monosaccharides, such as glucose or fructose; disaccharides, such as lactose or sucrose; oligosaccharides; polysaccharides, such as starch, cellulose, or lignocellulose, hemicellulose; one-carbon substrates, fatty acids; and any combination of these.

"Fermentation medium" as used herein means the mixture of water, sugars (fermentable carbon substrates), dissolved solids, fermentation product and all other constituents of the material in which the fermentation product is being made by the reaction of fermentable carbon substrates to fermentation products, water and carbon dioxide ($CO_2$) by the microorganisms present. From time to time, as used herein the term "fermentation broth", "fermentation mix" and "fermentation mixture" can be used synonymously with "fermentation medium."

The term "aerobic conditions" as used herein means growth conditions in the presence of oxygen.

The term "microaerobic conditions" as used herein means growth conditions with low levels of dissolved oxygen. For example, the oxygen level may be less than about 1% of air-saturation.

The term "anaerobic conditions" as used herein means growth conditions in the absence of oxygen.

The term "carbon substrate" refers to a carbon source capable of being metabolized by the recombinant host cells disclosed herein. Non-limiting examples of carbon substrates are provided herein and include, but are not limited to, monosaccharides, oligosaccharides, polysaccharides, ethanol, lactate, succinate, glycerol, carbon dioxide, methanol, glucose, fructose, sucrose, xylose, arabinose, dextrose, amino acids, and mixtures thereof.

The term "sucrose utilizing butanologen" as used herein refers to a microorganism capable of producing butanol from sucrose. Such microorganisms are typically recombinant microorganisms comprising an engineered butanol biosynthetic pathway. "Sucrose utilizing isobutanologen" as used herein refers to a microorganism capable of producing isobutanol from sucrose. Such microorganisms are typically recombinant microorganisms comprising an engineered isobutanol biosynthetic pathway.

As used herein, the term "yield" refers to the amount of product per amount of carbon source in g/g. The yield may be exemplified for glucose as the carbon source. It is understood unless otherwise noted that yield is expressed as a percentage of the theoretical yield. In reference to a microorganism or metabolic pathway, "theoretical yield" is defined as the maximum amount of product that can be generated per total amount of substrate as dictated by the stoichiometry of the metabolic pathway used to make the product. For example, the theoretical yield for one typical conversion of glucose to isopropanol is 0.33 g/g. As such, a yield of isopropanol from glucose of 29.7 g/g would be expressed as 90% of theoretical or 90% theoretical yield. It is understood that while in the present disclosure the yield is exemplified for glucose as a carbon source, the invention can be applied to other carbon sources and the yield may vary depending on the carbon source used. One skilled in the art can calculate yields on various carbon sources.

The term "effective titer" as used herein, refers to the total amount of C3-C6 alcohol produced by fermentation per liter of fermentation medium. The total amount of C3-C6 alcohol includes: (i) the amount of C3-C6 alcohol in the fermentation medium; (ii) the amount of C3-C6 alcohol recovered from the organic extractant; and (iii) the amount of C3-C6 alcohol recovered from the gas phase, if gas stripping is used.

The term "effective rate" as used herein, refers to the total amount of C3-C6 alcohol produced by fermentation per liter of fermentation medium per hour of fermentation.

The term "specific productivity" as used herein, refers to the g of C3-C6 alcohol produced per g of dry cell weight of cells per unit time.

As used herein the term "coding sequence" refers to a DNA sequence that encodes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The terms "derivative" and "analog" refer to a polypeptide differing from the enzymes of the invention, but retaining essential properties thereof. The term "derivative" may also refer to a host cells differing from the host cells of the invention, but retaining essential properties thereof. Generally, derivatives and analogs are overall closely similar, and, in many regions, identical to the enzymes of the invention. The terms "derived-from", "derivative" and "analog" when referring to enzymes of the invention include any polypeptides which retain at least some of the activity of the corresponding native polypeptide or the activity of its catalytic domain.

Derivatives of enzymes disclosed herein are polypeptides which may have been altered so as to exhibit features not found on the native polypeptide. Derivatives can be covalently modified by substitution (e.g. amino acid substitution), chemical, enzymatic, or other appropriate means with a moiety other than a naturally occurring amino acid (e.g., a detectable moiety such as an enzyme or radioisotope). Examples of derivatives include fusion proteins, or proteins which are based on a naturally occurring protein sequence, but which have been altered. For example, proteins can be designed by knowledge of a particular amino acid sequence, and/or a particular secondary, tertiary, and/or quaternary structure. Derivatives include proteins that are modified based on the knowledge of a previous sequence, natural or synthetic, which is then optionally modified, often, but not necessarily to confer some improved function. These sequences, or proteins, are then said to be derived from a particular protein or amino acid sequence. In some embodiments of the invention, a derivative must retain at least 50% identity, at least 60% identity, at least 70% identity, at least 80% identity, at least 90% identity, at least 95% identity, at least 97% identity, or at least 99% identity to the sequence the derivative is "derived-from." In some embodiments of the invention, an enzyme is said to be derived-from an enzyme naturally found in a particular species if, using molecular genetic techniques, the DNA sequence for part or all of the enzyme is amplified and placed into a new host cell.

Polypeptides and Polynucleotides for Use in the Invention

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. A polypeptide may be derived from a natural biological source or produced by recombinant technology, but is not necessarily translated from a designated nucleic acid sequence. It may be generated in any manner, including by chemical synthesis. The polypeptides used in this invention comprise full-length polypeptides and fragments thereof.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for the purposes of the invention, as are native or recombinant polypeptides which have been separated, fractionated, or partially or substantially purified by any suitable technique.

A polypeptide of the invention may be of a size of about 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

Also included as polypeptides of the present invention are derivatives, analogs, or variants of the foregoing polypeptides, and any combination thereof. The terms "active variant," "active fragment," "active derivative," and "analog" refer to polypeptides of the present invention and include any polypeptides that are capable of catalyzing the reduction of a lower alkyl aldehyde. Variants of polypeptides of the present invention include polypeptides with altered amino acid sequences due to amino acid substitutions, deletions, and/or insertions. Variants may occur naturally or be non-naturally occurring. Non-naturally occurring variants may be produced using art-known mutagenesis techniques. Variant polypeptides may comprise conservative or non-conservative amino acid substitutions, deletions and/or additions. Derivatives of polypeptides of the present invention are polypeptides which have been altered so as to exhibit additional features not found on the native polypeptide. Examples include fusion proteins. Variant polypeptides may also be referred to herein as "polypeptide analogs." As used herein a "derivative" of a polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

A "fragment" is a unique portion of a polypeptide or other enzyme used in the invention which is identical in sequence to but shorter in length than the parent full-length sequence. A fragment may comprise up to the entire length of the defined sequence, minus one amino acid residue. For example, a fragment may comprise from 5 to 1000 contiguous amino acid residues. A fragment may be at least 5, 10, 15, 20, 25, 30, 40, 50, 60, 75, 100, 150, 250 or at least 500 contiguous amino acid residues in length. Fragments may be preferentially selected from certain regions of a molecule. For example, a polypeptide fragment may comprise a certain length of contiguous amino acids selected from the first 100 or 200 amino acids of a polypeptide as shown in a certain defined sequence. Clearly these lengths are exemplary, and any length that is supported by the specification, including the Sequence Listing, tables, and figures, may be encompassed by the present embodiments.

Alternatively, recombinant variants encoding these same or similar polypeptides can be synthesized or selected by making use of the "redundancy" in the genetic code. Various codon substitutions, such as the silent changes which produce various restriction sites, may be introduced to optimize cloning into a plasmid or viral vector or expression in a host cell system.

Preferably, amino acid "substitutions" are the result of replacing one amino acid with another amino acid having similar structural and/or chemical properties, i.e., conservative amino acid replacements, or they can be result of replacing one amino acid with an amino acid having different structural and/or chemical properties, i.e., non-conservative amino acid replacements. "Conservative" amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. Alternatively, "non-conservative" amino acid substitutions can be made by selecting the differences in polarity, charge, solubility, hydrophobicity, hydrophilicity, or the amphipathic nature of any of these amino acids. "Insertions" or "deletions" are preferably in the range of about 1 to about 20 amino acids, more preferably 1 to 10 amino acids. The variation allowed may be experimentally determined by systematically making insertions, deletions, or substitutions of amino acids in a polypeptide molecule using recombinant DNA techniques and assaying the resulting recombinant variants for activity.

By a polypeptide having an amino acid or polypeptide sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the references sequence.

As a practical matter, whether any particular polypeptide is at least 80%, 85%, 90%, 95%, 96%, 97%, 98%, or 99% identical to a reference polypeptide can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al., *Comp. Appi. Biosci.* 6:237-245 (1990). In a sequence alignment, the query and subject sequences are either both nucleotide sequences or both amino acid sequences. The result of the global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty-0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case, the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to be made for the purposes of the present invention.

Polypeptides and other enzymes suitable for use in the present invention and fragments thereof are encoded by polynucleotides. The term "polynucleotide" is intended to encompass a singular nucleic acid as well as plural nucleic acids, and refers to an isolated nucleic acid molecule or construct, e.g., messenger RNA (mRNA), virally-derived RNA, or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. Polynucleotides according to the present invention further include such molecules produced synthetically. Polynucleotides of the invention may be native to the host cell or heterologous. In addition, a polynucleotide or a nucleic acid may be or may include a regulatory element such as a promoter, ribosome binding site, or a transcription terminator.

In certain embodiments, the polynucleotide or nucleic acid is DNA. In the case of DNA, a polynucleotide comprising a nucleic acid, which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. Other transcription control elements, besides a promoter, for example enhancers, operators, repressors, and transcription termination signals, can be operably associated with the polynucleotide. Suitable promoters and other transcription control regions are disclosed herein.

A polynucleotide sequence can be referred to as "isolated," in which it has been removed from its native environment. For example, a heterologous polynucleotide encoding a polypeptide or polypeptide fragment having enzymatic activity (e.g., the ability to convert a substrate to xylulose) contained in a vector is considered isolated for the purposes of the present invention. Further examples of an isolated polynucleotide include recombinant polynucleotides maintained in heterologous host cells or purified (partially or substantially) polynucleotides in solution. Isolated polynucleotides or nucleic acids according to the present invention further include such molecules produced synthetically. An isolated polynucleotide fragment in the form of a polymer of DNA can be comprised of one or more segments of cDNA, genomic DNA, or synthetic DNA.

The term "gene" refers to a nucleic acid fragment that is capable of being expressed as a specific protein, optionally including regulatory sequences preceding (5' non-coding sequences) and following (3' non-coding sequences) the coding sequence.

As used herein, a "coding region" or "ORF" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' non-translated regions, and the like, are not part of a coding region. "Suitable regulatory sequences" refer to nucleotide sequences located upstream (5' non-coding sequences), within, or downstream (3' non-coding sequences) of a coding sequence that influence the transcription, RNA processing or stability, or translation of the associated coding sequence. Regulatory sequences can include promoters, translation leader sequences, introns, polyadenylation recognition sequences, RNA processing sites, effector binding sites and stem-loop structures.

A variety of translation control elements are known to those of ordinary skill in the art. These include, but are not limited to ribosome binding sites, translation initiation and termination codons, and elements derived from viral systems (particularly an internal ribosome entry site, or IRES). In other embodiments, a polynucleotide of the present invention is RNA, for example, in the form of messenger RNA (mRNA). RNA of the present invention may be single stranded or double stranded.

Polynucleotide and nucleic acid coding regions of the present invention may be associated with additional coding regions which encode secretory or signal peptides, which direct the secretion of a polypeptide encoded by a polynucleotide of the present invention.

As used herein, the term "transformation" refers to the transfer of a nucleic acid fragment into the genome of a host organism, resulting in genetically stable inheritance. Host organisms containing the transformed nucleic acid fragments are referred to as "recombinant" or "transformed" organisms.

The term "expression," as used herein, refers to the transcription and stable accumulation of sense (mRNA) or antisense RNA derived from the nucleic acid fragment of the invention. Expression may also refer to translation of mRNA into a polypeptide.

The terms "plasmid," "vector," and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

The term "artificial" refers to a synthetic, or non-host cell derived composition, e.g., a chemically-synthesized oligonucleotide.

As used herein, "native" refers to the form of a polynucleotide, gene, or polypeptide as found in nature with its own regulatory sequences, if present.

The term "endogenous," when used in reference to a polynucleotide, a gene, or a polypeptide refers to a native polynucleotide or gene in its natural location in the genome of an organism, or for a native polypeptide, is transcribed and translated from this location in the genome.

The term "heterologous" when used in reference to a polynucleotide, a gene, or a polypeptide refers to a polynucleotide, gene, or polypeptide not normally found in the host organism. "Heterologous" also includes a native coding region, or portion thereof, that is reintroduced into the source organism in a form that is different from the corresponding native gene, e.g., not in its natural location in the organism's genome. The heterologous polynucleotide or gene may be introduced into the host organism by, e.g., gene transfer. A heterologous gene may include a native coding region with non-native regulatory regions that is reintroduced into the native host. A "transgene" is a gene that has been introduced into the genome by a transformation procedure.

The term "recombinant genetic expression element" refers to a nucleic acid fragment that expresses one or more specific proteins, including regulatory sequences preceding (5' non-coding sequences) and following (3' termination sequences) coding sequences for the proteins. A chimeric gene is a recombinant genetic expression element. The coding regions of an operon may form a recombinant genetic expression element, along with an operably linked promoter and termination region.

"Regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, enhancers, operators, repressors, transcription termination signals, translation leader sequences, introns, polyadenylation recognition sequences, RNA processing site, effector binding site and stem-loop structure.

The term "promoter" refers to a nucleic acid sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic nucleic acid segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". "Inducible promoters," on the other hand, cause a gene to be expressed when the promoter is induced or turned on by a promoter-specific signal or molecule. It is further recognized that since in most cases the exact boundaries of regulatory sequences have not been completely defined, DNA fragments of different lengths may have identical promoter activity. For example, it will be understood that "FBA1 promoter" can be used to refer to a fragment derived from the promoter region of the FBA1 gene.

The term "terminator" as used herein refers to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence. It is recognized that since in most cases the exact boundaries of regulatory sequences have not been completely defined, DNA fragments of different lengths may have identical terminator activity. For example, it will be understood that "CYC1 terminator" can be used to refer to a fragment derived from the terminator region of the CYC1 gene.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Such optimization includes replacing at least one, or more than one, or a significant number, of codons with one or more codons that are more frequently used in the genes of that organism.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 1

The Standard Genetic Code

| | T | C | A | G |
|---|---|---|---|---|
| T | TTT Phe (F) | TCT Ser (S) | TAT Tyr (Y) | TGT Cys (C) |
| | TTC Phe (F) | TCC Ser (S) | TAC Tyr (Y) | TGC |
| | TTA Leu (L) | TCA Ser (S) | TAA Ter | TGA Ter |
| | TTG Leu (L) | TCG Ser (S) | TAG Ter | TGG Trp (W) |
| C | CTT Leu (L) | CCT Pro (P) | CAT His (H) | CGT Arg (R) |
| | CTC Leu (L) | CCC Pro (P) | CAC His (H) | CGC Arg (R) |
| | CTA Leu (L) | CCA Pro (P) | CAA Gln (Q) | CGA Arg (R) |
| | CTG Leu (L) | CCG Pro (P) | CAG Gln (Q) | CGG Arg (R) |
| A | ATT Ile (I) | ACT Thr (T) | AAT Asn (N) | AGT Ser (S) |
| | ATC Ile (I) | ACC Thr (T) | AAC Asn (N) | AGC Ser (S) |
| | ATA Ile (I) | ACA Thr (T) | AAA Lys (K) | AGA Arg (R) |
| | ATG Met (M) | ACG Thr (T) | AAG Lys (K) | AGG Arg (R) |
| G | GTT Val (V) | GCT Ala (A) | GAT Asp (D) | GGT Gly (G) |
| | GTC Val (V) | GCC Ala (A) | GAC Asp (D) | GGC Gly (G) |
| | GTA Val (V) | GCA Ala (A) | GAA Glu (E) | GGA Gly (G) |
| | GTG Val (V) | GCG Ala (A) | GAG Glu (E) | GGG Gly (G) |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example, at the "Codon Usage Database" available at the Kazusa DNA Research Institute, Japan, and these tables can be adapted in a number of ways. See Nakamura, Y., et al. *Nucl. Acids Res.* 28:292(2000). Codon usage tables for yeast, calculated from GenBank Release 128.0 [15 Feb. 2002], are reproduced below as Table 2. This table uses mRNA nomenclature, and so instead of thymine (T) which is found in DNA, the tables use uracil (U) which is found in RNA. The Table has been adapted so that frequencies are calculated for each amino acid, rather than for all 64 codons.

TABLE 2

Codon Usage Table for *Saccharomyces cerevisiae* Genes

| Amino Acid | Codon | Number | Frequency per thousand |
|---|---|---|---|
| Phe | UUU | 170666 | 26.1 |
| Phe | UUC | 120510 | 18.4 |
| Leu | UUA | 170884 | 26.2 |
| Leu | UUG | 177573 | 27.2 |
| Leu | CUU | 80076 | 12.3 |
| Leu | CUC | 35545 | 5.4 |
| Leu | CUA | 87619 | 13.4 |
| Leu | CUG | 68494 | 10.5 |
| Ile | AUU | 196893 | 30.1 |
| Ile | AUC | 112176 | 17.2 |
| Ile | AUA | 116254 | 17.8 |
| Met | AUG | 136805 | 20.9 |
| Val | GUU | 144243 | 22.1 |
| Val | GUC | 76947 | 11.8 |
| Val | GUA | 76927 | 11.8 |
| Val | GUG | 70337 | 10.8 |
| Ser | UCU | 153557 | 23.5 |
| Ser | UCC | 92923 | 14.2 |
| Ser | UCA | 122028 | 18.7 |
| Ser | UCG | 55951 | 8.6 |
| Ser | AGU | 92466 | 14.2 |
| Ser | AGC | 63726 | 9.8 |
| Pro | CCU | 88263 | 13.5 |
| Pro | CCC | 44309 | 6.8 |
| Pro | CCA | 119641 | 18.3 |
| Pro | CCG | 34597 | 5.3 |
| Thr | ACU | 132522 | 20.3 |
| Thr | ACC | 83207 | 12.7 |
| Thr | ACA | 116084 | 17.8 |
| Thr | ACG | 52045 | 8.0 |
| Ala | GCU | 138358 | 21.2 |
| Ala | GCC | 82357 | 12.6 |
| Ala | GCA | 105910 | 16.2 |
| Ala | GCG | 40358 | 6.2 |
| Tyr | UAU | 122728 | 18.8 |
| Tyr | UAC | 96596 | 14.8 |
| His | CAU | 89007 | 13.6 |
| His | CAC | 50785 | 7.8 |
| Gln | CAA | 178251 | 27.3 |
| Gln | CAG | 79121 | 12.1 |
| Asn | AAU | 233124 | 35.7 |
| Asn | AAC | 162199 | 24.8 |
| Lys | AAA | 273618 | 41.9 |
| Lys | AAG | 201361 | 30.8 |

TABLE 2-continued

Codon Usage Table for *Saccharomyces cerevisiae* Genes

| Amino Acid | Codon | Number | Frequency per thousand |
|---|---|---|---|
| Asp | GAU | 245641 | 37.6 |
| Asp | GAC | 132048 | 20.2 |
| Glu | GAA | 297944 | 45.6 |
| Glu | GAG | 125717 | 19.2 |
| Cys | UGU | 52903 | 8.1 |
| Cys | UGC | 31095 | 4.8 |
| Trp | UGG | 67789 | 10.4 |
| Arg | CGU | 41791 | 6.4 |
| Arg | CGC | 16993 | 2.6 |
| Arg | CGA | 19562 | 3.0 |
| Arg | CGG | 11351 | 1.7 |
| Arg | AGA | 139081 | 21.3 |
| Arg | AGG | 60289 | 9.2 |
| Gly | GGU | 156109 | 23.9 |
| Gly | GGC | 63903 | 9.8 |
| Gly | GGA | 71216 | 10.9 |
| Gly | GGG | 39359 | 6.0 |
| Stop | UAA | 6913 | 1.1 |
| Stop | UAG | 3312 | 0.5 |
| Stop | UGA | 4447 | 0.7 |

By utilizing this or similar tables, one of ordinary skill in the art can apply the frequencies to any given polypeptide sequence, and produce a nucleic acid fragment of a codon-optimized coding region which encodes the polypeptide, but which uses codons optimal for a given species.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, WI, the backtranslation function in the VectorNT1 Suite, available from InforMax, Inc., Bethesda, MD, and the "backtranslate" function in the GCG--Wisconsin Package, available from Accelrys, Inc., San Diego, CA. In addition, various resources are publicly available to codon-optimize coding region sequences, e.g., the "JAVA Codon Adaptation Tool" (Grote, et al., Nucl. Acids Res. 33:W526-W531, 2005) and the "Codon optimization tool" available at Entelechon GmbH, Regensburg, Germany.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence.

As a practical matter, whether any particular nucleic acid molecule or polynucleotide is at least 80%, 85%, 90%, 95%, 96%, 97%, 98%, or 99% identical to a nucleotide sequence or polypeptide sequence of the present invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al., *Comp. Appl. Biosci.* 6:237-245 (1990). In a sequence alignment the query and subject sequences are both DNA sequences. An RNA sequence can be compared by converting U's to T's. The result of the global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the subject nucleotide sequences, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/aligned of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to be made for the purposes of the present invention.

Standard recombinant DNA and molecular cloning techniques are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et al., *Current Protocols in Molecular Biology*, published by Greene Publishing Assoc. and Wiley-Interscience (1987). Additional methods used here are in *Methods in Enzymology*, Volume 194, *Guide to Yeast Genetics and Molecular and Cell Biology* (Part A, 2004, Christine Guthrie and Gerald R. Fink (Eds.), Elsevier Academic Press, San Diego, Calif.). Other molecular tools and techniques are known in the art and include splicing by overlapping extension polymerase chain reaction (PCR) (Yu, et al. (2004) Fungal Genet. Biol. 41:973-981), positive selection for mutations at the URA3 locus of *Saccharomyces cerevisiae* (Boeke, J. D. et al. (1984) Mol. Gen. Genet. 197, 345-346; M A Romanos, et al. Nucleic Acids Res. 1991 Jan. 11; 19(1): 187), the cre-lox site-specific recombination system as well as mutant lox sites and FLP substrate mutations (Sauer, B. (1987) Mol Cell Biol 7: 2087-2096; Senecoff, et al. (1988) Journal of Molecular Biology, Volume 201, Issue 2, Pages 405-421; Albert, et al. (1995) The Plant Journal. Volume 7, Issue 4, pages 649-659), "seamless" gene deletion (Akada, et al. (2006) Yeast; 23(5):399-405), and gap repair methodology (Ma et al., *Genetics* 58:201-216; 1981).

The genetic manipulations of a recombinant host cell disclosed herein can be performed using standard genetic techniques and screening and can be made in any host cell that is suitable to genetic manipulation (*Methods in Yeast Genetics*, 2005, Cold Spring Harbor Laboratory Press, Cold Spring Harbor, N.Y., pp. 201-202). Construction of butanologens is described herein and in the art, for example in in PCT Pub. No. WO/2012/129555, incorporated herein by reference.

"qPCR" or "RT-PCR" is a PCT-based laboratory technique that simultaneously amplifies and quantifies a target gene.

Biosynthetic Pathways

Biosynthetic pathways for the production of isobutanol that may be used include those described in U.S. Pat. Nos. 7,851,188 and 7,993,889, which are incorporated herein by reference. Isobutanol pathways are referred to with their lettering in FIG. 1. In one embodiment, the isobutanol biosynthetic pathway comprises the following substrate to product conversions:

a) pyruvate to acetolactate, which may be catalyzed, for example, by acetolactate synthase;

b) acetolactate to 2,3-dihydroxyisovalerate, which may be catalyzed, for example, by ketol-acid reductoisomerase;

c) 2,3-dihydroxyisovalerate to α-ketoisovalerate, which may be catalyzed, for example, by dihydroxyacid dehydratase;

d) α-ketoisovalerate to isobutyraldehyde, which may be catalyzed, for example, by a branched-chain keto acid decarboxylase; and, e) isobutyraldehyde to isobutanol, which may be catalyzed, for example, by a branched-chain alcohol dehydrogenase.

In another embodiment, the isobutanol biosynthetic pathway comprises the following substrate to product conversions:

a) pyruvate to acetolactate, which may be catalyzed, for example, by acetolactate synthase;

b) acetolactate to 2,3-dihydroxyisovalerate, which may be catalyzed, for example, by ketol-acid reductoisomerase;

c) 2,3-dihydroxyisovalerate to α-ketoisovalerate, which may be catalyzed, for example, by dihydroxyacid dehydratase;

h) α-ketoisovalerate to valine, which may be catalyzed, for example, by transaminase or valine dehydrogenase;

i) valine to isobutylamine, which may be catalyzed, for example, by valine decarboxylase;

j) isobutylamine to isobutyraldehyde, which may be catalyzed by, for example, omega transaminase; and,
e) isobutyraldehyde to isobutanol, which may be catalyzed, for example, by a branched-chain alcohol dehydrogenase.

In another embodiment, the isobutanol biosynthetic pathway comprises the following substrate to product conversions:
a) pyruvate to acetolactate, which may be catalyzed, for example, by acetolactate synthase;
b) acetolactate to 2,3-dihydroxyisovalerate, which may be catalyzed, for example, by ketol-acid reductoisomerase;
c) 2,3-dihydroxyisovalerate to α-ketoisovalerate, which may be catalyzed, for example, by dihydroxyacid dehydratase;
f) α-ketoisovalerate to isobutyryl-CoA, which may be catalyzed, for example, by branched-chain keto acid dehydrogenase;
g) isobutyryl-CoA to isobutyraldehyde, which may be catalyzed, for example, by acetylating aldehyde dehydrogenase; and,
e) isobutyraldehyde to isobutanol, which may be catalyzed, for example, by a branched-chain alcohol dehydrogenase.

In another embodiment, the isobutanol biosynthetic pathway comprises the substrate to product conversions shown as steps k, g, and e in FIG. 1.

Biosynthetic pathways for the production of 1-butanol that may be used include those described in U.S. Appl. Pub. No. 2008/0182308, which is incorporated herein by reference. In one embodiment, the 1-butanol biosynthetic pathway comprises the following substrate to product conversions:
a) acetyl-CoA to acetoacetyl-CoA, which may be catalyzed, for example, by acetyl-CoA acetyl transferase;
b) acetoacetyl-CoA to 3-hydroxybutyryl-CoA, which may be catalyzed, for example, by 3-hydroxybutyryl-CoA dehydrogenase;
c) 3-hydroxybutyryl-CoA to crotonyl-CoA, which may be catalyzed, for example, by crotonase;
d) crotonyl-CoA to butyryl-CoA, which may be catalyzed, for example, by butyryl-CoA dehydrogenase;
e) butyryl-CoA to butyraldehyde, which may be catalyzed, for example, by butyraldehyde dehydrogenase; and,
f) butyraldehyde to 1-butanol, which may be catalyzed, for example, by butanol dehydrogenase.

Biosynthetic pathways for the production of 2-butanol that may be used include those described in U.S. Appl. Pub. No. 2007/0259410 and U.S. Appl. Pub. No. 2009/0155870, which are incorporated herein by reference. In one embodiment, the 2-butanol biosynthetic pathway comprises the following substrate to product conversions:
a) pyruvate to alpha-acetolactate, which may be catalyzed, for example, by acetolactate synthase;
b) alpha-acetolactate to acetoin, which may be catalyzed, for example, by acetolactate decarboxylase;
c) acetoin to 3-amino-2-butanol, which may be catalyzed, for example, acetoin aminase;
d) 3-amino-2-butanol to 3-amino-2-butanol phosphate, which may be catalyzed, for example, by aminobutanol kinase;
e) 3-amino-2-butanol phosphate to 2-butanone, which may be catalyzed, for example, by aminobutanol phosphate phosphorylase; and,
f) 2-butanone to 2-butanol, which may be catalyzed, for example, by butanol dehydrogenase.

In another embodiment, the 2-butanol biosynthetic pathway comprises the following substrate to product conversions:
a) pyruvate to alpha-acetolactate, which may be catalyzed, for example, by acetolactate synthase;
b) alpha-acetolactate to acetoin, which may be catalyzed, for example, by acetolactate decarboxylase;
c) acetoin to 2,3-butanediol, which may be catalyzed, for example, by butanediol dehydrogenase;
d) 2,3-butanediol to 2-butanone, which may be catalyzed, for example, by dial dehydratase; and,
e) 2-butanone to 2-butanol, which may be catalyzed, for example, by butanol dehydrogenase.

Biosynthetic pathways for the production of 2-butanone that may be used include those described in U.S. Appl. Pub. No. 2007/0259410 and U.S. Appl. Pub. No. 2009/0155870, which are incorporated herein by reference. In one embodiment, the 2-butanone biosynthetic pathway comprises the following substrate to product conversions:
a) pyruvate to alpha-acetolactate, which may be catalyzed, for example, by acetolactate synthase;
b) alpha-acetolactate to acetoin, which may be catalyzed, for example, by acetolactate decarboxylase;
c) acetoin to 3-amino-2-butanol, which may be catalyzed, for example, acetoin aminase;
d) 3-amino-2-butanol to 3-amino-2-butanol phosphate, which may be catalyzed, for example, by aminobutanol kinase; and,
e) 3-amino-2-butanol phosphate to 2-butanone, which may be catalyzed, for example, by aminobutanol phosphate phosphorylase.

In another embodiment, the 2-butanone biosynthetic pathway comprises the following substrate to product conversions:
a) pyruvate to alpha-acetolactate, which may be catalyzed, for example, by acetolactate synthase;
b) alpha-acetolactate to acetoin which may be catalyzed, for example, by acetolactate decarboxylase;
c) acetoin to 2,3-butanediol, which may be catalyzed, for example, by butanediol dehydrogenase;
d) 2,3-butanediol to 2-butanone, which may be catalyzed, for example, by dial dehydratase.

In one embodiment, the invention produces butanol from plant derived carbon sources, avoiding the negative environmental impact associated with standard petrochemical processes for butanol production. In one embodiment, the invention provides a method for the production of butanol using recombinant industrial host cells comprising a butanol pathway.

In some embodiments, the isobutanol biosynthetic pathway comprises at least one polynucleotide, at least two polynucleotides, at least three polynucleotides, or at least four polynucleotides that is/are heterologous to the host cell. In embodiments, each substrate to product conversion of an isobutanol biosynthetic pathway in a recombinant host cell is catalyzed by a heterologous polypeptide. In embodiments, the polypeptide catalyzing the substrate to product conversions of acetolactate to 2,3-dihydroxyisovalerate and/or the polypeptide catalyzing the substrate to product conversion of isobutyraldehyde to isobutanol are capable of utilizing NADH as a cofactor.

The terms "acetohydroxyacid synthase," "acetolactate synthase" and "acetolactate synthetase" (abbreviated "ALS") are used interchangeably herein to refer to an enzyme that catalyzes the conversion of pyruvate to acetolactate and $CO_2$. Example acetolactate synthases are known by the EC number 2.2.1.6 (Enzyme Nomenclature 1992, Academic Press, San Diego). These unmodified enzymes are available from a number of sources, including, but not limited to, *Bacillus subtilis* (GenBank Nos: CAB07802.1, Z99122 (SEQ ID NO:16), NCBI (National Center for Biotechnology Information)), CAB15618), *Klebsiella pneumoniae* (GenBank Nos: AAA25079, M73842, *Lactococcus lactis* (GenBank Nos: AAA25161, L16975), *S. cerevisiae* (SEQ ID NOs:130 and 131), *E. coli* K12 (SEQ ID NOs:132 and 133).

The term "ketol-acid reductoisomerase" ("KARI"), "acetohydroxy acid reductoisomerase" and "acetohydroxy acid isomeroreductase" will be used interchangeably and refer to enzymes capable of catalyzing the reaction of (S)-acetolactate to 2,3-dihydroxyisovalerate. Example KARI enzymes may be classified as EC number EC 1.1.1.86 (Enzyme Nomenclature 1992, Academic Press, San Diego), and are available from a vast array of microorganisms, including, but not limited to, *Escherichia coli* (GenBank Nos: NP_418222, NC_000913), *Saccharomyces cerevisiae* (GenBank Nos: NP_013459, NC_001144), *Methanococcus maripaludis* (GenBank Nos: CAF30210, BX957220), and *Bacillus subtilis* (GenBank Nos: CAB14789, Z99118). KARIs include *Anaerostipes caccae* KARI variants "K9G9," "K9D3" and "K9JB4P" (SEQ ID NOs:37, 38, and 182 respectively). Ketol-acid reductoisomerase (KARI) enzymes are described in U.S. Patent Appl. Pub. Nos. 20080261230 A1, 20090163376 A1, 20100197519 A1, PCT Appl. Pub. Nos. WO/2011/041415, and WO/2012/129555, which are incorporated herein by reference. Examples of KARIs disclosed therein are those from *Lactococcus lactis, Vibrio cholera, Pseudomonas aeruginosa* PAO1, and *Pseudomonas fluorescens* PF5 mutants. *Pseudomonas fluorescens* KARIs include SEQ ID NO:134. In some embodiments, the KARI utilizes NADH. In some embodiments, the KARI utilizes NADPH. In some embodiments, the KARI utilizes NADH or NADPH.

The term "acetohydroxy acid dehydratase" and "dihydroxyacid dehydratase" ("DHAD") refers to an enzyme that catalyzes the conversion of 2,3-dihydroxyisovalerate to α-ketoisovalerate. Example acetohydroxy acid dehydratases are known by the EC number 4.2.1.9. Such enzymes are available from a vast array of microorganisms, including, but not limited to, *E. coli* (GenBank Nos: YP_026248, NC_000913), *S. cerevisiae* (GenBank Nos: NP_012550, NC 001142), *M. maripaludis* (GenBank Nos: CAF29874, BX957219), *B. subtilis* (GenBank Nos: CAB14105, Z99115), *L. lactis* (SEQ ID NO:108), and *N. crassa*. US Appl. Pub. No. 20100081154 A1, and U.S. Pat. No. 7,851,188, which are incorporated herein by reference, describe dihydroxyacid dehydratases (DHADs), including a DHAD from *Streptococcus mutans* (SEQ ID NO:135). Example DHADs include variants of *S. mutans* DHAD, for example "L2V4" (SEQ ID NO:183).

The term "branched-chain α-keto acid decarboxylase" or "α-ketoacid decarboxylase" or "α-ketoisovalerate decarboxylase" or "2-ketoisovalerate decarboxylase" ("KIVD") refers to an enzyme that catalyzes the conversion of α-ketoisovalerate to isobutyraldehyde and $CO_2$. Example branched-chain α-keto acid decarboxylases are known by the EC number 4.1.1.72 and are available from a number of sources, including, but not limited to, *Lactococcus lactis* (GenBank Nos: AAS49166 (SEQ ID NO:141), AY548760; CAG34226, AJ746364, *Salmonella typhimurium* (GenBank Nos: NP_461346, NC_003197), *Clostridium acetobutylicum* (GenBank Nos: NP_149189, NC_001988), *M. caseolyticus* (SEQ ID NOs:118, 137), and *L. grayi* (SEQ ID NO:136).

The term "branched-chain alcohol dehydrogenase" ("ADH") refers to an enzyme that catalyzes the conversion of isobutyraldehyde to isobutanol. Example branched-chain alcohol dehydrogenases are known by the EC number 1.1.1.265, but may also be classified under other alcohol dehydrogenases (specifically, EC 1.1.1.1 or 1.1.1.2). Alcohol dehydrogenases may be NADPH dependent or NADH dependent. Such enzymes are available from a number of sources, including, but not limited to, *S. cerevisiae* (GenBank Nos: NP_010656, NC_001136; NP_014051, NC_001145), *E. coli* (GenBank Nos: NP_417484, NC_000913), *C. acetobutylicum* (GenBank Nos: NP_349892, NC_003030; NP_349891, NC_003030). U.S. Pat. No. 8,188,250, which is incorporated herein by reference, describes SadB, an alcohol dehydrogenase (ADH) from *Achromobacter xylosoxidans* (SEQ ID NO:139). Alcohol dehydrogenases also include horse liver ADH (SEQ ID NO:142) and *Beijerinkia indica* ADH (SEQ ID NO:138) (as described by U.S. Appl. Publ. No. 20110269199, which is incorporated herein by reference).

The term "butanol dehydrogenase" refers to a polypeptide (or polypeptides) having an enzyme activity that catalyzes the conversion of isobutyraldehyde to isobutanol or the conversion of 2-butanone and 2-butanol. Butanol dehydrogenases are a subset of a broad family of alcohol dehydrogenases. Butanol dehydrogenase may be NAD- or NADP-dependent. The NAD-dependent enzymes are known as EC 1.1.1.1 and are available, for example, from *Rhodococcus ruber* (GenBank Nos: CAD36475, AJ491307). The NADP dependent enzymes are known as EC 1.1.1.2 and are available, for example, from *Pyrococcus furiosus* (GenBank Nos: AAC25556, AF013169). Additionally, a butanol dehydrogenase is available from *Escherichia coli* (GenBank Nos: NP_417484, NC_000913) and a cyclohexanol dehydrogenase is available from *Acinetobacter* sp. (GenBank Nos: AAG10026, AF282240). The term "butanol dehydrogenase" also refers to an enzyme that catalyzes the conversion of butyraldehyde to 1-butanol, using either NADH or NADPH as cofactor. Butanol dehydrogenases are available from, for example, *C. acetobutylicum* (GenBank NOs: NP_149325, NC_001988; note: this enzyme possesses both aldehyde and alcohol dehydrogenase activity); NP_349891, NC_003030; and NP_349892, NC_003030), *E. coli* (GenBank NOs: NP_417-484, NC_000913), and *A. xylosoxidans* (SEQ ID NOs:47 and 48, as described in U.S. Pat. No. 8,188,250, which is incorporated herein by reference in its entirety.

The term "branched-chain keto acid dehydrogenase" refers to an enzyme that catalyzes the conversion of α-ketoisovalerate to isobutyryl-CoA (isobutyryl-coenzyme A), typically using $NAD^+$ (nicotinamide adenine dinucleotide) as an electron acceptor. Example branched-chain keto acid dehydrogenases are known by the EC number 1.2.4.4. Such branched-chain keto acid dehydrogenases are comprised of four subunits and sequences from all subunits are available from a vast array of microorganisms, including, but not limited to, *B. subtilis* (GenBank Nos: CAB14336, Z99116; CAB14335, Z99116; CAB14334, Z99116; and CAB14337, Z99116) and *Pseudomonas putida* (GenBank Nos: AAA65614, M57613; AAA65615, M57613; AAA65617, M57613; and AAA65618, M57613).

The term "acylating aldehyde dehydrogenase" refers to an enzyme that catalyzes the conversion of isobutyryl-CoA to isobutyraldehyde, typically using either NADH or NADPH as an electron donor. Example acylating aldehyde dehydrogenases are known by the EC numbers 1.2.1.10 and 1.2.1.57. Such enzymes are available from multiple sources, including, but not limited to, *Clostridium beijerinckii* (GenBank Nos: AAD31841, AF157306), *C. acetobutylicum* (GenBank Nos: NP_149325, NC_001988; NP_149199, NC_001988), *P. putida* (GenBank Nos: AAA89106, U13232), and *Thermus thermophilus* (GenBank Nos: YP_145486, NC_006461).

The term "transaminase" refers to an enzyme that catalyzes the conversion of α-ketoisovalerate to L-valine, using either alanine or glutamate as an amine donor. Example transaminases are known by the EC numbers 2.6.1.42 and 2.6.1.66. Such enzymes are available from a number of sources. Examples of sources for alanine-dependent enzymes include, but are not limited to, *E. coli* (GenBank Nos: YP_026231, NC_000913) and *Bacillus licheniformis* (GenBank Nos: YP_093743, NC_006322). Examples of sources for glutamate-dependent enzymes include, but are not limited to, *E. coli* (GenBank Nos: YP_026247, NC_000913), *S. cerevisiae* (GenBank Nos: NP_012682, NC_001142) and *Methanobacterium thermoautotrophicum* (GenBank Nos: NP_276546, NC_000916).

The term "valine dehydrogenase" refers to an enzyme that catalyzes the conversion of α-ketoisovalerate to L-valine, typically using NAD(P)H as an electron donor and ammonia as an amine donor. Example valine dehydrogenases are known by the EC numbers 1.4.1.8 and 1.4.1.9 and such enzymes are available from a number of sources, including, but not limited to, *Streptomyces coelicolor* (GenBank Nos: NP_628270, NC_003888) and *B. subtilis* (GenBank Nos: CAB14339, Z99116).

The term "valine decarboxylase" refers to an enzyme that catalyzes the conversion of L-valine to isobutylamine and $CO_2$. Example valine decarboxylases are known by the EC number 4.1.1.14. Such enzymes are found in *Streptomyces*, such as for example, *Streptomyces viridifaciens* (GenBank Nos: AAN10242, AY116644).

The term "omega transaminase" refers to an enzyme that catalyzes the conversion of isobutylamine to isobutyraldehyde using a suitable amino acid as an amine donor. Example omega transaminases are known by the EC number 2.6.1.18 and are available from a number of sources, including, but not limited to, *Alcaligenes denitrificans* (AAP92672, AY330220), *Ralstonia eutropha* (GenBank Nos: YP_294474, NC_007347), *Shewanella oneidensis* (GenBank Nos: NP_719046, NC_004347), and *P. putida* (GenBank Nos: AAN66223, AE016776).

The term "acetyl-CoA acetyltransferase" refers to an enzyme that catalyzes the conversion of two molecules of acetyl-CoA to acetoacetyl-CoA and coenzyme A (CoA). Example acetyl-CoA acetyltransferases are acetyl-CoA acetyltransferases with substrate preferences (reaction in the forward direction) for a short chain acyl-CoA and acetyl-CoA and are classified as E.C. 2.3.1.9 [Enzyme Nomenclature 1992, Academic Press, San Diego]; although, enzymes with a broader substrate range (E.C. 2.3.1.16) will be functional as well. Acetyl-CoA acetyltransferases are available from a number of sources, for example, *Escherichia coli* (GenBank Nos: NP_416728, NC_000913; NCBI (National Center for Biotechnology Information) amino acid sequence, NCBI nucleotide sequence), *Clostridium acetobutylicum* (GenBank Nos: NP_349476.1, NC_003030; NP_149242, NC_001988, *Bacillus subtilis* (GenBank Nos: NP_390297, NC_000964), and *Saccharomyces cerevisiae* (GenBank Nos: NP_015297, NC_001148).

The term "3-hydroxybutyryl-CoA dehydrogenase" refers to an enzyme that catalyzes the conversion of acetoacetyl-CoA to 3-hydroxybutyryl-CoA. Example hydroxybutyryl-CoA dehydrogenases may be reduced nicotinamide adenine dinucleotide (NADH)-dependent, with a substrate preference for (S)-3-hydroxybutyryl-CoA or (R)-3-hydroxybutyryl-CoA. Examples may be classified as E.C. 1.1.1.35 and E.C. 1.1.1.30, respectively. Additionally, 3-hydroxybutyryl-CoA dehydrogenases may be reduced nicotinamide adenine dinucleotide phosphate (NADPH)-dependent, with a substrate preference for (S)-3-hydroxybutyryl-CoA or (R)-3-hydroxybutyryl-CoA and are classified as E.C. 1.1.1.157 and E.C. 1.1.1.36, respectively. 3-Hydroxybutyryl-CoA dehydrogenases are available from a number of sources, for example, *C. acetobutylicum* (GenBank NOs: NP_349314, NC_003030), *B. subtilis* (GenBank NOs: AAB09614, U29084), *Ralstonia eutropha* (GenBank NOs: YP_294481, NC_007347), and *Alcaligenes eutrophus* (GenBank NOs: AAA21973, J04987).

The term "crotonase" refers to an enzyme that catalyzes the conversion of 3-hydroxybutyryl-CoA to crotonyl-CoA and $H_2O$. Example crotonases may have a substrate preference for (S)-3-hydroxybutyryl-CoA or (R)-3-hydroxybutyryl-CoA and may be classified as E.C. 4.2.1.17 and E.C. 4.2.1.55, respectively. Crotonases are available from a number of sources, for example, *E. coli* (GenBank NOs: NP_415911, NC_000913), *C. acetobutylicum* (GenBank NOs: NP_349318, NC_003030), *B. subtilis* (GenBank NOs: CAB13705, Z99113), and *Aeromonas caviae* (GenBank NOs: BAA21816, D88825).

The term "butyryl-CoA dehydrogenase" refers to an enzyme that catalyzes the conversion of crotonyl-CoA to butyryl-CoA. Example butyryl-CoA dehydrogenases may be NADH-dependent, NADPH-dependent, or flavin-dependent and may be classified as E.C. 1.3.1.44, E.C. 1.3.1.38, and E.C. 1.3.99.2, respectively. Butyryl-CoA dehydrogenases are available from a number of sources, for example, *C. acetobutylicum* (GenBank NOs: NP_347102, NC_003030), *Euglena gracilis* (GenBank NOs: Q5EU90), AY741582), *Streptomyces collinus* (GenBank NOs: AAA92890, U37135), and *Streptomyces coelicolor* (GenBank NOs: CAA22721, AL939127).

The term "butyraldehyde dehydrogenase" refers to an enzyme that catalyzes the conversion of butyryl-CoA to butyraldehyde, using NADH or NADPH as cofactor. Butyraldehyde dehydrogenases with a preference for NADH are known as E.C. 1.2.1.57 and are available from, for example, *Clostridium beijerinckii* (GenBank NOs: AAD31841, AF157306) and *C. acetobutylicum* (GenBank NOs: NP_149325, NC_001988).

The term "isobutyryl-CoA mutase" refers to an enzyme that catalyzes the conversion of butyryl-CoA to isobutyryl-CoA. This enzyme uses coenzyme $B_{12}$ as cofactor. Example isobutyryl-CoA mutases are known by the EC number 5.4.99.13. These enzymes are found in a number of *Streptomyces*, including, but not limited to, *Streptomyces cinnamonensis* (GenBank Nos: AAC08713, U67612; CAB59633, AJ246005), *S. coelicolor* (GenBank Nos: CAB70645, AL939123; CAB92663, AL939121), and *Streptomyces avermitilis* (GenBank Nos: NP_824008, NC_003155; NP_824637, NC_003155).

The term "acetolactate decarboxylase" refers to a polypeptide (or polypeptides) having an enzyme activity that catalyzes the conversion of alpha-acetolactate to acetoin. Example acetolactate decarboxylases are known as EC 4.1.1.5 and are available, for example, from *Bacillus subtilis* (GenBank Nos: AAA22223, L04470), *Klebsiella terrigena* (GenBank Nos: AAA25054, L04507) and *Klebsiella pneumoniae* (GenBank Nos: AAU43774, AY722056).

The term "acetoin aminase" or "acetoin transaminase" refers to a polypeptide (or polypeptides) having an enzyme activity that catalyzes the conversion of acetoin to 3-amino-2-butanol. Acetoin aminase may utilize the cofactor pyridoxal 5'-phosphate or NADH (reduced nicotinamide adenine dinucleotide) or NADPH (reduced nicotinamide adenine dinucleotide phosphate). The resulting product may have (R) or (S) stereochemistry at the 3-position. The pyridoxal phosphate-dependent enzyme may use an amino acid such as alanine or glutamate as the amino donor. The NADH- and NADPH-dependent enzymes may use ammonia as a second substrate. A suitable example of an NADH dependent acetoin aminase, also known as amino alcohol dehydrogenase, is described by Ito et al. (U.S. Pat. No. 6,432,688). An example of a pyridoxal-dependent acetoin aminase is the amine:pyruvate aminotransferase (also called amine:pyruvate transaminase) described by Shin and Kim (*J. Org. Chem.* 67:2848-2853 (2002)).

The term "acetoin kinase" refers to a polypeptide (or polypeptides) having an enzyme activity that catalyzes the conversion of acetoin to phosphoacetoin. Acetoin kinase may utilize ATP (adenosine triphosphate) or phosphoenolpyruvate as the phosphate donor in the reaction. Enzymes that catalyze the analogous reaction on the similar substrate dihydroxyacetone, for example, include enzymes known as EC 2.7.1.29 (Garcia-Alles et al. (2004) Biochemistry 43:13037-13046).

The term "acetoin phosphate aminase" refers to a polypeptide (or polypeptides) having an enzyme activity that catalyzes the conversion of phosphoacetoin to 3-amino-2-butanol O-phosphate. Acetoin phosphate aminase may use the cofactor pyridoxal 5'-phosphate, NADH or NADPH. The resulting product may have (R) or (S) stereochemistry at the 3-position. The pyridoxal phosphate-dependent enzyme may use an amino acid such as alanine or glutamate. The NADH and NADPH-dependent enzymes may use ammonia as a second substrate. Although there are no reports of enzymes catalyzing this reaction on phosphoacetoin, there is a pyridoxal phosphate-dependent enzyme that is proposed to carry out the analogous reaction on the similar substrate serinol phosphate (Yasuta et al. (2001) Appl. Environ. Microbial. 67:4999-5009.

The term "aminobutanol phosphate phospholyase", also called "amino alcohol O-phosphate lyase", refers to a polypeptide (or polypeptides) having an enzyme activity that catalyzes the conversion of 3-amino-2-butanol O-phosphate to 2-butanone. Amino butanol phosphate phospho-lyase may utilize the cofactor pyridoxal 5'-phosphate. There are reports of enzymes that catalyze the analogous reaction on the similar substrate 1-amino-2-propanol phosphate (Jones et al. (1973) Biochem J. 134:167-182). U.S. Appl. Pub. No. 2007/0259410 describes an aminobutanol phosphate phospho-lyase from the organism *Erwinia carotovora*.

The term "aminobutanol kinase" refers to a polypeptide (or polypeptides) having an enzyme activity that catalyzes the conversion of 3-amino-2-butanol to 3-amino-2butanol O-phosphate. Amino butanol kinase may utilize ATP as the phosphate donor. Although there are no reports of enzymes catalyzing this reaction on 3-amino-2-butanol, there are reports of enzymes that catalyze the analogous reaction on the similar substrates ethanolamine and 1-amino-2-propanol (Jones et al., supra). U.S. Appl. Pub. No. 2009/0155870 describes, in Example 14, an amino alcohol kinase of *Erwinia carotovora* subsp. *Atroseptica*.

The term "butanediol dehydrogenase" also known as "acetoin reductase" refers to a polypeptide (or polypeptides) having an enzyme activity that catalyzes the conversion of acetoin to 2,3-butanediol. Butanediol dehydrogenases are a subset of the broad family of alcohol dehydrogenases. Butanediol dehydrogenase enzymes may have specificity for production of (R)- or (S)-stereochemistry in the alcohol product. (S)-specific butanediol dehydrogenases are known as EC 1.1.1.76 and are available, for example, from *Klebsiella pneumoniae* (GenBank Nos: BBA13085, D86412). (R)-specific butanediol dehydrogenases are known as EC 1.1.1.4 and are available, for example, from *Bacillus cereus* (GenBank Nos. NP 830481, NC_004722; AAP07682, AE017000), and *Lactococcus lactis* (GenBank Nos. AAK04995, AE006323).

The term "butanediol dehydratase", also known as "dial dehydratase" or "propanediol dehydratase" refers to a polypeptide (or polypeptides) having an enzyme activity that catalyzes the conversion of 2,3-butanediol to 2-butanone. Butanediol dehydratase may utilize the cofactor adenosyl cobalamin (also known as coenzyme Bw or vitamin B12; although vitamin B12 may refer also to other forms of cobalamin that are not coenzyme B12). Adenosyl cobalamin-dependent enzymes are known as EC 4.2.1.28 and are available, for example, from *Klebsiella oxytoca* (GenBank Nos: AA08099 (alpha subunit), D45071; BAA08100 (beta subunit), D45071; and BBA08101 (gamma subunit), D45071 (Note all three subunits are required for activity), and *Klebsiella pneumonia* (GenBank Nos: AAC98384 (alpha subunit), AF102064; GenBank Nos: AAC98385 (beta subunit), AF102064, GenBank Nos: AAC98386 (gamma subunit), AF102064). Other suitable dial dehydratases include, but are not limited to, B12-dependent dial dehydratases available from *Salmonella typhimurium* (GenBank Nos: AAB84102 (large subunit), AF026270; GenBank Nos: AAB84103 (medium subunit), AF026270; GenBank Nos: AAB84104 (small subunit), AF026270); and *Lactobacillus collinoides* (GenBank Nos: CAC82541 (large subunit), AJ297723; GenBank Nos: CAC82542 (medium subunit); AJ297723; GenBank Nos: CAD01091 (small subunit), AJ297723); and enzymes from *Lactobacillus brevis* (particularly strains CNRZ 734 and CNRZ 735, Speranza et al., J. Agric. Food Chem. (1997) 45:3476-3480), and nucleotide sequences that encode the corresponding enzymes. Methods of dial dehydratase gene isolation are well known in the art (e.g., U.S. Pat. No. 5,686,276).

The term "pyruvate decarboxylase" refers to an enzyme that catalyzes the decarboxylation of pyruvic acid to acetaldehyde and carbon dioxide. Pyruvate decarboxylases are known by the EC number 4.1.1.1. These enzymes are found in a number of yeast, including *Saccharomyces cerevisiae* (GenBank Nos: CAA97575 (SEQ ID NO:1), CAA97705 (SEQ ID NO:2), CAA97091 (SEQ ID NO:3)).

The term "ethanol dehydrogenase" or "alcohol dehydrogenase" refers to an enzyme that catalyze the interconversion between aldehydes or ketones and alcohols, frequently using either NADH and/or NADPH as cofactors. Ethanol dehydrogenases comprise the EC numbers 1.1.1.1., 1.1.99.8., 1.1.1.244., 1.1.2.B1., 1.1.2.B2., 1.1.2.B3.

It will be appreciated that host cells comprising an isobutanol biosynthetic pathway as provided herein may further comprise one or more additional modifications. U.S. Appl. Pub. No. 20090305363 (incorporated by reference) discloses increased conversion of pyruvate to acetolactate by engineering yeast for expression of a cytosol-localized acetolactate synthase and substantial elimination of pyruvate decarboxylase activity. In some embodiments, the host cells comprise modifications to reduce glycerol-3-phosphate dehydrogenase activity and/or disruption in at least one gene encoding a polypeptide having pyruvate decarboxylase activity or a disruption in at least one gene encoding a regulatory element controlling pyruvate decarboxylase gene expression as described in U.S. Patent Appl. Pub. No. 20090305363 (incorporated herein by reference), modifications to a host cell that provide for increased carbon flux through an Entner-Doudoroff Pathway or reducing equivalents balance as described in U.S. Patent Appl. Pub. No. 20100120105 (incorporated herein by reference). Other modifications are described in PCT Pub. No. WO/2012/129555, incorporated herein by reference, and include integration of at least one polynucleotide encoding a polypeptide that catalyzes a step in a pyruvate-utilizing biosynthetic pathway. Other modifications include at least one deletion, mutation, and/or substitution in an endogenous polynucleotide encoding a polypeptide having acetolactate reductase activity. In embodiments, the polypeptide having acetolactate reductase activity is YMR226C (SEQ ID NOs:4, 5) of Saccharomyces cerevisiae or a homolog thereof. Additional modifications include a deletion, mutation, and/or substitution in an endogenous polynucleotide encoding a polypeptide having aldehyde dehydrogenase and/or aldehyde oxidase activity. In embodiments, the polypeptide having aldehyde dehydrogenase activity is ALD6 from Saccharomyces cerevisiae or a homolog thereof. A genetic modification which has the effect of reducing glucose repression wherein the yeast production host cell is pdc- is described in U.S. Appl. Publication No. 20110124060, incorporated herein by reference. In some embodiments, the pyruvate decarboxylase that is deleted or downregulated is selected from the group consisting of: PDC1, PDC5, PDC6, and combinations thereof. In some embodiments, the pyruvate decarboxylase is selected from those enzymes described in U.S. Patent Appl. Pub. No. 20090305363. In some embodiments, host cells contain a deletion or downregulation of a polynucleotide encoding a polypeptide that catalyzes the conversion of glyceraldehyde-3-phosphate to glycerate 1,3, bisphosphate. In some embodiments, the enzyme that catalyzes this reaction is glyceraldehyde-3-phosphate dehydrogenase.

Yeasts may have one or more genes encoding pyruvate decarboxylase. For example, there is one gene encoding pyruvate decarboxylase in Candida glabrata and Schizosaccharomyces pombe, while there are three isozymes of pyruvate decarboxylase encoded by the PDC1, PCD5, and PDC6 genes in Saccharomyces. In some embodiments, in the present yeast cells at least one PDC gene is inactivated. If the yeast cell used has more than one expressed (active) PDC gene, then each of the active PDC genes may be modified or inactivated thereby producing a pdc– cell. For example, in S. cerevisiae the PDC1, PDC5, and PDC6 genes may be modified or inactivated. If a PDC gene is not active under the fermentation conditions to be used then such a gene would not need to be modified or inactivated.

Other target genes, such as those encoding pyruvate decarboxylase proteins having at least 70-75%, at least 75-80%, at least 80-85%, at least 85%-90%, at least 90%-95%, or at least 96%, at least 97%, at least 98%, or at least 99% sequence identity to the pyruvate decarboxylases described in U.S. Patent Appl. Pub. No. 20090305363 may be identified in the literature and in bioinformatics databases well known to the skilled person.

Recombinant host cells may further comprise (a) at least one heterologous polynucleotide encoding a polypeptide having dihydroxy-acid dehydratase activity; and (b)(i) at least one deletion, mutation, and/or substitution in an endogenous gene encoding a polypeptide affecting Fe—S cluster biosynthesis; and/or (ii) at least one heterologous polynucleotide encoding a polypeptide affecting Fe—S cluster biosynthesis described in U.S. Patent Appl. Pub. No. US20120064561, incorporated herein by reference. In embodiments, the polypeptide affecting Fe—S cluster biosynthesis is encoded by AFT1, AFT2, FRA2, GRX3 or CCC1. AFT1 and AFT2 are described by WO/2001/103300, which is incorporated herein by reference. In embodiments, the polypeptide affecting Fe—S cluster biosynthesis is constitutive mutant AFT1 L99A, AFT1 L102A, AFT1 C291F, or AFT1 C293F.

In some embodiments, the host cell further comprises one or more polynucleotides that encode one or more enzymes having the following Enzyme Commission Numbers: EC 4.1.1.1 (PDC1, 5, and 6) (SEQ ID NOs:1, 2, and 3) and EC 1.1.1.1 (alcohol dehydrogenase).

In some embodiments of the invention, there are one or more inhibitors, antibiotics, or combinations thereof in the fermentation medium.

In some embodiments, the inhibitor is an inhibitor of an ethanol biosynthesis pathway. In some embodiments, the inhibitor inhibits pyruvate decarboxylase and/or alcohol dehydrogenase. In some embodiments, the inhibitor is selected from the group consisting of: the $XC_6H_4CH=CHCOCOOH$ class of inhibitors/substrate analogues, cinnamaldehydes, glyoxalic acid, ketomalonate, regulatory site inhibitors, p-chloromercuribenzoic acid (pCMB), 5,5'-dithiobis(2-nitrobenzoic acid) (DNTB), pyrazole, 4-pyrazolecarboxylic acid, 1-H -pyrazole-1-carboxamidine-HC1, 4-methylpyrazole, 1-bromo-2-butanone, pyrazole-3,5-dicarboxylic acid monohydrate, and mixtures thereof. In some embodiments, the $XC_6H_4CH=CHCOCOOH$ inhibitors/substrate analogue is CPB((E)-4-(4-chlorophenyl)-2-oxo-3-butenoic acid. In some embodiments the cinnamaldehyde is p-nitrocinnamaldehyde (NA). In some embodiments, the regulatory site inhibitors are iodoacetate, 1,3-dibromoacetone, 1-bromo-2-butanone. "Cinnamaldehyde" includes both trans-cinnamaldehydes and 4-nitrocinnamaldehydes. In some embodiments, copper (II) is added at a concentration of at least about 1.1 mM, at least about 11 mM, at least about 33 mM. In some embodiments, sulfometuron methyl is added at a concentration of at least about 0.001 mM, at least about 0.01 mM, at least about 0.1 mM. In some embodiments, sulfite is added at a concentration of at least about 0.6 mM, at least about 6.2 mM, at least about 62 mM. In some embodiments, formaldehyde is added at a concentration of at least about 0.09 mM, at least about 0.9 mM, at least about 2.7 mM. In some embodiments, pyrazole is added at a concentration of at least about 0.3 mM, at least about 3 mM, at least about 30 mM. In some embodiments, 4-methylpyrazole hydrochloride is added at a concentration of at least about 4.1 mM, at least about 41mM, at least about 123 mM. In some embodiments, 4-pyrazolecarboxylic acid is added at a concentration of at least about 10 mM, at least about 100 mM, at least about 300 mM. In some embodiments, 1-bromo-2-butanone is added at a concentration of at least about 0.0002 mM, at least about 0.002 mM, at least about 0.006 mM. In some embodiments, trans-cinnamaldehyde is added at a concentration of at least about 0.025 mM, at least about 0.25 mM, at least about 0.75 mM. In some embodiments, glyoxylic acid is added at a concentration of at least about 16.8 mM, at least about 168 mM, at least about 504 mM.

In some embodiments, the inhibitor is a chemical. In some embodiments, the chemical is selected from the group consisting of: fluoroacetate (dehH1), fluorophenyalanine, formaldehyde (SFA1), sulfite (FZF1-4), and trifluoroleucine (LEU4-1).

In some embodiments, the inhibitor is an inhibitor of an amino acid biosynthesis pathway. In some embodiments, the inhibitor is an acetohydroxy acid synthase (AHAS) inhibitor. In some embodiments, the inhibitor is a sulfonylurea herbicide. In some embodiments, the sulfonylurea herbicide is selected from the group consisting of: imidazolinones, triazolopyrimidines, pyrimidinyl oxybenzoates, sulfonylureas, sulfonylamino carbonyl triazolinones, and mixtures thereof. In some embodiments, the inhibitor is selected from the group consisting of: nicosulfuron methyl, metsulfuron methyl, chlorimuron ethyl, sulfometuron methyl, chlorsulfuron, thifensulfuron methyl, and mixtures thereof. In some embodiments, the sulfonylurea herbicide is an acetohydroxyacid synthase (AHAS) inhibitor).

In some embodiments, resistance to the sulfonyl urea is conferred by a polypeptide encoded by a heterologous polynucleotide. In some embodiments, the heterologous polynucleotide provides resistance to AHAS inhibitors and comprises a sequence having at least 80% identity to a sequence selected from the group consisting of: SEQ ID NO:130 (ILV2 gene from *S. cerevisiae* BY4700) and SEQ ID NO:132 (ALS I gene from *E. coli* K12). In some embodiments, the heterologous polypeptide provides resistance to AHAS inhibitors and comprises an amino acid sequence having at least 80% identity to an amino acid sequence selected from the group consisting of: SEQ ID NO:131 (ILV2 from *S. cerevisiae* BY4700) and SEQ ID NO:133 (ALS I from *E. coli* K12). In some embodiments, the polypeptide provides resistance to AHAS inhibitors and comprises an amino acid sequence selected from the group consisting of: SEQ ID NO:131 (ILV2 from *S. cerevisiae* BY4700) and SEQ ID NO:133 (ALS I gene from *E. coli* K12) or an active variant, fragment or derivative thereof. In some embodiments, the polypeptide is from a bacteria of the family Enterobacteriaceae. In some embodiments, the polypeptide is from a bacterial genus selected from the group consisting of: *Alishewanella, Alterococcus, Aquamonas, Aranicola, Arsenophonus, Azotivirga, Blochmannia, Brenneria, Buchnera, Budvicia, Buttiauxella, Cedecea, Citrobacter, Cronobacter, Dickeya, Edwardsiella, Enterobacter, Erwinia, Escherichia, Ewingella, Grimontella, Hafnia, Klebsiella, Kluyvera, Leclercia, Leminorella, Moellerella, Morganella, Obesumbacterium, Pantoea, Candidatus Phlomobacter, Photorhabdus, Poodoomaamaana, Plesiomonas, Pragia, Proteus, Providencia, Rahnella, Raoultella, Salmonella, Samsonia, Serratia, Shigella, Sodalis, Tatumella, Trabulsiella, Wigglesworthia, Xenorhabdus, Yersinia,* and *Yokenella*. In some embodiments, the polypeptide is from a microorganism of the genus *Saccharomyces*. In some embodiments, the AHAS enzymes can be mutated to confer sulfonyl urea resistance. In some embodiments, the *B. subtilis* AlsS enzyme is mutated to increase its sulfonyl urea resistance.

In some embodiments, the inhibitor of amino acid synthesis is glyphosate. In some embodiments, resistance to the glyphosate is conferred by a polypeptide that has 5-enolpyruvoyl-shikimate-3-phosphate synthetase (EPSPS) activity. In some embodiments, the polypeptide is encoded by a heterologous polynucleotide. In some embodiments, the inhibitor is a 5-enolpyruvoyl-shikimate-3-phosphate synthetase (EPSPS) inhibitor. In some embodiments, the inhibitor is a glyphosate derivative. In some embodiments, resistance to the glyphosate is conferred by a polypeptide that has glyphosate N-acetyltransferase activity. In some embodiments, the polypeptide is encoded by a heterologous polynucleotide. Sequences describing polypeptides with glyphosate N-acetyltransferase activity are described in, for example, U.S. Pat. No. 7,863,503, which is incorporated herein by reference.

In some embodiments, the antibiotic is selected from the group consisting of: aureobasidin A, bialaphos, cerulenin, chloramphenicol, cyclohexamide, geneticin/G418, hygromycin B, methotrexate, nourseothricin, phleomycin, triazole, and mixtures thereof. In some embodiments, a polypeptide confers resistance to one or more antibiotics. In some embodiments, the polypeptide is encoded by a heterologous polynucleotide.

In some embodiments a polypeptide confers resistance to the inhibitor or antibiotic. In some embodiments, the polypeptide is encoded by a polynucleotide. In some embodiments, the polypeptide conferring resistance to the inhibitor or antibiotic has one or more amino acid deletions when compared with the amino acid sequence of the corresponding native polypeptide. In some embodiments, the amino acid sequence of the polypeptide has one or more amino acid substitutions when compared with the amino acid sequence of the corresponding native polypeptide.

In some embodiments, the inhibitor is an α-isopropyl malate (a-IPM) synthase inhibitor. In some embodiments, the inhibitor is trifluoroleucine or a trifluoroleucine derivative. In some embodiments, the inhibitor is a 3-deoxy-D-arabino-heptolusonate-7-phosphate synthase (DAHPS) inhibitor. In some embodiments, the inhibitor is fluorophenyalanine or a fluorophenyalanine derivative. In some embodiments, the inhibitor is bismuth (III) or copper (II).

In some embodiments, the polypeptide confers tolerance to fluoroacetate. In some embodiments, the polypeptide confers tolerance to formaldehyde. In some embodiments, the polypeptide confers tolerance to sulfite.

In some embodiments, the polypeptide confers tolerance to an α-isopropyl malate (a-IPM) synthase inhibitor. In some embodiments, the polypeptide confers tolerance to trifluoroleucine or a trifluoroleucine derivative (isopropyl malate resistance). In some embodiments, the polynucleotide sequence encoding the polypeptide providing resistance to trifluoroleucine comprises a sequence having at least 80% identity to a sequence disclosed by: Chianelli, M. S., et al., *Cell. Mol. Biol.* 42(6):847-57 (1996) or Oba, T., et al., *Biosci. Biotechnol. Biochem.* 70(7):1776-9 (2006) and incorporated by reference. In some embodiments, the polypeptide confers tolerance to a 3-deoxy-D-arabino-heptolusonate-7-phosphate synthase (DAHPS) inhibitor. In some embodiments, the polynucleotide sequence encoding the polypeptide providing resistance to DAHPS comprises a sequence having at least 80% identity to a sequence disclosed by: Fukada, K., et al., *Agric. Biol. Chem.* 54:3151-3156 (1990); Meuris, P. 1974. *Genetics* 76:735-744 (1974); Shimura, K., et al., 1993. *Enzyme Microbiol. Technol.* 15:874-876 (1993) and incorporated by reference.

In some embodiments, the polypeptide confers tolerance to an antibiotic. In some embodiments, the polypeptide confers tolerance to an antibiotic selected from the group consisting of: aureobasidin A, bialaphos, cerulenin, chloramphenicol, cyclohexamide, geneticin, hygromycin B, methotrexate, nourseothricin, phleomycin, triazole, and mixtures thereof. In some embodiments, the polynucleotide sequence encoding the polypeptide comprises a sequence having at least 80% identity to a sequence selected from the group consisting of: SEQ ID NOs: 92 and 143-157 (Aureobasidin A resistance (AUR1-C) (SEQ ID NOs:143 and 144); bialiphos resistance protein (SEQ ID NOs:145 and 146); cerulenin resistance YML007W Chr 13 (SEQ ID NOs:147 and 148); Geneticin resistance (kanMX) (SEQ ID NOs:149 and 150); Hygromycin B resistance (HygR) (SEQ ID NOs:151 and 152); *Streptomyces noursei* nourseothricin resistance (natl) (SEQ ID NOs:153 and 154); phleomycin/zeocin binding protein (SEQ ID NOs:155 and 156); and Triazole resistance (cyp51A) (SEQ ID NOs:157 and 92).

In some embodiments, the inhibitor is inhibiting at least one enzyme selected from the group consisting of: 5-enolpyruvoyl-shikimate-3-phosphate synthetase, α-isopropyl malate synthase, 3-deoxy-D-arabino-heptolusonate-7-phosphate synthase and mixtures thereof. In some embodiments, the polynucleotide sequence encoding the polypeptide providing resistance to 5-enolpyruvoyl-shikimate-3-phosphate synthetase comprises a sequence having at least 80% identity to a sequence disclosed by: Cao G, et al., (2012) *PLoS ONE* 7(6): e38718 (2012) incorporated by reference. In some embodiments, the polynucleotide sequence encoding the polypeptide with glyphosate N-acetyltransferase activity comprises a sequence having at least 80% identity to a sequence disclosed by U.S. Pat. No. 7,666,644, which is incorporated herein by reference in its entirety and Siehl D.L., et al., *Pest Manag Sci.* 61(3):235-40 (2005) incorporated by reference. In some embodiments, the polynucleotide sequence encoding the polypeptide providing resistance to 3-phosphoshikimate 1-carboxylvinyltransferase comprises a sequence having at least 80% identity to a sequence disclosed by: Vande Berg B.J., et al., *Pest Manag Sci.* 64(4):340-5 (2008) incorporated by reference. In some embodiments, the polypeptide that provides resistance to the inhibitor is a formaldehyde dehydrogenase. In some embodiments, the polypeptide comprises an amino acid sequence of at least about 80% identity to SEQ ID NO:6 or 7.

In some embodiments, the polypeptide that confers resistance comprises an amino acid sequence of at least about 80% identity to SEQ ID NO:11 or SEQ ID NO:12. In some embodiments, the polypeptide that confers resistance is a 3-phosphoshikimate 1-carboxylvinyltransferase. In some embodiments, the polypeptide comprises an amino acid sequence of at least about 80% identity to SEQ ID NO:13.

In some embodiments, one or more AHAS inhibitors is present at a concentration from about 0.1 g/mL to about 2 g/mL, about 1.0 g/mL to about 0.1 g/mL, about 1 mg/mL to about 0.1 g/mL, or about 10 mg/mL to about 100 mg/mL. In some embodiments, one or more AHAS inhibitors is present at a concentration of 0.0125 mg/mL. In some embodiments, one or more AHAS inhibitors is present at a concentration of 1 mg/mL. In some embodiments, one or more AHAS inhibitors is present at a concentration of 2 mg/mL.

In some embodiments, glyphosate is at a concentration from about 0.1 μg/mL to about 2 g/mL, for example about 10 μg/mL, about 100 μg/mL, about 1 mg/mL, about 10 mg/mL, about 100 mg/mL, about 1 g/mL, or about 2 g/mL.

In some embodiments, the antibiotic is present at a concentration from about 2 ppm to about 500 ppm, for example about 5 ppm, about 20 ppm, about 50 ppm, about 100 ppm, about 150 ppm, about 200 ppm, about 300 ppm, about 400 ppm, or about 500 ppm.

In some embodiments, the addition inhibitors of amino acid synthesis, antibiotics, or combinations thereof results in death of at least 10%, 20%, 30%, 40%, 50%, 60%, 70%, 80%, 90% or 100% of the microbial contaminants in the fermentation mix.

In embodiments, the effective concentration of inhibitor for use in methods provided herein can be determined empirically for a given production strain, contaminant strain, and production process. Alternatively, minimal data may be obtained for a given system and used to determine appropriate concentrations for inhibitors. Such determination is disclosed and demonstrated herein (see Examples), and is readily available to one of skill in the art, equipped with this disclosure.

Briefly, as described herein, growth and/or production competitiveness may be improved by, for example, i) adding a genetic trait that provides growth and/or production competitiveness, or ii) by providing growth conditions that increase growth and/or production competitiveness, e.g. through the addition of selective inhibitors. While not wishing to be bound by theory, in the first case, increased growth competitiveness of a strain A carrying a genetic trait that provides growth competitiveness will have a higher biomass ratio after a growth phase compared to a competing strain B than an strain C isogenic to strain A without the genetic trait, i.e. $cx_{A\_mod}(t)/cx_{B\_mod}(t) > cx_C(t)/cx_B(t)$. In the later case, strain A will have a higher biomass ratio after a growth phase compared to a competing strain B under the conditions promoting growth competitiveness, i.e. $cx_A$ (t,c(inhibitor)>0 g/L)/$cx_B$ (t,c(inhibitor)>0 g/L)>$cx_A$(t,c(inhibitor)=0 g/L)/$cx_A$(t, c(inhibitor)=0 g/L). After a growth phase indicates that the biomass of strain A had to increase during the respective time interval, i.e. $cx_A(t) > cx_A(t_{start})$. While not wishing to be bound by theory, in the first case, increased production competitiveness of a strain A carrying a genetic trait that provides production competitiveness will have a higher product ratio compared to a product of a competing strain B than an strain C isogenic to strain A without the genetic trait, i.e. $cp_A(t)/cp_B(t) > cp_C(t)/cp_B(t)$. In the later case, strain A will have a higher product ratio compared to a product of a competing strain B, i.e. $cp_A$ (t,c(inhibitor)>0 g/L)/$cp_B$ (t,c(inhibitor)>0 g/L)>$cp_A$(t,c(inhibitor)=0 g/L)/$cp_B$(t, c(inhibitor)=0 g/L).

Under situations where substrates are not limiting, e.g. under glucose excess conditions, maximum specific growth rate of the strains under the given cultivation conditions (medium, temperature, etc.) will be a component for determining growth competitiveness. Changes in the given conditions (e.g. changing concentrations of products, substrates, signaling molecules, etc.) may result in different values of maximum specific growth rate, and the maximum specific growth rate of strains may be different in a given condition. Considering such factors and assuming a constant $\mu_{max}$ for an exponential growth phase, the biomass concentration during the exponential growth phase that started at $t_{lag}$ can be approximately described according to $$c_X(t) = c_X(t) \cdot e^{\mu_{max} \cdot (t - t_{lag})} \qquad \text{Eq. (1)}$$

Figure 18:
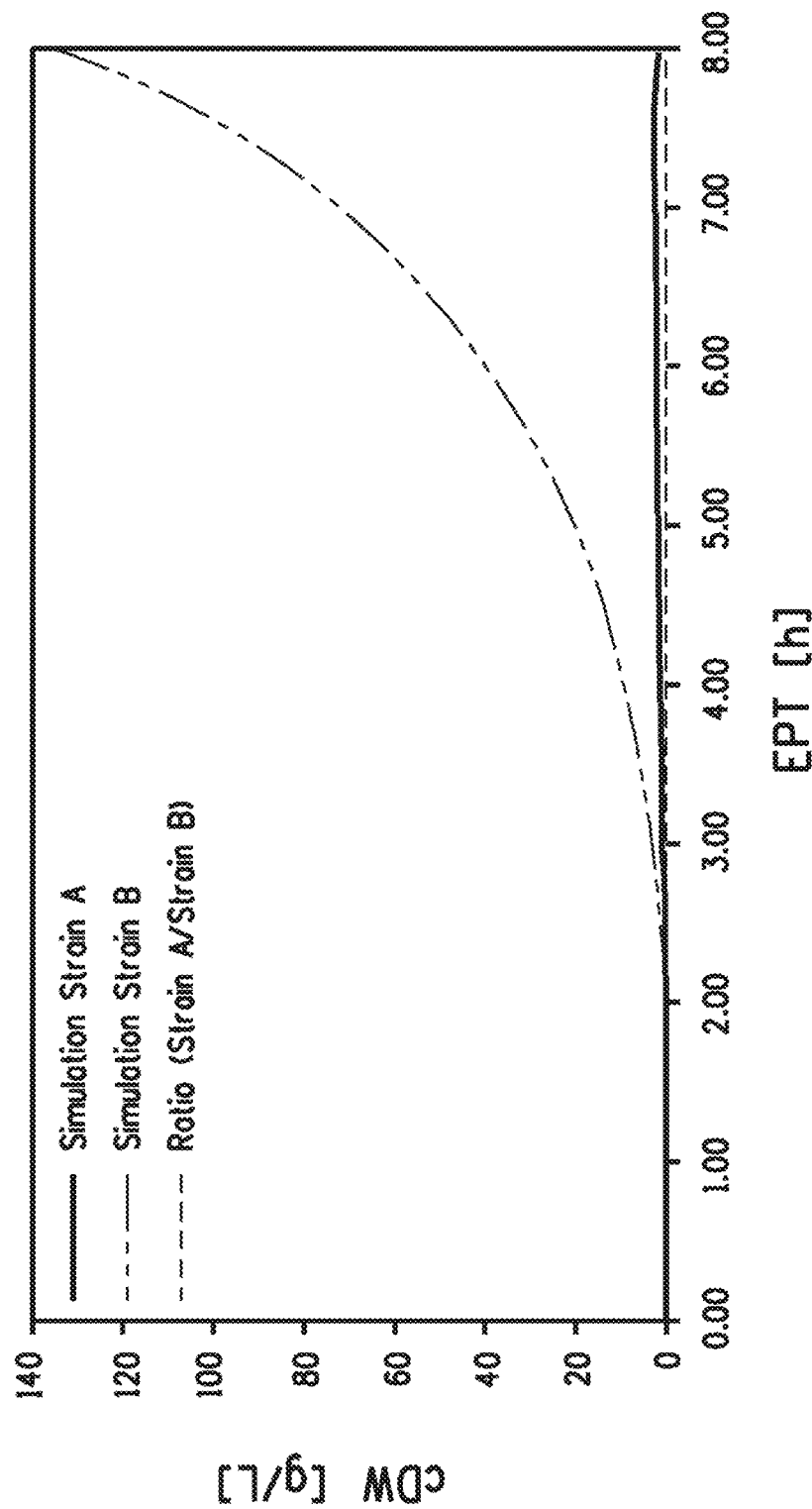
FIG. 18 depicts simulated growth curves of strains A and B growing in a mixed culture at a maximum specific growth rate of 0.16 l/h and 0.61 l/h, respectively. The ratio of the biomass of strains A vs. strain B is continuously decreasing during the cultivation and is below 3% at the end of the run.
Figure 19:
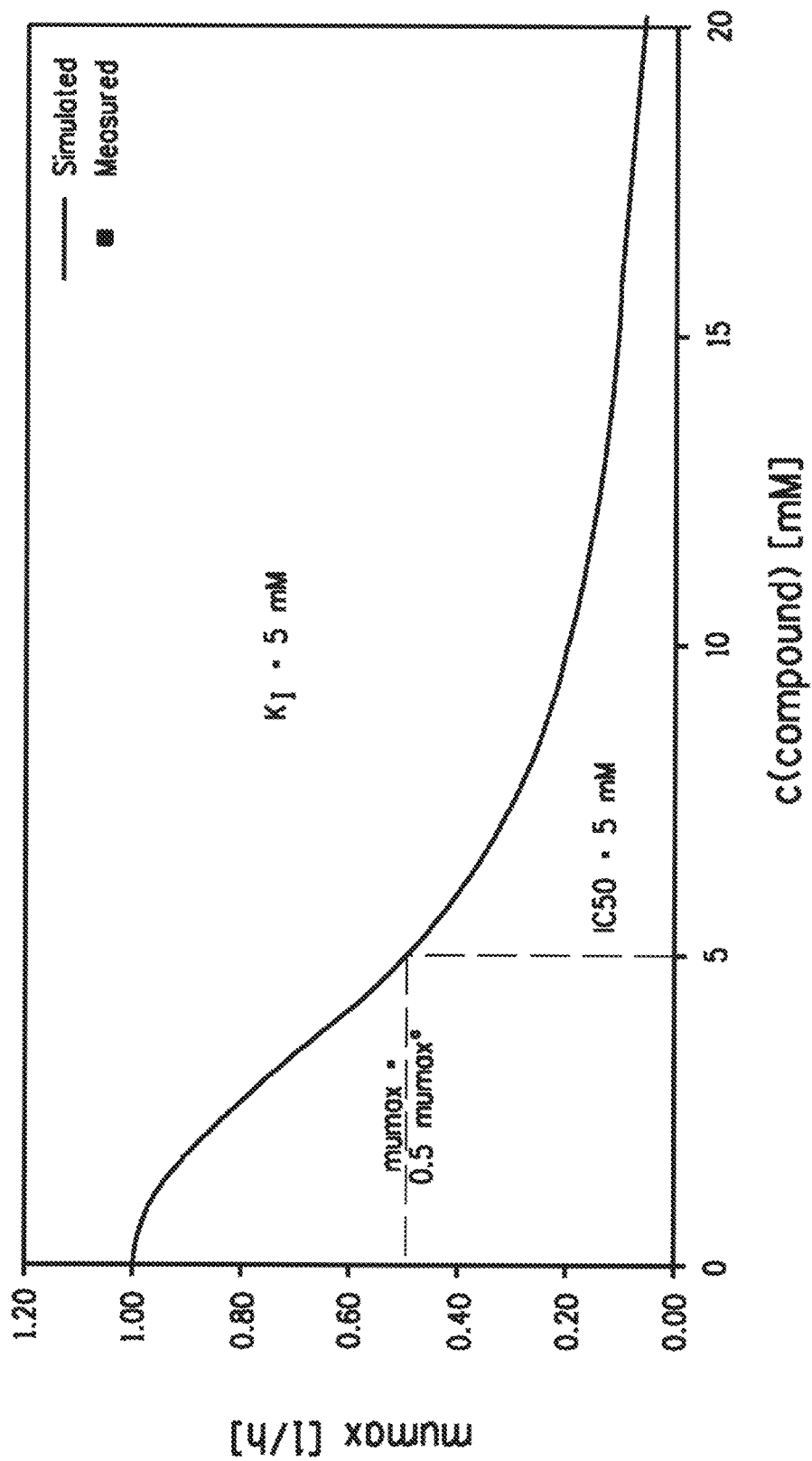
FIG. 19 depicts the predicted effect of an inhibitor c (compound) on the maximum specific growth rate of a hypothetical strain with a mumax without inhibitor addition ($\mu^°_{max}$) of 1.00 l/h, a $K_r$-value of 5 mM, and its behavior according a squared inhibition kinetics as described by equation (2).

Under aerobic, glucose-excess conditions and acetic acid in the medium, maximum specific growth rate of an exemplary ethanologen *S. cerevisiae* strain (PNY 827) was determined to be 0.61 l/h. In contrast, an isobutanologen *S. cerevisiae* strain (PNY 2129, constructed using PNY827) exhibited a maximum specific growth rate of 0.16 l/h. If an aerobic batch cultivation with a mixed culture consisting of both strains with a biomass ratio of 1:1, i.e. with a cell dry weight concentration of 1 g/L each, would be started, and both strains would be growing for 8 hours at $\mu_{max}$ without any lag phase, at the end of the process PNY 827 would account for approximately 131.6 g/L cell dry weight in the mixed culture, while PNY 2129 would account for only about 3.6 g/L. The ratio of biomass PNY 2129/PNY 827 would be below 3%. This phenomenon is illustrated in FIG. 18 where PNY 2129 is represented by strain A and PNY 827 by strain B.

In order to describe growth performance of a strain according to Eq. (1) under the influence of different inhibitor/mixture of inhibitors concentrations in a batch experiment, $\mu_{max}$ was determined in a way to incorporate effect of the inhibitor/mixture of inhibitors. According to the observed inhibition kinetics, usually a "squared" inhibition term according to Eq. (2) was applied, $$\mu_{max} = \frac{\mu^o_{max}}{\left(1 + \frac{c(I)^2}{K_I^2}\right)}, \quad \text{Eq. (2)}$$

with $\mu_{max}$ denoting a strain characteristic maximum specific growth rate at the inhibitor concentration c(I), and $\mu^o_{max}$ the maximum specific growth rate of the strain under the same conditions, but without inhibitor (c(inhibitor)=0 g/L). Finally $K_I$ represents an inhibitory constant $K_I$.

In some occasions, inhibition of a cellular process significantly reduces but not completely abolishes growth of the organism. This effect can sometimes be explained by the action of alternative cellular processes available to the organism. In this particular situation, the "squared" inhibition term according to Eq. (2) is insufficient to describe growth of the strain, and a hybrid modeling approach according to Eq. (3) was used instead according to $$\mu_{max} = \frac{\mu^o_{max\,1}}{\left(1 + \frac{c(I)^2}{K_I^2}\right)} + \mu^o_{max\,2}, \quad \text{Eq. (3)}$$

with $\mu_{max}$ denoting a strain characteristic maximum specific growth rate at the inhibitor concentration c(I), and the sum of $\mu^o_{max1}$ and $\mu^o_{max2}$ the maximum specific growth rate of the strain under the same conditions, but without inhibitor (c(inhibitor)=0 g/L). Finally $K_I$ represents an inhibitory constant $K_I$. Using such equations to fit minimal data collected for a given system allows for determination of strain-specific parameters, i.e. of a maximum specific growth rate without inhibitor ($\mu^o_{max}$ or sum of $\mu^o_{max1}$ and $\mu^o_{max2}$) and an inhibitory constant $K_I$. Based on these parameters, effect of inhibitor concentrations on maximum specific growth rate $\mu_{max}$ of a given production or contaminant strain can be made, as well as the IC50 value of the inhibitor on their growth be estimated. Equipped with this disclosure, one of skill in the art will be able to utilize parameters such as the IC50 to determine suitable concentrations of compounds for methods provided herein.

One embodiment is directed to a method for improving production competitiveness of a butanologen in a fermentation mix, wherein the method comprises contacting a genetically modified host cell and a fermentation medium comprising one or more inhibitors, antibiotics, or combinations thereof, as well as a contaminating organism, and wherein the improved production competitiveness is associated with a higher butanol yield on the consumed substrate.

One embodiment is directed to a method for improving production competitiveness of a butanologen in a fermentation mix, wherein the method comprises contacting a genetically modified host cell and a fermentation medium comprising one or more inhibitors, antibiotics, or combinations thereof, as well as an ethanologen yeast, and wherein the improved production competitiveness is associated with a higher butanol-to-ethanol ratio as compared to a cultivation without addition of one or more inhibitors, antibiotics, or combinations thereof.

One embodiment is directed to a method for improved production competitiveness of a butanologen in a fermentation mix, wherein the method comprises contacting a genetically modified host cell and a fermentation medium comprising one or more inhibitors, antibiotics, or combinations thereof, and wherein the addition of the one or more inhibitors, antibiotics, or combinations thereof results in less than a 20% loss in the yield of a lower alkyl alcohol produced by the host cell due to the presence of microbial contaminants. In some embodiments, the addition of the one or more inhibitors of amino acid synthesis, antibiotics, or combinations thereof results in less than a 10% loss in the yield of a lower alkyl alcohol produced by the host cell due to the presence of microbial contaminants.

It will be appreciated that compounds such as an inhibitor, antibiotic, or combinations thereof can be incorporated into a fermentation mix using any method known in the art. In embodiments, compounds are introduced by incorporation into a fermentation feed. In embodiments, compounds are introduced as a bolus or over the course of a fermentation process or a portion of the process as suitable for the compound and production process.

Alcohol Production

Disclosed herein are processes suitable for production of fermentation products from a carbon substrate. In one embodiment a lower alcohol is produced. In one embodiment, butanol is produced, and a butanologen is employed. In another embodiment, isobutanol is produced, and an isobutanologen is employed. In some embodiments, isobutanologens may comprise an isobutanol biosynthetic pathway, such as, but not limited to isobutanol biosynthetic pathways disclosed elsewhere herein. The ability to utilize carbon substrates to produce isobutanol can be confirmed using methods known in the art, including, but not limited to those described in U.S. Pat. Nos. 7,851,188 and 7,993,889 which are incorporated herein by reference. For example, to confirm isobutanol production, the concentration of isobutanol in the culture media can be determined by a number of methods known in the art. For example, a specific high performance liquid chromatography (HPLC) method utilized a Shodex SH-1011 column with a Shodex SH-G guard column, both purchased from Waters Corporation (Milford, Mass.), with refractive index (RI) detection. Chromatographic separation was achieved using 0.01 M $H_2SO_4$ as the mobile phase with a flow rate of 0.5 mL/min and a column temperature of 50° C. Isobutanol had a retention time of 46.6 min under the conditions used. Alternatively, gas chromatography (GC) methods are available. For example, a specific GC method utilized an HP-INNOWax column (30 m×0.53 mm id, 1 µm film thickness, Agilent Technologies, Wilmington, Del.), with a flame ionization detector (FID). The carrier gas was helium at a flow rate of 4.5 mL/min, measured at 150° C. with constant head pressure; injector split was 1:25 at 200° C.; oven temperature was 45° C. for 1 min, 45 to 220° C. at 10° C./min, and 220° C. for 5 min; and FID detection was employed at 240° C. with 26 mL/min helium makeup gas. The retention time of isobutanol was 4.5 min.

In some embodiments, the butanologen comprises an engineered butanol pathway. In some embodiments, the butanologen is an isobutanologen. In some embodiments, the butanologen is a yeast. In some embodiments, the butanologen is a member of a genus of *Saccharomyces, Schizosaccharomyces, Hansenula, Candida, Kluyveromyces, Yarrowia, Issatchenkia,* or *Pichia*. In some embodiments, the butanologen is *Saccharomyces cerevisiae*.

In some embodiments, the engineered isobutanologen contains one or more polypeptides selected from a group of enzymes having the following Enzyme Commission Numbers: EC 2.2.1.6, EC 1.1.1.86, EC 4.2.1.9, EC 4.1.1.72, EC 1.1.1.1, EC 1.1.1.265, EC 1.1.1.2, EC 1.2.4.4, EC 1.3.99.2, EC 1.2.1.57, EC 1.2.1.10, EC 2.6.1.66, EC 2.6.1.42, EC 1.4.1.9, EC 1.4.1.8, EC 4.1.1.14, EC 2.6.1.18, EC 2.3.1.9, EC 2.3.1.16, EC 1.1.130, EC 1.1.1.35, EC 1.1.1.157, EC 1.1.1.36, EC 4.2.1.17, EC 4.2.1.55, EC 1.3.1.44, EC 1.3.1.38, EC 5.4.99.13, EC 4.1.1.5, EC 2.7.1.29, EC 1.1.1.76, EC 1.2.1.57, and EC 4.2.1.28.

In some embodiments, the engineered isobutanologen contains one or more polypeptides selected from acetolactate synthase, acetohydroxy acid isomeroreductase, acetohydroxy acid dehydratase, branched-chain alpha-keto acid decarboxylase, branched-chain alcohol dehydrogenase, acylating aldehyde dehydrogenase, branched-chain keto acid dehydrogenase, butyryl-CoA dehydrogenase, transaminase, valine dehydrogenase, valine decarboxylase, omega transaminase, acetyl-CoA acetyltransferase, 3-hydroxybutyryl-CoA dehydrogenase, crotonase, butyryl-CoA dehydrogenase, isobutyryl-CoA mutase, acetolactate decarboxylase, acetonin aminase, butanol dehydrogenase, butyraldehyde dehydrogenase, acetoin kinase, acetoin phosphate aminase, aminobutanol phosphate phospholyase, aminobutanol kinase, butanediol dehydrogenase, and butanediol dehydratase.

In some embodiments, the carbon substrate is selected from the group consisting of: oligosaccharides, polysaccharides, monosaccharides, and mixtures thereof. In some embodiments, the carbon substrate is selected from the group consisting of: fructose, glucose, lactose, maltose, galactose, sucrose, starch, cellulose, feedstocks, ethanol, lactate, succinate, glycerol, corn mash, sugar cane, biomass, a C5 sugar, such as xylose and arabinose, and mixtures thereof.

In some embodiments, the engineered isobutanol pathway comprises the following substrate to product conversions:
a. pyruvate to acetolactate
b. acetolactate to 2,3-dihydroxyisovalerate
c. 2,3-dihydroxyisovalerate to α-ketoisovalerate
d. α-ketoisovalerate to isobutyraldehyde, and
e. isobutyraldehyde to isobutanol.

In some embodiments, one or more of the substrate to product conversions utilizes NADH or NADPH as a cofactor.

In some embodiments, enzymes from the biosynthetic pathway are localized to the cytosol. In some embodiments, enzymes from the biosynthetic pathway that are usually localized to the mitochondria are localized to the cytosol. In some embodiments, an enzyme from the biosynthetic pathway is localized to the cytosol by removing the mitochondrial targeting sequence. In some embodiments, mitochondrial targeting is eliminated by generating new start codons as described in e.g., U.S. Pat. Nos. 7,851,188 and 7,993,889, which are incorporated herein by reference in its entirety. In some embodiments, the enzyme from the biosynthetic pathway that is localized to the cytosol is DHAD. In some embodiments, the enzyme from the biosynthetic pathway that is localized to the cytosol is KARI.

In some embodiments, the butanologen produces butanol at least 90% of effective yield, at least 91% of effective yield, at least 92% of effective yield, at least 93% of effective yield, at least 94% of effective yield, at least 95% of effective yield, at least 96% of effective yield, at least 97% of effective yield, at least 98% of effective yield, or at least 99% of effective yield. In some embodiments, the butanologen produces butanol at least 55% to at least 75% of effective yield, at least 50% to at least 80% of effective yield, at least 45% to at least 85% of effective yield, at least 40% to at least 90% of effective yield, at least 35% to at least 95% of effective yield, at least 30% to at least 99% of effective yield, at least 25% to at least 99% of effective yield, at least 10% to at least 99% of effective yield or at least 10% to at least 100% of effective yield.

In some embodiments, the host cell produces ethanol at least 90% of effective yield, at least 91% of effective yield, at least 92% of effective yield, at least 93% of effective yield, at least 94% of effective yield, at least 95% of effective yield, at least 96% of effective yield, at least 97% of effective yield, at least 98% of effective yield, or at least 99% of effective yield. In some embodiments, the host cell produces ethanol at least 55% to at least 75% of effective yield, at least 50% to at least 80% of effective yield, at least 45% to at least 85% of effective yield, at least 40% to at least 90% of effective yield, at least 35% to at least 95% of effective yield, at least 30% to at least 99% of effective yield, at least 25% to at least 99% of effective yield, at least 10% to at least 99% of effective yield or at least 10% to at least 100% of effective yield.

In some embodiments, the host cell produces a C3-C6 alcohol at least 90% of effective yield, at least 91% of effective yield, at least 92% of effective yield, at least 93% of effective yield, at least 94% of effective yield, at least 95% of effective yield, at least 96% of effective yield, at least 97% of effective yield, at least 98% of effective yield, or at least 99% of effective yield. In some embodiments, the host cell produces a C3-C6 alcohol at least 55% to at least 75% of effective yield, at least 50% to at least 80% of effective yield, at least 45% to at least 85% of effective yield, at least 40% to at least 90% of effective yield, at least 35% to at least 95% of effective yield, at least 30% to at least 99% of effective yield, at least 25% to at least 99% of effective yield, at least 10% to at least 99% of effective yield or at least 10% to at least 100% of effective yield.

One embodiment of this invention is directed to a method for the production of a C3-C6 alcohol comprising:
a. providing a host cell with an engineered pyruvate-utilizing pathway and a polypeptide conferring resistance to one or more inhibitors, antibiotics or combinations thereof, wherein the engineered pyruvate-utilizing pathway is a C3-C6 alcohol biosynthetic pathway;
b. contacting the host cell with a fermentable carbon substrate in a fermentation medium under conditions whereby the C3-C6 alcohol is produced; and
c. recovering the C3-C6 alcohol.

In some embodiments, the fermentation medium comprises one or more inhibitors, antibiotics or combinations thereof.

In some embodiments, the C3-C6 alcohol is produced at a titer from about 5 g/L to about 100 g/L. In some embodiments, the C3-C6 alcohol is produced at a titer of at least 20 g/L. In some embodiments, the C3-C6 alcohol is selected from the group consisting of: butanol, isobutanol, propanol, and isopropanol.

One embodiment is a method for the production of ethanol comprising:
a. providing a host cell with a pyruvate-utilizing pathway and a polypeptide conferring resistance to one or more inhibitors, antibiotics or combinations thereof, wherein the pyruvate-utilizing pathway is an ethanol producing pathway;

b. contacting the host cell with a fermentable carbon substrate in a fermentation medium under conditions whereby the ethanol is produced; and c. recovering the ethanol.

In some embodiments, the invention provides a method for production of a fermentation product in a fermentation process comprising contacting a fermentation mix comprising a recombinant production microorganism which comprises a pyruvate-utilizing pathway with at least one compound which preferentially inhibits at least one contaminant microorganism. In some embodiments the inhibition is measured through a reduction in the specific growth rate. In some embodiments the inhibition is measured through a reduced specific product formation rate of the contaminant. In some embodiments, the specific growth rate of the at least one contaminant microorganism is reduced more than the specific growth rate of the recombinant production microorganism. In some embodiments, the production of the fermentation product of the at least one contaminant microorganism is reduced more than production of the fermentation product of the recombinant production microorganism.

In some embodiments, the major product of a production microorganism is ethanol. In some embodiments, the titer of ethanol that is produced may be at least about 80 g/L to at least about 120 g/L. In some embodiments, the titer of ethanol that is produced is least about 50 g/L, at least about 60 g/L, at least about 70 g/L, at least about 80 g/L, at least about 90 g/L, at least about 95 g/L, at least about 100 g/L, at least about 105 g/L, at least about 110 g/L, at least about 115 g/L, or at least about 120 g/L.

In some embodiments, the major product of a production microorganism is butanol. In some embodiments, the titer of butanol that is produced may be at least about 80 g/L to at least about 120 g/L. In some embodiments, the titer of butanol that is produced is least about 50 g/L, at least about 60 g/L, at least about 70 g/L, at least about 80 g/L, at least about 90 g/L, at least about 95 g/L, at least about 100 g/L, at least about 105 g/L, at least about 110 g/L, at least about 115 g/L, or at least about 120 g/L.

In some embodiments, the major product of a production microorganism is butanol, for example, isobutanol. In some embodiments, the major product of a contaminant microorganism is ethanol. The titer of ethanol may be less than that of butanol. In some embodiments, the titer of ethanol is less than about 20 g/L, 10 g/L, less than about 5 g/L, or less than about 2 g/L.

In embodiments, the major product of a production microorganism is butanol, for example isobutanol, and the major product of a contaminant microorganism is ethanol. In embodiments, the percentage of ethanol produced as a fraction of the amount of butanol produced is less than about 25%, less than about 20%, less than about 10%, less than about 5%, less than about 2%, or less than about 1%.

In some embodiments, butanol is contacted with a fatty acid and a lipase producing a fatty acid butyl ester ("FABE"), which may be used as a biodiesel fuel.

The reduction in contamination can be measured through any assay known in the art, including, but not limited to, standard plating assays, qPCR/RT-PCR, or by measuring fermentation titer, yield, or specific growth rate of a production microorganism in relation to a contaminant microorganism.

In some embodiments, reduction in contamination and increased production competitiveness of the butanologen is observed through measurement of the ratio of the desired fermentation product to the contaminant fermentation production (e.g. butanol to ethanol). As the contaminant microorganism is inhibited to a greater degree than the production microorganism is inhibited, by either specific inhibitors or different concentrations of those inhibitors, the ratio of the desired fermentation product to the contaminant fermentation product will increase. The production of fermentation product in the aqueous phase can be quantified by HPLC, as described in the General Methods Section.

In some embodiments, the reduction in contamination is observed through measurement of the specific growth rate of samples treated with varying concentrations of inhibitors in a cell suspension, and measuring the OD of the samples at designated time points.

In some embodiments, the reduction in contamination is seen through the use of plating assays. In some embodiments, early stationary phase cultures are used to inoculate top agar media which is poured onto petri plates. Filter disks containing different concentrations of inhibitor can be applied to the plate surface, and, after a period of incubation, zones of growth inhibition can be observed.

Host Cells and Microorganisms

The terms "host cell" and "microorganism" are synonymous and used interchangeably throughout. In embodiments, suitable host cells include any yeast host useful for genetic modification and recombinant gene expression. In some embodiments, the host cell is a butanologen. In some embodiments, the host cell is an isobutanologen. In some embodiments, the isobutanologen host cell can be a member of the genera *Schizosaccharomyces, Issatchenkia, Kluyveromyces, Yarrowia, Pichia, Candida, Hansenula, Aspergillus, Pachysolen, Rhodotorula, Zygosaccharomyces, Galactomyces, Torulaspora, Debayomyces, Williopsis, Dekkera, Kloeckera, Metschnikowia* or *Saccharomyces*. In other embodiments, the host cell can be *Saccharomyces cerevisiae, Schizosaccharomyces pombe, Kluyveromyces lactis, Kluyveromyces thermotolerans, Kluyveromyces marxianus, Candida glabrata, Candida albicans, Pichia stipitis, Yarrowia lipolytica, E. coli,* or *L. plantarum*. In still other embodiments, the host cell is a yeast host cell. In some embodiments, the host cell is a member of the genera *Saccharomyces*. In some embodiments, the host cell is *Kluyveromyces lactis, Candida glabrata* or *Schizosaccharomyces pombe*. In some embodiments, the host cell is *Saccharomyces cerevisiae*. *S. cerevisiae* yeast are known in the art and are available from a variety of sources, including, but not limited to, American Type Culture Collection (Rockville, Md.), Centraalbureau voor Schimmelcultures (CBS) Fungal Biodiversity Centre, LeSaffre, Gert Strand AB, Ferm Solutions, North American Bioproducts, Martrex, and Lallemand. *S. cerevisiae* include, but are not limited to, BY4741, CEN.PK 113-7D, Ethanol Red® yeast, Ferm Pro™ yeast, Bio-Ferm® XR yeast, Gert Strand Prestige Batch Turbo alcohol yeast, Gert Strand Pot Distillers yeast, Gert Strand Distillers Turbo yeast, FerMax™ Green yeast, FerMax™ Gold yeast, Thermosacc® yeast, BG-1, PE-2, CAT-1, CBS7959, CBS7960, and CBS7961.

*Saccharomyces cerevisiae* PNY860 (or PNY0860), described in Example 4, was deposited with the American Type Culture Collection (ATCC), 10801 University Boulevard, Manassas, Va., 20110 on Jul. 21, 2011, and assigned ATCC Accession No. PTA-12007.

*Saccharomyces cerevisiae* PNY827, described in Examples 3 and 13, was deposited with the American Type Culture Collection (ATCC), 10801 University Boulevard, Manassas, Va., 20110 on Sep. 22, 2011, and assigned ATCC Accession No. PTA-12105.

In some embodiments, the host cell expresses an engineered butanol biosynthetic pathway. From time to time, such a host cell is referred to as a "butanologen". In some embodiments, the butanologen is an isobutanologen expressing an engineered isobutanol biosynthetic pathway. In some embodiments, the butanologen is a bacteria, cyanobacteria or filamentous fungi. In some embodiments, the genus of the host cell is selected from the group consisting of: *Salmonella, Arthrobacter, Bacillus, Brevibacterium, Clostridium, Corynebacterium, Gluconobacter, Nocardia, Pseudomonas, Rhodococcus, Streptomyces, Zymomonas, Escherichia, Lactobacillus, Lactococcus, Enterococcus, Alcaligenes, Klebsiella, Paenibacillus*, and *Xanthomonas*.

Some embodiments comprise a genetically modified host cell comprising:
a. an engineered C3-C6 alcohol biosynthetic pathway; and,
b. a polypeptide that is resistant to inhibitors, antibiotics, or a combination thereof.

Carbon Substrates

Suitable carbon substrates may include, but are not limited to, monosaccharides such as fructose or glucose, oligosaccharides such as lactose, maltose, galactose, or sucrose, polysaccharides such as starch or cellulose or mixtures thereof and unpurified mixtures from renewable feedstocks such as cheese whey permeate, cornsteep liquor, sugar beet molasses, and barley malt. Other carbon substrates may include ethanol, lactate, succinate, or glycerol.

"Sugar" includes monosaccharides such as fructose or glucose, oligosaccharides such as lactose, maltose, galactose, or sucrose, polysaccharides such as starch or cellulose, C5 sugars such as xylose and arabinose, and mixtures thereof.

Additionally the carbon substrate may also be one-carbon substrates such as carbon dioxide, or methanol for which metabolic conversion into key biochemical intermediates has been demonstrated. In addition to one and two carbon substrates, methylotrophic organisms are also known to utilize a number of other carbon containing compounds such as methylamine, glucosamine and a variety of amino acids for metabolic activity. For example, methylotrophic yeasts are known to utilize the carbon from methylamine to form trehalose or glycerol (Bellion et al., *Microb. Growth C1 Compd.*, [*Int. Symp.*], 7th (1993), 415-32, Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485-489 (1990)). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, in some embodiments, the carbon substrates are glucose, fructose, and sucrose, or mixtures of these with C5 sugars such as xylose and arabinose for yeasts cells modified to use C5 sugars. Sucrose may be derived from renewable sugar sources such as sugar cane, sugar beets, cassava, sweet sorghum, and mixtures thereof. Glucose and dextrose may be derived from renewable grain sources through saccharification of starch based feedstocks including grains such as corn, wheat, rye, barley, oats, and mixtures thereof. In addition, fermentable sugars may be derived from renewable cellulosic or lignocellulosic biomass through processes of pretreatment and saccharification, as described, for example, in U.S. Patent Application Publication No. 20070031918 A1, which is incorporated herein by reference. Biomass includes materials comprising cellulose, and optionally further comprising hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

In some embodiments, the carbon substrate is glucose derived from corn. In some embodiments, the carbon substrate is glucose derived from wheat. In some embodiments, the carbon substrate is sucrose derived from sugar cane.

In addition to an appropriate carbon source, fermentation media must contain suitable minerals, salts, cofactors, buffers and other components, known to those skilled in the art, suitable for the growth of the cultures and promotion of an enzymatic pathway described herein.

Fermentation Conditions

Typically cells are grown at a temperature in the range of about 20° C. to about 40° C. in an appropriate medium. Suitable growth media in the present invention include common commercially prepared media such as Sabouraud Dextrose (SD) broth, Yeast Medium (YM) broth, or broth that includes yeast nitrogen base, ammonium sulfate, and dextrose (as the carbon/energy source) or YPD Medium, a blend of peptone, yeast extract, and dextrose in optimal proportions for growing most *Saccharomyces cerevisiae* strains. Other defined or synthetic growth media may also be used, and the appropriate medium for growth of the particular microorganism will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation are from about pH 5.0 to about pH 9.0. In one embodiment, about pH 6.0 to about pH 8.0 is used for the initial condition. Suitable pH ranges for the fermentation of yeast are typically from about pH 3.0 to about pH 9.0. In one embodiment, about pH 5.0 to about pH 8.0 is used for the initial condition. Suitable pH ranges for the fermentation of other microorganisms are from about pH 3.0 to about pH 7.5. In one embodiment, about pH 4.5 to about pH 6.5 is used for the initial condition.

Fermentations may be performed under aerobic or anaerobic conditions. In one embodiment, anaerobic or microaerobic conditions are used for fermentations.

Industrial Batch and Continuous Fermentations

Isobutanol, or other products, may be produced using a batch method of fermentation. A classical batch fermentation is a closed system where the composition of the medium is set at the beginning of the fermentation and not subject to artificial alterations during the fermentation. A variation on the standard batch system is the fed-batch system. Fed-batch fermentation processes are also suitable in the present invention and comprise a typical batch system with the exception that the substrate is added in increments as the fermentation progresses. Fed-batch systems are useful when catabolite repression is apt to inhibit the metabolism of the cells and where it is desirable to have limited amounts of substrate in the media. Batch and fed-batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.*, 36:227, (1992).

Isobutanol, or other products, may also be produced using continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth. Continuous fermentation allows for the modulation of one factor or any number of factors that affect cell growth or end product concentration. Methods of modulating nutrients and growth factors for continuous fermentation processes as well as techniques for maximizing the rate of product formation are well known in the art of industrial microbiology and a variety of methods are detailed by Brock, supra.

It is contemplated that the production of isobutanol, or other products, may be practiced using batch, fed-batch or continuous processes and that any known mode of fermentation would be suitable. Additionally, it is contemplated that cells may be immobilized on a substrate as whole cell catalysts or encapsulated within porous material (e.g. alginate beads) and subjected to fermentation conditions for isobutanol production.

Methods for Isobutanol Isolation from the Fermentation Medium

Bioproduced isobutanol may be isolated from the fermentation medium using methods known in the art for ABE fermentations (see, e.g., Durre, *Appl. Microbiol. Biotechnol.* 49:639-648 (1998), Groot et al., *Process. Biochem.* 27:61-75 (1992), and references therein). For example, solids may be removed from the fermentation medium by centrifugation, filtration, decantation, or the like. Then, the isobutanol may be isolated from the fermentation medium using methods such as distillation, azeotropic distillation, liquid-liquid extraction, adsorption, gas stripping, membrane evaporation, or pervaporation.

Because isobutanol forms a low boiling point, azeotropic mixture with water, distillation can be used to separate the mixture up to its azeotropic composition. Distillation may be used in combination with another separation method to obtain separation around the azeotrope. Methods that may be used in combination with distillation to isolate and purify butanol include, but are not limited to, decantation, liquid-liquid extraction, adsorption, and membrane-based techniques. Additionally, butanol may be isolated using azeotropic distillation using an entrainer (see, e.g., Doherty and Malone, *Conceptual Design of Distillation Systems*, McGraw Hill, New York, 2001).

The butanol-water mixture forms a heterogeneous azeotrope so that distillation may be used in combination with decantation to isolate and purify the isobutanol. In this method, the isobutanol containing fermentation broth is distilled to near the azeotropic composition. Then, the azeotropic mixture is condensed, and the isobutanol is separated from the fermentation medium by decantation. The decanted aqueous phase may be returned to the first distillation column as reflux. The isobutanol-rich decanted organic phase may be further purified by distillation in a second distillation column.

The isobutanol can also be isolated from the fermentation medium using liquid-liquid extraction in combination with distillation. In this method, the isobutanol is extracted from the fermentation broth using liquid-liquid extraction with a suitable solvent. The isobutanol-containing organic phase is then distilled to separate the butanol from the solvent.

Distillation in combination with adsorption can also be used to isolate isobutanol from the fermentation medium. In this method, the fermentation broth containing the isobutanol is distilled to near the azeotropic composition and then the remaining water is removed by use of an adsorbent, such as molecular sieves (Aden et al., *Lignocellulosic Biomass to Ethanol Process Design and Economics Utilizing Co-Current Dilute Acid Prehydrolysis and Enzymatic Hydrolysis for Corn Stover*, Report NREL/TP-510-32438, National Renewable Energy Laboratory, June 2002).

Additionally, distillation in combination with pervaporation may be used to isolate and purify the isobutanol from the fermentation medium. In this method, the fermentation broth containing the isobutanol is distilled to near the azeotropic composition, and then the remaining water is removed by pervaporation through a hydrophilic membrane (Guo et al., *J. Membr. Sci.* 245, 199-210 (2004)).

In situ product removal (ISPR) (also referred to as extractive fermentation) can be used to remove butanol (or other fermentative alcohol) from the fermentation vessel as it is produced, thereby allowing the microorganism to produce butanol at high yields. One method for ISPR for removing fermentative alcohol that has been described in the art is liquid-liquid extraction. In general, with regard to butanol fermentation, for example, the fermentation medium, which includes the microorganism, is contacted with an organic extractant at a time before the butanol concentration reaches a toxic level. The organic extractant and the fermentation medium form a biphasic mixture. The butanol partitions into the organic extractant phase, decreasing the concentration in the aqueous phase containing the microorganism, thereby limiting the exposure of the microorganism to the inhibitory butanol.

Liquid-liquid extraction can be performed, for example, according to the processes described in U.S. Patent Appl. Pub. No. 2009/0305370, the disclosure of which is hereby incorporated in its entirety. U.S. Patent Appl. Pub. No. 2009/0305370 describes methods for producing and recovering butanol from a fermentation broth using liquid-liquid extraction, the methods comprising the step of contacting the fermentation broth with a water immiscible extractant to form a two-phase mixture comprising an aqueous phase and an organic phase. Typically, the extractant can be an organic extractant selected from the group consisting of saturated, mono-unsaturated, poly-unsaturated (and mixtures thereof) $C_{12}$ to $C_{22}$ fatty alcohols, $C_{12}$ to $C_{22}$ fatty acids, esters of $C_{12}$ to $C_{22}$ fatty acids, $C_{12}$ to $C_{22}$ fatty aldehydes, and mixtures thereof. The extractant(s) for ISPR can be non-alcohol extractants. The ISPR extractant can be an exogenous organic extractant such as oleyl alcohol, behenyl alcohol, cetyl alcohol, lauryl alcohol, myristyl alcohol, stearyl alcohol, 1-undecanol, oleic acid, lauric acid, myristic acid, stearic acid, methyl myristate, methyl oleate, undecanal, lauric aldehyde, 20-methylundecanal, and mixtures thereof.

In some embodiments, an ester can be formed by contacting the alcohol in a fermentation medium with an organic acid (e.g., fatty acids) and a catalyst capable of esterfiying the alcohol with the organic acid. In such embodiments, the organic acid can serve as an ISPR extractant into which the alcohol esters partition. The organic acid can be supplied to the fermentation vessel and/or derived from the biomass supplying fermentable carbon fed to the fermentation vessel. Lipids present in the feedstock can be catalytically hydrolyzed to organic acid, and the same catalyst (e.g., enzymes) can esterify the organic acid with the alcohol. The catalyst can be supplied to the feedstock prior to fermentation, or can be supplied to the fermentation vessel before or contemporaneously with the supplying of the feedstock. When the catalyst is supplied to the fermentation vessel, alcohol esters can be obtained by hydrolysis of the lipids into organic acid and substantially simultaneous esterification of the organic acid with butanol present in the fermentation vessel. Organic acid and/or native oil not derived from the feedstock can also be fed to the fermentation vessel, with the native oil being hydrolyzed into organic acid. Any organic acid not esterified with the alcohol can serve as part of the ISPR extractant. The extractant containing alcohol esters can be separated from the fermentation medium, and the alcohol can be recovered from the extractant. The extractant can be recycled to the fermentation vessel. Thus, in the case of butanol production, for example, the conversion of the butanol to an ester reduces the free butanol concentration in the fermentation medium, shielding the microorganism from the toxic effect of increasing butanol concentration. In addition, unfractionated grain can be used as feedstock without separation of lipids therein, since the lipids can be catalytically hydrolyzed to organic acid, thereby decreasing the rate of build-up of lipids in the ISPR extractant. Other butanol product recovery and/or ISPR methods may be employed, including those described in U.S. Pat. No. 8,101,808, incorporated herein by reference.

In situ product removal can be carried out in a batch mode or a continuous mode. In a continuous mode of in situ product removal, product is continually removed from the reactor. In a batchwise mode of in situ product removal, a volume of organic extractant is added to the fermentation vessel and the extractant is not removed during the process. For in situ product removal, the organic extractant can contact the fermentation medium at the start of the fermentation forming a biphasic fermentation medium. Alternatively, the organic extractant can contact the fermentation medium after the microorganism has achieved a desired amount of growth, which can be determined by measuring the optical density of the culture. Further, the organic extractant can contact the fermentation medium at a time at which the product alcohol level in the fermentation medium reaches a preselected level. In the case of butanol production according to some embodiments of the present invention, the organic acid extractant can contact the fermentation medium at a time before the butanol concentration reaches a toxic level, so as to esterify the butanol with the organic acid to produce butanol esters and consequently reduce the concentration of butanol in the fermentation vessel. The ester-containing organic phase can then be removed from the fermentation vessel (and separated from the fermentation broth which constitutes the aqueous phase) after a desired effective titer of the butanol esters is achieved. In some embodiments, the ester-containing organic phase is separated from the aqueous phase after fermentation of the available fermentable sugar in the fermentation vessel is substantially complete.

Isobutanol titer in any phase can be determined by methods known in the art, such as via high performance liquid chromatography (HPLC) or gas chromatography, as described, for example in U.S. Patent Appl. Pub. No. US20090305370, which is incorporated herein by reference.

EXAMPLES

The present invention is further defined in the following Examples. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used in the Examples are well known in the art and are described by Sambrook et al. (Sambrook, J., Fritsch, E. F. and Maniatis, T. (Molecular Cloning: A Laboratory Manual; Cold Spring Harbor Laboratory Press, Cold Spring Harbor, 1989, here in referred to as Maniatis) and by Ausubel et al. (Ausubel et al., Current Protocols in Molecular Biology, pub. by Greene Publishing Assoc. and Wiley-Interscience, 1987).

Materials and methods suitable for the maintenance and growth of bacterial cultures are well known in the art. Techniques suitable for use in the following examples may be found as set out in Manual of Methods for General Bacteriology (Phillipp et al., eds., American Society for Microbiology, Washington, D.C., 1994) or by Thomas D. Brock in (Brock, Biotechnology: A Textbook of Industrial Microbiology, Second Edition, Sinauer Associates, Inc., Sunderland, Mass. (1989). All reagents, restriction enzymes and materials used for the growth and maintenance of bacterial cells were obtained from Sigma-Aldrich Chemicals (St. Louis, Mo.), BD Diagnostic Systems (Sparks, Md.), Invitrogen (Carlsbad, Calif.), HiMedia (Mumbai, India), SD Fine chemicals (India), or Takara Bio Inc. (Shiga, Japan), unless otherwise specified.

The meaning of abbreviations is as follows: "sec" means second(s), "min" means minute(s), "h" means hour(s), "nm" means nanometers, "uL" or "µl" means microliter(s), "mL" means milliliter(s), "mg/mL" means milligram per milliliter, "L" means liter(s), "nm" means nanometers, "mM" means millimolar, "M" means molar, "mmol" means millimole(s), "µmole" means micromole(s), "kg" means kilogram, "g" means gram(s), "µg" means microgram(s) and "ng" means nanogram(s), "PCR" means polymerase chain reaction, "OD" means optical density, "OD600" means the optical density measured at a wavelength of 600 nm, "kDa" means kilodaltons, "g" can also mean the gravitation constant, "bp" means base pair(s), "kbp" means kilobase pair(s), "kb" means kilobase, "%" means percent, "% w/v" means weight/volume percent, "% v/v" means volume/volume percent, "HPLC" means high performance liquid chromatography, "g/L" means gram per liter, "µg/L" means microgram per liter, "ng/µL" means nanogram per microliter, "pmol/µL" means picomol per microliter, "RPM" means rotation per minute, "µmol/min/mg" means micromole per minute per milligram, "w/v" means weight per volume, "v/v" means volume per volume.

Example 1

Construction of Expression Vectors for Isobutanol Pathway Gene Expression in *S. cerevisiae* pLH475-JEA1 Construction

The pLH475-JEA1 plasmid (SEQ ID NO:23) was constructed for expression of ALS and KARI in yeast. pLH475-JEA1 is a pHR81 vector (ATCC #87541) containing the following chimeric genes: (1) the CUP1 promoter (SEQ ID NO:24), acetolactate synthase coding region from *Bacillus subtilis* (AlsS; SEQ ID NO:25; protein SEQ ID NO:36) and CYC1 terminator2 (SEQ ID NO:27); (2) an ILV5 promoter (SEQ ID NO:28), Pf5.IlvC-JEA1 coding region (SEQ ID NO:29; protein SEQ ID NO:30 and ILV5 terminator (SEQ ID NO:31); and (3) the FBA1 promoter (SEQ ID NO:32), *S. cerevisiae* KARI coding region (ILV5; SEQ ID NO:33; protein SEQ ID NO:34) and CYC1 terminator (SEQ ID NO:35). The Pf5.IlvC-JEA1 coding region is a sequence encoding KARI derived from *Pseudomonas fluorescens* but containing mutations, that was described in commonly owned and co-pending US Patent Application Publication US20100197519A1, which is herein incorporated by reference (Pf5.IlvC-JEA1 encoded KARI: SEQ ID NO:29; protein SEQ ID NO:30)

Expression Vector pLH468

The pLH468 plasmid (SEQ ID NO:39) was constructed for expression of DHAD, KivD and HADH in yeast. Coding regions for *L. lactis* ketoisovalerate decarboxylase (KivD) (SEQ ID NO:141) and Horse liver alcohol dehydrogenase (HADH) (SEQ ID NO:40 and 142) were synthesized by DNA2.0 based on codons that were optimized for expression in *Saccharomyces cerevisiae* and provided in plasmids pKivDy-DNA2.0 and pHadhy-DNA2.0. Individual expression vectors for KivD and HADH were constructed. To assemble pLH467 (pRS426::$P_{TDH3}$-kivDy-TDH3t), vector pNY8 (SEQ ID NO:14; also named pRS426.GPD-ald-GPDt, described in commonly owned and co-pending US Patent App. Pub. US2008/0182308, Example 17, which is herein incorporated by reference) was digested with AscI and SfiI enzymes, thus excising the GPD promoter and the ald coding region. A TDH3 promoter fragment (SEQ ID NO:41) from pNY8 was PCR amplified to add an AscI site at the 5' end, and an SpeI site at the 3' end, using 5' primer OT1068 and 3' primer OT1067 (SEQ ID NOs:42 and 43). The AscI/SfiI digested pNY8 vector fragment was ligated with the TDH3 promoter PCR product digested with AscI and SpeI, and the Spa-SfiI fragment containing the codon optimized kivD coding region isolated from the vector pKivD-DNA2.0. The triple ligation generated vector pLH467 (pRS426::$P_{TDH3}$-kivDy-TDH3t). pLH467 (SEQ ID NO:44) was verified by restriction mapping and sequencing.

pLH435 (pRS425::$P_{GPM1}$-Hadhy-ADH1t) (SEQ ID NO:52) was derived from vector pRS425::GPM-sadB (SEQ ID NO:45) which is described in commonly owned and co-pending US Patent App. Pub No. US20090305363 A1, Example 3, which is herein incorporated by reference in its entirety. pRS425::GPM-sadB is the pRS425 vector (ATCC #77106) with a chimeric gene containing the GPM1 promoter (SEQ ID NO: 46), coding region from a butanol dehydrogenase of *Achromobacter xylosoxidans* (sadB; DNA SEQ ID NO:47; protein SEQ ID NO:48: disclosed in U.S. Pat. No. 8,188,250, which is herein incorporated by reference in its entirety), and ADH1 terminator (SEQ ID NO:49). pRS425::GPMp-sadB contains BbvI and PacI sites at the 5' and 3' ends of the sadB coding region, respectively. A Nha site was added at the 5' end of the sadB coding region by site-directed mutagenesis using primers OT1074 and OT1075 (SEQ ID NO:50 and 51) to generate vector pRS425-GPMp-sadB-NheI, which was verified by sequencing. pRS425::$P_{GPM1}$-sadB-NheI was digested with NheI and PacI to drop out the sadB coding region, and ligated with the NheI-PacI fragment containing the codon optimized HADH coding region from vector pHadhy-DNA2.0 to create pLH435.

To combine KivD and HADH expression cassettes in a single vector, yeast vector pRS411 (ATCC #87474) was digested with SacI and Not I, and ligated with the SacI-SalI fragment from pLH467 that contains the $P_{TDH3}$-kivDy-TDH3t cassette together with the SalI-NotI fragment from pLH435 that contains the $P_{GPM1}$-Hadhy-ADH1t cassette in a triple ligation reaction. This yielded the vector pRS411::$P_{TDH3}$-kivDy-$P_{GPM1}$-Hadhy (pLH441), which was verified by restriction mapping.

In order to generate a co-expression vector for all three genes in the lower isobutanol pathway: ilvD, kivDy and Hadhy, we used pRS423 FBA ilvD(Strep) (SEQ ID NO:53, which is described in commonly owned and co-pending US Patent App. Pub. US 20100081154A1, which is herein incorporated by reference in its entirety, as the source of the IlvD gene. This shuttle vector contains an F1 origin of replication (nt 1423 to 1879) for maintenance in *E. coli* and a 2 micron origin (nt 8082 to 9426) for replication in yeast. The vector has an FBA1 promoter (nt 2111 to 3108; SEQ ID NO:32) and FBA terminator (nt 4861 to 5860; SEQ ID NO:54). In addition, it carries the His marker (nt 504 to 1163) for selection in yeast and ampicillin resistance marker (nt 7092 to 7949) for selection in *E. coli*. The ilvD coding region (nt 3116 to 4828; SEQ ID NO:55; protein SEQ ID NO:56) from *Streptococcus mutans* UA159 (ATCC #700610) is between the FBA promoter and FBA terminator forming a chimeric gene for expression. In addition there is a lumio tag fused to the ilvD coding region (nt 4829-4849).

The first step was to linearize pRS423 FBA ilvD(Strep) (also called pRS423-FBA(SpeI)-IlvD(*Streptococcus mutans*)-Lumio) with SacI and SacII (with SacII site blunt ended using T4 DNA polymerase), to give a vector with total length of 9,482 bp. The second step was to isolate the kivDy-hADHy cassette from pLH441 with SacI and KpaI (with KpaI site blunt ended using T4 DNA polymerase), which gives a 6,063 bp fragment. This fragment was ligated with the 9,482 bp vector fragment from pRS423-FBA (SpeI)-IlvD(*Streptococcus mutans*)-Lumio. This generated vector pLH468 (pRS423::$P_{FBA1}$-ilvD(Strep)Lumio-FBA1t-$P_{TDH3}$-kivDy-TDH3t-$P_{GPM1}$-hadhy-ADH1t), which was confirmed by restriction mapping and sequencing.

Example 2

Construction of *S. cerevisiae* Host Strain Containing Disruptions in Pyruvate Decarboxylase and Hexokinase II This example describes insertion-inactivation of endogenous PDC1, PDC5, and PDC6 genes of *S. cerevisiae*. PDC1, PDC5, and PDC6 genes encode the three major isozymes of pyruvate decarboxylase. Hexokinase II, which is responsible for phosphorylation of glucose and transcriptional repression, is also inactivated. The resulting PDC/HXK2 inactivation strain (U.S. Publication No: 2011/0124060, which is incorporated herein by reference) was used as a host for expression vectors pLH475-JEA1 and pLH468 that were described in Example 2.

Construction of pdc6::$P_{GPM1}$-sadB Integration Cassette and PDC6 Deletion:

A pdc6::$P_{GPM1}$-sadB-ADH1t-URA3r integration cassette was made by joining the GPM-sadB-ADHt segment from pRS425::GPM-sadB (described above) to the URA3r gene from pUC19-URA3r. pUC19-URA3r (SEQ ID NO:57) contains the URA3 marker from pRS426 (ATCC #77107) flanked by 75 bp homologous repeat sequences to allow homologous recombination in vivo and removal of the URA3 marker. The two DNA segments were joined by SOE PCR (as described by Horton et al. (1989) *Gene* 77:61-68) using as template pRS425::GPM-sadB and pUC19-URA3r plasmid DNAs, with Phusion DNA polymerase (New England Biolabs Inc., Beverly, Mass.; catalog no. F-5405) and primers 114117-11A through 114117-11D (SEQ ID NOs:58, 59, 60 and 61), and 114117-13A and 114117-13B (SEQ ID NOs:62 and 63).

The outer primers for the SOE PCR (114117-13A and 114117-13B) contained 5' and 3' ~50 bp regions homologous to regions upstream and downstream of the PDC6 promoter and terminator, respectively. The completed cassette PCR fragment was transformed into BY4700 (ATCC #200866) and transformants were maintained on synthetic complete media lacking uracil and supplemented with 2% glucose at 30° C. using standard genetic techniques (*Methods in Yeast Genetics*, 2005, Cold Spring Harbor Laboratory Press, Cold Spring Harbor, N.Y., pp. 201-202). Transformants were screened by PCR using primers 112590-34G and 112590-34H (SEQ ID NOs:64 and 65), and 112590-34F and 112590-49E (SEQ ID NOs:66 and 67) to verify integration at the PDC6 locus with deletion of the PDC6 coding region. The URA3r marker was recycled by plating on synthetic complete media supplemented with 2% glucose and 5-FOA at 30° C. following standard protocols. Marker removal was confirmed by patching colonies from the 5-FOA plates onto SD −URA media to verify the absence of growth. The resulting identified strain has the genotype: BY4700 pdc6::$P_{GPM1}$-sadB-ADH1t.

Construction of pdc1::$P_{PDC1}$-ilvD Integration Cassette and PDC1 Deletion:

A pdc1::$P_{PDC1}$-ilvD-FBA1t-URA3r integration cassette was made by joining the ilvD-FBA1t segment from pLH468 (described above) to the URA3r gene from pUC19-URA3r by SOE PCR (as described by Horton et al. (1989) Gene 77:61-68) using as template pLH468 and pUC19-URA3r plasmid DNAs, with Phusion DNA polymerase (New England Biolabs Inc., Beverly, Mass.; catalog no. F-540S) and primers 114117-27A through 114117-27D (SEQ ID NOs:68, 69, 70 and 71).

The outer primers for the SOE PCR (114117-27A and 114117-27D) contained 5' and 3' ~50 bp regions homologous to regions downstream of the PDC1 promoter and downstream of the PDC1 coding sequence. The completed cassette PCR fragment was transformed into BY4700 pdc6::$P_{GPM1}$-sadB-ADH1t and transformants were maintained on synthetic complete media lacking uracil and supplemented with 2% glucose at 30° C. using standard genetic techniques (*Methods in Yeast Genetics*, 2005, Cold Spring Harbor Laboratory Press, Cold Spring Harbor, N.Y., pp. 201-202). Transformants were screened by PCR using primers 114117-36D and 135 (SEQ ID NOs:72 and 73), and primers 112590-49E and 112590-30F (SEQ ID NOs:67 and 74) to verify integration at the PDC1 locus with deletion of the PDC1 coding sequence. The URA3r marker was recycled by plating on synthetic complete media supplemented with 2% glucose and 5-FOA at 30° C. following standard protocols. Marker removal was confirmed by patching colonies from the 5-FOA plates onto SD −URA media to verify the absence of growth. The resulting identified strain "NYLA67" has the genotype: BY4700 pdc6::$P_{GPM1}$-sadB-ADH1t pdc1::$P_{PDC1}$-ilvD-FBA1t.

HIS3 Deletion

To delete the endogenous HIS3 coding region, a his3:: URA3r2 cassette was PCR-amplified from URA3r2 template DNA (SEQ ID NO:75). URA3r2 contains the URA3 marker from pRS426 (ATCC #77107) flanked by 500 bp homologous repeat sequences to allow homologous recombination in vivo and removal of the URA3 marker. PCR was done using Phusion DNA polymerase and primers 114117-45A and 114117-45B (SEQ ID NOs:76 and 77) which generated a ~2.3 kb PCR product. The HIS3 portion of each primer was derived from the 5' region upstream of the HIS3 promoter and 3' region downstream of the coding region such that integration of the URA3r2 marker results in replacement of the HIS3 coding region. The PCR product was transformed into NYLA67 using standard genetic techniques (*Methods in Yeast Genetics*, 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened to verify correct integration by replica plating of transformants onto synthetic complete media lacking histidine and supplemented with 2% glucose at 30° C. The URA3r marker was recycled by plating on synthetic complete media supplemented with 2% glucose and 5-FOA at 30° C. following standard protocols. Marker removal was confirmed by patching colonies from the 5-FOA plates onto SD −URA media to verify the absence of growth. The resulting identified strain, called NYLA73, has the genotype: BY4700 pdc6::$P_{GPM1}$-sadB-ADH1t pdc1::Pp$_{PDC1}$-ilvD-FBA1t dhis3.

Deletion of HXK2 (Hexokinase II):

A hxk2::URA3r cassette was PCR-amplified from URA3r2 template (described above) using Phusion DNA polymerase and primers 384 and 385 (SEQ ID NOs:78 and 79) which generated a ~2.3 kb PCR product. The HXK2 portion of each primer was derived from the 5' region upstream of the HXK2 promoter and 3' region downstream of the coding region such that integration of the URA3r2 marker results in replacement of the HXK2 coding region. The PCR product was transformed into NYLA73 using standard genetic techniques (*Methods in Yeast Genetics*, 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened by PCR to verify correct integration at the HXK2 locus with replacement of the HXK2 coding region using primers N869 and N871 (SEQ ID NOs:80 and 81). The URA3r2 marker was recycled by plating on synthetic complete media supplemented with 2% glucose and 5-FOA at 30° C. following standard protocols. Marker removal was confirmed by patching colonies from the 5-FOA plates onto SD −URA media to verify the absence of growth, and by PCR to verify correct marker removal using primers N946 and N947 (SEQ ID NOs:82 and 83). The resulting identified strain named NYLA83 has the genotype: BY4700 pdc6:: $P_{GPM1}$-sadB-ADH1t pdc1::$P_{PDC1}$-ilvD-FBA1t dhis3 dhxk2.

Construction of pdc5::kanMX Integration Cassette and PDC5 Deletion

A pdc5::kanMX4 cassette was PCR-amplified from strain YLR134W chromosomal DNA (ATCC No. 4034091) using Phusion DNA polymerase and primers PDC5::KanMXF and PDC5::KanMXR (SEQ ID NOs:84 and 85) which generated a ~2.2 kb PCR product. The PDC5 portion of each primer was derived from the 5' region upstream of the PDC5 promoter and 3' region downstream of the coding region such that integration of the kanMX4 marker results in replacement of the PDC5 coding region. The PCR product was transformed into NYLA83, and transformants were selected and screened as described above. The identified correct transformants named NYLA84 have the genotype: BY4700 pdc6::$P_{GPM1}$-sadB-ADH1t pdc1::$P_{PDC1}$-ilvD-FBA1t dhis3 dhxk2 pdc5::kanMX4.

Plasmid vectors pLH468 and pLH475-JEA1 were simultaneously transformed into strain NYLA84 (BY4700 pdc6:: $P_{GPM1}$-sadB-ADH1t pdc1::$P_{PDC1}$-ilvD-FBA1t dhis3 dhxk2 pdc5::kanMX4) using standard genetic techniques (*Methods in Yeast Genetics,* 2005, Cold Spring Harbor Laboratory Press, Cold Spring Harbor, N.Y.) and the resulting strain was maintained on synthetic complete media lacking histidine and uracil, and supplemented with 1% ethanol at 30° C.

Example 3

Construction of *S. cerevisiae* Host Strain Containing Disruptions in URA3, HIS3, and Insertion of Sulfonylurea-Resistant ILV2

This example describes inactivation of the URA3 and HIS3 genes of *S. cerevisiae*, and replacement of the native ILV2 gene with a variant that is resistant to sulfonylurea herbicides. The resulting strain will be used as a host for expression vectors pLH475-JEA1 and pLH468 that were described in Example 1.
URA3 Deletion To delete the endogenous URA3 coding region, a deletion cassette was PCR-amplified from pLA54 (SEQ ID NO:100) which contains a $P_{TEF1}$-kanMX-TEF1t cassette flanked by loxP sites to allow homologous recombination in vivo and subsequent removal of the KanMX marker. PCR was performed using Phusion DNA polymerase and primers BK505 and BK506 (SEQ ID NOs:101 and 102). The URA3 portion of each primer was derived from the 5' region 180 bp upstream of the URA3 ATG and 3' region 78 bp downstream of the coding region such that integration of the KanMX cassette results in replacement of the URA3 coding region. The PCR product was transformed into PNY827 (ATCC # PTA-12105), using standard genetic techniques (Methods in Yeast Genetics, 2005, Cold Spring Harbor Laboratory Press, Cold Spring Harbor, N.Y., pp. 201-202) and transformants were selected on rich media supplemented 2% glucose and 100 µg/ml Geneticin at 30° C. Transformants were screened by colony PCR with primers BK468 and LA492 (SEQ ID NOs:103 and 104) to verify presence of the integration cassette. A heterozygous URA3 mutant was obtained; NYLA98 MATa/α URA3/ura3::loxP-kanMX-loxP. To obtain haploids, NYLA98 was sporulated using standard methods (Codón AC, Gasent-Ramírez J M, Benítez T., *Appl Environ Microbiol.* 1995 PMID: 7574601). Tetrads were dissected using a micromanipulator and grown on rich media supplemented with 2% glucose. Tetrads containing four viable spores were patched onto synthetic complete media lacking uracil and supplemented with 2% glucose, and the mating type was verified by multiplex colony PCR using primers AK109-1, AK109-2, and AK109-3 (SEQ ID NOs:105, 106, and 107). The resulting identified haploid strain called NYLA103 has the genotype MATα ura3Δ::loxP-kanMX-loxP, and NYLA106 has the genotype MATa ura3Δ::loxP-kanMX-loxP.
HIS3 Deletion The four fragments for the PCR cassette for the scarless HIS3 deletion were amplified using Phusion High Fidelity PCR Master Mix (New England BioLabs; Ipswich, Mass.) and CEN.PK 113-7D genomic DNA as template, prepared with a Gentra Puregene Yeast/Bact kit (Qiagen; Valencia, Calif.). HIS3 Fragment A was amplified with primer oBP452 (SEQ ID NO: 89) and primer oBP453 (SEQ ID NO:109), containing a 5' tail with homology to the 5' end of HIS3 Fragment B. HIS3 Fragment B was amplified with primer oBP454 (SEQ ID NO:110), containing a 5' tail with homology to the 3' end of HIS3 Fragment A, and primer oBP455 (SEQ ID NO:90), containing a 5' tail with homology to the 5' end of HIS3 Fragment U. HIS3 Fragment U was amplified with primer oBP456 (SEQ ID NO:91, containing a 5' tail with homology to the 3' end of HIS3 Fragment B, and primer oBP457 (SEQ ID NO:86), containing a 5' tail with homology to the 5' end of HIS3 Fragment C. HIS3 Fragment C was amplified with primer oBP458 (SEQ ID NO:87), containing a 5' tail with homology to the 3' end of HIS3 Fragment U, and primer oBP459 (SEQ ID NO:88). PCR products were purified with a PCR Purification kit (Qiagen). HIS3 Fragment AB was created by overlapping PCR by mixing HIS3 Fragment A and HIS3 Fragment B and amplifying with primers oBP452 (SEQ ID NO:89) and oBP455 (SEQ ID NO:90). HIS3 Fragment UC was created by overlapping PCR by mixing HIS3 Fragment U and HIS3 Fragment C and amplifying with primers oBP456 (SEQ ID NO:91) and oBP459 (SEQ ID NO:88). The resulting PCR products were purified on an agarose gel followed by a Gel Extraction kit (Qiagen). The HIS3 ABUC cassette was created by overlapping PCR by mixing HIS3 Fragment AB and HIS3 Fragment UC and amplifying with primers oBP452 (SEQ ID NO:89) and oBP459 (SEQ ID NO:88). The final PCR product was purified with a PCR Purification kit (Qiagen).

To delete the endogenous HIS3 coding region, the "scarless" deletion cassette was transformed into NYLA106 using standard techniques and plated on synthetic complete media lacking uracil and supplemented with 2% glucose. Transformants were screened to verify correct integration by replica plating onto synthetic complete media lacking histidine and supplemented with 2% glucose at 30° C. Genomic DNA preps were made to verify the integration by PCR using primers BP460 and LA135 (SEQ ID NOs:93 and 94) for the 5' end and primers BP461 and LA92 (SEQ ID NOs:95 and 96) for the 3' end. The URA3 marker was recycled by plating on synthetic complete media supplemented with 2% glucose and 5-FOA at 30° C. following standard protocols. Marker removal was confirmed by patching colonies from the 5-FOA plates onto SD –URA media to verify the absence of growth. The resulting identified strain, called PNY2003, has the genotype MATa ura3Δ::loxP-kanMX-loxP his3Δ.
Deletion of PDC1:

To delete the endogenous PDC1 coding region, a deletion cassette was PCR-amplified from pLA59 (SEQ ID NO:97), which contains a URA3 marker flanked by degenerate loxP sites to allow homologous recombination in vivo and subsequent removal of the URA3 marker. PCR was done by using Phusion DNA polymerase and primers LA678 and LA679 (SEQ ID NOs:98 and 99). The PDC1 portion of each primer was derived from the 5' region 50 bp downstream of the PDC1 start codon and 3' region 50 bp upstream of the stop codon such that integration of the URA3 cassette results in replacement of the PDC1 coding region but leaves the first 50 bp and the last 50 bp of the coding region. The PCR product was transformed into strain PNY2003 using standard genetic techniques with selection on synthetic complete media lacking uracil and supplemented with 2% glucose at 30° C. Transformants were screened to verify correct integration by colony PCR using primers LA337 (SEQ ID NO:111), external to the 5' coding region and LA135 (SEQ ID NO:94), an internal to URA3. Positive transformants were then screened by colony PCR using primers LA692 and LA693 (SEQ ID NOs:112 and 113), which were internal to the PDC1 coding region. The URA3 marker was recycled by transforming with pRS423::$P_{GAL1}$-cre (SEQ ID NO:121) and plated on synthetic complete media lacking histidine and supplemented with 2% glucose at 30° C. Transformants were plated on YP supplemented with 0.5% galactose to induce expression of Cre recombinase. Marker removal was confirmed by patching colonies to synthetic complete media lacking uracil and supplemented with 2% glucose to verify absence of growth. The resulting identified strain, called PNY2008, has the genotype MATa ura3Δ::loxP-kanMX-loxP his3Δ pdc1Δ::loxP71/66.

Construction of ILV2-410 Integration Vector:

A fragment of the native ILV2 gene from *S. cerevisiae* BY4700 was PCR-amplified using Phusion DNA polymerase and primers LA684 and LA685 (SEQ ID NOs: 114 and 115). The ~2 kb PCR product was digested with BamHI and SphI and cloned into pUC19, and the resulting vector was named pUC19::ILV2 (SEQ ID No:17). Site-directed mutagenesis (QuickChange XL, Stratagene, CA) was used to introduce a C to T transition at base pair 574, resulting in a proline-to-serine substitution (Yadav et al. 1986 *PNAS*. 83:4418-4422). PfuUltra DNA polymerase (Stratagene, CA), primers LA682 and LA683 (SEQ ID NOs:116 and 117), and pUC19::ILV2 template were used to introduce the mutation following standard protocol. The PCR reaction was digested with DpnI to remove parental DNA, and the reaction was transformed into DH5α competent cells on LB-Amp (100 μg/ml). The presence of DNA containing the ILV2-410 allele was confirmed by DNA sequencing of plasmid DNA isolated from transformants. The resulting vector was named pUC19::ILV2-410.

The ILV2-410 fragment was digested from pUC19::ILV2-410 by BamHI SphI digest and subcloned into pLA59. pLA59 (SEQ ID No:97) is a pUC19 cloning vector that contains a loxP71-URA3-loxP66 cassette. The resulting vector, pLA59::ILV2-410 (SEQ ID NO:18), was used as template for PCR of the full integration cassette. The ILV2-410-loxP71-URA3-loxP66 integration cassette was PCR amplified from pLA59::ILV2-410 template using Phusion DNA polymerase and primers LA686 and LA687 (SEQ ID NOs:119 and 120), producing a ~3 kb product. The ILV2 portion of each primer was derived from the 5' region downstream of the ILV2 start codon and 3' region downstream of the stop codon such that integration of the URA3 cassette results in replacement of the native ILV2 coding region.

The PCR product was transformed into strain PNY2008 and plated on synthetic complete media lacking uracil and supplemented with 2% glucose at 30° C. The loxP71-URA3-loxP66 marker was recycled by transformation with pRS423::P$_{GAL1}$-cre (SEQ ID NO:121) and plating on synthetic complete media lacking histidine supplemented with 3% glucose at 30° C. Colonies were patched onto YP (1% galactose) plates at 30° C. to induce URA3 marker excision and were transferred onto YP (2% glucose) plates at 30° C. for recovery. Removal of the URA3 marker were confirmed by patching colonies from the YP (2% glucose) plates onto synthetic complete media lacking uracil supplemented with 2% glucose to verify the absence of growth. The resulting identified strain, called PNY2010, has the genotype MATa ura3Δ::loxP-kanMX-loxP his3Δ pdc1Δ::loxP71/66 ILV2-410::loxP71/66.

Example 4

Susceptibility of Wildtype *S. cerevisiae* Strains to Sulfonylurea Herbicides

This example describes experiments that demonstrate yeast strains, expressing wildtype acetolactate synthase, are resistant to many AHAS-inhibiting sulfonylurea herbicides. Strains tested in this experiment included: *S. cerevisiae* yeast strain PNY0860-1A), a haploid derived from sporulation of the yeast strain deposited with ATCC (ATCC #PTA-12007; *S. cerevisiae* yeast strain PNY827 (ATCC # PTA-12105); and *S. cerevisiae* strain CEN.PK 113-7D (Centraalbureau voor Schimmelcultures (CBS) Fungal Biodiversity Centre #8340).

The following AHAS inhibitors were resuspended in 10 mM KOH to give final concentrations of 2 mg/ml (w/v).

| | |
|---|---|
| Accent ™ | nicosulfuron methyl (V9360) |
| W4189-128 | research sample |
| Ally ™ | metsulfuron methyl (T6376) |
| Classic ™ | chlorimuron ethyl (F6025) |
| Oust ™ | sulfometuron methyl (SM) |
| Harmony ™ | thifensulfuron methyl |

Figure 2:
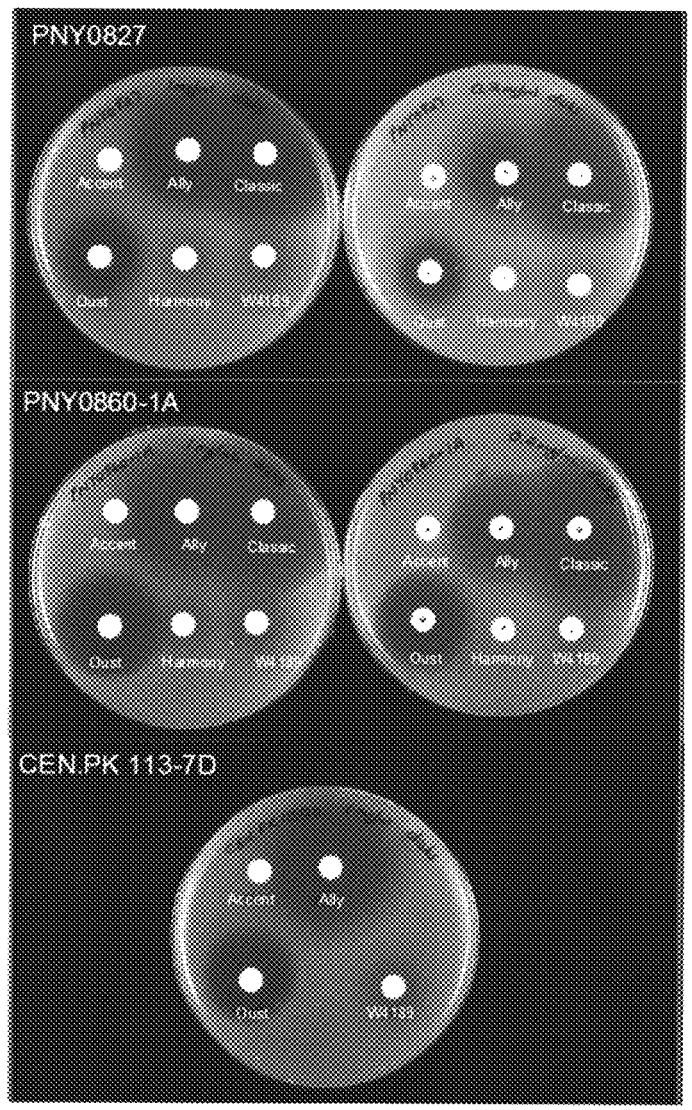
FIG. 2 depicts a growth inhibition assay measuring the ability of S. cerevisiae PNY0860-1A, PNY 827, and CEN.PK113-7D to grow in the presence of AHAS inhibitors.

The yeast strains were initially grown on synthetic complete liquid media lacking all amino acids and supplemented with 2% glucose at 30° C. Early stationary phase cultures (OD600 nm of ~5.0) were used to inoculate 40 ml of top agar media (synthetic complete lacking all amino acids with 0.7% agarose), which were poured into petri plates. Filter disks containing 20 μg AHAS inhibitor (20 p. 1 of a 1 mg/ml stock) or 10 μg AHAS inhibitor (20 μl of a 0.2 mg/ml stock) were added to the plate surface. Plates were incubated for 72 hours at 30° C. before visualization of zones of growth inhibition. Clear zones surrounding the AHAS-laced filter disks indicate inhibition of yeast growth. These results suggested that Classic, Ally, and (just herbicides inhibit growth of the yeast strains. Accent, Harmony, and W4189 did not inhibit the industrial yeast strains at the concentrations used in this experiment. (FIG. 2)

Example 5

Resistance of Engineered *S. cerevisiae* Strains Containing an ILV2 Variant Gene to Sulfonylurea Herbicides This example describes experiments that demonstrate yeast strains, expressing a resistant variant of acetolactate synthase, are resistant to the AHAS inhibitor sulfometuron methyl.

*S. cerevisiae* yeast strains PNY2008 and PNY2010 are described in Example 3. PNY2010 contains the ILV2-410 allele that confers resistance to sulfonylureas.

The yeast strains were initially grown on synthetic complete media supplemented with 2% glucose at 30° C. The strains were patched onto either synthetic complete media supplemented with 2% glucose at 30° C. or synthetic complete media supplemented with 2% glucose and 12.5 μg/ml sulfometuron methyl (prepared in 10 mM KOH as in Example 4). Plates were incubated for 48 hours at 30° C. before visualization. Strain PNY2008 was unable to grow on plates containing sulfometuron methyl, whereas strain PNY2010 grew normally due to the presence of the ILV2-410 allele.

Example 6

Production of Isobutanol in Recombinant *S. cerevisiae* NYLA84

The purpose of this example is to describe the production of isobutanol in the yeast strain NYLA84. The yeast strain comprises deletions of PDC1, PDC5, and PDC6, genes encoding three isozymes of pyruvate decarboxylase, and deletion of HXK2 encoding hexokinase II. The strain also contains constructs for heterologous expression of AlsS (acetolactate synthase), KARI (keto acid reductoisomerase), DHAD (dihydroxy acid dehydratase), KivD (ketoisovalerate decarboxylase), and SadB (secondary alcohol dehydrogenase).

Strain Construction

Plasmids pLH468 and pLH475-JEA1 were introduced into NYLA84, described in Example 3, by standard PEG/lithium acetate-mediated transformation methods. Transformants were selected on synthetic complete medium lacking glucose, histidine and uracil. Ethanol (1% v/v) was used as the carbon source. After three days, transformants were patched to synthetic complete medium lacking histidine and uracil supplemented with both 2% glucose and 0.5% ethanol as carbon sources. Freezer vials were made by dilution of log-phase cultures with 45% glycerol to a final glycerol concentration of 15% (w/v).

Production of Isobutanol 80 ml of synthetic complete medium lacking histidine and uracil supplemented with both 2% glucose and 0.5% ethanol as carbon sources was inoculated with a yeast strain.

Fermentation Conditions:

Medium (final concentration): 6.7 g/L, Yeast Nitrogen Base w/o amino acids (Difco); 2.8 g/L, Yeast Synthetic Drop-out Medium Supplement Without Histidine, Leucine, Tryptophan and Uracil (Sigma Y2001); 20 mL/L of 1% (w/v) L-Leucine; 4 mL/L of 1% (w/v) L-Tryptophan; 1 mL/L ergosterol/tween/ethanol solution; 0.2 mL/L Sigma DF204; 10 g/L glucose The fermenter was set to control at pH 5.5 with KOH, 30% dO, temperature 30° C., and airflow of 0.2 SLPM (or, 0.25 vvm). At inoculation, the airflow was set to 0.01 SLPM initially, then increased to 0.2 SLPM once growth was established. Glucose was maintained at 5-15 g/L throughout by manual addition.

Because efficient production of isobutanol with NYLA84 pLH486/pLH475 requires microaerobic conditions to enable redox balance in the biosynthetic pathway, air was continuously supplied to the fermenter at 0.25 vvm. Continuous aeration led to significant stripping of isobutanol from the aqueous phase of the fermenter. To quantify the loss of isobutanol due to stripping, the off-gas from the fermenter was directly sent to a mass spectrometer (Prima dB mass spectrometer, Thermo Electron Corp., Madison, Wis.) to quantify the amount of isobutanol in the gas stream. The isobutanol peaks at mass to charge ratios of 74 or 42 were monitored continuously to quantify the amount of isobutanol in the gas stream.

Figure 3:
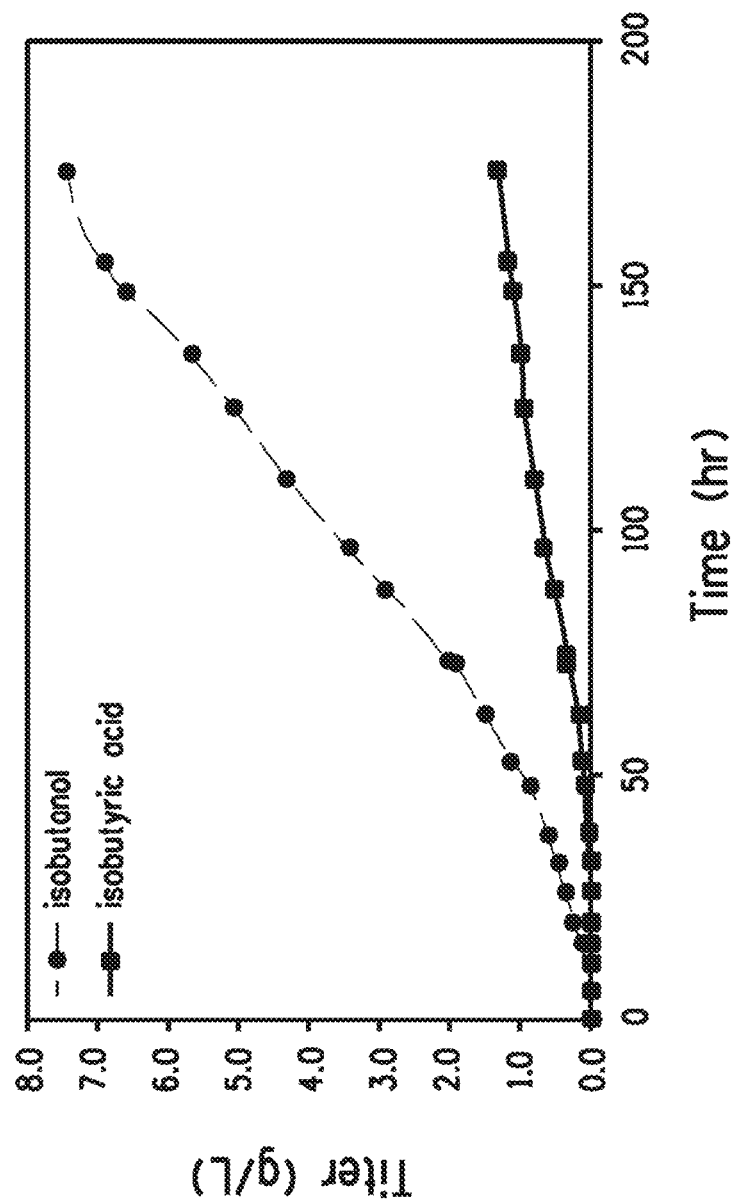
FIG. 3 depicts the production of isobutanol and isobutyric acid as a function of time for the strain NYLA84.

Glucose and organic acids in the aqueous phase were monitored during the fermentation using HPLC. Glucose was also monitored quickly using a glucose analyzer (YSI, Inc., Yellow Springs, Ohio). Isobutanol in the aqueous phase was quantified by HPLC as described in the General Methods Section herein above after the aqueous phase was removed periodically from the fermenter. The effective titer, corrected for the isobutanol lost due to stripping, was 7.5 g/L. The titer of isobutyric acid was 1.28 g/L. (FIG. 3)

Example 7 (Prophetic):

Resistance of Engineered S. cerevisiae Isobutanologens Containing an IL V2 Variant Gene to Sulfonylurea Herbicides This example describes experiments that demonstrate yeast strains that contain an engineered isobutanol production pathway which also express a resistant variant of acetolactate synthase, are resistant to the AHAS inhibitor sulfometuron methyl. Construction of strain NYLA84 is shown in Example 2.

The ILV2-410-loxP71-URA3-loxP66 integration cassette (described in Example 3) is PCR amplified from pLA59::ILV2-410 template using Phusion DNA polymerase and primers LA686 and LA687 (SEQ ID NOs:119 and 120), producing a ~3 kb product. The PCR product is transformed into strain NYLA84 and plated on synthetic complete media lacking uracil and supplemented with 1% ethanol at 30° C. The loxP71-URA3-loxP66 marker is recycled by transformation with pRS423::$P_{GAL1}$-cre (SEQ ID NO:121) and plating on synthetic complete media lacking histidine supplemented with 1% ethanol at 30° C. Colonies are patched onto YP (1% galactose) plates at 30° C. to induce URA3 marker excision and are transferred onto YP (1% ethanol) plates at 30° C. for recovery. Removal of the URA3 marker is confirmed by patching colonies from the YP (1% ethanol) plates onto synthetic complete media lacking uracil supplemented with 1% ethanol to verify the absence of growth. The resulting identified strain has the genotype NYLA84 ILV2-410::loxP71/66.

Plasmid vectors pLH468 and pLH475-JEA1 were simultaneously transformed into strain NYLA84 ILV2-410::loxP71/66 using standard genetic techniques (*Methods in Yeast Genetics*, 2005, Cold Spring Harbor Laboratory Press, Cold Spring Harbor, N.Y.) and the resulting strain was maintained on synthetic complete media lacking histidine and uracil, and supplemented with 1% ethanol at 30° C.

The yeast strains are initially grown on synthetic complete media lacking histidine and uracil, and supplemented with 1% ethanol at 30° C. After three days, transformants are patched to synthetic complete medium lacking histidine and uracil supplemented with both 2% glucose and 0.5% ethanol as carbon sources.

20 ml of synthetic complete medium lacking histidine and uracil supplemented with both 0.2% glucose and 0.5% ethanol as carbon sources at 30° C. is inoculated with the yeast strain. Each strain is diluted to an initial OD of 0.2 in tubes containing fresh synthetic complete medium lacking histidine and uracil supplemented with both 2% glucose and 0.5% ethanol as carbon sources. The AHAS inhibitor sulfometuron methyl is added to the tubes at concentrations ranging from 0 µg/ml to 50 µg/ml. The tubes are incubated overnight at 30° C. shaking at 220 rpm and are scored the following day for growth. Strains expressing cytosolic acetolactate synthase demonstrate higher resistance to sulfometuron methyl. Isobutanol in the aqueous phase is quantified by HPLC as described in the General Methods Section.

Example 8 (Prophetic):

Production of Isobutanol in Recombinant S. cerevisiae NYLA84 in the Presence of Wildtype Yeast Competitor and Sulfometuron Methyl Herbicide The purpose of this example is to describe the production of isobutanol in the yeast strain NYLA84 ILV2-410::loxP71/66 pLH468/pLH475-JEA1 when challenged with a wildtype yeast strain. The AHAS inhibitor sulfometuron methyl is added to prevent or retard growth of the wildtype yeast strain.

Strain Construction

Plasmids pLH468 and pLH475-JEA1 are introduced into NYLA84 ILV2-410::loxP71/66 pLH468/pLH475-JEA1, described in Example 7, by standard PEG/lithium acetate-mediated transformation methods. Transformants are selected on synthetic complete medium lacking glucose, histidine and uracil. Ethanol (1% v/v) is used as the carbon source. After three days, transformants are patched to synthetic complete medium lacking histidine and uracil supplemented with both 2% glucose and 0.5% ethanol as carbon sources.

Wildtype competitor strain Ethanol Red (Fermentis) is grown is synthetic complete medium supplemented with 2% glucose as carbon source.

Production of Isobutanol 80 ml of synthetic complete medium lacking histidine and uracil supplemented with both 2% glucose and 0.5% ethanol as carbon sources is inoculated with the yeast strain.

Fermentation Conditions:

Medium (final concentration): 6.7 g/L, Yeast Nitrogen Base w/o amino acids (Difco); 2.8 g/L, Yeast Synthetic Drop-out Medium Supplement Without Histidine, Leucine Tryptophan and Uracil (Sigma Y2001); 20 mL/L of 1% (w/v) L-Leucine; 4 mL/L of 1% (w/v) L-Tryptophan; 1 mL/L ergosterol/tween/ethanol solution; 0.2 mL/L Sigma DF204; 10 g/L glucose.

Both fermenters are inoculated with NYLA84 pLH486/pLH475 and Ethanol Red (at 0.5x number of cells as the NYLA84 strain). Sulfometuron methyl is added to one fermenter at a concentration found to be inhibitory (see Example 4). The fermenters are set to control at pH 5.5 with KOH, 30% dO, temperature 30° C., and airflow of 0.2 SLPM (or, 0.25 vvm). At inoculation, the airflow is set to 0.01 SLPM initially, then increased to 0.2 SLPM once growth is established. Glucose is maintained at 5-15 g/L throughout by manual addition.

Because efficient production of isobutanol with NYLA84 pLH486/pLH475 requires microaerobic conditions to enable redox balance in the biosynthetic pathway, air is continuously supplied to the fermenter at 0.25 vvm. Continuous aeration leads to significant stripping of isobutanol from the aqueous phase of the fermenter. To quantify the loss of isobutanol due to stripping, the off-gas from the fermenter is directly sent to a mass spectrometer (Prima dB mass spectrometer, Thermo Electron Corp., Madison, Wis.) to quantify the amount of isobutanol in the gas stream. The isobutanol peaks at mass to charge ratios of 74 or 42 are monitored continuously to quantify the amount of isobutanol in the gas stream.

Glucose and organic acids in the aqueous phase are monitored during the fermentation using HPLC. Glucose is also monitored quickly using a glucose analyzer (YSI, Inc., Yellow Springs, Ohio). Isobutanol in the aqueous phase is quantified by HPLC as described in the General Methods Section herein above, after the aqueous phase is removed periodically from the fermenter.

Example 9 (Prophetic):

Isobutanol Production in an Engineered S. cerevisiae Isobutanologens Containing a Heterologous Acetolactate Synthase that is Resistant to Sulfonylurea Herbicides This example describes experiments that demonstrate yeast strains, which contain an engineered isobutanol production pathway and express a heterologous acetolactate synthase that is resistant to sulfonylurea herbicides, are resistant to the AHAS inhibitor sulfometuron methyl. Construction of strain NYLA84 is shown in Example 2.

The enzyme ALS I (encoded by ilvB) from the enterobacteria Escherichia coli K12, which is intrinsically resistant to sulfonylurea herbicides, is PCR-amplified from E. coli K12 genomic DNA using Phusion DNA polymerase and primers T001 and T002 (SEQ ID NOs:122 and 123). The FBA1 promoter is PCR amplified from BY4700 genomic DNA using Phusion DNA polymerase and primers T003 and T004 (SEQ ID NOs:124 and 125). The FBA1 terminator is PCR amplified from BY4700 genomic DNA using Phusion DNA polymerase and primers T005 and T006 (SEQ ID NOs:126 and 127). The FBA1 promoter is digested with SphI KpnI, the ilvB gene is digested with KpnI NotI, and the FBA1 terminator is digested with NotI BamHI. The three fragments are ligated together and subcloned into vector pLA59 (described in Example 3) via SphI BamHI sites, creating vector pLA59::ilvB (SEQ ID NO:19).

The bdh1Δ::$P_{FBA1}$-ilvB-FBA1t-loxP71-URA3-loxP66 integration cassette is PCR amplified from pLA59::ilvB template (SEQ ID NO:19) using Phusion DNA polymerase and primers T007 and T008 (SEQ ID NOs:128 and 129). The BDH1 portion of each primer was derived from the 5' region 50 bp downstream of the BDH1 start codon and 3' region 50 bp upstream of the stop codon such that integration of the URA3 cassette results in replacement of the BDH1 coding region but leaves the first ~50 bp and the last ~50 bp of the coding region. The PCR product is transformed into strain NYLA84 and plated on synthetic complete media lacking uracil and supplemented with 1% ethanol at 30° C. The loxP71-URA3-loxP66 marker is recycled by transformation with pRS423::$P_{GAL1}$-cre (SEQ ID NO:121) and plating on synthetic complete media lacking histidine supplemented with 1% ethanol at 30° C. Colonies are patched onto YP (1% galactose) plates at 30° C. to induce URA3 marker excision and are transferred onto YP (1% ethanol) plates at 30° C. for recovery. Removal of the URA3 marker is confirmed by patching colonies from the YP (1% ethanol) plates onto synthetic complete media lacking uracil supplemented with 1% ethanol to verify the absence of growth. The resulting identified strain has the genotype NYLA84 bdh1::ilvB-loxP71/66.

Plasmid vectors pLH468 and pLH475-JEA1 are simultaneously transformed into strain NYLA84 bdh1::ilvB-loxP71/66 using standard genetic techniques (Methods in Yeast Genetics, 2005, Cold Spring Harbor Laboratory Press, Cold Spring Harbor, N.Y.) and the resulting strain is maintained on synthetic complete media lacking histidine and uracil, and supplemented with 1% ethanol at 30° C.

The yeast strains are initially grown on synthetic complete media lacking histidine and uracil, and supplemented with 1% ethanol at 30° C. After three days, transformants are patched to synthetic complete medium lacking histidine and uracil supplemented with both 2% glucose and 0.5% ethanol as carbon sources.

20 ml of synthetic complete medium lacking histidine and uracil supplemented with both 0.2% glucose and 0.5% ethanol as carbon sources at 30° C. is inoculated with the yeast strain. Each strain is diluted to an initial OD of 0.2 in tubes containing fresh synthetic complete medium lacking histidine and uracil supplemented with both 2% glucose and 0.5% ethanol as carbon sources. The AHAS inhibitor sulfometuron methyl is added to the tubes at concentrations ranging from 0 μg/ml to 50 μg/ml. The tubes are incubated overnight at 30° C. shaking at 220 rpm and are scored the following day for growth. Strains expressing cytosolic acetolactate synthase demonstrate higher resistance to sulfometuron methyl. Isobutanol in the aqueous phase is quantified by HPLC as described in the General Methods Section.

Enterobacterial ALS enzymes are described in LaRossa and Smul, *J. Bacteriol.* 160(1):391-394 (1984). LaRossa describes ALSI enzymes from *S. typhimurium* and *E. coli* that are resistant to sulfonylurea herbicides.

Materials and Methods for Examples 10 to 20

Yeast synthetic medium w/o amino acids, w/o glucose, w/o ethanol/Tween (2x) 13.4 g/l, Yeast Nitrogen Base w/o amino acids (Difco 0919-15-3); 40 mg/L thiamine; 40 mg/L niacin; 200 ml/L 1M MES buffer, pH=5.5

Supplement aa sol. without histidine and uracil (SAAS-1 10x): 18.5 g/L, Synthetic complete amino acid dropout (Kaiser)-His, -Ura (Formedium).

Na-acetate stock solution: 3 M sodium acetate solution
Glucose stock solution: 250 g/L glucose solution Inhibitor stock solutions: (1) copper (II) sulfate pentahydrate: $CuSO_4.5H_2O$ (MW 249.6 g/mol, CAS Number 7758-99-8): 150 mM; (2) formaldehyde solution (SIGMA F8775, 36.5-38% in H2O, MW 30.03 g/mol, CAS Number 50-00-0): 12.15 M; (3) sodium sulfite ($Na_2SO_3$, SIGMA-ALDRICH 50505, CAS Number 7757-83-7, MW 126.04 g/mol): 100 mM in SF11, 500 mM in SF12; (4) bismuth(III) citrate (CAS Number 813-93-4, [O2CCH2C(OH)(CO2)CH2CO2] Bi, MW 398.08 g/mol): saturated solution; (5) sulfometuron methyl (Fluka #34224, CAS Number 74222-97-2, $C_{15}H_{16}N_4O_5S$, MW 364.38 g/mol): 10 g/L in DMSO; (6) 4-pyrazolecarboxylic acid (Sigma-Aldrich, #300713, $C_4H_4N_2O_2$, MW: 112.09 g/mol, CAS Number: 37718-11-9: 1.0 M in SF12 (=112 mg/ml (DMSO)); (7) 4-methylpyrazole hydrochloride (Sigma, # M1387, $C_4H_6N_2.HCl$, MW: 118.56 g/mol, CAS: 56010-88-9): 1.0M in SF12 (=119 mg/ml (DMSO)); (8) pyrazole (Aldrich, # P56607, $C_3H_4N_2$, MW: 68.08 g/mol, CAS Number: 288-13-1): 0.5 M in SF12 (=34 mg/ml); (9) glyoxylic acid sodium salt monohydrate ($HC(O)COONa.H_2O$, MW: 114.03, CAS Number: 918149-31-2): 0.5 M in SF12 (=57 mg/ml); (10) pyrazole (Aldrich, # P56607, $C_3H_4N_2$, MW: 68.08 g/mol, CAS Number: 288-13-1): 0.5 M (=34 mg/ml) in SF13; (11) trans-cinnamaldehyde (Aldrich #239968, $C_6H_5CH=CHCHO$, MW: 132.16 g/mol, CAS: 14371-10-9, d=1.050 g/ml): SF12 and SF13=pure liquid, SF14=20 mM in DMSO; (12) 1-bromo-2-butanone (Sigma-Aldrich #243299, $C_2H_5COCH_2Br$, MW: 151.00 g/mol, CAS: 816-40-0, d=1.479 g/l): SF12 and SF13=pure liquid, SF14=10 mM in DMSO; (13) 4-nitrocinnamaldehyde (predominantly "trans" form, Aldrich #281670, $O_2NC_6H_4CH=CHCHO$, MW: 177.16 g/mol, CAS: 49678-08-2): SF12=pure substance was weighted and added to the culture SEED medium: 10,000 mL Yeast synthetic medium w/o aa, w/o glucose, w/o ethanol/Tween (2x); 2.000 mL Supplement aa sol. without histidine and uracil (SAAS-1 10x); 3.200 mL 250 g/L glucose solution (resulting in 40 g/l glucose); 0.046 mL Na-acetate stock solution; 4.754 mL H2O.

Example 10

Inhibition of Ethanologen Yeast PNY 827 by Copper(II)

Figure 4:
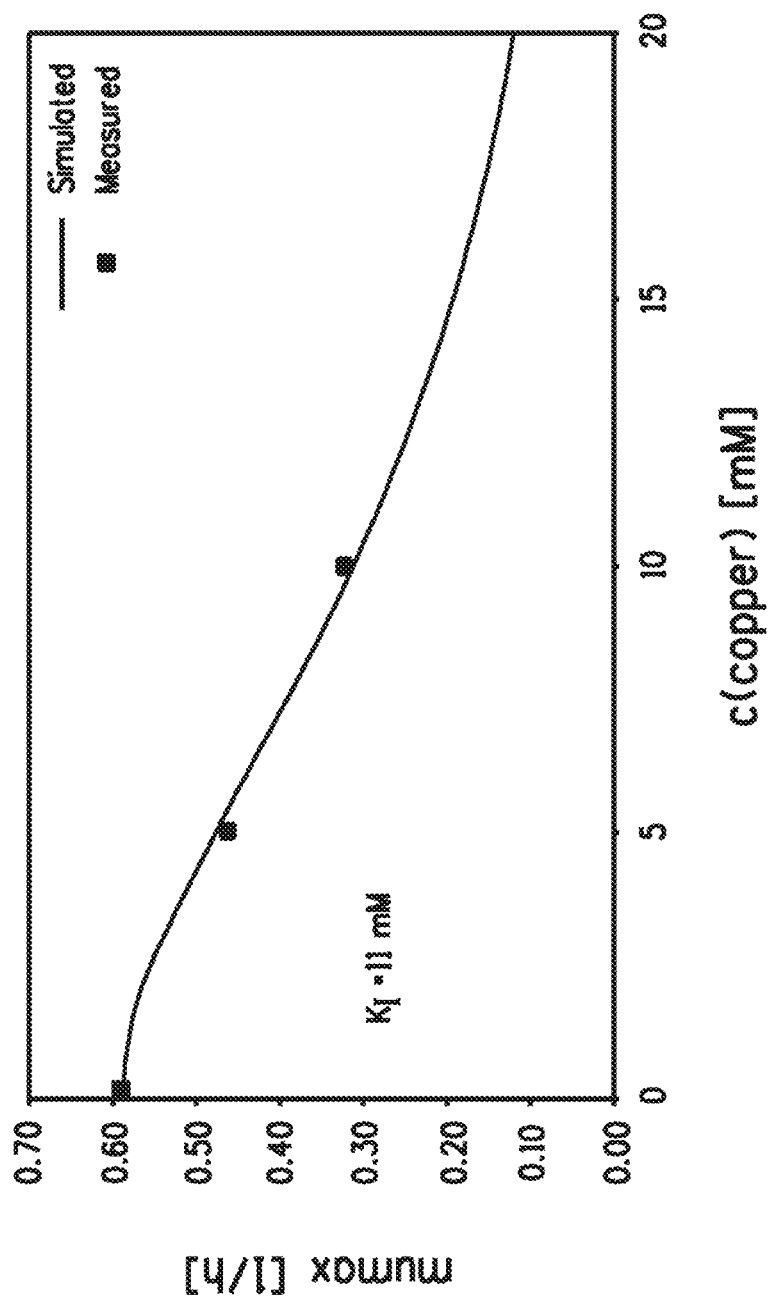
FIG. 4 depicts the μmax of PNY 827 in dependence on concentration of copper(2+) in the medium.
Figure 5:
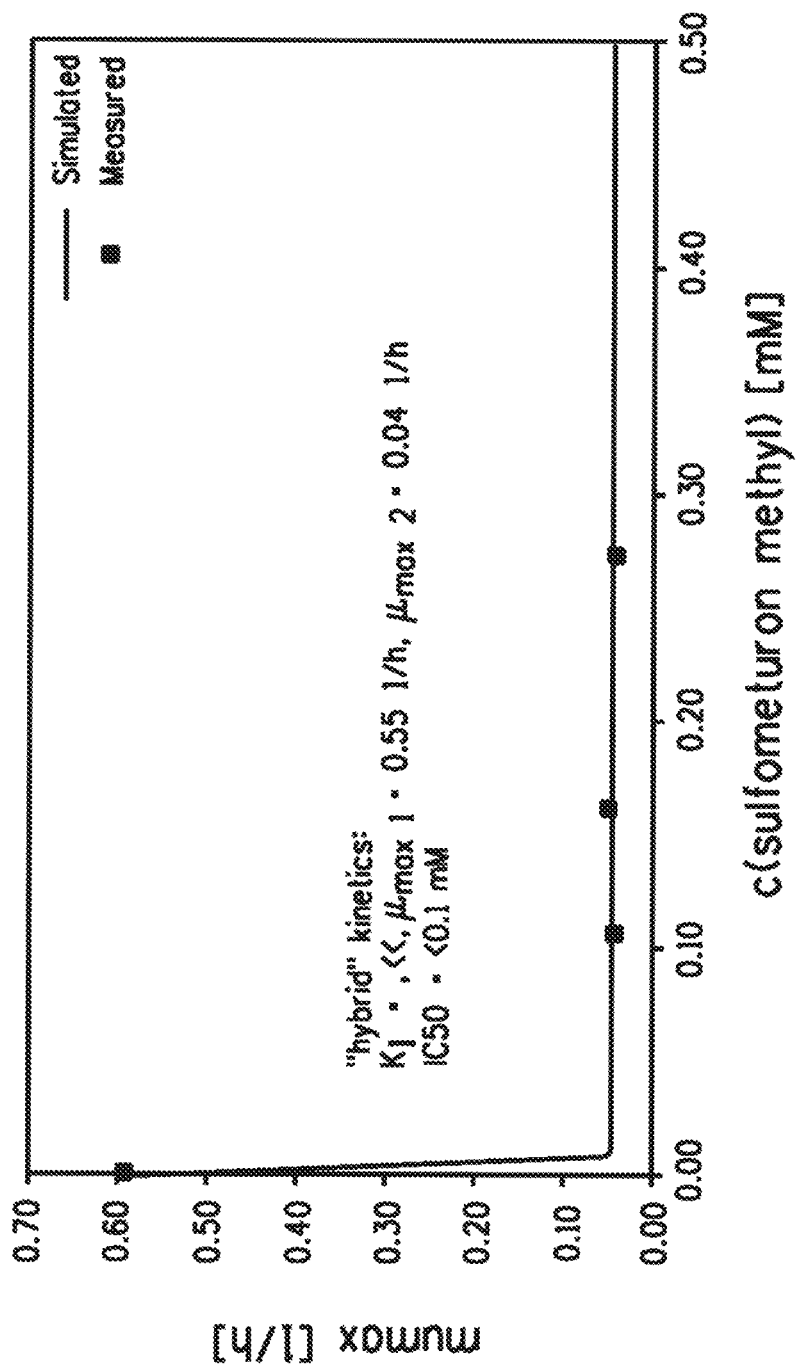
FIG. 5 depicts the μmax of PNY 827 in dependence on concentration of sulfometuron methyl in the medium.

The inhibitory effect of copper (II) on ethanologen yeast PNY 827 was investigated. Therefore a 125 ml aerobic shake flask was prepared with 20 ml SEED medium and inoculated with 1 ml of frozen glycerol stock culture of PNY 827. The culture was inoculated over night at 30° C. and 250 rpm in an Innova Laboratory Shaker (New Brunswick Scientific, Edison, N.J.). Subsequently, a sufficient amount of the seed culture was transferred into shake flasks containing 20 ml of production medium without copper or addition of copper at concentrations of 5 mM, 10 mM and 25 mM, to give an initial OD of approximately 0.1. The cultures were incubated at 250 rpm for 24 h in an Innova Laboratory Shaker (New Brunswick Scientific, Edison, N.J.) and samples of about 1 ml for OD determination withdrawn at designated hours. Optical density was measured with an Ultrospec 3000 spectrophotometer (Pharmacia Biotech) at λ=600 nm. In case cell dry weight concentrations were needed, an OD-DW-correlation of 0.33 gDW/OD was applied. Maximum specific growth rates $\mu_{max}$ were determined by applying the exponential regression function of Microsoft Excel (Microsoft Office Excel 2003, SP 3). Outliers were discarded until good fit of the regression curve with measurements was confirmed by visual inspection. Parameters of the inhibition kinetics were determined by least square minimization of the differences between measured and predicted $\mu_{max}$ values. Employed search algorithm was a quasi-Newton method with linear extrapolation from a tangent vector, as implemented in the solver routine of Microsoft Excel (Microsoft Office Excel 2003, SP 3). The solution with 25 mM showed precipitation and was not analyzed. At 5 mM of copper $\mu_{max}$ was determined to be 0.46 l/h. In the medium containing 10 mM of copper, maximum specific growth rate of $\mu_{max}$=0.33 l/h was found. Fitting the data to the "squared inhibition" kinetics yielded parameters of $\mu°_{max}$=0.58 l/h and a $K_I$ value of $K_I$=11 mM (FIG. 4). Decrease in $\mu_{max}$ with increasing copper (II) concentrations in the medium indicates inhibition of ethanologen yeast PNY 827 Inhibition kinetics were used and fitted parameters predict an $IC_{50}$ value of 11 mM. Data from the samples is seen in Table 3 below.

TABLE 3

Data for control samples and copper-inhibited experiments.

| sample | time | time [min] | time [h] | OD600 | dilution [1:x] | OD600corr [ ] | OD600corr [ ] |
|---|---|---|---|---|---|---|---|
| F1-ctrl-a | | | | | | | |
| 0 | 8:25 | 0 | 0.00 | 0.154 | 1 | 0.087 | |
| 1 | 9:25 | 60 | 1.00 | 0.157 | 1 | 0.090 | |
| 2 | 10:40 | 135 | 2.25 | 0.188 | 1 | 0.121 | 0.121 |
| 3 | 11:40 | 195 | 3.25 | 0.255 | 1 | 0.188 | 0.188 |
| 4 | 12:40 | 255 | 4.25 | 0.372 | 1 | 0.305 | 0.305 |
| 5 | 14:25 | 360 | 6.00 | 0.285 | 5 | 1.102 | 1.102 |
| 6 | 8:05 | 1420 | 23.67 | 0.672 | 20 | 12.157 | |
| F2-ctrl-b | | | | | | | |
| 0 | 8:25 | 0 | 0.00 | 0.154 | 1 | 0.087 | |
| 1 | 9:25 | 60 | 1.00 | 0.153 | 1 | 0.086 | |

TABLE 3-continued

Data for control samples and copper-inhibited experiments.

| sample | time | time [min] | time [h] | OD600 | dilution [1:x] | OD600corr [ ] | OD600corr [ ] |
|---|---|---|---|---|---|---|---|
| 2 | 10:40 | 135 | 2.25 | 0.187 | 1 | 0.120 | 0.120 |
| 3 | 11:40 | 195 | 3.25 | 0.251 | 1 | 0.184 | 0.184 |
| 4 | 12:40 | 255 | 4.25 | 0.371 | 1 | 0.304 | 0.304 |
| 5 | 14:25 | 360 | 6.00 | 0.281 | 5 | 1.082 | 1.082 |
| 6 | 8:05 | 1420 | 23.67 | 0.647 | 20 | 11.657 | |
| | | | | F5-cu-1 | | | |
| 0 | 8:25 | 0 | 0.00 | 0.336 | 1 | 0.097 | |
| 1 | 9:25 | 60 | 1.00 | 0.346 | 1 | 0.107 | 0.107 |
| 2 | 10:40 | 135 | 2.25 | 0.467 | 1 | 0.228 | 0.228 |
| 3 | 11:40 | 195 | 3.25 | 0.538 | 1 | 0.299 | 0.299 |
| 4 | 12:40 | 255 | 4.25 | 0.543 | 1 | 0.304 | |
| 5 | 14:25 | 360 | 6.00 | 0.152 | 5 | 0.265 | |
| 6 | 18:05 | 580 | 9.67 | 0.163 | 5 | 0.320 | |
| 6 | 8:05 | 1420 | 23.67 | 0.171 | 5 | 0.360 | |
| | | | | F6-cu-2 | | | |
| 0 | 8:25 | 0 | 0.00 | 0.389 | 1 | 0.115 | |
| 1 | 9:25 | 60 | 1.00 | 0.399 | 1 | 0.125 | |
| 2 | 10:40 | 135 | 2.25 | 0.401 | 1 | 0.127 | 0.127 |
| 3 | 11:40 | 195 | 3.25 | 0.437 | 1 | 0.163 | 0.163 |
| 4 | 12:40 | 255 | 4.25 | 0.521 | 1 | 0.247 | 0.247 |
| 5 | 14:25 | 360 | 6.00 | 0.158 | 5 | 0.260 | |
| 6 | 18:05 | 580 | 9.67 | 0.166 | 5 | 0.300 | |
| 6 | 8:05 | 1420 | 23.67 | 0.202 | 5 | 0.480 | |
| | | | | F7-cu-3 | | | | precipitation

Copper concentrations in the experiments were:
F1-ctrl-a: 0 mM;
F2-ctrl-b: 0 mM;
F5-cu-1: 5 mM;
F6-cu-2: 10 mM;
F7-cu-3: 25 mM.

Example 11

Inhibition of Ethanologen Yeast PNY 827 by Sulfometuron Methyl

The inhibitory effect of the sulfonylurea sulfometuron methyl on ethanologen yeast PNY 827 was investigated. Therefore a 125 ml aerobic shake flask was prepared with 20 ml SEED medium and inoculated with 1 ml of frozen glycerol stock culture of PNY 827. The culture was inoculated over night at 30° C. and 250 rpm in an Innova Laboratory Shaker (New Brunswick Scientific, Edison, N.J.). Subsequently, a sufficient amount of the seed culture was transferred into shake flasks containing 20 ml of production medium without sulfometuron methyl or addition of sulfometuron methyl at concentrations of 0.11 mM, 0.16 mM and 0.27, to give an initial OD of approximately 0.1. The cultures were incubated at 250 rpm for 24 h in an Innova Laboratory Shaker (New Brunswick Scientific, Edison, N.J.) and samples of about 1 ml for OD determination withdrawn at designated hours. Optical density was measured with an Ultrospec 3000 spectrophotometer (Pharmacia Biotech) at λ=600 nm. In case cell dry weight concentrations were needed, an OD-DW-correlation of 0.33 gDW/OD was applied. Maximum specific growth rates $\mu_{max}$ were determined by applying the exponential regression function of Microsoft Excel (Microsoft Office Excel 2003, SP 3). Outliers were discarded until good fit of the regression curve with measurements was confirmed by visual inspection. Parameters of the inhibition kinetics were determined by least square minimization of the differences between measured and predicted $\mu_{max}$ values. Employed search algorithm was a quasi-Newton method with linear extrapolation from a tangent vector, as implemented in the solver routine of Microsoft Excel (Microsoft Office Excel 2003, SP 3).

At all three applied concentrations of 0.11 mM, 0.16 mM and 0.27 mM of sulfometuron methyl a significant reduction in specific maximum growth rate was found, yielding $\mu_{max}$ values of 0.04 1/h, 0.05 1/h and 0.04 1/h, down from uninhibited maximum specific growth in the experiment of $\mu°_{max}$=0.59 1/h, respectively (5).

Sulfometuron methyl is poorly water soluble, consequently the compound was administered dissolved in DMSO. In order to make sure the observed inhibition did not result from DMSO, DMSO was added only ad 0.14 mM to a culture and a maximum specific growth rate of 0.56 1/h was found. Follow up experiments with DMSO point to a "squared inhibition" with a $K_I$ value of about 16 mM (data not shown). So while DMSO alone seems to have an inhibitory effect on growth, its inhibitory effects at concentrations of 0.06 mM, 0.08 mM and 0.14 mM, as used in the experiments with sulfometuron methyl, can be neglected. Fitting a "hybrid" inhibition kinetics model to the measurements yields values of $\mu°_{max\ 1}$=0.55 1/h and $\mu°_{max\ 2}$=0.04 1/h. Not sufficient data are available for accurate determination of $K_I$, but from the curve shape it can be concluded that the $K_I$ value is significantly below 0.1 mM. The "hybrid" inhibition kinetics model predicts an overall observable $\mu°_{max}$ of 0.59 1/h. Due to the underdetermined $K_I$ value, the $IC_{50}$ value cannot reliably be determined, but it can be concluded that it is significantly lower than 0.1 mM. Data from the samples is seen in Table 4 below.

TABLE 4

Data for control samples and sulfometuron methyl-inhibited experiments. Sulfometuron methyl concentrations in the experiments were: F1-ctrl-a: 0 mM; F2-ctrl-b: 0 mM; F12-sm-1: 0.11 mM; F13-sm-2: 0.16 mM; F14-sm-3: 0.27 mM.

| sample | time | time [min] | time [h] | OD600 | dilution [1:x] | OD600corr [ ] | OD600corr [ ] |
|---|---|---|---|---|---|---|---|
| \multicolumn{8}{c}{F1-ctrl-a} |
| 0 | 8:25 | 0 | 0.00 | 0.154 | 1 | 0.087 | |
| 1 | 9:25 | 60 | 1.00 | 0.157 | 1 | 0.090 | |
| 2 | 10:40 | 135 | 2.25 | 0.188 | 1 | 0.121 | 0.121 |
| 3 | 11:40 | 195 | 3.25 | 0.255 | 1 | 0.188 | 0.188 |
| 4 | 12:40 | 255 | 4.25 | 0.372 | 1 | 0.305 | 0.305 |
| 5 | 14:25 | 360 | 6.00 | 0.285 | 5 | 1.102 | 1.102 |
| 6 | 8:05 | 1420 | 23.67 | 0.672 | 20 | 12.157 | |
| \multicolumn{8}{c}{F2-ctrl-b} |
| 0 | 8:25 | 0 | 0.00 | 0.154 | 1 | 0.087 | |
| 1 | 9:25 | 60 | 1.00 | 0.153 | 1 | 0.086 | |
| 2 | 10:40 | 135 | 2.25 | 0.187 | 1 | 0.120 | 0.120 |
| 3 | 11:40 | 195 | 3.25 | 0.251 | 1 | 0.184 | 0.184 |
| 4 | 12:40 | 255 | 4.25 | 0.371 | 1 | 0.304 | 0.304 |
| 5 | 14:25 | 360 | 6.00 | 0.281 | 5 | 1.082 | 1.082 |
| 6 | 8:05 | 1420 | 23.67 | 0.647 | 20 | 11.657 | |
| \multicolumn{8}{c}{F12-sm-1} |
| 0 | 8:25 | 0 | 0.00 | 0.155 | 1 | 0.088 | |
| 1 | 9:25 | 60 | 1.00 | 0.160 | 1 | 0.093 | 0.093 |
| 2 | 10:40 | 135 | 2.25 | 0.165 | 1 | 0.098 | 0.098 |
| 3 | 11:40 | 195 | 3.25 | 0.170 | 1 | 0.103 | 0.103 |
| 4 | 12:40 | 255 | 4.25 | 0.175 | 1 | 0.108 | 0.108 |
| 5 | 14:25 | 360 | 6.00 | 0.182 | 1 | 0.115 | 0.115 |
| 6 | 17:50 | 565 | 9.42 | 0.222 | 1 | 0.155 | |
| 7 | 8:05 | 1420 | 23.67 | 0.272 | 5 | 1.037 | |
| \multicolumn{8}{c}{F13-sm-2} |
| 0 | 8:25 | 0 | 0.00 | 0.158 | 1 | 0.091 | |
| 1 | 9:25 | 60 | 1.00 | 0.160 | 1 | 0.093 | 0.093 |
| 2 | 10:40 | 135 | 2.25 | 0.166 | 1 | 0.099 | 0.099 |
| 3 | 11:40 | 195 | 3.25 | 0.171 | 1 | 0.104 | 0.104 |
| 4 | 12:40 | 255 | 4.25 | 0.175 | 1 | 0.108 | 0.108 |
| 5 | 14:25 | 360 | 6.00 | 0.184 | 1 | 0.117 | 0.117 |
| 6 | 17:50 | 565 | 9.42 | 0.219 | 1 | 0.152 | |
| 7 | 8:05 | 1420 | 23.67 | 0.467 | 1 | 0.400 | |
| \multicolumn{8}{c}{F14-sm-3} |
| 0 | 8:25 | 0 | 0.00 | 0.154 | 1 | 0.087 | |
| 1 | 9:25 | 60 | 1.00 | 0.157 | 1 | 0.090 | 0.090 |
| 2 | 10:40 | 135 | 2.25 | 0.164 | 1 | 0.097 | 0.097 |
| 3 | 11:40 | 195 | 3.25 | 0.164 | 1 | 0.097 | 0.097 |
| 4 | 12:40 | 255 | 4.25 | 0.166 | 1 | 0.099 | 0.099 |
| 5 | 14:25 | 360 | 6.00 | 0.177 | 1 | 0.110 | 0.110 |
| 6 | 17:50 | 565 | 9.42 | 0.201 | 1 | 0.134 | 0.134 |
| 7 | 8:05 | 1420 | 23.67 | 0.306 | 1 | 0.239 | 0.239 |

Example 12

Inhibition of Ethanologen Yeast PNY 827 by Sulfite

The inhibitory effect of sulfite on ethanologen yeast PNY 827 was investigated. Therefore a 125 ml aerobic shake flask was prepared with 20 ml SEED medium and inoculated with 1 ml of frozen glycerol stock culture of PNY 827. The culture was inoculated over night at 30° C. and 250 rpm in an Innova Laboratory Shaker (New Brunswick Scientific, Edison, N.J.). Subsequently, a sufficient amount of the seed culture was transferred into shake flasks containing 20 ml of production medium without sulfite or addition of sulfite at concentrations of 1 mM, 2 mM, 5 mM, 10 mM, 20 mM and 50 mM, to give an initial OD of approximately 0.1. The cultures were incubated at 250 rpm for 24 h in an Innova Laboratory Shaker (New Brunswick Scientific, Edison, N.J.) and samples of about 1 ml for OD determination withdrawn at designated hours. Optical density was measured with an Ultrospec 3000 spectrophotometer (Pharmacia Biotech) at $\lambda=600$ nm. In case cell dry weight concentrations were needed, an OD-DW-correlation of 0.33 gDW/OD was applied. Maximum specific growth rates $\mu_{max}$ were determined by applying the exponential regression function of Microsoft Excel (Microsoft Office Excel 2003, SP 3). Outliers were discarded until good fit of the regression curve with measurements was confirmed by visual inspection. Parameters of the inhibition kinetics were determined by least square minimization of the differences between measured and predicted $\mu_{max}$ values. Employed search algorithm was a quasi-Newton method with linear extrapolation from a tangent vector, as implemented in the solver routine of Microsoft Excel (Microsoft Office Excel 2003, SP 3).

Figure 6:
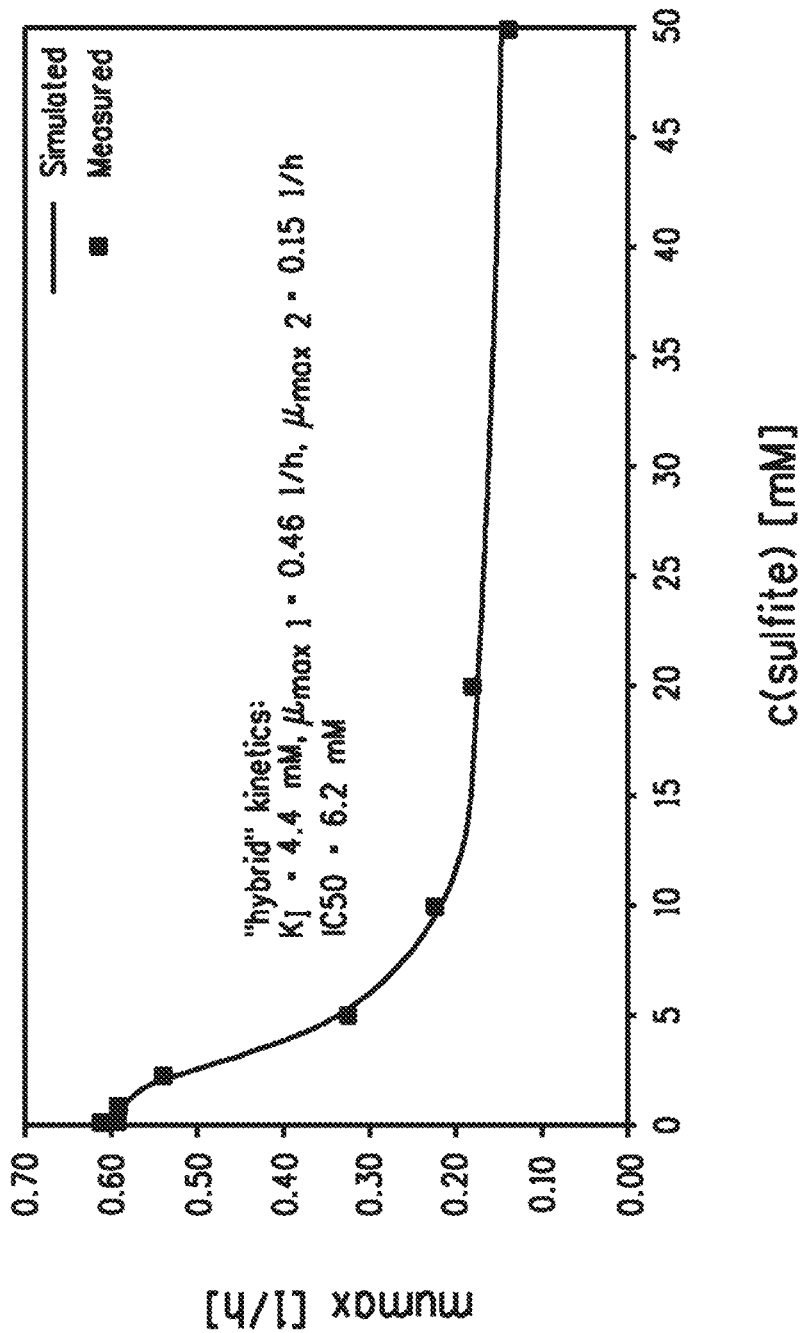
FIG. 6 depicts the μmax of PNY 827 in dependence on concentration of sulfite in the medium.

Sulfite concentrations of 1 mM, 2 mM, 5 mM, 10 mM, 20 mM and 50 mM resulted in maximum specific growth rates of 0.59 1/h, 0.54 1/h, 0.33 1/h, 0.23 1/h, 0.18 1/h and 0.14 1/h, respectively, indicating significant inhibitory effect of sulfite on ethanologen yeast PNY 807. Fitting the measured data to the "hybrid" inhibition kinetics model, values of $\mu°_{max\ 1}=0.46$ 1/h, $\mu°_{max\ 2}=0.15$ 1/h and KI=4.4 mM were determined. The "hybrid" inhibition kinetics model predicts an overall observable $\mu°_{max}=0.61$ 1/h and an IC50 value of 6.2 mM. Measured $\mu_{max}$ values and fitted dependency of $\mu_{max}$ on the concentration of sulfite in the medium is depicted in FIG. 6. Data from the samples is seen in Table 5 below.

TABLE 5

Data for control samples and sulfite-inhibited experiments. Sulfite concentrations in the experiments were: F1-ctrl-a: 0 mM; F2-ctrl-b: 0 mM; F8-su-1: 1 mM; F9-su-2: 2 mM; F10-su-3: 5 mM; F11-su-4: 10 mM; SF12-F1-CtrlA: 0 mM; SF12-F2-ctrlB: 0M; F3-su-1: 20 mM; F4-su-2: 50 mM.

| sample | time | time [min] | time [h] | OD600 | dilution [1:x] | OD600corr [ ] | OD600corr [ ] |
|---|---|---|---|---|---|---|---|
| \multicolumn{8}{c}{F1-ctrl-a} |
| 0 | 8:25 | 0 | 0.00 | 0.154 | 1 | 0.087 | |
| 1 | 9:25 | 60 | 1.00 | 0.157 | 1 | 0.090 | |
| 2 | 10:40 | 135 | 2.25 | 0.188 | 1 | 0.121 | 0.121 |
| 3 | 11:40 | 195 | 3.25 | 0.255 | 1 | 0.188 | 0.188 |
| 4 | 12:40 | 255 | 4.25 | 0.372 | 1 | 0.305 | 0.305 |
| 5 | 14:25 | 360 | 6.00 | 0.285 | 5 | 1.102 | 1.102 |
| 6 | 8:05 | 1420 | 23.67 | 0.672 | 20 | 12.157 | |
| \multicolumn{8}{c}{F2-ctrl-b} |
| 0 | 8:25 | 0 | 0.00 | 0.154 | 1 | 0.087 | |
| 1 | 9:25 | 60 | 1.00 | 0.153 | 1 | 0.086 | |
| 2 | 10:40 | 135 | 2.25 | 0.187 | 1 | 0.120 | 0.120 |
| 3 | 11:40 | 195 | 3.25 | 0.251 | 1 | 0.184 | 0.184 |
| 4 | 12:40 | 255 | 4.25 | 0.371 | 1 | 0.304 | 0.304 |
| 5 | 14:25 | 360 | 6.00 | 0.281 | 5 | 1.082 | 1.082 |
| 6 | 8:05 | 1420 | 23.67 | 0.647 | 20 | 11.657 | |
| \multicolumn{8}{c}{F8-su-1} |
| 0 | 8:25 | 0 | 0.00 | 0.148 | 1 | 0.081 | |
| 1 | 9:25 | 60 | 1.00 | 0.149 | 1 | 0.082 | |
| 2 | 10:40 | 135 | 2.25 | 0.188 | 1 | 0.121 | 0.121 |
| 3 | 11:40 | 195 | 3.25 | 0.252 | 1 | 0.185 | 0.185 |
| 4 | 12:40 | 255 | 4.25 | 0.374 | 1 | 0.307 | 0.307 |
| 5 | 14:25 | 360 | 6.00 | 0.285 | 5 | 1.102 | 1.102 |
| 6 | 8:05 | 1420 | 23.67 | 0.622 | 20 | 11.157 | |
| \multicolumn{8}{c}{F9-su-2} |
| 0 | 8:25 | 0 | 0.00 | 0.154 | 1 | 0.087 | |
| 1 | 9:25 | 60 | 1.00 | 0.153 | 1 | 0.086 | |
| 2 | 10:40 | 135 | 2.25 | 0.187 | 1 | 0.120 | 0.120 |

TABLE 5-continued

Data for control samples and sulfite-inhibited experiments.
Sulfite concentrations in the experiments were: F1-ctrl-a:
0 mM; F2-ctrl-b: 0 mM; F8-su-1: 1 mM; F9-su-2: 2 mM; F10-
su-3: 5 mM; F11-su-4: 10 mM; SF12-F1-CtrlA: 0 mM; SF12-
F2-ctrlB: 0M; F3-su-1: 20 mM; F4-su-2: 50 mM.

| sample | time | time [min] | time [h] | OD600 | dilution [1:x] | OD600corr [ ] | OD600corr [ ] |
|---|---|---|---|---|---|---|---|
| 3 | 11:40 | 195 | 3.25 | 0.240 | 1 | 0.173 | 0.173 |
| 4 | 12:40 | 255 | 4.25 | 0.332 | 1 | 0.265 | 0.265 |
| 5 | 14:25 | 360 | 6.00 | 0.242 | 5 | 0.887 | 0.887 |
| 6 | 8:05 | 1420 | 23.67 | 0.675 | 20 | 12.217 | |
| F10-su-3 | | | | | | | |
| 0 | 8:25 | 0 | 0.00 | 0.155 | 1 | 0.088 | |
| 1 | 9:25 | 60 | 1.00 | 0.157 | 1 | 0.090 | |
| 2 | 10:40 | 135 | 2.25 | 0.183 | 1 | 0.116 | 0.116 |
| 3 | 11:40 | 195 | 3.25 | 0.220 | 1 | 0.153 | 0.153 |
| 4 | 12:40 | 255 | 4.25 | 0.275 | 1 | 0.208 | 0.208 |
| 5 | 14:25 | 360 | 6.00 | 0.459 | 1 | 0.392 | 0.392 |
| 6 | 18:00 | 575 | 9.58 | 0.579 | 5 | 2.572 | |
| 7 | 8:05 | 1420 | 23.67 | 0.650 | 20 | 11.717 | |
| F11-su-4 | | | | | | | |
| 0 | 8:25 | 0 | 0.00 | 0.159 | 1 | 0.092 | |
| 1 | 9:25 | 60 | 1.00 | 0.152 | 1 | 0.085 | 0.085 |
| 2 | 10:40 | 135 | 2.25 | 0.178 | 1 | 0.111 | 0.111 |
| 3 | 11:40 | 195 | 3.25 | 0.207 | 1 | 0.140 | 0.140 |
| 4 | 12:40 | 255 | 4.25 | 0.242 | 1 | 0.175 | 0.175 |
| 5 | 14:25 | 360 | 6.00 | 0.335 | 1 | 0.268 | 0.268 |
| 6 | 18:00 | 575 | 9.58 | 0.285 | 5 | 1.102 | |
| 6 | 8:05 | 1420 | 23.67 | 0.636 | 20 | 11.437 | |
| SF12-F1-Ctrl-A | | | | | | | |
| 0 | 8:55 | 0 | 0.00 | 0.156 | 1 | 0.089 | |
| 1 | 10:25 | 90 | 1.50 | 0.170 | 1 | 0.103 | |
| 2 | 11:35 | 160 | 2.67 | 0.222 | 1 | 0.155 | 0.155 |
| 3 | 12:55 | 240 | 4.00 | 0.350 | 1 | 0.283 | 0.283 |
| 4 | 14:15 | 320 | 5.33 | 0.220 | 5 | 0.777 | 0.777 |
| 6 | 8:30 | 1395 | 23.25 | 0.648 | 20 | 11.677 | |
| SF12-F2-ctrl-B | | | | | | | |
| 0 | 8:55 | 0 | 0.00 | 0.162 | 1 | 0.095 | |
| 1 | 10:25 | 90 | 1.50 | 0.172 | 1 | 0.105 | |
| 2 | 11:35 | 160 | 2.67 | 0.223 | 1 | 0.156 | 0.156 |
| 3 | 12:55 | 240 | 4.00 | 0.354 | 1 | 0.287 | 0.287 |
| 4 | 14:15 | 320 | 5.33 | 0.228 | 5 | 0.817 | 0.817 |
| 5 | 8:30 | 1395 | 23.25 | 0.667 | 20 | 12.057 | |
| F3-su-1 | | | | | | | |
| 0 | 8:55 | 0 | 0.00 | 0.154 | 1 | 0.087 | |
| 1 | 10:25 | 90 | 1.50 | 0.166 | 1 | 0.099 | |
| 2 | 11:35 | 160 | 2.67 | 0.182 | 1 | 0.115 | 0.115 |
| 3 | 12:55 | 240 | 4.00 | 0.217 | 1 | 0.150 | 0.150 |
| 4 | 14:15 | 320 | 5.33 | 0.249 | 1 | 0.182 | 0.182 |
| 5 | 15:40 | 405 | 6.75 | 0.293 | 1 | 0.226 | 0.226 |
| 6 | 18:20 | 565 | 9.42 | 0.463 | 1 | 0.396 | 0.396 |
| 7 | 8:30 | 1395 | 23.25 | 0.549 | 20 | 9.697 | |
| F4-su-2 | | | | | | | |
| 0 | 8:55 | 0 | 0.00 | 0.155 | 1 | 0.088 | |
| 1 | 10:25 | 90 | 1.50 | 0.162 | 1 | 0.095 | |
| 2 | 11:35 | 160 | 2.67 | 0.183 | 1 | 0.116 | 0.116 |
| 3 | 12:55 | 240 | 4.00 | 0.202 | 1 | 0.135 | 0.135 |
| 4 | 14:15 | 320 | 5.33 | 0.228 | 1 | 0.161 | 0.161 |
| 5 | 15:40 | 405 | 6.75 | 0.259 | 1 | 0.192 | 0.192 |
| 6 | 18:20 | 565 | 9.42 | 0.362 | 1 | 0.295 | 0.295 |
| 7 | 8:30 | 1395 | 23.25 | 0.600 | 20 | 10.717 | |

Example 13

Inhibition of Ethanologen Yeast PNY 827 by Formaldehyde

The inhibitory effect of formaldehyde on ethanologen yeast PNY 827 was investigated. Therefore a 125 ml aerobic shake flask was prepared with 20 ml SEED medium and inoculated with 1 ml of frozen glycerol stock culture of PNY 827. The culture was inoculated over night at 30° C. and 250 rpm in an Innova Laboratory Shaker (New Brunswick Scientific, Edison, N.J.). Subsequently, a sufficient amount of the seed culture was transferred into shake flasks containing 20 ml of production medium without formaldehyde or addition of formaldehyde at concentrations of 1 mM, 2 mM, 5 mM and 10 mM, to give an initial OD of approximately 0.1. The cultures were incubated at 250 rpm for 24 h in an Innova Laboratory Shaker (New Brunswick Scientific, Edison, N.J.) and samples of about 1 ml for OD determination withdrawn at designated hours. Optical density was measured with an Ultrospec 3000 spectrophotometer (Pharmacia Biotech) at $\lambda$=600 nm. In case cell dry weight concentrations were needed, an OD-DW-correlation of 0.33 gDW/OD was applied. Maximum specific growth rates $\mu_{max}$ were determined by applying the exponential regression function of Microsoft Excel (Microsoft Office Excel 2003, SP 3). Outliers were discarded until good fit of the regression curve with measurements was confirmed by visual inspection. Parameters of the inhibition kinetics were determined by least square minimization of the differences between measured and predicted $\mu_{max}$ values. Employed search algorithm was a quasi-Newton method with linear extrapolation from a tangent vector, as implemented in the solver routine of Microsoft Excel (Microsoft Office Excel 2003, SP 3).

Figure 7:
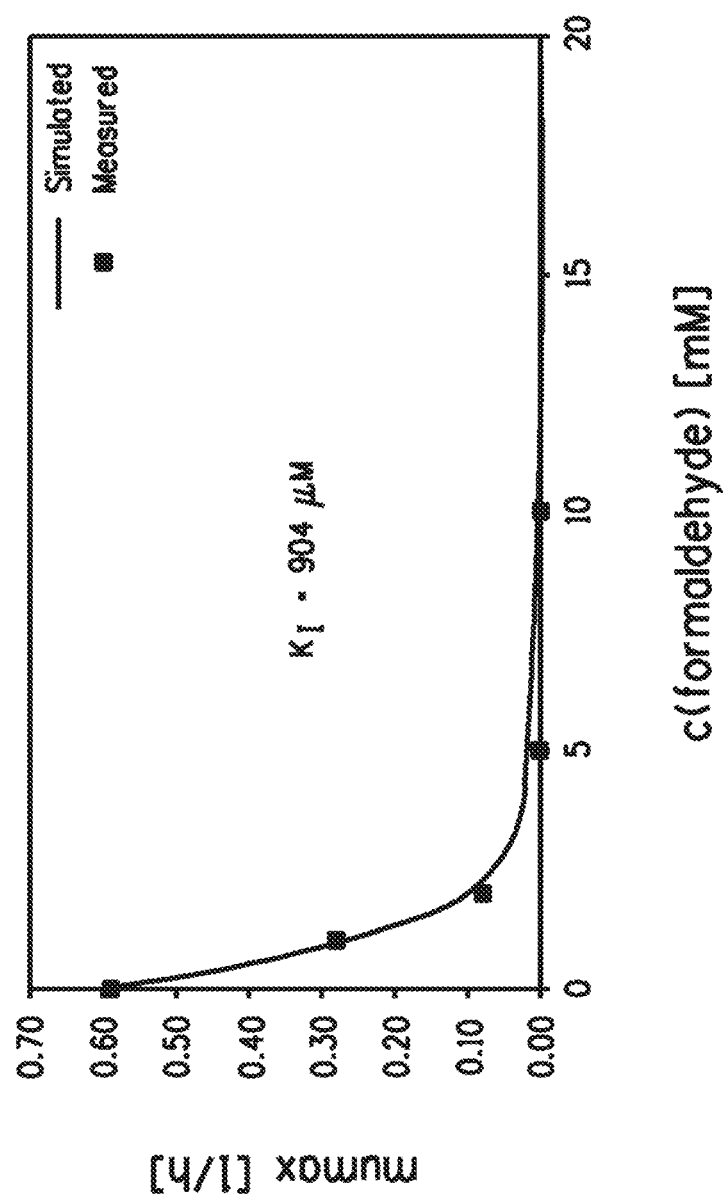
FIG. 7 depicts the μmax of PNY 827 in dependence on concentration of formaldehyde in the medium.

With the investigated formaldehyde concentrations of 1 mM, 2 mM, 5 mM and 10 mM, corresponding maximum specific growth rates of PNY827 were 0.28 l/h, 0.08 l/h, 0.00 l/h (no growth), and 0.00 l/h (no growth), respectively. Mumax values determined without inhibitor addition were 0.59 l/h and 0.59 l/h. Fitting the measured data to the "squared inhibition" kinetics model, a $K_I$ value of $K_I$=904 $\mu$M ($\mu°_{max}$=0.59 l/h) was found, indicating a very strong inhibition of S. cerevisiae by formaldehyde. The derived IC50 value is 0.9 mM. Measured $\mu_{max}$ values and fitted dependency of $\mu_{max}$ on the concentration of formaldehyde in the medium is depicted in FIG. 7. Data from the samples is seen in Table 6 below.

TABLE 6

Data for control samples and formaldehyde-inhibited experiments.
Formaldehyde concentrations in the experiments were: F1-
ctrl-a: 0 mM; F2-ctrl-b: 0 mM; F16-fa-1: 1 mM; F17-fa-2:
2 mM; F18-fa-3: 5 mM; F19-fa-4: 10 mM.

| sample | time | time [min] | time [h] | OD600 | dilution [1:x] | OD600corr [ ] | OD600corr [ ] |
|---|---|---|---|---|---|---|---|
| F1-ctrl-a | | | | | | | |
| 0 | 8:25 | 0 | 0.00 | 0.154 | 1 | 0.087 | |
| 1 | 9:25 | 60 | 1.00 | 0.157 | 1 | 0.090 | |
| 2 | 10:40 | 135 | 2.25 | 0.188 | 1 | 0.121 | 0.121 |
| 3 | 11:40 | 195 | 3.25 | 0.255 | 1 | 0.188 | 0.188 |
| 4 | 12:40 | 255 | 4.25 | 0.372 | 1 | 0.305 | 0.305 |
| 5 | 14:25 | 360 | 6.00 | 0.285 | 5 | 1.102 | 1.102 |
| 6 | 8:05 | 1420 | 23.67 | 0.672 | 20 | 12.157 | |
| F2-ctrl-b | | | | | | | |
| 0 | 8:25 | 0 | 0.00 | 0.154 | 1 | 0.087 | |
| 1 | 9:25 | 60 | 1.00 | 0.153 | 1 | 0.086 | |
| 2 | 10:40 | 135 | 2.25 | 0.187 | 1 | 0.120 | 0.120 |
| 3 | 11:40 | 195 | 3.25 | 0.251 | 1 | 0.184 | 0.184 |
| 4 | 12:40 | 255 | 4.25 | 0.371 | 1 | 0.304 | 0.304 |
| 5 | 14:25 | 360 | 6.00 | 0.281 | 5 | 1.082 | 1.082 |
| 6 | 8:05 | 1420 | 23.67 | 0.647 | 20 | 11.657 | |

TABLE 6-continued

Data for control samples and formaldehyde-inhibited experiments. Formaldehyde concentrations in the experiments were: F1-ctrl-a: 0 mM; F2-ctrl-b: 0 mM; F16-fa-1: 1 mM; F17-fa-2: 2 mM; F18-fa-3: 5 mM; F19-fa-4: 10 mM.

| sample | time | time [min] | time [h] | OD600 | dilution [1:x] | OD600corr [ ] | OD600corr [ ] |
|---|---|---|---|---|---|---|---|
| F16-fa-1 | | | | | | | |
| 0 | 8:35 | 0 | 0.00 | 0.157 | 1 | 0.090 | |
| 1 | 9:35 | 60 | 1.00 | 0.157 | 1 | 0.090 | |
| 2 | 10:50 | 135 | 2.25 | 0.165 | 1 | 0.098 | |
| 3 | 11:50 | 195 | 3.25 | 0.182 | 1 | 0.115 | 0.115 |
| 4 | 12:50 | 255 | 4.25 | 0.206 | 1 | 0.139 | 0.139 |
| 5 | 14:35 | 360 | 6.00 | 0.285 | 1 | 0.218 | 0.218 |
| 6 | 17:40 | 545 | 9.08 | 0.655 | 1 | 0.588 | 0.588 |
| 7 | 8:20 | 1425 | 23.75 | 0.657 | 20 | 11.857 | |
| F17-fa-2 | | | | | | | |
| 0 | 8:35 | 0 | 0.00 | 0.158 | 1 | 0.091 | |
| 1 | 9:35 | 60 | 1.00 | 0.158 | 1 | 0.091 | |
| 2 | 10:50 | 135 | 2.25 | 0.159 | 1 | 0.092 | |
| 3 | 11:50 | 195 | 3.25 | 0.160 | 1 | 0.093 | 0.093 |
| 4 | 12:50 | 255 | 4.25 | 0.165 | 1 | 0.098 | 0.098 |
| 5 | 14:35 | 360 | 6.00 | 0.177 | 1 | 0.110 | 0.110 |
| 6 | 17:40 | 545 | 9.08 | 0.211 | 1 | 0.144 | 0.144 |
| 7 | 8:20 | 1425 | 23.75 | 0.382 | 20 | 6.357 | |
| F18-fa-3 | | | | | | | |
| 0 | 8:35 | 0 | 0.00 | 0.157 | 1 | 0.090 | |
| 1 | 9:35 | 60 | 1.00 | 0.162 | 1 | 0.095 | |
| 2 | 10:50 | 135 | 2.25 | 0.161 | 1 | 0.094 | |
| 3 | 11:50 | 195 | 3.25 | 0.157 | 1 | 0.090 | 0.090 |
| 4 | 12:50 | 255 | 4.25 | 0.155 | 1 | 0.088 | 0.088 |
| 5 | 14:35 | 360 | 6.00 | 0.155 | 1 | 0.088 | 0.088 |
| 6 | 17:40 | 545 | 9.08 | 0.156 | 1 | 0.089 | 0.089 |
| 7 | 8:20 | 1425 | 23.75 | 0.160 | 1 | 0.093 | |
| F19-fa-4 | | | | | | | |
| 0 | 8:35 | 0 | 0.00 | 0.162 | 1 | 0.095 | |
| 1 | 9:35 | 60 | 1.00 | 0.168 | 1 | 0.101 | |
| 2 | 10:50 | 135 | 2.25 | 0.164 | 1 | 0.097 | |
| 3 | 11:50 | 195 | 3.25 | 0.163 | 1 | 0.096 | 0.096 |
| 4 | 12:50 | 255 | 4.25 | 0.160 | 1 | 0.093 | 0.093 |
| 5 | 14:35 | 360 | 6.00 | 0.161 | 1 | 0.094 | 0.094 |
| 6 | 17:40 | 545 | 9.08 | 0.162 | 1 | 0.095 | 0.095 |
| 7 | 8:20 | 1425 | 23.75 | 0.168 | 1 | 0.101 | |

Example 14

Inhibition of Ethanologen Yeast PNY 827 by 4-pyrazolecarboxylic acid

The inhibitory effect of 4-nitrocinnamaldehyde (predominantly trans) on ethanologen yeast PNY 827 was investigated. Therefore a 125 ml aerobic shake flask was prepared with 20 ml SEED medium and inoculated with 1 ml of frozen glycerol stock culture of PNY 827. The culture was inoculated over night at 30° C. and 250 rpm in an Innova Laboratory Shaker (New Brunswick Scientific, Edison, N.J.). Subsequently, a sufficient amount of the seed culture was transferred into shake flasks containing 20 ml of production medium without 4-pyrazolecarboxylic acid or addition of 4-nitrocinnamaldehyde at concentrations of 1 mM and 50 mM, to give an initial OD of approximately 0.1. The cultures were incubated at 250 rpm for 24 h in an Innova Laboratory Shaker (New Brunswick Scientific, Edison, N.J.) and samples of about 1 ml for OD determination withdrawn at designated hours. Optical density was measured with an Ultrospec 3000 spectrophotometer (Pharmacia Biotech) at λ=600 nm. In case cell dry weight concentrations were needed, an OD-DW-correlation of 0.33 gDW/OD was applied. Maximum specific growth rates $\mu_{max}$ were determined by applying the exponential regression function of Microsoft Excel (Microsoft Office Excel 2003, SP 3). Outliers were discarded until good fit of the regression curve with measurements was confirmed by visual inspection. Parameters of the inhibition kinetics were determined by least square minimization of the differences between measured and predicted $\mu_{max}$ values. Employed search algorithm was a quasi-Newton method with linear extrapolation from a tangent vector, as implemented in the solver routine of Microsoft Excel (Microsoft Office Excel 2003, SP 3).

Figure 8:
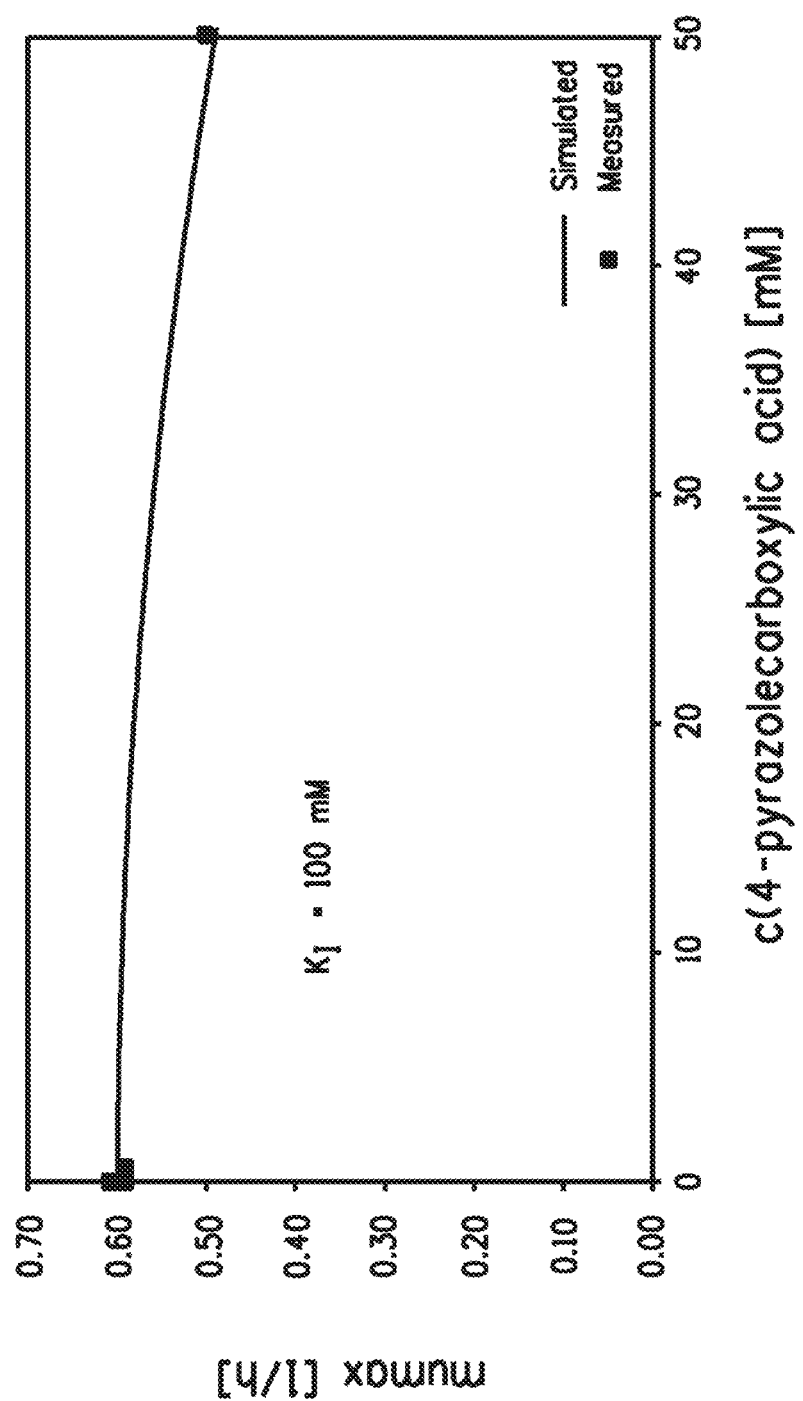
FIG. 8 depicts μmax of PNY 827 in dependence on concentration of 4-pyrazolecarboxylic acid in the medium.
Figure 9:
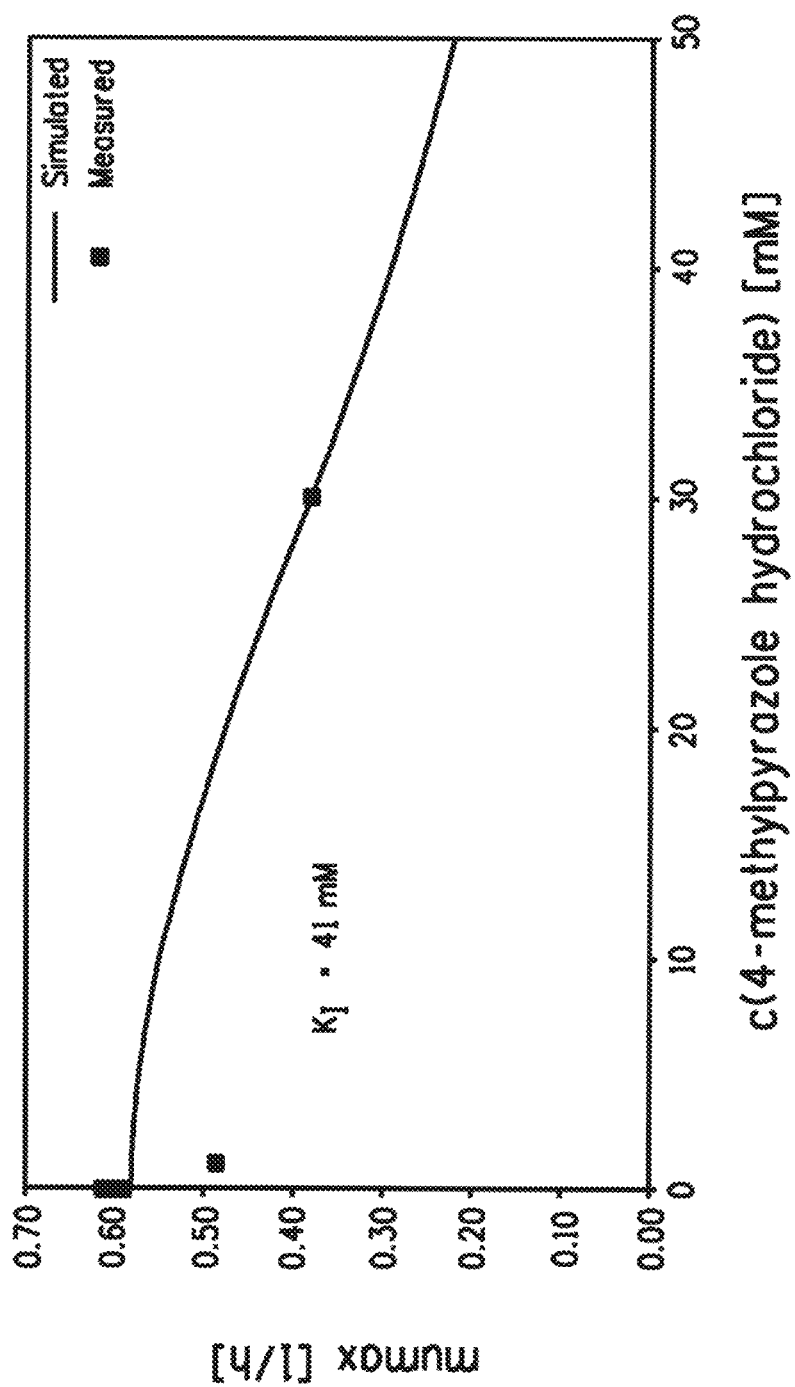
FIG. 9 depicts μmax of PNY 827 in dependence on concentration of 4-methylpyrazole hydrochloride in the medium.

The inhibitory effect of 4-pyrazolecarboxylic acid (PA) was investigated at 1 mM and 50 mM. 4-pyrazolecarboxylic acid was administered as a DMSO solution, resulting in DMSO concentrations in the cell suspension of 14 mM and 704 mM, respectively. Assuming an additive effect of 4-pyrazolecarboxylic acid and DMSO inhibition, observed maximum specific growth rate of the two cultures was corrected by 0.00 l/h and 0.27 l/h due to the effect of DMSO, resulting in 4-pyrazolecarboxylic acid-based mumax values of 0.59 l/h and 0.50 l/h derived from the observed values of 0.59 l/h and 0.23 l/h, respectively. Fitting the data to the "squared inhibition" kinetics (observed maximum specific growth rates without inhibitor addition were 0.59 l/h, 0.59 l/h, 0.60 l/h and 0.62 l/h) yielded parameters of $\mu°_{max}=0.60$ l/h and a KI value of KI=100 mM (FIG. 8), indicating only weak inhibitory effects of 4-pyrazolecarboxylic acid. Data from the samples is seen in Table 7 below.

TABLE 7

Data for control samples and 4-pyrazolecarboxylic acid - inhibited experiments. 4-pyrazolecarboxylic acid concentrations in the experiments were: F1-Ctrl-A: 0 mM; F2-ctrl-B: 0 mM; F12-pa-1: 1 mM; F13-pa-2: 50 mM.

| sample | time | time [min] | time [h] | OD600 | dilution [1:x] | OD600corr [ ] | OD600corr [ ] |
|---|---|---|---|---|---|---|---|
| F1-Ctrl-A | | | | | | | |
| 0 | 8:55 | 0 | 0.00 | 0.156 | 1 | 0.089 | |
| 1 | 10:25 | 90 | 1.50 | 0.170 | 1 | 0.103 | |
| 2 | 11:35 | 160 | 2.67 | 0.222 | 1 | 0.155 | 0.155 |
| 3 | 12:55 | 240 | 4.00 | 0.350 | 1 | 0.283 | 0.283 |
| 4 | 14:15 | 320 | 5.33 | 0.220 | 5 | 0.777 | 0.777 |
| 6 | 8:30 | 1395 | 23.25 | 0.648 | 20 | 11.677 | |
| F2-ctrl-B | | | | | | | |
| 0 | 8:55 | 0 | 0.00 | 0.162 | 1 | 0.095 | |
| 1 | 10:25 | 90 | 1.50 | 0.172 | 1 | 0.105 | |
| 2 | 11:35 | 160 | 2.67 | 0.223 | 1 | 0.156 | 0.156 |
| 3 | 12:55 | 240 | 4.00 | 0.354 | 1 | 0.287 | 0.287 |
| 4 | 14:15 | 320 | 5.33 | 0.228 | 5 | 0.817 | 0.817 |
| 5 | 8:30 | 1395 | 23.25 | 0.667 | 20 | 12.057 | |
| F12-pa-1 | | | | | | | |
| 0 | 8:55 | 0 | 0.00 | 0.156 | 1 | 0.089 | |
| 1 | 10:25 | 90 | 1.50 | 0.172 | 1 | 0.105 | |
| 2 | 11:35 | 160 | 2.67 | 0.227 | 1 | 0.160 | 0.160 |
| 3 | 12:55 | 240 | 4.00 | 0.361 | 1 | 0.294 | 0.294 |
| 4 | 14:15 | 320 | 5.33 | 0.217 | 5 | 0.762 | 0.762 |
| 5 | 8:30 | 1395 | 23.25 | 0.659 | 20 | 11.897 | |
| F13-pa-2 | | | | | | | |
| 0 | 8:55 | 0 | 0.00 | 0.157 | 1 | 0.090 | |
| 1 | 10:25 | 90 | 1.50 | 0.167 | 1 | 0.100 | 0.100 |
| 2 | 11:35 | 160 | 2.67 | 0.192 | 1 | 0.125 | 0.125 |
| 3 | 12:55 | 240 | 4.00 | 0.234 | 1 | 0.167 | 0.167 |
| 4 | 14:15 | 320 | 5.33 | 0.305 | 1 | 0.238 | 0.238 |
| 5 | 3:40 | 405 | 6.75 | 0.405 | 1 | 0.338 | 0.338 |
| 6 | 8:30 | 1395 | 23.25 | 0.655 | 20 | 11.817 | |

Example 15

Inhibition of Ethanologen Yeast PNY 827 by 4-methylpyrazole hydrochloride

The inhibitory effect of 4-methylpyrazole hydrochloride on ethanologen yeast PNY 827 was investigated. Therefore a 125 ml aerobic shake flask was prepared with 20 ml SEED medium and inoculated with 1 ml of frozen glycerol stock culture of PNY 827. The culture was inoculated over night at 30° C. and 250 rpm in an Innova Laboratory Shaker (New Brunswick Scientific, Edison, N.J.). Subsequently, a sufficient amount of the seed culture was transferred into shake flasks containing 20 ml of production medium without 4-methylpyrazole hydrochloride or addition of 4-methylpyrazole hydrochloride at concentrations of 1 mM and 30 mM, to give an initial OD of approximately 0.1. The cultures were incubated at 250 rpm for 24 h in an Innova Laboratory Shaker (New Brunswick Scientific, Edison, N.J.) and samples of about 1 ml for OD determination withdrawn at designated hours. Optical density was measured with an Ultrospec 3000 spectrophotometer (Pharmacia Biotech) at $\lambda=600$ nm. In case cell dry weight concentrations were needed, an OD-DW-correlation of 0.33 gDW/OD was applied. Maximum specific growth rates $\mu_{max}$ were determined by applying the exponential regression function of Microsoft Excel (Microsoft Office Excel 2003, SP 3). Outliers were discarded until good fit of the regression curve with measurements was confirmed by visual inspection. Parameters of the inhibition kinetics were determined by least square minimization of the differences between measured and predicted $\mu_{max}$ values. Employed search algorithm was a quasi-Newton method with linear extrapolation from a tangent vector, as implemented in the solver routine of Microsoft Excel (Microsoft Office Excel 2003, SP 3).

The inhibitory effect of 4-methylpyrazole hydrochloride was investigated at 1 mM and 30 mM. 4-methylpyrazole hydrochloride was administered as a DMSO solution, resulting in DMSO concentrations in the cell suspension of 14 mM and 423 mM, respectively. Assuming an additive effect of 4-methylpyrazole hydrochloride and DMSO inhibition, observed maximum specific growth rate of the two cultures was corrected by 0.00 l/h and 0.14 l/h due to the effect of DMSO, resulting in 4-methylpyrazole hydrochloride-based mumax values of 0.48 l/h and 0.38 l/h derived from the observed values of 0.48 l/h and 0.24 l/h, respectively. Fitting the data to the "squared inhibition" kinetics (observed maximum specific growth rates without inhibitor addition were 0.59 l/h, 0.59 l/h, 0.60 l/h and 0.62 l/h) yielded parameters of $\mu°_{max}=0.58$ l/h and a $K_I$ value of $K_I=41$ mM, indicating inhibitory effects of 4-methylpyrazole hydrochloride (9). Data from the samples is seen in Table 8 below.

TABLE 8

Data for control samples and 4-methylpyrazole hydrochloride acid-inhibited experiments. 4-methylpyrazole hydrochloride acid concentrations in the experiments were: F1-Ctrl-A: 0 mM; F2-ctrl-B: 0 mM; F14-mp-1: 1 mM; F15-mp-2: 30 mM.

| sample | time | time [min] | time [h] | OD600 | dilution [1:x] | OD600corr [ ] | OD600corr [ ] |
|---|---|---|---|---|---|---|---|
| F1-Ctrl-A | | | | | | | |
| 0 | 8:55 | 0 | 0.00 | 0.156 | 1 | 0.089 | |
| 1 | 10:25 | 90 | 1.50 | 0.170 | 1 | 0.103 | |
| 2 | 11:35 | 160 | 2.67 | 0.222 | 1 | 0.155 | 0.155 |
| 3 | 12:55 | 240 | 4.00 | 0.350 | 1 | 0.283 | 0.283 |
| 4 | 14:15 | 320 | 5.33 | 0.220 | 5 | 0.777 | 0.777 |
| 6 | 8:30 | 1395 | 23.25 | 0.648 | 20 | 11.677 | |
| F2-ctrl-B | | | | | | | |
| 0 | 8:55 | 0 | 0.00 | 0.162 | 1 | 0.095 | |
| 1 | 10:25 | 90 | 1.50 | 0.172 | 1 | 0.105 | |
| 2 | 11:35 | 160 | 2.67 | 0.223 | 1 | 0.156 | 0.156 |
| 3 | 12:55 | 240 | 4.00 | 0.354 | 1 | 0.287 | 0.287 |
| 4 | 14:15 | 320 | 5.33 | 0.228 | 5 | 0.817 | 0.817 |
| 5 | 8:30 | 1395 | 23.25 | 0.667 | 20 | 12.057 | |
| F14-mp-1 | | | | | | | |
| 0 | 8:55 | 0 | 0.00 | 0.163 | 1 | 0.096 | |
| 1 | 10:25 | 90 | 1.50 | 0.174 | 1 | 0.107 | 0.107 |
| 2 | 11:35 | 160 | 2.67 | 0.221 | 1 | 0.154 | 0.154 |
| 3 | 12:55 | 240 | 4.00 | 0.342 | 1 | 0.275 | 0.275 |
| 4 | 14:15 | 320 | 5.33 | 0.203 | 5 | 0.692 | 0.692 |
| 5 | 8:30 | 1395 | 23.25 | 0.626 | 20 | 11.237 | |
| F15-mp-2 | | | | | | | |
| 0 | 8:55 | 0 | 0.00 | 0.161 | 1 | 0.094 | |
| 1 | 10:25 | 90 | 1.50 | 0.172 | 1 | 0.105 | 0.105 |
| 2 | 11:35 | 160 | 2.67 | 0.189 | 1 | 0.122 | 0.122 |
| 3 | 12:55 | 240 | 4.00 | 0.237 | 1 | 0.170 | 0.170 |
| 4 | 14:15 | 320 | 5.33 | 0.305 | 1 | 0.238 | 0.238 |
| 5 | 3:40 | 405 | 6.75 | 0.434 | 1 | 0.367 | 0.367 |
| 6 | 8:30 | 1395 | 23.25 | 0.729 | 20 | 13.297 | |

Example 16

Inhibition of Ethanologen Yeast PNY 827 by Glyoxylic Acid

The inhibitory effect of glyoxylic acid on ethanologen yeast PNY 827 was investigated. Therefore a 125 ml aerobic shake flask was prepared with 20 ml SEED medium and inoculated with 1 ml of frozen glycerol stock culture of PNY 827. The culture was inoculated over night at 30° C. and 250 rpm in an Innova Laboratory Shaker (New Brunswick Scientific, Edison, N.J.). Subsequently, a sufficient amount of the seed culture was transferred into shake flasks containing 20 ml of production medium without glyoxylic acid or addition of glyoxylic acid at concentrations of 10 mM and 50 mM, to give an initial OD of approximately 0.1. The cultures were incubated at 250 rpm for 24 h in an Innova Laboratory Shaker (New Brunswick Scientific, Edison, N.J.) and samples of about 1 ml for OD determination withdrawn at designated hours. Optical density was measured with an Ultrospec 3000 spectrophotometer (Pharmacia Biotech) at $\lambda=600$ nm. In case cell dry weight concentrations were needed, an OD-DW-correlation of 0.33 gDW/OD was applied. Maximum specific growth rates $\mu_{max}$ were determined by applying the exponential regression function of Microsoft Excel (Microsoft Office Excel 2003, SP 3). Outliers were discarded until good fit of the regression curve with measurements was confirmed by visual inspection. Parameters of the inhibition kinetics were determined by least square minimization of the differences between measured and predicted $\mu_{max}$ values. Employed search algorithm was a quasi-Newton method with linear extrapolation from a tangent vector, as implemented in the solver routine of Microsoft Excel (Microsoft Office Excel 2003, SP 3).

Figure 10:
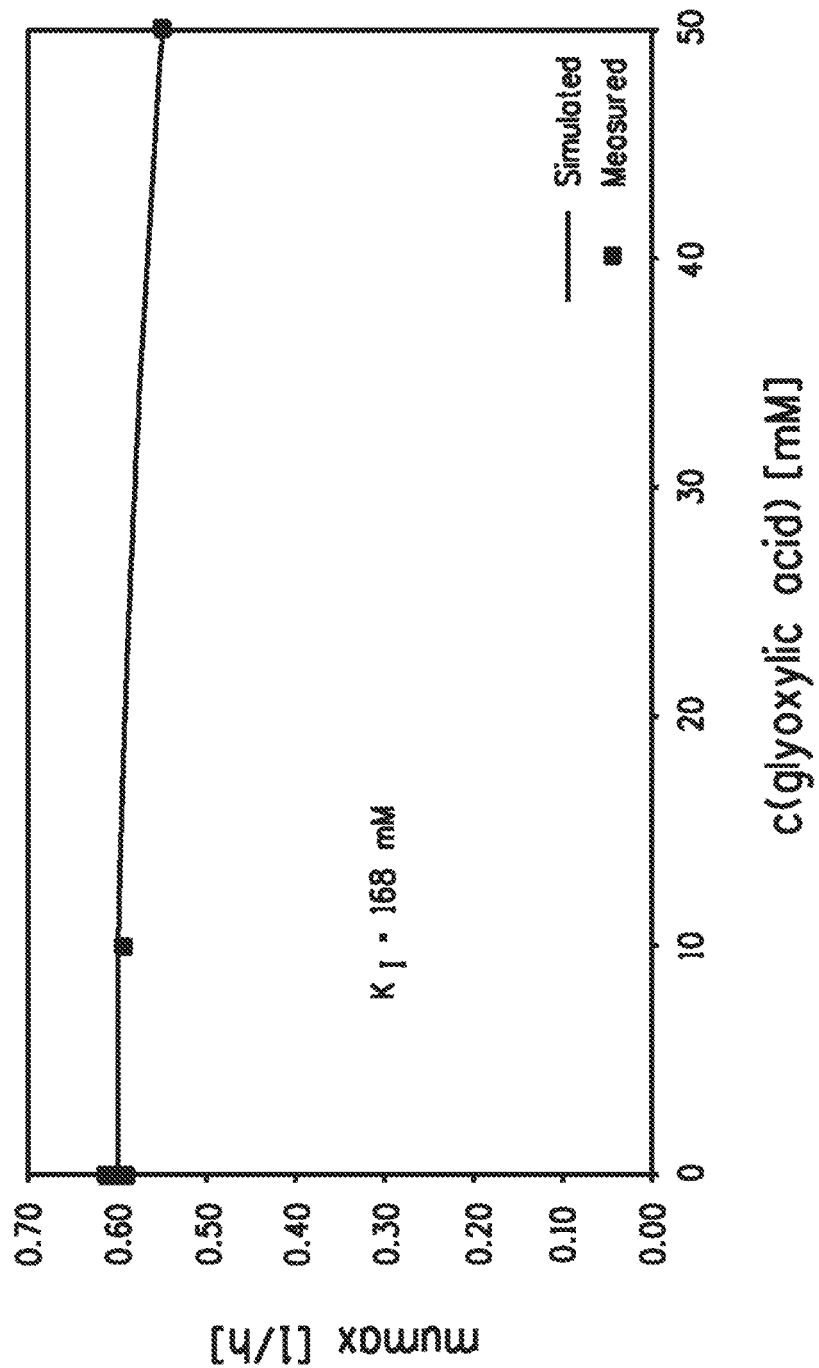
FIG. 10 depicts μmax of PNY 827 in dependence on concentration of glyoxylic acid in the medium.

The inhibitory effect of glyoxylic acid was investigated at 10 mM and 50 mM. At the two concentrations, mumax values of 0.59 l/h and 0.55 l/h were found, respectively. Fitting the data to the "squared inhibition" kinetics (observed maximum specific growth rates without inhibitor addition were 0.59 l/h, 0.59 l/h, 0.60 l/h and 0.62 l/h) yielded parameters of $\mu°_{max}$=0.60 l/h and a $K_I$ value of $K_I$=168 mM, indicating a weak inhibitory effect of extracellular glyoxylic acid on growth of ethanologen yeast (FIG. 10.). Data from the samples is seen in Table 9 below.

TABLE 9

Data for control samples and glyoxylic acid-inhibited experiments. Glyoxylic acid concentrations in the experiments were: F1-Ctrl-A: 0 mM; F2-ctrl-B: 0 mM; F18-ga-1: 10 mM; F19-ga-2: 50 mM.

| sample | time | time [min] | time [h] | OD600 | dilution [1:x] | OD600corr [ ] | OD600corr [ ] |
|---|---|---|---|---|---|---|---|
| F1-Ctrl-A | | | | | | | |
| 0 | 8:55 | 0 | 0.00 | 0.156 | 1 | 0.089 | |
| 1 | 10:25 | 90 | 1.50 | 0.170 | 1 | 0.103 | |
| 2 | 11:35 | 160 | 2.67 | 0.222 | 1 | 0.155 | 0.155 |
| 3 | 12:55 | 240 | 4.00 | 0.350 | 1 | 0.283 | 0.283 |
| 4 | 14:15 | 320 | 5.33 | 0.220 | 5 | 0.777 | 0.777 |
| 6 | 8:30 | 1395 | 23.25 | 0.648 | 20 | 11.677 | |
| F2-ctrl-B | | | | | | | |
| 0 | 8:55 | 0 | 0.00 | 0.162 | 1 | 0.095 | |
| 1 | 10:25 | 90 | 1.50 | 0.172 | 1 | 0.105 | |
| 2 | 11:35 | 160 | 2.67 | 0.223 | 1 | 0.156 | 0.156 |
| 3 | 12:55 | 240 | 4.00 | 0.354 | 1 | 0.287 | 0.287 |
| 4 | 14:15 | 320 | 5.33 | 0.228 | 5 | 0.817 | 0.817 |
| 5 | 8:30 | 1395 | 23.25 | 0.667 | 20 | 12.057 | |
| F18-ga-1 | | | | | | | |
| 0 | 8:55 | 0 | 0.00 | 0.161 | 1 | 0.094 | |
| 1 | 10:25 | 90 | 1.50 | 0.175 | 1 | 0.108 | |
| 2 | 11:35 | 160 | 2.67 | 0.226 | 1 | 0.159 | 0.159 |
| 3 | 12:55 | 240 | 4.00 | 0.361 | 1 | 0.294 | 0.294 |
| 4 | 14:15 | 320 | 5.33 | 0.217 | 5 | 0.762 | 0.762 |
| 5 | 8:30 | 1395 | 23.25 | 0.634 | 20 | 11.397 | |
| F19-ga-2 | | | | | | | |
| 0 | 8:55 | 0 | 0.00 | 0.157 | 1 | 0.090 | |
| 1 | 10:25 | 90 | 1.50 | 0.173 | 1 | 0.106 | |
| 2 | 11:35 | 160 | 2.67 | 0.222 | 1 | 0.155 | 0.155 |
| 3 | 12:55 | 240 | 4.00 | 0.337 | 1 | 0.270 | 0.270 |
| 4 | 14:15 | 320 | 5.33 | 0.199 | 5 | 0.672 | 0.672 |
| 5 | 8:30 | 1395 | 23.25 | 0.655 | 20 | 11.817 | |

Example 17

Inhibition of Ethanologen Yeast PNY 827 by Pyrazole

The inhibitory effect of pyrazole on ethanologen yeast PNY 827 was investigated. Therefore a 125 ml aerobic shake flask was prepared with 20 ml SEED medium and inoculated with 1 ml of frozen glycerol stock culture of PNY 827. The culture was inoculated over night at 30° C. and 250 rpm in an Innova Laboratory Shaker (New Brunswick Scientific, Edison, N.J.). Subsequently, a sufficient amount of the seed culture was transferred into shake flasks containing 20 ml of production medium without pyrazole or addition of pyrazole at concentrations of 1 mM, 5 mM, 10 mM, 25 mM and 50 mM, to give an initial OD of approximately 0.1. The cultures were incubated at 250 rpm for 24 h in an Innova Laboratory Shaker (New Brunswick Scientific, Edison, N.J.) and samples of about 1 ml for OD determination withdrawn at designated hours. Optical density was measured with an Ultrospec 3000 spectrophotometer (Pharmacia Biotech) at λ=600 nm. In case cell dry weight concentrations were needed, an OD-DW-correlation of 0.33 gDW/OD was applied. Maximum specific growth rates $\mu_{max}$ were determined by applying the exponential regression function of Microsoft Excel (Microsoft Office Excel 2003, SP 3). Outliers were discarded until good fit of the regression curve with measurements was confirmed by visual inspection. Parameters of the inhibition kinetics were determined by least square minimization of the differences between measured and predicted $\mu_{max}$ values. Employed search algorithm was a quasi-Newton method with linear extrapolation from a tangent vector, as implemented in the solver routine of Microsoft Excel (Microsoft Office Excel 2003, SP 3).

Figure 11:
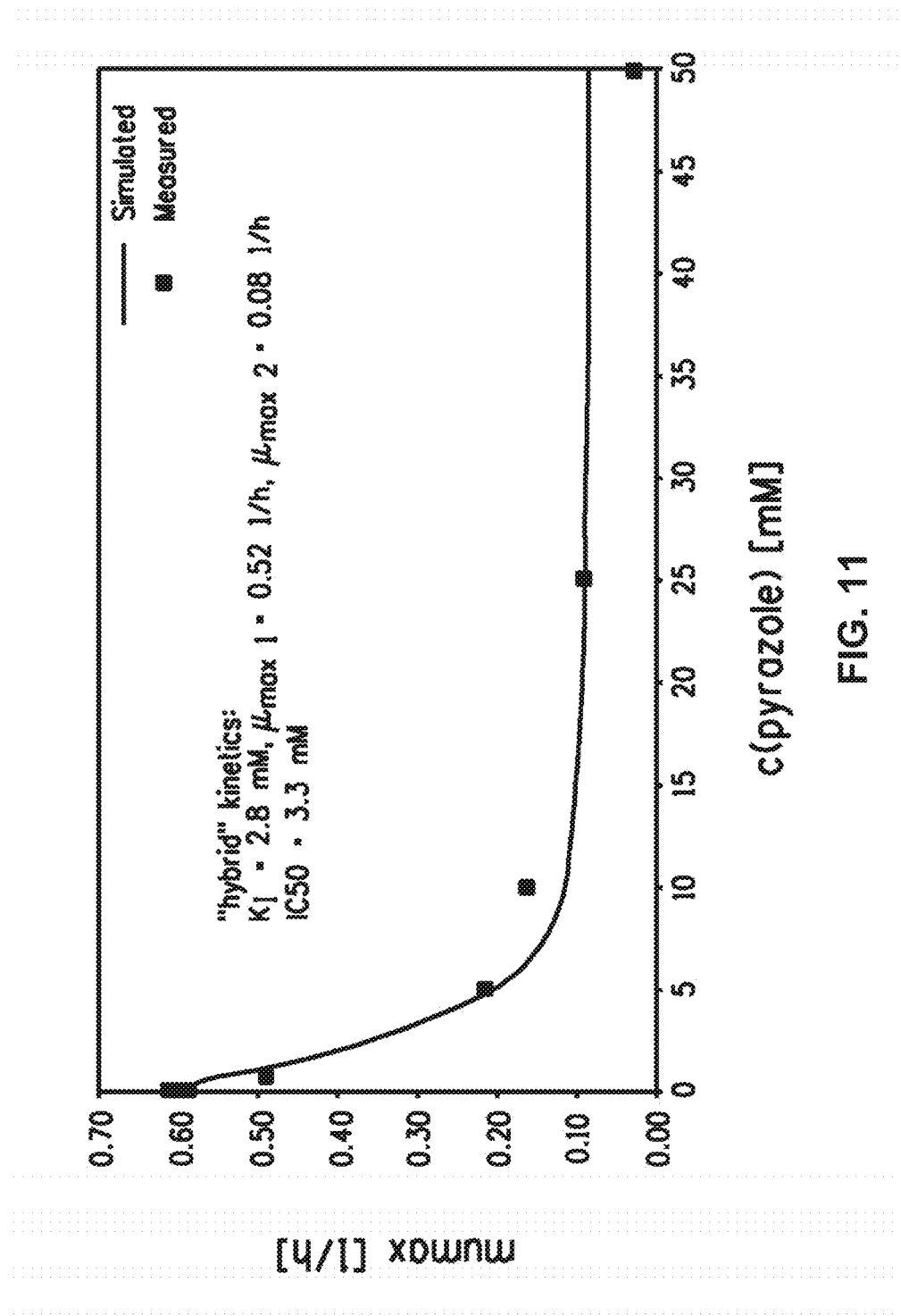
FIG. 11 depicts μmax of PNY 827 in dependence on concentration of pyrazole in the medium.

Pyrazole concentrations of 1 mM, 5 mM, 10 mM, 25 mM and 50 mM were tested, resulting in maximum specific growth rates of 0.54 l/h, 0.21 l/h, 0.12 l/h, 0.09 l/h and 0.08 l/h. Mumax values determined without inhibitor addition were 0.59 l/h, 0.59 l/h, 0.60 l/h, 0.62 l/h, 0.61 l/h and 0.62 l/h, respectively. Inhibitory effect of pyrazole on growth was best described by the hybrid growth model. If fitted to the "hybrid" inhibition kinetics model, values of $\mu°_{max\ 1}$=0.52 l/h, $\mu°_{max\ 2}$=0.08 l/h and $K_I$=2.8 mM were determined. The "hybrid" inhibition kinetics model predicts an overall observable $\mu°_{max}$=0.60 l/h and an $IC_{50}$ (inhibitor concentration with a specific growth rate of 50% $\mu°_{max}$) value of 3.3 mM. Measured $\mu_{max}$ values and fitted dependency of $\mu_{max}$ on the concentration of pyrazole in the medium is depicted in FIG. 11. Data from the samples is seen in Table 10 below.

TABLE 10

Data for control samples and pyrazole-inhibited experiments. Pyrazole concentrations in the experiments were: SF12-F1-Ctrl-A: 0 mM; SF12-F2-ctrl-B: 0 mM; F16-py-1: 1 mM; F17-py-2: 50 mM; F1-ctrl-A: 0 mM; F2-ctrl-B: 0 mM; F8-Py-5: 5 mM; F9-Py-10: 10 mM; F10-Py-25: 25 mM.

| sample | time | time [min] | time [h] | OD600 | dilution [1:x] | OD600corr [ ] | OD600corr [ ] |
|---|---|---|---|---|---|---|---|
| SF12-F1-Ctrl-A | | | | | | | |
| 0 | 8:55 | 0 | 0.00 | 0.156 | 1 | 0.089 | |
| 1 | 10:25 | 90 | 1.50 | 0.170 | 1 | 0.103 | |
| 2 | 11:35 | 160 | 2.67 | 0.222 | 1 | 0.155 | 0.155 |
| 3 | 12:55 | 240 | 4.00 | 0.350 | 1 | 0.283 | 0.283 |
| 4 | 14:15 | 320 | 5.33 | 0.220 | 5 | 0.777 | 0.777 |
| 6 | 8:30 | 1395 | 23.25 | 0.648 | 20 | 11.677 | |
| SF12-F2-ctrl-B | | | | | | | |
| 0 | 8:55 | 0 | 0.00 | 0.162 | 1 | 0.095 | |
| 1 | 10:25 | 90 | 1.50 | 0.172 | 1 | 0.105 | |
| 2 | 11:35 | 160 | 2.67 | 0.223 | 1 | 0.156 | 0.156 |
| 3 | 12:55 | 240 | 4.00 | 0.354 | 1 | 0.287 | 0.287 |
| 4 | 14:15 | 320 | 5.33 | 0.228 | 5 | 0.817 | 0.817 |
| 5 | 8:30 | 1395 | 23.25 | 0.667 | 20 | 12.057 | |
| F16-py-1 | | | | | | | |
| 0 | 8:55 | 0 | 0.00 | 0.155 | 1 | 0.088 | |
| 1 | 10:25 | 90 | 1.50 | 0.167 | 1 | 0.100 | |
| 2 | 11:35 | 160 | 2.67 | 0.199 | 1 | 0.132 | 0.132 |
| 3 | 12:55 | 240 | 4.00 | 0.277 | 1 | 0.210 | 0.210 |
| 4 | 14:15 | 320 | 5.33 | 0.444 | 1 | 0.377 | 0.377 |
| 5 | 3:40 | 405 | 6.75 | 0.262 | 5 | 0.987 | 0.987 |
| 6 | 8:30 | 1395 | 23.25 | 0.645 | 20 | 11.617 | |

TABLE 10-continued

Data for control samples and pyrazole-inhibited experiments.
Pyrazole concentrations in the experiments were: SF12-
F1-Ctrl-A: 0 mM; SF12-F2-ctrl-B: 0 mM; F16-py-1: 1 mM;
F17-py-2: 50 mM; F1-ctrl-A: 0 mM; F2-ctrl-B: 0 mM; F8-
Py-5: 5 mM; F9-Py-10: 10 mM; F10-Py-25: 25 mM.

| sample | time | time [min] | time [h] | OD600 | dilution [1:x] | OD600corr [ ] | OD600corr [ ] |
|---|---|---|---|---|---|---|---|
| F17-py-2 | | | | | | | |
| 0 | 8:55 | 0 | 0.00 | 0.164 | 1 | 0.097 | |
| 1 | 10:25 | 90 | 1.50 | 0.166 | 1 | 0.099 | 0.099 |
| 2 | 11:35 | 160 | 2.67 | 0.169 | 1 | 0.102 | 0.102 |
| 3 | 12:55 | 240 | 4.00 | 0.175 | 1 | 0.108 | 0.108 |
| 4 | 14:15 | 320 | 5.33 | 0.186 | 1 | 0.119 | 0.119 |
| 5 | 15:40 | 405 | 6.75 | 0.190 | 1 | 0.123 | 0.123 |
| 6 | 18:20 | 565 | 9.42 | 0.209 | 1 | 0.142 | 0.142 |
| 7 | 8:30 | 1395 | 23.25 | 0.302 | 1 | 0.235 | 0.235 |
| 0 | 8:55 | 0 | 0.00 | 0.164 | 1 | 0.097 | |
| 1 | 10:25 | 90 | 1.50 | 0.166 | 1 | 0.099 | 0.099 |
| 2 | 11:35 | 160 | 2.67 | 0.169 | 1 | 0.102 | 0.102 |
| 3 | 12:55 | 240 | 4.00 | 0.175 | 1 | 0.108 | 0.108 |
| 4 | 14:15 | 320 | 5.33 | 0.186 | 1 | 0.119 | 0.119 |
| 5 | 15:40 | 405 | 6.75 | 0.190 | 1 | 0.123 | 0.123 |
| 6 | 18:20 | 565 | 9.42 | 0.209 | 1 | 0.142 | 0.142 |
| 7 | 8:30 | 1395 | 23.25 | 0.302 | 1 | 0.235 | 0.235 |
| 0 | 8:55 | 0 | 0.00 | 0.164 | 1 | 0.097 | |
| 1 | 10:25 | 90 | 1.50 | 0.166 | 1 | 0.099 | 0.099 |
| 2 | 11:35 | 160 | 2.67 | 0.169 | 1 | 0.102 | 0.102 |
| 3 | 12:55 | 240 | 4.00 | 0.175 | 1 | 0.108 | 0.108 |
| 4 | 14:15 | 320 | 5.33 | 0.186 | 1 | 0.119 | 0.119 |
| 5 | 15:40 | 405 | 6.75 | 0.190 | 1 | 0.123 | 0.123 |
| 6 | 18:20 | 565 | 9.42 | 0.209 | 1 | 0.142 | 0.142 |
| 7 | 8:30 | 1395 | 23.25 | 0.302 | 1 | 0.235 | 0.235 |
| F1-ctrl-A | | | | | | | |
| 0 | 8:15 | 0 | 0.00 | 0.160 | 1 | 0.093 | |
| 1 | 9:45 | 90 | 1.50 | 0.169 | 1 | 0.102 | |
| 2 | 11:05 | 170 | 2.83 | 0.229 | 1 | 0.162 | 0.162 |
| 3 | 12:20 | 245 | 4.08 | 0.368 | 1 | 0.301 | 0.301 |
| 4 | 13:35 | 320 | 5.33 | 0.215 | 5 | 0.752 | 0.752 |
| 6 | 8:30 | 1455 | 24.25 | 0.644 | 20 | 11.597 | |
| F2-ctrl-B | | | | | | | |
| 0 | 8:15 | 0 | 0.00 | 0.159 | 1 | 0.092 | |
| 1 | 9:45 | 90 | 1.50 | 0.168 | 1 | 0.101 | |
| 2 | 11:05 | 170 | 2.83 | 0.228 | 1 | 0.161 | 0.161 |
| 3 | 12:20 | 245 | 4.08 | 0.372 | 1 | 0.305 | 0.305 |
| 4 | 13:35 | 320 | 5.33 | 0.215 | 5 | 0.752 | 0.752 |
| 5 | 8:30 | 1455 | 24.25 | 0.652 | 20 | 11.757 | |
| F8-Py-5 | | | | | | | |
| 0 | 8:15 | 0 | 0.00 | 0.163 | 1 | 0.096 | |
| 1 | 9:45 | 90 | 1.50 | 0.162 | 1 | 0.095 | 0.095 |
| 2 | 11:05 | 170 | 2.83 | 0.177 | 1 | 0.110 | 0.110 |
| 3 | 12:20 | 245 | 4.08 | 0.210 | 1 | 0.143 | 0.143 |
| 4 | 13:35 | 320 | 5.33 | 0.256 | 1 | 0.189 | 0.189 |
| 5 | 3:00 | 405 | 6.75 | 0.362 | 1 | 0.295 | 0.295 |
| 6 | 8:30 | 1455 | 24.25 | 0.551 | 20 | 9.737 | |
| F9-Py-10 | | | | | | | |
| 0 | 8:15 | 0 | 0.00 | 0.164 | 1 | 0.097 | |
| 1 | 9:45 | 90 | 1.50 | 0.166 | 1 | 0.099 | 0.099 |
| 2 | 11:05 | 170 | 2.83 | 0.181 | 1 | 0.114 | 0.114 |
| 3 | 12:20 | 245 | 4.08 | 0.205 | 1 | 0.138 | 0.138 |
| 4 | 13:35 | 320 | 5.33 | 0.238 | 1 | 0.171 | 0.171 |
| 5 | 3:00 | 405 | 6.75 | 0.289 | 1 | 0.222 | 0.222 |
| | 8:30 | 1455 | 24.25 | 0.475 | 20 | 8.217 | |
| F10-Py-25 | | | | | | | |
| 0 | 8:15 | 0 | 0.00 | 0.162 | 1 | 0.095 | |
| 1 | 9:45 | 90 | 1.50 | 0.159 | 1 | 0.092 | 0.092 |
| 2 | 11:05 | 170 | 2.83 | 0.167 | 1 | 0.100 | 0.100 |
| 3 | 12:20 | 245 | 4.08 | 0.181 | 1 | 0.114 | 0.114 |
| 4 | 13:35 | 320 | 5.33 | 0.194 | 1 | 0.127 | 0.127 |
| 5 | 3:00 | 405 | 6.75 | 0.211 | 1 | 0.144 | 0.144 |
| | 8:30 | 1455 | 24.25 | 0.374 | 20 | 6.197 | |

Example 18

Inhibition of Ethanologen Yeast PNY 827 by Cinnamaldehyde

The inhibitory effect of cinnamaldehyde on ethanologen yeast PNY 827 was investigated. Therefore a 125 ml aerobic shake flask was prepared with 20 ml SEED medium and inoculated with 1 ml of frozen glycerol stock culture of PNY 827. The culture was inoculated over night at 30° C. and 250 rpm in an Innova Laboratory Shaker (New Brunswick Scientific, Edison, N.J.). Subsequently, a sufficient amount of the seed culture was transferred into shake flasks containing 20 ml of production medium without cinnamaldehyde or addition of cinnamaldehyde at concentrations of 200 mM, 100 mM, 50 mM, 25 mM, 10 mM, 1 mM, 0.1 mM, 0.01 mM and 0.001 mM, to give an initial OD of approximately 0.1. The cultures were incubated at 250 rpm for 24 h in an Innova Laboratory Shaker (New Brunswick Scientific, Edison, N.J.) and samples of about 1 ml for OD determination withdrawn at designated hours. Optical density was measured with an Ultrospec 3000 spectrophotometer (Pharmacia Biotech) at $\lambda=600$ nm. In case cell dry weight concentrations were needed, an OD-DW-correlation of 0.33 gDW/OD was applied. Maximum specific growth rates $\mu_{max}$ were determined by applying the exponential regression function of Microsoft Excel (Microsoft Office Excel 2003, SP 3). Outliers were discarded until good fit of the regression curve with measurements was confirmed by visual inspection. Parameters of the inhibition kinetics were determined by least square minimization of the differences between measured and predicted $\mu_{max}$ values. Employed search algorithm was a quasi-Newton method with linear extrapolation from a tangent vector, as implemented in the solver routine of Microsoft Excel (Microsoft Office Excel 2003, SP 3).

Figure 12:
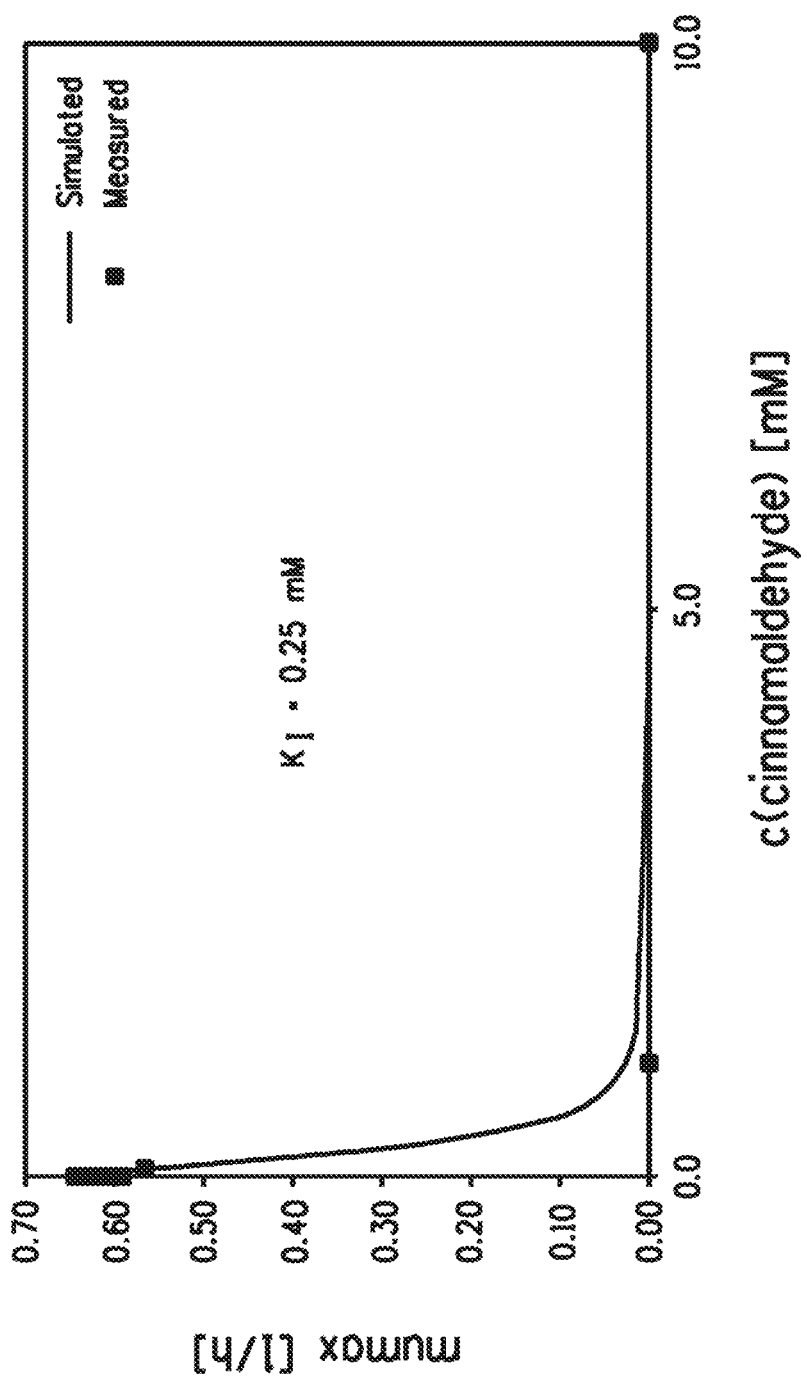
FIG. 12 depicts μmax of PNY 827 in dependence on concentration of cinnamaldehyde in the medium.

The inhibitory effect of cinnamaldehyde (CA) was investigated at 200 mM, 100 mM, 50 mM, 25 mM, 10 mM, 1 mM, 0.1 mM, 0.01 mM and 0.001 mM. For generating the concentrations of 0.1 mM, 0.01 mM and 0.001 mM, cinnamaldehyde was diluted with DMSO, resulting in DMSO concentrations in the cell suspension of 0.7 mM, 7 mM and 70 mM of DMSO, respectively. Assuming an additive effect of cinnamaldehyde and DMSO inhibition, observed maximum specific growth rates of the two cultures were corrected by 0.000 l/h, 0.000 l/h and 0.005 l/h due to the effect of DMSO, resulting in cinnamaldehyde-based mumax values of 0.64 l/h, 0.63 l/h and 0.55 l/h derived from the observed values of 0.64 l/h, 0.63 l/h and 0.55 l/h, respectively. At all the other concentrations, no DMSO was used in the stock solution of cinnamaldehyde. However, in none of the non-DMSO experiments any cell growth was observed. Fitting the data to the "squared inhibition" kinetics (observed maximum specific growth rates without inhibitor addition were 0.59 l/h, 0.59 l/h, 0.60 l/h, 0.62 l/h, 0.62 l/h and 0.62 l/h) yielded parameters of $\mu°_{max}=0.62$ l/h and a $K_I$ value of $K_I=0.25$ mM (FIG. 12). These findings indicate strong inhibition of growth of PNY 827 by trans-cinnamaldehyde with a derived IC50 of 0.25 mM. Data from the samples is seen in Table 11 below.

TABLE 11

Data for control samples and cinnamaldehyde-inhibited experiments. Cinnamaldehyde concentrations in the experiments were: SF12-F1-Ctrl-A: 0 mM; SF12-F2-ctrl-B: 0 mM; F7-ca-1: 50 mM; F8-ca-2: 100 mM; F9-ca-3: 200 mM; SF13-F1-ctrl-A: 0 mM; SF13-F2-ctrl-B: 0 mM; F3-Ca-1: 1 mM; F4-Ca-10: 10 mM; F5-Ca-25: 25 mM; F1-Ctrl-A: 0 mM; F2-ctrl-B: 0 mM; F3-Ca-a: 0.001 mM; F4-Ca-b: 0.01 mM; F5-Ca-c: 0.1 mM.

| sample | time | time [min] | time [h] | OD600 | dilution [1:x] | OD600corr [ ] | OD600corr [ ] |
|---|---|---|---|---|---|---|---|
| SF12-F1-Ctrl-A | | | | | | | |
| 0 | 8:55 | 0 | 0.00 | 0.156 | 1 | 0.089 | |
| 1 | 10:25 | 90 | 1.50 | 0.170 | 1 | 0.103 | |
| 2 | 11:35 | 160 | 2.67 | 0.222 | 1 | 0.155 | 0.155 |
| 3 | 12:55 | 240 | 4.00 | 0.350 | 1 | 0.283 | 0.283 |
| 4 | 14:15 | 320 | 5.33 | 0.220 | 5 | 0.777 | 0.777 |
| 6 | 8:30 | 1395 | 23.25 | 0.648 | 20 | 11.677 | |
| SF12-F2-ctrl-B | | | | | | | |
| 0 | 8:55 | 0 | 0.00 | 0.162 | 1 | 0.095 | |
| 1 | 10:25 | 90 | 1.50 | 0.172 | 1 | 0.105 | |
| 2 | 11:35 | 160 | 2.67 | 0.223 | 1 | 0.156 | 0.156 |
| 3 | 12:55 | 240 | 4.00 | 0.354 | 1 | 0.287 | 0.287 |
| 4 | 14:15 | 320 | 5.33 | 0.228 | 5 | 0.817 | 0.817 |
| 5 | 8:30 | 1395 | 23.25 | 0.667 | 20 | 12.057 | |
| F7-ca-1 | | | | | | | |
| 0 | 8:55 | 0 | 0.00 | 0.167 | 1 | 0.100 | |
| 1 | 10:25 | 90 | 1.50 | 0.168 | 1 | 0.101 | 0.101 |
| 2 | 11:35 | 160 | 2.67 | 0.172 | 1 | 0.105 | 0.105 |
| 3 | 12:55 | 240 | 4.00 | 0.171 | 1 | 0.104 | 0.104 |
| 4 | 14:15 | 320 | 5.33 | 0.171 | 1 | 0.104 | |
| 5 | 8:30 | 1395 | 23.25 | 0.144 | 1 | 0.077 | |
| F8-ca-2 | | | | | | | |
| 0 | 8:55 | 0 | 0.00 | 0.178 | 1 | 0.111 | |
| 1 | 10:25 | 90 | 1.50 | 0.179 | 1 | 0.112 | 0.112 |
| 2 | 11:35 | 160 | 2.67 | 0.175 | 1 | 0.108 | 0.108 |
| 3 | 12:55 | 240 | 4.00 | 0.174 | 1 | 0.107 | 0.107 |
| 4 | 14:15 | 320 | 5.33 | 0.170 | 1 | 0.103 | 0.103 |
| 5 | 8:30 | 1395 | 23.25 | 0.136 | 1 | 0.069 | |
| F9-ca-3 | | | | | | | |
| 0 | 8:55 | 0 | 0.00 | 0.175 | 1 | 0.108 | |
| 1 | 10:25 | 90 | 1.50 | 0.179 | 1 | 0.112 | 0.112 |
| 2 | 11:35 | 160 | 2.67 | 0.173 | 1 | 0.106 | 0.106 |
| 3 | 12:55 | 240 | 4.00 | 0.169 | 1 | 0.102 | 0.102 |
| 4 | 14:15 | 320 | 5.33 | 0.160 | 1 | 0.093 | 0.093 |
| 5 | 8:30 | 1395 | 23.25 | 0.122 | 1 | 0.055 | |
| SF13-F1-ctrl-A | | | | | | | |
| 0 | 8:15 | 0 | 0.00 | 0.160 | 1 | 0.093 | |
| 1 | 9:45 | 90 | 1.50 | 0.169 | 1 | 0.102 | |
| 2 | 11:05 | 170 | 2.83 | 0.229 | 1 | 0.162 | 0.162 |
| 3 | 12:20 | 245 | 4.08 | 0.368 | 1 | 0.301 | 0.301 |
| 4 | 13:35 | 320 | 5.33 | 0.215 | 5 | 0.752 | 0.752 |
| 6 | 8:30 | 1455 | 24.25 | 0.644 | 20 | 11.597 | |
| SF13 - F2-ctrl-B | | | | | | | |
| 0 | 8:15 | 0 | 0.00 | 0.159 | 1 | 0.092 | |
| 1 | 9:45 | 90 | 1.50 | 0.168 | 1 | 0.101 | |
| 2 | 11:05 | 170 | 2.83 | 0.228 | 1 | 0.161 | 0.161 |
| 3 | 12:20 | 245 | 4.08 | 0.372 | 1 | 0.305 | 0.305 |
| 4 | 13:35 | 320 | 5.33 | 0.215 | 5 | 0.752 | 0.752 |
| 5 | 8:30 | 1455 | 24.25 | 0.652 | 20 | 11.757 | |
| F3-Ca-1 | | | | | | | |
| 0 | 8:15 | 0 | 0.00 | 0.165 | 1 | 0.098 | |
| 1 | 9:45 | 90 | 1.50 | 0.164 | 1 | 0.097 | 0.097 |
| 2 | 11:05 | 170 | 2.83 | 0.165 | 1 | 0.098 | 0.098 |
| 3 | 12:20 | 245 | 4.08 | 0.167 | 1 | 0.100 | 0.100 |
| 4 | 13:35 | 320 | 5.33 | 0.167 | 1 | 0.100 | 0.100 |
| 5 | 8:30 | 1455 | 24.25 | 0.167 | 1 | 0.100 | 0.100 |
| F4-Ca-10 | | | | | | | |
| 0 | 8:15 | 0 | 0.00 | 0.167 | 1 | 0.100 | |
| 1 | 9:45 | 90 | 1.50 | 0.169 | 1 | 0.102 | |
| 2 | 11:05 | 170 | 2.83 | 0.170 | 1 | 0.103 | 0.103 |
| 3 | 12:20 | 245 | 4.08 | 0.174 | 1 | 0.107 | 0.107 |
| 4 | 13:35 | 320 | 5.33 | 0.172 | 1 | 0.105 | 0.105 |
| 5 | 8:30 | 1455 | 24.25 | 0.141 | 1 | 0.074 | 0.074 |
| F5-Ca-25 | | | | | | | |
| 0 | 8:15 | 0 | 0.00 | 0.171 | 1 | 0.104 | |
| 1 | 9:45 | 90 | 1.50 | 0.173 | 1 | 0.106 | 0.106 |
| 2 | 11:05 | 170 | 2.83 | 0.172 | 1 | 0.105 | 0.105 |
| 3 | 12:20 | 245 | 4.08 | 0.174 | 1 | 0.107 | 0.107 |
| 4 | 13:35 | 320 | 5.33 | 0.168 | 1 | 0.101 | 0.101 |
| 5 | 8:30 | 1455 | 24.25 | 0.140 | 1 | 0.073 | 0.073 |
| F1-Ctrl-A | | | | | | | |
| 0 | 8:25 | 0 | 0.00 | 0.167 | 1 | 0.100 | |
| 1 | 9:55 | 90 | 1.50 | 0.190 | 1 | 0.123 | |
| 2 | 11:15 | 170 | 2.83 | 0.264 | 1 | 0.197 | 0.197 |
| 3 | 12:35 | 250 | 4.17 | 0.452 | 1 | 0.385 | 0.385 |
| 4 | 13:40 | 315 | 5.25 | 0.246 | 5 | 0.907 | 0.907 |
| F2-ctrl-B | | | | | | | |
| 0 | 8:25 | 0 | 0.00 | 0.165 | 1 | 0.098 | |
| 1 | 9:55 | 90 | 1.50 | 0.190 | 1 | 0.123 | |
| 2 | 11:15 | 170 | 2.83 | 0.264 | 1 | 0.197 | 0.197 |
| 3 | 12:35 | 250 | 4.17 | 0.460 | 1 | 0.393 | 0.393 |
| 4 | 13:40 | 315 | 5.25 | 0.248 | 5 | 0.917 | 0.917 |
| F3-Ca-a | | | | | | | |
| 0 | 8:25 | 0 | 0.00 | 0.166 | 1 | 0.099 | |
| 1 | 9:55 | 90 | 1.50 | 0.192 | 1 | 0.125 | |
| 2 | 11:15 | 170 | 2.83 | 0.266 | 1 | 0.199 | 0.199 |
| 3 | 12:35 | 250 | 4.17 | 0.461 | 1 | 0.394 | 0.394 |
| 4 | 13:40 | 315 | 5.25 | 0.256 | 5 | 0.957 | 0.957 |
| F4-Ca-b | | | | | | | |
| 0 | 8:25 | 0 | 0.00 | 0.169 | 1 | 0.102 | |
| 1 | 9:55 | 90 | 1.50 | 0.190 | 1 | 0.123 | |
| 2 | 11:15 | 170 | 2.83 | 0.262 | 1 | 0.195 | 0.195 |
| 3 | 12:35 | 250 | 4.17 | 0.443 | 1 | 0.376 | 0.376 |
| 4 | 13:40 | 315 | 5.25 | 0.245 | 5 | 0.902 | 0.902 |
| F5-Ca-c | | | | | | | |
| 0 | 8:25 | 0 | 0.00 | 0.164 | 1 | 0.097 | |
| 1 | 9:55 | 90 | 1.50 | 0.186 | 1 | 0.119 | |
| 2 | 11:15 | 170 | 2.83 | 0.235 | 1 | 0.168 | 0.168 |
| 3 | 12:35 | 250 | 4.17 | 0.364 | 1 | 0.297 | 0.297 |
| 4 | 13:40 | 315 | 5.25 | 0.575 | 1 | 0.508 | 0.508 |
| 5 | 14:55 | 390 | 6.50 | 0.321 | 5 | 1.282 | 1.282 |

Example 19

Inhibition of Ethanologen Yeast PNY 827 by 1-bromo-2-butanone

The inhibitory effect of 1-bromo-2-butanone on ethanologen yeast PNY 827 was investigated. Therefore a 125 ml aerobic shake flask was prepared with 20 ml SEED medium and inoculated with 1 ml of frozen glycerol stock culture of PNY 827. The culture was inoculated overnight at 30° C. and 250 rpm in an Innova Laboratory Shaker (New Brunswick Scientific, Edison, N.J.). Subsequently, a sufficient amount of the seed culture was transferred into shake flasks containing 20 ml of production medium without 1-bromo-2-butanone or addition of 1-bromo-2-butanone at concentrations of 50 mM, 5 mM, 1 mM, 0.5 mM, 0.1 mM, 0.01 mM and 0.001 mM, to give an initial OD of approximately 0.1. The cultures were incubated at 250 rpm for 24 h in an Innova Laboratory Shaker (New Brunswick Scientific, Edison, N.J.) and samples of about 1 ml for OD determination withdrawn at designated hours. Optical density was measured with an Ultrospec 3000 spectrophotometer (Pharmacia Biotech) at λ=600 nm. In case cell dry weight concentrations were needed, an OD-DW-correlation of 0.33 gDW/OD was applied. Maximum specific growth rates $\mu_{max}$ were determined by applying the exponential regression function of Microsoft Excel (Microsoft Office Excel 2003, SP 3). Outliers were discarded until good fit of the regression curve with measurements was confirmed by visual inspection. Parameters of the inhibition kinetics were determined by least square minimization of the differences between measured and predicted $\mu_{max}$ values. Employed search algorithm was a quasi-Newton method with linear extrapolation from a tangent vector, as implemented in the solver routine of Microsoft Excel (Microsoft Office Excel 2003, SP 3).

Figure 13:
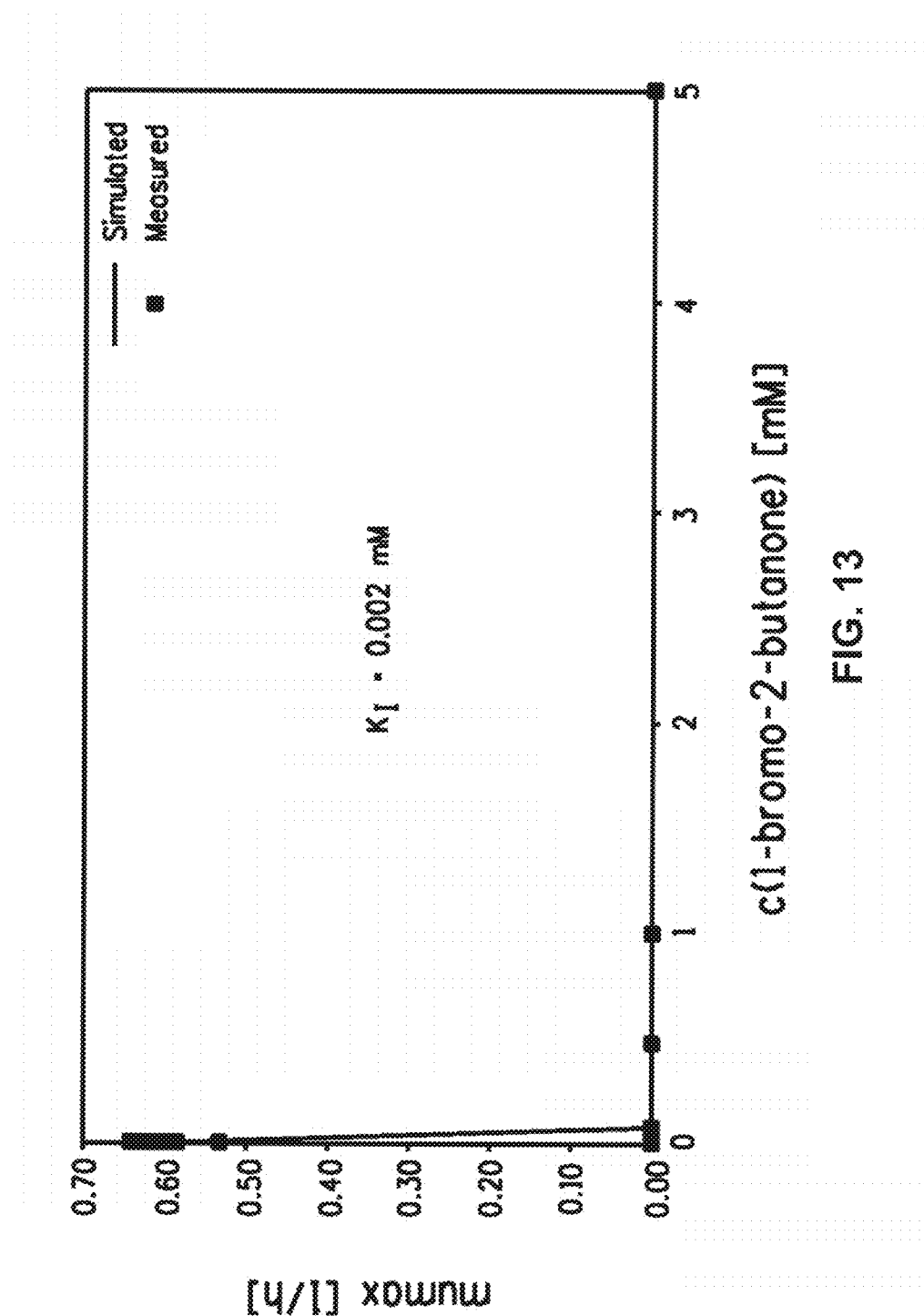
FIG. 13 depicts μmax of PNY 827 in dependence on concentration of 1-bromo-2-butanone in the medium.

The inhibitory effect of 1-bromo-2-butanone was investigated at 50 mM, 5 mM, 1 mM, 0.5 mM, 0.1 mM, 0.01 mM and 0.001 mM. For generating the concentrations of 0.1 mM, 0.01 mM and 0.001 mM, 1-bromo-2-butanone was diluted with DMSO, resulting in DMSO concentrations in the cell suspension of 0.7 mM, 7 mM and 70 mM of DMSO, respectively. Assuming an additive effect of 1-bromo-2-butanone and DMSO inhibition, observed maximum specific growth rates of the two cultures were corrected by 0.000 l/h, 0.000 l/h and 0.005 l/h due to the effect of DMSO, resulting in 1-bromo-2-butanone-based mumax values of 0.54 l/h, 0.00 l/h and 0.00 l/h derived from the observed values of 0.54 l/h, 0.00 l/h and 0.00 l/h, respectively. At all the other concentrations, no DMSO was used for dilution of 1-bromo-2-butanone. However, in all of the non-DMSO experiments no cell growth was observed. Fitting the data to the "squared inhibition" kinetics (observed maximum specific growth rates without inhibitor addition were 0.59 l/h, 0.59 l/h, 0.60 l/h, 0.62 l/h, 0.62 l/h and 0.62 l/h) yielded parameters of $\mu°_{max}$=0.61 l/h and a $K_I$ value of $K_I$=0.002 mM (FIG. 13). This corresponds to an IC50 value of 1-bromo-2-butanone on growth of 0.002 mM, indication of strong inhibition of ethanologen yeast by 1-bromo-2-butanone. Data from the samples is seen in Table 12 below.

TABLE 12

Data for control samples and 1-bromo-2-butanone-inhibited experiments, 1-bromo-2-butanone concentrations in the experiments were: SF12-F1-Ctrl-A: 0 mM; SF12-F2-ctrl-B: 0 mM; F10-bb-1: 5 mM; F11-bb-2: 50 mM; SF13-F1-ctrl-A: 0 mM; SF13-F2-ctrl-B: 0 mM; F6-Bb-0.5: 0.5 mM; F7-Bb-1: 1 mM; F1-Ctrl-A: 0 mM; F2-ctrl-B: 0 mM; F6-Bb-a: 0.001 mM; F7-Bb-b: 0.01 mM; F8-Bb-c: 0.1 mM.

| sample | time | time [min] | time [h] | OD600 | dilution [1:x] | OD600corr [ ] | OD600corr [ ] |
|---|---|---|---|---|---|---|---|
| SF12-F1-Ctrl-A | | | | | | | |
| 0 | 8:55 | 0 | 0.00 | 0.156 | 1 | 0.089 | |
| 1 | 10:25 | 90 | 1.50 | 0.170 | 1 | 0.103 | |
| 2 | 11:35 | 160 | 2.67 | 0.222 | 1 | 0.155 | 0.155 |
| 3 | 12:55 | 240 | 4.00 | 0.350 | 1 | 0.283 | 0.283 |
| 4 | 14:15 | 320 | 5.33 | 0.220 | 5 | 0.777 | 0.777 |
| 6 | 8:30 | 1395 | 23.25 | 0.648 | 20 | 11.677 | |
| SF12-F2-ctrl-B | | | | | | | |
| 0 | 8:55 | 0 | 0.00 | 0.162 | 1 | 0.095 | |
| 1 | 10:25 | 90 | 1.50 | 0.172 | 1 | 0.105 | |
| 2 | 11:35 | 160 | 2.67 | 0.223 | 1 | 0.156 | 0.156 |
| 3 | 12:55 | 240 | 4.00 | 0.354 | 1 | 0.287 | 0.287 |
| 4 | 14:15 | 320 | 5.33 | 0.228 | 5 | 0.817 | 0.817 |
| 5 | 8:30 | 1395 | 23.25 | 0.667 | 20 | 12.057 | |
| F10-bb-1 | | | | | | | |
| 0 | 8:55 | 0 | 0.00 | 0.161 | 1 | 0.094 | |
| 1 | 10:25 | 90 | 1.50 | 0.176 | 1 | 0.109 | 0.109 |
| 2 | 11:35 | 160 | 2.67 | 0.170 | 1 | 0.103 | 0.103 |
| 3 | 12:55 | 240 | 4.00 | 0.168 | 1 | 0.101 | 0.101 |
| 4 | 14:15 | 320 | 5.33 | 0.170 | 1 | 0.103 | 0.103 |
| 5 | 8:30 | 1395 | 23.25 | 0.171 | 1 | 0.104 | 0.104 |
| F11-bb-2 | | | | | | | |
| 0 | 8:55 | 0 | 0.00 | 0.261 | 1 | 0.194 | |
| 1 | 10:25 | 90 | 1.50 | 0.238 | 1 | 0.171 | 0.171 |
| 2 | 11:35 | 160 | 2.67 | 0.275 | 1 | 0.208 | 0.208 |
| 3 | 12:55 | 240 | 4.00 | 0.266 | 1 | 0.199 | 0.199 |
| 4 | 14:15 | 320 | 5.33 | 0.264 | 1 | 0.197 | 0.197 |
| 5 | 8:30 | 1395 | 23.25 | 0.161 | 1 | 0.094 | 0.094 |
| SF13-F1-ctrl-A | | | | | | | |
| 0 | 8:15 | 0 | 0.00 | 0.160 | 1 | 0.093 | |
| 1 | 9:45 | 90 | 1.50 | 0.169 | 1 | 0.102 | |
| 2 | 11:05 | 170 | 2.83 | 0.229 | 1 | 0.162 | 0.162 |
| 3 | 12:20 | 245 | 4.08 | 0.368 | 1 | 0.301 | 0.301 |
| 4 | 13:35 | 320 | 5.33 | 0.215 | 5 | 0.752 | 0.752 |
| 6 | 8:30 | 1455 | 24.25 | 0.644 | 20 | 11.597 | |
| SF13 - F2-ctrl-B | | | | | | | |
| 0 | 8:15 | 0 | 0.00 | 0.159 | 1 | 0.092 | |
| 1 | 9:45 | 90 | 1.50 | 0.168 | 1 | 0.101 | |
| 2 | 11:05 | 170 | 2.83 | 0.228 | 1 | 0.161 | 0.161 |
| 3 | 12:20 | 245 | 4.08 | 0.372 | 1 | 0.305 | 0.305 |
| 4 | 13:35 | 320 | 5.33 | 0.215 | 5 | 0.752 | 0.752 |
| 5 | 8:30 | 1455 | 24.25 | 0.652 | 20 | 11.757 | |
| F6-Bb-0.5 | | | | | | | |
| 0 | 8:15 | 0 | 0.00 | 0.165 | 1 | 0.098 | |
| 1 | 9:45 | 90 | 1.50 | 0.166 | 1 | 0.099 | 0.099 |
| 2 | 11:05 | 170 | 2.83 | 0.169 | 1 | 0.102 | 0.102 |
| 3 | 12:20 | 245 | 4.08 | 0.169 | 1 | 0.102 | 0.102 |
| 4 | 13:35 | 320 | 5.33 | 0.167 | 1 | 0.100 | 0.100 |
| 5 | 8:30 | 1455 | 24.25 | 0.169 | 1 | 0.102 | 0.102 |
| F7-Bb-1 | | | | | | | |
| 0 | 8:15 | 0 | 0.00 | 0.157 | 1 | 0.090 | |
| 1 | 9:45 | 90 | 1.50 | 0.161 | 1 | 0.094 | 0.094 |
| 2 | 11:05 | 170 | 2.83 | 0.160 | 1 | 0.093 | 0.093 |
| 3 | 12:20 | 245 | 4.08 | 0.160 | 1 | 0.093 | 0.093 |
| 4 | 13:35 | 320 | 5.33 | 0.158 | 1 | 0.091 | 0.091 |
| 5 | 8:30 | 1455 | 24.25 | 0.161 | 1 | 0.094 | 0.094 |
| F1-Ctrl-A | | | | | | | |
| 0 | 8:25 | 0 | 0.00 | 0.167 | 1 | 0.100 | |
| 1 | 9:55 | 90 | 1.50 | 0.190 | 1 | 0.123 | |
| 2 | 11:15 | 170 | 2.83 | 0.264 | 1 | 0.197 | 0.197 |
| 3 | 12:35 | 250 | 4.17 | 0.452 | 1 | 0.385 | 0.385 |
| 4 | 13:40 | 315 | 5.25 | 0.246 | 5 | 0.907 | 0.907 |
| F2-ctrl-B | | | | | | | |
| 0 | 8:25 | 0 | 0.00 | 0.165 | 1 | 0.098 | |
| 1 | 9:55 | 90 | 1.50 | 0.190 | 1 | 0.123 | |
| 2 | 11:15 | 170 | 2.83 | 0.264 | 1 | 0.197 | 0.197 |
| 3 | 12:35 | 250 | 4.17 | 0.460 | 1 | 0.393 | 0.393 |
| 4 | 13:40 | 315 | 5.25 | 0.248 | 5 | 0.917 | 0.917 |
| F6-Bb-a | | | | | | | |
| 0 | 8:25 | 0 | 0.00 | 0.165 | 1 | 0.098 | |
| 1 | 9:55 | 90 | 1.50 | 0.180 | 1 | 0.113 | |

TABLE 12-continued

Data for control samples and 1-bromo-2-butanone-inhibited experiments, 1-bromo-2-butanone concentrations in the experiments were: SF12-F1-Ctrl-A: 0 mM; SF12-F2-ctrl-B: 0 mM; F10-bb-1: 5 mM; F11-bb-2: 50 mM; SF13-F1-ctrl-A: 0 mM; SF13-F2-ctrl-B: 0 mM; F6-Bb-0.5: 0.5 mM; F7-Bb-1: 1 mM; F1-Ctrl-A: 0 mM; F2-ctrl-B: 0 mM; F6-Bb-a: 0.001 mM; F7-Bb-b: 0.01 mM; F8-Bb-c: 0.1 mM.

| sample | time | time [min] | time [h] | OD600 | dilution [1:x] | OD600corr [ ] | OD600corr [ ] |
|---|---|---|---|---|---|---|---|
| 2 | 11:15 | 170 | 2.83 | 0.219 | 1 | 0.152 | 0.152 |
| 3 | 12:35 | 250 | 4.17 | 0.314 | 1 | 0.247 | 0.247 |
| 4 | 13:40 | 315 | 5.25 | 0.500 | 1 | 0.433 | 0.433 |
| 5 | 14:55 | 390 | 6.50 | 0.287 | 5 | 1.112 | 1.112 |
| F7-Bb-b | | | | | | | |
| 0 | 8:25 | 0 | 0.00 | 0.166 | 1 | 0.099 | |
| 1 | 9:55 | 90 | 1.50 | 0.184 | 1 | 0.117 | 0.117 |
| 2 | 11:15 | 170 | 2.83 | 0.183 | 1 | 0.116 | 0.116 |
| 3 | 12:35 | 250 | 4.17 | 0.189 | 1 | 0.122 | 0.122 |
| 4 | 13:40 | 315 | 5.25 | 0.186 | 1 | 0.119 | 0.119 |
| 5 | 14:55 | 390 | 6.50 | 0.191 | 1 | 0.124 | 0.124 |
| F8-Bb-c | | | | | | | |
| 0 | 8:25 | 0 | 0.00 | 0.164 | 1 | 0.097 | |
| 1 | 9:55 | 90 | 1.50 | 0.168 | 1 | 0.101 | 0.101 |
| 2 | 11:15 | 170 | 2.83 | 0.166 | 1 | 0.099 | 0.099 |
| 3 | 12:35 | 250 | 4.17 | 0.170 | 1 | 0.103 | 0.103 |
| 4 | 13:40 | 315 | 5.25 | 0.170 | 1 | 0.103 | 0.103 |
| 5 | 14:55 | 390 | 6.50 | 0.170 | 1 | 0.103 | |

Example 20

Effect of Ethanol Dehydrogenase and Pyruvate Decarboxylase Inhibitors on Growth and Product Formation of Mixed Cultures of Ethanologen and Butanologen Yeast Effects of addition of ethanol dehydrogenase and pyruvate decarboxylase inhibitors on mixed cultures of ethanologen S. cerevisiae PNY 827 and the butanologen yeast S. cerevisiae PNY 2129 were investigated. Therefore two 125 ml aerobic shake flask were prepared with 20 ml SEED medium and each inoculated with 1 ml of frozen glycerol stock culture of PNY 2129 in the morning. Another 125 ml aerobic shake flask was prepared with 20 ml SEED medium and inoculated with 1 ml of frozen glycerol stock culture of PNY 827 in the afternoon. All cultures were incubated at 30° C. and 250 rpm overnight in an Innova Laboratory Shaker (New Brunswick Scientific, Edison, N.J.). In the morning, sufficient seed culture volume of each strain to give OD600 of 1.000 in the resuspended solution was separately transferred into 50 mL sterile centrifuge tubes and spun down at 9500 rpm for 20 min in an Eppendorf Centrifuge 5804R (Eppendorf, Hamburg, Germany). Supernatants were discarded and the cell pellets resuspended in 20 ml of 0.9% NaCl solution. Optical density was measured with an Ultrospec 3000 spectrophotometer (Pharmacia Biotech) at λ=600 nm. Subsequently "production" cultures were prepared in 25 ml Balch tubes by adding into each tube 6 ml Yeast synthetic w/o aa, w/o glucose, w/o ethanol, w/o Tween (2x), 1.2 ml supplement amino acid solution without histidine and uracil (SAAS-2 10x), 1.92 ml of 250 g/l glucose (ca. 40 g/l glucose) and 2.3 µl of 3M sodium acetate, as well as a specific amount of inoculum solutions, inhibitor solution and water according to the schema in Table 13:

TABLE 13

Schema showing strains and inhibitors solutions.

| | inoculum solution | | stock: | inhibitor solution | | |
|---|---|---|---|---|---|---|
| | PNY2129 [ul] | PNY827 [ul] | H2O [ul] | 300 mM Py [ul] | 2 mM (200 mM) Bb [ul] | 250 mM (2500 mM) Ca [ul] |
| T1-ctrl1 B | 1200 | | 1200 | | | |
| T2-ctrl2 B | 1200 | | 1200 | | | |
| T3-ctrl1 E | | 1200 | 1200 | | | |
| T4-ctrl2 E | | 1200 | 1200 | | | |
| T5-1:1-PyA | 600 | 600 | 1080 | 120 | | |
| T6-1:1-PyB | 600 | 600 | | 1200 | | |
| T7-11:1-PyA | 1100 | 100 | 1080 | 120 | | |
| T8-11:1-PyB | 1100 | 100 | | 1200 | | |
| T9-1:1-BbA | 600 | 600 | 1188 | | 12 | |
| T10-1:1-BbB | 600 | 600 | 1188 | | 12 | |
| T11-11:1-BbA | 1100 | 100 | 1188 | | 12 | |
| T12-11:1-BbB | 1100 | 100 | 1188 | | 12 | |
| T13-1:1-CaA | 600 | 600 | 1188 | | | 12 |
| T14-1:1-CaB | 600 | 600 | 1080 | | | 120 |
| T15-11:1-CaA | 1100 | 100 | 1188 | | | 12 |
| T16-11:1-CaB | 1100 | 100 | 1080 | | | 120 |
| T17-1:1-ctrl1 | 600 | 600 | 1200 | | | |
| T18-11:1-ctrl1 | 1100 | 100 | 1200 | | | |

Inhibitor solutions were trans-cinnamaldehyde (Aldrich, #239968, CAS: 14371-10-9) dissolved in water either ad 250 mM or 2500 mM, 1-bromo-2-butanone (Sigma-Aldrich, #243299, CAS: 816-40-0) dissolved in water either at 2 mM or 200 mM, and pyrazole (Aldrich, # P56607, CAS Number: 288-13-1), dissolved in water at 300 mM. Resulting inhibitor concentrations in the Balch tube cultures were pyrazole (PY): 3 mM (A) and 30 mM (B), 1-bromo-2-butanone (BB): 2 µM (A) and 200 µM (B), and trans-cinnamaldehyde (CA): 250 µM (A) and 25 mM (B), respectively. Each Balch tube was fitted with a butyl rubber septum and crimped to the tube with a sheet metal with circular opening to allow samples withdrawal by syringes. The cultures were mixed by a vial/tube rotator (Glas-Col, Terre-Haute, Ind.) that was placed in an Innova Laboratory Shaker (New Brunswick Scientific, Edison, N.J.) for keeping the temperature at 30° C. Samples of about 1 ml for OD determination and extracellular compound analysis were withdrawn at designated hours. Extracellular compound analysis in supernatant was accomplished by HPLC. An Aminex® HPX-87H column (Bio-Rad, Hercules, Calif.) was used in an isocratic method with 0.01N sulfuric acid as eluent on an Alliance® 2695 Separations Module (Waters Corp., Milford, Mass.). Flow rate was 0.60 mL/min, column temperature 40° C., injection volume 10 µL and run time 58 min. Detection was carried out with a refractive index detector (Waters 2414 RI, Waters Corp., Milford, Mass.) operated at 40° C. and an UV detector (Waters 2996 PDA, Waters Corp., Milford, Mass.) at 210 nm. Determined optical densities as well as concentrations of extracellular compounds at selected sampling time points can be found in Table 14.

Figure 14:
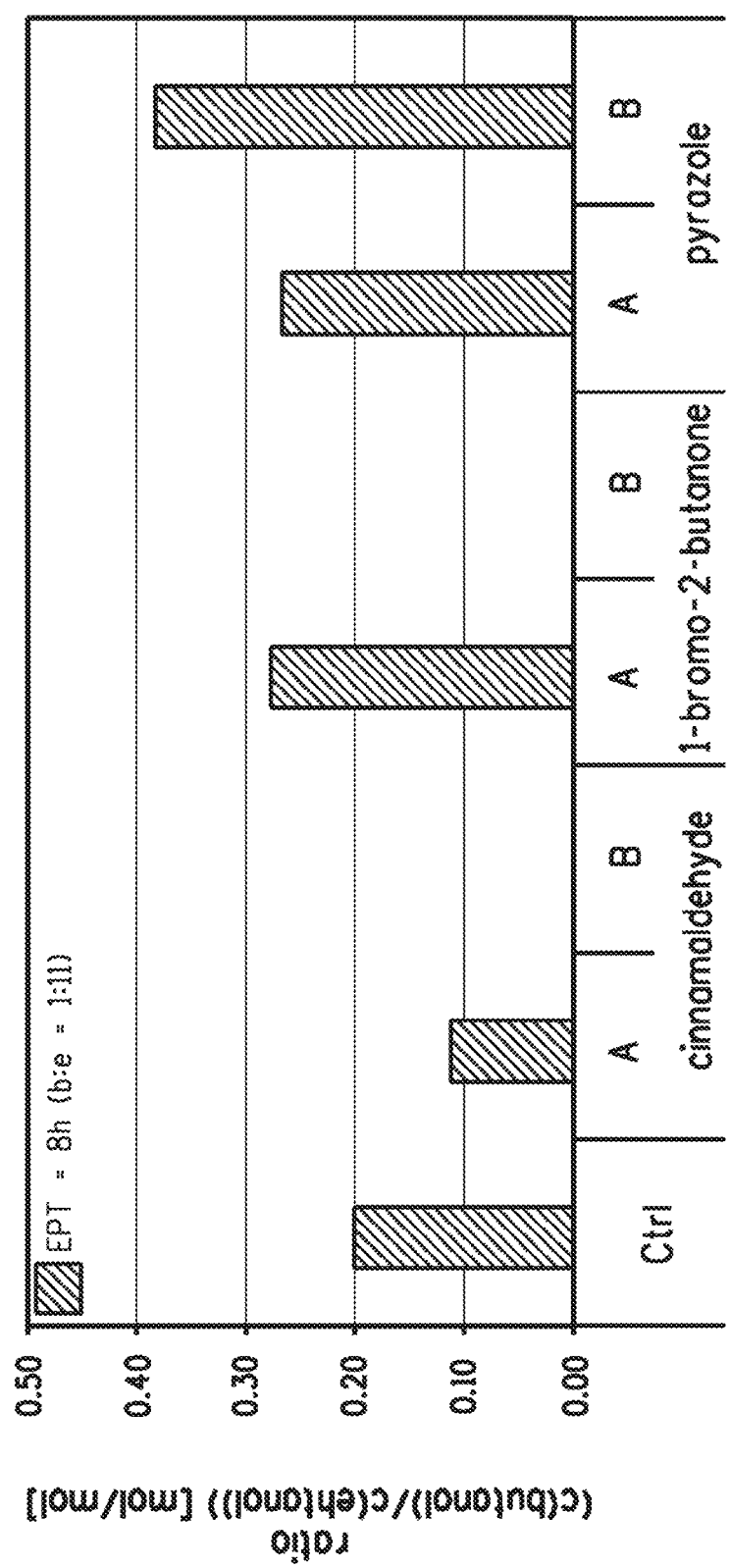
FIG. 14 depicts the ratio of the produced molar butanol to ethanol concentration at EPT=8 h in mixed cultures inoculated in an OD600 ratio of 1 ethanologen strain PNY 827 to 11 butanologen strain PNY 2129 in cultures without addition of an inhibitor ("Ctrl") and trans-cinnamaldehyde concentrations of 250 μM (A) and 25 mM (B), 1-bromo-2-butanone concentrations of 2 μM (A) and 200 μM (B), and pyrazole concentrations of 3 mM (A) and 30 mM (B).
Figure 15:
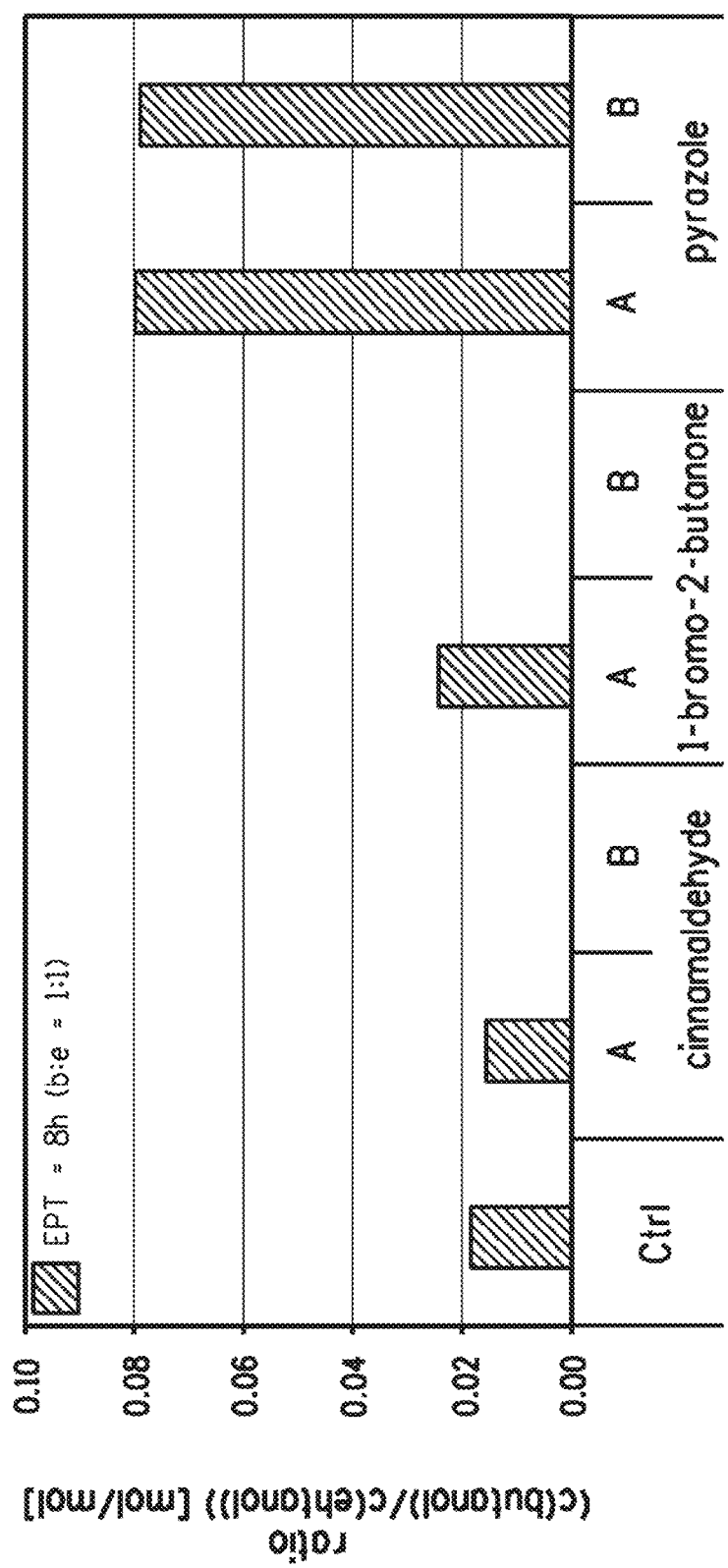
FIG. 15 depicts the ratio of the produced molar butanol to ethanol concentration at EPT=8 h in mixed cultures inoculated in an OD600 ratio of 1 ethanologen strain PNY 827 to 1 butanologen strain PNY 2129 in cultures without addition of an inhibitor ("Ctrl") and trans-cinnamaldehyde at concentrations of 250 μM (A) and 25 mM (B), 1-bromo-2-butanone at concentrations of 2 μM (A) and 200 μM (B), and pyrazole at concentrations of 3 mM (A) and 30 mM (B).
Figure 16:
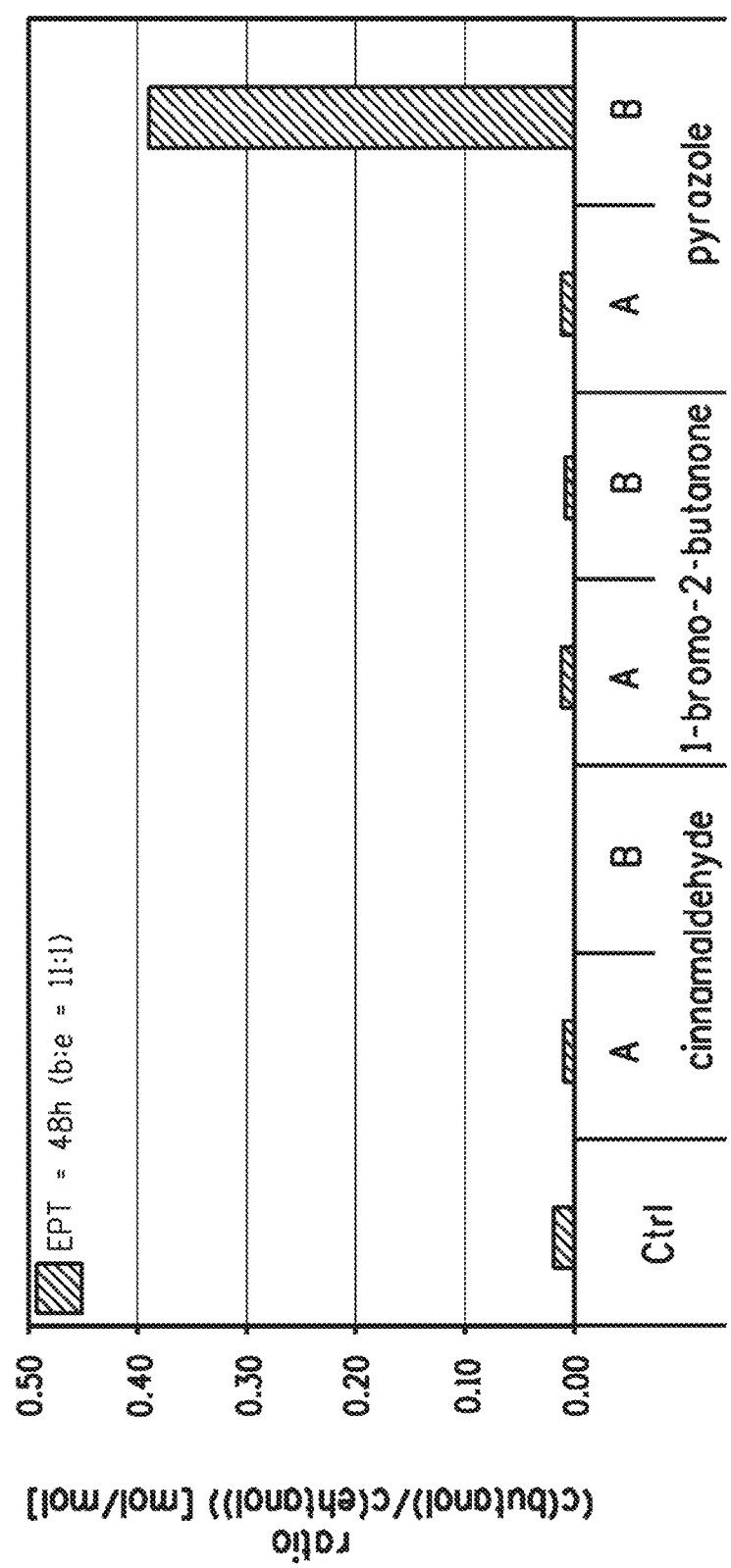
FIG. 16 depicts the ratio of the produced molar butanol to ethanol concentration at EPT=48 h in mixed cultures inoculated in an OD600 ratio of 1 ethanologen strain PNY 827 to 11 butanologen strain PNY 2129 in cultures without addition of an inhibitor ("Ctrl") and trans-cinnamaldehyde at concentrations of 250 μM (A) and 25 mM (B), 1-bromo-2-butanone at concentrations of 2 μM (A) and 200 μM (B), and pyrazole at concentrations of 3 mM (A) and 30 mM (B).
Figure 17:
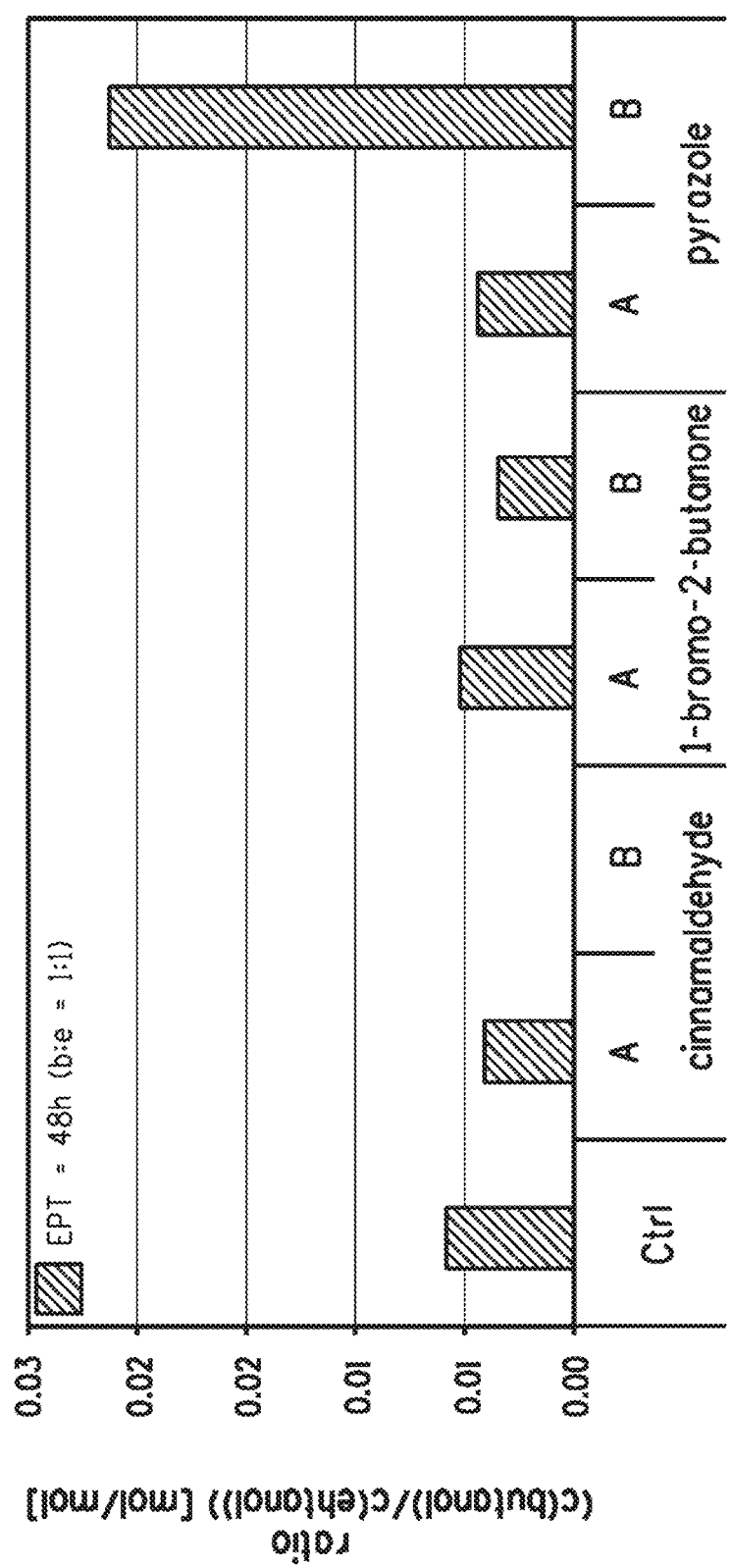
FIG. 17 depicts the ratio of the produced molar butanol to ethanol concentration at EPT=48 h in mixed cultures inoculated in an OD600 ratio of 1 ethanologen strain PNY 827 to 1 butanologen strain PNY 2129 in cultures without addition of an inhibitor ("Ctrl") and trans-cinnamaldehyde at concentrations of 250 μM (A) and 25 mM (B), 1-bromo-2-butanone at concentrations of 2 μM (A) and 200 μM (B), and pyrazole at concentrations of 3 mM (A) and 30 mM (B).

Butanol to ethanol formed in the mixed cultures with inhibitors was compared to the ratio of butanol to ethanol formed in the mixed cultures without inhibitor (Ctrl) at 8 hours (EPT=8 h, FIG. 14 and FIG. 15) and at 48 hours (EPT=48 h, FIG. 16 and FIG. 17) of the experiments inoculated with a butanologen-to-ethanologen ratio of 11:1 (b:e=11:1, FIG. 14 and FIG. 16) or 1:1 (b:e=1:1, FIG. 15 and FIG. 17).

No growth in both mixed cultures and at both time points was observed at the high concentration of trans-cinnamaldehyde of 25 mM (FIG. 14-FIG. 17). At the lower concentration of 250 μM, both mixed cultures grew and produced alcohols. However, at both sampling times (EPT=8 h and EPT=48 h) as well as at both inoculum ratios (1:1 and 1:11), the ratio of butanol vs. ethanol produced was lower with addition of trans-cinnamaldehyde than without addition (FIG. 14-FIG. 17).

With 1-bromo-2-butanone, no growth was observed in the 1:1 culture at the high concentration of 200 μM until EPT=8 h, only at EPT=48 h. At low concentration (2 μM), cultures with both inoculum ratios showed increased butanol-to-ethanol ratios at EPT=8 h, but not at EPT=48 h. The same findings apply to the culture with 1:11 ratio at the high concentration (FIG. 14-FIG. 17).

With pyrazole addition at both concentrations, 3 mM and 30 mM, cultures with inoculum ratios 1:1 as well as 1:11 showed dramatically increased butanol-to-ethanol ratios at EPT=8 h (FIG. 14 and FIG. 15). However, at EPT=48 h cultures with both inoculum ratios maintained significantly increased butanol:ethanol ratios only at the higher pyrazole concentration of 30 mM, but not at the lower concentration of 3 mM (FIG. 16 and FIG. 17).

TABLE 14

Optical density (OD) and extracellular compound concentrations at the different sampling time points (EPT = elapsed process time) of different pure and mixed cultures. Abbreviations used were: EtOH = ethanol, PYR = pyruvate, KIV = ketoisovalerate, DHIV = dihydroisovalerate, DHMB = 2,3-dihydroxy-2-metylbutyrate, GLY = glycerol, ACE = acetate, IBOOH = isobutyric acid, IBOH = isobutanol, m-BDO = meso-butanediol, d/l-BDO = d/l-butanediol, LAC = lactate, SUC = succinate.

| Sample [ ] | EPT [h] | OD [ ] | GLC [mM] | EtOH [mM] | PYR [mM] | KIV [mM] | DHIV + DHMB [mM] | GLY [mM] | ACE [mM] | IBOOH [mM] | IBOH [mM] | m-BDO [mM] | d/l-BDO [mM] | LAC [mM] | SUC [mM] |
|---|---|---|---|---|---|---|---|---|---|---|---|---|---|---|---|
| SF-17-T1-ctrl-1-B-0 | 0.00 | 0.115 | 226.0 | 0.0 | 0.0 | 0.0 | 0.0 | 0.1 | 6.8 | 0.0 | 0.0 | 0.0 | 0.0 | 0.0 | 0.0 |
| SF-17-T1-ctrl-1-B-3 | 3.00 | 0.159 | 223.4 | 0.0 | 0.0 | 0.2 | 0.0 | 0.2 | 6.7 | 0.0 | 0.6 | 0.0 | 0.0 | 0.0 | 0.0 |
| SF-17-T1-ctrl-1-B-6 | 6.00 | 0.210 | 221.3 | 0.0 | 0.1 | 0.2 | 0.0 | 0.3 | 6.7 | 0.3 | 1.4 | 0.0 | 0.0 | 0.0 | 0.0 |
| SF-17-T1-ctrl-1-B-8 | 8.00 | 0.247 | 222.4 | 0.0 | 0.1 | 0.4 | 0.0 | 0.4 | 6.5 | 0.4 | 2.4 | 0.0 | 0.0 | 0.0 | 0.0 |
| SF-17-T1-ctrl-1-B-24 | 24.00 | 1.382 | 178.0 | 1.2 | 1.8 | 3.1 | 0.6 | 2.8 | 4.4 | 2.5 | 24.8 | 0.0 | 0.0 | 0.1 | 0.3 |
| SF-17-T1-ctrl-1-B-31 | 31.00 | 1.747 | 147.9 | 2.0 | 2.2 | 3.8 | 1.2 | 5.2 | 4.1 | 3.1 | 39.7 | 0.0 | 0.5 | 0.1 | 0.5 |
| SF-17-T1-ctrl-1-B-48 | 48.00 | 1.917 | 106.9 | 3.6 | 2.9 | 4.4 | 1.9 | 11.9 | 3.0 | 3.3 | 69.1 | 0.0 | 1.3 | 0.2 | 0.5 |
| SF-17-T1-ctrl-1-B-0 | 0.00 | 0.109 | 226.0 | 0.0 | 0.0 | 0.0 | 0.0 | 0.1 | 6.8 | 0.0 | 0.0 | 0.0 | 0.0 | 0.0 | 0.0 |
| SF-17-T2-ctrl-2-B-3 | 3.00 | 0.157 | 223.4 | 0.0 | 0.0 | 0.1 | 0.0 | 0.2 | 6.7 | 0.0 | 0.6 | 0.0 | 0.0 | 0.0 | 0.0 |
| SF-17-T2-ctrl-2-B-6 | 6.00 | 0.209 | 222.0 | 0.0 | 0.1 | 0.2 | 0.0 | 0.3 | 6.7 | 0.2 | 1.4 | 0.0 | 0.0 | 0.0 | 0.0 |
| SF-17-T2-ctrl-2-B-8 | 8.00 | 0.239 | 221.1 | 0.0 | 0.1 | 0.4 | 0.0 | 0.4 | 6.5 | 0.3 | 2.4 | 0.0 | 0.0 | 0.0 | 0.0 |
| SF-17-T2-ctrl-2-B-24 | 24.00 | 1.197 | 183.6 | 0.0 | 1.6 | 2.9 | 0.4 | 2.6 | 4.4 | 2.9 | 22.2 | 0.0 | 0.0 | 0.0 | 0.2 |
| SF-17-T2-ctrl-2-B-31 | 31.00 | 1.627 | 152.0 | 2.1 | 2.1 | 3.9 | 1.1 | 4.9 | 4.0 | 3.3 | 38.1 | 0.0 | 0.5 | 0.0 | 0.5 |
| SF-17-T2-ctrl-2-B-48 | 48.00 | 1.867 | 104.7 | 4.0 | 3.0 | 4.6 | 2.0 | 11.2 | 2.9 | 3.3 | 69.7 | 0.0 | 1.4 | 0.3 | 0.5 |
| SF-17-T3-ctrl-1-E-0 | 0.00 | 0.088 | 224.0 | 0.0 | 0.0 | 0.0 | 0.0 | 0.0 | 7.1 | 0.0 | 0.0 | 0.0 | 0.0 | 0.0 | 0.0 |
| SF-17-T3-ctrl-1-E-3 | 3.00 | 0.222 | 221.8 | 4.5 | 0.0 | 0.0 | 0.0 | 0.4 | 6.8 | 0.0 | 0.0 | 0.0 | 0.0 | 0.0 | 0.0 |
| SF-17-T3-ctrl-1-E-6 | 6.00 | 1.317 | 206.1 | 30.3 | 0.1 | 0.0 | 0.0 | 1.6 | 6.6 | 0.0 | 0.0 | 0.0 | 0.0 | 0.0 | 0.0 |
| SF-17-T3-ctrl-1-A-8 | 8.00 | 3.637 | 162.9 | 103.8 | 0.5 | 0.0 | 0.0 | 5.7 | 6.3 | 0.0 | 0.0 | 0.0 | 0.2 | 0.0 | 0.3 |
| SF-17-T3-ctrl-1-E-24 | 24.00 | 9.497 | 0.0 | 378.5 | 2.5 | 0.0 | 0.0 | 18.6 | 9.5 | 0.0 | 0.0 | 0.0 | 0.5 | 0.4 | 0.5 |
| SF-17-T3-ctrl-1-E-31 | 31.00 | 11.997 | 0.0 | 372.7 | 2.6 | 0.0 | 0.0 | 18.6 | 10.8 | 0.0 | 0.5 | 0.0 | 0.4 | 0.0 | 0.5 |
| SF-17-T3-ctrl-1-E-48 | 48.00 | 11.897 | 0.0 | 382.0 | 2.3 | 0.0 | 0.0 | 18.6 | 11.0 | 0.0 | 0.0 | 0.0 | 0.3 | 0.3 | 0.6 |
| SF-17-T3-ctrl-1-E-0 | 0.00 | 0.088 | 224.0 | 0.0 | 0.0 | 0.0 | 0.0 | 0.0 | 7.1 | 0.0 | 0.0 | 0.0 | 0.0 | 0.0 | 0.0 |
| SF-17-T4-ctrl-2-E-3 | 3.00 | 0.225 | 221.7 | 4.6 | 0.0 | 0.0 | 0.0 | 0.4 | 6.8 | 0.0 | 0.0 | 0.0 | 0.0 | 0.0 | 0.0 |
| SF-17-T4-ctrl-2-E-6 | 6.00 | 1.352 | 207.3 | 30.6 | 0.1 | 0.0 | 0.0 | 1.6 | 6.8 | 0.0 | 0.0 | 0.0 | 0.0 | 0.0 | 0.0 |
| SF-17-T4-ctrl-1-B-8 | 8.00 | 3.727 | 161.8 | 104.8 | 0.5 | 0.0 | 0.0 | 5.6 | 6.4 | 0.0 | 0.0 | 0.0 | 0.2 | 0.0 | 0.3 |
| SF-17-T4-ctrl-2-E-24 | 24.00 | 11.847 | 0.0 | 377.1 | 2.5 | 0.0 | 0.0 | 17.0 | 12.1 | 0.0 | 0.0 | 0.0 | 0.4 | 0.4 | 0.5 |
| SF-17-T4-ctrl-2-E-31 | 31.00 | 11.547 | 0.0 | 367.9 | 2.4 | 0.0 | 0.0 | 17.1 | 13.0 | 0.0 | 0.6 | 0.0 | 0.4 | 0.4 | 0.5 |
| SF-17-T4-ctrl-2-E-48 | 48.00 | 11.747 | 0.0 | 378.7 | 2.3 | 0.0 | 0.0 | 16.9 | 13.6 | 0.0 | 0.5 | 0.0 | 0.3 | 0.3 | 0.4 |
| SF-17-T5-1:1-Py-A-0 | 0.00 | 0.104 | 224.0 | 0.0 | 0.0 | 0.0 | 0.0 | 0.1 | 6.8 | 0.0 | 0.0 | 0.0 | 0.0 | 0.0 | 0.0 |
| SF-17-T5-1:1-Py-A-3 | 3.00 | 0.141 | 222.8 | 1.3 | 0.0 | 0.0 | 0.0 | 0.7 | 6.8 | 0.0 | 0.0 | 0.0 | 0.0 | 0.0 | 0.0 |
| SF-17-T5-1:1-Py-A-6 | 6.00 | 0.273 | 218.1 | 5.4 | 0.1 | 0.1 | 0.0 | 2.5 | 6.9 | 0.0 | 0.0 | 0.0 | 0.0 | 0.0 | 0.0 |
| SF-17-T5-1:1-Py-A-8 | 8.00 | 0.504 | 210.2 | 14.8 | 0.2 | 0.1 | 0.0 | 6.4 | 6.8 | 0.0 | 0.6 | 0.4 | 0.0 | 0.0 | 0.0 |
| SF-17-T5-1:1-Py-A-24 | 24.00 | 9.777 | 0.0 | 346.4 | 2.9 | 0.1 | 0.0 | 37.0 | 10.3 | 0.1 | 1.6 | 0.9 | 1.5 | 0.4 | 0.4 |
| SF-17-T5-1:1-Py-A-31 | 31.00 | 10.647 | 0.0 | 337.3 | 2.8 | 0.1 | 0.0 | 37.0 | 11.7 | 0.3 | 1.6 | 0.9 | 1.6 | 0.3 | 0.4 |
| SF-17-T5-1:1-Py-A-48 | 48.00 | 10.797 | 0.0 | 347.2 | 2.7 | 0.1 | 0.0 | 37.1 | 12.7 | 0.0 | 1.6 | 0.9 | 1.7 | 0.3 | 0.5 |
| SF-17-T5-1:1-Py-A-0 | 0.00 | 0.103 | 224.0 | 0.0 | 0.0 | 0.0 | 0.0 | 0.1 | 6.8 | 0.0 | 0.0 | 0.0 | 0.0 | 0.0 | 0.0 |
| SF-17-T6-1:1-Py-B-3 | 3.00 | 0.125 | 222.4 | 0.0 | 0.0 | 0.0 | 0.0 | 0.7 | 6.8 | 0.0 | 0.0 | 0.0 | 0.0 | 0.0 | 0.0 |
| SF-17-T6-1:1-Py-B-6 | 6.00 | 0.149 | 220.7 | 1.4 | 0.0 | 0.1 | 0.0 | 2.0 | 6.8 | 0.0 | 0.0 | 0.2 | 0.0 | 0.0 | 0.0 |
| SF-17-T6-1:1-Py-B-8 | 8.00 | 0.173 | 218.7 | 2.4 | 0.1 | 0.1 | 0.0 | 3.9 | 7.0 | 0.0 | 0.2 | 0.3 | 0.0 | 0.0 | 0.0 |
| SF-17-T6-1:1-Py-B-24 | 24.00 | 0.602 | 175.8 | 24.6 | 2.0 | 0.3 | 0.0 | 32.7 | 7.5 | 0.0 | 2.1 | 2.5 | 0.0 | 0.0 | 0.0 |
| SF-17-T6-1:1-Py-B-31 | 31.00 | 0.727 | 149.4 | 46.0 | 3.8 | 0.4 | 0.0 | 48.4 | 8.2 | 0.0 | 2.5 | 3.2 | 0.7 | 0.0 | 0.0 |
| SF-17-T6-1:1-Py-B-48 | 48.00 | 1.477 | 68.8 | 140.3 | 9.1 | 0.5 | 0.0 | 88.0 | 10.0 | 0.0 | 3.0 | 3.8 | 2.0 | 0.0 | 0.6 |
| SF-17-T8-11:1-Py-B-0 | 0.00 | 0.110 | 223.6 | 0.0 | 0.0 | 0.0 | 0.0 | 0.1 | 6.8 | 0.0 | 0.0 | 0.0 | 0.0 | 0.0 | 0.0 |
| SF-17-T7-11:1-Py-A-3 | 3.00 | 0.146 | 223.6 | 0.0 | 0.0 | 0.1 | 0.0 | 0.3 | 6.8 | 0.0 | 0.0 | 0.0 | 0.0 | 0.0 | 0.0 |
| SF-17-T7-11:1-Py-A-6 | 6.00 | 0.174 | 224.2 | 0.9 | 0.0 | 0.1 | 0.0 | 0.8 | 6.7 | 0.3 | 0.4 | 0.0 | 0.0 | 0.0 | 0.0 |
| SF-17-T7-11:1-Py-A-8 | 8.00 | 0.216 | 221.3 | 2.5 | 0.1 | 0.2 | 0.0 | 1.6 | 6.6 | 0.4 | 0.7 | 0.0 | 0.0 | 0.0 | 0.0 |
| SF-17-T7-11:1-Py-A-24 | 24.00 | 9.517 | 0.0 | 345.0 | 3.0 | 0.3 | 0.0 | 37.3 | 8.8 | 0.8 | 3.4 | 0.0 | 1.2 | 0.4 | 0.5 |
| SF-17-T7-11:1-Py-A-31 | 31.00 | 10.047 | 0.0 | 336.0 | 2.9 | 0.3 | 0.0 | 37.4 | 10.1 | 0.8 | 3.4 | 0.9 | 1.4 | 0.4 | 0.5 |
| SF-17-T7-11:1-Py-A-48 | 48.00 | 11.347 |  | 344.2 | 2.8 | 0.2 | 0.0 | 37.2 | 11.4 | 0.6 | 3.5 | 0.9 | 1.4 | 0.3 | 0.5 |
| SF-17-T8-11:1-Py-B-0 | 0.00 | 0.108 | 223.6 | 0.0 | 0.0 | 0.0 | 0.0 | 0.1 | 6.8 | 0.0 | 0.0 | 0.0 | 0.0 | 0.0 | 0.0 |
| SF-17-T8-11:1-Py-B-3 | 3.00 | 0.136 | 223.2 | 0.0 | 0.0 | 0.1 | 0.0 | 0.3 | 6.8 | 0.0 | 0.0 | 0.0 | 0.0 | 0.0 | 0.0 |
| SF-17-T8-11:1-Py-B-6 | 6.00 | 0.150 | 224.5 | 0.4 | 0.0 | 0.2 | 0.0 | 0.7 | 6.7 | 0.3 | 0.2 | 0.0 | 0.0 | 0.0 | 0.0 |
| SF-17-T8-11:1-Py-B-8 | 8.00 | 0.161 | 222.1 | 0.7 | 0.0 | 0.2 | 0.0 | 1.1 | 6.8 | 0.3 | 0.2 | 0.0 | 0.0 | 0.0 | 0.0 |
| SF-17-T8-11:1-Py-B-24 | 24.00 | 0.277 | 209.8 | 6.0 | 0.4 | 0.6 | 0.0 | 6.6 | 6.6 | 0.8 | 1.8 | 0.0 | 0.0 | 0.0 | 0.0 |
| SF-17-T8-11:1-Py-B-31 | 31.00 | 0.327 | 205.2 | 10.2 | 0.6 | 0.8 | 0.0 | 10.7 | 6.7 | 1.1 | 3.6 | 0.3 | 0.0 | 0.0 | 0.0 |

TABLE 14-continued

Optical density (OD) and extracellular compound concentrations at the different sampling time points (EPT = elapsed process time) of different pure and mixed cultures. Abbreviations used were: EtOH = ethanol, PYR = pyruvate, KTV = ketoisovalerate, DHIV = dihydroisovalerate, DHMB = 2,3-dihydroxy-2-metylbutyrate, GLY = glycerol, ACE = acetate, IBOOH = isobutyric acid, IBOH = isobutanol, m-BDO = meso-butanediol, d/l-BDO = d/l-butanediol, LAC = lactate, SUC = succinate.

| Sample [ ] | EPT [h] | OD [ ] | GLC [mM] | EtOH [mM] | PYR [mM] | KIV [mM] | DHIV + DHMB [mM] | GLY [mM] | ACE [mM] | IBOOH [mM] | IBOH [mM] | m-BDO [mM] | d/l-BDO [mM] | LAC [mM] | SUC [mM] |
|---|---|---|---|---|---|---|---|---|---|---|---|---|---|---|---|
| SF-17-T8-11:1-Py-B-48 | 48.00 | 0.667 | 164.4 | 31.3 | 2.0 | 1.3 | 0.0 | 29.7 | 7.3 | 2.0 | 12.1 | 1.2 | 0.0 | 0.0 | 0.0 |
| SF-17-T9-1:1-Bb-A-0 | 0.00 | 0.104 | 224.2 | 0.0 | 0.0 | 0.0 | 0.0 | 0.1 | 6.9 | 0.0 | 0.0 | 0.0 | 0.0 | 0.0 | 0.0 |
| SF-17-T9-1:1-Bb-A-3 | 3.00 | 0.144 | 223.2 | 1.4 | 0.0 | 0.1 | 0.0 | 0.2 | 6.8 | 0.0 | 0.0 | 0.0 | 0.0 | 0.0 | 0.0 |
| SF-17-T9-1:1-Bb-A-6 | 6.00 | 0.330 | 219.1 | 7.3 | 0.0 | 0.1 | 0.0 | 0.7 | 6.6 | 0.0 | 0.4 | 0.0 | 0.0 | 0.0 | 0.0 |
| SF-17-T9-1:1-Bb-A-8 | 8.00 | 1.057 | 207.4 | 26.7 | 0.1 | 0.1 | 0.0 | 2.0 | 6.6 | 0.2 | 0.7 | 0.0 | 0.0 | 0.0 | 0.0 |
| SF-17-T9-1:1-Bb-A-24 | 24.00 | 9.877 | 0.0 | 371.9 | 2.7 | 0.2 | 0.0 | 20.5 | 9.9 | 0.5 | 2.0 | 0.0 | 0.3 | 0.3 | 0.5 |
| SF-17-T9-1:1-Bb-A-31 | 31.00 | 11.047 | 0.0 | 363.4 | 2.6 | 0.2 | 0.0 | 20.5 | 10.9 | 0.7 | 2.0 | 0.0 | 0.3 | 0.3 | 0.5 |
| SF-17-T9-1:1-Bb-A-48 | 48.00 | 12.247 | 0.0 | 375.3 | 2.5 | 0.2 | 0.0 | 20.4 | 11.8 | 0.7 | 2.0 | 0.4 | 0.4 | 0.3 | 0.6 |
| SF-17-T9-1:1-Bb-A-0 | 0.00 | 0.106 | 224.2 | 0.0 | 0.0 | 0.0 | 0.0 | 0.1 | 6.9 | 0.0 | 0.0 | 0.0 | 0.0 | 0.0 | 0.0 |
| SF-17-T10-1:1-Bb-B-3 | 3.00 | 0.114 | 223.7 | 0.0 | 0.0 | 0.0 | 0.0 | 0.2 | 6.8 | 0.0 | 0.0 | 0.0 | 0.0 | 0.0 | 0.0 |
| SF-17-T10-1:1-Bb-B-6 | 6.00 | 0.139 | 223.4 | 1.4 | 0.0 | 0.0 | 0.0 | 0.3 | 6.8 | 0.0 | 0.2 | 0.0 | 0.0 | 0.0 | 0.0 |
| SF-17-T10-1:1-Bb-B-8 | 8.00 | 0.189 | 223.8 | 3.8 | 0.0 | 0.1 | 0.0 | 0.4 | 6.8 | 0.0 | 0.3 | 0.0 | 0.0 | 0.0 | 0.0 |
| SF-17-T10-1:1-Bb-B-24 | 24.00 | 11.847 | 0.0 | 373.8 | 2.6 | 0.1 | 0.0 | 19.2 | 9.3 | 0.2 | 1.3 | 0.0 | 0.2 | 0.3 | 0.6 |
| SF-17-T10-1:1-Bb-B-31 | 31.00 | 11.447 | 0.0 | 364.2 | 2.6 | 0.1 | 0.0 | 19.4 | 11.0 | 0.0 | 1.3 | 0.3 | 0.3 | 0.3 | 0.6 |
| SF-17-T10-1:1-Bb-B-48 | 48.00 | 11.747 | 0.0 | 380.5 | 2.5 | 0.1 | 0.0 | 19.2 | 12.0 | 0.3 | 1.3 | 0.0 | 0.3 | 0.3 | 0.6 |
| SF-17-T12-11:1-Bb-B-0 | 0.00 | 0.110 | 223.9 | 0.0 | 0.0 | 0.0 | 0.0 | 0.1 | 6.8 | 0.0 | 0.0 | 0.0 | 0.0 | 0.0 | 0.0 |
| SF-17-T11-11:1-Bb-A-3 | 3.00 | 0.144 | 224.0 | 0.0 | 0.0 | 0.1 | 0.0 | 0.2 | 6.8 | 0.0 | 0.0 | 0.0 | 0.0 | 0.0 | 0.0 |
| SF-17-T11-11:1-Bb-A-6 | 6.00 | 0.187 | 222.0 | 1.0 | 0.0 | 0.0 | 0.0 | 0.4 | 6.6 | 0.0 | 0.6 | 0.0 | 0.0 | 0.0 | 0.0 |
| SF-17-T11-11:1-Bb-A-8 | 8.00 | 0.259 | 220.8 | 3.4 | 0.1 | 0.2 | 0.0 | 0.7 | 6.5 | 0.0 | 1.0 | 0.0 | 0.2 | 0.0 | 0.0 |
| SF-17-T11-11:1-Bb-A-24 | 24.00 | 10.797 | 0.0 | 363.4 | 2.8 | 0.5 | 0.0 | 22.3 | 8.4 | 1.0 | 4.4 | 0.0 | 0.2 | 0.3 | 0.5 |
| SF-17-T11-11:1-Bb-A-31 | 31.00 | 11.197 | 0.0 | 353.8 | 2.7 | 0.5 | 0.0 | 22.3 | 10.0 | 1.1 | 4.3 | 0.6 | 0.4 | 0.4 | 0.5 |
| SF-17-T11-11:1-Bb-A-48 | 48.00 | 11.497 | 0.0 | 365.6 | 2.7 | 0.4 | 0.0 | 22.2 | 11.3 | 1.4 | 4.5 | 0.6 | 0.5 | 0.3 | 0.5 |
| SF-17-T12-11:1-Bb-B-0 | 0.00 | 0.107 | 223.9 | 0.0 | 0.0 | 0.0 | 0.0 | 0.1 | 6.8 | 0.0 | 0.0 | 0.0 | 0.0 | 0.0 | 0.0 |
| SF-17-T12-11:1-Bb-B-3 | 3.00 | 0.123 | 222.4 | 0.0 | 0.0 | 0.0 | 0.0 | 0.2 | 6.7 | 0.0 | 0.0 | 0.0 | 0.0 | 0.0 | 0.0 |
| SF-17-T12-11:1-Bb-B-6 | 6.00 | 0.134 | 222.4 | 0.0 | 0.0 | 0.1 | 0.0 | 0.2 | 6.6 | 0.0 | 0.4 | 0.0 | 0.0 | 0.0 | 0.0 |
| SF-17-T12-11:1-Bb-B-8 | 8.00 | 0.138 | 225.8 | 0.0 | 0.0 | 0.1 | 0.0 | 0.3 | 6.9 | 0.0 | 0.5 | 0.0 | 0.0 | 0.0 | 0.0 |
| SF-17-T12-11:1-Bb-B-24 | 24.00 | 10.317 | 16.0 | 344.8 | 2.7 | 0.2 | 0.0 | 20.4 | 6.4 | 0.5 | 2.8 | 0.3 | 0.0 | 0.4 | 0.5 |
| SF-17-T12-11:1-Bb-B-31 | 31.00 | 11.447 | 0.0 | 360.8 | 2.7 | 0.2 | 0.0 | 21.4 | 9.1 | 0.5 | 2.8 | 0.0 | 0.2 | 0.3 | 0.6 |
| SF-17-T12-11:1-Bb-B-48 | 48.00 | 11.897 | 0.0 | 372.0 | 2.6 | 0.2 | 0.0 | 21.1 | 10.8 | 0.6 | 2.8 | 0.0 | 0.3 | 0.4 | 0.6 |
| SF-17-T14-1:1-Ca-B-0 | 0.00 | 0.106 | 233.7 | 0.0 | 0.0 | 0.0 | 0.0 | 0.1 | 7.2 | 0.0 | 0.0 | 0.0 | 0.0 | 0.0 | 0.0 |
| SF-17-T13-1:1-Ca-A-3 | 3.00 | 0.142 | 222.8 | 1.6 | 0.0 | 0.0 | 0.0 | 0.3 | 6.8 | 0.0 | 0.0 | 0.0 | 0.0 | 0.0 | 0.0 |
| SF-17-T13-1:1-Ca-A-6 | 6.00 | 0.388 | 217.9 | 9.6 | 0.0 | 0.0 | 0.0 | 0.8 | 6.6 | 0.0 | 0.3 | 0.0 | 0.0 | 0.0 | 0.0 |
| SF-17-T13-1:1-Ca-A-8 | 8.00 | 1.417 | 201.3 | 36.8 | 0.2 | 0.1 | 0.0 | 2.5 | 6.3 | 0.3 | 0.6 | 0.0 | 0.0 | 0.0 | 0.0 |
| SF-17-T13-1:1-Ca-A-24 | 24.00 | 11.347 | 0.0 | 374.9 | 2.7 | 0.1 | 0.0 | 18.4 | 11.2 | 0.5 | 1.7 | 0.0 | 0.2 | 0.4 | 0.5 |
| SF-17-T13-1:1-Ca-A-31 | 31.00 | 10.647 | 0.0 | 358.7 | 2.6 | 0.1 | 0.0 | 18.5 | 11.9 | 0.7 | 1.6 | 0.0 | 0.3 | 0.3 | 0.5 |
| SF-17-T13-1:1-Ca-A-48 | 48.00 | 12.097 | 0.0 | 369.5 | 2.5 | 0.1 | 0.0 | 18.4 | 13.0 | 0.7 | 1.6 | 0.2 | 0.2 | 0.3 | 0.5 |
| SF-17-T14-1:1-Ca-B-0 | 0.00 | n.d. | 233.7 | 0.0 | 0.0 | 0.0 | 0.0 | 0.1 | 7.2 | 0.0 | 0.0 | 0.0 | 0.0 | 0.0 | 0.0 |
| SF-17-T14-1:1-Ca-B-3 | 3.00 | n.d. | 233.9 | 0.0 | 0.0 | 0.0 | 0.0 | 0.1 | 7.2 | 0.0 | 0.0 | 0.0 | 0.0 | 0.0 | 0.0 |
| SF-17-T14-1:1-Ca-B-6 | 6.00 | n.d. | 233.4 | 0.0 | 0.0 | 0.0 | 0.0 | 0.0 | 7.1 | 0.0 | 0.0 | 0.0 | 0.0 | 0.0 | 0.0 |
| SF-17-T14-1:1-Ca-B-8 | 8.00 | n.d. | 237.4 | 0.0 | 0.0 | 0.0 | 0.0 | 0.1 | 7.2 | 0.0 | 0.0 | 0.0 | 0.0 | 0.0 | 0.0 |
| SF-17-T14-1:1-Ca-B-24 | 24.00 | n.d. | 234.0 | 0.0 | 0.0 | 0.0 | 0.0 | 0.0 | 7.2 | 0.0 | 0.0 | 0.0 | 0.0 | 0.0 | 0.0 |
| SF-17-T14-1:1-Ca-B-31 | 31.00 | n.d. | 234.0 | 0.0 | 0.0 | 0.0 | 0.0 | 0.1 | 7.1 | 0.0 | 0.0 | 0.0 | 0.0 | 0.0 | 0.0 |
| SF-17-T14-1:1-Ca-B-48 | 48.00 | n.d. | 234.7 | 0.0 | 0.0 | 0.0 | 0.0 | 0.0 | 7.5 | 0.0 | 0.0 | 0.0 | 0.0 | 0.0 | 0.0 |
| SF-17-T15-11:1-Ca-A-0 | 0.00 | 0.113 | 232.1 | 0.0 | 0.0 | 0.0 | 0.0 | 0.1 | 7.0 | 0.0 | 0.0 | 0.0 | 0.0 | 0.0 | 0.0 |
| SF-17-T15-11:1-Ca-A-3 | 3.00 | 0.141 | 231.6 | 0.0 | 0.0 | 0.0 | 0.0 | 0.2 | 7.0 | 0.0 | 0.0 | 0.0 | 0.0 | 0.0 | 0.0 |
| SF-17-T15-11:1-Ca-A-6 | 6.00 | 0.199 | 230.2 | 1.4 | 0.0 | 0.1 | 0.0 | 0.5 | 6.8 | 0.0 | 0.4 | 0.0 | 0.0 | 0.0 | 0.0 |
| SF-17-T15-11:1-Ca-A-8 | 8.00 | 0.387 | 228.2 | 6.5 | 0.1 | 0.2 | 0.0 | 1.0 | 6.8 | 0.6 | 0.8 | 0.0 | 0.0 | 0.0 | 0.0 |
| SF-17-T15-11:1-Ca-A-24 | 24.00 | 11.647 | 0.0 | 381.6 | 2.9 | 0.3 | 0.0 | 22.4 | 9.3 | 1.1 | 3.5 | 0.4 | 0.3 | 0.3 | 0.5 |
| SF-17-T15-11:1-Ca-A-31 | 31.00 | 10.397 | 0.0 | 366.1 | 2.9 | 0.3 | 0.0 | 22.6 | 10.7 | 1.5 | 3.5 | 0.4 | 0.2 | 0.4 | 0.5 |
| SF-17-T15-11:1-Ca-A-48 | 48.00 | 12.147 | 0.0 | 382.7 | 2.8 | 0.3 | 0.0 | 22.2 | 11.9 | 1.3 | 3.7 | 0.0 | 0.3 | 0.3 | 0.5 |
| SF-17-T15-11:1-Ca-A-0 | 0.00 | n.d. | 232.1 | 0.0 | 0.0 | 0.0 | 0.0 | 0.1 | 7.0 | 0.0 | 0.0 | 0.0 | 0.0 | 0.0 | 0.0 |
| SF-17-T16-11:1-Ca-B-3 | 3.00 | n.d. | 224.4 | 0.0 | 0.0 | 0.0 | 0.0 | 0.1 | 6.9 | 0.0 | 0.0 | 0.0 | 0.0 | 0.0 | 0.0 |
| SF-17-T16-11:1-Ca-B-6 | 6.00 | n.d. | 223.9 | 0.0 | 0.0 | 0.0 | 0.0 | 0.1 | 6.7 | 0.0 | 0.0 | 0.0 | 0.0 | 0.0 | 0.0 |
| SF-17-T16-11:1-Ca-B-8 | 8.00 | n.d. | 227.0 | 0.0 | 0.0 | 0.0 | 0.0 | 0.1 | 7.1 | 0.0 | 0.0 | 0.0 | 0.0 | 0.0 | 0.0 |
| SF-17-T16-11:1-Ca-B-24 | 24.00 | n.d. | 224.1 | 0.0 | 0.0 | 0.0 | 0.0 | 0.0 | 6.8 | 0.0 | 0.0 | 0.0 | 0.0 | 0.0 | 0.0 |
| SF-17-T16-11:1-Ca-B-31 | 31.00 | n.d. | 226.4 | 0.0 | 0.0 | 0.0 | 0.0 | 0.1 | 6.9 | 0.0 | 0.0 | 0.0 | 0.0 | 0.0 | 0.0 |
| SF-17-T16-11:1-Ca-B-48 | 48.00 | n.d. | 225.3 | 0.0 | 0.0 | 0.0 | 0.0 | 0.1 | 6.8 | 0.0 | 0.0 | 0.0 | 0.0 | 0.0 | 0.0 |
| SF-17-T17-1:1-ctrl-1-0 | 0.00 | 0.101 | 223.9 | 0.0 | 0.0 | 0.0 | 0.0 | 0.1 | 6.8 | 0.0 | 0.0 | 0.0 | 0.0 | 0.0 | 0.0 |
| SF-17-T17-1:1-ctrl-1-3 | 3.00 | 0.209 | 221.6 | 2.5 | 0.0 | 0.1 | 0.0 | 0.4 | 6.8 | 0.0 | 0.4 | 0.0 | 0.0 | 0.0 | 0.0 |
| SF-17-T17-1:1-ctrl-1-6 | 6.00 | 0.862 | 211.4 | 17.9 | 0.1 | 0.1 | 0.0 | 1.3 | 6.5 | 0.0 | 0.8 | 0.0 | 0.0 | 0.0 | 0.0 |
| SF-17-T17-1:1-ctrl-1-8 | 8.00 | 2.787 | 181.0 | 67.6 | 0.4 | 0.2 | 0.0 | 4.7 | 6.5 | 0.2 | 1.2 | 0.0 | 0.0 | 0.1 | 0.2 |
| SF-17-T17-1:1-ctrl-1-24 | 24.00 | 12.097 | 0.0 | 372.5 | 2.7 | 0.2 | 0.0 | 19.6 | 9.7 | 0.3 | 2.2 | 0.0 | 0.2 | 0.4 | 0.5 |
| SF-17-T17-1:1-ctrl-1-31 | 31.00 | 11.997 | 0.0 | 358.7 | 2.7 | 0.2 | 0.0 | 19.9 | 10.3 | 0.3 | 2.1 | 0.3 | 0.4 | 0.3 | 0.6 |
| SF-17-T17-1:1-ctrl-1-48 | 48.00 | 12.297 | 0.0 | 374.6 | 2.6 | 0.2 | 0.0 | 19.4 | 11.0 | 0.3 | 2.3 | 0.0 | 0.4 | 0.4 | 0.6 |
| SF-17-T17-1:1-ctrl-1-0 | 0.00 | 0.114 | 223.9 | 0.0 | 0.0 | 0.0 | 0.0 | 0.1 | 6.8 | 0.0 | 0.0 | 0.0 | 0.0 | 0.0 | 0.0 |
| SF-17-T18-11:1-ctrl-1-3 | 3.00 | 0.177 | 222.1 | 0.0 | 0.0 | 0.1 | 0.0 | 0.2 | 6.7 | 0.0 | 0.7 | 0.0 | 0.0 | 0.0 | 0.0 |
| SF-17-T18-11:1-ctrl-1-6 | 6.00 | 0.303 | 218.8 | 2.9 | 0.1 | 0.3 | 0.0 | 0.5 | 6.4 | 0.3 | 1.5 | 0.0 | 0.0 | 0.0 | 0.0 |
| SF-17-T18-11:1-ctrl-1-8 | 8.00 | 0.857 | 212.3 | 12.6 | 0.2 | 0.4 | 0.0 | 1.4 | 6.4 | 0.5 | 2.5 | 0.0 | 0.0 | 0.0 | 0.0 |
| SF-17-T18-11:1-ctrl-1-24 | 24.00 | 11.397 | 0.0 | 354.1 | 3.1 | 0.6 | 0.1 | 21.6 | 8.4 | 0.8 | 7.2 | 0.0 | 0.4 | 0.4 | 0.5 |

TABLE 14-continued

Optical density (OD) and extracellular compound concentrations at the different sampling time points (EPT = elapsed process time) of different pure and mixed cultures. Abbreviations used were: EtOH = ethanol, PYR = pyruvate, KTV = ketoisovalerate, DHIV = dihydroisovalerate, DHMB = 2,3-dihydroxy-2-metylbutyrate, GLY = glycerol, ACE = acetate, IBOOH = isobutyric acid, IBOH = isobutanol, m-BDO = meso-butanediol, d/l-BDO = d/l-butanediol, LAC = lactate, SUC = succinate.

| Sample [ ] | EPT [h] | OD [ ] | GLC [mM] | EtOH [mM] | PYR [mM] | KIV [mM] | DHIV + DHMB [mM] | GLY [mM] | ACE [mM] | IBOOH [mM] | IBOH [mM] | m-BDO [mM] | d/l-BDO [mM] | LAC [mM] | SUC [mM] |
|---|---|---|---|---|---|---|---|---|---|---|---|---|---|---|---|
| SF-17-T18-11:1-ctrl-1-31 | 31.00 | 10.947 | 0.0 | 351.4 | 3.1 | 0.6 | 0.1 | 21.9 | 9.6 | 1.0 | 7.1 | 0.8 | 0.5 | 0.4 | 0.5 |
| SF-17-T18-11:1-ctrl-1-48 | 48.00 | 11.797 | 0.0 | 355.5 | 3.0 | 0.6 | 0.1 | 21.4 | 10.5 | 0.8 | 7.3 | 0.9 | 0.7 | 0.3 | 0.5 |

Materials & Methods for Examples 21-25

Yeast synthetic medium w/o amino acids, w/o glucose, w/o ethanol/Tween (2×): 13.4 g/l, Yeast Nitrogen Base w/o amino acids (Difco 0919-15-3); 40 mg/L thiamine; 40 mg/L niacin; 200 ml/L 1M MES buffer, pH=5.5; Supplement aa sol. without histidine and uracil (SAAS-1 10×); 18.5 g/L, Synthetic complete amino acid dropout (Kaiser)-His, -Ura (Formedium).

SEED medium: 10.000 mL Yeast synthetic medium w/o aa, w/o glucose, w/o ethanol/Tween (2×); 2.000 mL Supplement aa sol. without histidine and uracil (SAAS-1 10×); 3.200 mL 250 g/L glucose solution (resulting in 40 g/l glucose); 0.046 mL Na-acetate stock solution; 4.754 mL H$_2$O Example 21 (Prophetic):

Construction of Isobutanologen Strains Expressing a Formaldehyde Dehydrogenase

*P. putida* fdhA (SEQ ID NO:7) (GI:1169603) and *S. cerevisiae* SFA1 (SEQ ID NO:6) (van den Berg et al., Yeast 13(6): 551-9 (1997)) are used to synthesize genes in vitro using codon-optimization algorithms for *S. cerevisiae* (e.g. DNA 2.0). The gene cassettes are designed to place 5' BamHI and 3' MluI restriction sites for subcloning of the coding sequences into expression plasmid pBTX1 (SEQ ID NO:15). pBTX1 is derived from the pRS413 vector backbone (ATCC #87518) and contains the FBA1 promoter, multiple cloning site (BamHI, MluI), and ADH1 terminator.

An isobutanologen is constructed by transformation of plasmids pBTX1::SFA1 and pLH804::L2V4 into the host strain PNY2145. Plasmid pLH804::L2V4 is derived from the pHR81 vector backbone (ATCC #87541) and contains: the *A. caccae* K9JB4P KARI driven by the ILV5 promoter and ILV5 terminator, and the *S. mutans* L2V4 DHAD driven by the TEF1(M7) promoter and FBA1 terminator (SEQ ID NO:22). Plasmids are introduced by lithium acetate transformation method (Methods in Yeast Genetics, 2005, page 113), and transformants are selected on synthetic complete medium, minus histidine and uracil, with 1% ethanol as carbon source. Transformants are then transferred to plates containing synthetic complete medium, minus histidine and uracil, with 2% glucose as carbon source and optionally ethanol (0.05%) or acetate (2 mM) as a C2 supplement. Freezer vials are made by dilution of log-phase cultures with 45% glycerol to a final glycerol concentration of 15% (w/v).

An isobutanologen is constructed by transformation of plasmids pBTX1::fdhA and pLH804::L2V4 into the host strain PNY2145. Plasmid pLH804::L2V4 is derived from the pHR81 vector backbone (ATCC #87541) and contains: the *A. caccae* K9JB4P KARI driven by the ILV5 promoter and ILV5 terminator, and the *S. mutans* L2V4 DHAD driven by the TEF1(M7) promoter and FBA1 terminator (SEQ ID NO:22). Plasmids are introduced by lithium acetate transformation method (Methods in Yeast Genetics, 2005, page 113), and transformants are selected on synthetic complete medium, minus histidine and uracil, with 1% ethanol as carbon source. Transformants are then transferred to plates containing synthetic complete medium, minus histidine and uracil, with 2% glucose as carbon source and optionally ethanol (0.05%) or acetate (2 mM) as a C2 supplement. Freezer vials are made by dilution of log-phase cultures with 45% glycerol to a final glycerol concentration of 15% (w/v).

Example 22 (Prophetic):

Construction of Isobutanologen Strains Expressing a Sulfonylurea-Resistant ALS (e.g. SMR1-410)

To construct an expression plasmid, the protein coding sequence for *S. cerevisiae* SMR1-410 (SEQ ID NO:9; nucleic acid sequence SEQ ID NO:8) is used to synthesize genes in vitro using codon-optimization algorithms for *S. cerevisiae* (e.g. DNA 2.0). The SMR1-410 gene cassette is designed to place 5' BamHI and 3' MluI restriction sites for subcloning of the coding sequences into expression plasmid pBTX1 (SEQ ID NO:15). pBTX1 is derived from the pRS413 vector backbone (ATCC #87518) and contains the FBA1 promoter, multiple cloning site (BamHI, MluI), and ADH1 terminator.

An isobutanologen is constructed by transformation of plasmids pBTX1::SMR1-410 and pLH804::L2V4 into the host strain PNY2145 (referenced in US Pat. Publ. No. 2014/0004526, which is incorporated herein by reference in its entirety, and described in Example 26). Plasmid pLH804::L2V4 is derived from the pHR81 vector backbone (ATCC #87541) and contains: the *A. caccae* K9JB4P KARI driven by the ILV5 promoter and ILV5 terminator, and the *S. mutans* L2V4 DHAD driven by the TEF1(M7) promoter and FBA1 terminator (SEQ ID NO:22). Plasmids are introduced by lithium acetate transformation method (Methods in Yeast Genetics, 2005, page 113), and transformants are selected on synthetic complete medium, minus histidine and uracil, with 1% ethanol as carbon source. Transformants are then transferred to plates containing synthetic complete medium, minus histidine and uracil, with 2% glucose as carbon source and optionally ethanol (0.05%) or acetate (2 mM) as a C2 supplement. Freezer vials are made by dilution of log-phase cultures with 45% glycerol to a final glycerol concentration of 15% (w/v).

Example 23 (Prophetic):

Construction of Isobutanologen Strains Expressing Genes Conferring Sulfite Resistance To construct expression plasmids, the protein coding sequences for *S. cerevisiae* FZF1-4 (SEQ ID NO:11) (Park, Lopez et al. 1999) and SSU1 (SEQ ID NO:12) are used to synthesize genes in vitro using codon-optimization algorithms for *S. cerevisiae* (e.g. DNA 2.0). SEQ ID NO:10 is the wild type protein sequence for FZF1. The gene cassettes are designed to place 5' BamHI and 3' MluI restriction sites for subcloning of the coding sequences into expression plasmid pBTX1 (SEQ ID NO:15). pBTX1 is derived from the pRS413 vector backbone (ATCC #87518) and contains the FBA1 promoter, multiple cloning site (BamHI, MluI), and ADH1 terminator.

An isobutanologen is constructed by transformation of plasmids pBTX1::FZF1-4 and pLH804::L2V4 into the host strain PNY2145 (described herein) that contains a deletion of the chromosomal FZF1 gene. The FZF1 deletion in PNY2145 is made using standard yeast deletions using a kanMX4 cassette (Brachmann, et al. Designer deletion strains derived from *Saccharomyces cerevisiae* S288C: a useful set of strains and plasmids for PCR-mediated gene disruption and other applications. Yeast. 14, 115-132 (1998). Plasmid pLH804::L2V4 is derived from the pHR81 vector backbone (ATCC #87541) and contains: the *A. caccae* K9JB4P KARI driven by the ILV5 promoter and ILV5 terminator, and the *S. mutans* L2V4 DHAD driven by the TEF1(M7) promoter and FBA1 terminator (SEQ ID NO:22). Plasmids are introduced by lithium acetate transformation method (Methods in Yeast Genetics, 2005, page 113), and transformants are selected on synthetic complete medium, minus histidine and uracil, with 1% ethanol as carbon source. Transformants are then transferred to plates containing synthetic complete medium, minus histidine and uracil, with 2% glucose as carbon source and optionally ethanol (0.05%) or acetate (2 mM) as a C2 supplement. Freezer vials are made by dilution of log-phase cultures with 45% glycerol to a final glycerol concentration of 15% (w/v).

An isobutanologen is constructed by transformation of plasmids pBTX1::SSU1and pLH804::L2V4 into the host strain PNY2145 (described herein). Plasmid pLH804::L2V4 is derived from the pHR81 vector backbone (ATCC #87541) and contains: the *A. caccae* K9JB4P KARI driven by the ILV5 promoter and ILV5 terminator, and the *S. mutans* L2V4 DHAD driven by the TEF1(M7) promoter and FBA1 terminator (SEQ ID NO:22). Plasmids are introduced by lithium acetate transformation method (Methods in Yeast Genetics, 2005, page 113), and transformants are selected on synthetic complete medium, minus histidine and uracil, with 1% ethanol as carbon source. Transformants are then transferred to plates containing synthetic complete medium, minus histidine and uracil, with 2% glucose as carbon source and optionally ethanol (0.05%) or acetate (2 mM) as a C2 supplement. Freezer vials are made by dilution of log-phase cultures with 45% glycerol to a final glycerol concentration of 15% (w/v).

Example 24 (Prophetic):

Construction of Isobutanologen Strains Expressing a Glyphosate Resistance 3-phosphoshikimate 1-carboxylvinyltransferase To construct an expression plasmid, the protein coding sequence for *Salmonella typhi* aroA$^{GLY+}$ (SEQ ID NO:13) (Stalker, et al., *J Biol Chem* 260(8): 4724-8 (1985)) is used to synthesize genes in vitro using codon-optimization algorithms for *S. cerevisiae* (e.g. DNA 2.0). The aroA$^{GLY+}$ gene cassette is designed to place 5' BamHI and 3' MluI restriction sites for subcloning of the coding sequences into expression plasmid pBTX1 (SEQ ID NO:15). pBTX1 is derived from the pRS413 vector backbone (ATCC #87518) and contains the FBA1 promoter, multiple cloning site (BamHI, MluI), and ADH1 terminator.

An isobutanologen is constructed by transformation of plasmids pBTX1::aroA$^{GLY+}$ and pLH804::L2V4 into the host strain PNY2145 (described herein). Plasmid pLH804::L2V4 is derived from the pHR81 vector backbone (ATCC #87541) and contains: the *A. caccae* K9JB4P KARI driven by the ILV5 promoter and ILV5 terminator, and the *S. mutans* L2V4 DHAD driven by the TEFL (M7) promoter and FBA1 terminator (SEQ ID NO:22). Plasmids are introduced by lithium acetate transformation method (Methods in Yeast Genetics, 2005, page 113), and transformants are selected on synthetic complete medium, minus histidine and uracil, with 1% ethanol as carbon source. Transformants are then transferred to plates containing synthetic complete medium, minus histidine and uracil, with 2% glucose as carbon source and optionally ethanol (0.05%) or acetate (2 mM) as a C2 supplement. Freezer vials are made by dilution of log-phase cultures with 45% glycerol to a final glycerol concentration of 15% (w/v).

Example 25 (Prophetic):

Genetic Engineering for Increased Inhibitor Tolerance in Butanologen Yeast

In some embodiments, the butanologen is engineered for increased inhibitor tolerance by expressing or overexpressing a formaldehyde dehydrogenase. The formaldehyde dehydrogenase is selected from one of the following EC groups: EC 1.1.1.284, EC 1.1.1.1, EC 1.2.1.46, EC 1.2.1.66, EC 3.1.2.12, EC 1.2.2.B1 and EC 1.2.2.B2. ED 1.2.2.B1 and EC 1.2.2.B2 are no official designators, but are defined by the BRENDA protein database. Especially suited formaldehyde dehydrogenases are:

SFA1 (YDL168W, ADH5): glutathione-dependent formaldehyde dehydrogenase (van den Berg et al., *Yeast* 13(6): 551-9 (1997)) (SEQ ID NO:6) and *Pseudomonas putida* glutathione-independent formaldehyde dehydrogenase (SEQ ID NO:7).

In some embodiments, the butanologen is engineered for increased inhibitor tolerance by expressing or overexpressing a sulfonylurea-resistant ALS (e.g. SMR1-410) (Yadav et al., *Proc Natl Acad Sci USA* 83(12): 4418-22 (1986)) (SEQ ID NO:9).

In some embodiments, the butanologen is engineered for increased inhibitor tolerance by expressing or overexpressing other sulfonylurea-resistant ALS enzymes that qualify for (over)expression.

In some embodiments, the butanologen is engineered for increased inhibitor tolerance by expressing or overexpressing sulfite resistance by convert FZF1 (SEQ ID NO:10) to FZF1-4 (SEQ ID NO:11) (Park et al., *Curr Genet* 36(6): 339-44. (1999)) or overexpressing SSU1 (SEQ ID NO:12).

FZF1 (YGL254W, NRC299, RSU1 2, SUL1) is a transcription factor involved in sulfite metabolism, sole identified regulatory target is SSU1, overexpression suppresses sulfite-sensitivity of many unrelated mutants due to hyperactivation of SSU1.

Overexpression of SSU1 (YPL092W, LPG16). SSU1 is a plasma membrane sulfite pump involved in sulfite metabolism and required for efficient sulfite efflux. Homolog enzymes may be considered for overexpression as well to confer increased tolerance/improved competitiveness.

In some embodiments, the butanologen is engineered for increased inhibitor tolerance by expressing or overexpressing a glyphosate resistance 3-phosphoshikimate 1-carboxylvinyltransferase (e.g. aroA$^{gly+}$) (SEQ ID NO:13) (Stalker et al., *J Biol Chem* 260(8): 4724-8 (1985)).

All other glyphosate resistant 3-phosphoshikimate 1-carboxyvinyltransferases qualify for expression or overexpression.

Example 26

Strain Construction

Construction of Strain PNY2115

*Saccharomyces cerevisiae* strain PNY0827 is used as the host cell for further genetic manipulation for PNY2115. PNY0827 refers to a strain derived from *Saccharomyces cerevisiae* which has been deposited at the ATCC under the Budapest Treaty on Sep. 22, 2011 at the American Type Culture Collection, Patent Depository 10801 University Boulevard, Manassas, Va. 20110-2209 and has the patent deposit designation PTA-12105.

Deletion of URA3 and Sporulation into Haploids

In order to delete the endogenous URA3 coding region, a deletion cassette was PCR-amplified from pLA54 (SEQ ID NO:158) which contains a P$_{TEF1}$-kanMX4-TEF1t cassette flanked by loxP sites to allow homologous recombination in vivo and subsequent removal of the KANMX4 marker. PCR was done by using Phusion High Fidelity PCR Master Mix (New England BioLabs; Ipswich, Mass.) and primers BK505 (SEQ ID NO:101) and BK506 (SEQ ID NO:102). The URA3 portion of each primer was derived from the 5' region 180 bp upstream of the URA3 ATG and 3' region 78 bp downstream of the coding region such that integration of the kanMX4 cassette results in replacement of the URA3 coding region. The PCR product was transformed into PNY0827 using standard genetic techniques (Methods in Yeast Genetics, 2005, Cold Spring Harbor Laboratory Press, Cold Spring Harbor, N.Y., pp. 201-202) and transformants were selected on YEP medium supplemented 2% glucose and 100 μg/ml Geneticin at 30° C. Transformants were screened by colony PCR with primers LA468 (SEQ ID NO:161) and LA492 (SEQ ID NO:104) to verify presence of the integration cassette. A heterozygous diploid was obtained: NYLA98, which has the genotype MATa/α URA3/ura3::loxP-kanMX4-loxP. To obtain haploids, NYLA98 was sporulated using standard methods (Codón A C, Gasent-Ramirez J M, Benítez T. Factors which affect the frequency of sporulation and tetrad formation in *Saccharomyces cerevisiae* baker's yeast. Appl Environ Microbiol. 1995 PMID: 7574601). Tetrads were dissected using a micromanipulator and grown on rich YPE medium supplemented with 2% glucose. Tetrads containing four viable spores were patched onto synthetic complete medium lacking uracil supplemented with 2% glucose, and the mating type was verified by multiplex colony PCR using primers AK109-1 (SEQ ID NO:105), AK109-2 (SEQ ID NO: 106), and AK109-3 (SEQ ID NO:107). The resulting identified haploid strain called NYLA103, which has the genotype: MATα ura3Δ::loxP-kanMX4-loxP, and NYLA106, which has the genotype: MATa ura3Δ::loxP-kanMX4-loxP.

Deletion of His3

To delete the endogenous HIS3 coding region, a scarless deletion cassette was used. The four fragments for the PCR cassette for the scarless HIS3 deletion were amplified using Phusion High Fidelity PCR Master Mix (New England BioLabs; Ipswich, Mass.) and CEN.PK 113-7D genomic DNA as template, prepared with a Gentra Puregene Yeast/Bact kit (Qiagen; Valencia, Calif.). HIS3 Fragment A was amplified with primer oBP452 (SEQ ID NO:89) and primer oBP453 (SEQ ID NO:109), containing a 5' tail with homology to the 5' end of HIS3 Fragment B. HIS3 Fragment B was amplified with primer oBP454 (SEQ ID NO:110), containing a 5' tail with homology to the 3' end of HIS3 Fragment A, and primer oBP455 (SEQ ID NO:90) containing a 5' tail with homology to the 5' end of HIS3 Fragment U. HIS3 Fragment U was amplified with primer oBP456 (SEQ ID NO:91), containing a 5' tail with homology to the 3' end of HIS3 Fragment B, and primer oBP457 (SEQ ID NO:86), containing a 5' tail with homology to the 5' end of HIS3 Fragment C. HIS3 Fragment C was amplified with primer oBP458 (SEQ ID NO:87), containing a 5' tail with homology to the 3' end of HIS3 Fragment U, and primer oBP459 (SEQ ID NO:88). PCR products were purified with a PCR Purification kit (Qiagen). HIS3 Fragment AB was created by overlapping PCR by mixing HIS3 Fragment A and HIS3 Fragment B and amplifying with primers oBP452 (SEQ ID NO:89) and oBP455 (SEQ ID NO:90). HIS3 Fragment UC was created by overlapping PCR by mixing HIS3 Fragment U and HIS3 Fragment C and amplifying with primers oBP456 (SEQ ID NO:91) and oBP459 (SEQ ID NO:88). The resulting PCR products were purified on an agarose gel followed by a Gel Extraction kit (Qiagen). The HIS3 ABUC cassette was created by overlapping PCR by mixing HIS3 Fragment AB and HIS3 Fragment UC and amplifying with primers oBP452 (SEQ ID NO:89) and oBP459 (SEQ ID NO:88). The PCR product was purified with a PCR Purification kit (Qiagen). Competent cells of NYLA106 were transformed with the HIS3 ABUC PCR cassette and were plated on synthetic complete medium lacking uracil supplemented with 2% glucose at 30° C. Transformants were screened to verify correct integration by replica plating onto synthetic complete medium lacking histidine and supplemented with 2% glucose at 30° C. Genomic DNA preps were made to verify the integration by PCR using primers oBP460 (SEQ ID NO:93) and LA135 (SEQ ID NO:94) for the 5' end and primers oBP461 (SEQ ID NO:95) and LA92 (SEQ ID NO:96) for the 3' end. The URA3 marker was recycled by plating on synthetic complete medium supplemented with 2% glucose and 5-FOA at 30° C. following standard protocols. Marker removal was confirmed by patching colonies from the 5-FOA plates onto SD –URA medium to verify the absence of growth. The resulting identified strain, called PNY2003 has the genotype: MATa ura3Δ::loxP-kanMX4-loxP his3Δ.

Deletion of PDC1

To delete the endogenous PDC1 coding region, a deletion cassette was PCR-amplified from pLA59 (SEQ ID NO:97), which contains a URA3 marker flanked by degenerate loxP sites to allow homologous recombination in vivo and subsequent removal of the URA3 marker. PCR was done by using Phusion High Fidelity PCR Master Mix (New England BioLabs; Ipswich, Mass.) and primers LA678 (SEQ ID NO:98) and LA679 (SEQ ID NO:99). The PDC1 portion of each primer was derived from the 5' region 50 bp downstream of the PDC1 start codon and 3' region 50 bp upstream of the stop codon such that integration of the URA3 cassette results in replacement of the PDC1 coding region but leaves the first 50 bp and the last 50 bp of the coding region. The PCR product was transformed into PNY2003 using standard genetic techniques and transformants were selected on synthetic complete medium lacking uracil and supplemented with 2% glucose at 30° C. Transformants were screened to verify correct integration by colony PCR using primers LA337 (SEQ ID NO:111), external to the 5' coding region and LA135 (SEQ ID NO:94), an internal primer to URA3.

Positive transformants were then screened by colony PCR using primers LA692 (SEQ ID NO: 112) and LA693 (SEQ ID NO:113), internal to the PDC1 coding region. The URA3 marker was recycled by transforming with pLA34 (SEQ ID NO:184) containing the CRE recombinase under the GAL1 promoter and plated on synthetic complete medium lacking histidine and supplemented with 2% glucose at 30° C. Transformants were plated on rich medium supplemented with 0.5% galactose to induce the recombinase. Marker removal was confirmed by patching colonies to synthetic complete medium lacking uracil and supplemented with 2% glucose to verify absence of growth. The resulting identified strain, called PNY2008 has the genotype: MATa ura3Δ::loxP-kanMX4-loxP his3Δ pdc1Δ::loxP71/66.

Deletion of PDC5

To delete the endogenous PDC5 coding region, a deletion cassette was PCR-amplified from pLA59 (SEQ ID NO:97), which contains a URA3 marker flanked by degenerate loxP sites to allow homologous recombination in vivo and subsequent removal of the URA3 marker. PCR was done by using Phusion High Fidelity PCR Master Mix (New England BioLabs; Ipswich, Mass.) and primers LA722 (SEQ ID NO:185) and LA733 (SEQ ID NO:186). The PDC5 portion of each primer was derived from the 5' region 50 bp upstream of the PDC5 start codon and 3' region 50 bp downstream of the stop codon such that integration of the URA3 cassette results in replacement of the entire PDC5 coding region. The PCR product was transformed into PNY2008 using standard genetic techniques and transformants were selected on synthetic complete medium lacking uracil and supplemented with 1% ethanol at 30° C. Transformants were screened to verify correct integration by colony PCR using primers LA453 (SEQ ID NO:187), external to the 5' coding region and LA135 (SEQ ID NO:94), an internal primer to URA3. Positive transformants were then screened by colony PCR using primers LA694 (SEQ ID NO:188) and LA695 (SEQ ID NO:189), internal to the PDC5 coding region. The URA3 marker was recycled by transforming with pLA34 (SEQ ID NO:184) containing the CRE recombinase under the GAL1 promoter and plated on synthetic complete medium lacking histidine and supplemented with 1% ethanol at 30° C. Transformants were plated on rich YEP medium supplemented with 1% ethanol and 0.5% galactose to induce the recombinase. Marker removal was confirmed by patching colonies to synthetic complete medium lacking uracil and supplemented with 1% ethanol to verify absence of growth. The resulting identified strain, called PNY2009 has the genotype: MATa ura3Δ::loxP-kanMX4-loxP his3Δ pdc1Δ::loxP71/66 pdc5Δ::loxP71/66.

Deletion of FRA2

The FRA2 deletion was designed to delete 250 nucleotides from the 3' end of the coding sequence, leaving the first 113 nucleotides of the FRA2 coding sequence intact. An in-frame stop codon was present 7 nucleotides downstream of the deletion. The four fragments for the PCR cassette for the scarless FRA2 deletion were amplified using Phusion High Fidelity PCR Master Mix (New England BioLabs; Ipswich, Mass.) and CEN.PK 113-7D genomic DNA as template, prepared with a Gentra Puregene Yeast/Bact kit (Qiagen; Valencia, Calif.). FRA2 Fragment A was amplified with primer oBP594 (SEQ ID NO:190) and primer oBP595 (SEQ ID NO:191), containing a 5' tail with homology to the 5' end of FRA2 Fragment B. FRA2 Fragment B was amplified with primer oBP596 (SEQ ID NO:192), containing a 5' tail with homology to the 3' end of FRA2 Fragment A, and primer oBP597 (SEQ ID NO:193), containing a 5' tail with homology to the 5' end of FRA2 Fragment U. FRA2 Fragment U was amplified with primer oBP598 (SEQ ID NO:194), containing a 5' tail with homology to the 3' end of FRA2 Fragment B, and primer oBP599 (SEQ ID NO:195), containing a 5' tail with homology to the 5' end of FRA2 Fragment C. FRA2 Fragment C was amplified with primer oBP600 (SEQ ID NO:196), containing a 5' tail with homology to the 3' end of FRA2 Fragment U, and primer oBP601 (SEQ ID NO:197). PCR products were purified with a PCR Purification kit (Qiagen). FRA2 Fragment AB was created by overlapping PCR by mixing FRA2 Fragment A and FRA2 Fragment B and amplifying with primers oBP594 (SEQ ID NO:190) and oBP597 (SEQ ID NO:193). FRA2 Fragment UC was created by overlapping PCR by mixing FRA2 Fragment U and FRA2 Fragment C and amplifying with primers oBP598 (SEQ ID NO:194) and oBP601 (SEQ ID NO:197). The resulting PCR products were purified on an agarose gel followed by a Gel Extraction kit (Qiagen). The FRA2 ABUC cassette was created by overlapping PCR by mixing FRA2 Fragment AB and FRA2 Fragment UC and amplifying with primers oBP594 (SEQ ID NO:190) and oBP601 (SEQ ID NO:197). The PCR product was purified with a PCR Purification kit (Qiagen).

To delete the endogenous FRA2 coding region, the scarless deletion cassette obtained above was transformed into PNY2009 using standard techniques and plated on synthetic complete medium lacking uracil and supplemented with 1% ethanol. Genomic DNA preps were made to verify the integration by PCR using primers oBP602 (SEQ ID NO:198) and LA135 (SEQ ID NO:94) for the 5' end, and primers oBP602 (SEQ ID NO:198) and oBP603 (SEQ ID NO:199) to amplify the whole locus. The URA3 marker was recycled by plating on synthetic complete medium supplemented with 1% ethanol and 5-FOA (5-Fluoroorotic Acid) at 30° C. following standard protocols. Marker removal was confirmed by patching colonies from the 5-FOA plates onto synthetic complete medium lacking uracil and supplemented with 1% ethanol to verify the absence of growth. The resulting identified strain, PNY2037, has the genotype: MATa ura3Δ::loxP-kanMX4-loxP his3Δ pdc1Δ::loxP71/66 pdc5Δ::loxP71/66 fra2Δ.

Addition of Native 2 Micron Plasmid

The loxP71-URA3-loxP66 marker was PCR-amplified using Phusion DNA polymerase (New England BioLabs; Ipswich, Mass.) from pLA59 (SEQ ID NO:97), and transformed along with the LA811×LA817 (SEQ ID NOs:200, 201) and LA812×LA818 (SEQ ID NOs:202, 203) 2-micron plasmid fragments (amplified from the native 2-micron plasmid from CEN.PK 113-7D; Centraalbureau voor Schimmelcultures (CBS) Fungal Biodiversity Centre) into strain PNY2037 on SE −URA plates at 30° C. The resulting strain PNY2037 2μ::loxP71-URA3-loxP66 was transformed with pLA34 (pRS423::cre) (also called, pLA34) (SEQ ID NO:184) and selected on SE −HIS −URA plates at 30° C. Transformants were patched onto YP-1% galactose plates and allowed to grow for 48 hrs at 30° C. to induce Cre recombinase expression. Individual colonies were then patched onto SE −URA, SE −HIS, and YPE plates to confirm URA3 marker removal. The resulting identified strain, PNY2050, has the genotype: MATa ura3Δ::loxP-kanMX4-loxP, his3Δ pdc1Δ::loxP71/66 pdc5Δ::loxP71/66 fra2Δ 2-micron.

Construction of PNY2115 from PNY2050

Construction of PNY2115 [MATa ura3Δ::loxP his3Δ pdc5Δ::loxP66/71 fra2Δ 2-micron plasmid (CEN.PK2) pdc1Δ::P[PDC1]-ALS|alsS_Bs-CYC1t-loxP71/66 pdc6Δ:: (UAS)PGK1-P[FBA1]-KIVD|Lg(y)-TDH3t-loxP71/66 adh1Δ::P[ADH1]-ADH|Bi(y)-ADHt-loxP71/66 fra2Δ::P

[ILV5]-ADH|Bi(y)-ADHt-loxP71/66 gpd2Δ::loxP71/66] from PNY2050 was as follows.

Pdc1Δ::P[PDC1]-ALS|alsS_Bs-CYC1t-loxP71/66

To integrate alsS into the pdc1Δ::loxP66/71 locus of PNY2050 using the endogenous PDC1 promoter, an integration cassette was PCR-amplified from pLA71 (SEQ ID NO:209), which contains the gene acetolactate synthase from the species *Bacillus subtilis* with a FBA1 promoter and a CYC1 terminator, and a URA3 marker flanked by degenerate loxP sites to allow homologous recombination in vivo and subsequent removal of the URA3 marker. PCR was done by using KAPA HiFi and primers 895 (SEQ ID NO:212) and 679 (SEQ ID NO:213). The PDC1 portion of each primer was derived from 60 bp of the upstream of the coding sequence and 50 bp that are 53 bp upstream of the stop codon. The PCR product was transformed into PNY2050 using standard genetic techniques and transformants were selected on synthetic complete media lacking uracil and supplemented with 1% ethanol at 30° C. Transformants were screened to verify correct integration by colony PCR using primers 681 (SEQ ID NO:214), external to the 3' coding region and 92 (SEQ ID NO:215), internal to the URA3 gene. Positive transformants were then prepped for genomic DNA and screened by PCR using primers N245 (SEQ ID NO:216) and N246 (SEQ ID NO:217). The URA3 marker was recycled by transforming with pLA34 (SEQ ID NO:184) containing the CRE recombinase under the GAL1 promoter and plated on synthetic complete media lacking histidine and supplemented with 1% ethanol at 30° C. Transformants were plated on rich media supplemented with 1% ethanol and 0.5% galactose to induce the recombinase. Marker removal was confirmed by patching colonies to synthetic complete media lacking uracil and supplemented with 1% ethanol to verify absence of growth. The resulting identified strain, called PNY2090 has the genotype MATa ura3Δ::loxP, his3Δ, pdc1Δ::loxP71/66, pdc5Δ::loxP71/66 fra2Δ 2-micron pdc1Δ::P[PDC1]-ALS|alsS_Bs-CYC1t-loxP71/66.

Pdc6Δ::(UAS)PGK1-P[FBA1]-KIVD|Lg(y)-TDH3t-loxP71/66

To delete the endogenous PDC6 coding region, an integration cassette was PCR-amplified from pLA78 (SEQ ID NO:210), which contains the kivD gene from the species *Listeria grayi* with a hybrid FBA1 promoter and a TDH3 terminator, and a URA3 marker flanked by degenerate loxP sites to allow homologous recombination in vivo and subsequent removal of the URA3 marker. PCR was done by using KAPA HiFi and primers 896 (SEQ ID NO:218) and 897 (SEQ ID NO:219). The PDC6 portion of each primer was derived from 60 bp upstream of the coding sequence and 59 bp downstream of the coding region. The PCR product was transformed into PNY2090 using standard genetic techniques and transformants were selected on synthetic complete media lacking uracil and supplemented with 1% ethanol at 30° C. Transformants were screened to verify correct integration by colony PCR using primers 365 (SEQ ID NO:220) and 366 (SEQ ID NO:221), internal primers to the PDC6 gene. Transformants with an absence of product were then screened by colony PCR N638 (SEQ ID NO:222), external to the 5' end of the gene, and 740 (SEQ ID NO:223), internal to the FBA1 promoter. Positive transformants were than the prepped for genomic DNA and screened by PCR with two external primers to the PDC6 coding sequence. Positive integrants would yield a 4720 bp product, while PDC6 wild type transformants would yield a 2130 bp product. The URA3 marker was recycled by transforming with pLA34 containing the CRE recombinase under the GAL1 promoter and plated on synthetic complete media lacking histidine and supplemented with 1% ethanol at 30° C. Transformants were plated on rich media supplemented with 1% ethanol and 0.5% galactose to induce the recombinase. Marker removal was confirmed by patching colonies to synthetic complete media lacking uracil and supplemented with 1% ethanol to verify absence of growth. The resulting identified strain is called PNY2093 and has the genotype MATa ura3Δ::loxP his3Δ pdc5Δ::loxP71/66 fra2Δ 2-micron pdc1Δ::P[PDC1]-ALS|alsS_Bs-CYC1t-loxP71/66 pdc6Δ::(UAS)PGK1-P[FBA1]-KIVD|Lg(y)-TDH3t-loxP71/66.

Adh1Δ::P[ADH1]-ADH|Bi(y)-ADHt-loxP71/66

To delete the endogenous ADH1 coding region and integrate BiADH using the endogenous ADH1 promoter, an integration cassette was PCR-amplified from pLA65 (SEQ ID NO:211), which contains the alcohol dehydrogenase from the species *Beijerinckii incida* with an ILV5 promoter and a ADH1 terminator, and a URA3 marker flanked by degenerate loxP sites to allow homologous recombination in vivo and subsequent removal of the URA3 marker. PCR was done by using KAPA HiFi and primers 856 (SEQ ID NO:224) and 857 (SEQ ID NO:225). The ADH1 portion of each primer was derived from the 5' region 50 bp upstream of the ADH1 start codon and the last 50 bp of the coding region. The PCR product was transformed into PNY2093 using standard genetic techniques and transformants were selected on synthetic complete media lacking uracil and supplemented with 1% ethanol at 30° C. Transformants were screened to verify correct integration by colony PCR using primers BK415 (SEQ ID NO:226), external to the 5' coding region and N1092 (SEQ ID NO:227), internal to the BiADH gene. Positive transformants were then screened by colony PCR using primers 413 (SEQ ID NO:160), external to the 3' coding region, and 92 (SEQ ID NO:215), internal to the URA3 marker. The URA3 marker was recycled by transforming with pLA34 (SEQ ID NO:184) containing the CRE recombinase under the GAL1 promoter and plated on synthetic complete media lacking histidine and supplemented with 1% ethanol at 30° C. Transformants were plated on rich media supplemented with 1% ethanol and 0.5% galactose to induce the recombinase. Marker removal was confirmed by patching colonies to synthetic complete media lacking uracil and supplemented with 1% ethanol to verify absence of growth. The resulting identified strain, called PNY2101 has the genotype MATa ura3Δ::loxP his3Δ pdc5Δ::loxP71/66 fra2Δ 2-micron pdc1Δ::P[PDC1]-ALS|alsS_Bs-CYC1t-loxP71/66 pdc6Δ::(UAS)PGK1-P[FBA1]-KIVD|Lg(y)-TDH3t-loxP71/66 adh1Δ::P[ADH1]-ADH|Bi(y)-ADHt-loxP71/66.

Fra2Δ::P[ILV5]-ADH|Bi(y)-ADHt-loxP71/66

To integrate BiADH into the flan locus of PNY2101, an integration cassette was PCR-amplified from pLA65 (SEQ ID NO:211), which contains the alcohol dehydrogenase from the species *Beijerinckii indica* with an ILV5 promoter and an ADH1 terminator, and a URA3 marker flanked by degenerate loxP sites to allow homologous recombination in vivo and subsequent removal of the URA3 marker. PCR was performed by using KAPA HiFi and primers 906 (SEQ ID NO:228) and 907 (SEQ ID NO:229). The FRA2 portion of each primer was derived from the first 60 bp of the coding sequence starting at the ATG and 56 bp downstream of the stop codon. The PCR product was transformed into PNY2101 using standard genetic techniques and transformants were selected on synthetic complete media lacking uracil and supplemented with 1% ethanol at 30° C. Transformants were screened to verify correct integration by colony PCR using primers 667 (SEQ ID NO:230), external to the 5' coding region and 749 (SEQ ID NO:159), internal to the ILV5 promoter. The URA3 marker was recycled by transforming with pLA34 (SEQ ID NO:184) containing the CRE recombinase under the GAL1 promoter and plated on synthetic complete media lacking histidine and supplemented with 1% ethanol at 30° C. Transformants were plated on rich media supplemented with 1% ethanol and 0.5% galactose to induce the recombinase. Marker removal was confirmed by patching colonies to synthetic complete media lacking uracil and supplemented with 1% ethanol to verify absence of growth. The resulting identified strain, called PNY2110 has the genotype MATa ura3Δ::loxP his3Δ pdc5Δ::loxP66/71 2-micron pdc1Δ::P[PDC1]-ALS|alsS_Bs-CYC1t-loxP71/66 pdc6Δ:(UAS)PGK1-P[FBA1]-KIVD|Lg(y)-TDH3t-loxP71/66 adh1Δ::P[ADH1]-ADH|Bi(y)-ADHt-loxP71/66 fra2Δ::P[ILV5]-ADH|Bi(y)-ADHt-loxP71/66.

GPD2 Deletion

To delete the endogenous GPD2 coding region, a deletion cassette was PCR amplified from pLA59 (SEQ ID NO:97), which contains a URA3 marker flanked by degenerate loxP sites to allow homologous recombination in vivo and subsequent removal of the URA3 marker. PCR was done by using KAPA HiFi and primers LA512 (SEQ ID NO:204) and LA513 (SEQ ID NO:205). The GPD2 portion of each primer was derived from the 5' region 50 bp upstream of the GPD2 start codon and 3' region 50 bp downstream of the stop codon such that integration of the URA3 cassette results in replacement of the entire GPD2 coding region. The PCR product was transformed into PNY2110 using standard genetic techniques and transformants were selected on synthetic complete medium lacking uracil and supplemented with 1% ethanol at 30° C. Transformants were screened to verify correct integration by colony PCR using primers LA516 (SEQ ID NO:206) external to the 5' coding region and LA135 (SEQ ID NO:94), internal to URA3. Positive transformants were then screened by colony PCR using primers LA514 (SEQ ID NO:207) and LA515 (SEQ ID NO:208), internal to the GPD2 coding region. The URA3 marker was recycled by transforming with pLA34 (SEQ ID NO:184) containing the CRE recombinase under the GAL1 promoter and plated on synthetic complete medium lacking histidine and supplemented with 1% ethanol at 30° C. Transformants were plated on rich medium supplemented with 1% ethanol and 0.5% galactose to induce the recombinase. Marker removal was confirmed by patching colonies to synthetic complete medium lacking uracil and supplemented with 1% ethanol to verify absence of growth. The resulting identified strain, called PNY2115, has the genotype MATa ura3Δ::loxP his3Δ pdc5Δ::loxP66/71 fra2Δ 2-micron pdc1Δ::P[PDC1]-ALS|alsS_Bs-CYC1t-loxP71/66 pdc6Δ::(UAS)PGK1-P[FBA1]-KIVD|Lg(y)-TDH3t-loxP71/66 adh1Δ::P[ADH1]-ADH|Bi(y)-ADHt-loxP71/66 fra2Δ::P[ILV5]-ADH|Bi(y)-ADHt-loxP71/66 gpd2Δ::loxP71/66.

Creation of PNY2145 from PNY2115

PNY2145 was constructed from PNY2115 by the additional integration of a phosphoketolase gene cassette at the pdc5Δ locus and by replacing the native AMN1 gene with a codon optimized verison of the ortholog from CEN.PK. Integration constructs are further described below.

pdc5Δ::FBA(L8)-xpk1-CYC1t-loxP71/66

The TEF(M4)-xpk1-CYC1t gene from pRS423::TEF(M4)-xpk1+ENO1-eutD (SEQ ID NO:162) was PCR amplified using primers N1341 and N1338 (SEQ ID NOs:163 and 164), generating a 3.1 kb product. The loxP-flanked URA3 gene cassette from pLA59 (SEQ ID NO:97) was amplified with primers N1033c and N1342 (SEQ ID NOs:165 and 166), generating a 1.6 kb product. The xpk1 and URA3 PCR products were fused by combining them without primers for an additional 10 cycles of PCR using Phusion DNA polymerase. The resulting reaction mix was then used as a template for a PCR reaction with KAPA Hi Fi and primers N1342 and N1364 (SEQ ID NOs:166 and 167). A 4.2 kb PCR product was recovered by purification from an electrophoresis agarose gel (Zymo kit). FBA promoter variant L8 (SEQ ID NO:168) was amplified using primers N1366 and N1368 (SEQ ID NOs:169 and 170). The xpk1::URA3 PCR product was combined with the FBA promoter by additional rounds of PCR. The resulting product was phosphorylated with polynucleotide kinase and ligated into pBR322 that had been digested with EcoRV and treated with calf intestinal phosphatase. The ligation reaction was transformed into E. coli cells (Stbl3 competent cells from Invitrogen). The integration cassette was confirmed by sequencing. To prepare DNA for integration, the plasmid was used as a template in a PCR reaction with Kapa HiFi and primers N1371 and N1372 (SEQ ID NOs:171 and 172). The PCR product was isolated by phenol-chloroform extraction and ethanol precipitation (using standard methods; e.g. Maniatas, et al.). Five micrograms of DNA were used to transform strain PNY2115. Transformants were selected on medium lacking uracil (synthetic complete medium minus uracil with 1% ethanol as the carbon source). Colonies were screened for the integration event using PCR (JumpStart) with primers BK93 and N1114 (SEQ ID NOs:173 and 174). Two clones were selected to carry forward. The URA3 marker was recycled by transforming with pJT254 (SEQ ID NO:175) containing the CRE recombinase under the GAL1 promoter and plating on synthetic complete medium lacking histidine and supplemented with 1% ethanol at 30° C. Transformants were grown in rich medium supplemented with 1% ethanol to derepress the recombinase. Marker removal was confirmed for single colony isolates by patching to synthetic complete medium lacking uracil and supplemented with 1% ethanol to verify absence of growth. Loss of the recombinase plasmid, pJT254, was confirmed by patching the colonies to synthetic complete medium lacking histidine and supplemented with 1% ethanol. Proper marker removal was confirmed by PCR (primers N160SeqF5 (SEQ ID NO:176) and BK380. One resulting clone was designated PNY2293.

amn1Δ::AMN1(y)-loxP71/66

To replace the endogenous copy of AMN1 with a codon-optimized version of the AMN1 gene from CEN.PK2, an integration cassette containing the CEN.PK AMN1 promoter, AMN1(y) gene (nucleic acid SEQ ID NO:177; amino acid SEQ ID NO:178), and CEN.PK AMN1 terminator was assembled by SOE PCR and subcloned into the shuttle vector pLA59. The AMN1(y) gene was ordered from DNA 2.0 with codon-optimization for S. cerevisiae. The completed pLA67 plasmid (SEQ ID NO:179) contained: 1) pUC19 vector backbone sequence containing an E. coli replication origin and ampicillin resistance gene; 2) URA3 selection marker flanked by loxP71 and loxP66 sites; and 3) $P_{AMN1(CEN.PK)}$-AMN1(y)-term$_{AMN1(CEN.PK)}$ expression cassette PCR amplification of the AMN1(y)-loxP71-URA3-loxP66 cassette was performed by using KAPA HiFi from Kapa Biosystems, Woburn, Mass. and primers LA712 (SEQ ID NO:180) and LA746 (SEQ ID NO:181). The PCR product was transformed into PNY2293 using standard genetic techniques and transformants were selected on synthetic complete medium lacking uracil and supplemented with 1% ethanol at 30° C. Transformants were observed under magnification for the absence of a clumping phenotype with respect to the control (PNY2293). The URA3 marker was recycled using the pJT254 Cre recombinase plasmid as described above. After marker recycle, clones were again observed under magnification to confirm absence of the clumping phenotype. A resulting identified strain, PNY2145, has the genotype: MATa ura3Δ::loxP his3Δ pdc5Δ::P[FBA(L8)]-XPK|xpk1_Lp-CYCt-loxP66/71 fra2Δ 2-micron plasmid (CEN.PK2) pdc1Δ::P[PDC1]-ALS|al-sS_Bs-CYC1t-loxP71/66 pdc6Δ::(UAS)PGK1-P[FBA1]-KIVD|Lg(y)-TDH3t-loxP71/66 adh1Δ::P[ADH1]-ADH|Bi(y)-ADHt-loxP71/66 fra2Δ::P[ILV5]-ADH|Bi(y)-ADHt-loxP71/66 gpd2Δ::loxP71/66 amn1Δ::AMN1(y).

INCORPORATION BY REFERENCE

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. A method for production of isobutanol in a fermentation process comprising:
providing a fermentation mix comprising a recombinant yeast production microorganism which comprises an engineered isobutanol biosynthetic pathway, a heterologous polynucleotide encoding a polypeptide having acetolactate synthase activity, wherein said polypeptide has the amino acid sequence of SEQ ID NO: 9 and confers resistant to sulfonylureas, and a heterologous polynucleotide encoding a polypeptide having 3-phosphoshikimate 1-carboxylvinyltransferase activity; and
contacting the fermentation mix with at least one sulfonylurea which preferentially inhibits at least one contaminant yeast microorganism, wherein a fermentation product of the contaminant yeast microorganism is ethanol;
wherein production competitiveness of the recombinant yeast production microorganism is associated with a higher isobutanol-to-ethanol ratio as compared to a fermentation process without addition of one or more inhibitors, antibiotics, or combinations thereof.

2. The method of claim 1, wherein the specific growth rate of the at least one contaminant yeast microorganism is reduced more than the specific growth rate of the recombinant yeast production microorganism.

3. The method of claim 1, wherein production of the fermentation product of the at least one contaminant yeast microorganism is reduced more than the isobutanol production of the recombinant yeast production microorganism.

4. The method of claim 1, wherein the contaminant yeast microorganism is *Saccharomyces cerevisiae*.

5. The method of claim 1, wherein the sulfonylurea is an inhibitor of an ethanol biosynthesis pathway.

6. The method of claim 1, wherein the sulfonylurea is an inhibitor of an amino acid biosynthesis pathway.

7. The method of claim 1, wherein the sulfonylurea is selected from a group consisting of: nicosulfuron methyl, metsulfuron methyl, chlorimuron ethyl, sulfometuron methyl, chlorsulfuron, thifensulfuron methyl, and mixtures thereof.

8. The method of claim 1, wherein the recombinant yeast production microorganism is selected from *Schizosaccharomyces, Issatchenkia, Kluyveromyces, Yarrowia, Pichia, Candida, Hansenula, Aspergillus, Pachysolen, Rhodotorula, Zygosaccharomyces, Galactomyces, Torulaspora, Debayomyces, Williopsis, Dekkera, Kloeckera, Metschnikowia,* and *Saccharomyces*.

9. The method of claim 1, wherein the isobutanol biosynthetic pathway comprises the following substrate to product conversions:
a) pyruvate to acetolactate;
b) acetolactate to 2,3-dihydroxyisovalerate;
c) 2,3-dihydroxyisovalerate to α-ketoisovalerate;
d) α-ketoisovalerate to isobutyraldehyde; and
e) isobutyraldehyde to isobutanol.

10. The method of claim 1, wherein the recombinant yeast production microorganism further comprises one or more of the following modifications:
a deletion in one or more endogenous polynucleotides encoding a polypeptide having pyruvate decarboxylase activity;

a deletion, mutation, or substitution in an endogenous polynucleotide encoding a polypeptide having acetolactate reductase activity;

a deletion, mutation, or substitution in an endogenous polynucleotide encoding a polypeptide having aldehyde dehydrogenase activity;

a deletion in an endogenous polynucleotide encoding a polypeptide having hexokinase activity;

a deletion in an endogenous polynucleotide encoding a polypeptide having glycerol-3-phosphate dehydrogenase activity; or a deletion in an endogenous gene encoding a polypeptide affecting Fe-S cluster biosynthesis, wherein the polypeptide is FRA2.

* * * * *

SEQUENCE LISTING

```
<160> NUMBER OF SEQ ID NOS: 230

<210> SEQ ID NO 1
<211> LENGTH: 563
<212> TYPE: PRT
<213> ORGANISM: Saccharomyces cerevisiae

<400> SEQUENCE: 1

Met Ser Glu Ile Thr Leu Gly Lys Tyr Leu Phe Glu Arg Leu Ser Gln
1               5                   10                  15

Val Asn Cys Asn Thr Val Phe Gly Leu Pro Gly Asp Phe Asn Leu Ser
            20                  25                  30

Leu Leu Asp Lys Leu Tyr Glu Val Lys Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ser Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Asn
    130                 135                 140

Ala Pro Ala Glu Ile Asp Arg Cys Ile Arg Thr Thr Tyr Thr Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Glu Thr Pro Ile Asp Leu Ser Leu Lys Pro Asn
            180                 185                 190

Asp Ala Glu Ala Glu Ala Glu Val Val Arg Thr Val Val Glu Leu Ile
        195                 200                 205

Lys Asp Ala Lys Asn Pro Val Ile Leu Ala Asp Ala Cys Ala Ser Arg
    210                 215                 220

His Asp Val Lys Ala Glu Thr Lys Lys Leu Met Asp Leu Thr Gln Phe
225                 230                 235                 240
```

```
Pro Val Tyr Val Thr Pro Met Gly Lys Gly Ala Ile Asp Glu Gln His
            245                 250                 255

Pro Arg Tyr Gly Gly Val Tyr Val Gly Thr Leu Ser Arg Pro Glu Val
            260                 265                 270

Lys Lys Ala Val Glu Ser Ala Asp Leu Ile Leu Ser Ile Gly Ala Leu
            275                 280                 285

Leu Ser Asp Phe Asn Thr Gly Ser Phe Ser Tyr Ser Tyr Lys Thr Lys
            290                 295                 300

Asn Ile Val Glu Phe His Ser Asp His Ile Lys Ile Arg Asn Ala Thr
305                 310                 315                 320

Phe Pro Gly Val Gln Met Lys Phe Ala Leu Gln Lys Leu Leu Asp Ala
                325                 330                 335

Ile Pro Glu Val Val Lys Asp Tyr Lys Pro Val Ala Val Pro Ala Arg
            340                 345                 350

Val Pro Ile Thr Lys Ser Thr Pro Ala Asn Thr Pro Met Lys Gln Glu
            355                 360                 365

Trp Met Trp Asn His Leu Gly Asn Phe Leu Arg Glu Gly Asp Ile Val
            370                 375                 380

Ile Ala Glu Thr Gly Thr Ser Ala Phe Gly Ile Asn Gln Thr Thr Phe
385                 390                 395                 400

Pro Thr Asp Val Tyr Ala Ile Val Gln Val Leu Trp Gly Ser Ile Gly
            405                 410                 415

Phe Thr Val Gly Ala Leu Leu Gly Ala Thr Met Ala Ala Glu Glu Leu
            420                 425                 430

Asp Pro Lys Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
            450                 455                 460

Tyr Ile Phe Val Leu Asn Asn Asn Gly Tyr Thr Ile Glu Lys Leu Ile
465                 470                 475                 480

His Gly Pro His Ala Glu Tyr Asn Glu Ile Gln Gly Trp Asp His Leu
                485                 490                 495

Ala Leu Leu Pro Thr Phe Gly Ala Arg Asn Tyr Glu Thr His Arg Val
            500                 505                 510

Ala Thr Thr Gly Glu Trp Glu Lys Leu Thr Gln Asp Lys Asp Phe Gln
            515                 520                 525

Asp Asn Ser Lys Ile Arg Met Ile Glu Val Met Leu Pro Val Phe Asp
            530                 535                 540

Ala Pro Gln Asn Leu Val Lys Gln Ala Gln Leu Thr Ala Ala Thr Asn
545                 550                 555                 560

Ala Lys Gln

<210> SEQ ID NO 2
<211> LENGTH: 563
<212> TYPE: PRT
<213> ORGANISM: Saccharomyces cerevisiae

<400> SEQUENCE: 2

Met Ser Glu Ile Thr Leu Gly Lys Tyr Leu Phe Glu Arg Leu Ser Gln
1               5                   10                  15

Val Asn Cys Asn Thr Val Phe Gly Leu Pro Gly Asp Phe Asn Leu Ser
            20                  25                  30

Leu Leu Asp Lys Leu Tyr Glu Val Lys Gly Met Arg Trp Ala Gly Asn
        35                  40                  45
```

```
Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                   80

Ala Leu Asn Gly Ile Ala Gly Ser Tyr Ala Glu His Val Gly Val Leu
                85                  90                  95

His Val Gly Val Pro Ser Ile Ser Ser Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Asn
    130                 135                 140

Ala Pro Ala Glu Ile Asp Arg Cys Ile Arg Thr Thr Tyr Thr Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Glu Thr Pro Ile Asp Leu Ser Leu Lys Pro Asn
            180                 185                 190

Asp Ala Glu Ala Glu Ala Val Val Arg Thr Val Val Glu Leu Ile
    195                 200                 205

Lys Asp Ala Lys Asn Pro Val Ile Leu Ala Asp Ala Cys Ala Ser Arg
    210                 215                 220

His Asp Val Lys Ala Glu Thr Lys Lys Leu Met Asp Leu Thr Gln Phe
225                 230                 235                 240

Pro Val Tyr Val Thr Pro Met Gly Lys Gly Ala Ile Asp Glu Gln His
                245                 250                 255

Pro Arg Tyr Gly Gly Val Tyr Val Gly Thr Leu Ser Arg Pro Glu Val
                260                 265                 270

Lys Lys Ala Val Glu Ser Ala Asp Leu Ile Leu Ser Ile Gly Ala Leu
    275                 280                 285

Leu Ser Asp Phe Asn Thr Gly Ser Phe Ser Tyr Ser Tyr Lys Thr Lys
    290                 295                 300

Asn Ile Val Glu Phe His Ser Asp His Ile Lys Ile Arg Asn Ala Thr
305                 310                 315                 320

Phe Pro Gly Val Gln Met Lys Phe Ala Leu Gln Lys Leu Leu Asp Ala
                325                 330                 335

Ile Pro Glu Val Val Lys Asp Tyr Lys Pro Val Ala Val Pro Ala Arg
                340                 345                 350

Val Pro Ile Thr Lys Ser Thr Pro Ala Asn Thr Pro Met Lys Gln Glu
            355                 360                 365

Trp Met Trp Asn His Leu Gly Asn Phe Leu Arg Glu Gly Asp Ile Val
        370                 375                 380

Ile Ala Glu Thr Gly Thr Ser Ala Phe Gly Ile Asn Gln Thr Thr Phe
385                 390                 395                 400

Pro Thr Asp Val Tyr Ala Ile Val Gln Val Leu Trp Gly Ser Ile Gly
                405                 410                 415

Phe Thr Val Gly Ala Leu Leu Gly Ala Thr Met Ala Ala Glu Glu Leu
                420                 425                 430

Asp Pro Lys Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
        450                 455                 460
```

```
Tyr Ile Phe Val Leu Asn Asn Gly Tyr Thr Ile Glu Lys Leu Ile
465                 470                 475                 480

His Gly Pro His Ala Glu Tyr Asn Glu Ile Gln Gly Trp Asp His Leu
            485                 490                 495

Ala Leu Leu Pro Thr Phe Gly Ala Arg Asn Tyr Glu Thr His Arg Val
            500                 505                 510

Ala Thr Thr Gly Glu Trp Glu Lys Leu Thr Gln Asp Lys Asp Phe Gln
            515                 520                 525

Asp Asn Ser Lys Ile Arg Met Ile Glu Val Met Leu Pro Val Phe Asp
530                 535                 540

Ala Pro Gln Asn Leu Val Lys Gln Ala Gln Leu Thr Ala Ala Thr Asn
545                 550                 555                 560

Ala Lys Gln

<210> SEQ ID NO 3
<211> LENGTH: 533
<212> TYPE: PRT
<213> ORGANISM: Saccharomyces cerevisiae

<400> SEQUENCE: 3

Met Ser Glu Ile Thr Leu Gly Lys Tyr Leu Phe Glu Arg Leu Lys Gln
1               5                   10                  15

Val Asn Val Asn Thr Ile Phe Gly Leu Pro Gly Asp Phe Asn Leu Ser
            20                  25                  30

Leu Leu Asp Lys Ile Tyr Glu Val Asp Gly Leu Arg Trp Ala Gly Asn
        35                  40                  45

Ala Asn Glu Leu Asn Ala Ala Tyr Ala Ala Asp Gly Tyr Ala Arg Ile
50                  55                  60

Lys Gly Leu Ser Val Leu Val Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ser Met Ile Thr Asp Ile Ala Thr
130                 135                 140

Ala Pro Ser Glu Ile Asp Arg Leu Ile Arg Thr Thr Phe Ile Thr Gln
145                 150                 155                 160

Arg Pro Ser Tyr Leu Gly Leu Pro Ala Asn Leu Val Asp Leu Lys Val
                165                 170                 175

Pro Gly Ser Leu Leu Glu Lys Pro Ile Asp Leu Ser Leu Lys Pro Asn
            180                 185                 190

Asp Pro Glu Ala Glu Lys Glu Val Ile Asp Thr Val Leu Glu Leu Ile
        195                 200                 205

Gln Asn Ser Lys Asn Pro Val Ile Leu Ser Asp Ala Cys Ala Ser Arg
210                 215                 220

His Asn Val Lys Lys Glu Thr Gln Lys Leu Ile Asp Leu Thr Gln Phe
225                 230                 235                 240

Pro Ala Phe Val Thr Pro Leu Gly Lys Gly Ser Ile Asp Glu Gln His
                245                 250                 255

Pro Arg Tyr Gly Gly Val Tyr Val Gly Thr Leu Ser Lys Gln Asp Val
            260                 265                 270
```

Lys Gln Ala Val Glu Ser Ala Asp Leu Ile Leu Ser Val Gly Ala Leu
            275                 280                 285

Leu Ser Asp Phe Asn Thr Gly Ser Phe Ser Tyr Ser Tyr Lys Thr Lys
            290                 295                 300

Asn Val Val Glu Phe His Ser Asp Tyr Val Lys Val Lys Asn Ala Thr
305                 310                 315                 320

Phe Leu Gly Val Gln Met Lys Phe Ala Leu Gln Asn Leu Leu Lys Val
                325                 330                 335

Ile Pro Asp Val Val Lys Gly Tyr Lys Ser Val Pro Val Pro Thr Lys
            340                 345                 350

Thr Pro Ala Asn Lys Gly Val Pro Ala Ser Thr Pro Leu Lys Gln Glu
            355                 360                 365

Trp Leu Trp Asn Glu Leu Ser Lys Phe Leu Gln Glu Gly Asp Val Ile
            370                 375                 380

Ile Ser Glu Thr Gly Thr Ser Ala Phe Gly Ile Asn Gln Thr Ile Phe
385                 390                 395                 400

Pro Lys Asp Ala Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430

Asp Pro Asn Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
            450                 455                 460

Tyr Leu Phe Val Leu Asn Asn Asp Gly Tyr Thr Ile Glu Lys Leu Ile
465                 470                 475                 480

His Gly Pro His Ala Glu Tyr Asn Glu Ile Gln Thr Trp Asp His Leu
                485                 490                 495

Ala Leu Leu Pro Ala Phe Gly Ala Lys Lys Tyr Glu Asn His Lys Ile
            500                 505                 510

Ala Thr Thr Gly Glu Trp Asp Ala Leu Thr Thr Asp Ser Glu Phe Gln
            515                 520                 525

Lys Asn Ser Val Ile
            530

<210> SEQ ID NO 4
<211> LENGTH: 804
<212> TYPE: DNA
<213> ORGANISM: Saccharomyces cerevisiae

<400> SEQUENCE: 4
atgtcccaag gtagaaaagc tgcagaaaga ttggctaaga agactgtcct cattacaggt        60
gcatctgctg gtattggtaa ggcgaccgca ttagagtact ggaggcatc caatggtgat       120 atgaaactga tcttggctgc tagaagatta gaaaagctcg aggaattgaa gagaccatt       180 gatcaagagt ttccaaacgc aaaagttcat gtggcccagc tggatatcac tcaagcagaa       240
aaaatcaagc ccttcattga aacttgcca caagagttca aggatattga cattctggtg       300
aacaatgccg aaaggctct tggcagtgac cgtgtgggcc agatcgcaac ggaggatatc       360
caggacgtgt ttgacaccaa cgtcacggct ttaatcaata tcacacaagc tgtactgccc       420
atattccaag ccaagaattc aggagatatt gtaaatttgg gttcaatcgc tggcagagac       480
gcatacccaa caggttctat ctattgtgcc tctaagtttg ccgtgggggc gttcactgat       540
agtttgagaa aggagctcat caacactaaa attagagtca ttctaattgc accagggcta       600

-continued

```
gtcgagactg aattttcact agttagatac agaggtaacg aggaacaagc caagaatgtt   660
tacaaggata ctaccccatt gatggctgat gacgtggctg atctgatcgt ctatgcaact   720
tccagaaaac aaaatactgt aattgcagac actttaatct tccaacaaa ccaagcgtca    780 cctcatcata tcttccgtgg ataa                                          804
```

<210> SEQ ID NO 5
<211> LENGTH: 267
<212> TYPE: PRT
<213> ORGANISM: Saccharomyces cerevisiae

<400> SEQUENCE: 5

```
Met Ser Gln Gly Arg Lys Ala Ala Glu Arg Leu Ala Lys Lys Thr Val
1               5                   10                  15

Leu Ile Thr Gly Ala Ser Ala Gly Ile Gly Lys Ala Thr Ala Leu Glu
            20                  25                  30

Tyr Leu Glu Ala Ser Asn Gly Asp Met Lys Leu Ile Leu Ala Ala Arg
        35                  40                  45

Arg Leu Glu Lys Leu Glu Glu Leu Lys Lys Thr Ile Asp Gln Glu Phe
    50                  55                  60

Pro Asn Ala Lys Val His Val Ala Gln Leu Asp Ile Thr Gln Ala Glu
65                  70                  75                  80

Lys Ile Lys Pro Phe Ile Glu Asn Leu Pro Gln Glu Phe Lys Asp Ile
                85                  90                  95

Asp Ile Leu Val Asn Asn Ala Gly Lys Ala Leu Gly Ser Asp Arg Val
            100                 105                 110

Gly Gln Ile Ala Thr Glu Asp Ile Gln Asp Val Phe Asp Thr Asn Val
        115                 120                 125

Thr Ala Leu Ile Asn Ile Thr Gln Ala Val Leu Pro Ile Phe Gln Ala
    130                 135                 140

Lys Asn Ser Gly Asp Ile Val Asn Leu Gly Ser Ile Ala Gly Arg Asp
145                 150                 155                 160

Ala Tyr Pro Thr Gly Ser Ile Tyr Cys Ala Ser Lys Phe Ala Val Gly
                165                 170                 175

Ala Phe Thr Asp Ser Leu Arg Lys Glu Leu Ile Asn Thr Lys Ile Arg
            180                 185                 190

Val Ile Leu Ile Ala Pro Gly Leu Val Glu Thr Glu Phe Ser Leu Val
        195                 200                 205

Arg Tyr Arg Gly Asn Glu Glu Gln Ala Lys Asn Val Tyr Lys Asp Thr
    210                 215                 220

Thr Pro Leu Met Ala Asp Asp Val Ala Asp Leu Ile Val Tyr Ala Thr
225                 230                 235                 240

Ser Arg Lys Gln Asn Thr Val Ile Ala Asp Thr Leu Ile Phe Pro Thr
                245                 250                 255

Asn Gln Ala Ser Pro His His Ile Phe Arg Gly
            260                 265
```

<210> SEQ ID NO 6
<211> LENGTH: 386
<212> TYPE: PRT
<213> ORGANISM: Saccharomyces cerevisiae

<400> SEQUENCE: 6

```
Met Ser Ala Ala Thr Val Gly Lys Pro Ile Lys Cys Ile Ala Ala Val
1               5                   10                  15

Ala Tyr Asp Ala Lys Lys Pro Leu Ser Val Glu Glu Ile Thr Val Asp
```

```
                  20                  25                  30
Ala Pro Lys Ala His Glu Val Arg Ile Lys Ile Glu Tyr Thr Ala Val
                35                  40                  45

Cys His Thr Asp Ala Tyr Thr Leu Ser Gly Ser Asp Pro Glu Gly Leu
 50                  55                  60

Phe Pro Cys Val Leu Gly His Glu Gly Ala Gly Ile Val Glu Ser Val
 65                  70                  75                  80

Gly Asp Asp Val Ile Thr Val Lys Pro Gly Asp His Val Ile Ala Leu
                 85                  90                  95

Tyr Thr Ala Glu Cys Gly Lys Cys Lys Phe Cys Thr Ser Gly Lys Thr
                100                 105                 110

Asn Leu Cys Gly Ala Val Arg Ala Thr Gln Gly Lys Gly Val Met Pro
            115                 120                 125

Asp Gly Thr Thr Arg Phe His Asn Ala Lys Gly Glu Asp Ile Tyr His
            130                 135                 140

Phe Met Gly Cys Ser Thr Phe Ser Glu Tyr Thr Val Val Ala Asp Val
145                 150                 155                 160

Ser Val Val Ala Ile Asp Pro Lys Ala Pro Leu Asp Ala Ala Cys Leu
                165                 170                 175

Leu Gly Cys Gly Val Thr Thr Gly Phe Gly Ala Ala Leu Lys Thr Ala
            180                 185                 190

Asn Val Gln Lys Gly Asp Thr Val Ala Val Phe Gly Cys Gly Thr Val
            195                 200                 205

Gly Leu Ser Val Ile Gln Gly Ala Lys Leu Arg Gly Ala Ser Lys Ile
            210                 215                 220

Ile Ala Ile Asp Ile Asn Asn Lys Lys Gln Tyr Cys Ser Gln Phe
225                 230                 235                 240

Gly Ala Thr Asp Phe Val Asn Pro Lys Glu Asp Leu Ala Lys Asp Gln
                245                 250                 255

Thr Ile Val Glu Lys Leu Ile Glu Met Thr Asp Gly Gly Leu Asp Phe
            260                 265                 270

Thr Phe Asp Cys Thr Gly Asn Thr Lys Ile Met Arg Asp Ala Leu Glu
            275                 280                 285

Ala Cys His Lys Gly Trp Gly Gln Ser Ile Ile Gly Val Ala Ala
            290                 295                 300

Ala Gly Glu Glu Ile Ser Thr Arg Pro Phe Gln Leu Val Thr Gly Arg
305                 310                 315                 320

Val Trp Lys Gly Ser Ala Phe Gly Gly Ile Lys Gly Arg Ser Glu Met
                325                 330                 335

Gly Gly Leu Ile Lys Asp Tyr Gln Lys Gly Ala Leu Lys Val Glu Glu
            340                 345                 350

Phe Ile Thr His Arg Arg Pro Phe Lys Glu Ile Asn Gln Ala Phe Glu
            355                 360                 365

Asp Leu His Asn Gly Asp Cys Leu Arg Thr Val Leu Lys Ser Asp Glu
            370                 375                 380

Ile Lys
385

<210> SEQ ID NO 7
<211> LENGTH: 399
<212> TYPE: PRT
<213> ORGANISM: Pseudomonas putida

<400> SEQUENCE: 7
```

```
Met Ser Gly Asn Arg Gly Val Val Tyr Leu Gly Ser Gly Lys Val Glu
1               5                   10                  15
Val Gln Lys Ile Asp Tyr Pro Lys Met Gln Asp Pro Arg Gly Lys Lys
            20                  25                  30
Ile Glu His Gly Val Ile Leu Lys Val Val Ser Thr Asn Ile Cys Gly
            35                  40                  45
Ser Asp Gln His Met Val Arg Gly Arg Thr Thr Ala Gln Val Gly Leu
        50                  55                  60
Val Leu Gly His Glu Ile Thr Gly Glu Val Ile Glu Lys Gly Arg Asp
65                  70                  75                  80
Val Glu Asn Leu Gln Ile Gly Asp Leu Val Ser Val Pro Phe Asn Val
                85                  90                  95
Ala Cys Gly Arg Cys Arg Ser Cys Lys Glu Met His Thr Gly Val Cys
            100                 105                 110
Leu Thr Val Asn Pro Ala Arg Ala Gly Gly Ala Tyr Gly Tyr Val Asp
            115                 120                 125
Met Gly Asp Trp Thr Gly Gln Ala Glu Tyr Leu Leu Val Pro Tyr
        130                 135                 140
Ala Asp Phe Asn Leu Leu Lys Leu Pro Asp Arg Asp Lys Ala Met Glu
145                 150                 155                 160
Lys Ile Arg Asp Leu Thr Cys Leu Ser Asp Ile Leu Pro Thr Gly Tyr
                165                 170                 175
His Gly Ala Val Thr Ala Gly Val Gly Pro Gly Ser Thr Val Tyr Val
            180                 185                 190
Ala Gly Ala Gly Pro Val Gly Leu Ala Ala Ala Ser Ala Arg Leu
        195                 200                 205
Leu Gly Ala Ala Val Val Ile Val Gly Asp Leu Asn Pro Ala Arg Leu
210                 215                 220
Ala His Ala Lys Ala Gln Gly Phe Glu Ile Ala Asp Leu Ser Leu Asp
225                 230                 235                 240
Thr Pro Leu His Glu Gln Ile Ala Ala Leu Leu Gly Glu Pro Glu Val
                245                 250                 255
Asp Cys Ala Val Asp Ala Val Gly Phe Glu Ala Arg Gly His Gly His
            260                 265                 270
Glu Gly Ala Lys His Glu Ala Pro Ala Thr Val Leu Asn Ser Leu Met
        275                 280                 285
Gln Val Thr Arg Val Ala Gly Lys Ile Gly Ile Pro Gly Leu Tyr Val
        290                 295                 300
Thr Glu Asp Pro Gly Ala Val Asp Ala Ala Lys Ile Gly Ser Leu
305                 310                 315                 320
Ser Ile Arg Phe Gly Leu Gly Trp Ala Lys Ser His Ser Phe His Thr
                325                 330                 335
Gly Gln Thr Pro Val Met Lys Tyr Asn Arg Ala Leu Met Gln Ala Ile
            340                 345                 350
Met Trp Asp Arg Ile Asn Ile Ala Glu Val Val Gly Val Gln Val Ile
        355                 360                 365
Ser Leu Asp Asp Ala Pro Arg Gly Tyr Gly Glu Phe Asp Ala Gly Val
    370                 375                 380
Pro Lys Lys Phe Val Ile Asp Pro His Lys Thr Phe Ser Ala Ala
385                 390                 395
```

<210> SEQ ID NO 8
<211> LENGTH: 2064
<212> TYPE: DNA

<213> ORGANISM: Saccharomyces cerevisiae

<400> SEQUENCE: 8

```
atgatcagac aatctacgct aaaaaacttc gctattaagc gttgctttca acatatagca      60
taccgcaaca cacctgccat gagatcagta gctctcgcgc agcgctttta tagttcgtct     120
tcccgttatt acagtgcgtc tccattacca gcctctaaaa ggccagagcc tgctccaagt     180
ttcaatgttg atccattaga acagcccgct gaaccttcaa aattggctaa gaaactacgc     240
gctgagcctg acatggatac ctctttcgtc ggtttaactg gtggtcaaat atttaacgaa     300
atgatgtcca gacaaaacgt tgatactgta tttggttatc caggtggtgc tatcctacct     360
gtttacgatg ccattcataa cagtgataaa ttcaacttcg ttcttccaaa acacgaacaa     420
ggtgccggtc acatggcaga aggctacgcc agagcttctg gtaaaccagg tgttgtcttg     480
gttacttctg gccaggtgc caccaatgtc gttactccaa tggcagatgc ctttgcagac     540
gggattccaa tggttgtctt tacagggcaa gtctcaacta gtgctatcgg tactgatgct     600
ttccaagagg ctgacgtcgt tggtatttct agatcttgta cgaaatggaa tgtcatggtc     660
aagtccgtgg aagaattgcc attgcgtatt aacgaggctt tgaaattgc cacgagcggt     720
agaccgggac cagtcttggt cgatttacca aggatgttaa cagcagctat cttaagaaat     780
ccaattccaa caaaaacaac tcttccatca aacgcactaa accaattaac cagtcgcgca     840
caagatgaat ttgtcatgca aagtatcaat aaagcagcag atttgatcaa cttggcaaag     900
aaacctgtct tatacgtcgg tgctggtatt ttaaaccatg cagatggtcc aagattacta     960
aaagaattaa gtgaccgtgc tcaaatacct gtcaccacta ctttacaagg tttaggttca    1020
ttcgaccaag aagatccaaa atcattggat atgcttggta tgcacggttg tgctactgcc    1080
aacctggcag tgcaaaatgc cgacttgata attgcagttg gtgctagatt cgacgaccgt    1140
gtcactggta atatttctaa attcgctcca gaagctcgtc gtgcagctgc cgagggtaga    1200
ggtggtatta ttcatttcga ggttagtcca aaaaacataa acaaggttgt tcaaactcaa    1260
atagcagtgg aaggtgatgc tacgaccaat ctgggcaaaa tgatgtcaaa gattttccca    1320
gttaaggaga ggtctgaatg gtttgctcaa ataaataaat ggaagaagga atacccatac    1380
gcttatatgg aggagactcc aggatctaaa attaaaccac agacggttat aaagaaacta    1440
tccaaggttg ccaacgacac aggaagacat gtcattgtta caacgggtgt ggggcaacat    1500
caaatgtggg ctgctcaaca ctggacatgg agaaatccac atactttcat cacatcaggt    1560
ggtttaggta cgatgggtta cggtctccct gccgccatcg gtgctcaagt tgcaaagcca    1620
gaatctttgg ttattgacat tgatggtgac gcatccttta acatgactct aacggaattg    1680
agttctgccg ttcaagctgg tactccagtg aagattttga ttttgaacaa tgaagagcaa    1740
ggtatggtta ctcaatggca atccctgttc tacgaacatc gttattccca cacacatcaa    1800
ttgaaccctg atttcataaa actagcggag gctatgggtt taaaaggttt aagagtcaag    1860
aagcaagagg aattggacgc taagttgaaa gaattcgttt ctaccaaggg cccagttttg    1920
cttgaagtgg aagttgataa aaaagttcct gttttgccaa tggtggcagg tggtagcgt    1980
ctagacgagt tcataaattt tgacccagaa gttgaaagac aacagactga attacgtcat    2040
aagcgtacag gcggtaagca ctga                                            2064
```

<210> SEQ ID NO 9
<211> LENGTH: 687
<212> TYPE: PRT
<213> ORGANISM: Saccharomyces cerevisiae

<400> SEQUENCE: 9

```
Met Ile Arg Gln Ser Thr Leu Lys Asn Phe Ala Ile Lys Arg Cys Phe
1               5                   10                  15

Gln His Ile Ala Tyr Arg Asn Thr Pro Ala Met Arg Ser Val Ala Leu
            20                  25                  30

Ala Gln Arg Phe Tyr Ser Ser Ser Arg Tyr Tyr Ser Ala Ser Pro
        35                  40                  45

Leu Pro Ala Ser Lys Arg Pro Glu Pro Ala Pro Ser Phe Asn Val Asp
    50                  55                  60

Pro Leu Glu Gln Pro Ala Glu Pro Ser Lys Leu Ala Lys Lys Leu Arg
65                  70                  75                  80

Ala Glu Pro Asp Met Asp Thr Ser Phe Val Gly Leu Thr Gly Gly Gln
                85                  90                  95

Ile Phe Asn Glu Met Met Ser Arg Gln Asn Val Asp Thr Val Phe Gly
                100                 105                 110

Tyr Pro Gly Gly Ala Ile Leu Pro Val Tyr Asp Ala Ile His Asn Ser
            115                 120                 125

Asp Lys Phe Asn Phe Val Leu Pro Lys His Glu Gln Gly Ala Gly His
        130                 135                 140

Met Ala Glu Gly Tyr Ala Arg Ala Ser Gly Lys Pro Gly Val Val Leu
145                 150                 155                 160

Val Thr Ser Gly Pro Gly Ala Thr Asn Val Val Thr Pro Met Ala Asp
                165                 170                 175

Ala Phe Ala Asp Gly Ile Pro Met Val Val Phe Thr Gly Gln Val Ser
            180                 185                 190

Thr Ser Ala Ile Gly Thr Asp Ala Phe Gln Glu Ala Asp Val Val Gly
        195                 200                 205

Ile Ser Arg Ser Cys Thr Lys Trp Asn Val Met Val Lys Ser Val Glu
    210                 215                 220

Glu Leu Pro Leu Arg Ile Asn Glu Ala Phe Glu Ile Ala Thr Ser Gly
225                 230                 235                 240

Arg Pro Gly Pro Val Leu Val Asp Leu Pro Lys Asp Val Thr Ala Ala
                245                 250                 255

Ile Leu Arg Asn Pro Ile Pro Thr Lys Thr Thr Leu Pro Ser Asn Ala
            260                 265                 270

Leu Asn Gln Leu Thr Ser Arg Ala Gln Asp Glu Phe Val Met Gln Ser
        275                 280                 285

Ile Asn Lys Ala Ala Asp Leu Ile Asn Leu Ala Lys Lys Pro Val Leu
    290                 295                 300

Tyr Val Gly Ala Gly Ile Leu Asn His Ala Asp Gly Pro Arg Leu Leu
305                 310                 315                 320

Lys Glu Leu Ser Asp Arg Ala Gln Ile Pro Val Thr Thr Thr Leu Gln
                325                 330                 335

Gly Leu Gly Ser Phe Asp Gln Glu Asp Pro Lys Ser Leu Asp Met Leu
            340                 345                 350

Gly Met His Gly Cys Ala Thr Ala Asn Leu Ala Val Gln Asn Ala Asp
        355                 360                 365

Leu Ile Ile Ala Val Gly Ala Arg Phe Asp Asp Arg Val Thr Gly Asn
    370                 375                 380

Ile Ser Lys Phe Ala Pro Glu Ala Arg Arg Ala Ala Glu Gly Arg
385                 390                 395                 400

Gly Gly Ile Ile His Phe Glu Val Ser Pro Lys Asn Ile Asn Lys Val
```

```
                    405                 410                 415
Val Gln Thr Gln Ile Ala Val Glu Gly Asp Ala Thr Thr Asn Leu Gly
                420                 425                 430

Lys Met Met Ser Lys Ile Phe Pro Val Lys Glu Arg Ser Glu Trp Phe
            435                 440                 445

Ala Gln Ile Asn Lys Trp Lys Lys Glu Tyr Pro Tyr Ala Tyr Met Glu
        450                 455                 460

Glu Thr Pro Gly Ser Lys Ile Lys Pro Gln Thr Val Ile Lys Lys Leu
465                 470                 475                 480

Ser Lys Val Ala Asn Asp Thr Gly Arg His Val Ile Val Thr Thr Gly
                485                 490                 495

Val Gly Gln His Gln Met Trp Ala Ala Gln His Trp Thr Trp Arg Asn
                500                 505                 510

Pro His Thr Phe Ile Thr Ser Gly Gly Leu Gly Thr Met Gly Tyr Gly
            515                 520                 525

Leu Pro Ala Ala Ile Gly Ala Gln Val Ala Lys Pro Glu Ser Leu Val
        530                 535                 540

Ile Asp Ile Asp Gly Asp Ala Ser Phe Asn Met Thr Leu Thr Glu Leu
545                 550                 555                 560

Ser Ser Ala Val Gln Ala Gly Thr Pro Val Lys Ile Leu Ile Leu Asn
                565                 570                 575

Asn Glu Glu Gln Gly Met Val Thr Gln Trp Gln Ser Leu Phe Tyr Glu
                580                 585                 590

His Arg Tyr Ser His Thr His Gln Leu Asn Pro Asp Phe Ile Lys Leu
            595                 600                 605

Ala Glu Ala Met Gly Leu Lys Gly Leu Arg Val Lys Lys Gln Glu Glu
        610                 615                 620

Leu Asp Ala Lys Leu Lys Glu Phe Val Ser Thr Lys Gly Pro Val Leu
625                 630                 635                 640

Leu Glu Val Glu Val Asp Lys Lys Val Pro Val Leu Pro Met Val Ala
                645                 650                 655

Gly Gly Ser Gly Leu Asp Glu Phe Ile Asn Phe Asp Pro Glu Val Glu
                660                 665                 670

Arg Gln Gln Thr Glu Leu Arg His Lys Arg Thr Gly Gly Lys His
            675                 680                 685

<210> SEQ ID NO 10
<211> LENGTH: 299
<212> TYPE: PRT
<213> ORGANISM: Saccharomyces cerevisiae

<400> SEQUENCE: 10

Met Thr Asp Ile Gly Arg Thr Lys Ser Arg Asn Tyr Lys Cys Ser Phe
1               5                   10                  15

Asp Gly Cys Glu Lys Val Tyr Asn Arg Pro Ser Leu Leu Gln Gln His
                20                  25                  30

Gln Asn Ser His Thr Asn Gln Lys Pro Tyr His Cys Asp Glu Pro Gly
            35                  40                  45

Cys Gly Lys Lys Phe Ile Arg Pro Cys His Leu Arg Val His Lys Trp
        50                  55                  60

Thr His Ser Gln Ile Lys Pro Lys Ala Cys Thr Leu Cys Gln Lys Arg
65                  70                  75                  80

Phe Val Thr Asn Gln Gln Leu Arg Arg His Leu Asn Ser His Glu Arg
                85                  90                  95
```

```
Lys Ser Lys Leu Ala Ser Arg Ile Asp Arg Lys His Glu Gly Val Asn
            100                 105                 110

Ala Asn Val Lys Ala Glu Leu Asn Gly Lys Glu Gly Phe Asp Pro
        115                 120                 125

Lys Leu Pro Ser Gly Ser Pro Met Cys Gly Glu Glu Phe Ser Gln Gly
    130                 135                 140

His Leu Pro Gly Tyr Asp Asp Met Gln Val Leu Gln Cys Pro Tyr Lys
145                 150                 155                 160

Ser Cys Gln Lys Val Thr Ser Phe Asn Asp Asp Leu Ile Asn His Met
                165                 170                 175

Leu Gln His His Ile Ala Ser Lys Leu Val Val Pro Ser Gly Asp Pro
            180                 185                 190

Ser Leu Lys Glu Ser Leu Pro Thr Ser Glu Lys Ser Ser Ser Thr Asp
        195                 200                 205

Thr Thr Ser Ile Pro Gln Leu Ser Phe Ser Thr Thr Gly Thr Ser Ser
    210                 215                 220

Ser Glu Ser Val Asp Ser Thr Thr Ala Gln Thr Pro Thr Asp Pro Glu
225                 230                 235                 240

Ser Tyr Trp Ser Asp Asn Arg Cys Lys His Ser Asp Cys Gln Glu Leu
                245                 250                 255

Ser Pro Phe Ala Ser Val Phe Asp Leu Ile Asp His Tyr Asp His Thr
            260                 265                 270

His Ala Phe Ile Pro Glu Thr Leu Val Lys Tyr Ser Tyr Ile His Leu
        275                 280                 285

Tyr Lys Pro Ser Val Trp Asp Leu Phe Glu Tyr
    290                 295

<210> SEQ ID NO 11
<211> LENGTH: 299
<212> TYPE: PRT
<213> ORGANISM: Artificial Sequence
<220> FEATURE:
<223> OTHER INFORMATION: FZF1-4

<400> SEQUENCE: 11

Met Thr Asp Ile Gly Arg Thr Lys Ser Arg Asn Tyr Lys Cys Ser Phe
1               5                   10                  15

Asp Gly Cys Glu Lys Val Tyr Asn Arg Pro Ser Leu Leu Gln Gln His
            20                  25                  30

Gln Asn Ser His Thr Asn Gln Lys Pro Tyr His Cys Asp Glu Pro Gly
        35                  40                  45

Cys Gly Lys Lys Phe Ile Arg Pro Tyr His Leu Arg Val His Lys Trp
    50                  55                  60

Thr His Ser Gln Ile Lys Pro Lys Ala Cys Thr Leu Cys Gln Lys Arg
65                  70                  75                  80

Phe Val Thr Asn Gln Gln Leu Arg Arg His Leu Asn Ser His Glu Arg
                85                  90                  95

Lys Ser Lys Leu Ala Ser Arg Ile Asp Arg Lys His Glu Gly Val Asn
            100                 105                 110

Ala Asn Val Lys Ala Glu Leu Asn Gly Lys Glu Gly Phe Asp Pro
        115                 120                 125

Lys Leu Pro Ser Gly Ser Pro Met Cys Gly Glu Glu Phe Ser Gln Gly
    130                 135                 140

His Leu Pro Gly Tyr Asp Asp Met Gln Val Leu Gln Cys Pro Tyr Lys
145                 150                 155                 160
```

```
Ser Cys Gln Lys Val Thr Ser Phe Asn Asp Asp Leu Ile Asn His Met
                165                 170                 175

Leu Gln His His Ile Ala Ser Lys Leu Val Val Pro Ser Gly Asp Pro
            180                 185                 190

Ser Leu Lys Glu Ser Leu Pro Thr Ser Glu Lys Ser Ser Ser Thr Asp
        195                 200                 205

Thr Thr Ser Ile Pro Gln Leu Ser Phe Ser Thr Gly Thr Ser Ser
    210                 215                 220

Ser Glu Ser Val Asp Ser Thr Thr Ala Gln Thr Pro Thr Asp Pro Glu
225                 230                 235                 240

Ser Tyr Trp Ser Asp Asn Arg Cys Lys His Ser Asp Cys Gln Glu Leu
                245                 250                 255

Ser Pro Phe Ala Ser Val Phe Asp Leu Ile Asp His Tyr Asp His Thr
            260                 265                 270

His Ala Phe Ile Pro Glu Thr Leu Val Lys Tyr Ser Tyr Ile His Leu
        275                 280                 285

Tyr Lys Pro Ser Val Trp Asp Leu Phe Glu Tyr
    290                 295
```

<210> SEQ ID NO 12
<211> LENGTH: 458
<212> TYPE: PRT
<213> ORGANISM: Saccharomyces cerevisiae

<400> SEQUENCE: 12

```
Met Val Ala Asn Trp Val Leu Ala Leu Thr Arg Gln Phe Asp Pro Phe
1               5                   10                  15

Met Phe Met Met Val Met Gly Val Gly Ile Ser Ser Asn Ile Leu Tyr
                20                  25                  30

Ser Phe Pro Tyr Pro Ala Arg Trp Leu Arg Ile Cys Ser Tyr Ile Met
            35                  40                  45

Phe Ala Ile Ala Cys Leu Ile Phe Ile Ala Val Gln Ala Leu Gln Ile
        50                  55                  60

Leu His Leu Ile Val Tyr Ile Lys Glu Lys Ser Phe Arg Glu Tyr Phe
65                  70                  75                  80

Asn Asp Phe Phe Arg Asn Met Lys His Asn Leu Phe Trp Gly Thr Tyr
                85                  90                  95

Pro Met Gly Leu Val Thr Ile Ile Asn Phe Leu Gly Ala Leu Ser Lys
            100                 105                 110

Ala Asn Thr Thr Lys Ser Pro Thr Asn Ala Arg Asn Leu Met Ile Phe
        115                 120                 125

Val Tyr Val Leu Trp Trp Tyr Asp Leu Ala Val Cys Leu Val Ile Ala
130                 135                 140

Trp Gly Ile Ser Phe Leu Ile Trp His Asp Tyr Tyr Pro Leu Glu Gly
145                 150                 155                 160

Ile Gly Asn Tyr Pro Ser Tyr Asn Ile Lys Met Ala Ser Glu Asn Met
                165                 170                 175

Lys Ser Val Leu Leu Leu Asp Ile Ile Pro Leu Val Val Val Ala Ser
            180                 185                 190

Ser Cys Gly Thr Phe Thr Met Ser Glu Ile Phe Phe His Ala Phe Asn
        195                 200                 205

Arg Asn Ile Gln Leu Ile Thr Leu Val Ile Cys Ala Leu Thr Trp Leu
        210                 215                 220

His Ala Ile Ile Phe Val Phe Ile Leu Ile Ala Ile Tyr Phe Trp Ser
225                 230                 235                 240
```

```
Leu Tyr Ile Asn Lys Ile Pro Pro Met Thr Gln Val Phe Thr Leu Phe
                245                 250                 255

Leu Leu Leu Gly Pro Met Gly Gln Gly Ser Phe Gly Val Leu Leu Leu
            260                 265                 270

Thr Asp Asn Ile Lys Lys Tyr Ala Gly Lys Tyr Tyr Pro Thr Asp Asn
        275                 280                 285

Ile Thr Arg Glu Gln Glu Ile Leu Thr Ile Ala Val Pro Trp Cys Phe
    290                 295                 300

Lys Ile Leu Gly Met Val Ser Ala Met Ala Leu Leu Ala Met Gly Tyr
305                 310                 315                 320

Phe Phe Thr Val Ile Ser Val Val Ser Ile Leu Ser Tyr Tyr Asn Lys
                325                 330                 335

Lys Glu Ile Glu Asn Glu Thr Gly Lys Val Lys Arg Val Tyr Thr Phe
            340                 345                 350

His Lys Gly Phe Trp Gly Met Thr Phe Pro Met Gly Thr Met Ser Leu
        355                 360                 365

Gly Asn Glu Glu Leu Tyr Val Gln Tyr Asn Gln Tyr Val Pro Leu Tyr
    370                 375                 380

Ala Phe Arg Val Leu Gly Thr Ile Tyr Gly Gly Val Cys Val Cys Trp
385                 390                 395                 400

Ser Ile Leu Cys Leu Leu Cys Thr Leu His Glu Tyr Ser Lys Lys Met
                405                 410                 415

Leu His Ala Ala Arg Lys Ser Ser Leu Phe Ser Ser Gly Thr Glu
            420                 425                 430

Lys Thr Thr Val Ser Pro Tyr Asn Ser Ile Glu Ser Val Glu Glu Ser
        435                 440                 445

Asn Ser Ala Leu Asp Phe Thr Arg Leu Ala
450                 455

<210> SEQ ID NO 13
<211> LENGTH: 427
<212> TYPE: PRT
<213> ORGANISM: Salmonella typhi

<400> SEQUENCE: 13

Met Glu Ser Leu Thr Leu Gln Pro Ile Ala Arg Val Asp Gly Ala Ile
1               5                   10                  15

Asn Leu Pro Gly Ser Lys Ser Val Ser Asn Arg Ala Leu Leu Leu Ala
            20                  25                  30

Ala Leu Ala Cys Gly Lys Thr Val Leu Thr Asn Leu Leu Asp Ser Asp
        35                  40                  45

Asp Val Arg His Met Leu Asn Ala Leu Ser Ala Leu Gly Ile Asn Tyr
    50                  55                  60

Thr Leu Ser Ala Asp Arg Thr Arg Cys Asp Ile Thr Gly Asn Gly Gly
65                  70                  75                  80

Pro Leu Arg Ala Ser Gly Thr Leu Glu Leu Phe Leu Gly Asn Ala Gly
                85                  90                  95

Thr Ala Met Arg Pro Leu Ala Ala Ala Leu Cys Leu Gly Gln Asn Glu
            100                 105                 110

Ile Val Leu Thr Gly Glu Pro Arg Met Lys Glu Arg Pro Ile Gly His
        115                 120                 125

Leu Val Asp Ser Leu Arg Gln Gly Gly Ala Asn Ile Asp Tyr Leu Glu
    130                 135                 140

Gln Glu Asn Tyr Pro Pro Leu Arg Leu Arg Gly Gly Phe Ile Gly Gly
```

```
            145                 150                 155                 160
Asp Ile Glu Val Asp Gly Ser Val Ser Gln Phe Leu Thr Ala Leu
                165                 170                 175
Leu Met Thr Ala Pro Leu Ala Pro Glu Asp Thr Ile Ile Arg Val Lys
                180                 185                 190
Gly Glu Leu Val Ser Lys Pro Tyr Ile Asp Ile Thr Leu Asn Leu Met
                195                 200                 205
Lys Thr Phe Gly Val Glu Ile Ala Asn His His Tyr Gln Gln Phe Val
            210                 215                 220
Val Lys Gly Gly Gln Gln Tyr His Ser Pro Gly Arg Tyr Leu Val Glu
225                 230                 235                 240
Gly Asp Ala Ser Ser Ala Ser Tyr Phe Leu Ala Ala Gly Ala Ile Lys
                245                 250                 255
Gly Gly Thr Val Lys Val Thr Gly Ile Gly Arg Lys Ser Met Gln Gly
                260                 265                 270
Asp Ile Arg Phe Ala Asp Val Leu Glu Lys Met Gly Ala Thr Ile Thr
            275                 280                 285
Trp Gly Asp Asp Phe Ile Ala Cys Thr Arg Gly Glu Leu His Ala Ile
            290                 295                 300
Asp Met Asp Met Asn His Ile Pro Asp Ala Ala Met Thr Ile Ala Thr
305                 310                 315                 320
Thr Ala Leu Phe Ala Lys Gly Thr Thr Thr Leu Arg Asn Ile Tyr Asn
                325                 330                 335
Trp Arg Val Lys Glu Thr Asp Arg Leu Phe Ala Met Ala Thr Glu Leu
                340                 345                 350
Arg Lys Val Gly Ala Glu Val Glu Glu Gly His Asp Tyr Ile Arg Ile
            355                 360                 365
Thr Pro Pro Ala Lys Leu Gln His Ala Asp Ile Gly Tyr Asn Asp
            370                 375                 380
His Arg Met Ala Met Cys Phe Ser Leu Val Ala Leu Ser Asp Thr Pro
385                 390                 395                 400
Val Thr Ile Leu Asp Pro Lys Cys Thr Ala Lys Thr Phe Pro Asp Tyr
                405                 410                 415
Phe Glu Gln Leu Ala Arg Met Ser Thr Pro Ala
                420                 425

<210> SEQ ID NO 14
<211> LENGTH: 9089
<212> TYPE: DNA
<213> ORGANISM: artificial sequence
<220> FEATURE:
<223> OTHER INFORMATION: constructed plasmid

<400> SEQUENCE: 14
tcgcgcgttt cggtgatgac ggtgaaaacc tctgacacat gcagctcccg gagacggtca    60
cagcttgtct gtaagcggat gccgggagca gacaagcccg tcaggcgcgc tcagcgggtg   120
ttggcgggtg tcggggctgg cttaactatg cggcatcaga gcagattgta ctgagagtgc   180
accataccac agcttttcaa ttcaattcat cattttttt ttattctttt tttgatttc    240
ggtttctttg aaatttttt gattcggtaa tctccgaaca aaggaagaa cgaaggaagg   300
agcacagact tagattggta tatatacgca tatgtagtgt tgaagaaaca tgaaattgcc   360
cagtattctt aacccaactg cacagaacaa aaacctgcag gaaacgaaga taatcatgt   420
cgaaagctac atataaggaa cgtgctgcta ctcatcctag tcctgttgct gccaagctat   480
```

```
ttaatatcat gcacgaaaag caaacaaact tgtgtgcttc attggatgtt cgtaccacca    540
aggaattact ggagttagtt gaagcattag gtcccaaaat ttgtttacta aaaacacatg    600
tggatatctt gactgatttt tccatggagg gcacagttaa gccgctaaag gcattatccg    660
ccaagtacaa tttttactc ttcgaagaca gaaaatttgc tgacattggt aatacagtca     720
aattgcagta ctctgcgggt gtatacagaa tagcagaatg ggcagacatt acgaatgcac    780
acggtgtggt gggcccaggt attgttagcg gtttgaagca ggcggcagaa gaagtaacaa    840
aggaacctag aggccttttg atgttagcag aattgtcatg caagggctcc ctatctactg    900
gagaatatac taagggtact gttgacattg cgaagagcga caaagatttt gttatcggct    960
ttattgctca aagagacatg ggtggaagag atgaaggtta cgattggttg attatgacac   1020
ccggtgtggg tttagatgac aagggagacg cattgggtca acagtataga accgtggatg   1080
atgtggtctc tacaggatct gacattatta ttgttggaag aggactattt gcaaagggaa   1140
gggatgctaa ggtagagggt gaacgttaca gaaaagcagg ctgggaagca tatttgagaa   1200
gatgcggcca gcaaaactaa aaaactgtat tataagtaaa tgcatgtata ctaaactcac   1260
aaattagagc ttcaatttaa ttatatcagt tattaccta tgcggtgtga aataccgcac     1320
agatgcgtaa ggagaaaata ccgcatcagg aaattgtaaa cgttaatatt ttgttaaaat   1380
tcgcgttaaa tttttgttaa atcagctcat ttttaacca ataggccgaa atcggcaaaa     1440
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560 gcgatgccc actacgtgaa ccatcaccct aatcaagttt ttggggtcg aggtgccgta      1620 aagcactaaa tcggaaccct aaagggagcc cccgatttag agcttgacgg ggaaagccgg   1680
cgaacgtggc gagaaaggaa gggaagaaag cgaaaggagc gggcgctagg gcgctggcaa   1740
gtgtagcggt cacgctgcgc gtaaccacca cacccgccgc gcttaatgcg ccgctacagg   1800
gcgcgtcgcg ccattcgcca ttcaggctgc gcaactgttg ggaagggcga tcggtgcggg   1860
cctcttcgct attacgccag ctggcgaaag ggggatgtgc tgcaaggcga ttaagttggg   1920
taacgccagg gttttcccag tcacgacgtt gtaaaacgac ggccagtgag cgcgcgtaat   1980
acgactcact atagggcgaa ttgggtaccg ggccccccct cgaggtcgac tggccattaa   2040
tctttcccat attagatttc gccaagccat gaaagttcaa gaaaggtctt tagacgaatt   2100
acccttcatt tctcaaactg gcgtcaaggg atcctggtat ggttttatcg tttatttct    2160 ggttcttata gcatcgtttt ggacttctct gttcccatta ggcggttcag gagccagcgc   2220
agaatcattc tttgaaggat acttatcctt tccaattttg attgtctgtt acgttggaca   2280
taaactgtat actagaaatt ggactttgat ggtgaaacta gaagatatgg atcttgatac   2340
cggcagaaaa caagtagatt tgactcttcg tagggaagaa atgaggattg agcgagaaac   2400
attagcaaaa agatccttcg taacaagatt tttacatttc tggtgttgaa gggaaagata   2460
tgagctatac agcggaattt ccatatcact cagattttgt tatctaattt tttccttccc   2520
acgtccgcgg gaatctgtgt atattactgc atctagatat atgttatctt atcttggcgc   2580
gtacatttaa ttttcaacgt attctataag aaattgcggg agttttttc atgtagatga    2640 tactgactgc acgcaaatat aggcatgatt tataggcatg atttgatggc tgtaccgata   2700
ggaacgctaa gagtaacttc agaatcgtta tcctggcgga aaaaattcat ttgtaaactt   2760
taaaaaaaaa agccaatatc cccaaaatta ttaagagcgc ctccattatt aactaaaatt   2820
tcactcagca tccacaatgt atcaggtatc tactacagat attacatgtg gcgaaaaaga   2880
```

```
caagaacaat gcaatagcgc atcaagaaaa aacacaaagc tttcaatcaa tgaatcgaaa    2940
atgtcattaa aatagtatat aaattgaaac taagtcataa agctataaaa agaaaattta    3000
tttaaatgca agatttaaag taaattcacg gccctgcagg ccctaacctg ctaggacaca    3060
acgtctttgc ctggtaaagt ttctagctga cgtgattcct tcacctgtgg atccggcaat    3120
tgtaaaggtt gtgaaaccct cagcttcata accgacacct gcaaatgact ttgcattctt    3180
aacaaagata gttgtatcaa tttcacgttc gaatctatta aggttatcga tgttcttaga    3240
ataaatgtag gcggaatgtt ttctattctg ctcagctatc ttggcgtatt taatggcttc    3300
atcaatgtcc ttcactctaa ctataggcaa aattggcatc atcaactccg tcataacgaa    3360
cggatggttt gcgttgactt cacaaataat acactttaca ttacttggtg actctacatc    3420
tatttcatcc aaaaacagtt tagcgtcctt accaacccac ttcttattaa tgaaatattc    3480
ttgagtttca ttgttctttt gaagaacaag gtctatcagc ttggatactt ggtcttcatt    3540
gataatgacg gcgttgtttt tcaacatgtt agagatcaga tcatctgcaa cgttttcaaa    3600
cacgaacact tctttttccg cgatacaagg aagattgttg tcaaacgaac aaccttcaat    3660
aatgcttctg ccggccttct cgatatctgc tgtatcgtct acaataaccg gaggattacc    3720
cgcgccagct ccgatggcct ttttaccaga attaagaagg ttttttacca tacccgggcc    3780
acccgtaccg cacaacaatt ttatggatgg atgtttgata atagcgtcta aactttccat    3840
agttgggttc tttatagtag tgacaaggtt ttcaggtcca ccacagctaa ttatggcttt    3900
gtttatcatt tctactgcga aagcgacaca ctttttggcg catgggtgac cattaaaatac   3960 aactgcattc cccgcagcta tcatacctat agaattgcag ataacggttt ctgttggatt    4020
cgtgcttgga gttatagcgc cgataactcc gtatggactc atttcaacca ctgttagtcc    4080
attatcgccg gaccatgctg ttgttgtcag atcttcagtg cctggggtat acttggccac    4140
taattcatgt ttcaagattt tatcctcata ccttcccatg tgggtttcct ccaggatcat    4200
tgtggctaag acctctttat tctgtaatgc ggcttttctt atttcggtga ttattttctc    4260
tctttgttcc tttgtgtagt gtagggaaag aatcttttgt gcatgtactg cagaagaaat    4320
ggcattctca acattttcaa atactccaaa acatgaagag ttatctttgt aattctttaa    4380
gttgatgttt tcaccattag tcttcacttt caagtctttg gtggttggga ttaaggtatc    4440
tttatccatg gtgtttgttt atgtgtgttt attcgaaact aagttcttgg tgttttaaaa    4500
ctaaaaaaaa gactaactat aaaagtagaa tttaagaagt ttaagaaata gatttacaga    4560
attacaatca ataccaccg tctttatata cttattagtc aagtagggga ataatttcag    4620
ggaactggtt tcaacctttt ttttcagctt tttccaaatc agagagagca gaaggtaata    4680
gaaggtgtaa gaaaatgaga tagatacatg cgtgggtcaa ttgccttgtg tcatcattta    4740
ctccaggcag gttgcatcac tccattgagg ttgtgcccgt tttttgcctg tttgtgcccc    4800
tgttctctgt agttgcgcta agagaatgga cctatgaact gatggttggt gaagaaaaca    4860 atatttggt gctgggattc ttttttttc tggatgccag cttaaaaagc gggctccatt     4920
atatttagtg gatgccagga ataaactgtt cacccagaca cctacgatgt tatatattct    4980
gtgtaacccg ccccctattt tgggcatgta cgggttacag cagaattaaa aggctaattt    5040
tttgactaaa taaagttagg aaaatcacta ctattaatta tttacgtatt ctttgaaatg    5100
gcagtattga taatgataaa ctcgaactga aaaagcgtgt tttttattca aaatgattct    5160
aactccctta cgtaatcaag gaatcttttt gccttggcct ccgcgtcatt aaacttcttg    5220
```

```
ttgttgacgc taacattcaa cgctagtata tattcgtttt tttcaggtaa gttcttttca    5280
acgggtctta ctgatgaggc agtcgcgtct gaacctgtta agaggtcaaa tatgtcttct    5340
tgaccgtacg tgtcttgcat gttattagct ttgggaattt gcatcaagtc ataggaaaat    5400
ttaaatcttg gctctcttgg gctcaaggtg acaaggtcct cgaaaatagg gcgcgcccca    5460
ccgcggtgga gctccagctt tgttcccctt tagtgagggt taattgcgcg cttggcgtaa    5520
tcatggtcat agctgtttcc tgtgtgaaat tgttatccgc tcacaattcc acacaacata    5580
ggagccggaa gcataaagtg taaagcctgg ggtgcctaat gagtgaggta actcacatta    5640
attgcgttgc gctcactgcc cgcttttcag tcgggaaacc tgtcgtgcca gctgcattaa    5700
tgaatcggcc aacgcgcggg gagaggcggt ttgcgtattg ggcgctcttc cgcttcctcg    5760
ctcactgact cgctgcgctc ggtcgttcgg ctgcggcgag cggtatcagc tcactcaaag    5820
gcggtaatac ggttatccac agaatcaggg gataacgcag gaaagaacat gtgagcaaaa    5880
ggccagcaaa aggccaggaa ccgtaaaaag gccgcgttgc tggcgttttt ccataggctc    5940
cgcccccctg acgagcatca caaaaatcga cgctcaagtc agaggtggcg aaacccgaca    6000
ggactataaa gataccaggc gtttccccct ggaagctccc tcgtgcgctc tcctgttccg    6060
accctgccgc ttaccggata cctgtccgcc tttctccctt cgggaagcgt ggcgctttct    6120
catagctcac gctgtaggta tctcagttcg gtgtaggtcg ttcgctccaa gctgggctgt    6180
gtgcacgaac cccccgttca gcccgaccgc tgcgccttat ccggtaacta tcgtcttgag    6240
tccaacccgg taagacacga cttatcgcca ctggcagcag ccactggtaa caggattagc    6300
agagcgaggt atgtaggcgg tgctacagag ttcttgaagt ggtggcctaa ctacggctac    6360
actagaagga cagtatttgg tatctgcgct ctgctgaagc cagttacctt cggaaaaaga    6420
gttggtagct cttgatccgg caaacaaacc accgctggta gcggtggttt ttttgtttgc    6480
aagcagcaga ttacgcgcag aaaaaaagga tctcaagaag atcctttgat cttttctacg    6540
gggtctgacg ctcagtggaa cgaaaactca cgttaaggga ttttggtcat gagattatca    6600
aaaaggatct tcacctagat ccttttaaat taaaaatgaa gttttaaatc aatctaaagt    6660
atatatgagt aaacttggtc tgacagttac caatgcttaa tcagtgaggc acctatctca    6720
gcgatctgtc tatttcgttc atccatagtt gcctgactcc ccgtcgtgta gataactacg    6780
atacgggagg gcttaccatc tggccccagt gctgcaatga taccgcgaga cccacgctca    6840
ccggctccag atttatcagc aataaaccag ccagccggaa gggccgagcg cagaagtggt    6900
cctgcaactt tatccgcctc catccagtct attaattgtt gccgggaagc tagagtaagt    6960
agttcgccag ttaatagttt gcgcaacgtt gttgccattg ctacaggcat cgtggtgtca    7020
cgctcgtcgt ttggtatggc ttcattcagc tccggttccc aacgatcaag gcgagttaca    7080
tgatccccca tgttgtgcaa aaaagcggtt agctccttcg gtcctccgat cgttgtcaga    7140
agtaagttgg ccgcagtgtt atcactcatg gttatggcag cactgcataa ttctcttact    7200
gtcatgccat ccgtaagatg cttttctgtg actggtgagt actcaaccaa gtcattctga    7260
gaatagtgta tgcggcgacc gagttgctct tgcccggcgt caatacggga taataccgcg    7320
ccacatagca gaactttaaa agtgctcatc attggaaaac gttcttcggg gcgaaaactc    7380
tcaaggatct taccgctgtt gagatccagt tcgatgtaac ccactcgtgc acccaactga    7440
tcttcagcat cttttacttt caccagcgtt tctgggtgag caaaaacagg aaggcaaaat    7500
gccgcaaaaa agggaataag ggcgacacgg aaatgttgaa tactcatact cttcctttt    7560 caatattatt gaagcattta tcagggttat tgtctcatga gcggatacat atttgaatgt    7620
```

| | |
|---|---|
| atttagaaaa ataaacaaat aggggttccg cgcacatttc cccgaaaagt gccacctgaa | 7680 |
| cgaagcatct gtgcttcatt ttgtagaaca aaaatgcaac gcgagagcgc taattttttca | 7740 |
| aacaaagaat ctgagctgca tttttacaga acagaaatgc aacgcgaaag cgctattta | 7800 |
| ccaacgaaga atctgtgctt cattttttgta aaacaaaaat gcaacgcgag agcgctaatt | 7860 |
| tttcaaacaa agaatctgag ctgcattttt acagaacaga atgcaacgc gagagcgcta | 7920 |
| ttttaccaac aaagaatcta acttcttttt ttgttctaca aaaatgcatc ccgagagcgc | 7980 |
| tatttttcta acaaagcatc ttagattact tttttttctcc tttgtgcgct ctataatgca | 8040 |
| gtctcttgat aacttttttgc actgtaggtc cgttaaggtt agaagaaggc tactttggtg | 8100 |
| tctatttttct cttccataaa aaaagcctga ctccacttcc cgcgtttact gattactagc | 8160 |
| gaagctgcgg gtgcatttttt tcaagataaa ggcatccccg attatattct ataccgatgt | 8220 |
| ggattgcgca actttgtga acagaaagtg atagcgttga tgattcttca ttggtcagaa | 8280 |
| aattatgaac ggtttcttct attttgtctc tatatactac gtataggaaa tgtttacatt | 8340 |
| ttcgtattgt tttcgattca ctctatgaat agttcttact acaatttttt tgtctaaaga | 8400 |
| gtaatactag agataaacat aaaaaatgta gaggtcgagt ttagatgcaa gttcaaggag | 8460 |
| cgaaaggtgg atgggtaggt tatatagga tatagcacag agatatatag caaagagata | 8520 |
| cttttgagca atgtttgtgg aagcggtatt cgcaatattt tagtagctcg ttacagtccg | 8580 |
| gtgcgttttt ggttttttga aagtgcgtct tcagagcgct tttggttttc aaaagcgctc | 8640 |
| tgaagttcct atactttcta gagaatagga acttcggaat aggaacttca aagcgtttcc | 8700 |
| gaaaacgagc gcttccgaaa atgcaacgcg agctgcgcac atacagctca ctgttcacgt | 8760 |
| cgcacctata tctgcgtgtt gcctgtatat atatatacat gagaagaacg gcatagtgcg | 8820 |
| tgtttatgct taaatgcgta cttatatgcg tctatttatg taggatgaaa ggtagtctag | 8880 |
| tacctcctgt gatattatcc cattccatgc ggggtatcgt atgcttcctt cagcactacc | 8940 |
| ctttagctgt tctatatgct gccactcctc aattggatta gtctcatcct tcaatgctat | 9000 |
| catttccttt gatattggat catactaaga aaccattatt atcatgacat taacctataa | 9060 |
| aaataggcgt atcacgaggc cctttcgtc | 9089 |

<210> SEQ ID NO 15
<211> LENGTH: 5956
<212> TYPE: DNA
<213> ORGANISM: Artificial Sequence
<220> FEATURE:
<223> OTHER INFORMATION: pBTX1 plasmid

<400> SEQUENCE: 15

| | |
|---|---|
| tcgaggtcga cggtatcgat aagcttgata tcgaattcct gcagcccggg ggatctgaaa | 60 |
| tgaataacaa tactgacagt actaaataat tgcctacttg gcttcacata cgttgcatac | 120 |
| gtcgatatag ataataatga taatgacagc aggattatcg taatacgtaa tagttgaaaa | 180 |
| tctcaaaaat gtgtgggtca ttacgtaaat aatgatagga atgggattct tctatttttc | 240 |
| cttttttccat tctagcagcc gtcgggaaaa cgtggcatcc tctctttcgg gctcaattgg | 300 |
| agtcacgctg ccgtgagcat cctctctttc catatctaac aactgagcac gtaaccaatg | 360 |
| gaaaagcatg agcttagcgt tgctccaaaa aagtattgga tggttaatac catttgtctg | 420 |
| ttctcttctg actttgactc ctcaaaaaaa aaaaatctac aatcaacaga tcgcttcaat | 480 |
| tacgccctca caaaaacttt tttccttctt cttcgcccac gttaaatttt atccctcatg | 540 |

```
ttgtctaacg gatttctgca cttgatttat tataaaaaga caaagacata atacttctct    600
atcaatttca gttattgttc ttccttgcgt tattcttctg ttcttctttt tcttttgtca    660
tatataacca taaccaagta atacatattc aaatctagag ggatccctga ggttaattaa    720
acgcgtgagt aagcgaattt cttatgattt atgattttta ttattaaata agttataaaa    780
aaaataagtg tatacaaatt ttaaagtgac tcttaggttt taaaacgaaa attcttattc    840
ttgagtaact ctttcctgta ggtcaggttg ctttctcagg tatagcatga ggtcgctctt    900
attgaccaca cctctaccgg catgccgagc aaatgcctgc aaatcgctcc ccatttcacc    960
caattgtaga tatgctaact ccagcaatga gttgatgaat ctcggtgtgt attttatgtc   1020
ctcagaggac aacacctgtg gtactagttc tagagcggcc gccaccgcgg tggagctcca   1080
gcttttgttc cctttagtga gggttaattg cgcgcttggc gtaatcatgg tcatagctgt   1140
ttcctgtgtg aaattgttat ccgctcacaa ttccacacaa cataggagcc ggaagcataa   1200
agtgtaaagc ctggggtgcc taatgagtga ggtaactcac attaattgcg ttgcgctcac   1260
tgcccgcttt ccagtcggga aacctgtcgt gccagctgca ttaatgaatc ggccaacgcg   1320
cggggagagg cggtttgcgt attgggcgct cttccgcttc ctcgctcact gactcgctgc   1380
gctcggtcgt tcggctgcgg cgagcggtat cagctcactc aaaggcggta atacggttat   1440
ccacagaatc aggggataac gcaggaaaga acatgtgagc aaaaggccag caaaaggcca   1500
ggaaccgtaa aaaggccgcg ttgctggcgt ttttccatag gctccgcccc cctgacgagc   1560
atcacaaaaa tcgacgctca agtcagaggt ggcgaaaccc gacaggacta taaagatacc   1620
aggcgtttcc ccctggaagc tccctcgtgc gctctcctgt tccgaccctg ccgcttaccg   1680
gatacctgtc cgcctttctc ccttcgggaa gcgtggcgct ttctcatagc tcacgctgta   1740
ggtatctcag ttcggtgtag gtcgttcgct ccaagctggg ctgtgtgcac gaaccccccg   1800
ttcagcccga ccgctgcgcc ttatccggta actatcgtct tgagtccaac ccggtaagac   1860
acgacttatc gccactggca gcagccactg gtaacaggat tagcagagcg aggtatgtag   1920
gcggtgctac agagttcttg aagtggtggc ctaactacgg ctacactaga aggacagtat   1980
ttggtatctg cgctctgctg aagccagtta ccttcggaaa aagagttggt agctcttgat   2040
ccggcaaaca aaccaccgct ggtagcggtg gtttttttgt ttgcaagcag cagattacgc   2100
gcagaaaaaa aggatctcaa gaagatcctt tgatcttttc tacggggtct gacgctcagt   2160
ggaacgaaaa ctcacgttaa gggattttgg tcatgagatt atcaaaaagg atcttcacct   2220
agatcctttt aaattaaaaa tgaagtttta aatcaatcta agtatatat gagtaaactt   2280
ggtctgacag ttaccaatgc ttaatcagtg aggcacctat ctcagcgatc tgtctatttc   2340
gttcatccat agttgcctga ctccccgtcg tgtagataac tacgatacgg gagggcttac   2400
catctggccc cagtgctgca atgataccgc gagacccacg ctcaccggct ccagatttat   2460
cagcaataaa ccagccagcc ggaagggccg agcgcagaag tggtcctgca actttatccg   2520
cctccatcca gtctattaat tgttgccggg aagctagagt aagtagttcg ccagttaata   2580
gtttgcgcaa cgttgttgcc attgctacag gcatcgtggt gtcacgctcg tcgtttggta   2640
tggcttcatt cagctccggt tcccaacgat caaggcgagt tacatgatcc cccatgttgt   2700
gcaaaaaagc ggttagctcc ttcggtcctc cgatcgttgt cagaagtaag ttggccgcag   2760
tgttatcact catggttatg gcagcactgc ataattctct tactgtcatg ccatccgtaa   2820
gatgcttttc tgtgactggt gagtactcaa ccaagtcatt ctgagaatag tgtatgcggc   2880
gaccgagttg ctcttgcccg gcgtcaatac gggataatac cgcgccacat agcagaactt   2940
```

```
taaaaagtgct catcattgga aaacgttctt cggggcgaaa actctcaagg atcttaccgc    3000
tgttgagatc cagttcgatg taacccactc gtgcacccaa ctgatcttca gcatctttta    3060 cttttcaccag cgtttctggg tgagcaaaaa caggaaggca aaatgccgca aaaagggaa    3120 taagggcgac acgaaatgt tgaatactca tactcttcct ttttcaatat tattgaagca    3180
tttatcaggg ttattgtctc atgagcggat acatatttga atgtatttag aaaaataaac    3240 aaatagggt tccgcgcaca tttccccgaa aagtgccacc tgggtccttt tcatcacgtg    3300
ctataaaaat aattataatt taaattttt aatataaata tataaattaa aaatagaaag    3360 taaaaaaga aattaaagaa aaaatagttt ttgttttccg aagatgtaaa agactctagg    3420
gggatcgcca acaaatacta cctttatct tgctcttcct gctctcaggt attaatgccg    3480
aattgtttca tcttgtctgt gtagaagacc acacacgaaa atcctgtgat tttacatttt    3540
acttatcgtt aatcgaatgt atatctattt aatctgcttt tcttgtctaa taaatatata    3600
tgtaaagtac gcttttgtt gaattttttt aaacctttgt ttattttttt ttcttcattc    3660
cgtaactctt ctaccttctt tatttacttt ctaaaatcca aatacaaaac ataaaaataa    3720
ataaacacag agtaaattcc caaattattc catcattaaa agatacgagg cgcgtgtaag    3780
ttacaggcaa gcgatccgtc ctaagaaacc attattatca tgacattaac ctataaaaat    3840
aggcgtatca cgaggccctt tcgtctcgcg cgtttcggtg atgacggtga aaacctctga    3900
cacatgcagc tcccggagac ggtcacagct tgtctgtaag cggatgccgg gagcagacaa    3960
gcccgtcagg gcgcgtcagc gcgtgttggc gggtgtcggg gctggcttaa ctatgcggca    4020
tcagagcaga ttgtactgag agtgcaccat aaattcccgt tttaagagct tggtgagcgc    4080
taggagtcac tgccaggtat cgtttgaaca cggcattagt cagggaagtc ataacacagt    4140
cctttcccgc aattttcttt ttctattact cttggcctcc tctagtacac tctatatttt    4200
tttatgcctc ggtaatgatt ttcattttt ttttcccct agcggatgac tcttttttt    4260 tcttagcgat tggcattatc acataatgaa ttatacatta tataaagtaa tgtgatttct    4320
tcgaagaata tactaaaaaa tgagcaggca agataaacga aggcaaagat gacgagcag    4380 aaagccctag taaagcgtat tacaaatgaa accaagattc agattgcgat ctcttaaag    4440 ggtggtcccc tagcgataga gcactcgatc ttcccagaaa aagaggcaga agcagtagca    4500
gaacaggcca cacaatcgca agtgattaac gtccacacag gtatagggtt tctgaccat    4560 atgatacatg ctctggccaa gcattccggc tggtcgctaa tcgttgagtg cattggtgac    4620
ttacacatag acgaccatca caccactgaa gactgcggga ttgctctcgg tcaagctttt    4680
aaagaggccc tactggcgcg tggagtaaaa aggtttggat caggatttgc gcctttggat    4740
gaggcacttt ccagacggt ggtagatctt tcgaacaggc cgtacgcagt tgtcgaactt    4800
ggtttgcaaa gggagaaagt aggagatctc tcttgcgaga tgatcccgca ttttcttgaa    4860
agctttgcag aggctagcag aattaccctc cacgttgatt gtctgcgagg caagaatgat    4920
catcaccgta gtgagagtgc gttcaaggct cttgcggttg ccataagaga agccacctcg    4980
cccaatggta ccaacgatgt tccctccacc aaaggtgttc ttatgtagtg acaccgatta    5040
tttaaagctg cagcatacga tatatataca tgtgtatata tgtataccta tgaatgtcag    5100
taagtatgta tacgaacagt atgatactga agatgacaag gtaatgcatc attctatacg    5160
tgtcattctg aacgaggcgc gctttccttt tttcttttg cttttctttt tttttctct    5220 tgaactcgac ggatctatgc ggtgtgaaat accgcacaga tgcgtaagga gaaaataccg    5280
```

-continued

```
catcaggaaa ttgtaaacgt taatattttg ttaaaattcg cgttaaattt ttgttaaatc    5340
agctcatttt ttaaccaata ggccgaaatc ggcaaaatcc cttataaatc aaaagaatag    5400
accgagatag ggttgagtgt tgttccagtt tggaacaaga gtccactatt aaagaacgtg    5460
gactccaacg tcaaagggcg aaaaaccgtc tatcagggcg atggcccact acgtgaacca    5520
tcaccctaat caagtttttt ggggtcgagg tgccgtaaag cactaaatcg gaaccctaaa    5580
gggagccccc gatttagagc ttgacgggga agccggcga acgtggcgag aaaggaaggg    5640
aagaaagcga aaggagcggg cgctagggcg ctggcaagtg tagcggtcac gctgcgcgta    5700
accaccacac ccgccgcgct taatgcgccg ctacagggcg cgtcgcgcca ttcgccattc    5760
aggctgcgca actgttggga agggcgatcg gtgcgggcct cttcgctatt acgccagctg    5820
gcgaaagggg gatgtgctgc aaggcgatta agttgggtaa cgccagggtt ttcccagtca    5880
cgacgttgta aaacgacggc cagtgagcgc gcgtaatacg actcactata gggcgaattg    5940
ggtaccgggc cccccc                                                    5956
```

<210> SEQ ID NO 16
<211> LENGTH: 570
<212> TYPE: PRT
<213> ORGANISM: Bacillus subtilis

<400> SEQUENCE: 16

```
Met Thr Lys Ala Thr Lys Glu Gln Lys Ser Leu Val Lys Asn Arg Gly
1               5                   10                  15

Ala Glu Leu Val Val Asp Cys Leu Val Glu Gln Gly Val Thr His Val
                20                  25                  30

Phe Gly Ile Pro Gly Ala Lys Ile Asp Ala Val Phe Asp Ala Leu Gln
            35                  40                  45

Asp Lys Gly Pro Glu Ile Ile Val Ala Arg His Glu Gln Asn Ala Ala
        50                  55                  60

Phe Met Ala Gln Ala Val Gly Arg Leu Thr Gly Lys Pro Gly Val Val
65                  70                  75                  80

Leu Val Thr Ser Gly Pro Gly Ala Ser Asn Leu Ala Thr Gly Leu Leu
                85                  90                  95

Thr Ala Asn Thr Glu Gly Asp Pro Val Val Ala Leu Ala Gly Asn Val
            100                 105                 110

Ile Arg Ala Asp Arg Leu Lys Arg Thr His Gln Ser Leu Asp Asn Ala
        115                 120                 125

Ala Leu Phe Gln Pro Ile Thr Lys Tyr Ser Val Glu Val Gln Asp Val
    130                 135                 140

Lys Asn Ile Pro Glu Ala Val Thr Asn Ala Phe Arg Ile Ala Ser Ala
145                 150                 155                 160

Gly Gln Ala Gly Ala Ala Phe Val Ser Phe Pro Gln Asp Val Val Asn
                165                 170                 175

Glu Val Thr Asn Thr Lys Asn Val Arg Ala Val Ala Ala Pro Lys Leu
            180                 185                 190

Gly Pro Ala Ala Asp Asp Ala Ile Ser Ala Ala Ile Ala Lys Ile Gln
        195                 200                 205

Thr Ala Lys Leu Pro Val Val Leu Val Gly Met Lys Gly Gly Arg Pro
    210                 215                 220

Glu Ala Ile Lys Ala Val Arg Lys Leu Leu Lys Val Gln Leu Pro
225                 230                 235                 240

Phe Val Glu Thr Tyr Gln Ala Ala Gly Thr Leu Ser Arg Asp Leu Glu
                245                 250                 255
```

-continued

```
Asp Gln Tyr Phe Gly Arg Ile Gly Leu Phe Arg Asn Gln Pro Gly Asp
                260                 265                 270
Leu Leu Leu Glu Gln Ala Asp Val Val Leu Thr Ile Gly Tyr Asp Pro
            275                 280                 285
Ile Glu Tyr Asp Pro Lys Phe Trp Asn Ile Asn Gly Asp Arg Thr Ile
        290                 295                 300
Ile His Leu Asp Glu Ile Ile Ala Asp Ile Asp His Ala Tyr Gln Pro
305                 310                 315                 320
Asp Leu Glu Leu Ile Gly Asp Ile Pro Ser Thr Ile Asn His Ile Glu
                325                 330                 335
His Asp Ala Val Lys Val Glu Phe Ala Glu Arg Glu Gln Lys Ile Leu
            340                 345                 350
Ser Asp Leu Lys Gln Tyr Met His Glu Gly Glu Gln Val Pro Ala Asp
        355                 360                 365
Trp Lys Ser Asp Arg Ala His Pro Leu Glu Ile Val Lys Glu Leu Arg
    370                 375                 380
Asn Ala Val Asp Asp His Val Thr Val Thr Cys Asp Ile Gly Ser His
385                 390                 395                 400
Ala Ile Trp Met Ser Arg Tyr Phe Arg Ser Tyr Glu Pro Leu Thr Leu
                405                 410                 415
Met Ile Ser Asn Gly Met Gln Thr Leu Gly Val Ala Leu Pro Trp Ala
            420                 425                 430
Ile Gly Ala Ser Leu Val Lys Pro Gly Glu Lys Val Val Ser Val Ser
        435                 440                 445
Gly Asp Gly Gly Phe Leu Phe Ser Ala Met Glu Leu Glu Thr Ala Val
    450                 455                 460
Arg Leu Lys Ala Pro Ile Val His Ile Val Trp Asn Asp Ser Thr Tyr
465                 470                 475                 480
Asp Met Val Ala Phe Gln Gln Leu Lys Lys Tyr Asn Arg Thr Ser Ala
                485                 490                 495
Val Asp Phe Gly Asn Ile Asp Ile Val Lys Tyr Ala Glu Ser Phe Gly
            500                 505                 510
Ala Thr Gly Leu Arg Val Glu Ser Pro Asp Gln Leu Ala Asp Val Leu
        515                 520                 525
Arg Gln Gly Met Asn Ala Glu Gly Pro Val Ile Ile Asp Val Pro Val
    530                 535                 540
Asp Tyr Ser Asp Asn Ile Asn Leu Ala Ser Asp Lys Leu Pro Lys Glu
545                 550                 555                 560
Phe Gly Glu Leu Met Lys Thr Lys Ala Leu
                565                 570
```

<210> SEQ ID NO 17
<211> LENGTH: 4531
<212> TYPE: DNA
<213> ORGANISM: Artificial Sequence
<220> FEATURE:
<223> OTHER INFORMATION: pUC19 ILV2

<400> SEQUENCE: 17

```
gatcccactt gaattgaact tattattcat ctatgactta attttagccg tcattagttt    60
tttagaaaaa aatatatata gtatatacga aaaaaatata catgactacc gatttggtag   120
aatgtcatat ataagaagca cgattaaata ataataaagt ctgcattttt tactgaaaat   180
gcttttgaaa taaatgtttt tgaaattcag tgcttaccgc ctgtacgctt atgacgtaat   240
```

```
tcagtctgtt gtctttcaac ttctgggtca aaatttatga actcgtctag accgctacca    300
cctgccacca ttggcaaaac aggaactttt ttatcaactt ccacttcaag caaaactggg    360
cccttggtag aaacgaattc tttcaactta gcgtccaatt cctcttgctt cttgactctt    420
aaacctttta aacccatagc ctccgctagt tttatgaaat cagggttcaa ttgatgtgtg    480
tgggaataac gatgttcgta gaacagggat tgccattgag taaccatacc ttgctcttca    540
ttgttcaaaa tcaaaatctt cactggagta ccagcttgaa cggcagaact caattccgtt    600
agagtcatgt taaggatgc gtcaccatca atgtcaataa ccaaagattc tggctttgca     660
acttgagcac cgatggcggc agggagaccg taacccatcg tacctaaacc acctgatgtg    720
atgaaagtat gtggatttct ccatgtccag tgttgagcag cccacatttg atgttgcccc    780
acacccgttg taacaatgac atgtcttcct gtgtcgttgg caaccttgga tagtttcttt    840
ataaccgtct gtggtttaat tttagatcct ggagtctcct ccatataagc gtatgggtat    900
tccttcttcc atttatttat ttgagcaaac cattcagacc tctccttaac tgggaaaatc    960
tttgacatca ttttgcccag attggtcgta gcatcacctt ccactgctat ttgagtttga   1020
acaaccttgt ttatgttttt tggactaacc tcgaaatgaa taataccacc tctaccctcg   1080
gcagctgcac gacgagcttc tggagcgaat ttagaaatat taccagtgac acggtcgtcg   1140
aatctagcac caactgcaat tatcaagtcg gcattttgca ctgccaggtt ggcagtagca   1200
caaccgtgca taccaagcat atccaatgat tttggatctt cttggtcgaa tgaacctaaa   1260
ccttgtaaag tagtggtgac aggtatttga gcacggtcac ttaattcttt tagtaatctt   1320
ggaccatctg catggtttaa aataccagca ccgacgtata agacaggttt ctttgccaag   1380
ttgatcaaat ctgctgcttt attgatactt tgcatgacaa attcatcttg tgcgcgactg   1440
gttaattggt ttagtgcgtt tgatggaaga gttgtttttg ttggaattgg atttcttaag   1500
atagctgctg taacatcctt tggtaaatcg accaagactg gtcccggtct accgctcgtg   1560
gcaatttcaa aagcctcgtt aatacgcaat ggcaattctt ccacggactt gaccatgaca   1620
ttccatttcg tacaagatct agaaatacca acgacgtcag cctcttggaa agcatcagta   1680
ccgatagcac tagttgggac ttgccctgta aagacaacca ttggaatccc gtctgcaaag   1740
gcatctgcca ttggagtaac gacattggtg gcacctggcc cagaagtaac caagacaaca   1800
cctggtttac cagaagctct ggcgtagcct tctgccatgt gaccggcacc ttgttcgtgt   1860
tttggaaggc atgcaagctt ggcgtaatca tggtcatagc tgtttcctgt gtgaaattgt   1920
tatccgctca caattccaca caacatacga gccggaagca taagtgtaa agcctggggt    1980
gcctaatgag tgagctaact cacattaatt gcgttgcgct cactgcccgc tttccagtcg   2040
ggaaacctgt cgtgccagct gcattaatga atcggccaac gcgcgggag aggcggtttg    2100
cgtattgggc gctcttccgc ttcctcgctc actgactcgc tgcgctcggt cgttcggctg   2160
cggcgagcgg tatcagctca ctcaaaggcg gtaatacggt tatccacaga atcaggggat   2220
aacgcaggaa agaacatgtg agcaaaaggc cagcaaaagg ccaggaaccg taaaaaggcc   2280
gcgttgctgg cgttttccca taggctccgc cccctgacg agcatcacaa aaatcgacgc    2340
tcaagtcaga ggtggcgaaa cccgacagga ctataaagat accaggcgtt ccccctgga    2400
agctccctcg tgcgctctcc tgttccgacc ctgccgctta ccggatacct gtccgccttt   2460
ctcccttcgg gaagcgtggc gctttctcat agctcacgct gtaggtatct cagttcggtg   2520
taggtcgttc gctccaagct gggctgtgtg cacgaacccc ccgttcagcc cgaccgctgc   2580
gccttatccg gtaactatcg tcttgagtcc aacccggtaa gacacgactt atcgccactg   2640
```

```
gcagcagcca ctggtaacag gattagcaga gcgaggtatg taggcggtgc tacagagttc   2700
ttgaagtggt ggcctaacta cggctacact agaaggacag tatttggtat ctgcgctctg   2760
ctgaagccag ttaccttcgg aaaaagagtt ggtagctctt gatccggcaa acaaaccacc   2820
gctggtagcg gtggttttt tgtttgcaag cagcagatta cgcgcagaaa aaaggatct   2880 caagaagatc ctttgatctt ttctacgggg tctgacgctc agtggaacga aaactcacgt   2940
taagggattt tggtcatgag attatcaaaa aggatcttca cctagatcct tttaaattaa   3000
aaatgaagtt ttaaatcaat ctaaagtata tatgagtaaa cttggtctga cagttaccaa   3060
tgcttaatca gtgaggcacc tatctcagcg atctgtctat ttcgttcatc catagttgcc   3120
tgactccccg tcgtgtagat aactacgata cgggagggct taccatctgg ccccagtgct   3180
gcaatgatac cgcgagaccc acgctcaccg gctccagatt tatcagcaat aaaccagcca   3240
gccggaaggg ccgagcgcag aagtggtcct gcaactttat ccgcctccat ccagtctatt   3300
aattgttgcc gggaagctag agtaagtagt tcgccagtta atagtttgcg caacgttgtt   3360
gccattgcta caggcatcgt ggtgtcacgc tcgtcgtttg gtatggcttc attcagctcc   3420
ggttcccaac gatcaaggcg agttacatga tcccccatgt tgtgcaaaaa agcggttagc   3480
tccttcggtc ctccgatcgt tgtcagaagt aagttggccg cagtgttatc actcatggtt   3540
atggcagcac tgcataattc tcttactgtc atgccatccg taagatgctt ttctgtgact   3600
ggtgagtact caaccaagtc attctgagaa tagtgtatgc ggcgaccgag ttgctcttgc   3660
ccggcgtcaa tacgggataa taccgcgcca catagcagaa ctttaaaagt gctcatcatt   3720
ggaaaacgtt cttcggggcg aaaactctca aggatcttac cgctgttgag atccagttcg   3780
atgtaaccca ctcgtgcacc caactgatct tcagcatctt ttactttcac cagcgtttct   3840
gggtgagcaa aaacaggaag gcaaaatgcc gcaaaaaagg aataagggc gacacggaaa   3900 tgttgaatac tcatactctt cctttttcaa tattattgaa gcatttatca gggttattgt   3960
ctcatgagcg gatacatatt tgaatgtatt tagaaaaata acaaataggg gttccgcgc   4020 acatttcccc gaaaagtgcc acctgacgtc taagaaacca ttattatcat gacattaacc   4080
tataaaaata ggcgtatcac gaggcccttt cgtctcgcgc gtttcggtga tgacggtgaa   4140
aacctctgac acatgcagct cccggagacg gtcacagctt gtctgtaagc ggatgccggg   4200
agcagacaag cccgtcaggg cgcgtcagcg ggtgttggcg ggtgtcgggg ctggcttaac   4260
tatgcggcat cagagcagat tgtactgaga gtgcaccata tgcggtgtga ataccgcac   4320 agatgcgtaa ggagaaaata ccgcatcagg cgccattcgc cattcaggct gcgcaactgt   4380
tgggaagggc gatcggtgcg ggcctcttcg ctattacgcc agctggcgaa agggggatgt   4440
gctgcaaggc gattaagttg ggtaacgcca gggttttccc agtcacgacg ttgtaaaacg   4500
acggccagtg aattcgagct cggtacccgg g   4531
```

<210> SEQ ID NO 18
<211> LENGTH: 6074
<212> TYPE: DNA
<213> ORGANISM: Artificial Sequence
<220> FEATURE:
<223> OTHER INFORMATION: pLA59 ILV2-410

<400> SEQUENCE: 18

```
gatccgcatt gcggattacg tattctaatg ttcagtaccg ttcgtataat gtatgctata     60
cgaagttatg cagattgtac tgagagtgca ccataccacc ttttcaattc atcatttttt    120
```

-continued

```
ttttattctt ttttttgatt tcggtttcct tgaaattttt ttgattcggt aatctccgaa      180
cagaaggaag aacgaaggaa ggagcacaga cttagattgg tatatatacg catatgtagt      240
gttgaagaaa catgaaattg cccagtattc ttaacccaac tgcacagaac aaaaacctgc      300
aggaaacgaa gataaatcat gtcgaaagct acatataagg aacgtgctgc tactcatcct      360
agtcctgttg ctgccaagct atttaatatc atgcacgaaa agcaaacaaa cttgtgtgct      420
tcattggatg ttcgtaccac caaggaatta ctggagttag ttgaagcatt aggtcccaaa      480
atttgtttac taaaaacaca tgtggatatc ttgactgatt tttccatgga gggcacagtt      540
aagccgctaa aggcattatc cgccaagtac aattttttac tcttcgaaga cagaaaattt      600
gctgacattg gtaatacagt caaattgcag tactctgcgg gtgtatacag aatagcagaa      660
tgggcagaca ttacgaatgc acacggtgtg gtgggcccag gtattgttag cggtttgaag      720
caggcggcag aagaagtaac aaaggaacct agaggccttt tgatgttagc agaattgtca      780
tgcaagggct ccctatctac tggagaatat actaagggta ctgttgacat tgcgaagagc      840
gacaaagatt ttgttatcgg ctttattgct caaagagaca tgggtggaag agatgaaggt      900
tacgattggt tgattatgac acccggtgtg ggtttagatg acaagggaga cgcattgggt      960
caacagtata gaaccgtgga tgatgtggtc tctacaggat ctgacattat tattgttgga     1020
agaggactat ttgcaaaggg aagggatgct aaggtagagg gtgaacgtta cagaaaagca     1080
ggctgggaag catatttgag aagatgcggc cagcaaaact aaaaaactgt attataagta     1140
aatgcatgta tactaaactc acaaattaga gcttcaattt aattatatca gttattaccc     1200
tatgcggtgt gaaataccgc acagatgcgt aaggagaaaa taccgcatca ggaaattgta     1260
aacgttaata ttttgttaaa attcgcgtta aatttttgtt aaatcagctc attttttaac     1320
caataggccg aaatcggcaa atcccttat aaatcaaaag aatagaccga gatagggttg     1380
agtgttgttc cagtttggaa caagagtcca ctattaaaga acgtggactc caacgtcaaa     1440
gggcgaaaaa ccgtctatca gggcgatggc ccactacgtg aaccatcacc ctaatcaaga     1500
taacttcgta atgtatgc tatacgaacg gtaccagtga tgatacaacg agttagccaa     1560
ggtgaattca ctggccgtcg ttttacaacg tcgtgactgg gaaaaccctg gcgttaccca     1620
acttaatcgc cttgcagcac atccccttt cgccagctgg cgtaatagcg aagaggcccg     1680
caccgatcgc ccttcccaac agttgcgcag cctgaatggc gaatggcgcc tgatgcggta     1740
ttttctcctt acgcatctgt gcggtatttc acaccgcata tggtgcactc tcagtacaat     1800
ctgctctgat gccgcatagt taagccagcc ccgacacccg ccaacacccg ctgacgcgcc     1860
ctgacgggct tgtctgctcc cggcatccgc ttacagacaa gctgtgaccg tctccgggag     1920
ctgcatgtgt cagaggtttt caccgtcatc accgaaacgc gcgagacgaa agggcctcgt     1980
gatacgccta ttttatagg ttaatgtcat gataataatg gtttcttaga cgtcaggtgg     2040
cacttttcgg ggaaatgtgc gcggaacccc tatttgttta ttttctaaa tacattcaaa     2100 tatgtatccg ctcatgagac aataaccctg ataaatgctt caataatatt gaaaaaggaa     2160
gagtatgagt attcaacatt tccgtgtcgc ccttattccc ttttttgcgg catttttgcct     2220 tcctgttttt gctcacccag aaacgctggt gaaagtaaaa gatgctgaag atcagttggg     2280
tgcacgagtg ggttacatcg aactggatct caacagcggt aagatccttg agagttttcg     2340
ccccgaagaa cgttttccaa tgatgagcac ttttaaagtt ctgctatgtg gcgcggtatt     2400
atcccgtatt gacgccgggc aagagcaact cggtcgccgc atacactatt ctcagaatga     2460
cttggttgag tactcaccag tcacagaaaa gcatcttacg gatggcatga cagtaagaga     2520
```

```
attatgcagt gctgccataa ccatgagtga taacactgcg gccaacttac ttctgacaac  2580
gatcggagga ccgaaggagc taaccgcttt tttgcacaac atgggggatc atgtaactcg  2640
ccttgatcgt tgggaaccgg agctgaatga agccatacca aacgacgagc gtgacaccac  2700
gatgcctgta gcaatggcaa caacgttgcg caaactatta actggcgaac tacttactct  2760
agcttcccgg caacaattaa tagactggat ggaggcggat aaagttgcag gaccacttct  2820
gcgctcggcc cttccggctg gctggtttat tgctgataaa tctggagccg tgagcgtgg  2880
gtctcgcggt atcattgcag cactgggggcc agatggtaag ccctcccgta tcgtagttat  2940
ctacacgacg gggagtcagg caactatgga tgaacgaaat agacagatcg ctgagatagg  3000
tgcctcactg attaagcatt ggtaactgtc agaccaagtt tactcatata ctttagat   3060
tgatttaaaa cttcattttt aatttaaaag gatctaggtg aagatccttt ttgataatct  3120
catgaccaaa atcccttaac gtgagttttc gttccactga gcgtcagacc ccgtagaaaa  3180
gatcaaagga tcttcttgag atcctttttt tctgcgcgta atctgctgct tgcaaacaaa  3240
aaaaccaccg ctaccagcgg tggtttgttt gccggatcaa gagctaccaa ctctttttcc  3300
gaaggtaact ggcttcagca gagcgcagat accaaatact gtccttctag tgtagccgta  3360
gttaggccac cacttcaaga actctgtagc accgcctaca tacctcgctc tgctaatcct  3420
gttaccagtg gctgctgcca gtggcgataa gtcgtgtctt accgggttgg actcaagacg  3480
atagttaccg gataaggcgc agcggtcggg ctgaacgggg ggttcgtgca cacagcccag  3540
cttggagcga acgacctaca ccgaactgag atacctacag cgtgagctat gagaaagcgc  3600
cacgcttccc gaagggagaa aggcggacag gtatccggta agcggcaggg tcggaacagg  3660
agagcgcacg agggagcttc caggggggaaa cgcctggtat ctttatagtc ctgtcgggtt  3720
tcgccacctc tgacttgagc gtcgattttt gtgatgctcg tcagggggggc ggagcctatg  3780
gaaaaacgcc agcaacgcgg cctttttacg gttcctggcc ttttgctggc cttttgctca  3840
catgttcttt cctgcgttat cccctgattc tgtggataac cgtattaccg cctttgagtg  3900
agctgatacc gctcgccgca gccgaacgac cgagcgcagc gagtcagtga gcgaggaagc  3960
ggaagagcgc ccaatacgca aaccgcctct ccccgcgcgt tggccgattc attaatgcag  4020
ctggcacgac aggtttcccg actggaaagc gggcagtgag cgcaacgcaa ttaatgtgag  4080
ttagctcact cattaggcac cccaggcttt acactttatg cttccggctc gtatgttgtg  4140
tggaattgtg agcggataac aatttcacac aggaaacagc tatgaccatg attacgccaa  4200
gcttgcatgc cttccaaaac acgaacaagg tgccggtcac atggcagaag gctacgccag  4260
agcttctggt aaaccaggtg ttgtcttggt tacttctggg ccaggtgcca ccaatgtcgt  4320
tactccaatg gcagatgcct ttgcagacgg gattccaatg gttgtcttta cagggcaagt  4380
ctcaactagt gctatcggta ctgatgcttt ccaagaggct gacgtcgttg gtatttctag  4440
atcttgtacg aaatgaatg tcatggtcaa gtccgtggaa gaattgccat tgcgtattaa  4500
cgaggctttt gaaattgcca cgagcggtag accgggacca gtcttggtcg atttaccaaa  4560
ggatgttaca gcagctatct taagaaatcc aattccaaca aaaacaactc ttccatcaaa  4620
cgcactaaac caattaacca gtcgcgcaca agatgaattt gtcatgcaaa gtatcaataa  4680
agcagcagat ttgatcaact ggcaaagaa acctgtctta tacgtcggtg ctggtatttt  4740
aaaccatgca gatggccaa gattactaaa agaattaagt gaccgtgctc aaatacctgt  4800
caccactact ttacaaggtt taggttcatt cgaccaagaa gatccaaaat cattggatat  4860
```

```
gcttggtatg cacggttgtg ctactgccaa cctggcagtg caaaatgccg acttgataat    4920
tgcagttggt gctagattcg acgaccgtgt cactggtaat atttctaaat tcgctccaga    4980
agctcgtcgt gcagctgccg agggtagagg tggtattatt catttcgagg ttagtccaaa    5040
aaacataaac aaggttgttc aaactcaaat agcagtggaa ggtgatgcta cgaccaatct    5100
gggcaaaatg atgtcaaaga ttttcccagt taaggagagg tctgaatggt ttgctcaaat    5160
aaataaatgg aagaaggaat acccatacgc ttatatggag gagactccag gatctaaaat    5220
taaaccacag acggttataa agaaactatc caaggttgcc aacgacacag aagacatgt     5280 cattgttaca acgggtgtgg ggcaacatca aatgtgggct gctcaacact ggacatggag    5340
aaatccacat actttcatca catcaggtgg tttaggtacg atgggttacg gtctccctgc    5400
cgccatcggt gctcaagttg caaagccaga atctttggtt attgacattg atggtgacgc    5460
atcctttaac atgactctaa cggaattgag ttctgccgtt caagctggta ctccagtgaa    5520
gattttgatt ttgaacaatg aagagcaagg tatggttact caatggcaat ccctgttcta    5580
cgaacatcgt tattcccaca cacatcaatt gaaccctgat ttcataaaac tagcggaggc    5640
tatgggttta aaaggtttaa gagtcaagaa gcaagaggaa ttggacgcta agttgaaaga    5700
attcgtttct accaagggcc cagttttgct tgaagtggaa gttgataaaa aagttcctgt    5760
tttgccaatg gtggcaggtg gtagcggtct agacgagttc ataaattttg acccagaagt    5820
tgaaagacaa cagactgaat tacgtcataa gcgtacaggc ggtaagcact gaatttcaaa    5880
aacatttatt tcaaaagcat tttcagtaaa aaatgcagac tttattatta tttaatcgtg    5940
cttcttatat atgacattct accaaatcgg tagtcatgta tatttttttc gtatatactt    6000
tatatatttt tttctaaaaa actaatgacg gctaaaatta agtcatagat gaataataag    6060
ttcaattcaa gtgg                                                       6074

<210> SEQ ID NO 19
<211> LENGTH: 6827
<212> TYPE: DNA
<213> ORGANISM: Artificial Sequence
<220> FEATURE:
<223> OTHER INFORMATION: pLA59 ilvB

<400> SEQUENCE: 19
cgcctacttg gcttcacata cgttgcatac gtcgatatag ataataatga taatgacagc      60
aggattatcg taatacgtaa tagttgaaaa tctcaaaaat gtgtgggtca ttacgtaaat     120
aatgatagga atgggattct tctatttttc cttttttccat tctagcagcc gtcgggaaaa    180
cgtggcatcc tctctttcgg gctcaattgg agtcacgctg ccgtgagcat cctctctttc    240
catatctaac aactgagcac gtaaccaatg gaaaagcatg agcttagcgt tgctccaaaa    300
aagtattgga tggttaatac catttgtctg ttctcttctg actttgactc ctcaaaaaaa    360
aaaaatctac aatcaacaga tcgcttcaat tacgccctca caaaaacttt ttccttctt     420 cttcgcccac gttaaatttt atccctcatg ttgtctaacg gatttctgca cttgatttat    480
tataaaaaga caaagacata atacttctct atcaatttca gttattgttc ttccttgcgt    540
tattcttctg ttcttctttt tcttttgtca tatataacca taccaagta atacatattc     600 aaggtaccat ggcaagttcg ggcacaacat cgacgcgtaa gcgctttacc ggcgcagaat    660
ttatcgttca tttcctggaa cagcagggca ttaagattgt gacaggcatt ccgggcggtt    720
ctatcctgcc tgtttacgat gccttaagcc aaagcacgca aatccgccat attctggccc    780
gtcatgaaca gggcgcgggc tttatcgctc agggaatggc gcgaccgac ggtaaaccgg    840
```

```
cggtctgtat ggcctgtagc ggaccgggtg cgactaacct ggtgaccgcc attgccgatg    900
cgcggctgga ctccatcccg ctgatttgca tcactggtca ggttcccgcc tcgatgatcg    960
gcaccgacgc cttccaggaa gtggacacct acggcatctc tatccccatc accaaacaca   1020
actatctggt cagacatatc gaagaactcc cgcaggtcat gagcgatgcc ttccgcattg   1080
cgcaatcagg ccgcccaggc ccggtgtgga tagacattcc taaggatgtg caaacggcag   1140
tttttgagat tgaaacacag cccgctatgg cagaaaaagc cgccgccccc gcctttagcg   1200
aagaaagcat tcgtgacgca gcggcgatga ttaacgctgc caaacgcccg gtgctttatc   1260
tgggcggcgg tgtgatcaat cgcccgcac gggtgcgtga actggcggag aaagcgcaac   1320
tgcctaccac catgacttta atggcgctgg gcatgttgcc aaaagcgcat ccgttgtcgc   1380
tgggtatgct ggggatgcac ggcgtgcgca gcaccaacta tttttgcag gaggcggatt   1440 tgttgatagt gctcggtgcg cgttttgatg accgggcgat tggcaaaacc gagcagttct   1500
gtccgaatgc caaaatcatt catgtcgata tcgaccgtgc agagctgggt aaaatcaagc   1560
agccgcacgt ggcgattcag gcggatgttg atgacgtgct ggcgcagttg atcccgctgg   1620
tggaagcgca accgcgtgca gagtggcacc agttggtagc ggatttgcag cgtgagtttc   1680
cgtgtccaat cccgaaagcg tgcgatccgt taagccatta cggcctgatc aacgccgttg   1740
ccgcctgtgt cgatgacaat gcaattatca ccaccgacgt tggtcagcat cagatgtgga   1800
ccgcgcaagc ttatccgctc aatcgcccac gccagtggct gacctccggt gggctgggca   1860
cgatgggttt tggcctgcct gcggcgattg gcgctgcgct ggcgaacccg gatcgcaaag   1920
tgttgtgttt ctccggcgac ggcagcctga tgatgaatat tcaggagatg gcgaccgcca   1980
gtgaaaatca gctggatgtc aaaatcattc tgatgaacaa cgaagcgctg gggctggtgc   2040
atcagcaaca gagtctgttc tacgagcaag gcgttttgc cgccacctat ccgggcaaaa   2100
tcaactttat gcagattgcc gccggattcg gcctcgaaac ctgtgatttg aataacgaag   2160
ccgatccgca ggcttcattg caggaaatca tcaatcgccc tggcccggcg ctgatccatg   2220
tgcgcattga tgccgaagaa aaagtttacc cgatggtgcc gccaggtgcg gcgaatactg   2280
aaatggtggg ggaataagcg gccgcgttaa ttcaaattaa ttgatatagt ttttttaatga   2340 gtattgaatc tgtttagaaa taatggaata ttatttttat ttatttattt atattattgg   2400
tcggctcttt tcttctgaag gtcaatgaca aaatgatatg aaggaaataa tgatttctaa   2460
aattttacaa cgtaagatat ttttacaaaa gcctagctca tcttttgtca tgcactattt   2520
tactcacgct tgaaattaac ggccagtcca ctgcggagtc atttcaaagt catcctaatc   2580
gatctatcgt ttttgatagc tcattttgga gttcgcggga tccgcattgc ggattacgta   2640
ttctaatgtt cagtaccgtt cgtataatgt atgctatacg aagttatgca gattgtactg   2700
agagtgcacc ataccacctt ttcaattcat catttttttt ttattctttt ttttgatttc   2760
ggtttccttg aaatttttt gattcggtaa tctccgaaca gaaggaagaa cgaaggaagg   2820
agcacagact tagattggta tatatacgca tatgtagtgt tgaagaaaca tgaaattgcc   2880
cagtattctt aacccaactg cacagaacaa aaacctgcag gaaacgaaga taatcatgt   2940 cgaaagctac atataaggaa cgtgctgcta ctcatcctag tcctgttgct gccaagctat   3000
ttaatatcat gcacgaaaag caaacaaact tgtgtgcttc attggatgtt cgtaccacca   3060
aggaattact ggagttagtt gaagcattag gtcccaaaat ttgtttacta aaaacacatg   3120
tggatatctt gactgatttt tccatggagg gcacagttaa gccgctaaag gcattatccg   3180
```

```
ccaagtacaa ttttttactc ttcgaagaca gaaaatttgc tgacattggt aatacagtca    3240
aattgcagta ctctgcgggt gtatacgaaa tagcagaatg ggcagacatt acgaatgcac    3300
acggtgtggt gggcccaggt attgttagcg gtttgaagca ggcggcagaa gaagtaacaa    3360
aggaacctag aggccttttg atgttagcag aattgtcatg caagggctcc ctatctactg    3420
gagaatatac taagggtact gttgacattg cgaagagcga caaagatttt gttatcggct    3480
ttattgctca aagagacatg ggtggaagag atgaaggtta cgattggttg attatgacac    3540
ccggtgtggg tttagatgac aagggagacg cattgggtca acagtataga accgtggatg    3600
atgtggtctc tacaggatct gacattatta ttgttggaag aggactattt gcaaagggaa    3660
gggatgctaa ggtagagggt gaacgttaca gaaaagcagg ctgggaagca tatttgagaa    3720
gatgcggcca gcaaaactaa aaaactgtat tataagtaaa tgcatgtata ctaaactcac    3780
aaattagagc ttcaatttaa ttatatcagt tattacccta tgcggtgtga aataccgcac    3840
agatgcgtaa ggagaaaata ccgcatcagg aaattgtaaa cgttaatatt ttgttaaaat    3900
tcgcgttaaa ttttttgttaa atcagctcat ttttttaacca ataggccgaa atcggcaaaa    3960 tccccttataa atcaaaagaa tagaccgaga taggggttgag tgttgttcca gtttggaaca    4020
agagtccact attaaagaac gtggactcca acgtcaaagg gcgaaaaacc gtctatcagg    4080
gcgatggccc actacgtgaa ccatcaccct aatcaagata acttcgtata atgtatgcta    4140
tacgaacggt accagtgatg atacaacgag ttagccaagg tgaattcact ggccgtcgtt    4200
ttacaacgtc gtgactggga aaaccctggc gttacccaac ttaatcgcct gcagcacat    4260 ccccctttcg ccagctggcg taatagcgaa gaggcccgca ccgatcgccc ttcccaacag    4320
ttgcgcagcc tgaatggcga atggcgcctg atgcggtatt ttctccttac gcatctgtgc    4380
ggtatttcac accgcatatg gtgcactctc agtacaatct gctctgatgc cgcatagtta    4440
agccagcccc gacacccgcc aacacccgct gacgcgccct gacgggcttg tctgctcccg    4500
gcatccgctt acagacaagc tgtgaccgtc tccgggagct gcatgtgtca gaggttttca    4560
ccgtcatcac cgaaacgcgc gagacgaaag gcctcgtga tacgcctatt tttataggtt    4620
aatgtcatga taataatggt ttcttagacg tcaggtggca cttttcgggg aaatgtgcgc    4680
ggaaccccta tttgtttatt tttctaaata cattcaaata tgtatccgct catgagacaa    4740
taaccctgat aaatgcttca ataatattga aaaaggaaga gtatgagtat tcaacatttc    4800
cgtgtcgccc ttattccctt ttttgcggca ttttgccttc ctgtttttgc tcacccagaa    4860
acgctggtga agtaaaaga tgctgaagat cagttgggtg cacgagtggg ttacatcgaa    4920
ctggatctca acagcggtaa gatccttgag agttttcgcc ccgaagaacg ttttccaatg    4980
atgagcactt ttaaagttct gctatgtggc gcggtattat cccgtattga cgccgggcaa    5040
gagcaactcg gtcgccgcat acactattct cagaatgact tggttgagta ctcaccagtc    5100
acagaaaagc atcttacgga tggcatgaca gtaagagaat tatgcagtgc tgccataacc    5160
atgagtgata acactgcggc caacttactt ctgacaacga tcggaggacc gaaggagcta    5220
accgcttttt tgcacaacat gggggatcat gtaactcgcc ttgatcgttg ggaaccggag    5280
ctgaatgaag ccataccaaa cgacgagcgt gacaccacga tgcctgtagc aatggcaaca    5340
acgttgcgca aactattaac tggcgaacta cttactctag cttcccggca acaattaata    5400
gactggatgg aggcggataa agttgcagga ccacttctgc gctcggccct tccggctggc    5460
tggtttattg ctgataaatc tggagccggt gagcgtgggt ctcgcggtat cattgcagca    5520
ctggggccag atggtaagcc ctcccgtatc gtagttatct acacgacggg gagtcaggca    5580
```

```
actatggatg aacgaaatag acagatcgct gagataggtg cctcactgat taagcattgg    5640
taactgtcag accaagttta ctcatatata ctttagattg atttaaaact tcattttttaa   5700 tttaaaagga tctaggtgaa gatccttttt gataatctca tgaccaaaat cccttaacgt    5760
gagttttcgt tccactgagc gtcagacccc gtagaaaaga tcaaaggatc ttcttgagat    5820
cctttttttc tgcgcgtaat ctgctgcttg caaacaaaaa aaccaccgct accagcggtg    5880
gtttgtttgc cggatcaaga gctaccaact cttttccga aggtaactgg cttcagcaga     5940
gcgcagatac caaatactgt ccttctagtg tagccgtagt taggccacca cttcaagaac    6000
tctgtagcac cgcctacata cctcgctctg ctaatcctgt taccagtggc tgctgccagt    6060
ggcgataagt cgtgtcttac cgggttggac tcaagacgat agttaccgga taaggcgcag    6120
cggtcgggct gaacggggggt tcgtgcaca cagcccagct tggagcgaac gacctacacc    6180
gaactgagat acctacagcg tgagctatga gaaagcgcca cgcttcccga agggagaaag    6240
gcggacaggt atccggtaag cggcagggtc ggaacaggag agcgcacgag ggagcttcca    6300
gggggaaacg cctggtatct ttatagtcct gtcgggtttc gccacctctg acttgagcgt    6360
cgatttttgt gatgctcgtc aggggggcgg agcctatgga aaaacgccag caacgcggcc    6420 ttttttacggt tcctggcctt ttgctggcct tttgctcaca tgttctttcc tgcgttatcc    6480
cctgattctg tggataaccg tattaccgcc tttgagtgag ctgataccgc tcgccgcagc    6540
cgaacgaccg agcgcagcga gtcagtgagc gaggaagcgg aagagcgccc aatacgcaaa    6600
ccgcctctcc ccgcgcgttg gccgattcat taatgcagct ggcacgacag gtttcccgac    6660
tggaaagcgg gcagtgagcg caacgcaatt aatgtgagtt agctcactca ttaggcaccc    6720
caggctttac actttatgct tccggctcgt atgttgtgtg gaattgtgag cggataacaa    6780
tttcacacag gaaacagcta tgaccatgat tacgccaagc ttgcatg                  6827
```

<210> SEQ ID NO 20
<211> LENGTH: 1713
<212> TYPE: DNA
<213> ORGANISM: Lactococcus lactis

<400> SEQUENCE: 20

```
ctataaatca gtcacacagc cttcactggc tgggcgcgtg agtttagcaa atttagcaag      60
aaccccacgc gttgctttag gagcaggttt ttgataattg gcacgtcgtc tagcaatctc     120
atcgtcagca accttcaaac taatgctgtt attgaccgca tcaatctcga taatatcatc    180
atcttcgacc aagccaatca atccgccctc aaccgcttcg gggacaatgt ggccaaccac    240
aaagccatgt gtgccaccag agaaacgtcc gtcagtaatc aaagcacaag attttccaag    300
acctgctcca atcaaggctg aggtcggttt taacatttct ggcattcctg gcctccgac     360 tggaccgata ttacggatga cagcgacatc tcctgcgtgc aaacgacctg actcaattcc    420
gtcaataaaa tgttgttcgc catcaaagac acgggccgtt cctttaaaaa attcgccttc    480
ttttccagaa attttgtgcca cagaaccacc ttcagcaaga ttgccataaa gaatttgcaa    540
atgacctgtt gctttgattg gattttcaag tggtcgcata atgtcttggc tttcaaagtc    600
caaatccagt gctgttttaa catttcagc tagagtttta ccagtaaccg tcaaacagtc     660
gccgtgaagc ttgccctctt tgagcaaata tttcaaaaca gcaggcacgc caccaatttt    720
gtgcaaatct tccaccatgt acttgccact tggcttgaag tcgccaagca caggcgtgac    780
atcggaaata cgttgaaaat catcttgcgt aatttcgaca ccgatggcat tagccatggc    840
```

-continued

```
aatgatatga agcacagcat tagttgaacc accgagaacc atgacgatcg ttatggcatt     900
ttcaaaagct tccttggtca tgatatcgct tggcttgatg tcttttttcta gcaaattttt    960
gattgccaga ccaatttcat cacattcgtc ttcttttttct tgactgaccg ctggatttga    1020
agatgaataa ggtaaactca ttcctaaagt ttcaatagca gcagccaggg tattggcagt     1080
gtacattcct ccgcaagcac cttgtcctgg aatggcattg caaataacgc catgataatc     1140
ttcatcagaa atatttccag tgatttttttg ccccagagct tcaaaggccg aaacaatatt    1200
taacttttcg cctttgtatt cgccatgttc aatcgttcca ccataaacca taattgacgg     1260
acgattgagc cgagccatac cgataattga gcctggcata ttttttgtcac aaccgggaac    1320
agcgacaatt gcatcgtaat attcggcacc agcgttggtt tcaatgctgt cagcaataac     1380
ttcacgactg accaaggaat atctcatgcc aagttttccg ttggcaatcc catcagaaac     1440
cccaatcgtg tgaaattgaa gtccaatcag tccgtcagtt tgattgacag aattttttgat   1500
tttactacca agtgtcccca agtgcatgtt acagggattt ccgtcccaat ccatgctgac     1560
gattccgacc tgagcttttt tgaagtcctc atctttaaaa ccaatgccat agtacatggc    1620
ttgggtcgct ggctgtgttg ggtcttgtgt caatgttttt gaatacttat tgagctctat     1680
tgattcaact tttccgttat atttgaattc cat                                   1713
```

<210> SEQ ID NO 21
<211> LENGTH: 570
<212> TYPE: PRT
<213> ORGANISM: Lactococcus lactis

<400> SEQUENCE: 21

```
Met Glu Phe Lys Tyr Asn Gly Lys Val Glu Ser Ile Glu Leu Asn Lys
1               5                   10                  15

Tyr Ser Lys Thr Leu Thr Gln Asp Pro Thr Gln Pro Ala Thr Gln Ala
            20                  25                  30

Met Tyr Tyr Gly Ile Gly Phe Lys Asp Glu Asp Phe Lys Lys Ala Gln
        35                  40                  45

Val Gly Ile Val Ser Met Asp Trp Asp Gly Asn Pro Cys Asn Met His
    50                  55                  60

Leu Gly Thr Leu Gly Ser Lys Ile Lys Asn Ser Val Asn Gln Thr Asp
65                  70                  75                  80

Gly Leu Ile Gly Leu Gln Phe His Thr Ile Gly Val Ser Asp Gly Ile
                85                  90                  95

Ala Asn Gly Lys Leu Gly Met Arg Tyr Ser Leu Val Ser Arg Glu Val
            100                 105                 110

Ile Ala Asp Ser Ile Glu Thr Asn Ala Gly Ala Glu Tyr Tyr Asp Ala
        115                 120                 125

Ile Val Ala Val Pro Gly Cys Asp Lys Asn Met Pro Gly Ser Ile Ile
    130                 135                 140

Gly Met Ala Arg Leu Asn Arg Pro Ser Ile Met Val Tyr Gly Gly Thr
145                 150                 155                 160

Ile Glu His Gly Glu Tyr Lys Gly Glu Lys Leu Asn Ile Val Ser Ala
                165                 170                 175

Phe Glu Ala Leu Gly Gln Lys Ile Thr Gly Asn Ile Ser Asp Glu Asp
            180                 185                 190

Tyr His Gly Val Ile Cys Asn Ala Ile Pro Gly Gln Gly Ala Cys Gly
        195                 200                 205

Gly Met Tyr Thr Ala Asn Thr Leu Ala Ala Ala Ile Glu Thr Leu Gly
    210                 215                 220
```

Met Ser Leu Pro Tyr Ser Ser Asn Pro Ala Val Ser Gln Glu Lys
225                 230                 235                 240

Glu Asp Glu Cys Asp Glu Ile Gly Leu Ala Ile Lys Asn Leu Leu Glu
            245                 250                 255

Lys Asp Ile Lys Pro Ser Asp Ile Met Thr Lys Glu Ala Phe Glu Asn
            260                 265                 270

Ala Ile Thr Ile Val Met Val Leu Gly Gly Ser Thr Asn Ala Val Leu
            275                 280                 285

His Ile Ile Ala Met Ala Asn Ala Ile Gly Val Glu Ile Thr Gln Asp
            290                 295                 300

Asp Phe Gln Arg Ile Ser Asp Val Thr Pro Val Leu Gly Asp Phe Lys
305                 310                 315                 320

Pro Ser Gly Lys Tyr Met Val Glu Asp Leu His Lys Ile Gly Gly Val
                325                 330                 335

Pro Ala Val Leu Lys Tyr Leu Leu Lys Glu Gly Lys Leu His Gly Asp
            340                 345                 350

Cys Leu Thr Val Thr Gly Lys Thr Leu Ala Glu Asn Val Lys Thr Ala
            355                 360                 365

Leu Asp Leu Asp Phe Glu Ser Gln Asp Ile Met Arg Pro Leu Glu Asn
370                 375                 380

Pro Ile Lys Ala Thr Gly His Leu Gln Ile Leu Tyr Gly Asn Leu Ala
385                 390                 395                 400

Glu Gly Gly Ser Val Ala Lys Ile Ser Gly Lys Glu Gly Glu Phe Phe
                405                 410                 415

Lys Gly Thr Ala Arg Val Phe Asp Gly Glu Gln His Phe Ile Asp Gly
            420                 425                 430

Ile Glu Ser Gly Arg Leu His Ala Gly Asp Val Ala Val Ile Arg Asn
            435                 440                 445

Ile Gly Pro Val Gly Gly Pro Gly Met Pro Glu Met Leu Lys Pro Thr
            450                 455                 460

Ser Ala Leu Ile Gly Ala Gly Leu Gly Lys Ser Cys Ala Leu Ile Thr
465                 470                 475                 480

Asp Gly Arg Phe Ser Gly Gly Thr His Gly Phe Val Val Gly His Ile
                485                 490                 495

Val Pro Glu Ala Val Glu Gly Gly Leu Ile Gly Leu Val Glu Asp Asp
            500                 505                 510

Asp Ile Ile Glu Ile Asp Ala Val Asn Asn Ser Ile Ser Leu Lys Val
            515                 520                 525

Ala Asp Asp Glu Ile Ala Arg Arg Arg Ala Asn Tyr Gln Lys Pro Ala
530                 535                 540

Pro Lys Ala Thr Arg Gly Val Leu Ala Lys Phe Ala Lys Leu Thr Arg
545                 550                 555                 560

Pro Ala Ser Glu Gly Cys Val Thr Asp Leu
                565                 570

<210> SEQ ID NO 22
<211> LENGTH: 12298
<212> TYPE: DNA
<213> ORGANISM: Artificial Sequence
<220> FEATURE:
<223> OTHER INFORMATION: pLH804 L2V4

<400> SEQUENCE: 22
tcccattacc gacatttggg cgctatacgt gcatatgttc atgtatgtat ctgtatttaa    60

```
aacactttg tattattttt cctcatatat gtgtataggt ttatacggat gatttaatta      120
ttacttcacc acccttattt tcaggctgat atcttagcct tgttactaga ttaatcatgt      180
aattagttat gtcacgctta cattcacgcc ctccccccac atccgctcta accgaaaagg      240
aaggagttag acaacctgaa gtctaggtcc ctatttattt ttttatagtt atgttagtat      300
taagaacgtt atttatattt caaattttc ttttttttct gtacagacgc gtgtacgcat      360
gtaacattat actgaaaacc ttgcttgaga aggttttggg acgctcgaag gctttaattt      420
gcgggcggcc gcacctggta aaacctctag tggagtagta gatgtaatca atgaagcgga      480
agccaaaaga ccagagtaga ggcctataga agaaactgcg atacctttg tgatggctaa      540 acaaacagac atcttttat atgttttac ttctgtatat cgtgaagtag taagtgataa      600
gcgaatttgg ctaagaacgt tgtaagtgaa caagggacct cttttgcctt tcaaaaaagg      660
attaaatgga gttaatcatt gagatttagt tttcgttaga ttctgtatcc ctaaataact      720
cccttacccg acgggaaggc acaaaagact tgaataatag caaacggcca gtagccaaga      780
ccaaataata ctagagttaa ctgatggtct taaacaggca ttacgtggtg aactccaaga      840
ccaatataca aaatatcgat aagttattct tgcccaccaa tttaaggagc ctacatcagg      900
acagtagtac cattcctcag agaagaggta tacataacaa gaaaatcgcg tgaacacctt      960
atataactta gcccgttatt gagctaaaaa accttgcaaa atttcctatg aataagaata     1020
cttcagacgt gataaaaatt tactttctaa ctcttctcac gctgcccta tctgttcttc      1080 cgctctaccg tgagaaataa agcatcgagt acggcagttc gctgtcactg aactaaaaca     1140
ataaggctag ttcgaatgat gaacttgctt gctgtcaaac ttctgagttg ccgctgatgt     1200
gacactgtga caataaattc aaaccggtta tagcggtctc ctccggtacc ggttctgcca     1260
cctccaatag agctcagtag gagtcagaac ctctgcggtg gctgtcagtg actcatccgc     1320
gtttcgtaag ttgtgcgcgt gcacatttcg cccgttcccg ctcatcttgc agcaggcgga     1380
aattttcatc acgctgtagg acgcaaaaaa aaataatta atcgtacaag aatcttggaa     1440
aaaaaattga aaaatttgt ataaagggga tgacctaact tgactcaatg gcttttacac     1500
ccagtatttt cccttctctt gtttgttaca attatagaag caagacaaaa acatatagac     1560
aacctattcc taggagttat attttttac cctaccagca atataagtaa aaaactgttt     1620
aaacagtatg gaagaatgta agatggctaa gatttactac caagaagact gtaacttgtc     1680
cttgttggat ggtaagacta tcgccgttat cggttacggt tctcaaggtc acgctcatgc     1740
cctgaatgct aaggaatccg gttgtaacgt tatcattggt ttatacgaag gtgcggagga     1800
gtggaaaaga gctgaagaac aaggtttcga agtctacacc gctgctgaag ctgctaagaa     1860
ggctgacatc attatgatct tgatcccaga tgaaaagcag gctaccatgt acaaaaacga     1920
catcgaacca aacttggaag ccggtaacat gttgatgttc gctcacggtt tcaacatcca     1980
tttcggttgt attgttccac caaggacgt tgatgtcact atgatcgctc aaagggtcc      2040 aggtcacacc gttagatccg aatacgaaga aggtaaaggt gtcccatgct tggttgctgt     2100
cgaacaagac gctactggca aggctttgga tatggctttg gcctacgctt tagccatcgg     2160
tggtgctaga gccggtgtct tggaaactac cttcagaacc gaaactgaaa ccgacttgtt     2220
cggtgaacaa gctgttttat gtggtggtgt ctgcgctttg atgcaggccg ttttgaaac      2280 cttggttgaa gccggttacg acccaagaaa cgcttacttc gaatgtatcc acgaaatgaa     2340
gttgatcgtt gacttgatct accaatctgg ttttctccggt atgcgttact ctatctccaa     2400
cactgctgaa tacggtgact acattaccgg tccaaagatc attactgaag ataccaagaa     2460
```

```
ggctatgaag aagattttgt ctgacattca agatggtacc tttgccaagg acttcttggt    2520
tgacatgtct gatgctggtt cccaggtcca cttcaaggct atgagaaagt tggcctccga    2580
acacccagct gaagttgtcg gtgaagaaat tagatccttg tactcctggt ccgacgaaga    2640
caagttgatt aacaactgag gccctgcagg ccagaggaaa ataatatcaa gtgctggaaa    2700 cttttttctct tggaattttt gcaacatcaa gtcatagtca attgaattga cccaatttca    2760 cattttaagat ttttttttttt tcatccgaca tacatctgta cactaggaag ccctgttttt    2820
ctgaagcagc ttcaaatata tatatttttt acatatttat tatgattcaa tgaacaatct    2880
aattaaatcg aaaacaagaa ccgaaacgcg aataaataat ttatttagat ggtgacaagt    2940
gtataagtcc tcatcgggac agctacgatt tctctttcgg ttttggctga gctactggtt    3000
gctgtgacgc agcggcatta gcgcggcgtt atgagctacc ctcgtggcct gaaagatggc    3060
gggaataaag cggaactaaa aattactgac tgagccatat tgaggtcaat ttgtcaactc    3120
gtcaagtcac gtttggtgga cggcccctt ccaacgaatc gtatatacta acatgcgcgc    3180
gcttcctata tacacatata catatatata tatatatata tgtgtgcgtg tatgtgtaca    3240
cctgtattta atttccttac tcgcgggttt ttcttttttc tcaattcttg gcttcctctt    3300
tctcgagcgg accggatcct cgcgaactcc aaaatgagct atcaaaaacg atagatcgat    3360
taggatgact ttgaaatgac tccgcagtgg actggccgtt aatttcaagc gtgagtaaaa    3420
tagtgcatga caaaagatga gctaggcttt tgtaaaaata tcttacgttg taaaatttta    3480
gaaatcatta tttccttcat atcatttttgt cattgacctt cagaagaaaa gagccgacca    3540
ataatataaa taaataaata aaaataatat tccattattt ctaaacagat tcaatactca    3600
ttaaaaaact atatcaatta atttgaatta acttaattaa ttattttttg ccagtttctt    3660
caggcttcca aaagtctgtt acggctcccc tagaagcaga cgaaacgatg tgagcatatt    3720
taccaaggat accgcgtgaa tagagcggtg gcaattcaat ggtctcttga cgatgtttta    3780
actcttcatc ggagatatca aagtgtaatt ccttagtgtc ttggtcaata gtgactatgt    3840
ctcctgtttg caggtaggcg attggaccgc catcttgtgc ttcaggagcg atatgaccca    3900
cgacaagacc ataagtacca cctgagaagc ggccatctgt cagaagggca acttttttcac    3960 cttgcccttt accaacaatc attgatgaaa gggaaagcat ttcaggcata ccaggaccgc    4020
cctttggtcc tacaaaacgt acgacaacaa catcaccatc aacaatatca tcattcaaga    4080
cagcttcaat ggcttcttct tcagaattaa agaccttagc aggaccgaca tgacgacgca    4140
cttttacacc agaaactttg gcaacggcac cgtctggagc caagttacca tggagaataa    4200
tgaccggacc atcttcacgt ttaggatttt caagcggcat aataaccttt tgaccaggtg    4260
ttaaatcatc aaaagccttc aaattttcag cgactgtttt gccagtacaa gtgatacggt    4320
caccatgaag gaagccattt ttaaggagat atttcataac tgctggtacc cctccgacct    4380
tgtaaaggtc ttggaataca tattgaccag aaggtttcaa atcagccaaa tgaggaactt    4440
tttcttggaa agtattgaaa tcatcaagtg tcaattccac attagcagca tgggcaatag    4500
ctaagaggtg aagggttgag ttggttgaac ctcccagagc catagttaca gtaatagcat    4560
cttcaaaagc ttcacgcgtt aaaatgtcag aaggttttaa gcccatttcg agcatttga    4620 caacagcgcg accagcttct tcaatatctg cttttctttc tgcggattca gccgggtgag    4680
aagatgaacc cggaaggcta agtcccaaaa cttcaatagc tgtcgccatt tgttagcag    4740 tatacatacc accgcagcct ccaggaccgg gacaagcatt acattccaaa gctttaactt    4800
```

```
cttctttggt catatcgccg tggttccaat ggccgacacc ttcaaagaca gagactaaat    4860
cgatatcttt gccgtctaaa ttaccaggtg caattgttcc gccgtaagca aaaatggctg    4920
ggatatccat gttagccata gcgataacag aaccgggcat gtttttatca caaccgccaa    4980
tggctacaaa agcatccgca ttatgacctc ccatggctgc ttcaatagaa tctgcaataa    5040
tatcacgaga tgtcaaggag aaacgcattc cttgggttcc catggcgatt ccatcagaaa    5100
ccgtgattgt tccgaactga actggccaag caccagcttc cttaacaccg actttggcta    5160
gtttaccaaa gtcatgtaag tggatattac aaggtgtgtt ttcagcccaa gttgaaatga    5220
caccgacgat aggttttcca aagtcttcat cttgcatacc agttcacgc aacatagcac     5280
gattaggtga tttaaccatt gaatcgtaaa cagaactacg atttcttaag tctttaagag    5340
ttttttgtc agtcatactc acgtgaaact tagattagat tgctatgctt tctttccaat     5400
gagcaagaag taaaaaagt tgtaatagaa caggaaaaat gaagctgaaa cttgagaaat     5460
tgaagaccgt ttgttaactc aaatatcaat gggaggtcgt cgaaagagaa caaaatcgaa    5520
aaaaagttt tcaagagaaa gaaacgtgat aaaaattttt attgccttct ccgacgaaga    5580
aaaagggacg aggcggtctc ttttccttt tccaaacctt tagtacgggt aattaacggc    5640
accctagagg aaggaggagg gggaatttag tatgctgtgc ttgggtgttt tgaagtggta    5700
cggcggtgcg cggagtccga gaaaatctgg aagagtaaaa aaggagtaga cattttga    5760
agctatgccg gcagatctat ttaaatggcg cgccgacgtc aggtggcact tttcggggaa    5820
atgtgcgcgg aaccctatt tgtttatttt tctaaataca ttcaaatatg tatccgctca    5880
tgagacaata accctgataa atgcttcaat aatattgaaa aaggaagagt atgagtattc    5940
aacatttccg tgtcgccctt attccttttt tgcggcatt ttgccttcct gtttttgctc      6000
acccagaaac gctggtgaaa gtaaaagatg ctgaagatca gttgggtgca cgagtgggtt    6060
acatcgaact ggatctcaac agcggtaaga tccttgagag ttttcgcccc gaagaacgtt    6120
ttccaatgat gagcactttt aaagttctgc tatgtggcgc ggtattatcc cgtattgacg    6180
ccgggcaaga gcaactcggt cgccgcatac actattctca gaatgacttg gttgagtact    6240
caccagtcac agaaaagcat cttacggatg gcatgacagt aagagaatta tgcagtgctg    6300
ccataaccat gagtgataac actgcggcca acttacttct gacaacgatc ggaggaccga    6360
aggagctaac cgcttttttg cacaacatgg ggatcatgt aactcgcctt gatcgttggg     6420
aaccggagct gaatgaagcc ataccaaacg acgagcgtga ccacgatg cctgtagcaa      6480
tggcaacaac gttgcgcaaa ctattaactg gcgaactact tactctagct tcccggcaac    6540
aattaataga ctggatggag gcggataaag ttgcaggacc acttctgcgc tcggcccttc    6600
cggctggctg gttattgct gataaatctg gagccggtga gcgtgggtct cgcggtatca     6660
ttgcagcact ggggccagat ggtaagccct cccgtatcgt agttatctac acgacgggga    6720
gtcaggcaac tatggatgaa cgaaatagac agatcgctga ataggtgcc tcactgatta    6780
agcattggta actgtcagac caagtttact catatatact ttagattgat ttaaaacttc    6840
atttttaatt taaaaggatc taggtgaaga tccttttga taatctcatg accaaaatcc     6900
cttaacgtga gttttcgttc cactgagcgt cagacccgt agaaaagatc aaaggatctt     6960
cttgagatcc ttttttctg cgcgtaatct gctgcttgca acaaaaaaa ccaccgctac      7020
cagcggtggt ttgtttgccg gatcaagagc taccaactct ttttccgaag gtaactggct    7080
tcagcagagc gcagatacca aatactgttc ttctagtgta gccgtagtta ggccaccact    7140
tcaagaactc tgtagcaccg cctacatacc tcgctctgct aatcctgtta ccagtggctg    7200
```

```
ctgccagtgg cgataagtcg tgtcttaccg ggttggactc aagacgatag ttaccggata   7260
aggcgcagcg gtcgggctga acgggggggtt cgtgcacaca gcccagcttg gagcgaacga   7320
cctacaccga actgagatac ctacagcgtg agctatgaga aagcgccacg cttcccgaag   7380
ggagaaaggc ggacaggtat ccggtaagcg gcagggtcgg aacaggagag cgcacgaggg   7440
agcttccagg gggaaacgcc tggtatcttt atagtcctgt cgggtttcgc cacctctgac   7500
ttgagcgtcg attttttgtga tgctcgtcag ggggcggag cctatggaaa aacgccagca   7560
acgcggcctt tttacggttc ctggcctttt gctggccttt tgctcacatg ttctttcctg   7620
cgttatcccc tgattctgtg gataaccgta ttaccgcctt tgagtgagct gataccgctc   7680
gccgcagccg aacgaccgag cgcagcgagt cagtgagcga ggaagcggaa gagcgcccaa   7740
tacgcaaacc gcctctcccc gcgcgttggc cgattcatta atgcagctgg cacgacaggt   7800
ttcccgactg gaaagcgggc agtgagcgca acgcaattaa tgtgagttag ctcactcatt   7860 aggcaccccca ggctttacac tttatgcttc cggctcgtat gttgtgtgga attgtgagcg   7920
gataacaatt tcacacagga aacagctatg accatgatta cgccaagctt tttctttcca   7980 atttttttttt tttcgtcatt ataaaaatca ttacgaccga gattcccggg taataactga   8040
tataattaaa ttgaagctct aatttgtgag tttagtatac atgcatttac ttataataca   8100
gttttttagt tttgctggcc gcatcttctc aaatatgctt cccagcctgc ttttctgtaa   8160 cgttcacccct ctaccttagc atcccttccc tttgcaaata gtcctcttcc aacaataata   8220
atgtcagatc ctgtagagac cacatcatcc acggttctat actgttgacc caatgcgtct   8280
cccttgtcat ctaaacccac accgggtgtc ataatcaacc aatcgtaacc ttcatctctt   8340
ccacccatgt ctctttgagc aataaagccg ataacaaaat ctttgtcgct cttcgcaatg   8400
tcaacagtac ccttagtata ttctccagta gatagggagc ccttgcatga caattctgct   8460
aacatcaaaa ggcctctagg ttcctttgtt acttcttctg ccgcctgctt caaaccgcta   8520
acaatacctg ggcccaccac accgtgtgca ttcgtaatgt ctgcccattc tgctattctg   8580
tatacacccg cagagtactg caatttgact gtattaccaa tgtcagcaaa ttttctgtct   8640
tcgaagagta aaaaattgta cttggcggat aatgccttta gcggcttaac tgtgccctcc   8700
atggaaaaat cagtcaagat atccacatgt gttttttagta aacaaatttt gggacctaat   8760
gcttcaacta actccagtaa ttccttggtg gtacgaacat ccaatgaagc acacaagttt   8820
gtttgctttt cgtgcatgat attaaatagc ttggcagcaa caggactagg atgagtagca   8880
gcacgttcct tatatgtagc tttcgacatg atttatcttc gtttcctgca ggttttttgtt   8940 ctgtgcagtt gggttaagaa tactgggcaa tttcatgttt cttcaacact acatatgcgt   9000
atatatacca atctaagtct gtgctccttc cttcgttctt ccttctgttc ggagattacc   9060
gaatcaaaaa aatttcaagg aaaccgaaat caaaaaaaag aataaaaaaa aaatgatgaa   9120
ttgaaaagct tgcatgcctg caggtcgact ctagtatact ccgtctactg tacgatacac   9180
ttccgctcag gtccttgtcc tttaacgagg ccttaccact cttttgttac tctattgatc   9240
cagctcagca aaggcagtgt gatctaagat tctatcttcg cgatgtagta aaactagcta   9300
gaccgagaaa gagactagaa atgcaaaagg cacttctaca atggctgcca tcattattat   9360
ccgatgtgac gctgcatttt tttttttttt tttttttttt tttttttttt tttttttttt   9420 tttttttttgt acaaatatca taaaaaaaga gaatctttt aagcaaggat ttcttaact   9480 tcttcggcga cagcatcacc gacttcggtg gtactgttgg aaccacctaa atcaccagtt   9540
```

```
ctgatacctg catccaaaac cttttaact gcatcttcaa tggctttacc ttcttcaggc    9600
aagttcaatg acaatttcaa catcattgca gcagacaaga tagtggcgat agggttgacc    9660
ttattctttg gcaaatctgg agcggaacca tggcatggtt cgtacaaacc aaatgcggtg    9720
ttcttgtctg gcaaagaggc caaggacgca gatggcaaca acccaagga gcctgggata    9780
acggaggctt catcggagat gatatcacca acatgttgc tggtgattat ataccattt    9840
aggtgggttg ggttcttaac taggatcatg gcggcagaat caatcaattg atgttgaact    9900
ttcaatgtag ggaattcgtt cttgatggtt cctccacag ttttctcca taatcttgaa    9960
gaggccaaaa cattagcttt atccaaggac caaataggca atggtggctc atgttgtagg   10020
gccatgaaag cggccattct tgtgattctt tgcacttctg gaacggtgta ttgttcacta   10080
tcccaagcga caccatcacc atcgtcttcc tttctcttac caaagtaaat acctcccact   10140
aattctctaa caacaacgaa gtcagtacct ttagcaaatt gtggcttgat tggagataag   10200
tctaaaagag agtcggatgc aaagttacat ggtcttaagt tggcgtacaa ttgaagttct   10260
ttacggattt ttagtaaacc ttgttcaggt ctaacactac cggtacccca tttaggacca   10320
cccacagcac ctaacaaaac ggcatcagcc ttcttggagg cttccagcgc ctcatctgga   10380
agtggaacac ctgtagcatc gatagcagca ccaccaatta aatgattttc gaaatcgaac   10440
ttgacattgg aacgaacatc agaaatagct ttaagaacct taatggcttc ggctgtgatt   10500
tcttgaccaa cgtggtcacc tggcaaaacg acgatcttct tagggcaga cattacaatg   10560
gtatatcctt gaaatatata taaaaaaaa aaaaaaaaa aaaaaaaaa atgcagcttc   10620
tcaatgatat tcgaatacgc tttgaggaga tacagcctaa tatccgacaa actgttttac   10680
agatttacga tcgtacttgt tacccatcat tgaattttga acatccgaac ctgggagttt   10740
tccctgaaac agatagtata tttgaacctg tataataata tatagtctag cgctttacgg   10800
aagacaatgt atgtatttcg gttcctggag aaactattgc atctattgca taggtaatct   10860
tgcacgtcgc atccccggtt cattttctgc gtttccatct tgcacttcaa tagcatatct   10920
ttgttaacga agcatctgtg cttcattttg tagaacaaaa atgcaacgcg agagcgctaa   10980
ttttcaaac aaagaatctg agctgcattt ttacagaaca gaaatgcaac gcgaaagcgc   11040
tattttacca acgaagaatc tgtgcttcat ttttgtaaaa caaaaatgca acgcgagagc   11100
gctaatttt caaacaaaga atctgagctg cattttaca gaacagaaat gcaacgcgag   11160
agcgctattt taccaacaaa gaatctatac ttctttttg ttctacaaaa atgcatcccg   11220
agagcgctat ttttctaaca aagcatctta gattactttt tttctccttt gtgcgctcta   11280
taatgcagtc tcttgataac ttttgcact gtaggtccgt taaggttaga agaaggctac   11340
tttggtgtct attttctctt ccataaaaa agcctgactc cacttcccgc gtttactgat   11400
tactagcgaa gctgcgggtg catttttca agataaaggc atccccgatt atattctata   11460
ccgatgtgga ttgcgcatac tttgtgaaca gaaagtgata gcgttgatga ttcttcattg   11520
gtcagaaaat tatgaacggt ttcttctatt ttgtctctat atactacgta taggaaatgt   11580
ttacatttc gtattgtttt cgattcactc tatgaatagt tcttactaca attttttgt   11640
ctaaagagta atactagaga taaacataaa aaatgtagag gtcgagttta gatgcaagtt   11700
caaggagcga aaggtggatg ggtaggttat atagggatat agcacagaga tatatagcaa   11760
agagatactt ttgagcaatg tttgtggaag cggtattcgc aatattttag tagctcgtta   11820
cagtccggtg cgttttggt ttttgaaag tgcgtcttca gagcgctttt ggttttcaaa   11880
agcgctctga agttcctata ctttctagag aataggaact tcggaatagg aacttcaaag   11940
```

```
cgtttccgaa acgagcgct tccgaaaatg caacgcgagc tgcgcacata cagctcactg    12000
ttcacgtcgc acctatatct gcgtgttgcc tgtatatata tatacatgag aagaacggca    12060
tagtgcgtgt ttatgcttaa atgcgtactt atatgcgtct atttatgtag gatgaaaggt    12120
agtctagtac ctcctgtgat attatcccat tccatgcggg gtatcgtatg cttccttcag    12180 cactacccctt tagctgttct atatgctgcc actcctcaat tggattagtc tcatccttca    12240
atgctatcat ttcctttgat attggatcat atgcatagta ccgagaaact agaggatc      12298

<210> SEQ ID NO 23
<211> LENGTH: 16387
<212> TYPE: DNA
<213> ORGANISM: Artificial sequence
<220> FEATURE:
<223> OTHER INFORMATION: pLH475-JEA1 plasmid

<400> SEQUENCE: 23
tcccattacc gacatttggg cgctatacgt gcatatgttc atgtatgtat ctgtatttaa      60 aacactttg tattattttt cctcatatat gtgtataggt ttatacggat gatttaatta     120
ttacttcacc acccttttatt tcaggctgat atcttagcct tgttactagt tagaaaaaga    180 cattttttgct gtcagtcact gtcaagagat tcttttgctg gcatttcttc tagaagcaaa    240
aagagcgatg cgtcttttcc gctgaaccgt tccagcaaaa aagactacca acgcaatatg    300
gattgtcaga atcatataaa agagaagcaa ataactcctt gtcttgtatc aattgcatta    360
taatatcttc ttgttagtgc aatatcatat agaagtcatc gaaatagata ttaagaaaaa    420
caaactgtac aatcaatcaa tcaatcatcg ctgaggatgt tgacaaaagc aacaaaagaa    480
caaaaatccc ttgtgaaaaa cagaggggcg gagcttgttg ttgattgctt agtggagcaa    540
ggtgtcacac atgtatttgg cattccaggt gcaaaaattg atgcggtatt tgacgcttta    600
caagataaag gacctgaaat tatcgttgcc cggcacgaac aaaacgcagc attcatggcc    660
caagcagtcg gccgtttaac tggaaaaccg ggagtcgtgt tagtcacatc aggaccgggt    720
gcctctaact tggcaacagg cctgctgaca gcgaacactg aaggagaccc tgtcgttgcg    780
cttgctggaa acgtgatccg tgcagatcgt ttaaaacgga cacatcaatc tttggataat    840
gcggcgctat tccagccgat tacaaaatac agtgtagaag ttcaagatgt aaaaaatata    900
ccggaagctg ttacaaatgc atttaggata gcgtcagcag ggcaggctgg ggccgctttt    960
gtgagctttc gcaagatgt tgtgaatgaa gtcacaaata cgaaaaacgt gcgtgctgtt   1020
gcagcgccaa aactcggtcc tgcagcagat gatgcaatca gtgcggccat agcaaaaatc   1080
caaacagcaa aacttcctgt cgttttggtc ggcatgaaag gcggaagacc ggaagcaatt   1140
aaagcggttc gcaagctttt gaaaaaggtt cagcttccat tgttgaaac atatcaagct   1200 gccggtaccc tttctagaga tttagaggat caatattttg gccgtatcgg tttgttccgc   1260
aaccagcctg gcgattact gctagagcag gcagatgttg ttctgacgat cggctatgac   1320
ccgattgaat atgatccgaa attctggaat atcaatggag accggacaat tatccattta   1380
gacgagatta tcgctgacat tgatcatgct taccagcctg atcttgaatt gatcggtgac   1440
attccgtcca cgatcaatca tatcgaacac gatgctgtga agtgaatt tgcagagcgt   1500 gagcagaaaa tcctttctga tttaaaacaa tatatgcatg aaggtgagca ggtgcctgca   1560
gattggaaat cagacagagc gcaccctctt gaaatcgtta aagagttgcg taatgcagtc   1620
gatgatcatg ttacagtaac ttgcgatatc ggttcgcacg ccatttggat gtcacgttat   1680
```

```
ttccgcagct acgagccgtt aacattaatg atcagtaacg gtatgcaaac actcggcgtt    1740
gcgcttcctt gggcaatcgg cgcttcattg gtgaaaccgg gagaaaaagt ggtttctgtc    1800
tctggtgacg gcggtttctt attctcagca atggaattag agacagcagt tcgactaaaa    1860
gcaccaattg tacacattgt atggaacgac agcacatatg acatggttgc attccagcaa    1920
ttgaaaaaat ataaccgtac atctgcggtc gatttcggaa atatcgatat cgtgaaatat    1980
gcggaaagct tcggagcaac tggcttgcgc gtagaatcac cagaccagct ggcagatgtt    2040
ctgcgtcaag gcatgaacgc tgaaggtcct gtcatcatcg atgtcccggt tgactacagt    2100
gataacatta atttagcaag tgacaagctt ccgaaagaat tcggggaact catgaaaacg    2160
aaagctctct agttaattaa tcatgtaatt agttatgtca cgcttacatt cacgccctcc    2220
ccccacatcc gctctaaccg aaaaggaagg agttagacaa cctgaagtct aggtccctat    2280 ttatttttt atagttatgt tagtattaag aacgttattt atatttcaaa tttttctttt    2340
ttttctgtac agacgcgtgt acgcatgtaa cattatactg aaaaccttgc ttgagaaggt    2400
tttgggacgc tcgaaggctt taatttgcgg gcggccgctc tagaactagt accacaggtg    2460
ttgtcctctg aggacataaa atacacaccg agattcatca actcattgct ggagttagca    2520
tatctacaat tgggtgaaat ggggagcgat ttgcaggcat ttgctcggca tgccggtaga    2580
ggtgtggtca ataagagcga cctcatgcta tacctgagaa agcaacctga cctacaggaa    2640
agagttactc aagaataaga atttttcgttt taaaacctaa gagtcacttt aaaatttgta    2700
tacacttatt ttttttataa cttatttaat aataaaaatc ataaatcata agaaattcgc    2760
ttactcttaa ttaatcaagc atctaaaaca caaccgttgg aagcgttgga aaccaactta    2820
gcatacttgg atagagtacc tcttgtgtaa cgaggtggag gtgcaaccca actttgttta    2880
cgttgagcca tttccttatc agagactaat aggtcaatct tgttattatc agcatcaatg    2940
ataatctcat cgccgtctct gaccaacccg ataggaccac cttcagcggc ttcgggaaca    3000
atgtggccga ttaagaaccc gtgagaacca ccagagaatc taccatcagt caacaatgca    3060
acatctttac ccaaaccgta acccatcaga gcagaggaag gctttagcat tcaggcata    3120 cctggtgcac ctcttggacc ttcatatctg ataacaacaa cggttttttc acccttcttg    3180
atttcacctc tttccaaggc ttcaataaag gcaccttcct cttcgaacac acgtgctcta    3240
cccttgaagt aagtaccttc cttaccggta attttaccca cagctccacc tggtgccaat    3300
gaaccgtaca gaatttgcaa gtgaccgttg gccttgattg ggtgggagag tggcttaata    3360
atctcttgtc cttcaggtag gcttggtgct ttctttgcac gttctgccaa agtgtcaccg    3420
gtaacagtca ttgtgttacc gtgcaacatg ttgttttcat atagatactt aatcacagat    3480
tgggtaccac caacgttaat caaatcggcc atgacgtatt taccagaagg tttgaagtca    3540
ccgatcaatg gtgtagtatc actgattctt tggaaatcat ctggtgacaa cttgacaccc    3600
gcagagtgag caacagccac caaatgcaaa acagcattag tggacccacc ggttgcaacg    3660
acataagtaa tggcgttttc aaaagcctct tttgtgagga tatcacgagg taaaataccc    3720
aattccattg tcttcttgat gtattcacca atgttgtcac actcagctaa cttctccttg    3780
gaaacggctg ggaaggaaga ggagtttgga atggtcaaac ctagcacttc agcggcagaa    3840
gccattgtgt tggcagtata cataccacca caagaaccag gacctgggca tgcatgttcc    3900
acaacatctt ctctttcttc ttcagtgaat tgcttggaaa tatattcacc gtaggattgg    3960
aacgcagaga cgatatcgat gttttttagag atcctgttaa aacctctagt ggagtagtag    4020
atgtaatcaa tgaagcggaa gccaaaagac cagagtagag gcctatagaa gaaactgcga    4080
```

```
tacctttttgt gatggctaaa caaacagaca tctttttata tgtttttact tctgtatatc   4140
gtgaagtagt aagtgataag cgaatttggc taagaacgtt gtaagtgaac aagggacctc   4200
ttttgccttt caaaaaagga ttaaatggag ttaatcattg agatttagtt ttcgttagat   4260
tctgtatccc taaataactc ccttacccga cgggaaggca caaagactt gaataatagc    4320
aaacggccag tagccaagac caaataatac tagagttaac tgatggtctt aaacaggcat   4380
tacgtggtga actccaagac caatatacaa aatatcgata agttattctt gcccaccaat   4440
ttaaggagcc tacatcagga cagtagtacc attcctcaga gaagaggtat acataacaag   4500
aaaatcgcgt gaacacctta tataacttag cccgttattg agctaaaaaa ccttgcaaaa   4560
tttcctatga ataagaatac ttcagacgtg ataaaaattt actttctaac tcttctcacg   4620
ctgcccctat ctgttcttcc gctctaccgt gagaaataaa gcatcgagta cggcagttcg   4680
ctgtcactga actaaaacaa taaggctagt tcgaatgatg aacttgcttg ctgtcaaact   4740
tctgagttgc cgctgatgtg acactgtgac aataaaattca aaccggttat agcggtctcc   4800
tccggtaccg gttctgccac ctccaataga gctcagtagg agtcagaacc tctgcggtgg   4860
ctgtcagtga ctcatccgcg tttcgtaagt tgtgcgcgtg cacatttcgc ccgttcccgc   4920
tcatcttgca gcaggcggaa attttcatca cgctgtagga cgcaaaaaaa aataattaa    4980
tcgtacaaga atcttggaaa aaaaattgaa aaattttgta taaagggat gacctaactt    5040
gactcaatgg cttttacacc cagtattttc cctttccttg tttgttacaa ttatagaagc   5100
aagacaaaaa catatagaca acctattcct aggagttata tttttttacc ctaccagcaa   5160
tataagtaaa aaactagtat gaaagttttc tacgataaag actgcgacct gtcgatcatc   5220
caaggtaaga aagttgccat catcggcttc ggttcccagg gccacgctca agcactcaac   5280
ctgaaggatt ccggcgtaga cgtgactgtt ggcctgccta aaggctttgc tgatgtagcc   5340
aaggctgaag cccacggctt taaagtgacc gacgttgctg cagccgttgc cggtgccgac   5400
ttggtcatga tcctgattcc ggacgagttc cagtcccagc tgtacaagaa cgaaatcgag   5460
ccgaacatca agaagggcgc cactctggcc ttctcccacg gcttcgcgat ccactacaac   5520
caggttgtgc ctcgtgccga cctcgacgtg atcatgatcg cgccgaaggc tccaggccac   5580
accgtacgtt ccgagttcgt caagggcgga ggtattcctg acctgatcgc gatctaccag   5640
gacgtttccg gcaacgccaa gaacgtcgcc ctgtcctacg ccgcaggcgt gggcggcggc   5700
cgtaccggca tcatcgaaac caccttcaag gacgagactg aaaccgacct gttcggtgag   5760
caggctgttc tgtgtggcgg taccgtcgag ctggtcaaag ccggtttcga accctggtt   5820
gaagctggct acgctccaga aatggcctac ttcgagtgcc tgcacgaact gaagctgatc   5880
gttgacctca tgtacgaagg cggtatcgcc aacatgaact actcgatctc caacaacgct   5940
gaatacggcg agtacgtgac tggtccagaa gtcatcaacg ccgaatcccg tcaggccatg   6000
cgcaatgctc tgaagcgcat ccaggacggc gaatacgcga agatgttcat cagcgaaggc   6060
gctaccggct acccatcgat gaccgccaag cgtcgtaaca acgctgctca cggtatcgaa   6120
atcatcggcg agcaactgcg ctcgatgatg ccttggatcg gtgccaacaa atcgtcgac    6180
aaagccaaga actaaggccc tgcaggccta tcaagtgctg gaactttttt ctcttggaat   6240
ttttgcaaca tcaagtcata gtcaattgaa ttgacccaat tcacattta agatttttt    6300
tttttcatcc gacatacatc tgtacactag gaagccctgt ttttctgaag cagcttcaaa   6360
tatatatatt ttttacatat ttattatgat tcaatgaaca atctaattaa atcgaaaaca   6420
```

-continued

| | |
|---|---|
| agaaccgaaa cgcgaataaa taatttattt agatggtgac aagtgtataa gtcctcatcg | 6480 |
| ggacagctac gatttctctt tcggttttgg ctgagctact ggttgctgtg acgcagcggc | 6540 |
| attagcgcgg cgttatgagc taccctcgtg gcctgaaaga tggcgggaat aaagcggaac | 6600 |
| taaaaattac tgactgagcc atattgaggt caatttgtca actcgtcaag tcacgtttgg | 6660 |
| tggacggccc ctttccaacg aatcgtatat actaacatgc gcgcgcttcc tatatacaca | 6720 |
| tatacatata tatatatata tatatgtgtg cgtgtatgtg tacacctgta tttaatttcc | 6780 |
| ttactcgcgg gttttctttt tttctcaatt cttggcttcc tctttctcga gtatataatt | 6840 |
| tttcaggtaa aatttagtac gatagtaaaa tacttctcga actcgtcaca tatacgtgta | 6900 |
| cataatgtct gaaccagctc aaaagaaaca aaaggttgct aacaactctc tagagcggcc | 6960 |
| gcccgcaaat taaagccttc gagcgtccca aaaccttctc aagcaaggtt ttcagtataa | 7020 |
| tgttacatgc gtacacgcgt ctgtacagaa aaaaagaaa aatttgaaat ataaataacg | 7080 |
| ttcttaatac taacataact ataaaaaaat aaatagggac ctagacttca ggttgtctaa | 7140 |
| ctccttcctt ttcggttaga gcggatgtgg ggggagggcg tgaatgtaag cgtgacataa | 7200 |
| ctaattacat gattaattaa ttattggttt tctggtctca actttctgac ttccttacca | 7260 |
| accttccaga tttccatgtt tctgatggtg tctaattcct tttctagctt ttctctgtag | 7320 |
| tcaggttgag agttgaattc caaagatctc ttggtttcgg taccgttctt ggtagattcg | 7380 |
| tacaagtctt ggaaacagg cttcaaagca ttcttgaaga ttgggtacca gtccaaagca | 7440 |
| cctcttctgg cggtggtgga acaagcatcg tacatgtaat ccataccgta cttaccgatc | 7500 |
| aatgggtata gagattgggt agcttcttcg acggtttcgt tgaaagcttc agatggggag | 7560 |
| tgaccgtttt ctctcaagac gtcgtattga gccaagaaca taccgtggat accacccatt | 7620 |
| aaacaacctc tttcaccgta caagtcagag ttgacttctc tttcgaaagt ggtttggtaa | 7680 |
| acgtaaccgg aaccaatggc aacggccaaa gcttgggcct tttcgtgagc cttaccggtg | 7740 |
| acatcgttcc agacgcgta agaagagtta ataccacgac cttccttgaa caaagatctg | 7800 |
| acagttctac cggaacccctt tggagcaacc aagataacat ctaagtcctt tggtggttca | 7860 |
| acgtgagtca agtccttgaa gactggggag aaaccgtggg agaagtacaa agtcttaccc | 7920 |
| ttggtcaaca atggcttgat agcaggccag gtttctgatt gagcggcatc ggacaacaag | 7980 |
| ttcataacgt aactacctct cttgatagca tcttcaacag tgaacaagtt cttgcctgga | 8040 |
| acccaaccgt cttcgatggc agccttccaa gaagcaccat ctttacggac accaatgata | 8100 |
| acgttcaaac cgttgtctct caagttcaaa ccttgaccgt aaccttggga accgtaaccg | 8160 |
| atcaaagcaa aagtgtcgtt cttgaagtag tccaacaact tttctcttgg ccagtcagct | 8220 |
| ctttcgtaga cggtttcaac agtaccaccg aagttgattt gcttcaacat cctcagctct | 8280 |
| agatttgaat atgtattact tggttatggt tatatatgac aaaagaaaaa gaagaacaga | 8340 |
| agaataacgc aaggaagaac aataactgaa attgatagag aagtattatg tctttgtctt | 8400 |
| tttataataa atcaagtgca gaaatccgtt agacaacatg agggataaaa tttaacgtgg | 8460 |
| gcgaagaaga aggaaaaaag ttttgtgag ggcgtaattg aagcgatctg ttgattgtag | 8520 |
| attttttttt tttgaggagt caaagtcaga agagaacaga caaatggtat taaccatcca | 8580 |
| atacttttt ggagcaacgc taagctcatg cttttccatt ggttacgtgc tcagttgtta | 8640 |
| gatatgaaa gagaggatgc tcacggcagc gtgactccaa ttgagcccga aagagaggat | 8700 |
| gccacgtttt cccgacggct gctagaatgg aaaaaggaaa aatagaagaa tcccattcct | 8760 |
| atcattattt acgtaatgac ccacacattt ttgagatttt caactattac gtattacgat | 8820 |

```
aatcctgctg tcattatcat tattatctat atcgacgtat gcaacgtatg tgaagccaag    8880
taggcaatta tttagtactg tcagtattgt tattcatttc agatctatcc gcggtggagc    8940
tcgaattcac tggccgtcgt tttacaacgt cgtgactggg aaaaccctgg cgttacccaa    9000
cttaatcgcc ttgcagcaca tccccctttc gccagctggc gtaatagcga agaggcccgc    9060
accgatcgcc cttcccaaca gttgcgcagc ctgaatggcg aatggcgcct gatgcggtat    9120
tttctcctta cgcatctgtg cggtatttca caccgcatac gtcaaagcaa ccatagtacg    9180
cgccctgtag cggcgcatta agcgcggcgg gtgtggtggt tacgcgcagc gtgaccgcta    9240
cacttgccag cgccttagcg cccgctcctt tcgctttctt cccttccttt ctcgccacgt    9300
tcgccggctt tccccgtcaa gctctaaatc gggggctccc tttagggttc cgatttagtg    9360
ctttacggca cctcgacccc aaaaaacttg atttgggtga tggttcacgt agtgggccat    9420
cgccctgata gacggttttt cgccctttga cgttggagtc cacgttcttt aatagtggac    9480
tcttgttcca aactggaaca acactcaact ctatctcggg ctattctttt gatttataag    9540
ggattttgcc gatttcggtc tattggttaa aaaatgagct gatttaacaa aaatttaacg    9600
cgaattttaa caaaatatta acgtttacaa ttttatggtg cactctcagt acaatctgct    9660
ctgatgccgc atagttaagc cagccccgac acccgccaac acccgctgac gcgccctgac    9720
gggcttgtct gctcccggca tccgcttaca gacaagctgt gaccgtctcc gggagctgca    9780
tgtgtcagag gttttcaccg tcatcaccga aacgcgcgag acgaaagggc ctcgtgatac    9840
gcctattttt ataggttaat gtcatgataa taatggtttc ttagacgtca ggtggcactt    9900
ttcggggaaa tgtgcgcgga acccctattt gtttattttt ctaaatacat tcaaatatgt    9960
atccgctcat gagacaataa ccctgataaa tgcttcaata atattgaaaa aggaagagta   10020
tgagtattca acatttccgt gtcgccctta ttcccttttt tgcggcattt tgccttcctg   10080
tttttgctca cccagaaacg ctggtgaaag taaaagatgc tgaagatcag ttgggtgcac   10140
gagtgggtta catcgaactg gatctcaaca gcggtaagat ccttgagagt tttcgccccg   10200
aagaacgttt tccaatgatg agcactttta aagttctgct atgtggcgcg gtattatccc   10260
gtattgacgc cgggcaagag caactcggtc gccgcataca ctattctcag aatgacttgg   10320
ttgagtactc accagtcaca gaaaagcatc ttacggatgg catgacagta agagaattat   10380
gcagtgctgc cataaccatg agtgataaca ctgcggccaa cttacttctg acaacgatcg   10440
gaggaccgaa ggagctaacc gcttttttgc acaacatggg ggatcatgta actcgccttg   10500
atcgttggga accggagctg aatgaagcca taccaaacga cgagcgtgac accacgatgc   10560
ctgtagcaat ggcaacaacg ttgcgcaaac tattaactgg cgaactactt actctagctt   10620
cccggcaaca attaatagac tggatggagg cggataaagt tgcaggacca cttctgcgct   10680
cggcccttcc ggctggctgg tttattgctg ataaatctgg agccggtgag cgtgggtctc   10740
gcggtatcat tgcagcactg gggccagatg gtaagccctc ccgtatcgta gttatctaca   10800
cgacggggag tcaggcaact atggatgaac gaaatagaca gatcgctgag ataggtgcct   10860
cactgattaa gcattggtaa ctgtcagacc aagtttactc atatatactt tagattgatt   10920
taaaacttca tttttaattt aaaaggatct aggtgaagat cctttttgat aatctcatga   10980
ccaaaatccc ttaacgtgag ttttcgttcc actgagcgtc agaccccgta gaaaagatca   11040
aaggatcttc ttgagatcct ttttttctgc gcgtaatctg ctgcttgcaa acaaaaaaac   11100
caccgctacc agcggtggtt tgtttgccgg atcaagagct accaactctt tttccgaagg   11160
```

```
taactggctt cagcagagcg cagataccaa atactgttct tctagtgtag ccgtagttag    11220
gccaccactt caagaactct gtagcaccgc ctacatacct cgctctgcta atcctgttac    11280
cagtggctgc tgccagtggc gataagtcgt gtcttaccgg gttggactca agacgatagt    11340
taccggataa ggcgcagcgg tcgggctgaa cggggggttc gtgcacacag cccagcttgg    11400
agcgaacgac ctacaccgaa ctgagatacc tacagcgtga gctatgagaa agcgccacgc    11460
ttcccgaagg gagaaaggcg acaggtatc cggtaagcgg cagggtcgga acaggagagc     11520
gcacgaggga gcttccaggg ggaaacgcct ggtatcttta tagtcctgtc gggtttcgcc    11580
acctctgact tgagcgtcga ttttttgtgat gctcgtcagg ggggcggagc ctatggaaaa    11640
acgccagcaa cgcggccttt ttacggttcc tggccttttg ctggcctttt gctcacatgt    11700
tctttcctgc gttatcccct gattctgtgg ataaccgtat taccgccttt gagtgagctg    11760
ataccgctcg ccgcagccga acgaccgagc gcagcgagtc agtgagcgag gaagcggaag    11820
agcgcccaat acgcaaaccg cctctccccg cgcgttggcc gattcattaa tgcagctggc    11880
acgacaggtt cccgactgg aaagcgggca gtgagcgcaa cgcaattaat gtgagttagc     11940
tcactcatta ggcaccccag gctttacact ttatgcttcc ggctcgtatg ttgtgtggaa    12000
ttgtgagcgg ataacaattt cacacaggaa acagctatga ccatgattac gccaagcttt    12060
ttctttccaa ttttttttttt ttcgtcatta taaaaatcat tacgaccgag attcccgggt    12120
aataactgat ataattaaat tgaagctcta atttgtgagt ttagtataca tgcatttact    12180
tataatacag ttttttagtt ttgctggccg catcttctca aatatgcttc ccagcctgct    12240
tttctgtaac gttcaccctc taccttagca tcccttccct ttgcaaatag tcctcttcca    12300
acaataataa tgtcagatcc tgtagagacc acatcatcca cggttctata ctgttgaccc    12360
aatgcgtctc ccttgtcatc taaacccaca ccgggtgtca taatcaacca atcgtaacct    12420
tcatctcttc cacccatgtc tctttgagca ataaagccga taacaaaatc tttgtcgctc    12480
ttcgcaatgt caacagtacc cttagtatat tctccagtag atagggagcc cttgcatgac    12540
aattctgcta acatcaaaag gcctctaggt tcctttgtta cttcttctgc cgcctgcttc    12600
aaaccgctaa caatacctgg gcccaccaca ccgtgtgcat tcgtaatgtc tgcccattct    12660
gctattctgt atacacccgc agagtactgc aatttgactg tattaccaat gtcagcaaat    12720
tttctgtctt cgaagagtaa aaaattgtac ttggcggata atgcctttag cggcttaact    12780
gtgccctcca tggaaaaatc agtcaagata tccacatgtg ttttttagtaa acaaattttg    12840
ggacctaatg cttcaactaa ctccagtaat tccttggtgg tacgaacatc caatgaagca    12900
cacaagtttg tttgcttttc gtgcatgata ttaaatagct tggcagcaac aggactagga    12960
tgagtagcag cacgttcctt atatgtagct ttcgacatga tttatcttcg tttcctgcag    13020
gttttttgttc tgtgcagttg ggttaagaat actgggcaat ttcatgtttc ttcaacacta    13080
catatgcgta tataaccaa tctaagtctg tgctccttcc ttcgttcttc cttctgttcg      13140
gagattaccg aatcaaaaaa atttcaagga aaccgaaatc aaaaaaaaga ataaaaaaaa    13200
aatgatgaat tgaaaagctt gcatgcctgc aggtcgactc tagtatactc cgtctactgt    13260
acgatacact tccgctcagg tccttgtcct ttaacgaggc cttaccactc ttttgttact    13320
ctattgatcc agctcagcaa aggcagtgtg atctaagatt ctatcttcgc gatgtagtaa    13380
aactagctag accgagaaag agactagaaa tgcaaaaggc acttctacaa tggctgccat    13440
cattattatc cgatgtgacg ctgcattttt tttttttttt tttttttttt tttttttttt    13500
tttttttttt ttttttttgta caaatatcat aaaaaaagag aatcttttta agcaaggatt    13560
```

```
ttcttaactt cttcggcgac agcatcaccg acttcggtgg tactgttgga accacctaaa    13620
tcaccagttc tgatacctgc atccaaaacc tttttaactg catcttcaat ggctttacct    13680
tcttcaggca agttcaatga caatttcaac atcattgcag cagacaagat agtggcgata    13740
gggttgacct tattctttgg caaatctgga gcggaaccat ggcatggttc gtacaaacca    13800
aatgcggtgt tcttgtctgg caaagaggcc aaggacgcag atggcaacaa acccaaggag    13860
cctgggataa cggaggcttc atcggagatg atatcaccaa acatgttgct ggtgattata    13920
ataccattta ggtgggttgg gttcttaact aggatcatgg cggcagaatc aatcaattga    13980
tgttgaactt tcaatgtagg gaattcgttc ttgatggttt cctccacagt ttttctccat    14040
aatcttgaag aggccaaaac attagcttta tccaaggacc aaataggcaa tggtggctca    14100
tgttgtaggg ccatgaaagc ggccattctt gtgattcttt gcacttctgg aacggtgtat    14160
tgttcactat cccaagcgac accatcacca tcgtcttcct ttctcttacc aaagtaaata    14220
cctcccacta attctctaac aacaacgaag tcagtacctt tagcaaattg tggcttgatt    14280
ggagataagt ctaaaagaga gtcggatgca aagttacatg gtcttaagtt ggcgtacaat    14340
tgaagttctt tacggatttt tagtaaacct tgttcaggtc taacactacc ggtaccccat    14400
ttaggaccac ccacagcacc taacaaaacg gcatcagcct tcttggaggc ttccagcgcc    14460
tcatctggaa gtggaacacc tgtagcatcg atagcagcac caccaattaa atgatttttcg    14520 aaatcgaact tgacattgga acgaacatca gaaatagctt taagaacctt aatggcttcg    14580
gctgtgattt cttgaccaac gtggtcacct ggcaaaacga cgatcttctt aggggcagac    14640
attacaatgg tatatccttg aaatatatat aaaaaaaaaa aaaaaaaaaa aaaaaaaaaa    14700
tgcagcttct caatgatatt cgaatacgct tgaggagat acagcctaat atccgacaaa    14760
ctgttttaca gatttacgat cgtacttgtt acccatcatt gaattttgaa catccgaacc    14820
tgggagtttt ccctgaaaca gatagtatat ttgaacctgt ataataatat atagtctagc    14880
gctttacgga agacaatgta tgtatttcgg ttcctggaga aactattgca tctattgcat    14940
aggtaatctt gcacgtcgca tccccggttc attttctgcg tttccatctt gcacttcaat    15000
agcatatctt tgttaacgaa gcatctgtgc ttcattttgt agaacaaaaa tgcaacgcga    15060
gagcgctaat ttttcaaaca aagaatctga gctgcatttt tacagaacag aaatgcaacg    15120
cgaaagcgct atttttaccaa cgaagaatct gtgcttcatt tttgtaaaac aaaaatgcaa    15180
cgcgagagcg ctaatttttc aaacaaagaa tctgagctgc attttttacag aacagaaatg    15240 caacgcgaga gcgctatttt accaacaaag aatctatact tctttttttgt tctacaaaaa    15300 tgcatcccga gagcgctatt tttctaacaa agcatcttag attacttttt ttctcctttg    15360
tgcgctctat aatgcagtct cttgataact ttttgcactg taggtccgtt aaggttagaa    15420
gaaggctact ttggtgtcta ttttctcttc cataaaaaaa gcctgactcc acttcccgcg    15480
tttactgatt actagcgaag ctgcgggtgc atttttccaa gataaaggca tccccgatta    15540
tattctatac cgatgtggat tgcgcatact ttgtgaacag aaagtgatag cgttgatgat    15600
tcttcattgg tcagaaaatt atgaacggtt tcttctattt tgtctctata tactacgtat    15660
aggaaatgtt tacattttcg tattgttttc gattcactct atgaatagtt cttactacaa    15720 ttttttttgtc taaagagtaa tactagagat aaacataaaa aatgtagagg tcgagtttag    15780
atgcaagttc aaggagcgaa aggtggatgg gtaggttata tagggatata gcacagagat    15840
atatagcaaa gagatacttt tgagcaatgt ttgtggaagc ggtattcgca atattttagt    15900
```

```
agctcgttac agtccggtgc gttttttggtt ttttgaaagt gcgtcttcag agcgcttttg    15960
gttttcaaaa gcgctctgaa gttcctatac tttctagaga ataggaactt cggaatagga    16020
acttcaaagc gtttccgaaa acgagcgctt ccgaaaatgc aacgcgagct gcgcacatac    16080
agctcactgt tcacgtcgca cctatatctg cgtgttgcct gtatatatat atacatgaga    16140
agaacggcat agtgcgtgtt tatgcttaaa tgcgtactta tatgcgtcta tttatgtagg    16200
atgaaaggta gtctagtacc tcctgtgata ttatcccatt ccatgcgggg tatcgtatgc    16260
ttccttcagc actacccttt agctgttcta tatgctgcca ctcctcaatt ggattagtct    16320
catccttcaa tgctatcatt tcctttgata ttggatcata tgcatagtac cgagaaacta    16380
gaggatc                                                             16387

<210> SEQ ID NO 24
<211> LENGTH: 448
<212> TYPE: DNA
<213> ORGANISM: Artificial Sequence
<220> FEATURE:
<223> OTHER INFORMATION: Saccharomyces cerevisiae CUP1 promoter

<400> SEQUENCE: 24
cccattaccg acatttgggc gctatacgtg catatgttca tgtatgtatc tgtatttaaa      60
acacttttgt attatttttc ctcatatatg tgtataggtt tatacggatg atttaattat     120
tacttcacca cccctttattt caggctgata tcttagcctt gttactagtt agaaaaagac    180 attttttgctg tcagtcactg tcaagagatt cttttgctgg catttcttct agaagcaaaa    240
agagcgatgc gtctttttccg ctgaaccgtt ccagcaaaaa agactaccaa cgcaatatgg    300
attgtcagaa tcatataaaa gagaagcaaa taactccttg tcttgtatca attgcattat    360
aatatcttct tgttagtgca atatcatata gaagtcatcg aaatagatat taagaaaaac    420
aaactgtaca atcaatcaat caatcatc                                       448

<210> SEQ ID NO 25
<211> LENGTH: 1716
<212> TYPE: DNA
<213> ORGANISM: Bacillus subtilis

<400> SEQUENCE: 25
atgttgacaa aagcaacaaa agaacaaaaa tcccttgtga aaaacagagg ggcggagctt      60
gttgttgatt gcttagtgga gcaaggtgtc acacatgtat ttggcattcc aggtgcaaaa    120
attgatgcgg tatttgacgc tttacaagat aaaggacctg aaattatcgt tgcccggcac    180
gaacaaaacg cagcattcat ggcccaagca gtcggccgtt taactggaaa accgggagtc    240
gtgttagtca catcaggacc gggtgcctct aacttggcaa caggcctgct gacagcgaac    300
actgaaggag accctgtcgt tgcgcttgct ggaaacgtga tccgtgcaga tcgtttaaaa    360
cggacacatc aatctttgga taatgcggcg ctattccagc cgattacaaa atacagtgta    420
gaagttcaag atgtaaaaaa tataccggaa gctgttacaa atgcatttag gatagcgtca    480
gcagggcagg ctggggccgc ttttgtgagc tttccgcaag atgttgtgaa tgaagtcaca    540
aatacgaaaa acgtgcgtgc tgttgcagcg ccaaaactcg gtcctgcagc agatgatgca    600
atcagtgcgg ccatagcaaa aatccaaaca gcaaaacttc ctgtcgtttt ggtcggcatg    660
aaaggcggaa gaccggaagc aattaaagcg gttcgcaagc ttttgaaaaa ggttcagctt    720
ccatttgttg aaacatatca agctgccggt acccttttcta gagatttaga ggatcaatat    780
tttggccgta tcggtttgtt ccgcaaccag cctggcgatt tactgctaga gcaggcagat    840
```

```
gttgttctga cgatcggcta tgacccgatt gaatatgatc cgaaattctg gaatatcaat    900
ggagaccgga caattatcca tttagacgag attatcgctg acattgatca tgcttaccag    960
cctgatcttg aattgatcgg tgacattccg tccacgatca atcatatcga acacgatgct   1020
gtgaaagtgg aatttgcaga gcgtgagcag aaaatccttt ctgatttaaa acaatatatg   1080
catgaaggtg agcaggtgcc tgcagattgg aaatcagaca gagcgcaccc tcttgaaatc   1140
gttaaagagt tgcgtaatgc agtcgatgat catgttacag taacttgcga tatcggttcg   1200
cacgccattt ggatgtcacg ttatttccgc agctacgagc cgttaacatt aatgatcagt   1260
aacggtatgc aaacactcgg cgttgcgctt ccttgggcaa tcggcgcttc attggtgaaa   1320
ccgggagaaa aagtggtttc tgtctctggt gacggcggtt tcttattctc agcaatggaa   1380
ttagagacag cagttcgact aaaagcacca attgtacaca ttgtatggaa cgacagcaca   1440
tatgacatgg ttgcattcca gcaattgaaa aaatataacc gtacatctgc ggtcgatttc   1500
ggaaatatcg atatcgtgaa atatgcggaa agcttcggag caactggctt gcgcgtagaa   1560
tcaccagacc agctggcaga tgttctgcgt caaggcatga acgctgaagg tcctgtcatc   1620
atcgatgtcc cggttgacta cagtgataac attaatttag caagtgacaa gcttccgaaa   1680
gaattcgggg aactcatgaa aacgaaagct ctctag                             1716

<210> SEQ ID NO 26
<211> LENGTH: 571
<212> TYPE: PRT
<213> ORGANISM: Bacillus subtilis

<400> SEQUENCE: 26

Met Leu Thr Lys Ala Thr Lys Glu Gln Lys Ser Leu Val Lys Asn Arg
1               5                   10                  15

Gly Ala Glu Leu Val Val Asp Cys Leu Val Glu Gln Gly Val Thr His
                20                  25                  30

Val Phe Gly Ile Pro Gly Ala Lys Ile Asp Ala Val Phe Asp Ala Leu
            35                  40                  45

Gln Asp Lys Gly Pro Glu Ile Ile Val Ala Arg His Glu Gln Asn Ala
        50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

Ala Ala Leu Phe Gln Pro Ile Thr Lys Tyr Ser Val Glu Val Gln Asp
    130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
        195                 200                 205

Gln Thr Ala Lys Leu Pro Val Val Leu Val Gly Met Lys Gly Gly Arg
```

```
                210                 215                 220
Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
                260                 265                 270

Asp Leu Leu Leu Glu Gln Ala Asp Val Val Leu Thr Ile Gly Tyr Asp
                275                 280                 285

Pro Ile Glu Tyr Asp Pro Lys Phe Trp Asn Ile Asn Gly Asp Arg Thr
290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
                325                 330                 335

Glu His Asp Ala Val Lys Val Glu Phe Ala Glu Arg Glu Gln Lys Ile
                340                 345                 350

Leu Ser Asp Leu Lys Gln Tyr Met His Glu Gly Glu Gln Val Pro Ala
                355                 360                 365

Asp Trp Lys Ser Asp Arg Ala His Pro Leu Glu Ile Val Lys Glu Leu
370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
                420                 425                 430

Ala Ile Gly Ala Ser Leu Val Lys Pro Gly Glu Lys Val Val Ser Val
                435                 440                 445

Ser Gly Asp Gly Gly Phe Leu Phe Ser Ala Met Glu Leu Glu Thr Ala
450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
                500                 505                 510

Gly Ala Thr Gly Leu Arg Val Glu Ser Pro Asp Gln Leu Ala Asp Val
                515                 520                 525

Leu Arg Gln Gly Met Asn Ala Glu Gly Pro Val Ile Ile Asp Val Pro
530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
                565                 570

<210> SEQ ID NO 27
<211> LENGTH: 250
<212> TYPE: DNA
<213> ORGANISM: Artificial Sequence
<220> FEATURE:
<223> OTHER INFORMATION: Saccharomyces cerevisiae CYC1 terminator 2

<400> SEQUENCE: 27
ccgcaaatta aagccttcga gcgtcccaaa accttctcaa gcaaggtttt cagtataatg    60
```

```
ttacatgcgt acacgcgtct gtacagaaaa aaagaaaaa tttgaaatat aaataacgtt     120
cttaatacta acataactat aaaaaaataa atagggacct agacttcagg ttgtctaact    180 ccttccttt cggttagagc ggatgtgggg ggagggcgtg aatgtaagcg tgacataact     240
aattacatga                                                          250
```

<210> SEQ ID NO 28
<211> LENGTH: 1181
<212> TYPE: DNA
<213> ORGANISM: Artificial Sequence
<220> FEATURE:
<223> OTHER INFORMATION: Saccharomyces cerevisiae ILV5 promoter

<400> SEQUENCE: 28

```
taaaacctct agtggagtag tagatgtaat caatgaagcg gaagccaaaa gaccagagta     60
gaggcctata gaagaaactg cgatacccttt tgtgatggct aaacaaacag acatctttt    120 atatgtttt acttctgtat atcgtgaagt agtaagtgat aagcgaattt ggctaagaac    180
gttgtaagtg aacaagggac ctcttttgcc tttcaaaaaa ggattaaatg gagttaatca    240
ttgagattta gttttcgtta gattctgtat ccctaaataa ctcccttacc cgacgggaag    300
gcacaaaaga cttgaataat agcaaacggc cagtagccaa gaccaaataa tactagagtt    360
aactgatggt cttaaacagg cattacgtgg tgaactccaa gaccaatata caaaatatcg    420
ataagttatt cttgcccacc aatttaagga gcctacatca ggacagtagt accattcctc    480
agagaagagg tatacataac aagaaaatcg cgtgaacacc ttatataact tagcccgtta    540
ttgagctaaa aaaccttgca aaatttccta tgaataagaa tacttcagac gtgataaaaa    600
tttactttct aactcttctc acgctgcccc tatctgttct tccgctctac cgtgagaaat    660
aaagcatcga gtacggcagt tcgctgtcac tgaactaaaa caataaggct agttcgaatg    720
atgaacttgc ttgctgtcaa acttctgagt tgccgctgat gtgacactgt gacaataaat    780
tcaaaccggt tatagcggtc tcctccggta ccggttctgc cacctccaat agagctcagt    840
aggagtcaga acctctgcgg tggctgtcag tgactcatcc gcgtttcgta agttgtgcgc    900
gtgcacattt cgcccgttcc cgctcatctt gcagcaggcg gaaattttca tcacgctgta    960
ggacgcaaaa aaaaataat taatcgtaca agaatcttgg aaaaaaaatt gaaaatttt    1020 gtataaaagg gatgacctaa cttgactcaa tggcttttac acccagtatt ttccctttcc    1080
ttgtttgtta caattataga agcaagacaa aaacatatag acaacctatt cctaggagtt    1140 atatttttt acctaccag caatataagt aaaaaactag t                        1181
```

<210> SEQ ID NO 29
<211> LENGTH: 1017
<212> TYPE: DNA
<213> ORGANISM: Artificial Sequence
<220> FEATURE:
<223> OTHER INFORMATION: Pf5.IlvC-JEA1 coding region

<400> SEQUENCE: 29

```
atgaaagttt tctacgataa agactgcgac ctgtcgatca tccaaggtaa gaaagttgcc     60
atcatcggct tcggttccca gggccacgct caagcactca acctgaagga ttccggcgta    120
gacgtgactg ttggcctgcc taaaggcttt gctgatgtag ccaaggctga agcccacggc    180
tttaaagtga ccgacgttgc tgcagccgtt gccggtgccg acttggtcat gatcctgatt    240
ccggacgagt tccagtccca gctgtacaag aacgaaatcg agccgaacat caagaagggc    300
```

```
gccactctgg ccttctccca cggcttcgcg atccactaca accaggttgt gcctcgtgcc     360
gacctcgacg tgatcatgat cgcgccgaag gctccaggcc acaccgtacg ttccgagttc     420
gtcaagggcg gaggtattcc tgacctgatc gcgatctacc aggacgtttc cggcaacgcc     480
aagaacgtcg ccctgtccta cgccgcaggc gtgggcggcg ccgtaccgg catcatcgaa      540 accaccttca aggacgagac tgaaaccgac ctgttcggtg agcaggctgt tctgtgtggc     600
ggtaccgtcg agctggtcaa agccggtttc gaaaccctgg ttgaagctgg ctacgctcca     660
gaaatggcct acttcgagtg cctgcacgaa ctgaagctga tcgttgacct catgtacgaa     720
ggcggtatcg ccaacatgaa ctactcgatc tccaacaacg ctgaatacgg cgagtacgtg     780
actggtccag aagtcatcaa cgccgaatcc cgtcaggcca tgcgcaatgc tctgaagcgc     840
atccaggacg cgaatacgc gaagatgttc atcagcgaag cgctaccgg ctacccatcg       900 atgaccgcca agcgtcgtaa caacgctgct cacggtatcg aaatcatcgg cgagcaactg     960
cgctcgatga tgccttggat cggtgccaac aaaatcgtcg acaaagccaa gaactaa       1017
```

<210> SEQ ID NO 30
<211> LENGTH: 338
<212> TYPE: PRT
<213> ORGANISM: Artificial Sequence
<220> FEATURE:
<223> OTHER INFORMATION: Pf5.IlvC-JEA1 coding region

<400> SEQUENCE: 30

```
Met Lys Val Phe Tyr Asp Lys Asp Cys Asp Leu Ser Ile Ile Gln Gly
1               5                   10                  15

Lys Lys Val Ala Ile Ile Gly Phe Gly Ser Gln Gly His Ala Gln Ala
            20                  25                  30

Leu Asn Leu Lys Asp Ser Gly Val Asp Val Thr Val Gly Leu Pro Lys
        35                  40                  45

Gly Phe Ala Asp Val Ala Lys Ala Glu Ala His Gly Phe Lys Val Thr
    50                  55                  60

Asp Val Ala Ala Val Ala Gly Ala Asp Leu Val Met Ile Leu Ile
65                  70                  75                  80

Pro Asp Glu Phe Gln Ser Gln Leu Tyr Lys Asn Glu Ile Glu Pro Asn
                85                  90                  95

Ile Lys Lys Gly Ala Thr Leu Ala Phe Ser His Gly Phe Ala Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Val Ser Gly Asn Ala
145                 150                 155                 160

Lys Asn Val Ala Leu Ser Tyr Ala Ala Gly Val Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Thr Val Glu Leu Val Lys Ala
        195                 200                 205

Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240
```

```
Gly Gly Ile Ala Asn Met Asn Tyr Ser Ile Ser Asn Ala Glu Tyr
                245                 250                 255

Gly Glu Tyr Val Thr Gly Pro Glu Val Ile Asn Ala Glu Ser Arg Gln
            260                 265                 270

Ala Met Arg Asn Ala Leu Lys Arg Ile Gln Asp Gly Glu Tyr Ala Lys
            275                 280                 285

Met Phe Ile Ser Glu Gly Ala Thr Gly Tyr Pro Ser Met Thr Ala Lys
            290                 295                 300

Arg Arg Asn Asn Ala Ala His Gly Ile Glu Ile Gly Glu Gln Leu
305                 310                 315                 320

Arg Ser Met Met Pro Trp Ile Gly Ala Asn Lys Ile Val Asp Lys Ala
                325                 330                 335

Lys Asn
```

<210> SEQ ID NO 31
<211> LENGTH: 759
<212> TYPE: DNA
<213> ORGANISM: Artificial Sequence
<220> FEATURE:
<223> OTHER INFORMATION: Saccharomyces cerevisiae ILV5 terminator

<400> SEQUENCE: 31

```
ggccctgcag gcctatcaag tgctggaaac ttttctctt ggaattttg caacatcaag      60
tcatagtcaa ttgaattgac ccaatttcac atttaagatt ttttttttt catccgacat    120
acatctgtac actaggaagc cctgttttc tgaagcagct tcaaatatat atttttta      180
catatttatt atgattcaat gaacaatcta attaaatcga aaacaagaac cgaaacgcga    240
ataaataatt tatttagatg gtgacaagtg tataagtcct catcgggaca gctacgattt    300
ctctttcggt tttggctgag ctactggttg ctgtgacgca gcggcattag cgcggcgtta    360
tgagctaccc tcgtggcctg aaagatggcg ggaataaagc ggaactaaaa attactgact    420
gagccatatt gaggtcaatt tgtcaactcg tcaagtcacg tttggtggac ggccccttc     480
caacgaatcg tatatactaa catgcgcgcg cttcctatat acacatatac atatatatat    540
atatatatat gtgtgcgtgt atgtgtacac ctgtatttaa tttccttact cgcgggtttt    600
tctttttct caattcttgg cttcctcttt ctcgagtata aattttttca ggtaaaattt    660
agtacgatag taaaatactt ctcgaactcg tcacatatac gtgtacataa tgtctgaacc    720
agctcaaaag aaacaaaagg ttgctaacaa ctctctaga                          759
```

<210> SEQ ID NO 32
<211> LENGTH: 643
<212> TYPE: DNA
<213> ORGANISM: Artificial Sequence
<220> FEATURE:
<223> OTHER INFORMATION: Saccharomyces cerevisiae FBA1 promoter

<400> SEQUENCE: 32

```
gaaatgaata acaatactga cagtactaaa taattgccta cttggcttca catacgttgc     60
atacgtcgat atagataata atgataatga cagcaggatt atcgtaatac gtaatagttg   120
aaaatctcaa aaatgtgtgg gtcattacgt aaataatgat aggaatggga ttcttctatt   180
tttccttttt ccattctagc agccgtcggg aaaacgtggc atcctctctt tcgggctcaa   240
ttggagtcac gctgccgtga gcatcctctc tttccatatc taacaactga gcacgtaacc   300
aatgaaaaag catgagctta gcgttgctcc aaaaaagtat tggatggtta ataccatttg   360
tctgttctct tctgactttg actcctcaaa aaaaaaaat ctacaatcaa cagatcgctt   420
```

```
caattacgcc ctcacaaaaa ctttttttcct tcttcttcgc ccacgttaaa ttttatccct    480
catgttgtct aacggatttc tgcacttgat ttattataaa aagacaaaga cataatactt    540
ctctatcaat ttcagttatt gttcttcctt gcgttattct tctgttcttc tttttctttt    600
gtcatatata accataacca agtaatacat attcaaatct aga                      643
```

<210> SEQ ID NO 33
<211> LENGTH: 1188
<212> TYPE: DNA
<213> ORGANISM: Saccharomyces cerevisiae

<400> SEQUENCE: 33

```
atgttgagaa ctcaagccgc cagattgatc tgcaactccc gtgtcatcac tgctaagaga     60
acctttgctt tggccacccg tgctgctgct tacagcagac cagctgcccg tttcgttaag    120
ccaatgatca ctacccgtgg tttgaagcaa atcaacttcg gtggtactgt tgaaaccgtc    180
tacgaaagag ctgactggcc aagagaaaag ttgttggact acttcaagaa cgacactttt    240
gctttgatcg gttacggttc ccaaggttac ggtcaaggtt tgaacttgag agacaacggt    300
ttgaacgtta tcattggtgt ccgtaaagat ggtgcttctt ggaaggctgc catcgaagac    360
ggttgggttc caggcaagaa cttgttcact gttgaagatg ctatcaagag aggtagttac    420
gttatgaact gttgtccga tgccgctcaa tcagaaacct ggcctgctat caagccattg    480
ttgaccaagg gtaagacttt gtacttctcc cacggtttct ccccagtctt caaggacttg    540
actcacgttg aaccaccaaa ggacttagat gttatcttgg ttgctccaaa gggttccggt    600
agaactgtca gatctttgtt caaggaaggt cgtggtatta actcttctta cgccgtctgg    660
aacgatgtca ccggtaaggc tcacgaaaag gcccaagctt tggccgttgc cattggttcc    720
ggttacgttt accaaaccac tttcgaaaga gaagtcaact ctgacttgta cggtgaaaga    780
ggttgtttaa tgggtggtat ccacggtatg ttcttggctc aatacgacgt cttgagagaa    840
aacggtcact ccccatctga agcttttcaac gaaaccgtcg aagaagctac ccaatctcta    900
tacccattga tcggtaagta cggtatggat tacatgtacg atgcttgttc caccaccgcc    960
agaagaggtg ctttggactg gtacccaatc ttcaagaatg ctttgaagcc tgttttccaa   1020
gacttgtacg aatctaccaa gaacggtacc gaaaccaaga gatctttgga attcaactct   1080
caacctgact acagagaaaa gctagaaaag gaattagaca ccatcagaaa catggaaatc   1140
tggaaggttg gtaaggaagt cagaaagttg agaccagaaa accaataa                1188
```

<210> SEQ ID NO 34
<211> LENGTH: 395
<212> TYPE: PRT
<213> ORGANISM: Saccharomyces cerevisiae

<400> SEQUENCE: 34

```
Met Leu Arg Thr Gln Ala Ala Arg Leu Ile Cys Asn Ser Arg Val Ile
1               5                   10                  15

Thr Ala Lys Arg Thr Phe Ala Leu Ala Thr Arg Ala Ala Ala Tyr Ser
            20                  25                  30

Arg Pro Ala Ala Arg Phe Val Lys Pro Met Ile Thr Thr Arg Gly Leu
        35                  40                  45

Lys Gln Ile Asn Phe Gly Gly Thr Val Glu Thr Val Tyr Glu Arg Ala
    50                  55                  60

Asp Trp Pro Arg Glu Lys Leu Leu Asp Tyr Phe Lys Asn Asp Thr Phe
65                  70                  75                  80
```

Ala Leu Ile Gly Tyr Gly Ser Gln Gly Tyr Gly Gln Gly Leu Asn Leu
            85                  90                  95

Arg Asp Asn Gly Leu Asn Val Ile Ile Gly Val Arg Lys Asp Gly Ala
           100                 105                 110

Ser Trp Lys Ala Ala Ile Glu Asp Gly Trp Val Pro Gly Lys Asn Leu
           115                 120                 125

Phe Thr Val Glu Asp Ala Ile Lys Arg Gly Ser Tyr Val Met Asn Leu
           130                 135                 140

Leu Ser Asp Ala Ala Gln Ser Glu Thr Trp Pro Ala Ile Lys Pro Leu
145                 150                 155                 160

Leu Thr Lys Gly Lys Thr Leu Tyr Phe Ser His Gly Phe Ser Pro Val
               165                 170                 175

Phe Lys Asp Leu Thr His Val Glu Pro Pro Lys Asp Leu Asp Val Ile
               180                 185                 190

Leu Val Ala Pro Lys Gly Ser Gly Arg Thr Val Arg Ser Leu Phe Lys
               195                 200                 205

Glu Gly Arg Gly Ile Asn Ser Ser Tyr Ala Val Trp Asn Asp Val Thr
               210                 215                 220

Gly Lys Ala His Glu Lys Ala Gln Ala Leu Ala Val Ala Ile Gly Ser
225                 230                 235                 240

Gly Tyr Val Tyr Gln Thr Thr Phe Glu Arg Glu Val Asn Ser Asp Leu
               245                 250                 255

Tyr Gly Glu Arg Gly Cys Leu Met Gly Gly Ile His Gly Met Phe Leu
               260                 265                 270

Ala Gln Tyr Asp Val Leu Arg Glu Asn Gly His Ser Pro Ser Glu Ala
               275                 280                 285

Phe Asn Glu Thr Val Glu Glu Ala Thr Gln Ser Leu Tyr Pro Leu Ile
               290                 295                 300

Gly Lys Tyr Gly Met Asp Tyr Met Tyr Asp Ala Cys Ser Thr Thr Ala
305                 310                 315                 320

Arg Arg Gly Ala Leu Asp Trp Tyr Pro Ile Phe Lys Asn Ala Leu Lys
               325                 330                 335

Pro Val Phe Gln Asp Leu Tyr Glu Ser Thr Lys Asn Gly Thr Glu Thr
               340                 345                 350

Lys Arg Ser Leu Glu Phe Asn Ser Gln Pro Asp Tyr Arg Glu Lys Leu
               355                 360                 365

Glu Lys Glu Leu Asp Thr Ile Arg Asn Met Glu Ile Trp Lys Val Gly
               370                 375                 380

Lys Glu Val Arg Lys Leu Arg Pro Glu Asn Gln
385                 390                 395

<210> SEQ ID NO 35
<211> LENGTH: 244
<212> TYPE: DNA
<213> ORGANISM: Artificial Sequence
<220> FEATURE:
<223> OTHER INFORMATION: Saccharomyces cerevisiae CYC1 terminator

<400> SEQUENCE: 35
attaaagcct tcgagcgtcc caaaaccttc tcaagcaagg ttttcagtat aatgttacat      60
gcgtacacgc gtctgtacag aaaaaaaaga aaaatttgaa atataaataa cgttcttaat    120
actaacataa ctataaaaaa ataaataggg acctagactt caggttgtct aactccttcc    180
ttttcggtta gagcggatgt gggggggaggg cgtgaatgta agcgtgacat aactaattac    240
atga                                                                    244

<210> SEQ ID NO 36
<211> LENGTH: 570
<212> TYPE: PRT
<213> ORGANISM: Bacillus subtilis

<400> SEQUENCE: 36

Met Thr Lys Ala Thr Lys Glu Gln Lys Ser Leu Val Lys Asn Arg Gly
1               5                   10                  15

Ala Glu Leu Val Val Asp Cys Leu Val Glu Gln Gly Val Thr His Val
                20                  25                  30

Phe Gly Ile Pro Gly Ala Lys Ile Asp Ala Val Phe Asp Ala Leu Gln
            35                  40                  45

Asp Lys Gly Pro Glu Ile Ile Val Ala Arg His Glu Gln Asn Ala Ala
        50                  55                  60

Phe Met Ala Gln Ala Val Gly Arg Leu Thr Gly Lys Pro Gly Val Val
65                  70                  75                  80

Leu Val Thr Ser Gly Pro Gly Ala Ser Asn Leu Ala Thr Gly Leu Leu
                85                  90                  95

Thr Ala Asn Thr Glu Gly Asp Pro Val Val Ala Leu Ala Gly Asn Val
                100                 105                 110

Ile Arg Ala Asp Arg Leu Lys Arg Thr His Gln Ser Leu Asp Asn Ala
            115                 120                 125

Ala Leu Phe Gln Pro Ile Thr Lys Tyr Ser Val Glu Val Gln Asp Val
        130                 135                 140

Lys Asn Ile Pro Glu Ala Val Thr Asn Ala Phe Arg Ile Ala Ser Ala
145                 150                 155                 160

Gly Gln Ala Gly Ala Ala Phe Val Ser Phe Pro Gln Asp Val Val Asn
                165                 170                 175

Glu Val Thr Asn Thr Lys Asn Val Arg Ala Val Ala Ala Pro Lys Leu
                180                 185                 190

Gly Pro Ala Ala Asp Asp Ala Ile Ser Ala Ala Ile Ala Lys Ile Gln
            195                 200                 205

Thr Ala Lys Leu Pro Val Val Leu Val Gly Met Lys Gly Gly Arg Pro
        210                 215                 220

Glu Ala Ile Lys Ala Val Arg Lys Leu Leu Lys Lys Val Gln Leu Pro
225                 230                 235                 240

Phe Val Glu Thr Tyr Gln Ala Ala Gly Thr Leu Ser Arg Asp Leu Glu
                245                 250                 255

Asp Gln Tyr Phe Gly Arg Ile Gly Leu Phe Arg Asn Gln Pro Gly Asp
                260                 265                 270

Leu Leu Leu Glu Gln Ala Asp Val Val Leu Thr Ile Gly Tyr Asp Pro
            275                 280                 285

Ile Glu Tyr Asp Pro Lys Phe Trp Asn Ile Asn Gly Asp Arg Thr Ile
        290                 295                 300

Ile His Leu Asp Glu Ile Ala Asp Ile Asp His Ala Tyr Gln Pro
305                 310                 315                 320

Asp Leu Glu Leu Ile Gly Asp Ile Pro Ser Thr Ile Asn His Ile Glu
                325                 330                 335

His Asp Ala Val Lys Val Glu Phe Ala Glu Arg Glu Gln Lys Ile Leu
                340                 345                 350

Ser Asp Leu Lys Gln Tyr Met His Glu Gly Glu Gln Val Pro Ala Asp
            355                 360                 365

-continued

```
Trp Lys Ser Asp Arg Ala His Pro Leu Glu Ile Val Lys Glu Leu Arg
    370                 375                 380
Asn Ala Val Asp Asp His Val Thr Val Thr Cys Asp Ile Gly Ser His
385                 390                 395                 400
Ala Ile Trp Met Ser Arg Tyr Phe Arg Ser Tyr Glu Pro Leu Thr Leu
                405                 410                 415
Met Ile Ser Asn Gly Met Gln Thr Leu Gly Val Ala Leu Pro Trp Ala
            420                 425                 430
Ile Gly Ala Ser Leu Val Lys Pro Gly Glu Lys Val Val Ser Val Ser
        435                 440                 445
Gly Asp Gly Gly Phe Leu Phe Ser Ala Met Glu Leu Glu Thr Ala Val
    450                 455                 460
Arg Leu Lys Ala Pro Ile Val His Ile Val Trp Asn Asp Ser Thr Tyr
465                 470                 475                 480
Asp Met Val Ala Phe Gln Gln Leu Lys Lys Tyr Asn Arg Thr Ser Ala
                485                 490                 495
Val Asp Phe Gly Asn Ile Asp Ile Val Lys Tyr Ala Glu Ser Phe Gly
            500                 505                 510
Ala Thr Gly Leu Arg Val Glu Ser Pro Asp Gln Leu Ala Asp Val Leu
        515                 520                 525
Arg Gln Gly Met Asn Ala Glu Gly Pro Val Ile Ile Asp Val Pro Val
    530                 535                 540
Asp Tyr Ser Asp Asn Ile Asn Leu Ala Ser Asp Lys Leu Pro Lys Glu
545                 550                 555                 560
Phe Gly Glu Leu Met Lys Thr Lys Ala Leu
                565                 570

<210> SEQ ID NO 37
<211> LENGTH: 343
<212> TYPE: PRT
<213> ORGANISM: Anaerostipes caccae

<400> SEQUENCE: 37

Met Glu Glu Cys Lys Met Ala Lys Ile Tyr Tyr Gln Glu Asp Cys Asn
1               5                   10                  15
Leu Ser Leu Leu Asp Gly Lys Thr Ile Ala Val Ile Gly Tyr Gly Ser
            20                  25                  30
Gln Gly His Ala His Ala Leu Asn Ala Lys Glu Ser Gly Cys Asn Val
        35                  40                  45
Ile Ile Gly Leu Tyr Glu Gly Ala Lys Glu Trp Lys Arg Ala Glu Glu
    50                  55                  60
Gln Gly Phe Glu Val Tyr Thr Ala Ala Glu Ala Ala Lys Lys Ala Asp
65                  70                  75                  80
Ile Ile Met Ile Leu Ile Asn Asp Glu Lys Gln Ala Thr Met Tyr Lys
                85                  90                  95
Asn Asp Ile Glu Pro Asn Leu Glu Ala Gly Asn Met Leu Met Phe Ala
            100                 105                 110
His Gly Phe Asn Ile His Phe Gly Cys Ile Val Pro Pro Lys Asp Val
        115                 120                 125
Asp Val Thr Met Ile Ala Pro Lys Gly Pro Gly His Thr Val Arg Ser
    130                 135                 140
Glu Tyr Glu Glu Gly Lys Gly Val Pro Cys Leu Val Ala Val Glu Gln
145                 150                 155                 160
Asp Ala Thr Gly Lys Ala Leu Asp Met Ala Leu Ala Tyr Ala Leu Ala
                165                 170                 175
```

```
Ile Gly Gly Ala Arg Ala Gly Val Leu Glu Thr Thr Phe Arg Thr Glu
            180                 185                 190

Thr Glu Thr Asp Leu Phe Gly Glu Gln Ala Val Leu Cys Gly Gly Val
        195                 200                 205

Cys Ala Leu Met Gln Ala Gly Phe Glu Thr Leu Val Glu Ala Gly Tyr
    210                 215                 220

Asp Pro Arg Asn Ala Tyr Phe Glu Cys Ile His Glu Met Lys Leu Ile
225                 230                 235                 240

Val Asp Leu Ile Tyr Gln Ser Gly Phe Ser Gly Met Arg Tyr Ser Ile
                245                 250                 255

Ser Asn Thr Ala Glu Tyr Gly Asp Tyr Ile Thr Gly Pro Lys Ile Ile
            260                 265                 270

Thr Glu Asp Thr Lys Lys Ala Met Lys Lys Ile Leu Ser Asp Ile Gln
        275                 280                 285

Asp Gly Thr Phe Ala Lys Asp Phe Leu Val Asp Met Ser Asp Ala Gly
    290                 295                 300

Ser Gln Val His Phe Lys Ala Met Arg Lys Leu Ala Ser Glu His Pro
305                 310                 315                 320

Ala Glu Val Val Gly Glu Ile Arg Ser Leu Tyr Ser Trp Ser Asp
                325                 330                 335

Glu Asp Lys Leu Ile Asn Asn
            340

<210> SEQ ID NO 38
<211> LENGTH: 343
<212> TYPE: PRT
<213> ORGANISM: Anaerostipes caccae

<400> SEQUENCE: 38

Met Glu Glu Cys Lys Met Ala Lys Ile Tyr Tyr Gln Glu Asp Cys Asn
1               5                   10                  15

Leu Ser Leu Leu Asp Gly Lys Thr Ile Ala Val Ile Gly Tyr Gly Ser
            20                  25                  30

Gln Gly His Ala His Ala Leu Asn Ala Lys Glu Ser Gly Cys Asn Val
        35                  40                  45

Ile Ile Gly Leu Tyr Glu Gly Ala Lys Asp Trp Lys Arg Ala Glu Glu
    50                  55                  60

Gln Gly Phe Glu Val Tyr Thr Ala Ala Glu Ala Lys Lys Ala Asp
65                  70                  75                  80

Ile Ile Met Ile Leu Ile Asn Asp Glu Lys Gln Ala Thr Met Tyr Lys
                85                  90                  95

Asn Asp Ile Glu Pro Asn Leu Glu Ala Gly Asn Met Leu Met Phe Ala
            100                 105                 110

His Gly Phe Asn Ile His Phe Gly Cys Ile Val Pro Pro Lys Asp Val
        115                 120                 125

Asp Val Thr Met Ile Ala Pro Lys Gly Pro Gly His Thr Val Arg Ser
    130                 135                 140

Glu Tyr Glu Glu Gly Lys Gly Val Pro Cys Leu Val Ala Val Glu Gln
145                 150                 155                 160

Asp Ala Thr Gly Lys Ala Leu Asp Met Ala Leu Ala Tyr Ala Leu Ala
                165                 170                 175

Ile Gly Gly Ala Arg Ala Gly Val Leu Glu Thr Thr Phe Arg Thr Glu
            180                 185                 190

Thr Glu Thr Asp Leu Phe Gly Glu Gln Ala Val Leu Cys Gly Gly Val
```

```
            195                 200                 205
Cys Ala Leu Met Gln Ala Gly Phe Glu Thr Leu Val Glu Ala Gly Tyr
    210                 215                 220

Asp Pro Arg Asn Ala Tyr Phe Glu Cys Ile His Glu Met Lys Leu Ile
225                 230                 235                 240

Val Asp Leu Ile Tyr Gln Ser Gly Phe Ser Gly Met Arg Tyr Ser Ile
                245                 250                 255

Ser Asn Thr Ala Glu Tyr Gly Asp Tyr Ile Thr Gly Pro Lys Ile Ile
            260                 265                 270

Thr Glu Asp Thr Lys Lys Ala Met Lys Lys Ile Leu Ser Asp Ile Gln
        275                 280                 285

Asp Gly Thr Phe Ala Lys Asp Phe Leu Val Asp Met Ser Asp Ala Gly
    290                 295                 300

Ser Gln Val His Phe Lys Ala Met Arg Lys Leu Ala Ser Glu His Pro
305                 310                 315                 320

Ala Glu Val Val Gly Glu Glu Ile Arg Ser Leu Tyr Ser Trp Ser Asp
                325                 330                 335

Glu Asp Lys Leu Ile Asn Asn
            340

<210> SEQ ID NO 39
<211> LENGTH: 15539
<212> TYPE: DNA
<213> ORGANISM: Artificial
<220> FEATURE:
<223> OTHER INFORMATION: pLH468

<400> SEQUENCE: 39
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accataaatt cccgttttaa gagcttggtg agcgctagga gtcactgcca ggtatcgttt     240
gaacacggca ttagtcaggg aagtcataac acagtccttt ccgcaatttt cttttttcta     300
ttactcttgg cctcctctag tacactctat attttttat gcctcggtaa tgattttcat     360
ttttttttt ccacctagcg gatgactctt ttttttctt agcgattggc attatcacat     420
aatgaattat acattatata agtaatgtg atttcttcga agaatatact aaaaaatgag     480
caggcaagat aaacgaaggc aaagatgaca gagcagaaag ccctagtaaa gcgtattaca     540
aatgaaacca agattcagat tgcgatctct ttaaagggtg gtcccctagc gatagagcac     600
tcgatcttcc cagaaaaaga ggcagaagca gtagcagaac aggccacaca atcgcaagtg     660
attaacgtcc acacaggtat agggtttctg gaccatatga tacatgctct ggccaagcat     720
tccggctggt cgctaatcgt tgagtgcatt ggtgacttac acatagacga ccatcacacc     780
actgaagact gcgggattgc tctcggtcaa gcttttaaag aggccctagg ggccgtgcgt     840
ggagtaaaaa ggtttggatc aggatttgcg cctttggatg aggcactttc cagagcggtg     900
gtagatcttt cgaacaggcc gtacgcagtt gtcgaacttg gtttgcaaag ggagaaagta     960
ggagatctct cttgcgagat gatcccgcat tttcttgaaa gctttgcaga ggctagcaga    1020
attaccctcc acgttgattg tctgcgaggc aagaatgatc atcaccgtag tgagagtgcg    1080
ttcaaggctc ttgcggttgc cataagagaa gccacctcgc ccaatggtac caacgatgtt    1140
ccctccacca aggtgttct tatgtagtga caccgattat ttaaagctgc agcatacgat    1200
```

```
atatatacat gtgtatatat gtataccat gaatgtcagt aagtatgtat acgaacagta    1260
tgatactgaa gatgacaagg taatgcatca ttctatacgt gtcattctga acgaggcgcg    1320 ctttccttt ttcttttgc ttttctttt ttttctctt gaactcgacg gatctatgcg    1380
gtgtgaaata ccgcacagat gcgtaaggag aaaataccgc atcaggaaat tgtaagcgtt    1440
aatattttgt taaaattcgc gttaaatttt tgttaaatca gctcattttt taaccaatag    1500
gccgaaatcg gcaaaatccc ttataaatca aagaataga ccgagatagg gttgagtgtt    1560
gttccagttt ggaacaagag tccactatta agaacgtgg actccaacgt caagggcga    1620 aaaaccgtct atcagggcga tggcccacta cgtgaaccat caccctaatc aagtttttg    1680 gggtcgaggt gccgtaaagc actaaatcgg aaccctaaag ggagccccg atttagagct    1740 tgacggggaa agccggcgaa cgtggcgaga aggaaggga agaaagcgaa aggagcgggc    1800
gctagggcgc tggcaagtgt agcggtcacg ctgcgcgtaa ccaccacacc cgccgcgctt    1860
aatgcgccgc tacagggcgc gtccattcgc cattcaggct gcgcaactgt tgggaagggc    1920
gcggtgcggg cctcttcgct attacgccag ctggcgaaag gggatgtgc tgcaaggcga    1980 ttaagttggg taacgccagg ttttcccag tcacgacgtt gtaaaacgac ggccagtgag    2040
cgcgcgtaat acgactcact ataggggaa ttgggtaccg gccccccct cgaggtcgac    2100 ggcgcgccac tggtagagag cgactttgta tgccccaatt gcgaaacccg cgatatcctt    2160
ctcgattctt tagtacccga ccaggacaag gaaaaggagg tcgaaacgtt tttgaagaaa    2220
caagaggaac tacacggaag ctctaaagat ggcaaccagc cagaaactaa gaaaatgaag    2280
ttgatggatc caactggcac cgctggcttg aacaacaata ccagccttcc aacttctgta    2340
aataacggcg gtacgccagt gccaccagta ccgttacctt tcggtatacc tccttccccc    2400
atgtttccaa tgccccttcat gcctccaacg gctactatca caaatcctca tcaagctgac    2460
gcaagcccta agaatgaat aacaatactg acagtactaa ataattgcct acttggcttc    2520
acatacgttg catacgtcga tatagataat aatgataatg acagcaggat tatcgtaata    2580
cgtaatagct gaaaatctca aaaatgtgtg ggtcattacg taaataatga taggaatggg    2640
attcttctat ttttccttt tccattctag cagccgtcgg gaaaacgtgg catcctctct    2700
ttcgggctca attggagtca cgctgccgtg agcatcctct ctttccatat ctaacaactg    2760
agcacgtaac caatggaaaa gcatgagctt agcgttgctc caaaaaagta ttggatggtt    2820 ataccatt gtctgttctc ttctgacttt gactcctcaa aaaaaaat ctacaatcaa    2880 cagatcgctt caattacgcc ctcacaaaaa cttttttcct tcttcttcgc ccacgttaaa    2940
ttttatccct catgttgtct aacggatttc tgcacttgat ttattataaa aagacaaaga    3000
cataatactt ctctatcaat ttcagttatt gttcttcctt gcgttattct tctgttcttc    3060 tttttcttt gtcatatata accataacca agtaatacat attcaaacta gtatgactga    3120 caaaaaact cttaaagact taagaaatcg tagttctgtt tacgattcaa tggttaaatc    3180
acctaatcgt gctatgttgc gtgcaactgg tatgcaagat gaagactttg aaaaacctat    3240
cgtcggtgtc atttcaactt gggctgaaaa cacaccttgt aatatccact tacatgactt    3300
tggtaaacta gccaaagtcg gtgttaagga agctggtgct tggccagttc agttcggaac    3360
aatcacggtt tctgatggaa tcgccatggg aaccccaagga atgcgtttct ccttgacatc    3420
tcgtgatatt attgcagatt ctattgaagc agccatggga ggtcataatg cggatgcttt    3480
tgtagccatt ggcggttgtg ataaaaacat gccccggttct gttatcgcta tggctaacat    3540
ggatatccca gccatttttg cttacggcgg aacaattgca cctggtaatt tagacggcaa    3600
```

```
agatatcgat ttagtctctg tctttgaagg tgtcggccat tggaaccacg gcgatatgac    3660
caaagaagaa gttaaagctt tggaatgtaa tgcttgtccc ggtcctggag gctgcggtgg    3720
tatgtatact gctaacacaa tggcgacagc tattgaagtt ttgggactta gccttccggg    3780
ttcatcttct cacccggctg aatccgcaga aagaaagca gatattgaag aagctggtcg    3840
cgctgttgtc aaaatgctcg aaatgggctt aaaaccttct gacattttaa cgcgtgaagc    3900
ttttgaagat gctattactg taactatggc tctgggaggg tcaaccaact caaccttca    3960 cctcttagct attgcccatg ctgctaatgt ggaattgaca cttgatgatt tcaatacttt    4020
ccaagaaaaa gttcctcatt tggctgattt gaaaccttct ggtcaatatg tattccaaga    4080
cctttacaag gtcggagggg taccagcagt tatgaaatat ctccttaaaa atggcttcct    4140
tcatggtgac cgtatcactt gtactggcaa aacagtcgct gaaaatttga aggcttttga    4200
tgatttaaca cctggtcaaa aggttattat gccgcttgaa aatcctaaac gtgaagatgg    4260
tccgctcatt attctccatg gtaacttggc tccagacggt gccgttgcca agtttctgg    4320 tgtaaaagtg cgtcgtcatg tcggtcctgc taaggtcttt aattctgaag aagaagccat    4380
tgaagctgtc ttgaatgatg atattgttga tggtgatgtt gttgtcgtac gttttgtagg    4440
accaaagggc ggtcctggta tgcctgaaat gctttccctt tcatcaatga ttgttggtaa    4500
agggcaaggt gaaaaagttg cccttctgac agatggccgc ttctcaggtg gtacttatgg    4560
tcttgtcgtg ggtcatatcg ctcctgaagc acaagatggc ggtccaatcg cctacctgca    4620
aacaggagac atagtcacta ttgaccaaga cactaaggaa ttcactttg atatctccga    4680 tgaagagtta aaacatcgtc aagagaccat tgaattgcca ccgctctatt cacgcggtat    4740
ccttggtaaa tatgctcaca tcgtttcgtc tgcttctagg ggagccgtaa cagacttttg    4800
gaagcctgaa gaaactggca aaaaatgttg tcctggttgc tgtggttaag cggccgcgtt    4860
aattcaaatt aattgatata gttttttaat gagtattgaa tctgtttaga ataatggaa    4920 tattatttt atttatttat ttatattatt ggtcggctct tttcttctga aggtcaatga    4980
caaaatgata tgaaggaaat aatgattct aaaattttac aacgtaagat attttacaa    5040 aagcctagct catcttttgt catgcactat tttactcacg cttgaaatta acggccagtc    5100
cactgcggag tcatttcaaa gtcatcctaa tcgatctatc gttttgata gctcattttg    5160 gagttcgcga ttgtcttctg ttattcacaa ctgttttaat ttttatttca ttctggaact    5220
cttcgagttc tttgtaaagt ctttcatagt agcttacttt atcctccaac atatttaact    5280
tcatgtcaat ttcggctctt aaattttcca catcatcaag ttcaacatca tcttttaact    5340
tgaatttatt ctctagctct tccaaccaag cctcattgct ccttgattta ctggtgaaaa    5400
gtgatacact ttgcgcgcaa tccaggtcaa aactttcctg caaagaattc accaatttct    5460
cgacatcata gtacaatttg ttttgttctc ccatcacaat ttaatatacc tgatggattc    5520
ttatgaagcg ctgggtaatg gacgtgtcac tctacttcgc cttttccct actccttta    5580 gtacggaaga caatgctaat aaataagagg gtaataataa tattattaat cggcaaaaaa    5640
gattaaacgc caagcgttta attatcagaa agcaaacgtc gtaccaatcc ttgaatgctt    5700
cccaattgta tattaagagt catcacagca acatattctt gttattaaat taattattat    5760 tgattttga tattgtataa aaaaaccaaa tatgtataaa aaagtgaat aaaaaatacc    5820 aagtatggag aaatatatta gaagtctata cgttaaacca cccggcccc ccctcgaggt    5880 cgacggtatc gataagcttg atatcgaatt cctgcagccc gggggatcca ctagttctag    5940
```

```
agcggccgct ctagaactag taccacaggt gttgtcctct gaggacataa aatacacacc    6000
gagattcatc aactcattgc tggagttagc atatctacaa ttgggtgaaa tggggagcga    6060
tttgcaggca tttgctcggc atgccggtag aggtgtggtc aataagagcg acctcatgct    6120
atacctgaga aagcaacctg acctacagga aagagttact caagaataag aattttcgtt    6180
ttaaaaccta agagtcactt taaaatttgt atacacttat tttttttata acttatttaa    6240
taataaaaat cataaatcat aagaaattcg cttactctta attaatcaaa aagttaaaat    6300
tgtacgaata gattcaccac ttcttaacaa atcaaaccct tcattgattt tctcgaatgg    6360
caatacatgt gtaattaaag gatcaagagc aaacttcttc gccataaagt cggcaacaag    6420
ttttggaaca ctatccttgc tcttaaaacc gccaaatata gctcccttcc atgtacgacc    6480
gcttagcaac agcataggat tcatcgacaa attttgtgaa tcaggaggaa cacctacgat    6540
cacactgact ccatatgcct cttgacagca ggacaacgca gttaccatag tatcaagacg    6600
gcctataact tcaaaagaga aatcaactcc accgtttgac atttcagtaa ggacttcttg    6660
tattggtttc ttataatctt gagggttaac acattcagta gccccgacct ccttagcttt    6720
tgcaaatttg tccttattga tgtctacacc tataatcctc gctgcgcctg cagctttaca    6780
ccccataata acgcttagtc ctactcctcc taaaccgaat actgcacaag tcgaaccctg    6840
tgtaaccttt gcaactttaa ctgcggaacc gtaaccggtg gaaaatccgc accctatcaa    6900
gcaaactttt tccagtggtg aagctgcatc gattttagcg acagatatct cgtccaccac    6960
tgtgtattgg gaaaatgtag aagtaccaag gaaatggtgt ataggtttcc ctctgcatgt    7020
aaatctgctt gtaccatcct gcatagtacc tctaggcata gacaaatcat ttttaaggca    7080
gaaattaccc tcaggatgtt tgcagactct acacttacca cattgaggag tgaacagtgg    7140
gatcacttta tcaccaggac gaacagtggt aacaccttca cctatggatt caacgattcc    7200
ggcagcctcg tgtcccgcga ttactggcaa aggagtaact agagtgccac tcaccacatg    7260
gtcgtcggat ctacagattc cggtggcaac catcttgatt ctaacctcgt gtgcttttgg    7320
tggcgctact tctacttctt ctatgctaaa cggcttttc tcttcccaca aaactgccgc    7380
tttacactta ataactttac cggctgttga catcctcagc tagctattgt aatatgtgtg    7440
tttgtttgga ttattaagaa gaataattac aaaaaaaatt acaaaggaag gtaattacaa    7500
cagaattaag aaaggacaag aaggaggaag agaatcagtt cattatttct tctttgttat    7560
ataacaaacc caagtagcga tttggccata cattaaaagt tgagaaccac cctccctggc    7620
aacagccaca actcgttacc attgttcatc acgatcatga aactcgctgt cagctgaaat    7680
ttcacctcag tggatctctc tttttattct tcatcgttcc actaaccttt ttccatcagc    7740
tggcagggaa cggaaagtgg aatcccattt agcgagcttc ctcttttctt caagaaaaga    7800
cgaagcttgt gtgtgggtgc gcgcgctagt atctttccac attaagaaat ataccataaa    7860
ggttacttag acatcactat ggctatatat atatatatat atatatgtaa cttagcacca    7920
tcgcgcgtgc atcactgcat gtgttaaccg aaaagtttgg cgaacacttc accgacacgg    7980
tcatttagat ctgtcgtctg cattgcacgt cccttagcct taaatcctag gcgggagcat    8040
tctcgtgtaa ttgtgcagcc tgcgtagcaa ctcaacatag cgtagtctac ccagtttttc    8100
aagggtttat cgttagaaga ttctcccttt tcttcctgct cacaaatctt aaagtcatac    8160
attgcacgac taaatgcaag catgcggatc cccgggctg caggaattcg atatcaagct    8220
tatcgatacc gtcgactggc cattaatctt tcccatatta gatttcgcca agccatgaaa    8280
gttcaagaaa ggtctttaga cgaattaccc ttcatttctc aaactggcgt caagggatcc    8340
```

```
tggtatggtt ttatcgtttt atttctggtt cttatagcat cgttttggac ttctctgttc    8400
ccattaggcg gttcaggagc cagcgcagaa tcattctttg aaggatactt atcctttcca    8460
attttgattg tctgttacgt tggacataaa ctgtatacta gaaattggac tttgatggtg    8520
aaactagaag atatggatct tgataccggc agaaaacaag tagatttgac tcttcgtagg    8580
gaagaaatga ggattgagcg agaaacatta gcaaaaagat ccttcgtaac aagatttta     8640
catttctggt gttgaaggga aagatatgag ctatacagcg gaatttccat atcactcaga    8700
ttttgttatc taattttttc cttcccacgt ccgcgggaat ctgtgtatat tactgcatct    8760
agatatatgt tatcttatct tggcgcgtac atttaatttt caacgtattc tataagaaat    8820
tgcgggagtt tttttcatgt agatgatact gactgcacgc aaatataggc atgatttata    8880
ggcatgattt gatggctgta ccgataggaa cgctaagagt aacttcagaa tcgttatcct    8940
ggcggaaaaa attcatttgt aaactttaaa aaaaaagcc aatatcccca aaattattaa     9000
gagcgcctcc attattaact aaaatttcac tcagcatcca caatgtatca ggtatctact    9060
acagatatta catgtggcga aaaagacaag aacaatgcaa tagcgcatca agaaaaaaca    9120
caaagctttc aatcaatgaa tcgaaaatgt cattaaaata gtatataaat tgaaactaag    9180
tcataaagct ataaaagaa aatttattta aatgcaagat ttaaagtaaa ttcacggccc     9240
tgcaggcctc agctcttgtt ttgttctgca ataacttac ccatcttttt caaaacttta     9300
ggtgcaccct cctttgctag aataagttct atccaataca tcctatttgg atctgcttga    9360
gcttctttca tcacggatac gaattcattt tctgttctca caattttgga cacaactctg    9420
tcttccgttg ccccgaaact ttctggcagt tttgagtaat tccacatagg aatgtcatta    9480
taactctggt tcggaccatg aatttccctc tcaaccgtgt aaccatcgtt attaatgata    9540
aagcagattg ggtttatctt ctctctaatg gctagtccta attcttggac agtcagttgc    9600
aatgatccat ctccgataaa caataaatgt ctagattctt tatctgcaat ttggctgcct    9660
agagctgcgg ggaaagtgta tcctatagat ccccacaagg gttgaccaat aaaatgtgat    9720
ttcgatttca gaaatataga tgaggcaccg aagaaagaag tgccttgttc agccacgatc    9780
gtctcattac tttgggtcaa attttcgaca gcttgccaca gtctatcttg tgacaacagc    9840
gcgttagaag gtacaaaatc ttcttgcttt ttatctatgt acttgccttt atattcaatt    9900
tcggacaagt caagaagaga tgatatcagg gattcgaagt cgaaattttg gattctttcg    9960
ttgaaaattt taccttcatc gatattcaag gaaatcattt tattttcatt aagatggtga   10020
gtaaatgcac ccgtactaga atcggtaagc tttacaccca acataagaat aaaatcagca   10080
gattccacaa attccttcaa gtttggctct gacagagtac cgttgtaaat ccccaaaaat   10140
gagggcaatg cttcatcaac agatgattta ccaaagttca aagtagtaat aggtaactta   10200
gtctttgaaa taaactgagt aacagtcttc tctaggccga acgatataat ttcatggcct   10260
gtgattacaa ttggtttctt ggcattcttc agactttcct gtattttgtt cagaatctct   10320
tgatcagatg tattcgacgt ggaattttcc ttcttaagag gcaaggatgg ttttcagcc    10380
ttagcggcag ctacatctac aggtaaattg atgtaaaccg gctttctttc ctttagtaag   10440
gcagacaaca ctctatcaat ttcaacagtt gcattctcgg ctgtcaataa agtcctggca   10500
gcagtaaccg gttcgtgcat cttcataaag tgcttgaaat caccatcagc caacgtatgg   10560
tgaacaaact taccttcgtt ctgcactttc gaggtaggag atcccacgat ctcaacaaca   10620
ggcaggttct cagcatagga gcccgctaag ccattaactg cggataattc gccaacacca   10680
```

```
aatgtagtca agaatgccgc agccttttc gttcttgcgt acccgtcggc catataggag    10740
gcatttaact cattagcatt tcccacccat ttcatatctt tgtgtgaaat aatttgatct    10800
agaaattgca aattgtagtc acctggtact ccgaatattt cttctatacc taattcgtgt    10860
aatctgtcca acagatagtc acctactgta tacattttgt ttactagttt atgtgtgttt    10920
attcgaaact aagttcttgg tgttttaaaa ctaaaaaaaa gactaactat aaaagtagaa    10980
tttaagaagt ttaagaaata gatttacaga attacaatca ataccaccg tctttatata     11040
cttattagtc aagtagggga ataatttcag ggaactggtt tcaaccttt ttttcagctt     11100
tttccaaatc agagagagca gaaggtaata gaaggtgtaa gaaatgaga tagatacatg     11160
cgtgggtcaa ttgccttgtg tcatcattta ctccaggcag gttgcatcac tccattgagg    11220
ttgtgcccgt ttttgcctg tttgtgcccc tgttctctgt agttgcgcta agagaatgga     11280
cctatgaact gatggttggt gaagaaaaca atattttggt gctgggattc ttttttttc     11340
tggatgccag cttaaaaagc gggctccatt atatttagtg gatgccagga ataaactgtt    11400
cacccagaca cctacgatgt tatatattct gtgtaacccg cccctattt tgggcatgta     11460
cgggttacag cagaattaaa aggctaattt tttgactaaa taaagttagg aaaatcacta    11520
ctattaatta tttcgtatt ctttgaaatg gcagtattga taatgataaa ctcgaactga     11580
aaaagcgtgt ttttattca aaatgattct aactcccta cgtaatcaag gaatctttt      11640
gccttggcct ccgcgtcatt aaacttcttg ttgttgacgc taacattcaa cgctagtata    11700
tattcgtttt ttcaggtaa gttcttttca acgggtctta ctgatgaggc agtcgcgtct    11760
gaacctgtta agaggtcaaa tatgtcttct tgaccgtacg tgtcttgcat gttattagct    11820
ttgggaattt gcatcaagtc ataggaaaat ttaaatcttg gctctcttgg gctcaaggtg    11880
acaaggtcct cgaaaatagg gcgcgcccca ccgcggtgga gctccagctt ttgttccctt    11940
tagtgagggt taattgcgcg cttggcgtaa tcatggtcat agctgttcc tgtgtgaaat     12000
tgttatccgc tcacaattcc acacaacata cgagccggaa gcataaagtg taaagcctgg    12060
ggtgcctaat gagtgagcta actcacatta attgcgttgc gctcactgcc gctttccag    12120
tcgggaaacc tgtcgtgcca gctgcattaa tgaatcggcc aacgcgcggg gagaggcggt    12180
ttgcgtattg ggcgctcttc cgcttcctcg ctcactgact cgctgcgctc ggtcgttcgg    12240
ctgcggcgag cggtatcagc tcactcaaag gcggtaatac ggttatccac agaatcaggg    12300
gataacgcag gaaagaacat gtgagcaaaa ggccagcaaa aggccaggaa ccgtaaaaag    12360
gccgcgttgc tggcgttttt ccataggctc cgcccccctg acgagcatca caaaaatcga    12420
cgctcaagtc agaggtggcg aaacccgaca ggactataaa gataccaggc gtttccccct    12480
ggaagctccc tcgtgcgctc tcctgttccg accctgccgc ttaccggata cctgtccgcc    12540
tttctccctt cgggaagcgt ggcgctttct catagctcac gctgtaggta tctcagttcg    12600
gtgtaggtcg ttcgctccaa gctgggctgt gtgcacgaac ccccgttca gcccgaccgc    12660
tgcgccttat ccggtaacta tcgtcttgag tccaacccgg taagacacga cttatcgcca    12720
ctggcagcag ccactggtaa caggattagc agagcgaggt atgtaggcgg tgctacagag    12780
ttcttgaagt ggtggcctaa ctacggctac actagaagaa cagtatttgg tatctgcgct    12840
ctgctgaagc cagttacctt cggaaaaaga gttggtagct cttgatccgg caaacaaacc    12900
accgctggta gcggtggttt ttttgtttgc aagcagcaga ttacgcgcag aaaaaagga    12960
tctcaagaag atcctttgat cttttctacg gggtctgacg ctcagtggaa cgaaaactca    13020
cgttaaggga ttttggtcat gagattatca aaaaggatct tcacctagat ccttttaaat    13080
```

```
taaaaatgaa gttttaaatc aatctaaagt atatatgagt aaacttggtc tgacagttac   13140
caatgcttaa tcagtgaggc acctatctca gcgatctgtc tatttcgttc atccatagtt   13200
gcctgactcc ccgtcgtgta gataactacg atacgggagg gcttaccatc tggccccagt   13260
gctgcaatga taccgcgaga cccacgctca ccggctccag atttatcagc aataaaccag   13320
ccagccggaa gggccgagcg cagaagtggt cctgcaactt tatccgcctc catccagtct   13380
attaattgtt gccgggaagc tagagtaagt agttcgccag ttaatagttt gcgcaacgtt   13440
gttgccattg ctacaggcat cgtggtgtca cgctcgtcgt ttggtatggc ttcattcagc   13500
tccggttccc aacgatcaag gcgagttaca tgatccccca tgttgtgcaa aaagcggtt   13560 agctccttcg gtcctccgat cgttgtcaga agtaagttgg ccgcagtgtt atcactcatg   13620
gttatggcag cactgcataa ttctcttact gtcatgccat ccgtaagatg cttttctgtg   13680
actggtgagt actcaaccaa gtcattctga gaatagtgta tgcggcgacc gagttgctct   13740
tgcccggcgt caatacggga taataccgcg ccacatagca gaactttaaa agtgctcatc   13800
attggaaaac gttcttcggg gcgaaaactc tcaaggatct taccgctgtt gagatccagt   13860
tcgatgtaac ccactcgtgc acccaactga tcttcagcat cttttacttt caccagcgtt   13920
tctgggtgag caaaaacagg aaggcaaaat gccgcaaaaa agggaataag ggcgacacgg   13980
aaatgttgaa tactcatact cttccttttt caatattatt gaagcattta tcagggttat   14040
tgtctcatga gcggatacat atttgaatgt atttagaaaa ataaacaaat aggggttccg   14100
cgcacatttc cccgaaaagt gccacctgaa cgaagcatct gtgcttcatt ttgtagaaca   14160
aaaatgcaac gcgagagcgc taattttttca acaaagaat ctgagctgca ttttttacaga   14220 acagaaatgc aacgcgaaag cgctatttta ccaacgaaga atctgtgctt cattttttgta   14280 aaacaaaaat gcaacgcgag agcgctaatt tttcaaacaa agaatctgag ctgcattttt   14340
acagaacaga aatgcaacgc gagagcgcta ttttaccaac aaagaatcta tacttctttt   14400
ttgttctaca aaaatgcatc ccgagagcgc tatttttcta caaagcatc ttagattact   14460 ttttttctcc tttgtgcgct ctataatgca gtctcttgat aactttttgc actgtaggtc   14520
cgttaaggtt agaagaaggc tactttggtg tctattttct cttccataaa aaagcctga   14580 ctccacttcc cgcgtttact gattactagc gaagctgcgg gtgcattttt tcaagataaa   14640
ggcatccccg attatattct ataccgatgt ggattgcgca tactttgtga acagaaagtg   14700
atagcgttga tgattcttca ttggtcagaa aattatgaac ggtttcttct atttgtctc   14760 tatatactac gtataggaaa tgtttacatt ttcgtattgt tttcgattca ctctatgaat   14820
agttcttact acaatttttt tgtctaaaga gtaatactag agataaacat aaaaaatgta   14880
gaggtcgagt ttagatgcaa gttcaaggag cgaaaggtgg atgggtaggt tatataggga   14940
tatagcacag agatatatag caaagagata cttttgagca atgtttgtgg aagcggtatt   15000
cgcaatattt tagtagctcg ttacagtccg gtgcgttttt ggtttttttga aagtgcgtct   15060 tcagagcgct tttggttttc aaaagcgctc tgaagttcct atactttcta gagaatagga   15120
acttcggaat aggaacttca aagcgtttcc gaaaacgagc gcttccgaaa atgcaacgcg   15180
agctgcgcac atacagctca ctgttcacgt cgcacctata tctgcgtgtt gcctgtatat   15240
atatatacat gagaagaacg gcatagtgcg tgtttatgct taaatgcgta cttatatgcg   15300
tctatttatg taggatgaaa ggtagtctag tacctcctgt gatattatcc cattccatgc   15360
ggggtatcgt atgcttcctt cagcactacc ctttagctgt tctatatgct gccactcctc   15420
```

```
<210> SEQ ID NO 40
<211> LENGTH: 1128
<212> TYPE: DNA
<213> ORGANISM: Artificial Sequence
<220> FEATURE:
<223> OTHER INFORMATION: Codon-optimized polynucleotide sequence-Horse-
      liver ADH

<400> SEQUENCE: 40
atgtcaacag ccggtaaagt tattaagtgt aaagcggcag ttttgtggga agagaaaaag      60
ccgtttagca tagaagaagt agaagtagcg ccaccaaaag cacacgaggt tagaatcaag     120
atggttgcca ccggaatctg tagatccgac gaccatgtgg tgagtggcac tctagttact     180
cctttgccag taatcgcggg acacgaggct gccggaatcg ttgaatccat aggtgaaggt     240
gttaccactt tcgtcctggt gataaagtg atcccactgt tcactcctca atgtggtaag     300
tgtagagtct gcaaacatcc tgagggtaat ttctgcctta aaaatgattt gtctatgcct     360
agaggtacta tgcaggatgg tacaagcaga tttacatgca gagggaaacc tatacaccat     420
ttccttggta cttctacatt tcccaatac acagtggtgg acgagatatc tgtcgctaaa     480
atcgatgcag cttcaccact ggaaaaagtt tgcttgatag ggtgcggatt tccaccggt     540
tacggttccg cagttaaagt tgcaaaggtt acacagggtt cgacttgtgc agtattcggt     600
ttaggaggag taggactaag cgttattatg gggtgtaaag ctgcaggcgc agcgaggatt     660
ataggtgtag acatcaataa ggacaaattt gcaaaagcta aggaggtcgg ggctactgaa     720
tgtgttaacc ctcaagatta taagaaacca atacaagaag tccttactga atgtcaaac     780
ggtggagttg atttctcttt tgaagttata ggccgtcttg atactatggt aactgcgttg     840
tcctgctgtc aagaggcata tggagtcagt gtgatcgtag tgttcctcc tgattcacaa     900
aatttgtcga tgaatcctat gctgttgcta agcggtcgta catggaaggg agctatattt     960
ggcggtttta agagcaagga tagtgttcca aaacttgttg ccgactttat ggcgaagaag    1020
tttgctcttg atcctttaat tacacatgta ttgccattcg agaaaatcaa tgaagggttt    1080
gatttgttaa aagtggtga atctattcgt acaattttaa cttttga                   1128

<210> SEQ ID NO 41
<211> LENGTH: 1023
<212> TYPE: DNA
<213> ORGANISM: Artificial Sequence
<220> FEATURE:
<223> OTHER INFORMATION: Saccharomyces cerevisiae TDH3 promoter

<400> SEQUENCE: 41
caccgcggtg gggcgcgccc tattttcgag gaccttgtca ccttgagccc aagagagcca      60
agatttaaat ttcctatga cttgatgcaa attcccaaag ctaataacat gcaagacacg     120
tacggtcaag aagacatatt tgacctctta acaggttcag acgcgactgc ctcatcagta     180
agaccccgttg aaaagaactt acctgaaaaa acgaatatata tactagcgtt gaatgttagc    240
gtcaacaaca agaagtttaa tgacgcggag gccaaggcaa aagattcct tgattacgta     300
agggagttag aatcattttg aataaaaaac acgcttttttc agttcgagtt tatcattatc     360
aatactgcca tttcaaagaa tacgtaaata attaatagta gtgattttcc taactttatt     420
tagtcaaaaa attagccttt taattctgct gtaacccgta catgcccaaa atagggggcg     480
```

```
ggttacacag aatatataac atcgtaggtg tctgggtgaa cagtttattc ctggcatcca    540
ctaaatataa tggagcccgc tttttaagct ggcatccaga aaaaaaaaga atcccagcac    600
caaaatattg ttttcttcac caaccatcag ttcataggtc cattctctta gcgcaactac    660
agagaacagg ggcacaaaca ggcaaaaaac gggcacaacc tcaatggagt gatgcaacct    720
gcctggagta aatgatgaca caaggcaatt gacccacgca tgtatctatc tcattttctt    780
acaccttcta ttaccttctg ctctctctga tttggaaaaa gctgaaaaaa aaggttgaaa    840
ccagttccct gaaattattc ccctacttga ctaataagta tataaagacg gtaggtattg    900
attgtaattc tgtaaatcta tttcttaaac ttcttaaatt ctacttttat agttagtctt    960
ttttttagtt ttaaaacacc aagaacttag tttcgaataa acacacataa actagtaaac   1020
aaa                                                                 1023

<210> SEQ ID NO 42
<211> LENGTH: 21
<212> TYPE: DNA
<213> ORGANISM: Artificial Sequence
<220> FEATURE:
<223> OTHER INFORMATION: Primer OT1068

<400> SEQUENCE: 42
caaaagctga gctccaccgc g                                               21

<210> SEQ ID NO 43
<211> LENGTH: 44
<212> TYPE: DNA
<213> ORGANISM: Artificial Sequence
<220> FEATURE:
<223> OTHER INFORMATION: Primer OT1067

<400> SEQUENCE: 43
gtttactagt ttatgtgtgt ttattcgaaa ctaagttctt ggtg                       44

<210> SEQ ID NO 44
<211> LENGTH: 9333
<212> TYPE: DNA
<213> ORGANISM: Artificial Sequence
<220> FEATURE:
<223> OTHER INFORMATION: pLH467

<400> SEQUENCE: 44
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accataccac agcttttcaa ttcaattcat cattttttttt ttattctttt ttttgatttc    240
ggtttctttg aaatttttttt gattcggtaa tctccgaaca gaaggaagaa cgaaggaagg    300
agcacagact tagattggta tatatacgca tatgtagtgt tgaagaaaca tgaaattgcc    360
cagtattctt aacccaactg cacagaacaa aaacctgcag gaaacgaaga taaatcatgt    420
cgaaagctac atataaggaa cgtgctgcta ctcatcctag tcctgttgct gccaagctat    480
ttaatatcat gcacgaaaag caaacaaact tgtgtgcttc attggatgtt cgtaccacca    540
aggaattact ggagttagtt gaagcattag gtcccaaaat ttgtttacta aaaacacatg    600
tggatatctt gactgatttt tccatggagg gcacagttaa gccgctaaag gcattatccg    660
ccaagtacaa ttttttactc ttcgaagaca gaaaatttgc tgacattggt aatacagtca    720
aattgcagta ctctgcgggt gtatacagaa tagcagaatg ggcagacatt acgaatgcac    780
```

| | |
|---|---|
| acggtgtggt gggcccaggt attgttagcg gtttgaagca ggcggcagaa gaagtaacaa | 840 |
| aggaacctag aggcctttg atgttagcag aattgtcatg caagggctcc ctatctactg | 900 |
| gagaatatac taagggtact gttgacattg cgaagagcga caaagatttt gttatcggct | 960 |
| ttattgctca aagagacatg ggtggaagag atgaaggtta cgattggttg attatgacac | 1020 |
| ccggtgtggg tttagatgac aagggagacg cattgggtca acagtataga accgtggatg | 1080 |
| atgtggtctc tacaggatct gacattatta ttgttggaag aggactattt gcaaagggaa | 1140 |
| gggatgctaa ggtagagggt gaacgttaca gaaaagcagg ctgggaagca tatttgagaa | 1200 |
| gatgcggcca gcaaaactaa aaaactgtat tataagtaaa tgcatgtata ctaaactcac | 1260 |
| aaattagagc ttcaatttaa ttatatcagt tattacccta tgcggtgtga ataccgcac | 1320 |
| agatgcgtaa ggagaaaata ccgcatcagg aaattgtaaa cgttaatatt ttgttaaaat | 1380 |
| tcgcgttaaa ttttgttaa atcagctcat tttttaacca ataggccgaa atcggcaaaa | 1440 |
| tcccttataa atcaaaagaa tagaccgaga tagggttgag tgttgttcca gtttggaaca | 1500 |
| agagtccact attaaagaac gtggactcca acgtcaaagg gcgaaaaacc gtctatcagg | 1560 |
| gcgatggccc actacgtgaa ccatcaccct aatcaagttt tttggggtcg aggtgccgta | 1620 |
| aagcactaaa tcggaacccct aaagggagcc cccgatttag agcttgacgg ggaaagccgg | 1680 |
| cgaacgtggc gagaaaggaa gggaagaaag cgaaaggagc gggcgctagg gcgctggcaa | 1740 |
| gtgtagcggt cacgctgcgc gtaaccacca cacccgccgc gcttaatgcg ccgctacagg | 1800 |
| gcgcgtcgcg ccattcgcca ttcaggctgc gcaactgttg ggaagggcga tcggtgcggg | 1860 |
| cctcttcgct attacgccag ctggcgaaag ggggatgtgc tgcaaggcga ttaagttggg | 1920 |
| taacgccagg gttttcccag tcacgacgtt gtaaaacgac ggccagtgag cgcgcgtaat | 1980 |
| acgactcact ataggggcgaa ttgggtaccg ggccccccct cgaggtcgac tggccattaa | 2040 |
| tctttcccat attagatttc gccaagccat gaaagttcaa gaaaggtctt tagacgaatt | 2100 |
| acccttcatt tctcaaactg gcgtcaaggg atcctggtat ggttttatcg tttttatttct | 2160 |
| ggttcttata gcatcgtttt ggacttctct gttcccatta ggcggttcag gagccagcgc | 2220 |
| agaatcattc tttgaaggat acttatcctt tccaattttg attgtctgtt acgttggaca | 2280 |
| taaactgtat actagaaatt ggactttgat ggtgaaacta aagatatgg atcttgatac | 2340 |
| cggcagaaaa caagtagatt tgactcttcg tagggaagaa atgaggattg agcgagaaac | 2400 |
| attagcaaaa agatccttcg taacaagatt tttacatttc tggtgttgaa gggaaagata | 2460 |
| tgagctatac agcggaattt ccatatcact cagattttgt tatctaattt tttccttccc | 2520 |
| acgtccgcgg gaatctgtgt atattactgc atctagatat atgttatctt atcttggcgc | 2580 |
| gtacatttaa ttttcaacgt attctataag aaattgcggg agtttttttc atgtagatga | 2640 |
| tactgactgc acgcaaatat aggcatgatt tataggcatg atttgatggc tgtaccgata | 2700 |
| ggaacgctaa gagtaacttc agaatcgtta tcctggcgga aaaattcat ttgtaaactt | 2760 |
| taaaaaaaaa agccaatatc cccaaaatta ttaagagcgc ctccattatt aactaaaatt | 2820 |
| tcactcagca tccacaatgt atcaggtatc tactacagat attacatgtg gcgaaaaaga | 2880 |
| caagaacaat gcaatagcgc atcaagaaaa aacacaaagc tttcaatcaa tgaatcgaaa | 2940 |
| atgtcattaa aatagtatat aaattgaaac taagtcataa agctataaaa agaaaattta | 3000 |
| tttaaatgca agatttaaag taaattcacg gccctgcagg cctcagctct tgttttgttc | 3060 |
| tgcaaataac ttacccatct ttttcaaaac tttaggtgca ccctccttg ctagaataag | 3120 |

```
ttctatccaa tacatcctat ttggatctgc ttgagcttct tcatcacgg  atacgaattc    3180 attttctgtt ctcacaattt tggacacaac tctgtcttcc gttgcccga  aactttctgg    3240 cagttttgag taattccaca taggaatgtc attataactc tggttcggac catgaatttc    3300
cctctcaacc gtgtaaccat cgttattaat gataaagcag attgggttta tcttctctct    3360
aatggctagt cctaattctt ggacagtcag ttgcaatgat ccatctccga taaacaataa    3420
atgtctagat tctttatctg caatttggct gcctagagct gcggggaaag tgtatcctat    3480
agatccccac aagggttgac caataaaatg tgatttcgat ttcagaaata tagatgaggc    3540
accgaagaaa gaagtgcctt gttcagccac gatcgtctca ttactttggg tcaaattttc    3600
gacagcttgc cacagtctat cttgtgacaa cagcgcgtta gaaggtacaa aatcttcttg    3660 cttttatct atgtacttgc ctttatattc aatttcggac aagtcaagaa gagatgatat     3720
cagggattcg aagtcgaaat tttggattct ttcgttgaaa attttacctt catcgatatt    3780
caaggaaatc attttatttt cattaagatg gtgagtaaat gcacccgtac tagaatcggt    3840
aagctttaca cccaacataa gaataaaatc agcagattcc acaaattcct tcaagtttgg    3900
ctctgacaga gtaccgttgt aaatccccaa aaatgagggc aatgcttcat caacagatga    3960
tttaccaaag ttcaaagtag taataggtaa cttagtcttt gaaataaact gagtaacagt    4020
cttctctagg ccgaacgata taatttcatg gcctgtgatt acaattggtt tcttggcatt    4080
cttcagactt tcctgtattt tgttcagaat ctcttgatca gatgtattcg acgtggaatt    4140
ttccttctta agaggcaagg atggtttttc agccttagcg gcagctacat ctacaggtaa    4200
attgatgtaa accggcttc tttccttag taaggcagac aacactctat caatttcaac      4260
agttgcattc tcggctgtca ataaagtcct ggcagcagta accggttcgt gcatcttcat    4320
aaagtgcttg aaatcaccat cagccaacgt atggtgaaca aacttacctt cgttctgcac    4380
tttcgaggta ggagatccca cgatctcaac aacaggcagg ttctcagcat aggagcccgc    4440
taagccatta actgcggata attcgccaac accaaatgta gtcaagaatg ccgcagcctt    4500
tttcgttctt gcgtacccgt cggccatata ggaggcattt aactcattag catttcccac    4560
ccatttcata tctttgtgtg aaataatttg atctagaaat tgcaaattgt agtcacctgg    4620
tactccgaat atttcttcta tacctaattc gtgtaatctg tccaacagat agtcacctac    4680
tgtatacatt ttgtttacta gtttatgtgt gtttattcga aactaagttc ttggtgtttt    4740
aaaactaaaa aaaagactaa ctataaaagt agaatttaag aagtttaaga aatagattta    4800
cagaattaca atcaataacct accgtcttta tatacttatt agtcaagtag gggataatt     4860 tcagggaact ggtttcaacc ttttttttca gcttttccca aatcagagag agcagaaggt    4920
aatagaaggt gtaagaaaat gagatagata catgcgtggg tcaattgcct tgtgtcatca    4980
tttactccag gcaggttgca tcactccatt gaggttgtgc ccgttttttg cctgtttgtg    5040
cccctgttct ctgtagttgc gctaagagaa tggacctatg aactgatggt tggtgaagaa    5100
aacaatattt tggtgctggg attctttttt tttctggatg ccagcttaaa aagcgggctc    5160
cattatattt agtggatgcc aggaataaac tgttcaccca gacacctacg atgttatata    5220
ttctgtgtaa cccgcccct attttgggca tgtacgggtt acagcagaat taaaaggcta    5280
attttttgac taaataaagt taggaaaatc actactatta attatttacg tattctttga    5340
aatggcagta ttgataatga taaactcgaa ctgaaaaagc gtgtttttta ttcaaaatga    5400
ttctaactcc cttacgtaat caaggaatct ttttgccttg gcctccgcgt cattaaactt    5460
cttgttgttg acgctaacat tcaacgctag tatatattcg ttttttttcag gtaagttctt    5520
```

```
ttcaacgggt cttactgatg aggcagtcgc gtctgaacct gttaagaggt caaatatgtc    5580
ttcttgaccg tacgtgtctt gcatgttatt agctttggga atttgcatca agtcatagga    5640
aaatttaaat cttggctctc ttgggctcaa ggtgacaagg tcctcgaaaa tagggcgcgc    5700
cccaccgcgg tggagctcca gcttttgttc cctttagtga gggttaattg cgcgcttggc    5760
gtaatcatgg tcatagctgt ttcctgtgtg aaattgttat ccgctcacaa ttccacacaa    5820
cataggagcc ggaagcataa agtgtaaagc ctggggtgcc taatgagtga ggtaactcac    5880
attaattgcg ttgcgctcac tgcccgcttt ccagtcggga aacctgtcgt gccagctgca    5940
ttaatgaatc ggccaacgcg cggggagagg cggtttgcgt attgggcgct cttccgcttc    6000
ctcgctcact gactcgctgc gctcggtcgt tcggctgcgg cgagcggtat cagctcactc    6060
aaaggcggta atacggttat ccacagaatc aggggataac gcaggaaaga acatgtgagc    6120
aaaaggccag caaaaggcca ggaaccgtaa aaaggccgcg ttgctggcgt ttttccatag    6180
gctccgcccc cctgacgagc atcacaaaaa tcgacgctca agtcagaggt ggcgaaaccc    6240
gacaggacta taaagatacc aggcgtttcc ccctggaagc tccctcgtgc gctctcctgt    6300
tccgaccctg ccgcttaccg gatacctgtc cgcctttctc ccttcgggaa gcgtggcgct    6360
ttctcatagc tcacgctgta ggtatctcag ttcggtgtag tcgttcgct ccaagctggg    6420 ctgtgtgcac gaaccccccg ttcagcccga ccgctgcgcc ttatccggta actatcgtct    6480
tgagtccaac ccggtaagac acgacttatc gccactggca gcagccactg gtaacaggat    6540
tagcagagcg aggtatgtag gcggtgctac agagttcttg aagtggtggc ctaactacgg    6600
ctacactaga aggacagtat ttggtatctg cgctctgctg aagccagtta ccttcggaaa    6660
aagagttggt agctcttgat ccggcaaaca aaccaccgct ggtagcggtg gtttttttgt    6720
ttgcaagcag cagattacgc gcagaaaaaa aggatctcaa gaagatcctt tgatcttttc    6780
tacggggtct gacgctcagt ggaacgaaaa ctcacgttaa gggattttgg tcatgagatt    6840
atcaaaaagg atcttcacct agatcctttt aaattaaaaa tgaagtttta atcaatcta    6900 aagtatatat gagtaaactt ggtctgacag ttaccaatgc ttaatcagtg aggcaccta    6960 ctcagcgatc tgtctatttc gttcatccat agttgcctga ctccccgtcg tgtagataac    7020
tacgatacgg gagggcttac catctggccc cagtgctgca atgataccgc gagacccacg    7080
ctcaccggct ccagatttat cagcaataaa ccagccagcc ggaagggccg agcgcagaag    7140
tggtcctgca actttatccg cctccatcca gtctattaat tgttgccggg aagctagagt    7200
aagtagttcg ccagttaata gtttgcgcaa cgttgttgcc attgctacag gcatcgtggt    7260
gtcacgctcg tcgtttggta tggcttcatt cagctccggt tcccaacgat caaggcgagt    7320
tacatgatcc cccatgttgt gcaaaaaagc ggttagctcc ttcggtcctc cgatcgttgt    7380
cagaagtaag ttggccgcag tgttatcact catggttatg gcagcactgc ataattctct    7440
tactgtcatg ccatccgtaa gatgcttttc tgtgactggt gagtactcaa ccaagtcatt    7500
ctgagaatag tgtatgcggc gaccgagttg ctcttgcccg gcgtcaatac gggataatac    7560
cgcgccacat agcagaactt taaaagtgct catcattgga aaacgttctt cggggcgaaa    7620
actctcaagg atcttaccgc tgttgagatc cagttcgatg taacccactc gtgcacccaa    7680
ctgatcttca gcatctttta ctttcaccag cgtttctggg tgagcaaaaa caggaaggca    7740
aaatgccgca aaaagggaa taagggcgac acggaaatgt tgaatactca tactcttcct    7800 tttcaatat tattgaagca tttatcaggg ttattgtctc atgagcggat acatatttga    7860
```

```
atgtatttag aaaaataaac aaatagggt tccgcgcaca tttccccgaa aagtgccacc      7920
tgaacgaagc atctgtgctt cattttgtag aacaaaaatg caacgcgaga gcgctaattt      7980
ttcaaacaaa gaatctgagc tgcatttta cagaacagaa atgcaacgcg aaagcgctat      8040
tttaccaacg aagaatctgt gcttcatttt tgtaaaacaa aaatgcaacg cgagagcgct      8100 aattttcaa acaaagaatc tgagctgcat ttttacagaa cagaaatgca acgcgagagc      8160 gctatttac caacaagaa tctatacttc tttttgttc tacaaaaatg catcccgaga      8220
gcgctatttt tctaacaaag catcttagat tactttttt ctcctttgtg cgctctataa      8280
tgcagtctct tgataacttt ttgcactgta ggtccgttaa ggttagaaga aggctacttt      8340
ggtgtctatt ttctcttcca taaaaaaagc ctgactccac ttcccgcgtt tactgattac      8400
tagcgaagct gcgggtgcat ttttcaaga taaaggcatc cccgattata ttctataccg      8460
atgtggattg cgcatacttt gtgaacagaa agtgatagcg ttgatgattc ttcattggtc      8520
agaaaattat gaacggtttc ttctattttg tctctatata ctacgtatag gaatgttta      8580 cattttcgta ttgttttcga ttcactctat gaatagttct tactacaatt ttttgtcta      8640 aagagtaata ctagagataa acataaaaaa tgtagaggtc gagtttagat gcaagttcaa      8700
ggagcgaaag gtggatgggt aggttatata gggatatagc acagagatat atagcaaaga      8760 gatactttg agcaatgttt gtggaagcgg tattcgcaat attttagtag ctcgttacag      8820
tccggtgcgt ttttggtttt ttgaaagtgc gtcttcagag cgcttttggt tttcaaaagc      8880
gctctgaagt tcctatactt tctagagaat aggaacttcg gaataggaac ttcaaagcgt      8940
ttccgaaaac gagcgcttcc gaaaatgcaa cgcgagctgc gcacatacag ctcactgttc      9000
acgtcgcacc tatatctgcg tgttgcctgt atatatatat acatgagaag aacggcatag      9060
tgcgtgttta tgcttaaatg cgtacttata tgcgtctatt tatgtaggat gaaaggtagt      9120
ctagtacctc ctgtgatatt atcccattcc atgcggggta tcgtatgctt ccttcagcac      9180 tacccttag ctgttctata tgctgccact cctcaattgg attagtctca tccttcaatg      9240
ctatcatttc ctttgatatt ggatcatact aagaaaccat tattatcatg acattaacct      9300
ataaaaatag gcgtatcacg aggcccttc gtc                                   9333
```

<210> SEQ ID NO 45
<211> LENGTH: 8994
<212> TYPE: DNA
<213> ORGANISM: Artificial Sequence
<220> FEATURE:
<223> OTHER INFORMATION: Synthetic construct pRS425::GPM-sadB

<400> SEQUENCE: 45

```
ctagttctag agcggccgcc accgcggtgg agctccagct tttgttccct ttagtgaggg       60
ttaattgcgc gcttggcgta atcatggtca tagctgtttc ctgtgtgaaa ttgttatccg      120
ctcacaattc cacacaacat aggagccgga agcataaagt gtaaagcctg gggtgcctaa      180
tgagtgaggt aactcacatt aattgcgttg cgctcactgc ccgctttcca gtcgggaaac      240
ctgtcgtgcc agctgcatta atgaatcggc caacgcgcgg ggagaggcgg tttgcgtatt      300
gggcgctctt ccgcttcctc gctcactgac tcgctgcgct cggtcgttcg gctgcggcga      360
gcggtatcag ctcactcaaa ggcggtaata cggttatcca cagaatcagg ggataacgca      420
ggaaagaaca tgtgagcaaa aggccagcaa aaggccagga accgtaaaaa ggccgcgttg      480
ctggcgtttt tccataggct ccgcccccct gacgagcatc acaaaaatcg acgctcaagt      540
cagaggtggc gaaacccgac aggactataa agataccagg cgtttccccc tggaagctcc      600
```

```
ctcgtgcgct ctcctgttcc gaccctgccg cttaccggat acctgtccgc ctttctccct   660
tcgggaagcg tggcgctttc tcatagctca cgctgtaggt atctcagttc ggtgtaggtc   720
gttcgctcca agctgggctg tgtgcacgaa ccccccgttc agcccgaccg ctgcgcctta   780
tccggtaact atcgtcttga gtccaacccg gtaagacacg acttatcgcc actggcagca   840
gccactggta acaggattag cagagcgagg tatgtaggcg gtgctacaga gttcttgaag   900
tggtggccta actacggcta cactagaagg acagtatttg gtatctgcgc tctgctgaag   960
ccagttacct tcggaaaaag agttggtagc tcttgatccg gcaaacaaac caccgctggt   1020
agcggtggtt tttttgtttg caagcagcag attacgcgca gaaaaaaagg atctcaagaa   1080
gatcctttga tcttttctac ggggtctgac gctcagtgga acgaaaactc acgttaaggg   1140
attttggtca tgagattatc aaaaaggatc ttcacctaga tccttttaaa ttaaaaatga   1200
agttttaaat caatctaaag tatatatgag taaacttggt ctgacagtta ccaatgctta   1260
atcagtgagg cacctatctc agcgatctgt ctatttcgtt catccatagt tgcctgactc   1320
cccgtcgtgt agataactac gatacgggag ggcttaccat ctggccccag tgctgcaatg   1380
ataccgcgag acccacgctc accggctcca gatttatcag caataaacca gccagccgga   1440
agggccgagc gcagaagtgg tcctgcaact ttatccgcct ccatccagtc tattaattgt   1500
tgccgggaag ctagagtaag tagttcgcca gttaatagtt tgcgcaacgt tgttgccatt   1560
gctacaggca tcgtggtgtc acgctcgtcg tttggtatgg cttcattcag ctccggttcc   1620
caacgatcaa ggcgagttac atgatccccc atgttgtgca aaaaagcggt tagctccttc   1680
ggtcctccga tcgttgtcag aagtaagttg gccgcagtgt tatcactcat ggttatggca   1740
gcactgcata attctcttac tgtcatgcca tccgtaagat gcttttctgt gactggtgag   1800
tactcaacca agtcattctg agaatagtgt atgcggcgac cgagttgctc ttgcccggcg   1860
tcaatacggg ataataccgc gccacatagc agaactttaa aagtgctcat cattggaaaa   1920
cgttcttcgg ggcgaaaact ctcaaggatc ttaccgctgt tgagatccag ttcgatgtaa   1980
cccactcgtg cacccaactg atcttcagca tcttttactt tcaccagcgt ttctgggtga   2040
gcaaaaacag gaaggcaaaa tgccgcaaaa aagggaataa gggcgacacg gaaatgttga   2100
atactcatac tcttcctttt tcaatattat tgaagcattt atcagggtta ttgtctcatg   2160
agcggataca tatttgaatg tatttagaaa aataaacaaa taggggttcc gcgcacattt   2220
ccccgaaaag tgccacctga cgaagcatc tgtgcttcat tttgtagaac aaaaatgcaa   2280 cgcgagagc ctaattttttc aaacaaagaa tctgagctgc atttttacag aacagaaatg   2340
caacgcgaaa gcgctatttt accaacgaag aatctgtgct tcattttgt aaaacaaaaa   2400 tgcaacgcga gagcgctaat ttttcaaaca agaatctga gctgcatttt tacagaacag   2460
aaatgcaacg cgagagcgct attttaccaa caaagaatct atacttcttt tttgttctac   2520
aaaaatgcat cccgagagcg ctattttttct aacaaagcat cttagattac ttttttttctc   2580 ctttgtgcgc tctataatgc agtctcttga taacttttttg cactgtaggt ccgttaaggt   2640
tagaagaagg ctactttggt gtctattttc tcttccataa aaaagcctg actccacttc   2700 ccgcgtttac tgattactag cgaagctgcg ggtgcatttt ttcaagataa aggcatcccc   2760
gattatattc tataccgatg tggattgcgc atactttgtg aacagaaagt gatagcgttg   2820
atgattcttc attggtcaga aaattatgaa cggtttcttc tattttgtct ctatatacta   2880
cgtataggaa atgtttacat tttcgtattg ttttcgattc actctatgaa tagttcttac   2940
```

```
tacaatttttt ttgtctaaag agtaatacta gagataaaca taaaaaatgt agaggtcgag   3000
tttagatgca agttcaagga gcgaaaggtg gatgggtagg ttatataggg atatagcaca   3060
gagatatata gcaaagagat acttttgagc aatgtttgtg gaagcggtat tcgcaatatt   3120
ttagtagctc gttacagtcc ggtgcgtttt tggttttttg aaagtgcgtc ttcagagcgc   3180
ttttggtttt caaaagcgct ctgaagttcc tatactttct agagaatagg aacttcggaa   3240
taggaacttc aaagcgtttc cgaaaacgag cgcttccgaa aatgcaacgc gagctgcgca   3300
catacagctc actgttcacg tcgcacctat atctgcgtgt tgcctgtata tatatataca   3360
tgagaagaac ggcatagtgc gtgtttatgc ttaaatgcgt acttatatgc gtctatttat   3420
gtaggatgaa aggtagtcta gtacctcctg tgatattatc ccattccatg cggggtatcg   3480
tatgcttcct tcagcactac ccttttagctg ttctatatgc tgccactcct caattggatt   3540
agtctcatcc ttcaatgcta tcatttcctt tgatattgga tcatactaag aaaccattat   3600
tatcatgaca ttaacctata aaaataggcg tatcacgagg cccttttcgtc tcgcgcgttt   3660 cggtgatgac ggtgaaaacc tctgacacat gcagctcccg gagacggtca cagcttgtct   3720
gtaagcggat gccgggagca gacaagcccg tcagggcgcg tcagcgggtg ttggcgggtg   3780
tcggggctgg cttaactatg cggcatcaga gcagattgta ctgagagtgc accatatcga   3840
ctacgtcgta aggccgtttc tgacagagta aaattcttga gggaactttc accattatgg   3900
gaaatgcttc aagaaggtat tgacttaaac tccatcaaat ggtcaggtca ttgagtgttt   3960
tttatttgtt gtattttttt ttttttagag aaaatcctcc aatatcaaat taggaatcgt   4020
agtttcatga ttttctgtta cacctaactt tttgtgtggt gccctcctcc ttgtcaatat   4080
taatgttaaa gtgcaattct ttttccttat cacgttgagc cattagtatc aatttgctta   4140
cctgtattcc tttactatcc tccttttcct ccttcttgat aaatgtatgt agattgcgta   4200
tatagtttcg tctaccctat gaacatattc cattttgtaa tttcgtgtcg tttctattat   4260
gaatttcatt tataaagttt atgtacaaat atcataaaaa aagagaatct ttttaagcaa   4320
ggattttctt aacttcttcg gcgacagcat caccgacttc ggtggtactg ttggaaccac   4380
ctaaatcacc agttctgata cctgcatcca aaaccttttt aactgcatct tcaatggcct   4440
taccttcttc aggcaagttc aatgacaatt tcaacatcat tgcagcagac aagatagtgg   4500
cgatagggtc aaccttattc tttggcaaat ctggagcaga accgtggcat ggttcgtaca   4560
aaccaaatgc ggtgttcttg tctggcaaag aggccaagga cgcagatggc aacaaaccca   4620
aggaacctgg gataacggag gcttcatcgg agatgatatc accaaacatg ttgctggtga   4680
ttataatacc atttaggtgg gttgggttct taactaggat catggcggca gaatcaatca   4740
attgatgttg aaccttcaat gtagggaatt cgttcttgat ggtttcctcc acagtttttc   4800
tccataatct tgaagaggcc aaaagattag ctttatccaa ggaccaaata ggcaatggtg   4860
gctcatgttg tagggccatg aaagcggcca ttcttgtgat tctttgcact tctggaacgg   4920
tgtattgttc actatcccaa gcgacaccat caccatcgtc ttcctttctc ttaccaaagt   4980
aaatacctcc cactaattct ctgacaacaa cgaagtcagt acctttagca aattgtggct   5040
tgattggaga taagtctaaa agagagtcgg atgcaaagtt acatggtctt aagttggcgt   5100
acaattgaag ttctttacgg attttttagta aaccttgttc aggtctaaca ctaccggtac   5160
cccatttagg accagccaca gcacctaaca aaacggcatc aaccttcttg gaggcttcca   5220
gcgcctcatc tggaagtggg acacctgtag catcgatagc agcaccacca attaaatgat   5280
tttcgaaatc gaacttgaca ttggaacgaa catcagaaat agctttaaga accttaatgg   5340
```

```
cttcggctgt gatttcttga ccaacgtggt cacctggcaa aacgacgatc ttccttagggg   5400 cagacatagg ggcagacatt agaatggtat atccttgaaa tatatatata tattgctgaa   5460
atgtaaaagg taagaaaagt tagaaagtaa gacgattgct aaccacctat tggaaaaaac   5520
aataggtcct taaataatat tgtcaacttc aagtattgtg atgcaagcat ttagtcatga   5580
acgcttctct attctatatg aaaagccggt tccggcctct cacctttcct ttttctccca   5640
atttttcagt tgaaaaggt atatgcgtca ggcgacctct gaaattaaca aaaaatttcc   5700
agtcatcgaa tttgattctg tgcgatagcg cccctgtgtg ttctcgttat gttgaggaaa   5760
aaaataatgg ttgctaagag attcgaactc ttgcatctta cgatacctga gtattcccac   5820
agttaactgc ggtcaagata tttcttgaat caggcgcctt agaccgctcg gccaaacaac   5880
caattacttg ttgagaaata gagtataatt atcctataaa tataacgttt ttgaacacac   5940
atgaacaagg aagtacagga caattgattt tgaagagaat gtggattttg atgtaattgt   6000
tgggattcca ttttaataa ggcaataata ttaggtatgt ggatatacta gaagttctcc   6060
tcgaccgtcg atatgcggtg tgaaataccg cacagatgcg taaggagaaa ataccgcatc   6120
aggaaattgt aaacgttaat attttgttaa aattcgcgtt aaattttgt taaatcagct   6180 catttttta ccataggcc gaaatcggca aaatcccta taaatcaaaa gaatagaccg   6240 agataggggtt gagtgttgtt ccagtttgga acaagagtcc actattaaag aacgtggact   6300
ccaacgtcaa agggcgaaaa accgtctatc agggcgatgg cccactacgt gaaccatcac   6360
cctaatcaag ttttttgggg tcgaggtgcc gtaaagcact aaatcggaac cctaaaggga   6420
gcccccgatt tagagcttga cggggaaagc cggcgaacgt ggcgagaaag gaagggaaga   6480
aagcgaaagg agcgggcgct agggcgctgg caagtgtagc ggtcacgctg cgcgtaacca   6540
ccacacccgc cgcgcttaat gcgccgctac agggcgcgtc gcgccattcg ccattcaggc   6600
tgcgcaactg ttgggaaggg cgatcggtgc gggcctcttc gctattacgc cagctggcga   6660
aagggggatg tgctgcaagg cgattaagtt gggtaacgcc agggttttcc cagtcacgac   6720
gttgtaaaac gacggccagt gagcgcgcgt aatacgactc actataggc gaattgggta   6780 ccgggcccc cctcgaggtc gacggtatcg ataagcttga tatcgaattc ctgcagcccg   6840
ggggatccgc atgcttgcat ttagtcgtgc aatgtatgac tttaagattt gtgagcagga   6900
agaaaaggga gaatcttcta acgataaacc cttgaaaaac tgggtagact acgctatgtt   6960
gagttgctac gcaggctgca caattacacg agaatgctcc cgcctaggat ttaaggctaa   7020
gggacgtgca atgcagacga cagatctaaa tgaccgtgtc ggtgaagtgt tcgccaaact   7080
tttcggttaa cacatgcagt gatgcacgcg cgatggtgct aagttacata tatatatata   7140
tatatatata tagccatagt gatgtctaag taacctttat ggtatatttc ttaatgtgga   7200
aagatactag cgcgcgcacc cacacacaag cttcgtctttt tcttgaagaa aagaggaagc   7260
tcgctaaatg ggattccact ttccgttccc tgccagctga tggaaaaagg ttagtggaac   7320
gatgaagaat aaaagagag atccactgag gtgaaatttc agctgacagc gagtttcatg   7380
atcgtgatga acaatggtaa cgagttgtgg ctgttgccag ggagggtggt tctcaacttt   7440
taatgtatgg ccaaatcgct acttgggttt gttatataac aaagaagaaa taatgaactg   7500
attctcttcc tccttcttgt cctttcttaa ttctgttgta attaccttcc tttgtaattt   7560 ttttgtaat tattcttctt aataatccaa acaaacacac atattacaat agctagctga   7620
ggatgaaggc attagtttat catggggatc acaaaatttc gttagaagac aaaccaaaac   7680
```

```
ccactctgca gaaaccaaca gacgttgtgg ttagggtgtt gaaaacaaca atttgcggta    7740
ctgacttggg aatatacaaa ggtaagaatc ctgaagtggc agatggcaga atcctgggtc    7800
atgagggcgt tggcgtcatt gaagaagtgg gcgaatccgt gacacaattc aaaaaggggg    7860
ataaagtttt aatctcctgc gttactagct gtggatcgtg tgattattgc aagaagcaac    7920
tgtattcaca ctgtagagac ggtggctgga ttttaggtta catgatcgac ggtgtccaag    7980
ccgaatacgt cagaatacca catgctgaca attcattgta taagatcccg caaactatcg    8040
atgatgaaat tgcagtacta ctgtccgata ttttacctac tggacatgaa attggtgttc    8100
aatatggtaa cgttcaacca ggcgatgctg tagcaattgt aggagcaggt cctgttggaa    8160
tgtcagtttt gttaactgct caattttact cgcctagtac cattattgtt atcgacatgg    8220
acgaaaaccg tttacaatta gcgaaggagc ttggggccac acacactatt aactccggta    8280
ctgaaaatgt tgtcgaagct gtgcatcgta tagcagccga aggagtggat gtagcaatag    8340
aagctgttgg tatacccgca acctgggaca tctgtcagga aattgtaaaa cccggcgctc    8400
atattgccaa cgtgggagtt catggtgtta aggtggactt tgaaattcaa aagttgtgga    8460
ttaagaatct aaccatcacc actggtttgg ttaacactaa tactaccccca atgttgatga    8520 aggtagcctc tactgataaa ttgcctttaa agaaaatgat tactcacagg tttgagttag    8580
ctgaaatcga acacgcatat caggttttct tgaatggcgc taaagaaaaa gctatgaaga    8640
ttattctatc taatgcaggt gccgcctaat taattaagag taagcgaatt tcttatgatt    8700
tatgattttt attattaaat aagttataaa aaaataagt gtatacaaat tttaaagtga    8760
ctcttaggtt ttaaaacgaa aattcttatt cttgagtaac tctttcctgt aggtcaggtt    8820
gctttctcag gtatagcatg aggtcgctct tattgaccac acctctaccg gcatgccgag    8880
caaatgcctg caaatcgctc cccatttcac ccaattgtag atatgctaac tccagcaatg    8940
agttgatgaa tctcggtgtg tattttatgt cctcagagga caacacctgt ggta         8994
```

<210> SEQ ID NO 46
<211> LENGTH: 753
<212> TYPE: DNA
<213> ORGANISM: Artificial Sequence
<220> FEATURE:
<223> OTHER INFORMATION: Saccharomyces cerevisiae GPM1 promoter

<400> SEQUENCE: 46

```
gcatgcttgc atttagtcgt gcaatgtatg actttaagat ttgtgagcag gaagaaaagg      60
gagaatcttc taacgataaa cccttgaaaa actgggtaga ctacgctatg ttgagttgct     120
acgcaggctg cacaattaca cgagaatgct cccgcctagg atttaaggct aagggacgtg     180
caatgcagac gacagatcta aatgaccgtg tcggtgaagt gttcgccaaa cttttcggtt     240
aacacatgca gtgatgcacg cgcgatggtg ctaagttaca tatatatata tatagccata     300
gtgatgtcta agtaaccttt atggtatatt tcttaatgtg gaaagatact agcgcgcgca     360
cccacacaca agcttcgtct tttcttgaag aaaagaggaa gctcgctaaa tgggattcca     420
ctttccgttc cctgccagct gatggaaaaa ggttagtgga acgatgaaga ataaaaagag     480
agatccactg aggtgaaatt tcagctgaca gcgagtttca tgatcgtgat gaacaatggt     540
aacgagttgt ggctgttgcc agggagggtg gttctcaact tttaatgtat ggccaaatcg     600
ctacttgggt ttgttatata acaaagaaga aataatgaac tgattctctt cctccttctt     660
gtcctttctt aattctgttg taattacctt cctttgtaat tttttttgta attattcttc     720
ttaataatcc aaacaaacac acatattaca ata                                  753
```

<210> SEQ ID NO 47
<211> LENGTH: 1047
<212> TYPE: DNA
<213> ORGANISM: Achromobacter xylosoxidans

<400> SEQUENCE: 47

```
atgaaagctc tggtttatca cggtgaccac aagatctcgc ttgaagacaa gcccaagccc      60
acccttcaaa agcccacgga tgtagtagta cgggttttga agaccacgat ctgcggcacg     120
gatctcggca tctacaaagg caagaatcca gaggtcgccg acgggcgcat cctgggccat     180
gaagggtag cgtcatcga ggaagtgggc gagagtgtca cgcagttcaa gaaaggcgac      240
aaggtcctga tttcctgcgt cacttcttgc ggctcgtgcg actactgcaa gaagcagctt     300
tactcccatt gccgcgacgg cgggtggatc ctgggttaca tgatcgatgg cgtgcaggcc     360
gaatacgtcc gcatcccgca tgccgacaac agcctctaca agatccccca gacaattgac     420
gacgaaatcg ccgtcctgct gagcgacatc ctgcccaccg ccacgaaaat cggcgtccag     480
tatgggaatg tccagccggg cgatgcggtg gctattgtcg gcgcgggccc cgtcggcatg     540
tccgtactgt tgaccgccca gttctactcc ccctcgacca tcatcgtgat cgacatggac     600
gagaatcgcc tccagctcgc caaggagctc ggggcaacgc acaccatcaa ctccggcacg     660
gagaacgttg tcgaagccgt gcataggatt gcggcagagg gagtcgatgt tgcgatcgag     720
gcggtgggca taccggcgac tttgggacatc tgccaggaga tcgtcaagcc cggcgcgcac     780
atcgccaacg tcggcgtgca tggcgtcaag gttgacttcg agattcagaa gctctggatc     840
aagaacctga cgatcaccac gggactggtg aacacgaaca cgacgcccat gctgatgaag     900
gtcgcctcga ccgacaagct tccgttgaag aagatgatta cccatcgctt cgagctggcc     960
gagatcgagc acgcctatca ggtattcctc aatggcgcca aggagaaggc gatgaagatc    1020
atcctctcga acgcaggcgc tgcctga                                          1047
```

<210> SEQ ID NO 48
<211> LENGTH: 348
<212> TYPE: PRT
<213> ORGANISM: Achromobacter xylosoxidans

<400> SEQUENCE: 48

```
Met Lys Ala Leu Val Tyr His Gly Asp His Lys Ile Ser Leu Glu Asp
1               5                   10                  15

Lys Pro Lys Pro Thr Leu Gln Lys Pro Thr Asp Val Val Arg Val
            20                  25                  30

Leu Lys Thr Thr Ile Cys Gly Thr Asp Leu Gly Ile Tyr Lys Gly Lys
        35                  40                  45

Asn Pro Glu Val Ala Asp Gly Arg Ile Leu Gly His Glu Gly Val Gly
    50                  55                  60

Val Ile Glu Glu Val Gly Glu Ser Val Thr Gln Phe Lys Lys Gly Asp
65                  70                  75                  80

Lys Val Leu Ile Ser Cys Val Thr Ser Cys Gly Ser Cys Asp Tyr Cys
                85                  90                  95

Lys Lys Gln Leu Tyr Ser His Cys Arg Asp Gly Gly Trp Ile Leu Gly
            100                 105                 110

Tyr Met Ile Asp Gly Val Gln Ala Glu Tyr Val Arg Ile Pro His Ala
        115                 120                 125

Asp Asn Ser Leu Tyr Lys Ile Pro Gln Thr Ile Asp Asp Glu Ile Ala
    130                 135                 140
```

```
Val Leu Leu Ser Asp Ile Leu Pro Thr Gly His Glu Ile Gly Val Gln
145                 150                 155                 160

Tyr Gly Asn Val Gln Pro Gly Asp Ala Val Ala Ile Val Gly Ala Gly
                165                 170                 175

Pro Val Gly Met Ser Val Leu Leu Thr Ala Gln Phe Tyr Ser Pro Ser
            180                 185                 190

Thr Ile Ile Val Ile Asp Met Asp Glu Asn Arg Leu Gln Leu Ala Lys
                195                 200                 205

Glu Leu Gly Ala Thr His Thr Ile Asn Ser Gly Thr Glu Asn Val Val
210                 215                 220

Glu Ala Val His Arg Ile Ala Ala Glu Gly Val Asp Val Ala Ile Glu
225                 230                 235                 240

Ala Val Gly Ile Pro Ala Thr Trp Asp Ile Cys Gln Glu Ile Val Lys
                245                 250                 255

Pro Gly Ala His Ile Ala Asn Val Gly Val His Gly Val Lys Val Asp
            260                 265                 270

Phe Glu Ile Gln Lys Leu Trp Ile Lys Asn Leu Thr Ile Thr Thr Gly
            275                 280                 285

Leu Val Asn Thr Asn Thr Thr Pro Met Leu Met Lys Val Ala Ser Thr
290                 295                 300

Asp Lys Leu Pro Leu Lys Lys Met Ile Thr His Arg Phe Glu Leu Ala
305                 310                 315                 320

Glu Ile Glu His Ala Tyr Gln Val Phe Leu Asn Gly Ala Lys Glu Lys
                325                 330                 335

Ala Met Lys Ile Ile Leu Ser Asn Ala Gly Ala Ala
            340                 345
```

<210> SEQ ID NO 49
<211> LENGTH: 316
<212> TYPE: DNA
<213> ORGANISM: Artificial Sequence
<220> FEATURE:
<223> OTHER INFORMATION: Saccharomyces cerevisiae ADH1 terminator

<400> SEQUENCE: 49

```
gagtaagcga atttcttatg atttatgatt tttattatta ataagttat aaaaaaaata    60
agtgtataca aattttaaag tgactcttag gttttaaaac gaaaattctt attcttgagt  120
aactctttcc tgtaggtcag gttgctttct caggtatagc atgaggtcgc tcttattgac  180
cacacctcta ccggcatgcc gagcaaatgc ctgcaaatcg ctccccattt cacccaattg  240
tagatatgct aactccagca atgagttgat gaatctcggt gtgtatttta tgtcctcaga  300
ggacaacacc tgtggt                                                  316
```

<210> SEQ ID NO 50
<211> LENGTH: 39
<212> TYPE: DNA
<213> ORGANISM: Artificial Sequence
<220> FEATURE:
<223> OTHER INFORMATION: Primer OT1074

<400> SEQUENCE: 50

```
cacacatatt acaatagcta gctgaggatg aaagctctg                          39
```

<210> SEQ ID NO 51
<211> LENGTH: 39
<212> TYPE: DNA
<213> ORGANISM: Artificial Sequence
```

```
<220> FEATURE:
<223> OTHER INFORMATION: Primer OT1075

<400> SEQUENCE: 51
cagagctttc atcctcagct agctattgta atatgtgtg                          39

<210> SEQ ID NO 52
<211> LENGTH: 9075
<212> TYPE: DNA
<213> ORGANISM: Artificial Sequence
<220> FEATURE:
<223> OTHER INFORMATION: pLH435

<400> SEQUENCE: 52
ctagttctag agcggccgcc accgcggtgg agctccagct tttgttccct ttagtgaggg     60
ttaattgcgc gcttggcgta atcatggtca tagctgtttc ctgtgtgaaa ttgttatccg    120
ctcacaattc cacacaacat aggagccgga agcataaagt gtaaagcctg ggtgcctaa    180 tgagtgaggt aactcacatt aattgcgttg cgctcactgc ccgctttcca gtcgggaaac   240
ctgtcgtgcc agctgcatta atgaatcggc caacgcgcgg ggagaggcgg tttgcgtatt   300
gggcgctctt ccgcttcctc gctcactgac tcgctgcgct cggtcgttcg gctgcggcga   360
gcggtatcag ctcactcaaa ggcggtaata cggttatcca cagaatcagg ggataacgca   420
ggaaagaaca tgtgagcaaa aggccagcaa aaggccagga accgtaaaaa ggccgcgttg   480
ctggcgtttt tccataggct ccgcccccct gacgagcatc acaaaaatcg acgctcaagt   540
cagaggtggc gaaacccgac aggactataa agataccagg cgtttccccc tggaagctcc   600
ctcgtgcgct ctcctgttcc gaccctgccg cttaccggat acctgtccgc ctttctccct   660
tcgggaagcg tggcgctttc tcatagctca cgctgtaggt atctcagttc ggtgtaggtc   720
gttcgctcca agctgggctg tgtgcacgaa ccccccgttc agcccgaccg ctgcgcctta   780
tccggtaact atcgtcttga gtccaacccg gtaagacacg acttatcgcc actggcagca   840
gccactggta acaggattag cagagcgagg tatgtaggcg gtgctacaga gttcttgaag   900
tggtggccta actacggcta cactagaagg acagtatttg gtatctgcgc tctgctgaag   960
ccagttacct tcggaaaaag agttggtagc tcttgatccg gcaaacaaac caccgctggt  1020
agcggtggtt tttttgtttg caagcagcag attacgcgca gaaaaaaagg atctcaagaa  1080
gatcctttga tcttttctac ggggtctgac gctcagtgga acgaaaactc acgttaaggg  1140
attttggtca tgagattatc aaaaaggatc ttcacctaga tccttttaaa ttaaaaatga  1200
agttttaaat caatctaaag tatatatgag taaacttggt ctgacagtta ccaatgctta  1260
atcagtgagg cacctatctc agcgatctgt ctatttcgtt catccatagt tgcctgactc  1320
cccgtcgtgt agataactac gatacgggag ggcttaccat ctggccccag tgctgcaatg  1380
ataccgcgag acccacgctc accggctcca gatttatcag caataaacca gccagccgga  1440
agggccgagc gcagaagtgg tcctgcaact ttatccgcct ccatccagtc tattaattgt  1500
tgccgggaag ctagagtaag tagttcgcca gttaatagtt tgcgcaacgt tgttgccatt  1560
gctacaggca tcgtggtgtc acgctcgtcg tttggtatgg cttcattcag ctccggttcc  1620
caacgatcaa ggcgagttac atgatccccc atgttgtgca aaaaagcggt tagctccttc  1680
ggtcctccga tcgttgtcag aagtaagttg gccgcagtgt tatcactcat ggttatggca  1740
gcactgcata attctcttac tgtcatgcca tccgtaagat gcttttctgt gactggtgag  1800
tactcaacca agtcattctg agaatagtgt atgcggcgac cgagttgctc ttgcccggcg  1860
```

-continued

```
tcaatacggg ataataccgc gccacatagc agaactttaa aagtgctcat cattggaaaa    1920
cgttcttcgg ggcgaaaact ctcaaggatc ttaccgctgt tgagatccag ttcgatgtaa    1980
cccactcgtg cacccaactg atcttcagca tcttttactt tcaccagcgt ttctgggtga    2040
gcaaaaacag gaaggcaaaa tgccgcaaaa aagggaataa gggcgacacg gaaatgttga    2100
atactcatac tcttcctttt tcaatattat tgaagcattt atcagggtta ttgtctcatg    2160
agcggataca tatttgaatg tatttagaaa aataaacaaa taggggttcc gcgcacattt    2220
ccccgaaaag tgccacctga acgaagcatc tgtgcttcat tttgtagaac aaaaatgcaa    2280
cgcgagagcg ctaattttc aaacaaagaa tctgagctgc attttacag aacagaaatg    2340 caacgcgaaa gcgctatttt accaacgaag aatctgtgct tcattttgt aaaacaaaaa    2400 tgcaacgcga gagcgctaat ttttcaaaca agaatctga gctgcatttt tacagaacag    2460
aaatgcaacg cgagagcgct attttaccaa caaagaatct atacttcttt tttgttctac    2520
aaaaatgcat cccgagagcg ctattttct aacaaagcat cttagattac ttttttctc    2580 ctttgtgcgc tctataatgc agtctcttga taacttttg cactgtaggt ccgttaaggt    2640
tagaagaagg ctactttggt gtctattttc tcttccataa aaaagcctg actccacttc    2700 ccgcgtttac tgattactag cgaagctgcg ggtgcatttt ttcaagataa aggcatcccc    2760
gattatattc tataccgatg tggattgcgc atactttgtg aacagaaagt gatagcgttg    2820
atgattcttc attggtcaga aaattatgaa cggtttcttc tattttgtct ctatatacta    2880
cgtataggaa atgtttacat tttcgtattg ttttcgattc actctatgaa tagttcttac    2940
tacaattttt ttgtctaaag agtaaatacta gagataaaca taaaaatgt agaggtcgag    3000 tttagatgca agttcaagga gcgaaaggtg gatgggtagg ttatataggg atatagcaca    3060
gagatatata gcaaagagat acttttgagc aatgtttgtg gaagcggtat tcgcaatatt    3120
ttagtagctc gttacagtcc ggtgcgtttt tggttttttg aaagtgcgtc ttcagagcgc    3180
ttttggtttt caaaagcgct ctgaagttcc tatactttct agagaatagg aacttcggaa    3240
taggaacttc aaagcgtttc cgaaaacgag cgcttccgaa aatgcaacgc gagctgcgca    3300
catacagctc actgttcacg tcgcacctat atctgcgtgt tgcctgtata tatatataca    3360
tgagaagaac ggcatagtgc gtgtttatgc ttaaatgcgt acttatatgc gtctatttat    3420
gtaggatgaa aggtagtcta gtacctcctg tgatattatc ccattccatg cggggtatcg    3480
tatgcttcct tcagcactac cctttagctg ttctatatgc tgccactcct caattggatt    3540
agtctcatcc ttcaatgcta tcatttcctt tgatattgga tcatactaag aaaccattat    3600
tatcatgaca ttaacctata aaaataggcg tatcacgagg ccctttcgtc tcgcgcgttt    3660
cggtgatgac ggtgaaaacc tctgacacat gcagctcccg gagacggtca cagcttgtct    3720
gtaagcggat gccgggagca gacaagcccg tcagggcgcg tcagcgggtg ttggcgggtg    3780
tcggggctgg cttaactatg cggcatcaga gcagattgta ctgagagtgc accatatcga    3840
ctacgtcgta aggccgtttc tgacagagta aaattcttga gggaactttc accattatgg    3900
gaaatgcttc aagaaggtat tgacttaaac tccatcaaat ggtcaggtca ttgagtgttt    3960
tttatttgtt gtattttttt tttttagag aaaatcctcc aatatcaaat taggaatcgt    4020
agtttcatga ttttctgtta cacctaactt tttgtgtggt gccctcctcc ttgtcaatat    4080
taatgttaaa gtgcaattct ttttccttat cacgttgagc cattagtatc aatttgctta    4140
cctgtattcc tttactatcc tcctttttct ccttcttgat aaatgtatgt agattgcgta    4200
tatagtttcg tctaccctat gaacatattc catttgtaa tttcgtgtcg tttctattat    4260
```

```
gaatttcatt tataaagttt atgtacaaat atcataaaaa aagagaatct ttttaagcaa      4320
ggattttctt aacttcttcg gcgacagcat caccgacttc ggtggtactg ttggaaccac      4380
ctaaatcacc agttctgata cctgcatcca aaaccttttt aactgcatct tcaatggcct      4440
taccttcttc aggcaagttc aatgacaatt tcaacatcat tgcagcagac aagatagtgg      4500
cgatagggtc aaccttattc tttggcaaat ctggagcaga accgtggcat ggttcgtaca      4560
aaccaaatgc ggtgttcttg tctggcaaag aggccaagga cgcagatggc aacaaaccca      4620
aggaacctgg gataacggag gcttcatcgg agatgatatc accaaacatg ttgctggtga      4680
ttataatacc atttaggtgg gttgggttct taactaggat catggcggca gaatcaatca      4740
attgatgttg aaccttcaat gtagggaatt cgttcttgat ggtttcctcc acagttttc      4800 tccataatct tgaagaggcc aaaagattag ctttatccaa ggaccaaata ggcaatggtg      4860
gctcatgttg tagggccatg aaagcggcca ttcttgtgat tctttgcact tctggaacgg      4920
tgtattgttc actatcccaa gcgacaccat caccatcgtc ttccttctc ttaccaaagt      4980 aaatacctcc cactaattct ctgacaacaa cgaagtcagt accttagca aattgtggct      5040 tgattggaga taagtctaaa agagagtcgg atgcaaagtt acatggtctt aagttggcgt      5100
acaattgaag ttcttacgg atttttagta aaccttgttc aggtctaaca ctaccggtac      5160
cccatttagg accagccaca gcacctaaca aaacggcatc aaccttcttg gaggcttcca      5220
gcgcctcatc tggaagtggg acacctgtag catcgatagc agcaccacca attaaatgat      5280
tttcgaaatc gaacttgaca ttggaacgaa catcagaaat agcttaaga accttaatgg      5340 cttcggctgt gatttcttga ccaacgtggt cacctggcaa aacgacgatc ttcttagggg      5400
cagacatagg ggcagacatt agaatggtat atccttgaaa tatatatata tattgctgaa      5460
atgtaaaagg taagaaaagt tagaaagtaa gacgattgct aaccacctat tggaaaaaac      5520
aataggtcct taaataatat tgtcaacttc aagtattgtg atgcaagcat ttagtcatga      5580
acgcttctct attctatatg aaaagccggt tccggcctct cacctttcct ttttctccca      5640
atttttcagt tgaaaaaggt atatgcgtca ggcgacctct gaaattaaca aaaaatttcc      5700
agtcatcgaa tttgattctg tgcgatagcg ccctgtgtg ttctcgttat gttgaggaaa      5760
aaaataatgg ttgctaagag attcgaactc ttgcatctta cgatacctga gtattcccac      5820
agttaactgc ggtcaagata tttcttgaat caggcgcctt agaccgctcg gccaaacaac      5880
caattacttg ttgagaaata gagtataatt atcctataaa tataacgttt ttgaacacac      5940
atgaacaagg aagtacagga caattgattt tgaagagaat gtggattttg atgtaattgt      6000
tgggattcca ttttaataa ggcaataata ttaggtatgt ggatatacta gaagttctcc      6060
tcgaccgtcg atatgcggtg tgaaataccg cacagatgcg taaggagaaa ataccgcatc      6120
aggaaattgt aaacgttaat attttgttaa aattcgcgtt aaattttgt taaatcagct      6180 catttttaa ccaataggcc gaaatcggca aaatccctta taaatcaaaa gaatagaccg      6240
agatagggtt gagtgttgtt ccagtttgga acaagagtcc actattaaag aacgtggact      6300
ccaacgtcaa agggcgaaaa accgtctatc agggcgatgg cccactacgt gaaccatcac      6360
cctaatcaag ttttttgggg tcgaggtgcc gtaaagcact aaatcggaac cctaaaggga      6420
gcccccgatt tagagcttga cggggaaagc cggcgaacgt ggcgagaaag gaagggaaga      6480
aagcgaaagg agcgggcgct agggcgctgg caagtgtagc ggtcacgctg cgcgtaacca      6540
ccacacccgc cgcgcttaat gcgccgctac agggcgcgtc gcgccattcg ccattcaggc      6600
```

```
tgcgcaactg ttgggaaggg cgatcggtgc gggcctcttc gctattacgc cagctggcga    6660 aaggggatg tgctgcaagg cgattaagtt gggtaacgcc agggttttcc cagtcacgac     6720
gttgtaaaac gacggccagt gagcgcgcgt aatacgactc actatagggc gaattgggta    6780 ccggccccc cctcgaggtc gacggtatcg ataagcttga tatcgaattc ctgcagcccg     6840
ggggatccgc atgcttgcat ttagtcgtgc aatgtatgac tttaagattt gtgagcagga    6900
agaaaaggga gaatcttcta acgataaacc cttgaaaaac tgggtagact acgctatgtt    6960
gagttgctac gcaggctgca caattacacg agaatgctcc cgcctaggat ttaaggctaa    7020
gggacgtgca atgcagacga cagatctaaa tgaccgtgtc ggtgaagtgt tcgccaaact    7080
tttcggttaa cacatgcagt gatgcacgcg cgatggtgct aagttacata tatatatata    7140
tatatatata tagccatagt gatgtctaag taacctttat ggtatatttc ttaatgtgga    7200
aagatactag cgcgcgcacc cacacacaag cttcgtcttt tcttgaagaa aagaggaagc    7260
tcgctaaatg ggattccact ttccgttccc tgccagctga tggaaaaagg ttagtggaac    7320
gatgaagaat aaaagagag atccactgag gtgaaatttc agctgacagc gagtttcatg     7380
atcgtgatga acaatggtaa cgagttgtgg ctgttgccag ggagggtggt tctcaacttt    7440
taatgtatgg ccaaatcgct acttgggttt gttatataac aaagaagaaa taatgaactg    7500
attctcttcc tccttcttgt cctttcttaa ttctgttgta attaccttcc tttgtaattt    7560
tttttgtaat tattcttctt aataatccaa acaaacacac atattacaat agctagctga    7620
ggatgtcaac agccggtaaa gttattaagt gtaaagcggc agttttgtgg aagagaaaa     7680 agccgtttag catagaagaa gtagaagtag cgccaccaaa agcacacgag ttagaatca     7740 agatggttgc caccggaatc tgtagatccg acgaccatgt ggtgagtggc actctagtta    7800
ctcctttgcc agtaatcgcg ggacacgagg ctgccggaat cgttgaatcc ataggtgaag    7860
gtgttaccac tgttcgtcct ggtgataaag tgatcccact gttcactcct caatgtggta    7920
agtgtagagt ctgcaaacat cctgagggta atttctgcct taaaaatgat ttgtctatgc    7980
ctagaggtac tatgcaggat ggtacaagca gatttacatg cagagggaaa cctatacacc    8040
atttccttgg tacttctaca tttttcccaat acacagtggt ggacgagata tctgtcgcta    8100
aaatcgatgc agcttcacca ctggaaaaag tttgcttgat agggtgcgga ttttccaccg    8160
gttacggttc cgcagttaaa gttgcaaagg ttacacaggg ttcgacttgt gcagtattcg    8220
gtttaggagg agtaggacta agcgttatta tggggtgtaa agctgcaggc gcagcgagga    8280
ttataggtgt agacatcaat aaggacaaat ttgcaaaagc taaggaggtc ggggctactg    8340
aatgtgttaa ccctcaagat tataagaaac caatacaaga agtccttact gaaatgtcaa    8400
acggtggagt tgatttctct tttgaagtta taggccgtct tgatactatg gtaactgcgt    8460
tgtcctgctg tcaagaggca tatggagtca gtgtgatcgt aggtgttcct cctgattcac    8520
aaaatttgtc gatgaatcct atgctgttgc taagcggtcg tacatggaag ggagctatat    8580
ttggcggttt taagagcaag gatagtgttc caaaacttgt tgccgacttt atggcgaaga    8640
agtttgctct tgatccttta attacacatg tattgccatt cgagaaaatc aatgaagggt    8700
ttgatttgtt aagaagtggt gaatctattc gtacaatttt aacttttga ttaattaaga     8760 gtaagcgaat ttcttatgat ttatgatttt tattattaaa taagttataa aaaaaataag    8820
tgtatacaaa tttaaagtg actcttaggt tttaaaacga aaattcttat tcttgagtaa     8880 ctcttttcctg taggtcaggt tgcttttctca ggtatagcat gaggtcgctc ttattgacca   8940
cacctctacc ggcatgccga gcaaatgcct gcaaatcgct ccccatttca cccaattgta    9000
```

```
gatatgctaa ctccagcaat gagttgatga atctcggtgt gtattttatg tcctcagagg    9060
acaacacctg tggta                                                      9075

<210> SEQ ID NO 53
<211> LENGTH: 9491
<212> TYPE: DNA
<213> ORGANISM: Artificial Sequence
<220> FEATURE:
<223> OTHER INFORMATION: Synthetic construct pRS423 FBA ilvD(Strep)

<400> SEQUENCE: 53
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accataaatt cccgttttaa gagcttggtg agcgctagga gtcactgcca ggtatcgttt     240
gaacacggca ttagtcaggg aagtcataac acagtccttt cccgcaattt tcttttctcta    300 ttactcttgg cctcctctag tacactctat attttttat gcctcggtaa tgattttcat      360
tttttttttt cccctagcgg atgactcttt tttttctta gcgattggca ttatcacata      420
atgaattata cattatataa agtaatgtga tttcttcgaa gaatatacta aaaaatgagc     480
aggcaagata aacgaaggca aagatgacag agcagaaagc cctagtaaag cgtattacaa     540
atgaaaccaa gattcagatt gcgatctctt taaagggtgg tcccctagcg atagagcact     600
cgatcttccc agaaaaagag gcagaagcag tagcagaaca ggccacacaa tcgcaagtga     660
ttaacgtcca cacaggtata gggtttctgg accatatgat acatgctctg gccaagcatt     720
ccggctggtc gctaatcgtt gagtgcattg gtgacttaca catagacgac catcacacca     780
ctgaagactg cgggattgct ctcggtcaag cttttaaaga ggccctactg gcgcgtggag     840
taaaaaggtt tggatcagga tttgcgcctt tggatgaggc actttccaga gcggtggtag     900
atctttcgaa caggccgtac gcagttgtcg aacttggttt gcaaagggag aaagtaggag     960
atctctcttg cgagatgatc ccgcatttct tgaaagcttt tgcagaggct agcagaatta    1020
ccctccacgt tgattgtctg cgaggcaaga atgatcatca ccgtagtgag agtgcgttca    1080
aggctcttgc ggttgccata agagaagcca cctcgcccaa tggtaccaac gatgttccct    1140
ccaccaaagg tgttcttatg tagtgacacc gattatttaa agctgcagca tacgatatat    1200
atacatgtgt atatatgtat acctatgaat gtcagtaagt atgtatacga acagtatgat    1260
actgaagatg acaaggtaat gcatcattct atacgtgtca ttctgaacga ggcgcgcttt    1320 cctttttttct ttttgctttt tcttttttttt tctcttgaac tcgacggatc tatgcggtgt    1380
gaaataccgc acagatgcgt aaggagaaaa taccgcatca ggaaattgta aacgttaata    1440
ttttgttaaa attcgcgtta aattttgtt aaatcagctc attttttaac caataggccg    1500
aaatcggcaa aatcccttat aaatcaaaag aatagaccga gatagggttg agtgttgttc    1560
cagtttggaa caagagtcca ctattaaaga acgtggactc caacgtcaaa gggcgaaaaa    1620
ccgtctatca gggcgatggc ccactacgtg aaccatcacc ctaatcaagt ttttttgggt    1680
cgaggtgccg taaagcacta atcggaacc ctaaagggag cccccgattt agagcttgac     1740
ggggaaagcc ggcgaacgtg gcgagaaagg aagggaagaa agcgaaagga gcgggcgcta    1800
gggcgctggc aagtgtagcg gtcacgctgc gcgtaaccac cacacccgcc gcgcttaatg    1860
cgccgctaca gggcgcgtcg cgccattcgc cattcaggct gcgcaactgt tgggaagggc    1920
```

```
gatcggtgcg ggcctcttcg ctattacgcc agctggcgaa aggggatgt gctgcaaggc    1980
gattaagttg ggtaacgcca gggttttccc agtcacgacg ttgtaaaacg acggccagtg    2040
agcgcgcgta atacgactca ctatagggcg aattgggtac cgggccccc ctcgaggtcg    2100
acggcgcgcc actggtagag agcgactttg tatgccccaa ttgcgaaacc cgcgatatcc    2160
ttctcgattc tttagtaccc gaccaggaca aggaaaagga ggtcgaaacg ttttttgaaga    2220
aacaagagga actacacgga agctctaaag atggcaacca gccagaaact aagaaaatga    2280
agttgatgga tccaactggc accgctggct tgaacaacaa taccagcctt ccaacttctg    2340
taaataacgg cggtacgcca gtgccaccag taccgttacc tttcggtata cctcctttcc    2400
ccatgtttcc aatgcccttc atgcctccaa cggctactat cacaaatcct catcaagctg    2460
acgcaagccc taagaaatga ataacaatac tgacagtact aaataattgc ctacttggct    2520
tcacatacgt tgcatacgtc gatatagata ataatgataa tgacagcagg attatcgtaa    2580
tacgtaatag ttgaaaatct caaaaatgtg tgggtcatta cgtaataat gataggaatg    2640
ggattcttct attttttcctt tttccattct agcagccgtc gggaaaacgt ggcatcctct    2700
ctttcgggct caattggagt cacgctgccg tgagcatcct ctctttccat atctaacaac    2760
tgagcacgta accaatggaa aagcatgagc ttagcgttgc tccaaaaaag tattggatgg    2820
ttaataccat ttgtctgttc tcttctgact ttgactcctc aaaaaaaaaa aatctacaat    2880
caacagatcg cttcaattac gccctcacaa aaactttttt ccttcttctt cgcccacgtt    2940
aaatttatc cctcatgttg tctaacggat ttctgcactt gatttattat aaaaagacaa    3000
agacataata cttctctatc aatttcagtt attgttcttc cttgcgttat tcttctgttc    3060
ttcttttttct tttgtcatat ataaccataa ccaagtaata catattcaaa ctagtatgac    3120
tgacaaaaaa actcttaaag acttaagaaa tcgtagttct gtttacgatt caatggttaa    3180
atcacctaat cgtgctatgt tgcgtgcaac tggtatgcaa gatgaagact ttgaaaaacc    3240
tatcgtcggt gtcatttcaa cttgggctga aaacacacct tgtaatatcc acttacatga    3300
ctttggtaaa ctagccaaag tcggtgttaa ggaagctggt gcttggccag ttcagttcgg    3360
aacaatcacg gttctgatg gaatcgccat gggaacccaa ggaatgcgtt tctccttgac    3420
atctcgtgat attattgcag attctattga agcagccatg ggaggtcata atgcggatgc    3480
ttttgtagcc attggcggtt gtgataaaaa catgcccggt tctgttatcg ctatggctaa    3540
catggatatc ccagccattt tgcttacgg cggaacaatt gcacctggta atttagacgg    3600
caaagatatc gatttagtct ctgtctttga aggtgtcggc cattggaacc acggcgatat    3660
gaccaaagaa gaagttaaag ctttggaatg taatgcttgt cccggtcctg gaggctgcgg    3720
tggtatgtat actgctaaca caatggcgac agctattgaa gttttgggac ttagccttcc    3780
gggttcatct tctcacccgg ctgaatccgc agaaaagaaa gcagatattg aagaagctgg    3840
tcgcgctgtt gtcaaaatgc tcgaaatggg cttaaaacct tctgacttt taacgcgtga    3900
agcttttgaa gatgctatta ctgtaactat ggctctggga ggttcaacca actcaaccct    3960
tcacctctta gctattgccc atgctgctaa tgtggaattg acacttgatg atttcaatac    4020
tttccaagaa aaagttcctc atttggctga tttgaaacct tctggtcaat atgtattcca    4080
agacctttac aaggtcggag gggtaccagc agttatgaaa tatctcctta aaaatggctt    4140
ccttcatggt gaccgtatca cttgtactgg caaaacagtc gctgaaaatt tgaaggcttt    4200
tgatgattta acacctggtc aaaaggttat tatgccgctt gaaaatccta acgtgaaga    4260
tggtccgctc attattctcc atggtaactt ggctccagac ggtgccgttg ccaaagtttc    4320
```

```
tggtgtaaaa gtgcgtcgtc atgtcggtcc tgctaaggtc tttaattctg aagaagaagc    4380
cattgaagct gtcttgaatg atgatattgt tgatggtgat gttgttgtcg tacgttttgt    4440
aggaccaaag ggcggtcctg gtatgcctga aatgctttcc ctttcatcaa tgattgttgg    4500
taaagggcaa ggtgaaaaag ttgcccttct gacagatggc cgcttctcag gtggtactta    4560
tggtcttgtc gtgggtcata tcgctcctga agcacaagat ggcggtccaa tcgcctacct    4620
gcaaacagga gacatagtca ctattgacca agacactaag gaattacact ttgatatctc    4680
cgatgaagag ttaaaacatc gtcaagagac cattgaattg ccaccgctct attcacgcgg    4740
tatccttggt aaatatgctc acatcgtttc gtctgcttct aggggagccg taacagactt    4800
ttggaagcct gaagaaactg gcaaaaaatg ttgtcctggt tgctgtggtt aagcggccgc    4860
gttaattcaa attaattgat atagtttttt aatgagtatt gaatctgttt agaaataatg    4920
gaatattatt tttatttatt tatttatatt attggtcggc tcttttcttc tgaaggtcaa    4980
tgacaaaatg atatgaagga aataatgatt tctaaaattt tacaacgtaa gatattttta    5040
caaaagccta gctcatcttt tgtcatgcac tattttactc acgcttgaaa ttaacggcca    5100
gtccactgcg gagtcatttc aaagtcatcc taatcgatct atcgtttttg atagctcatt    5160
ttggagttcg cgattgtctt ctgttattca caactgtttt aattttatt tcattctgga    5220 actcttcgag ttctttgtaa agtctttcat agtagcttac tttatcctcc aacatattta    5280
acttcatgtc aatttcggct cttaaatttt ccacatcatc aagttcaaca tcatctttta    5340
acttgaattt attctctagc tcttccaacc aagcctcatt gctccttgat ttactggtga    5400
aaagtgatac actttgcgcg caatccaggt caaaactttc ctgcaaagaa ttcaccaatt    5460
tctcgacatc atagtacaat ttgtttttgtt ctcccatcac aatttaatat acctgatgga    5520
ttcttatgaa gcgctgggta atggacgtgt cactctactt cgcctttttc cctactcctt    5580
ttagtacgga agacaatgct aataaataag agggtaataa taatattatt aatcggcaaa    5640
aaagattaaa cgccaagcgt ttaattatca gaaagcaaac gtcgtaccaa tccttgaatg    5700
cttcccaatt gtatattaag agtcatcaca gcaacatatt cttgttatta aattaattat    5760
tattgatttt tgatattgta taaaaaaacc aaatatgtat aaaaaaagtg aataaaaaat    5820
accaagtatg gagaaatata ttagaagtct atacgttaaa ccaccgcggt ggagctccag    5880
cttttgttcc ctttagtgag ggttaattgc gcgcttggcg taatcatggt catagctgtt    5940
tcctgtgtga aattgttatc cgctcacaat tccacacaac ataggagccg gaagcataaa    6000
gtgtaaagcc tggggtgcct aatgagtgag gtaactcaca ttaattgcgt tgcgctcact    6060
gcccgctttc cagtcgggaa acctgtcgtg ccagctgcat taatgaatcg gccaacgcgc    6120
ggggagaggc ggtttgcgta ttgggcgctc ttccgcttcc tcgctcactg actcgctgcg    6180
ctcggtcgtt cggctgcggc gagcggtatc agctcactca aaggcggtaa tacggttatc    6240
cacagaatca ggggataacg caggaaagaa catgtgagca aaaggccagc aaaaggccag    6300
gaaccgtaaa aaggccgcgt tgctggcgtt tttccatagg ctccgccccc ctgacgagca    6360
tcacaaaaat cgacgctcaa gtcagaggtg gcgaaacccg acaggactat aaagatacca    6420
ggcgtttccc cctggaagct ccctcgtgcg ctctcctgtt ccgaccctgc cgcttaccgg    6480
atacctgtcc gcctttctcc cttcgggaag cgtggcgctt tctcatagct cacgctgtag    6540
gtatctcagt tcggtgtagg tcgttcgctc caagctgggc tgtgtgcacg aaccccccgt    6600
tcagcccgac cgctgcgcct tatccggtaa ctatcgtctt gagtccaacc cggtaagaca    6660
```

```
cgacttatcg ccactggcag cagccactgg taacaggatt agcagagcga ggtatgtagg    6720
cggtgctaca gagttcttga agtggtggcc taactacggc tacactagaa ggacagtatt    6780
tggtatctgc gctctgctga agccagttac cttcggaaaa agagttggta gctcttgatc    6840
cggcaaacaa accaccgctg gtagcggtgg ttttttttgtt tgcaagcagc agattacgcg    6900
cagaaaaaaa ggatctcaag aagatccttt gatcttttct acggggtctg acgctcagtg    6960
gaacgaaaac tcacgttaag ggattttggt catgagatta tcaaaaagga tcttcaccta    7020 gatccttttta aattaaaaat gaagttttaa atcaatctaa agtatatatg agtaaacttg    7080
gtctgacagt taccaatgct taatcagtga ggcacctatc tcagcgatct gtctatttcg    7140
ttcatccata gttgcctgac tccccgtcgt gtagataact acgatacggg agggcttacc    7200
atctggcccc agtgctgcaa tgataccgcg agacccacgc tcaccggctc cagatttatc    7260
agcaataaac cagccagccg gaagggccga gcgcagaagt ggtcctgcaa ctttatccgc    7320
ctccatccag tctattaatt gttgccggga agctagagta agtagttcgc cagttaatag    7380
tttgcgcaac gttgttgcca ttgctacagg catcgtggtg tcacgctcgt cgtttggtat    7440
ggcttcattc agctccggtt cccaacgatc aaggcgagtt acatgatccc ccatgttgtg    7500
caaaaaagcg gttagctcct tcggtcctcc gatcgttgtc agaagtaagt tggccgcagt    7560
gttatcactc atggttatgg cagcactgca taattctctt actgtcatgc catccgtaag    7620
atgcttttct gtgactggtg agtactcaac caagtcattc tgagaatagt gtatgcggcg    7680
accgagttgc tcttgcccgg cgtcaatacg ggataatacc gcgccacata gcagaacttt    7740
aaaagtgctc atcattggaa aacgttcttc ggggcgaaaa ctctcaagga tcttaccgct    7800
gttgagatcc agttcgatgt aacccactcg tgcacccaac tgatcttcag catctttttac    7860 tttcaccagc gtttctgggt gagcaaaaac aggaaggcaa aatgccgcaa aaaagggaat    7920
aagggcgaca cggaaatgtt gaatactcat actcttcctt tttcaatatt attgaagcat    7980
ttatcagggt tattgtctca tgagcggata catatttgaa tgtatttaga aaaataaaca    8040 aatagggtt ccgcgcacat ttccccgaaa agtgccacct gaacgaagca tctgtgcttc    8100
attttgtaga acaaaaatgc aacgcgagag cgctaatttt tcaaacaaag aatctgagct    8160
gcatttttac agaacagaaa tgcaacgcga aagcgctatt ttaccaacga agaatctgtg    8220
cttcattttt gtaaaacaaa aatgcaacgc gagagcgcta attttcaaa caaagaatct    8280 gagctgcatt tttacagaac agaaatgcaa cgcgagagcg ctattttacc aacaaagaat    8340
ctatacttct tttttgttct acaaaaatgc atcccgagag cgctatttttt ctaacaaagc    8400 atcttagatt acttttttttc cctttgtgc gctctataat gcagtctctt gataacttttt    8460 tgcactgtag gtccgttaag gttagaagaa ggctactttg gtgtctatttt tctcttccat    8520 aaaaaaagcc tgactccact tcccgcgttt actgattact agcgaagctg cgggtgcatt    8580
ttttcaagat aaaggcatcc ccgattatat tctataccga tgtggattgc gcatactttg    8640
tgaacagaaa gtgatagcgt tgatgattct tcattggtca gaaaattatg aacggtttct    8700
tctattttgt ctctatatac tacgtatagg aaatgtttac attttcgtat tgttttcgat    8760
tcactctatg aatagttctt actacaattt ttttgtctaa agagtaatac tagagataaa    8820
cataaaaaat gtagaggtcg agtttagatg caagttcaag gagcgaaagg tggatgggta    8880
ggttatatag ggatatagca cagagatata tagcaaagag atacttttga gcaatgtttg    8940
tggaagcggt attcgcaata ttttagtagc tcgttacagt ccggtgcgtt tttggttttt    9000
tgaaagtgcg tcttcagagc gcttttggtt ttcaaaagcg ctctgaagtt cctatacttt    9060
```

```
ctagagaata ggaacttcgg aataggaact tcaaagcgtt tccgaaaacg agcgcttccg    9120
aaaatgcaac gcgagctgcg cacatacagc tcactgttca cgtcgcacct atatctgcgt    9180
gttgcctgta tatatatata catgagaaga acggcatagt gcgtgtttat gcttaaatgc    9240
gtacttatat gcgtctattt atgtaggatg aaaggtagtc tagtacctcc tgtgatatta    9300
tcccattcca tgcggggtat cgtatgcttc cttcagcact acccttagc tgttctatat     9360 gctgccactc ctcaattgga ttagtctcat ccttcaatgc tatcatttcc tttgatattg    9420
gatcatctaa gaaaccatta ttatcatgac attaacctat aaaaataggc gtatcacgag    9480
gccctttcgt c                                                          9491

<210> SEQ ID NO 54
<211> LENGTH: 1000
<212> TYPE: DNA
<213> ORGANISM: Artificial Sequence
<220> FEATURE:
<223> OTHER INFORMATION: FBA1 terminator nt 4861 to 5860

<400> SEQUENCE: 54
gttaattcaa attaattgat atagttttt  aatgagtatt gaatctgttt agaaataatg      60
gaatatattt tttatttatt tatttatatt attggtcggc tcttttcttc tgaaggtcaa    120
tgacaaaatg atatgaagga aataatgatt tctaaaattt tacaacgtaa gatattttta    180
caaaagccta gctcatcttt tgtcatgcac tattttactc acgcttgaaa ttaacggcca    240
gtccactgcg gagtcatttc aaagtcatcc taatcgatct atcgttttg atagctcatt     300 ttggagttcg cgattgtctt ctgttattca caactgtttt aattttttatt tcattctgga   360 actcttcgag ttctttgtaa agtctttcat agtagcttac tttatcctcc aacatattta    420
acttcatgtc aatttcggct cttaaatttt ccacatcatc aagttcaaca tcatctttta    480
acttgaattt attctctagc tcttccaacc aagcctcatt gctccttgat ttactggtga    540
aaagtgatac actttgcgcg caatccaggt caaaactttc ctgcaaagaa ttcaccaatt    600
tctcgacatc atagtacaat ttgttttgtt ctcccatcac aatttaatat acctgatgga    660
ttcttatgaa gcgctgggta atggacgtgt cactctactt cgccttttc cctactcctt     720 ttagtacgga agacaatgct aataaataag agggtaataa taatattatt aatcggcaaa    780
aaagattaaa cgccaagcgt ttaattatca gaaagcaaac gtcgtaccaa tccttgaatg    840
cttcccaatt gtatattaag agtcatcaca gcaacatatt cttgttatta aattaattat    900
tattgatttt tgatattgta taaaaaaacc aaatatgtat aaaaaaagtg aataaaaaat    960
accaagtatg gagaaatata ttagaagtct atacgttaaa                         1000

<210> SEQ ID NO 55
<211> LENGTH: 1713
<212> TYPE: DNA
<213> ORGANISM: Streptococcus mutans

<400> SEQUENCE: 55
atgactgaca aaaaaactct taaagactta agaaatcgta gttctgttta cgattcaatg     60
gttaaatcac ctaatcgtgc tatgttgcgt gcaactggta tgcaagatga agactttgaa    120
aaacctatcg tcggtgtcat ttcaacttgg gctgaaaaca caccttgtaa tatccactta    180
catgactttg gtaaactagc caaagtcggt gttaaggaag ctggtgcttg ccagttcag    240 ttcggaacaa tcacggtttc tgatggaatc gccatgggaa cccaaggaat gcgtttctcc   300
```

```
ttgacatctc gtgatattat tgcagattct attgaagcag ccatgggagg tcataatgcg    360
gatgcttttg tagccattgg cggttgtgat aaaaacatgc ccggttctgt tatcgctatg    420
gctaacatgg atatcccagc cattttttgct tacggcggaa caattgcacc tggtaattta   480
gacggcaaag atatcgattt agtctctgtc tttgaaggtg tcggccattg gaaccacggc    540
gatatgacca agaagaagt taaagctttg gaatgtaatg cttgtcccgg tcctggaggc     600
tgcggtggta tgtatactgc taacacaatg gcgacagcta ttgaagtttt gggacttagc    660
cttccgggtt catcttctca cccggctgaa tccgcagaaa agaaagcaga tattgaagaa    720
gctggtcgcg ctgttgtcaa atgctcgaa atgggcttaa accttctga cattttaacg     780
cgtgaagctt ttgaagatgc tattactgta actatggctc tgggaggttc aaccaactca   840
acccttcacc tcttagctat tgcccatgct gctaatgtgg aattgacact tgatgatttc    900
aatactttcc aagaaaaagt tcctcatttg gctgatttga accttctgg tcaatatgta    960
ttccaagacc tttacaaggt cggaggggta ccagcagtta tgaaatatct ccttaaaaat   1020
ggcttccttc atggtgaccg tatcacttgt actggcaaaa cagtcgctga aaatttgaag   1080
gcttttgatg atttaacacc tggtcaaaag gttattatgc cgcttgaaaa tcctaaacgt   1140
gaagatggtc cgctcattat tctccatggt aacttggctc cagacggtgc cgttgccaaa   1200
gtttctggtg taaaagtgcg tcgtcatgtc ggtcctgcta aggtctttaa ttctgaagaa   1260
gaagccattg aagctgtctt gaatgatgat attgttgatg gtgatgttgt tgtcgtacgt   1320
tttgtaggac caaagggcgg tcctggtatg cctgaaatgc tttcccttt c atcaatgatt 1380
gttggtaaag gcaaggtga aaaagttgcc cttctgacag atggccgctt ctcaggtggt   1440
acttatggtc ttgtcgtggg tcatatcgct cctgaagcac aagatggcgg tccaatcgcc   1500
tacctgcaaa caggagacat agtcactatt gaccaagaca ctaaggaatt acactttgat   1560
atctccgatg aagagttaaa acatcgtcaa gagaccattg aattgccacc gctctattca   1620
cgcggtatcc ttggtaaata tgctcacatc gtttcgtctg cttctagggg agccgtaaca   1680
gacttttgga agcctgaaga aactggcaaa aaa                                1713
```

<210> SEQ ID NO 56
<211> LENGTH: 571
<212> TYPE: PRT
<213> ORGANISM: Streptococcus mutans

<400> SEQUENCE: 56

```
Met Thr Asp Lys Lys Thr Leu Lys Asp Leu Arg Asn Arg Ser Ser Val
1               5                   10                  15

Tyr Asp Ser Met Val Lys Ser Pro Asn Arg Ala Met Leu Arg Ala Thr
            20                  25                  30

Gly Met Gln Asp Glu Asp Phe Glu Lys Pro Ile Val Gly Val Ile Ser
        35                  40                  45

Thr Trp Ala Glu Asn Thr Pro Cys Asn Ile His Leu His Asp Phe Gly
    50                  55                  60

Lys Leu Ala Lys Val Gly Val Lys Glu Ala Gly Ala Trp Pro Val Gln
65                  70                  75                  80

Phe Gly Thr Ile Thr Val Ser Asp Gly Ile Ala Met Gly Thr Gln Gly
                85                  90                  95

Met Arg Phe Ser Leu Thr Ser Arg Asp Ile Ile Ala Asp Ser Ile Glu
            100                 105                 110

Ala Ala Met Gly Gly His Asn Ala Asp Ala Phe Val Ala Ile Gly Gly
        115                 120                 125
```

```
Cys Asp Lys Asn Met Pro Gly Ser Val Ile Ala Met Ala Asn Met Asp
            130                 135                 140

Ile Pro Ala Ile Phe Ala Tyr Gly Gly Thr Ile Ala Pro Gly Asn Leu
145                 150                 155                 160

Asp Gly Lys Asp Ile Asp Leu Val Ser Val Phe Glu Gly Val Gly His
                165                 170                 175

Trp Asn His Gly Asp Met Thr Lys Glu Glu Val Lys Ala Leu Glu Cys
            180                 185                 190

Asn Ala Cys Pro Gly Pro Gly Gly Cys Gly Gly Met Tyr Thr Ala Asn
            195                 200                 205

Thr Met Ala Thr Ala Ile Glu Val Leu Gly Leu Ser Leu Pro Gly Ser
    210                 215                 220

Ser Ser His Pro Ala Glu Ser Ala Glu Lys Lys Ala Asp Ile Glu Glu
225                 230                 235                 240

Ala Gly Arg Ala Val Val Lys Met Leu Glu Met Gly Leu Lys Pro Ser
                245                 250                 255

Asp Ile Leu Thr Arg Glu Ala Phe Glu Asp Ala Ile Thr Val Thr Met
                260                 265                 270

Ala Leu Gly Gly Ser Thr Asn Ser Thr Leu His Leu Leu Ala Ile Ala
            275                 280                 285

His Ala Ala Asn Val Glu Leu Thr Leu Asp Asp Phe Asn Thr Phe Gln
    290                 295                 300

Glu Lys Val Pro His Leu Ala Asp Leu Lys Pro Ser Gly Gln Tyr Val
305                 310                 315                 320

Phe Gln Asp Leu Tyr Lys Val Gly Gly Val Pro Ala Val Met Lys Tyr
                325                 330                 335

Leu Leu Lys Asn Gly Phe Leu His Gly Asp Arg Ile Thr Cys Thr Gly
                340                 345                 350

Lys Thr Val Ala Glu Asn Leu Lys Ala Phe Asp Asp Leu Thr Pro Gly
            355                 360                 365

Gln Lys Val Ile Met Pro Leu Glu Asn Pro Lys Arg Glu Asp Gly Pro
    370                 375                 380

Leu Ile Ile Leu His Gly Asn Leu Ala Pro Asp Gly Ala Val Ala Lys
385                 390                 395                 400

Val Ser Gly Val Lys Val Arg Arg His Val Gly Pro Ala Lys Val Phe
                405                 410                 415

Asn Ser Glu Glu Glu Ala Ile Glu Ala Val Leu Asn Asp Asp Ile Val
                420                 425                 430

Asp Gly Asp Val Val Val Val Arg Phe Val Gly Pro Lys Gly Gly Pro
            435                 440                 445

Gly Met Pro Glu Met Leu Ser Leu Ser Ser Met Ile Val Gly Lys Gly
    450                 455                 460

Gln Gly Glu Lys Val Ala Leu Leu Thr Asp Gly Arg Phe Ser Gly Gly
465                 470                 475                 480

Thr Tyr Gly Leu Val Val Gly His Ile Ala Pro Glu Ala Gln Asp Gly
                485                 490                 495

Gly Pro Ile Ala Tyr Leu Gln Thr Gly Asp Ile Val Thr Ile Asp Gln
            500                 505                 510

Asp Thr Lys Glu Leu His Phe Asp Ile Ser Asp Glu Glu Leu Lys His
    515                 520                 525

Arg Gln Glu Thr Ile Glu Leu Pro Pro Leu Tyr Ser Arg Gly Ile Leu
530                 535                 540
```

Gly Lys Tyr Ala His Ile Val Ser Ser Ala Ser Arg Gly Ala Val Thr
545                 550                 555                 560

Asp Phe Trp Lys Pro Glu Glu Thr Gly Lys Lys
                565                 570

<210> SEQ ID NO 57
<211> LENGTH: 4280
<212> TYPE: DNA
<213> ORGANISM: Artificial Sequence
<220> FEATURE:
<223> OTHER INFORMATION: pUC19-URA3r

<400> SEQUENCE: 57

| | | | | | |
|---|---|---|---|---|---|
| ggggatcctc | tagagtcgac | ctgcaggcat | gcaagcttgg | cgtaatcatg | gtcatagctg | 60 |
| tttcctgtgt | gaaattgtta | tccgctcaca | attccacaca | acatacgagc | cggaagcata | 120 |
| aagtgtaaag | cctggggtgc | ctaatgagtg | agctaactca | cattaattgc | gttgcgctca | 180 |
| ctgcccgctt | tccagtcggg | aaacctgtcg | tgccagctgc | attaatgaat | cggccaacgc | 240 |
| gcggggagag | gcggtttgcg | tattgggcgc | tcttccgctt | cctcgctcac | tgactcgctg | 300 |
| cgctcggtcg | ttcggctgcg | gcgagcggta | tcagctcact | caaaggcggt | aatacggtta | 360 |
| tccacagaat | caggggataa | cgcaggaaag | aacatgtgag | caaaaggcca | gcaaaaggcc | 420 |
| aggaaccgta | aaaaggccgc | gttgctggcg | tttttccata | ggctccgccc | ccctgacgag | 480 |
| catcacaaaa | atcgacgctc | aagtcagagg | tggcgaaacc | cgacaggact | ataaagatac | 540 |
| caggcgtttc | ccctggaag | ctccctcgtg | cgctctcctg | ttccgaccct | gccgcttacc | 600 |
| ggatacctgt | ccgcctttct | cccttcggga | agcgtggcgc | tttctcatag | ctcacgctgt | 660 |
| aggtatctca | gttcggtgta | ggtcgttcgc | tccaagctgg | gctgtgtgca | cgaacccccc | 720 |
| gttcagcccg | accgctgcgc | cttatccggt | aactatcgtc | ttgagtccaa | cccggtaaga | 780 |
| cacgacttat | cgccactggc | agcagccact | ggtaacagga | ttagcagagc | gaggtatgta | 840 |
| ggcggtgcta | cagagttctt | gaagtggtgg | cctaactacg | gctacactag | aaggacagta | 900 |
| tttggtatct | gcgctctgct | gaagccagtt | accttcggaa | aaagagttgg | tagctcttga | 960 |
| tccggcaaac | aaaccaccgc | tggtagcggt | ggtttttttg | tttgcaagca | gcagattacg | 1020 |
| cgcagaaaaa | aaggatctca | agaagatcct | ttgatctttt | ctacggggtc | tgacgctcag | 1080 |
| tggaacgaaa | actcacgtta | agggattttg | gtcatgagat | tatcaaaaag | gatcttcacc | 1140 |
| tagatccttt | taaattaaaa | atgaagtttt | aaatcaatct | aaagtatata | tgagtaaact | 1200 |
| tggtctgaca | gttaccaatg | cttaatcagt | gaggcaccta | tctcagcgat | ctgtctattt | 1260 |
| cgttcatcca | tagttgcctg | actccccgtc | gtgtagataa | ctacgatacg | ggagggctta | 1320 |
| ccatctggcc | ccagtgctgc | aatgataccg | cgagacccac | gctcaccggc | tccagattta | 1380 |
| tcagcaataa | accagccagc | cggaagggcc | gagcgcagaa | gtggtcctgc | aactttatcc | 1440 |
| gcctccatcc | agtctattaa | ttgttgccgg | gaagctagag | taagtagttc | gccagttaat | 1500 |
| agtttgcgca | acgttgttgc | cattgctaca | ggcatcgtgg | tgtcacgctc | gtcgtttggt | 1560 |
| atggcttcat | tcagctccgg | ttcccaacga | tcaaggcgag | ttacatgatc | ccccatgttg | 1620 |
| tgcaaaaaag | cggttagctc | cttcggtcct | ccgatcgttg | tcagaagtaa | gttggccgca | 1680 |
| gtgttatcac | tcatggttat | ggcagcactg | cataattctc | ttactgtcat | gccatccgta | 1740 |
| agatgctttt | ctgtgactgg | tgagtactca | accaagtcat | tctgagaata | gtgtatgcgg | 1800 |
| cgaccgagtt | gctcttgccc | ggcgtcaata | cgggataata | ccgcgccaca | tagcagaact | 1860 |
| ttaaaagtgc | tcatcattgg | aaaacgttct | tcggggcgaa | aactctcaag | gatcttaccg | 1920 |

```
ctgttgagat ccagttcgat gtaacccact cgtgcaccca actgatcttc agcatctttt    1980
actttcacca gcgtttctgg gtgagcaaaa acaggaaggc aaaatgccgc aaaaaaggga    2040
ataagggcga cacggaaatg ttgaatactc atactcttcc tttttcaata ttattgaagc    2100
atttatcagg gttattgtct catgagcgga tacatatttg aatgtattta gaaaaataaa    2160
caaatagggg ttccgcgcac atttccccga aaagtgccac ctgacgtcta agaaaccatt    2220
attatcatga cattaaccta taaaaatagg cgtatcacga ggccctttcg tctcgcgcgt    2280
ttcggtgatg acggtgaaaa cctctgacac atgcagctcc cggagacggt cacagcttgt    2340
ctgtaagcga tgccgggag cagacaagcc cgtcagggcg cgtcagcggg tgttggcggg     2400
tgtcggggct ggcttaacta tgcggcatca gagcagattg tactgagagt gcaccatatg    2460
cggtgtgaaa taccgcacag atgcgtaagg agaaaatacc gcatcaggcg ccattcgcca    2520
ttcaggctgc gcaactgttg ggaagggcga tcggtgcggg cctcttcgct attacgccag    2580
ctggcgaaag gggatgtgc tgcaaggcga ttaagttggg taacgccagg ttttcccag     2640 tcacgacgtt gtaaaacgac ggccagtgaa ttcgagctcg gtaccccgg ctctgagaca    2700 gtagtaggtt agtcatcgct ctaccgacgc gcaggaaaag aaagaagcat tgcggattac    2760
gtattctaat gttcagcccg cggaacgcca gcaaatcacc acccatgcgc atgatactga    2820
gtcttgtaca cgctgggctt ccagtgtact gagagtgcac cataccacag cttttcaatt    2880
caattcatca tttttttttt attctttttt ttgatttcgg tttctttgaa attttttga    2940 ttcggtaatc tccgaacaga aggaagaacg aaggaaggag cacagactta gattggtata    3000
tatacgcata tgtagtgttg aagaaacatg aaattgccca gtattcttaa cccaactgca    3060
cagaacaaaa acctgcagga aacgaagata aatcatgtcg aaagctacat ataaggaacg    3120
tgctgctact catcctagtc ctgttgctgc caagctattt aatatcatgc acgaaaagca    3180
aacaaacttg tgtgcttcat ggatgttcg taccaccaag gaattactgg agttagttga    3240
agcattaggt cccaaaattt gtttactaaa aacacatgtg gatatcttga ctgattttc     3300 catggagggc acagttaagc cgctaaaggc attatccgcc aagtacaatt ttttactctt    3360
cgaagacaga aaatttgctg acattggtaa tacagtcaaa ttgcagtact ctgcgggtgt    3420
atacagaata gcagaatggg cagacattac gaatgcacac ggtgtggtgg gcccaggtat    3480
tgttagcggt ttgaagcagg cggcagaaga agtaacaaag gaacctagag ccttttgat    3540 gttagcagaa ttgtcatgca agggctccct atctactgga gaatatacta agggtactgt    3600
tgacattgcg aagagcgaca aagattttgt tatcggcttt attgctcaaa gagacatggg    3660
tggaagagat gaaggttacg attggttgat tatgacaccc ggtgtgggtt agatgacaa     3720 gggagacgca ttgggtcaac agtatagaac cgtggatgat gtggtctcta caggatctga    3780
cattattatt gttggaagag gactatttgc aaagggaagg gatgctaagg tagagggtga    3840
acgttacaga aaagcaggct gggaagcata tttgagaaga tgcggccagc aaaactaaaa    3900
aactgtatta agtaaatg catgtatact aaactcacaa attagagctt caatttaatt     3960
atatcagtta ttaccctatg cggtgtgaaa taccgcacag atgcgtaagg agaaaatacc    4020
gcatcaggaa attgtaaacg ttaatatttt gttaaaattc gcgttaaatt tttgttaaat    4080
cagctcattt tttaaccaat aggccgaaat cggcaaaatc ttcagcccgc ggaacgccag    4140
caaatcacca cccatgcgca tgatactgag tcttgtacac gctgggcttc cagtgatgat    4200
acaacgagtt agccaaggtg agcacggatg tctaaattag aattacgttt taatatcttt    4260
```

```
ttttccatat ctagggctag                                        4280
```

<210> SEQ ID NO 58
<211> LENGTH: 30
<212> TYPE: DNA
<213> ORGANISM: Artificial Sequence
<220> FEATURE:
<223> OTHER INFORMATION: Primer 114117-11A

<400> SEQUENCE: 58

```
gcatgcttgc atttagtcgt gcaatgtatg                               30
```

<210> SEQ ID NO 59
<211> LENGTH: 54
<212> TYPE: DNA
<213> ORGANISM: Artificial Sequence
<220> FEATURE:
<223> OTHER INFORMATION: Primer 114117-11B

<400> SEQUENCE: 59

```
gaacattaga atacgtaatc cgcaatgcac tagtaccaca ggtgttgtcc tctg    54
```

<210> SEQ ID NO 60
<211> LENGTH: 54
<212> TYPE: DNA
<213> ORGANISM: Artificial Sequence
<220> FEATURE:
<223> OTHER INFORMATION: Primer 114117-11C

<400> SEQUENCE: 60

```
cagaggacaa cacctgtggt actagtgcat tgcggattac gtattctaat gttc    54
```

<210> SEQ ID NO 61
<211> LENGTH: 28
<212> TYPE: DNA
<213> ORGANISM: Artificial Sequence
<220> FEATURE:
<223> OTHER INFORMATION: Primer 114117-11D

<400> SEQUENCE: 61

```
caccttggct aactcgttgt atcatcac                                 28
```

<210> SEQ ID NO 62
<211> LENGTH: 100
<212> TYPE: DNA
<213> ORGANISM: Artificial Sequence
<220> FEATURE:
<223> OTHER INFORMATION: Primer 114117-13A

<400> SEQUENCE: 62

```
ttttaagccg aatgagtgac agaaaaagcc cacaacttat caagtgatat tgaacaaagg    60
gcgaaacttc gcatgcttgc atttagtcgt gcaatgtatg                         100
```

<210> SEQ ID NO 63
<211> LENGTH: 98
<212> TYPE: DNA
<213> ORGANISM: Artificial Sequence
<220> FEATURE:
<223> OTHER INFORMATION: Primer 114117-13B

<400> SEQUENCE: 63

```
cccaattggt aaatattcaa caagagacgc gcagtacgta acatgcgaat tgcgtaattc    60
acggcgataa caccttggct aactcgttgt atcatcac                            98
```

```
<210> SEQ ID NO 64
<211> LENGTH: 29
<212> TYPE: DNA
<213> ORGANISM: Artificial Sequence
<220> FEATURE:
<223> OTHER INFORMATION: Primer 112590-34G

<400> SEQUENCE: 64
caaaagccca tgtcccacac caaaggatg                                  29

<210> SEQ ID NO 65
<211> LENGTH: 26
<212> TYPE: DNA
<213> ORGANISM: Artificial Sequence
<220> FEATURE:
<223> OTHER INFORMATION: Primer 112590-34H

<400> SEQUENCE: 65
caccatcgcg cgtgcatcac tgcatg                                     26

<210> SEQ ID NO 66
<211> LENGTH: 28
<212> TYPE: DNA
<213> ORGANISM: Artificial Sequence
<220> FEATURE:
<223> OTHER INFORMATION: Primer 112590-34F

<400> SEQUENCE: 66
tcggtttttg caatatgacc tgtgggcc                                   28

<210> SEQ ID NO 67
<211> LENGTH: 22
<212> TYPE: DNA
<213> ORGANISM: Artificial Sequence
<220> FEATURE:
<223> OTHER INFORMATION: Primer 112590-49E

<400> SEQUENCE: 67
gagaagatgc ggccagcaaa ac                                         22

<210> SEQ ID NO 68
<211> LENGTH: 99
<212> TYPE: DNA
<213> ORGANISM: artificial sequence
<220> FEATURE:
<223> OTHER INFORMATION: Primer 114117-27A

<400> SEQUENCE: 68
tcctttctca attattattt tctactcata acctcacgca aaataacaca gtcaaatcaa    60
tcaaagtatg actgacaaaa aaactcttaa agacttaag                           99

<210> SEQ ID NO 69
<211> LENGTH: 77
<212> TYPE: DNA
<213> ORGANISM: artificial sequence
<220> FEATURE:
<223> OTHER INFORMATION: Primer 114117-27B

<400> SEQUENCE: 69
gaacattaga atacgtaatc cgcaatgctt ctttcttttc cgtttaacgt atagacttct    60
aatatatttc tccatac                                                   77

<210> SEQ ID NO 70
<211> LENGTH: 45
<212> TYPE: DNA
```

```
<213> ORGANISM: artificial sequence
<220> FEATURE:
<223> OTHER INFORMATION: Primer 114117-27C

<400> SEQUENCE: 70
aaacggaaaa gaaagaagca ttgcggatta cgtattctaa tgttc            45

<210> SEQ ID NO 71
<211> LENGTH: 88
<212> TYPE: DNA
<213> ORGANISM: artificial sequence
<220> FEATURE:
<223> OTHER INFORMATION: Primer 114117-27D

<400> SEQUENCE: 71 tattttcgt tacataaaaa tgcttataaa actttaacta ataattagag attaaatcgc    60
caccttggct aactcgttgt atcatcac                                      88

<210> SEQ ID NO 72
<211> LENGTH: 27
<212> TYPE: DNA
<213> ORGANISM: Artificial Sequence
<220> FEATURE:
<223> OTHER INFORMATION: Primer 114117-36D

<400> SEQUENCE: 72
gacttttgga agcctgaaga aactggc                                       27

<210> SEQ ID NO 73
<211> LENGTH: 20
<212> TYPE: DNA
<213> ORGANISM: artificial sequence
<220> FEATURE:
<223> OTHER INFORMATION: Primer 135

<400> SEQUENCE: 73
cttggcagca acaggactag                                               20

<210> SEQ ID NO 74
<211> LENGTH: 26
<212> TYPE: DNA
<213> ORGANISM: Artificial Sequence
<220> FEATURE:
<223> OTHER INFORMATION: 112590-30F

<400> SEQUENCE: 74
ccaggccaat tcaacagact gtcggc                                        26

<210> SEQ ID NO 75
<211> LENGTH: 2347
<212> TYPE: DNA
<213> ORGANISM: Artificial Sequence
<220> FEATURE:
<223> OTHER INFORMATION: URA3r2 template DNA

<400> SEQUENCE: 75
gcattgcgga ttacgtattc taatgttcag gtgctggaag aagagctgct taaccgccgc    60
gcccagggtg aagatccacg ctactttacc ctgcgtcgtc tggatttcgg cggctgtcgt   120
ctttcgctgg caacgccggt tgatgaagcc tgggacggtc cgctctcctt aaacggtaaa   180
cgtatcgcca cctcttatcc tcacctgctc aagcgttatc tcgaccagaa aggcatctct   240
tttaaatcct gcttactgaa cggttctgtt gaagtcgccc cgcgtgccgg actggcggat   300
gcgatttgcg atctggtttc accggtgcc acgctggaag ctaacggcct gcgcgaagtc   360
```

```
gaagttatct atcgctcgaa agcctgcctg attcaacgcg atggcgaaat ggaagaatcc    420
aaacagcaac tgatcgacaa actgctgacc cgtattcagg gtgtgatcca ggcgcgcgaa    480
tcaaaataca tcatgatgca cgcaccgacc gaacgtctgg atgaagtcat ggtacctact    540
gagagtgcac cataccacag cttttcaatt caattcatca tttttttttt attctttttt    600
ttgatttcgg tttctttgaa attttttga ttcggtaatc tccgaacaga aggaagaacg     660
aaggaaggag cacagactta gattggtata tatacgcata tgtagtgttg aagaaacatg    720
aaattgccca gtattcttaa cccaactgca cagaacaaaa acctgcagga aacgaagata    780
aatcatgtcg aaagctacat ataaggaacg tgctgctact catcctagtc ctgttgctgc    840
caagctattt aatatcatgc acgaaaagca acaaacttg  tgtgcttcat ggatgttcg     900 taccaccaag gaattactgg agttagttga agcattaggc cccaaaattt gtttactaaa    960
aacacatgtg gatatcttga ctgattttc  catggagggc acagttaagc cgctaaaggc   1020
attatccgcc aagtacaatt ttttactctt cgaagacaga aaatttgctg acattggtaa   1080
tacagtcaaa ttgcagtact ctgcgggtgt atacagaata gcagaatggg cagacattac   1140
gaatgcacac ggtgtggtgg gcccaggtat tgttagcggt ttgaagcagg cggcagaaga   1200
agtaacaaag gaacctagag gccttttgat gttagcagaa ttgtcatgca agggctccct   1260
atctactgga gaatatacta agggtactgt tgacattgcg aagagcgaca agattttgt    1320 tatcggcttt attgctcaaa gagacatggg tggaagagat gaaggttacg attggttgat   1380
tatgacaccc ggtgtggggtt tagatgacaa gggagacgca ttgggtcaac agtatagaac   1440
cgtggatgat gtggtctcta caggatctga cattattatt gttggaagag gactatttgc   1500
aaagggaagg gatgctaagg tagagggtga acgttacaga aaagcaggct gggaagcata   1560
tttgagaaga tgcggccagc aaaactaaaa aactgtatta taagtaaatg catgtatact   1620
aaactcacaa attagagctt caatttaatt atatcagtta ttaccctatg cggtgtgaaa   1680
taccgcacag atgcgtaagg agaaaatacc gcatcaggaa attgtaaacg ttaatatttt   1740
gttaaaattc gcgttaaatt tttgttaaat cagctcattt tttaaccaat aggccgaaat   1800
cggcaaaatc tctagagtgc tggaagaaga gctgcttaac cgccgcgccc agggtgaaga   1860
tccacgctac tttaccctgc gtcgtctgga tttcggcggc tgtcgtcttt cgctggcaac   1920
gccggttgat gaagcctggg acggtccgct tccttaaaac ggtaaacgta tcgccacctc   1980
ttatcctcac ctgctcaagc gttatctcga ccagaaaggc atctctttta aatcctgctt   2040
actgaacggt tctgttgaag tcgccccgcg tgccggactg gcggatgcga tttgcgatct   2100
ggtttccacc ggtgccacgc tggaagctaa cggcctgcgc gaagtcgaag ttatctatcg   2160
ctcgaaagcc tgcctgattc aacgcgatgg cgaaatggaa gaatccaaac agcaactgat   2220
cgacaaactg ctgacccgta ttcagggtgt gatccaggcg cgcgaatcaa aatacatcat   2280
gatgcacgca ccgaccgaac gtctggatga agtcatccag tgatgataca acgagttagc   2340
caaggtg                                                            2347
```

<210> SEQ ID NO 76
<211> LENGTH: 80
<212> TYPE: DNA
<213> ORGANISM: Artificial Sequence
<220> FEATURE:
<223> OTHER INFORMATION: Primer 114117-45A

<400> SEQUENCE: 76
cttcgaagaa tatactaaaa aatgagcagg caagataaac gaaggcaaag gcattgcgga    60
ttacgtattc taatgttcag                                                80

<210> SEQ ID NO 77
<211> LENGTH: 81
<212> TYPE: DNA
<213> ORGANISM: Artificial Sequence
<220> FEATURE:
<223> OTHER INFORMATION: Primer 114117-45B

<400> SEQUENCE: 77
tatacacatg tatatatatc gtatgctgca gctttaaata atcggtgtca caccttggct    60
aactcgttgt atcatcactg g                                              81

<210> SEQ ID NO 78
<211> LENGTH: 90
<212> TYPE: DNA
<213> ORGANISM: Artificial Sequence
<220> FEATURE:
<223> OTHER INFORMATION: Primer 384

<400> SEQUENCE: 78
atggttcatt taggtccaaa aaaaccacaa gccagaaagg gttccatggc cgatgtgcca    60
gcattgcgga ttacgtattc taatgttcag                                     90

<210> SEQ ID NO 79
<211> LENGTH: 91
<212> TYPE: DNA
<213> ORGANISM: Artificial Sequence
<220> FEATURE:
<223> OTHER INFORMATION: Primer 385

<400> SEQUENCE: 79
ttaagcaccg atgataccaa cggacttacc ttcagcaatt ctttttggg ccaaagcagc     60 caccttggct aactcgttgt atcatcactg g                                   91

<210> SEQ ID NO 80
<211> LENGTH: 24
<212> TYPE: DNA
<213> ORGANISM: Artificial Sequence
<220> FEATURE:
<223> OTHER INFORMATION: Primer N869

<400> SEQUENCE: 80
ctaggatgag tagcagcacg ttcc                                           24

<210> SEQ ID NO 81
<211> LENGTH: 26
<212> TYPE: DNA
<213> ORGANISM: Artificial Sequence
<220> FEATURE:
<223> OTHER INFORMATION: Primer N871

<400> SEQUENCE: 81
ccaattccgt gatgtctctt tgttgc                                         26

<210> SEQ ID NO 82
<211> LENGTH: 20
<212> TYPE: DNA
<213> ORGANISM: Artificial Sequence
<220> FEATURE:
<223> OTHER INFORMATION: Primer N946

<400> SEQUENCE: 82
gtgaacgagt tcacaaccgc                                                  20

<210> SEQ ID NO 83
<211> LENGTH: 22
<212> TYPE: DNA
<213> ORGANISM: Artificial Sequence
<220> FEATURE:
<223> OTHER INFORMATION: Primer N947

<400> SEQUENCE: 83
gttcgttcca gaattatcac gc                                               22

<210> SEQ ID NO 84
<211> LENGTH: 26
<212> TYPE: DNA
<213> ORGANISM: Artificial Sequence
<220> FEATURE:
<223> OTHER INFORMATION: Primer PDC5:KanMXF

<400> SEQUENCE: 84
gacttgaata atgcagcggc gcttgc                                           26

<210> SEQ ID NO 85
<211> LENGTH: 30
<212> TYPE: DNA
<213> ORGANISM: Artificial Sequence
<220> FEATURE:
<223> OTHER INFORMATION: Primer PDC5::KanMXR

<400> SEQUENCE: 85
ccaccctctt caattagcta agatcatagc                                       30

<210> SEQ ID NO 86
<211> LENGTH: 49
<212> TYPE: DNA
<213> ORGANISM: Artificial sequence
<220> FEATURE:
<223> OTHER INFORMATION: Primer oBP457

<400> SEQUENCE: 86
ccagaaaccc tatacctgtg tggacgtaag gccatgaagc ttttctttt                  49

<210> SEQ ID NO 87
<211> LENGTH: 49
<212> TYPE: DNA
<213> ORGANISM: Artificial sequence
<220> FEATURE:
<223> OTHER INFORMATION: Primer oBP458

<400> SEQUENCE: 87
attggaaaga aaagcttca tggccttacg tccacacagg tatagggtt                   49

<210> SEQ ID NO 88
<211> LENGTH: 22
<212> TYPE: DNA
<213> ORGANISM: Artificial sequence
<220> FEATURE:
<223> OTHER INFORMATION: Primer oBP459

<400> SEQUENCE: 88
cataagaaca cctttggtgg ag                                               22

<210> SEQ ID NO 89
<211> LENGTH: 24
<212> TYPE: DNA

```
<213> ORGANISM: Artificial sequence
<220> FEATURE:
<223> OTHER INFORMATION: Primer oBP452

<400> SEQUENCE: 89
ttctcgacgt gggcctttttt cttg                                          24

<210> SEQ ID NO 90
<211> LENGTH: 49
<212> TYPE: DNA
<213> ORGANISM: Artificial sequence
<220> FEATURE:
<223> OTHER INFORMATION: Primer oBP455

<400> SEQUENCE: 90
tatggaccct gaaaccacag ccacattgta accaccacga cggttgttg                49

<210> SEQ ID NO 91
<211> LENGTH: 49
<212> TYPE: DNA
<213> ORGANISM: Artificial sequence
<220> FEATURE:
<223> OTHER INFORMATION: Primer oBP456

<400> SEQUENCE: 91
tttagcaaca accgtcgtgg tggttacaat gtggctgtgg tttcagggt                49

<210> SEQ ID NO 92
<211> LENGTH: 512
<212> TYPE: PRT
<213> ORGANISM: Aspergillus niger

<400> SEQUENCE: 92
```

Met Ala Leu Leu Ala Val Ala Gly Val Tyr Ala Phe Ala Ala Leu Leu
1               5                   10                  15

Val Ala Ile Val Leu Asn Val Thr Arg Gln Leu Leu Phe Arg Asn Glu
            20                  25                  30

Lys Glu Pro Pro Val Val Phe His Trp Ile Pro Phe Leu Gly Ser Thr
        35                  40                  45

Ile Ser Tyr Gly Met Asp Pro Tyr Thr Phe Phe Phe Ser Cys Arg Lys
    50                  55                  60

Lys Tyr Gly Asp Ile Phe Thr Phe Val Leu Leu Gly Gln Lys Thr Thr
65                  70                  75                  80

Val Tyr Leu Gly Val Gln Gly Asn Asp Phe Ile Leu Asn Gly Lys Leu
                85                  90                  95

Lys Asp Val Ser Ala Glu Glu Val Tyr Ser Pro Leu Thr Thr Pro Val
            100                 105                 110

Phe Gly Ser Asp Val Val Tyr Asp Cys Pro Asn Ser Lys Leu Met Glu
        115                 120                 125

Gln Lys Lys Phe Ile Lys Phe Gly Leu Thr Gln Ala Ala Leu Glu Ser
    130                 135                 140

His Val Gln Leu Ile Glu Lys Glu Thr Leu Asp Tyr Leu Arg Asp Ser
145                 150                 155                 160

Pro Arg Phe Asn Gly Ala Ser Gly Val Ile Asp Ile Pro Ala Ala Met
                165                 170                 175

Ala Glu Ile Thr Ile Tyr Thr Ala Ala Arg Ala Leu Gln Gly Glu Glu
            180                 185                 190

Val Arg Lys Lys Leu Thr Ala Glu Phe Ala Glu Leu Tyr His Asp Leu
        195                 200                 205

```
Asp Lys Gly Phe Ser Pro Ile Asn Phe Met Leu Pro Trp Ala Pro Leu
    210                 215                 220
Pro His Asn Arg Lys Arg Asp Ala Ala His Ala Arg Met Arg Glu Ile
225                 230                 235                 240
Tyr Thr Asp Ile Ile Asn Glu Arg Arg Lys Asn Pro Asp Glu Lys
                245                 250                 255
Ser Asp Met Ile Trp Asn Leu Met His Cys Thr Tyr Lys Ser Gly Gln
                260                 265                 270
Pro Val Pro Asp Lys Glu Ile Ala His Met Met Ile Thr Leu Leu Met
            275                 280                 285
Ala Gly Gln His Ser Ser Ser Ile Ser Ser Trp Ile Met Leu Arg
290                 295                 300
Leu Ala Ser Glu Pro Gln Val Leu Glu Glu Leu Tyr Gln Glu Gln Leu
305                 310                 315                 320
Ala Ser Leu Ser Asn Arg Asn Gly Val Phe Glu Pro Leu Gln Tyr Gln
                325                 330                 335
Asp Leu Asp Lys Leu Pro Phe Leu Gln Ser Val Ile Lys Glu Thr Leu
            340                 345                 350
Arg Ile His Ser Ser Ile His Ser Ile Met Arg Lys Val Lys Asn Pro
                355                 360                 365
Leu Pro Val Pro Gly Thr Ser Tyr Ile Ile Pro Glu Asp His Val Leu
370                 375                 380
Leu Ala Ser Pro Gly Val Thr Ala Leu Ser Asp Glu Tyr Phe Pro Asn
385                 390                 395                 400
Ala Thr Arg Trp Asp Pro His Arg Trp Glu Asn Gln Pro Asp Lys Glu
                405                 410                 415
Glu Asp Gly Glu Met Val Asp Tyr Gly Tyr Gly Ser Val Ser Lys Gly
            420                 425                 430
Thr Ala Ser Pro Tyr Leu Pro Phe Gly Ala Gly Arg His Arg Cys Ile
                435                 440                 445
Gly Glu Lys Phe Ala Tyr Val Asn Leu Gly Val Ile Ile Ala Thr Ile
        450                 455                 460
Val Arg His Leu Lys Leu Phe Asn Val Asp Gly Arg Lys Gly Val Pro
465                 470                 475                 480
Gly Thr Asp Tyr Ser Thr Leu Phe Ser Gly Pro Met Lys Pro Ala Ile
                485                 490                 495
Val Gly Trp Glu Arg Arg Phe Pro Asp Asn Ile Lys Gly Ser Met Asn
                500                 505                 510

<210> SEQ ID NO 93
<211> LENGTH: 22
<212> TYPE: DNA
<213> ORGANISM: Artificial sequence
<220> FEATURE:
<223> OTHER INFORMATION: Primer BP460

<400> SEQUENCE: 93
aggattatca ttcataagtt tc                                              22

<210> SEQ ID NO 94
<211> LENGTH: 20
<212> TYPE: DNA
<213> ORGANISM: Artificial sequence
<220> FEATURE:
<223> OTHER INFORMATION: Primer LA135

<400> SEQUENCE: 94
```
cttggcagca acaggactag                                                    20

<210> SEQ ID NO 95
<211> LENGTH: 23
<212> TYPE: DNA
<213> ORGANISM: Artificial sequence
<220> FEATURE:
<223> OTHER INFORMATION: Primer BP461

<400> SEQUENCE: 95
ttcttggagc tgggacatgt ttg                                                23

<210> SEQ ID NO 96
<211> LENGTH: 22
<212> TYPE: DNA
<213> ORGANISM: Artificial sequence
<220> FEATURE:
<223> OTHER INFORMATION: Primer LA92

<400> SEQUENCE: 96
gagaagatgc ggccagcaaa ac                                                 22

<210> SEQ ID NO 97
<211> LENGTH: 4242
<212> TYPE: DNA
<213> ORGANISM: Artificial
<220> FEATURE:
<223> OTHER INFORMATION: pLA59

<400> SEQUENCE: 97
aaacgccagc aacgcggcct ttttacggtt cctggccttt tgctggcctt ttgctcacat        60
gttctttcct gcgttatccc ctgattctgt ggataaccgt attaccgcct tgagtgagc       120
tgataccgct cgccgcagcc gaacgaccga gcgcagcgag tcagtgagcg aggaagcgga      180
agagcgccca atacgcaaac cgcctctccc cgcgcgttgg ccgattcatt aatgcagctg      240
gcacgacagg tttcccgact ggaaagcggg cagtgagcgc aacgcaatta atgtgagtta     300
gctcactcat taggcacccc aggctttaca ctttatgctt ccggctcgta tgttgtgtgg     360
aattgtgagc ggataacaat ttcacacagg aaacagctat gaccatgatt acgccaagct    420
tgcatgcctg caggtcgact ctagaggatc cgcaatgcgg atccgcattg cggattacgt    480
attctaatgt tcagtaccgt tcgtataatg tatgctatac gaagttatgc agattgtact    540
gagagtgcac cataccacct tttcaattca tcatttttt tttattcttt tttttgattt      600
cggtttcctt gaaattttt tgattcggta atctccgaac agaaggaaga acgaaggaag      660
gagcacagac ttagattggt atatatacgc atatgtagtg ttgaagaaac atgaaattgc     720
ccagtattct aacccaact gcacagaaca aaaacctgca ggaaacgaag ataaatcatg      780
tcgaaagcta catataagga acgtgctgct actcatccta gtcctgttgc tgccaagcta    840
tttaatatca tgcacgaaaa gcaaacaaac ttgtgtgctt cattggatgt tcgtaccacc     900
aaggaattac tggagttagt tgaagcatta ggtcccaaaa tttgtttact aaaaacacat    960
gtggatatct tgactgattt ttccatggag ggcacagtta agccgctaaa ggcattatcc   1020
gccaagtaca atttttact cttcgaagac agaaaatttg ctgacattgg taatacagtc    1080
aaattgcagt actctgcggg tgtatacaga atagcagaat gggcagacat tacgaatgca   1140
cacggtgtgg tgggcccagg tattgttagc ggtttgaagc aggcggcaga agaagtaaca   1200
aaggaaccta gaggcctttt gatgttagca gaattgtcat gcaagggctc cctatctact   1260
ggagaatata ctaagggtac tgttgacatt gcgaagagcg acaaagattt gttatcggc    1320

```
tttattgctc aaagagacat gggtggaaga gatgaaggtt acgattggtt gattatgaca    1380
cccggtgtgg gtttagatga caagggagac gcattgggtc aacagtatag aaccgtggat    1440
gatgtggtct ctacaggatc tgacattatt attgttggaa gaggactatt tgcaaaggga    1500
agggatgcta aggtagaggg tgaacgttac agaaaagcag gctgggaagc atatttgaga    1560
agatgcggcc agcaaaacta aaaaactgta ttataagtaa atgcatgtat actaaactca    1620
caaattagag cttcaattta attatatcag ttattaccct atgcggtgtg aaataccgca    1680
cagatgcgta aggagaaaat accgcatcag gaaattgtaa acgttaatat tttgttaaaa    1740
ttcgcgttaa attttgtta aatcagctca ttttttaacc aataggccga atcggcaaa    1800 atcccttata aatcaaaaga atagaccgag atagggttga gtgttgttcc agtttggaac    1860
aagagtccac tattaaagaa cgtggactcc aacgtcaaag ggcgaaaaac cgtctatcag    1920
ggcgatggcc cactacgtga accatcaccc taatcaagat aacttcgtat aatgtatgct    1980
atacgaacgg taccagtgat gatacaacga gttagccaag gtgaattcac tggccgtcgt    2040
tttacaacgt cgtgactggg aaaaccctgg cgttacccaa cttaatcgcc ttgcagcaca    2100
tccccctttc gccagctggc gtaatagcga agaggcccgc accgatcgcc cttcccaaca    2160
gttgcgcagc ctgaatggcg aatggcgcct gatgcggtat tttctcctta cgcatctgtg    2220
cggtatttca caccgcatat ggtgcactct cagtacaatc tgctctgatg ccgcatagtt    2280
aagccagccc cgacacccgc caacacccgc tgacgcgccc tgacgggctt gtctgctccc    2340
ggcatccgct tacagacaag ctgtgaccgt ctccgggagc tgcatgtgtc agaggttttc    2400
accgtcatca ccgaaacgcg cgagacgaaa gggcctcgtg atacgcctat ttttataggt    2460
taatgtcatg ataataatgg tttcttagac gtcaggtggc acttttcggg gaaatgtgcg    2520
cggaacccct atttgtttat ttttctaaat acattcaaat atgtatccgc tcatgagaca    2580
ataaccctga taaatgcttc aataatattg aaaaaggaag agtatgagta ttcaacattt    2640
ccgtgtcgcc cttattccct tttttgcggc attttgcctt cctgttttg ctcacccaga    2700 aacgctggtg aaagtaaaag atgctgaaga tcagttgggt gcacgagtgg gttacatcga    2760
actggatctc aacagcggta agatccttga gagttttcgc cccgaagaac gttttccaat    2820
gatgagcact tttaaagttc tgctatgtgg cgcggtatta tcccgtattg acgccgggca    2880
agagcaactc ggtcgccgca tacactattc tcagaatgac ttggttgagt actcaccagt    2940
cacagaaaag catcttacgg atggcatgac agtaagagaa ttatgcagtg ctgccataac    3000
catgagtgat aacactgcgg ccaacttact tctgacaacg atcggaggac cgaaggagct    3060
aaccgctttt ttgcacaaca tgggggatca tgtaactcgc cttgatcgtt gggaaccgga    3120
gctgaatgaa gccataccaa acgacgagcg tgacaccacg atgcctgtag caatggcaac    3180
aacgttgcgc aaactattaa ctggcgaact acttactcta gcttcccggc aacaattaat    3240
agactggatg gaggcggata agttgcagg accacttctg cgctcggccc ttccggctgg    3300
ctggtttatt gctgataaat ctggagccgg tgagcgtggg tctcgcggta tcattgcagc    3360
actggggcca gatggtaagc cctcccgtat cgtagttatc tacacgacgg ggagtcaggc    3420
aactatggat gaacgaaata gacagatcgc tgagataggt gcctcactga ttaagcattg    3480
gtaactgtca gaccaagttt actcatatat actttagatt gatttaaaac ttcatttta    3540 atttaaaagg atctaggtga agatcctttt tgataatctc atgaccaaaa tcccttaacg    3600
tgagttttcg ttccactgag cgtcagaccc cgtagaaaag atcaaaggat cttcttgaga    3660
```

```
tcctttttttt ctgcgcgtaa tctgctgctt gcaaacaaaa aaaccaccgc taccagcggt    3720
ggtttgtttg ccggatcaag agctaccaac tcttttttccg aaggtaactg gcttcagcag    3780
agcgcagata ccaaatactg tccttctagt gtagccgtag ttaggccacc acttcaagaa    3840
ctctgtagca ccgcctacat acctcgctct gctaatcctg ttaccagtgg ctgctgccag    3900
tggcgataag tcgtgtctta ccgggttgga ctcaagacga tagttaccgg ataaggcgca    3960
gcggtcgggc tgaacggggg gttcgtgcac acagcccagc ttggagcgaa cgacctacac    4020
cgaactgaga tacctacagc gtgagctatg agaaagcgcc acgcttcccg aagggagaaa    4080
ggcggacagg tatccggtaa gcggcagggt cggaacagga gagcgcacga gggagcttcc    4140
agggggaaac gcctggtatc tttatagtcc tgtcgggttt cgccacctct gacttgagcg    4200
tcgatttttg tgatgctcgt caggggggcg gagcctatgg aa                      4242

<210> SEQ ID NO 98
<211> LENGTH: 80
<212> TYPE: DNA
<213> ORGANISM: Artificial
<220> FEATURE:
<223> OTHER INFORMATION: LA678

<400> SEQUENCE: 98
caacgttaac accgttttcg gtttgccagg tgacttcaac ttgtccttgt gcattgcgga    60
ttacgtattc taatgttcag                                                80

<210> SEQ ID NO 99
<211> LENGTH: 81
<212> TYPE: DNA
<213> ORGANISM: Artificial
<220> FEATURE:
<223> OTHER INFORMATION: LA679

<400> SEQUENCE: 99
gtggagcatc gaagactggc aacatgattt caatcattct gatcttagag caccttggct    60
aactcgttgt atcatcactg g                                              81

<210> SEQ ID NO 100
<211> LENGTH: 4586
<212> TYPE: DNA
<213> ORGANISM: Artificial sequence
<220> FEATURE:
<223> OTHER INFORMATION: pLA54 template DNA

<400> SEQUENCE: 100
gggtaccgag ctcgaattca ctggccgtcg ttttacaacg tcgtgactgg gaaaaccctg    60
gcgttaccca acttaatcgc cttgcagcac atccccccttt cgccagctgg cgtaatagcg    120
aagaggcccg caccgatcgc ccttcccaac agttgcgcag cctgaatggc gaatggcgcc    180
tgatgcggta ttttctcctt acgcatctgt gcggtatttc acaccgcata tggtgcactc    240
tcagtacaat ctgctctgat gccgcatagt taagccagcc ccgacacccg ccaacacccg    300
ctgacgcgcc ctgacgggct tgtctgctcc cggcatccgc ttacagacaa gctgtgaccg    360
tctccgggag ctgcatgtgt cagaggtttt accgtcatc accgaaacgc gcgagacgaa    420
agggcctcgt gatacgccta ttttttatagg ttaatgtcat gataataatg gtttcttaga    480
cgtcaggtgg cacttttcgg ggaaatgtgc gcggaacccc tatttgttta ttttttctaaa    540 tacattcaaa tatgtatccg ctcatgagac aataaccctg ataaatgctt caataatatt    600 gaaaaggaa gagtatgagt attcaacatt tccgtgtcgc ccttattccc tttttttgcgg    660
```

-continued

```
cattttgcct tcctgtttt gctcacccag aaacgctggt gaaagtaaaa gatgctgaag       720
atcagttggg tgcacgagtg ggttacatcg aactggatct caacagcggt aagatccttg       780
agagttttcg ccccgaagaa cgttttccaa tgatgagcac ttttaaagtt ctgctatgtg       840
gcgcggtatt atcccgtatt gacgccgggc aagagcaact cggtcgccgc atacactatt       900
ctcagaatga cttggttgag tactcaccag tcacagaaaa gcatcttacg gatggcatga       960
cagtaagaga attatgcagt gctgccataa ccatgagtga taacactgcg gccaacttac      1020
ttctgacaac gatcggagga ccgaaggagc taaccgcttt tttgcacaac atggggatc       1080 atgtaactcg ccttgatcgt tgggaaccgg agctgaatga agccatacca aacgacgagc      1140
gtgacaccac gatgcctgta gcaatggcaa caacgttgcg caaactatta actggcgaac      1200
tacttactct agcttcccgg caacaattaa tagactggat ggaggcggat aaagttgcag      1260
gaccacttct gcgctcggcc cttccggctg gctggtttat tgctgataaa tctggagccg      1320
gtgagcgtgg gtctcgcggt atcattgcag cactggggcc agatggtaag ccctcccgta      1380
tcgtagttat ctacacgacg gggagtcagg caactatgga tgaacgaaat agacagatcg      1440
ctgagatagg tgcctcactg attaagcatt ggtaactgtc agaccaagtt tactcatata      1500
tactttagat tgatttaaaa cttcattttt aatttaaaag gatctaggtg aagatccttt      1560
ttgataatct catgaccaaa atcccttaac gtgagttttc gttccactga gcgtcagacc      1620
ccgtagaaaa gatcaaagga tcttcttgag atccttttt tctgcgcgta atctgctgct      1680
tgcaaacaaa aaaaccaccg ctaccagcgg tggtttgttt gccggatcaa gagctaccaa      1740
ctctttttcc gaaggtaact ggcttcagca gagcgcagat accaaatact gtccttctag      1800
tgtagccgta gttaggccac cacttcaaga actctgtagc accgcctaca tacctcgctc      1860
tgctaatcct gttaccagtg gctgctgcca gtggcgataa gtcgtgtctt accgggttgg      1920
actcaagacg atagttaccg gataaggcgc agcggtcggg ctgaacgggg gttcgtgca       1980 cacagcccag cttggagcga acgacctaca ccgaactgag atacctacag cgtgagctat      2040
gagaaagcgc cacgcttccc gaagggagaa aggcggacag gtatccggta agcggcaggg      2100
tcggaacagg agagcgcacg agggagcttc caggggaaa cgcctggtat ctttatagtc       2160
ctgtcgggtt tcgccacctc tgacttgagc gtcgatttt gtgatgctcg tcaggggggc       2220
ggagcctatg gaaaaacgcc agcaacgcgg cctttttacg gttcctggcc ttttgctggc      2280
cttttgctca catgttcttt cctgcgttat cccctgattc tgtggataac cgtattaccg      2340
cctttgagtg agctgatacc gctcgccgca gccgaacgac cgagcgcagc gagtcagtga      2400
gcgaggaagc ggaagagcgc ccaatacgca aaccgcctct ccccgcgcgt tggccgattc      2460
attaatgcag ctggcacgac aggtttcccg actggaaagc gggcagtgag cgcaacgcaa      2520
ttaatgtgag ttagctcact cattaggcac cccaggcttt acactttatg cttccggctc      2580
gtatgttgtg tggaattgtg agcggataac aatttcacac aggaaacagc tatgaccatg      2640
attacgccaa gcttgcatgc ctgcaggtcg actctagagg atccccgcat tgcggattac      2700
gtattctaat gttcagataa cttcgtatag catacattat acgaagttat ctagggattc      2760
ataaccattt tctcaatcga attacacaga acacaccgta caaacctctc tatcataact      2820
acttaatagt cacacacgta ctcgtctaaa tacacatcat cgtcctacaa gttcatcaaa      2880
gtgttggaca gacaactata ccagcatgga tctcttgtat cggttctttt ctcccgctct      2940
ctcgcaataa caatgaacac tgggtcaatc atagcctaca caggtgaaca gagtagcgtt      3000
```

```
tatacagggt ttatacggtg attcctacgg caaaaatttt tcatttctaa aaaaaaaaag    3060 aaaaatttt ctttccaacg ctagaaggaa agaaaaatc taattaaatt gatttggtga      3120
ttttctgaga gttcccttt tcatatatcg aattttgaat ataaaggag atcgaaaaaa      3180 tttttctatt caatctgttt tctggtttta tttgatagtt ttttgtgta ttattattat     3240 ggattagtac tggtttatat gggttttct gtaaacttc tttttatttt agtttgttta      3300
atcttatttt gagttacatt atagttccct aactgcaaga gaagtaacat aaaactcga     3360 gatgggtaag gaaaagactc acgtttcgag gccgcgatta aattccaaca tggatgctga   3420
tttatatggg tataaatggg ctcgcgataa tgtcgggcaa tcaggtgcga caatctatcg    3480
attgtatggg aagcccgatg cgccagagtt gtttctgaaa catggcaaag gtagcgttgc    3540
caatgatgtt acagatgaga tggtcagact aaactggctg acggaattta tgcctcttcc    3600
gaccatcaag cattttatcc gtactcctga tgatgcatgg ttactcacca ctgcgatccc    3660
cggcaaaaca gcattccagg tattagaaga atatcctgat tcaggtgaaa atattgttga   3720
tgcgctggca gtgttcctgc gccggttgca ttcgattcct gtttgtaatt gtccttttaa   3780
cagcgatcgc gtatttcgtc tcgctcaggc gcaatcacga atgaataacg gtttggttga   3840
tgcgagtgat tttgatgacg agcgtaatgg ctggcctgtt gaacaagtct ggaaagaaat    3900
gcataagctt ttgccattct caccggattc agtcgtcact catggtgatt tctcacttga    3960
taaccttatt tttgacgagg ggaaattaat aggttgtatt gatgttggac gagtcggaat    4020
cgcagaccga taccaggatc ttgccatcct atggaactgc ctcggtgagt tttctccttc    4080
attacagaaa cggcttttc aaaaatatgg tattgataat cctgatatga ataaattgca    4140
gtttcatttg atgctcgatg agttttcta gtttaactt gatactacta gattttttct     4200
cttcatttat aaaattttg gttataattg aagcttaga agtatgaaaa aatccttttt     4260
tttcattctt tgcaaccaaa ataagaagct tctttattc attgaaatga tgaatataaa    4320
cctaacaaaa gaaaaagact cgaatatcaa acattaaaaa aaaataaaag aggttatctg    4380
ttttcccatt tagttggagt ttgcattttc taatagatag aactctcaat taatgtggat    4440
ttagtttctc tgttcgtttt ttttgtttt gttctcactg tatttacatt tctatttagt    4500
atttagttat tcatataatc tataacttcg tatagcatac attatacgaa gttatccagt    4560
gatgatacaa cgagttagcc aaggtg                                         4586

<210> SEQ ID NO 101
<211> LENGTH: 80
<212> TYPE: DNA
<213> ORGANISM: Artificial
<220> FEATURE:
<223> OTHER INFORMATION: BK505 primer

<400> SEQUENCE: 101
ttccggtttc tttgaaattt ttttgattcg gtaatctccg agcagaagga gcattgcgga    60
ttacgtattc taatgttcag                                                80

<210> SEQ ID NO 102
<211> LENGTH: 81
<212> TYPE: DNA
<213> ORGANISM: Artificial
<220> FEATURE:
<223> OTHER INFORMATION: BK506 primer

<400> SEQUENCE: 102
gggtaataac tgatataatt aaattgaagc tctaatttgt gagtttagta caccttggct    60
```

```
aactcgttgt atcatcactg g                                                        81
```

<210> SEQ ID NO 103
<211> LENGTH: 38
<212> TYPE: DNA
<213> ORGANISM: Artificial sequence
<220> FEATURE:
<223> OTHER INFORMATION: BK468 Primer

<400> SEQUENCE: 103

```
gcctcgagtt ttaatgttac ttctcttgca gttaggga                                      38
```

<210> SEQ ID NO 104
<211> LENGTH: 31
<212> TYPE: DNA
<213> ORGANISM: Artificial
<220> FEATURE:
<223> OTHER INFORMATION: LA492 primer

<400> SEQUENCE: 104

```
gctaaattcg agtgaaacac aggaagacca g                                             31
```

<210> SEQ ID NO 105
<211> LENGTH: 23
<212> TYPE: DNA
<213> ORGANISM: Artificial
<220> FEATURE:
<223> OTHER INFORMATION: AK109-1

<400> SEQUENCE: 105

```
agtcacatca agatcgttta tgg                                                      23
```

<210> SEQ ID NO 106
<211> LENGTH: 23
<212> TYPE: DNA
<213> ORGANISM: Artificial
<220> FEATURE:
<223> OTHER INFORMATION: AK109-2

<400> SEQUENCE: 106

```
gcacggaata tgggactact tcg                                                      23
```

<210> SEQ ID NO 107
<211> LENGTH: 23
<212> TYPE: DNA
<213> ORGANISM: Artificial
<220> FEATURE:
<223> OTHER INFORMATION: AK109-3

<400> SEQUENCE: 107

```
actccacttc aagtaagagt ttg                                                      23
```

<210> SEQ ID NO 108
<211> LENGTH: 548
<212> TYPE: PRT
<213> ORGANISM: Lactococcus lactis

<400> SEQUENCE: 108

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

-continued

```
Glu Leu Asn Ala Ser Tyr Met Ala Asp Gly Tyr Ala Arg Thr Lys Lys
 50                  55                  60

Ala Ala Ala Phe Leu Thr Thr Phe Gly Val Gly Glu Leu Ser Ala Val
 65                  70                  75                  80

Asn Gly Leu Ala Gly Ser Tyr Ala Glu Asn Leu Pro Val Val Glu Ile
                     85                  90                  95

Val Gly Ser Pro Thr Ser Lys Val Gln Asn Glu Gly Lys Phe Val His
                100                 105                 110

His Thr Leu Ala Asp Gly Asp Phe Lys His Phe Met Lys Met His Glu
            115                 120                 125

Pro Val Thr Ala Ala Arg Thr Leu Leu Thr Ala Glu Asn Ala Thr Val
            130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Lys Ala Glu Lys Pro
                165                 170                 175

Ser Leu Pro Leu Lys Lys Glu Asn Ser Thr Ser Asn Thr Ser Asp Gln
                180                 185                 190

Glu Ile Leu Asn Lys Ile Gln Glu Ser Leu Lys Asn Ala Lys Lys Pro
                195                 200                 205

Ile Val Ile Thr Gly His Glu Ile Ile Ser Phe Gly Leu Glu Lys Thr
210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
                260                 265                 270

Ala Asp Phe Ile Leu Met Leu Gly Val Lys Leu Thr Asp Ser Ser Thr
            275                 280                 285

Gly Ala Phe Thr His His Leu Asn Glu Asn Lys Met Ile Ser Leu Asn
            290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
            355                 360                 365

Ser Asn Glu Thr Ile Val Ala Glu Gln Gly Thr Ser Phe Phe Gly Ala
            370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
            435                 440                 445

Pro Ile Cys Phe Ile Ile Asn Asn Asp Gly Tyr Thr Val Glu Arg Glu
450                 455                 460
```

```
Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
                500                 505                 510

Gln Ala Asp Pro Asn Arg Met Tyr Trp Ile Glu Leu Ile Leu Ala Lys
            515                 520                 525

Glu Gly Ala Pro Lys Val Leu Lys Met Gly Lys Leu Phe Ala Glu
        530                 535                 540

Gln Asn Lys Ser
545
```

<210> SEQ ID NO 109  
<211> LENGTH: 49  
<212> TYPE: DNA  
<213> ORGANISM: Artificial sequence  
<220> FEATURE:  
<223> OTHER INFORMATION: Primer oBP453

<400> SEQUENCE: 109
tgcagcttta ataatcggt gtcactactt tgccttcgtt tatcttgcc            49

<210> SEQ ID NO 110  
<211> LENGTH: 49  
<212> TYPE: DNA  
<213> ORGANISM: Artificial sequence  
<220> FEATURE:  
<223> OTHER INFORMATION: Primer oBP454

<400> SEQUENCE: 110
gagcaggcaa gataaacgaa ggcaaagtag tgacaccgat tatttaaag            49

<210> SEQ ID NO 111  
<211> LENGTH: 23  
<212> TYPE: DNA  
<213> ORGANISM: Artificial sequence  
<220> FEATURE:  
<223> OTHER INFORMATION: Primer LA337

<400> SEQUENCE: 111
ctcatttgaa tcagcttatg gtg                                        23

<210> SEQ ID NO 112  
<211> LENGTH: 24  
<212> TYPE: DNA  
<213> ORGANISM: Artificial sequence  
<220> FEATURE:  
<223> OTHER INFORMATION: LA692

<400> SEQUENCE: 112
ggaagtcatt gacaccatct tggc                                       24

<210> SEQ ID NO 113  
<211> LENGTH: 24  
<212> TYPE: DNA  
<213> ORGANISM: Artificial sequence  
<220> FEATURE:  
<223> OTHER INFORMATION: Primer LA693

<400> SEQUENCE: 113
agaagctggg acagcagcgt tagc                                       24

```
<210> SEQ ID NO 114
<211> LENGTH: 41
<212> TYPE: DNA
<213> ORGANISM: Artificial sequence
<220> FEATURE:
<223> OTHER INFORMATION: Primer LA684

<400> SEQUENCE: 114
aatcactgca tgccttccaa aacacgaaca aggtgccggt c                 41

<210> SEQ ID NO 115
<211> LENGTH: 45
<212> TYPE: DNA
<213> ORGANISM: Artificial sequence
<220> FEATURE:
<223> OTHER INFORMATION: Primer LA685

<400> SEQUENCE: 115
ttaagtagga tcccacttga attgaactta ttattcatct atgac             45

<210> SEQ ID NO 116
<211> LENGTH: 38
<212> TYPE: DNA
<213> ORGANISM: Artificial sequence
<220> FEATURE:
<223> OTHER INFORMATION: Primer LA682

<400> SEQUENCE: 116
gtctttacag ggcaagtctc aactagtgct atcggtac                    38

<210> SEQ ID NO 117
<211> LENGTH: 38
<212> TYPE: DNA
<213> ORGANISM: Artificial sequence
<220> FEATURE:
<223> OTHER INFORMATION: Primer LA683

<400> SEQUENCE: 117
gtaccgatag cactagttga gacttgccct gtaaagac                    38

<210> SEQ ID NO 118
<211> LENGTH: 546
<212> TYPE: PRT
<213> ORGANISM: Macrococcus caseolyticus

<400> SEQUENCE: 118

Met Lys Gln Arg Ile Gly Gln Tyr Leu Ile Asp Ala Leu His Val Asn
1               5                   10                  15

Gly Val Asp Lys Ile Phe Gly Val Pro Gly Asp Phe Thr Leu Ala Phe
            20                  25                  30

Leu Asp Asp Ile Ile Arg His Asp Asn Val Glu Trp Val Gly Asn Thr
        35                  40                  45

Asn Glu Leu Asn Ala Ala Tyr Ala Ala Asp Gly Tyr Ala Arg Val Asn
    50                  55                  60

Gly Leu Ala Ala Val Ser Thr Thr Phe Gly Val Gly Glu Leu Ser Ala
65                  70                  75                  80

Val Asn Gly Ile Ala Gly Ser Tyr Ala Glu Arg Val Pro Val Ile Lys
                85                  90                  95

Ile Ser Gly Gly Pro Ser Ser Val Ala Gln Gln Glu Gly Arg Tyr Val
            100                 105                 110

His His Ser Leu Gly Glu Gly Ile Phe Asp Ser Tyr Ser Lys Met Tyr
        115                 120                 125
```

```
Ala His Ile Thr Ala Thr Thr Thr Ile Leu Ser Val Asp Asn Ala Val
    130                 135                 140

Asp Glu Ile Asp Arg Val Ile His Cys Ala Leu Lys Glu Lys Arg Pro
145                 150                 155                 160

Val His Ile His Leu Pro Ile Asp Val Ala Leu Thr Glu Ile Glu Ile
            165                 170                 175

Pro His Ala Pro Lys Val Tyr Thr His Glu Ser Gln Asn Val Asp Ala
        180                 185                 190

Tyr Ile Gln Ala Val Glu Lys Lys Leu Met Ser Ala Lys Gln Pro Val
    195                 200                 205

Ile Ile Ala Gly His Glu Ile Asn Ser Phe Lys Leu His Glu Gln Leu
210                 215                 220

Glu Gln Phe Val Asn Gln Thr Asn Ile Pro Val Ala Gln Leu Ser Leu
225                 230                 235                 240

Gly Lys Ser Ala Phe Asn Glu Glu Asn Glu His Tyr Leu Gly Ile Tyr
                245                 250                 255

Asp Gly Lys Ile Ala Lys Glu Asn Val Arg Glu Tyr Val Asp Asn Ala
            260                 265                 270

Asp Val Ile Leu Asn Ile Gly Ala Lys Leu Thr Asp Ser Ala Thr Ala
    275                 280                 285

Gly Phe Ser Tyr Lys Phe Asp Thr Asn Asn Ile Ile Tyr Ile Asn His
290                 295                 300

Asn Asp Phe Lys Ala Glu Asp Val Ile Ser Asp Asn Val Ser Leu Ile
305                 310                 315                 320

Asp Leu Val Asn Gly Leu Asn Ser Ile Asp Tyr Arg Asn Glu Thr His
                325                 330                 335

Tyr Pro Ser Tyr Gln Arg Ser Asp Met Lys Tyr Glu Leu Asn Asp Ala
            340                 345                 350

Pro Leu Thr Gln Ser Asn Tyr Phe Lys Met Met Asn Ala Phe Leu Glu
    355                 360                 365

Lys Asp Asp Ile Leu Leu Ala Glu Gln Gly Thr Ser Phe Phe Gly Ala
370                 375                 380

Tyr Asp Leu Ser Leu Tyr Lys Gly Asn Gln Phe Ile Gly Gln Pro Leu
385                 390                 395                 400

Trp Gly Ser Ile Gly Tyr Thr Phe Pro Ser Leu Leu Gly Ser Gln Leu
                405                 410                 415

Ala Asp Met His Arg Arg Asn Ile Leu Leu Ile Gly Asp Gly Ser Leu
            420                 425                 430

Gln Leu Thr Val Gln Ala Leu Ser Thr Met Ile Arg Lys Asp Ile Lys
    435                 440                 445

Pro Ile Ile Phe Val Ile Asn Asn Asp Gly Tyr Thr Val Glu Arg Leu
450                 455                 460

Ile His Gly Met Glu Glu Pro Tyr Asn Asp Ile Gln Met Trp Asn Tyr
465                 470                 475                 480

Lys Gln Leu Pro Glu Val Phe Gly Gly Lys Asp Thr Val Lys Val His
                485                 490                 495

Asp Ala Lys Thr Ser Asn Glu Leu Lys Thr Val Met Asp Ser Val Lys
            500                 505                 510

Ala Asp Lys Asp His Met His Phe Ile Glu Val His Met Ala Val Glu
    515                 520                 525

Asp Ala Pro Lys Lys Leu Ile Asp Ile Ala Lys Ala Phe Ser Asp Ala
530                 535                 540

Asn Lys
```

<210> SEQ ID NO 119
<211> LENGTH: 28
<212> TYPE: DNA
<213> ORGANISM: Artificial sequence
<220> FEATURE:
<223> OTHER INFORMATION: LA686

<400> SEQUENCE: 119

```
cttccaaaac acgaacaagg tgccggtc                                            28
```

<210> SEQ ID NO 120
<211> LENGTH: 97
<212> TYPE: DNA
<213> ORGANISM: Artificial sequence
<220> FEATURE:
<223> OTHER INFORMATION: LA687

<400> SEQUENCE: 120

```
gttaaaacac accatttgaa tacatatgct acgtatccac tttagattta tcaaatacta        60
ccaactcacc ttggctaact cgttgtatca tcactgg                                  97
```

<210> SEQ ID NO 121
<211> LENGTH: 7555
<212> TYPE: DNA
<213> ORGANISM: Artificial
<220> FEATURE:
<223> OTHER INFORMATION: pRS423::PGAL1-cre

<400> SEQUENCE: 121

```
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg       120
ttggcgggtg tcggggctgg cttaactatg cggcatcaga gcagattgta ctgagagtgc       180
accataaatt cccgttttaa gagcttggtg agcgctagga gtcactgcca ggtatcgttt       240
gaacacggca ttagtcaggg aagtcataac acagtccttt ccgcaatttt ctttttccta       300
ttactcttgg cctcctctag tacactctat attttttat gcctcggtaa tgattttcat        360
tttttttttt cccctagcgg atgactcttt tttttcttta gcgattggca ttatcacata       420
atgaattata cattatataa agtaatgtga tttcttcgaa gaatatacta aaaaatgagc       480
aggcaagata aacgaaggca aagatgacag agcagaaagc cctagtaaag cgtattacaa       540
atgaaaccaa gattcagatt gcgatctctt taaagggtgg tcccctagcg atagagcact       600
cgatcttccc agaaaaagag gcagaagcag tagcagaaca ggccacacaa tcgcaagtga       660
ttaacgtcca cacaggtata gggtttctgg accatatgat acatgctctg gccaagcatt       720
ccggctggtc gctaatcgtt gagtgcattg gtgacttaca catagacgac catcacacca       780
ctgaagactg cgggattgct ctcggtcaag cttttaaaga ggccctactg gcgcgtggag       840
taaaaaggtt tggatcagga tttgcgcctt ggatgaggc actttccaga gcggtggtag        900
atctttcgaa caggccgtac gcagttgtcg aacttggttt gcaaagggag aaagtaggag       960
atctctcttg cgagatgatc ccgcattttc ttgaaagctt tgcagaggct agcagaatta      1020
ccctccacgt tgattgtctg cgaggcaaga atgatcatca ccgtagtgag agtgcgttca      1080
aggctcttgc ggttgccata agagaagcca cctcgcccaa tggtaccaac gatgttccct      1140
ccaccaaagg tgttcttatg tagtgacacc gattatttaa agctgcagca tacgatatat      1200
atacatgtgt atatatgtat acctatgaat gtcagtaagt atgtatacga acagtatgat      1260
```

-continued

```
actgaagatg acaaggtaat gcatcattct atacgtgtca ttctgaacga ggcgcgcttt    1320 cctttttct ttttgctttt tctttttttt tctcttgaac tcgacggatc tatgcggtgt     1380
gaaataccgc acagatgcgt aaggagaaaa taccgcatca ggaaattgta acgttaata    1440 ttttgttaaa attcgcgtta aatttttgtt aaatcagctc attttttaac caataggccg    1500
aaatcggcaa aatcccttat aaatcaaaag aatagaccga datagggttg agtgttgttc    1560
cagtttggaa caagagtcca ctattaaaga acgtggactc caacgtcaaa gggcgaaaaa    1620
ccgtctatca gggcgatggc ccactacgtg aaccatcacc ctaatcaagt ttttgggt     1680 cgaggtgccg taaagcacta atcggaacc ctaaagggag cccccgattt agagcttgac     1740
ggggaaagcc ggcgaacgtg gcgagaaagg aagggaagaa agcgaaagga gcgggcgcta    1800 gggcgctgg aagtgtagcg gtcacgctgc gcgtaaccac cacacccgcc gcgcttaatg     1860
cgccgctaca gggcgcgtcg cgccattcgc cattcaggct gcgcaactgt tgggaagggc    1920
gatcggtgcg ggcctcttcg ctattacgcc agctggcgaa aggggatgt gctgcaaggc    1980 gattaagttg ggtaacgcca gggttttccc agtcacgacg ttgtaaaacg acggccagtg    2040
agcgcgcgta atacgactca ctatagggcg aattgggtac cgggcccccc ctcgaggtcg    2100
acggtatcga taagcttgat tagaagccgc cgagcgggcg acagccctcc gacggaagac    2160
tctcctccgt gcgtcctcgt cttcaccggt cgcgttcctg aaacgcagat gtgcctcgcg    2220
ccgcactgct ccgaacaata aagattctac aatactagct tttatggtta tgaagaggaa    2280
aaattggcag taacctggcc ccacaaacct tcaaattaac gaatcaaatt aacaaccata    2340
ggatgataat gcgattagtt ttttagcctt atttctgggg taattaatca gcgaagcgat    2400
gatttttgat ctattaacag atatataaat ggaaaagctg cataaccact ttaactaata    2460 cttttcaacat tttcagtttg tattacttct tattcaaatg tcataaaagt atcaacaaaa    2520
aattgttaat atacctctat actttaacgt caaggagaaa aatgtccaat ttactgcccg    2580
tacaccaaaa tttgcctgca ttaccggtcg atgcaacgag tgatgaggtt cgcaagaacc    2640
tgatggacat gttcagggat cgccaggcgt tttctgagca tacctggaaa atgcttctgt    2700
ccgtttgccg gtcgtgggcg gcatggtgca agttgaataa ccggaaatgg tttcccgcag    2760
aacctgaaga tgttcgcgat tatcttctat atcttcaggc gcgcggtctg gcagtaaaaa    2820
ctatccagca acatttgggc cagctaaaca tgcttcatcg tcggtccggg ctgccacgac    2880
caagtgacag caatgctgtt tcactggtta tgcggcggat ccgaaaagaa aacgttgatg    2940
ccggtgaacg tgcaaaacag gctctagcgt tcgaacgcac tgatttcgac caggttcgtt    3000
cactcatgga aaatagcgat cgctgccagg atatacgtaa tctggcattt ctggggattg    3060
cttataacac cctgttacgt atagccgaaa ttgccaggat cagggttaaa gatatctcac    3120
gtactgacgg tgggagaatg ttaatccata ttggcagaac gaaaacgctg gttagcaccg    3180
caggtgtaga gaaggcactt agcctggggg taactaaact ggtcgagcga tggatttccg    3240
tctctggtgt agctgatgat ccgaataact acctgttttg ccgggtcaga aaaaatggtg    3300
ttgccgcgcc atctgccacc agccagctat caactcgcgc cctggaaggg atttttgaag    3360
caactcatcg attgatttac ggcgctaagg atgactctgg tcagagatac ctggcctggt    3420
ctggacacag tgcccgtgtc ggagccgcgc gagatatggc ccgcgctgga gtttcaatac    3480
cggagatcat gcaagctggt ggctggacca atgtaaatat tgtcatgaac tatatccgta    3540
acctggatag tgaaacaggg gcaatggtgc gcctgctgga agatggcgat taggagtaag    3600
```

```
cgaatttctt atgatttatg attttttatta ttaaataagt tataaaaaaa ataagtgtat    3660
acaaatttta aagtgactct taggttttaa aacgaaaatt cttattcttg agtaactctt    3720
tcctgtaggt caggttgctt tctcaggtat agcatgaggt cgctcttatt gaccacacct    3780
ctaccggcat gccgagcaaa tgcctgcaaa tcgctcccca tttcacccaa ttgtagatat    3840
gctaactcca gcaatgagtt gatgaatctc ggtgtgtatt ttatgtcctc agaggacaac    3900
acctgtggtg ttctagagcg gccgccaccg cggtggagct ccagcttttg ttccctttag    3960
tgagggttaa ttgcgcgctt ggcgtaatca tggtcatagc tgtttcctgt gtgaaattgt    4020
tatccgctca caattccaca acatagga gccggaagca taaagtgtaa agcctggggt      4080
gcctaatgag tgaggtaact cacattaatt gcgttgcgct cactgcccgc tttccagtcg    4140
ggaaacctgt cgtgccagct gcattaatga atcggccaac gcgcggggag aggcggtttg    4200
cgtattgggc gctcttccgc ttcctcgctc actgactcgc tgcgctcggt cgttcggctg    4260
cggcgagcgg tatcagctca ctcaaaggcg gtaatacggt tatccacaga atcaggggat    4320
aacgcaggaa agaacatgtg agcaaaaggc cagcaaaagg ccaggaaccg taaaaaggcc    4380
gcgttgctgg cgtttttcca taggctccgc cccctgacg agcatcacaa aaatcgacgc    4440
tcaagtcaga ggtggcgaaa cccgacagga ctataaagat accaggcgtt ccccctgga    4500 agctccctcg tgcgctctcc tgttccgacc ctgccgctta ccggatacct gtccgccttt    4560
ctcccttcgg gaagcgtggc gctttctcat agctcacgct gtaggtatct cagttcggtg    4620
taggtcgttc gctccaagct gggctgtgtg cacgaacccc ccgttcagcc cgaccgctgc    4680
gccttatccg gtaactatcg tcttgagtcc aacccggtaa gacacgactt atcgccactg    4740
gcagcagcca ctggtaacag gattagcaga gcgaggtatg taggcggtgc tacagagttc    4800
ttgaagtggt ggcctaacta cggctacact agaaggacag tatttggtat ctgcgctctg    4860
ctgaagccag ttaccttcgg aaaaagagtt ggtagctctt gatccggcaa acaaaccacc    4920
gctggtagcg gtggtttttt tgtttgcaag cagcagatta cgcgcagaaa aaaggatct    4980 caagaagatc ctttgatctt ttctacgggg tctgacgctc agtggaacga aaactcacgt    5040
taagggattt tggtcatgag attatcaaaa aggatcttca cctagatcct ttttaaatta    5100
aaatgaagtt ttaaatcaat ctaaagtata tatgagtaaa cttggtctga cagttaccaa    5160
tgcttaatca gtgaggcacc tatctcagcg atctgtctat ttcgttcatc catagttgcc    5220
tgactccccg tcgtgtagat aactacgata cgggagggct taccatctgg ccccagtgct    5280
gcaatgatac cgcgagaccc acgctcaccg gctccagatt tatcagcaat aaaccagcca    5340
gccggaaggg ccgagcgcag aagtggtcct gcaactttat ccgcctccat ccagtctatt    5400
aattgttgcc gggaagctag agtaagtagt tcgccagtta atagtttgcg caacgttgtt    5460
gccattgcta caggcatcgt ggtgtcacgc tcgtcgtttg gtatggcttc attcagctcc    5520
ggttcccaac gatcaaggcg agttacatga tcccccatgt tgtgcaaaaa agcggttagc    5580
tccttcggtc ctccgatcgt tgtcagaagt aagttggccg cagtgttatc actcatggtt    5640
atggcagcac tgcataattc tcttactgtc atgccatccg taagatgctt ttctgtgact    5700
ggtgagtact caaccaagtc attctgagaa tagtgtatgc ggcgaccgag ttgctcttgc    5760
ccggcgtcaa tacgggataa taccgcgcca catagcagaa ctttaaaagt gctcatcatt    5820
ggaaaacgtt cttcggggcg aaaactctca aggatcttac cgctgttgag atccagttcg    5880
atgtaaccca ctcgtgcacc caactgatct tcagcatctt ttactttcac cagcgtttct    5940
gggtgagcaa aaacaggaag gcaaaatgcc gcaaaaaagg gaataagggc gacacggaaa    6000
```

```
tgttgaatac tcatactctt ccttttcaa tattattgaa gcattatca gggttattgt    6060
ctcatgagcg gatacatatt tgaatgtatt tagaaaaata aacaaatagg ggttccgcgc    6120
acatttcccc gaaaagtgcc acctgaacga agcatctgtg cttcattttg tagaacaaaa    6180
atgcaacgcg agagcgctaa ttttcaaac aaagaatctg agctgcattt ttacagaaca    6240
gaaatgcaac gcgaaagcgc tattttacca acgaagaatc tgtgcttcat ttttgtaaaa    6300
caaaatgca acgcgagagc gctaattttt caaacaaaga atctgagctg cattttaca    6360
gaacagaaat gcaacgcgag agcgctattt taccaacaaa gaatctatac ttctttttg    6420
ttctacaaaa atgcatcccg agagcgctat ttttctaaca aagcatctta gattactttt    6480
tttctccttt gtgcgctcta taatgcagtc tcttgataac ttttgcact gtaggtccgt    6540
taaggttaga agaaggctac tttggtgtct attttctctt ccataaaaaa agcctgactc    6600
cacttcccgc gttactgat tactagcgaa gctgcgggtg catttttca agataaaggc    6660
atccccgatt atattctata ccgatgtgga ttgcgcatac tttgtgaaca gaaagtgata    6720
gcgttgatga ttcttcattg gtcagaaaat tatgaacggt ttcttctatt ttgtctctat    6780
atactacgta taggaaatgt ttacattttc gtattgtttt cgattcactc tatgaatagt    6840
tcttactaca attttttgt ctaaagagta atactagaga taaacataaa aaatgtagag    6900
gtcgagttta gatgcaagtt caaggagcga aaggtggatg ggtaggttat atagggatat    6960
agcacagaga tatatagcaa agagatactt ttgagcaatg tttgtggaag cggtattcgc    7020
aatatttag tagctcgtta cagtccggtg cgttttggt ttttgaaag tgcgtcttca    7080
gagcgctttt ggttttcaaa agcgctctga agttcctata ctttctagag aataggaact    7140
tcggaatagg aacttcaaag cgtttccgaa aacgagcgct tccgaaatg caacgcgagc    7200
tgcgcacata cagctcactg ttcacgtcgc acctatatct gcgtgttgcc tgtatatata    7260
tatacatgag aagaacggca tagtgcgtgt ttatgcttaa atgcgtactt atatgcgtct    7320
atttatgtag gatgaaaggt agtctagtac ctcctgtgat attatcccat tccatgcggg    7380
gtatcgtatg cttccttcag cactacccctt tagctgttct atatgctgcc actcctcaat    7440
tggattagtc tcatccttca atgctatcat ttcctttgat attggatcat ctaagaaacc    7500
attattatca tgacattaac ctataaaaat aggcgtatca cgaggcccctt tcgtc         7555
```

<210> SEQ ID NO 122
<211> LENGTH: 30
<212> TYPE: DNA
<213> ORGANISM: Artificial Sequence
<220> FEATURE:
<223> OTHER INFORMATION: Primer T001

<400> SEQUENCE: 122
tcaaggtacc atggcaagtt cgggcacaac                                      30

<210> SEQ ID NO 123
<211> LENGTH: 32
<212> TYPE: DNA
<213> ORGANISM: Artificial Sequence
<220> FEATURE:
<223> OTHER INFORMATION: Primer T002

<400> SEQUENCE: 123
taacgcggcc gcttattccc ccaccatttc ag                                   32

<210> SEQ ID NO 124

```
<211> LENGTH: 36
<212> TYPE: DNA
<213> ORGANISM: Artificial Sequence
<220> FEATURE:
<223> OTHER INFORMATION: Primer T003

<400> SEQUENCE: 124
atcattgcat gcgcctactt ggcttcacat acgttg                        36

<210> SEQ ID NO 125
<211> LENGTH: 28
<212> TYPE: DNA
<213> ORGANISM: Artificial Sequence
<220> FEATURE:
<223> OTHER INFORMATION: Primer T004

<400> SEQUENCE: 125
catggtacct tgaatatgta ttacttgg                                 28

<210> SEQ ID NO 126
<211> LENGTH: 36
<212> TYPE: DNA
<213> ORGANISM: Artificial Sequence
<220> FEATURE:
<223> OTHER INFORMATION: Primer T005

<400> SEQUENCE: 126
ataagcggcc gcgttaattc aaattaattg atatag                        36

<210> SEQ ID NO 127
<211> LENGTH: 36
<212> TYPE: DNA
<213> ORGANISM: Artificial Sequence
<220> FEATURE:
<223> OTHER INFORMATION: Primer T006

<400> SEQUENCE: 127
ttagattgga tcccgcgaac tccaaaatga gctatc                        36

<210> SEQ ID NO 128
<211> LENGTH: 94
<212> TYPE: DNA
<213> ORGANISM: Artificial Sequence
<220> FEATURE:
<223> OTHER INFORMATION: Primer T007

<400> SEQUENCE: 128
atgagagctt tggcatattt caagaagggt gatattcact tcactaatga tatccctagg  60
ccaggcctac ttggcttcac atacgttgca tacg                          94

<210> SEQ ID NO 129
<211> LENGTH: 91
<212> TYPE: DNA
<213> ORGANISM: Artificial Sequence
<220> FEATURE:
<223> OTHER INFORMATION: Primer T008

<400> SEQUENCE: 129
ttacttcatt tcaccgtgat tgttaggcgt caatagaatc ttaacgttgg attccttgtg  60
caccttggct aactcgttgt atcatcactg g                             91

<210> SEQ ID NO 130
<211> LENGTH: 2064
<212> TYPE: DNA
<213> ORGANISM: Saccharomyces cerevisiae
```

<400> SEQUENCE: 130

```
atgatcagac aatctacgct aaaaaacttc gctattaagc gttgctttca acatatagca      60
taccgcaaca cacctgccat gagatcagta gctctcgcgc agcgcttttta tagttcgtct    120
tcccgttatt acagtgcgtc tccattacca gcctctaaaa ggccagagcc tgctccaagt    180
ttcaatgttg atccattaga acagcccgct gaaccttcaa aattggctaa gaaactacgc    240
gctgagcctg acatggatac ctctttcgtc ggtttaactg gtggtcaaat atttaacgaa    300
atgatgtcca gacaaaacgt tgatactgta tttggttatc caggtggtgc tatcctacct    360
gtttacgatg ccattcataa cagtgataaa ttcaacttcg ttcttccaaa acacgaacaa    420
ggtgccggtc acatggcaga aggctacgcc agagcttctg gtaaaccagg tgttgtcttg    480
gttacttctg gccaggtgc caccaatgtc gttactccaa tggcagatgc ctttgcagac    540
gggattccaa tggttgtctt tacagggcaa gtcccaacta gtgctatcgg tactgatgct    600
ttccaagagg ctgacgtcgt tggtatttct agatcttgta cgaaatggaa tgtcatggtc    660
aagtccgtgg aagaattgcc attgcgtatt aacgaggctt ttgaaattgc cacgagcggt    720
agaccgggac cagtcttggt cgatttacca aaggatgtta cagcagctat cttaagaaat    780
ccaattccaa caaaaacaac tcttccatca aacgcactaa accaattaac cagtcgcgca    840
caagatgaat tgtcatgca agtatcaat aaagcagcag atttgatcaa cttggcaaag    900
aaacctgtct tatacgtcgg tgctggtatt ttaaaccatg cagatggtcc aagattacta    960
aaagaattaa gtgaccgtgc tcaaatacct gtcaccacta ctttacaagg tttaggttca   1020
ttcgaccaag aagatccaaa atcattggat atgcttggta tgcacggttg tgctactgcc   1080
aacctggcag tgcaaaatgc cgacttgata attgcagttg gtgctagatt cgacgaccgt   1140
gtcactggta atatttctaa attcgctcca gaagctcgtc gtgcagctgc cgagggtaga   1200
ggtggtatta ttcatttcga ggttagtcca aaaaacataa acaaggttgt tcaaactcaa   1260
atagcagtgg aaggtgatgc tacgaccaat ctgggcaaaa tgatgtcaaa gattttccca   1320
gttaaggaga ggtctgaatg gtttgctcaa ataaatagat ggaagaagga atacccatac   1380
gcttatatgg aggagactcc aggatctaaa attaaaccac agacggttat aaagaaacta   1440
tccaaggttg ccaacgacac aggaagacat gtcattgtta caacgggtgt ggggcaacat   1500
caaatgtggg ctgctcaaca ctggacatgg agaaatccac atactttcat cacatcaggt   1560
ggtttaggta cgatgggtta cggtctccct gccgccatcg gtgctcaagt tgcaaagcca   1620
gaatctttgg ttattgacat tgatggtgac gcatccttta catgactct aacggaattg   1680
agttctgccg ttcaagctgg tactccagtg aagattttga ttttgaacaa tgaagagcaa   1740
ggtatggtta ctcaatggca atccctgttc tacgaacatc gttattccca cacacatcaa   1800
ttgaaccctg atttcataaa actagcggag gctatgggtt taaaaggttt aagagtcaag   1860
aagcaagagg aattggacgc taagttgaaa gaattcgttt ctaccaaggg cccagttttg   1920
cttgaagtgg aagttgataa aaaagttcct gttttgccaa tggtggcagg tggtagcggt   1980
ctagacgagt tcataaattt tgacccagaa gttgaaagac aacagactga attacgtcat   2040
aagcgtacag gcggtaagca ctga                                          2064
```

<210> SEQ ID NO 131
<211> LENGTH: 687
<212> TYPE: PRT
<213> ORGANISM: Saccharomyces cerevisiae

```
<400> SEQUENCE: 131

Met Ile Arg Gln Ser Thr Leu Lys Asn Phe Ala Ile Lys Arg Cys Phe
1               5                   10                  15

Gln His Ile Ala Tyr Arg Asn Thr Pro Ala Met Arg Ser Val Ala Leu
            20                  25                  30

Ala Gln Arg Phe Tyr Ser Ser Ser Arg Tyr Tyr Ser Ala Ser Pro
        35                  40                  45

Leu Pro Ala Ser Lys Arg Pro Glu Pro Ala Pro Ser Phe Asn Val Asp
    50                  55                  60

Pro Leu Glu Gln Pro Ala Glu Pro Ser Lys Leu Ala Lys Lys Leu Arg
65                  70                  75                  80

Ala Glu Pro Asp Met Asp Thr Ser Phe Val Gly Leu Thr Gly Gly Gln
                85                  90                  95

Ile Phe Asn Glu Met Met Ser Arg Gln Asn Val Asp Thr Val Phe Gly
                100                 105                 110

Tyr Pro Gly Gly Ala Ile Leu Pro Val Tyr Asp Ala Ile His Asn Ser
            115                 120                 125

Asp Lys Phe Asn Phe Val Leu Pro Lys His Glu Gln Gly Ala Gly His
    130                 135                 140

Met Ala Glu Gly Tyr Ala Arg Ala Ser Gly Lys Pro Gly Val Val Leu
145                 150                 155                 160

Val Thr Ser Gly Pro Gly Ala Thr Asn Val Val Thr Pro Met Ala Asp
                165                 170                 175

Ala Phe Ala Asp Gly Ile Pro Met Val Val Phe Thr Gly Gln Val Pro
                180                 185                 190

Thr Ser Ala Ile Gly Thr Asp Ala Phe Gln Glu Ala Asp Val Val Gly
            195                 200                 205

Ile Ser Arg Ser Cys Thr Lys Trp Asn Val Met Val Lys Ser Val Glu
    210                 215                 220

Glu Leu Pro Leu Arg Ile Asn Glu Ala Phe Glu Ile Ala Thr Ser Gly
225                 230                 235                 240

Arg Pro Gly Pro Val Leu Val Asp Leu Pro Lys Asp Val Thr Ala Ala
                245                 250                 255

Ile Leu Arg Asn Pro Ile Pro Thr Lys Thr Thr Leu Pro Ser Asn Ala
                260                 265                 270

Leu Asn Gln Leu Thr Ser Arg Ala Gln Asp Glu Phe Val Met Gln Ser
            275                 280                 285

Ile Asn Lys Ala Ala Asp Leu Ile Asn Leu Ala Lys Lys Pro Val Leu
    290                 295                 300

Tyr Val Gly Ala Gly Ile Leu Asn His Ala Asp Gly Pro Arg Leu Leu
305                 310                 315                 320

Lys Glu Leu Ser Asp Arg Ala Gln Ile Pro Val Thr Thr Thr Leu Gln
                325                 330                 335

Gly Leu Gly Ser Phe Asp Gln Glu Asp Pro Lys Ser Leu Asp Met Leu
                340                 345                 350

Gly Met His Gly Cys Ala Thr Ala Asn Leu Ala Val Gln Asn Ala Asp
            355                 360                 365

Leu Ile Ile Ala Val Gly Ala Arg Phe Asp Asp Arg Val Thr Gly Asn
    370                 375                 380

Ile Ser Lys Phe Ala Pro Glu Ala Arg Arg Ala Ala Ala Glu Gly Arg
385                 390                 395                 400

Gly Gly Ile Ile His Phe Glu Val Ser Pro Lys Asn Ile Asn Lys Val
                405                 410                 415
```

```
Val Gln Thr Gln Ile Ala Val Glu Gly Asp Ala Thr Asn Leu Gly
            420                 425                 430

Lys Met Met Ser Lys Ile Phe Pro Val Lys Glu Arg Ser Glu Trp Phe
            435                 440                 445

Ala Gln Ile Asn Lys Trp Lys Lys Glu Tyr Pro Tyr Ala Tyr Met Glu
        450                 455                 460

Glu Thr Pro Gly Ser Lys Ile Lys Pro Gln Thr Val Ile Lys Lys Leu
465                 470                 475                 480

Ser Lys Val Ala Asn Asp Thr Gly Arg His Val Ile Val Thr Thr Gly
                485                 490                 495

Val Gly Gln His Gln Met Trp Ala Ala Gln His Trp Thr Trp Arg Asn
                500                 505                 510

Pro His Thr Phe Ile Thr Ser Gly Gly Leu Gly Thr Met Gly Tyr Gly
            515                 520                 525

Leu Pro Ala Ala Ile Gly Ala Gln Val Ala Lys Pro Glu Ser Leu Val
            530                 535                 540

Ile Asp Ile Asp Gly Asp Ala Ser Phe Asn Met Thr Leu Thr Glu Leu
545                 550                 555                 560

Ser Ser Ala Val Gln Ala Gly Thr Pro Val Lys Ile Leu Ile Leu Asn
                565                 570                 575

Asn Glu Glu Gln Gly Met Val Thr Gln Trp Gln Ser Leu Phe Tyr Glu
            580                 585                 590

His Arg Tyr Ser His Thr His Gln Leu Asn Pro Asp Phe Ile Lys Leu
            595                 600                 605

Ala Glu Ala Met Gly Leu Lys Gly Leu Arg Val Lys Lys Gln Glu Glu
            610                 615                 620

Leu Asp Ala Lys Leu Lys Glu Phe Val Ser Thr Lys Gly Pro Val Leu
625                 630                 635                 640

Leu Glu Val Glu Val Asp Lys Lys Val Pro Val Leu Pro Met Val Ala
                645                 650                 655

Gly Gly Ser Gly Leu Asp Glu Phe Ile Asn Phe Asp Pro Glu Val Glu
            660                 665                 670

Arg Gln Gln Thr Glu Leu Arg His Lys Arg Thr Gly Gly Lys His
            675                 680                 685

<210> SEQ ID NO 132
<211> LENGTH: 1689
<212> TYPE: DNA
<213> ORGANISM: Escherichia coli

<400> SEQUENCE: 132
atggcaagtt cgggcacaac atcgacgcgt aagcgcttta ccggcgcaga atttatcgtt     60
catttcctgg aacagcaggg cattaagatt gtgacaggca ttccgggcgg ttctatcctg    120
cctgtttacg atgccttaag ccaaagcacg caaatccgcc atattctggc ccgtcatgaa    180
cagggcgcgg gctttatcgc tcagggaatg gcgcgcaccg acgtaaaacc ggcggtctgt    240
atggcctgta gcggaccggg tgcgactaac ctggtgaccg ccattgccga tgcgcggctg    300
gactccatcc cgctgatttg catcactggt caggttcccg cctcgatgat cggcaccgac    360
gccttccagg aagtggacac ctacggcatc tctatcccca tcaccaaaca caactatctg    420
gtcagacata tcgaagaact cccgcaggtc atgagcgatg ccttccgcat tgcgcaatca    480
ggccgcccag gccggtgtg gatagacatt cctaaggatg tgcaaacggc agttttgag     540 attgaaacac agcccgctat ggcagaaaaa gccgccgccc ccgcctttag cgaagaaagc    600
```

```
attcgtgacg cagcggcgat gattaacgct gccaaacgcc cggtgctttta tctgggcggc    660
ggtgtgatca atgcgcccgc acgggtgcgt gaactggcgg agaaagcgca actgcctacc    720
accatgactt taatggcgct gggcatgttg ccaaaagcgc atccgttgtc gctgggtatg    780
ctggggatgc acggcgtgcg cagcaccaac tatattttgc aggaggcgga tttgttgata    840
gtgctcggtg cgcgttttga tgaccgggcg attggcaaaa ccgagcagtt ctgtccgaat    900
gccaaaatca ttcatgtcga tatcgaccgt gcagagctgg gtaaaatcaa gcagccgcac    960
gtggcgattc aggcggatgt tgatgacgtg ctggcgcagt tgatcccgct ggtggaagcg   1020
caaccgcgtg cagagtggca ccagttggta gcggatttgc agcgtgagtt ccgtgtcca   1080
atcccgaaag cgtgcgatcc gttaagccat tacggcctga tcaacgccgt tgccgcctgt   1140
gtcgatgaca atgcaattat caccaccgac gttggtcagc atcagatgtg gaccgcgcaa   1200
gcttatccgc tcaatcgccc acgccagtgg ctgacctccg gtgggctggg cacgatgggt   1260
tttggcctgc ctgcggcgat tggcgctgcg ctggcgaacc cggatcgcaa agtgttgtgt   1320
ttctccggcg acggcagcct gatgatgaat attcaggaga tggcgaccgc cagtgaaaat   1380
cagctggatg tcaaaatcat tctgatgaac aacgaagcgc tggggctggt gcatcagcaa   1440
cagagtctgt tctacgagca aggcgttttt gccgccacct atccgggcaa aatcaacttt   1500
atgcagattg ccgccggatt cggcctcgaa acctgtgatt tgaataacga agccgatccg   1560
caggcttcat tgcaggaaat catcaatcgc cctggcccgg cgctgatcca tgtgcgcatt   1620
gatgccgaag aaaaagttta cccgatggtg ccgccaggtg cggcgaatac tgaaatggtg   1680
ggggaataa                                                          1689
```

<210> SEQ ID NO 133
<211> LENGTH: 562
<212> TYPE: PRT
<213> ORGANISM: Escherichia coli

<400> SEQUENCE: 133

Met Ala Ser Ser Gly Thr Thr Ser Thr Arg Lys Arg Phe Thr Gly Ala
1               5                   10                  15

Glu Phe Ile Val His Phe Leu Glu Gln Gln Gly Ile Lys Ile Val Thr
            20                  25                  30

Gly Ile Pro Gly Gly Ser Ile Leu Pro Val Tyr Asp Ala Leu Ser Gln
        35                  40                  45

Ser Thr Gln Ile Arg His Ile Leu Ala Arg His Glu Gln Gly Ala Gly
    50                  55                  60

Phe Ile Ala Gln Gly Met Ala Arg Thr Asp Gly Lys Pro Ala Val Cys
65                  70                  75                  80

Met Ala Cys Ser Gly Pro Gly Ala Thr Asn Leu Val Thr Ala Ile Ala
                85                  90                  95

Asp Ala Arg Leu Asp Ser Ile Pro Leu Ile Cys Ile Thr Gly Gln Val
            100                 105                 110

Pro Ala Ser Met Ile Gly Thr Asp Ala Phe Gln Glu Val Asp Thr Tyr
        115                 120                 125

Gly Ile Ser Ile Pro Ile Thr Lys His Asn Tyr Leu Val Arg His Ile
    130                 135                 140

Glu Glu Leu Pro Gln Val Met Ser Asp Ala Phe Arg Ile Ala Gln Ser
145                 150                 155                 160

Gly Arg Pro Gly Pro Val Trp Ile Asp Ile Pro Lys Asp Val Gln Thr
                165                 170                 175

Ala Val Phe Glu Ile Glu Thr Gln Pro Ala Met Ala Glu Lys Ala Ala
            180                 185                 190

Ala Pro Ala Phe Ser Glu Glu Ser Ile Arg Asp Ala Ala Ala Met Ile
        195                 200                 205

Asn Ala Ala Lys Arg Pro Val Leu Tyr Leu Gly Gly Val Ile Asn
210                 215                 220

Ala Pro Ala Arg Val Arg Glu Leu Ala Glu Lys Ala Gln Leu Pro Thr
225                 230                 235                 240

Thr Met Thr Leu Met Ala Leu Gly Met Leu Pro Lys Ala His Pro Leu
                245                 250                 255

Ser Leu Gly Met Leu Gly Met His Gly Val Arg Ser Thr Asn Tyr Ile
            260                 265                 270

Leu Gln Glu Ala Asp Leu Leu Ile Val Leu Gly Ala Arg Phe Asp Asp
        275                 280                 285

Arg Ala Ile Gly Lys Thr Glu Gln Phe Cys Pro Asn Ala Lys Ile Ile
290                 295                 300

His Val Asp Ile Asp Arg Ala Glu Leu Gly Lys Ile Lys Gln Pro His
305                 310                 315                 320

Val Ala Ile Gln Ala Asp Val Asp Val Leu Ala Gln Leu Ile Pro
                325                 330                 335

Leu Val Glu Ala Gln Pro Arg Ala Glu Trp His Gln Leu Val Ala Asp
            340                 345                 350

Leu Gln Arg Glu Phe Pro Cys Pro Ile Pro Lys Ala Cys Asp Pro Leu
        355                 360                 365

Ser His Tyr Gly Leu Ile Asn Ala Val Ala Ala Cys Val Asp Asp Asn
370                 375                 380

Ala Ile Ile Thr Thr Asp Val Gly Gln His Gln Met Trp Thr Ala Gln
385                 390                 395                 400

Ala Tyr Pro Leu Asn Arg Pro Arg Gln Trp Leu Thr Ser Gly Gly Leu
                405                 410                 415

Gly Thr Met Gly Phe Gly Leu Pro Ala Ala Ile Gly Ala Ala Leu Ala
            420                 425                 430

Asn Pro Asp Arg Lys Val Leu Cys Phe Ser Gly Asp Gly Ser Leu Met
        435                 440                 445

Met Asn Ile Gln Glu Met Ala Thr Ala Ser Glu Asn Gln Leu Asp Val
450                 455                 460

Lys Ile Ile Leu Met Asn Asn Glu Ala Leu Gly Leu Val His Gln Gln
465                 470                 475                 480

Gln Ser Leu Phe Tyr Glu Gln Gly Val Phe Ala Ala Thr Tyr Pro Gly
                485                 490                 495

Lys Ile Asn Phe Met Gln Ile Ala Ala Gly Phe Gly Leu Glu Thr Cys
            500                 505                 510

Asp Leu Asn Asn Glu Ala Asp Pro Gln Ala Ser Leu Gln Glu Ile Ile
        515                 520                 525

Asn Arg Pro Gly Pro Ala Leu Ile His Val Arg Ile Asp Ala Glu Glu
530                 535                 540

Lys Val Tyr Pro Met Val Pro Pro Gly Ala Ala Asn Thr Glu Met Val
545                 550                 555                 560

Gly Glu

<210> SEQ ID NO 134
<211> LENGTH: 338
<212> TYPE: PRT

<213> ORGANISM: Pseudomonas fluorescens

<400> SEQUENCE: 134

| | | | | | | | | | | | | | | | |
|---|---|---|---|---|---|---|---|---|---|---|---|---|---|---|---|
| Met | Lys | Val | Phe | Tyr | Asp | Lys | Asp | Cys | Asp | Leu | Ser | Ile | Ile | Gln | Gly |
| 1 | | | | 5 | | | | 10 | | | | | 15 | | |
| Lys | Lys | Val | Ala | Ile | Ile | Gly | Tyr | Gly | Ser | Gln | Gly | His | Ala | Gln | Ala |
| | | | 20 | | | | | 25 | | | | | 30 | | |
| Cys | Asn | Leu | Lys | Asp | Ser | Gly | Val | Asp | Val | Thr | Val | Gly | Leu | Arg | Lys |
| | | | 35 | | | | | 40 | | | | | 45 | | |
| Gly | Ser | Ala | Thr | Val | Ala | Lys | Ala | Glu | Ala | His | Gly | Leu | Lys | Val | Thr |
| | 50 | | | | | 55 | | | | | 60 | | | | |
| Asp | Val | Ala | Ala | Val | Ala | Gly | Ala | Asp | Leu | Val | Met | Ile | Leu | Thr |
| 65 | | | | | 70 | | | | 75 | | | | | 80 |
| Pro | Asp | Glu | Phe | Gln | Ser | Gln | Leu | Tyr | Lys | Asn | Glu | Ile | Glu | Pro | Asn |
| | | | | 85 | | | | | 90 | | | | | 95 | |
| Ile | Lys | Lys | Gly | Ala | Thr | Leu | Ala | Phe | Ser | His | Gly | Phe | Ala | Ile | His |
| | | | 100 | | | | | 105 | | | | | 110 | | |
| Tyr | Asn | Gln | Val | Val | Pro | Arg | Ala | Asp | Leu | Asp | Val | Ile | Met | Ile | Ala |
| | | | 115 | | | | | 120 | | | | | 125 | | |
| Pro | Lys | Ala | Pro | Gly | His | Thr | Val | Arg | Ser | Glu | Phe | Val | Lys | Gly | Gly |
| | 130 | | | | | 135 | | | | | 140 | | | | |
| Gly | Ile | Pro | Asp | Leu | Ile | Ala | Ile | Tyr | Gln | Asp | Ala | Ser | Gly | Asn | Ala |
| 145 | | | | | 150 | | | | | 155 | | | | | 160 |
| Lys | Asn | Val | Ala | Leu | Ser | Tyr | Ala | Ala | Gly | Val | Gly | Gly | Gly | Arg | Thr |
| | | | | 165 | | | | | 170 | | | | | 175 | |
| Gly | Ile | Ile | Glu | Thr | Thr | Phe | Lys | Asp | Glu | Thr | Glu | Thr | Asp | Leu | Phe |
| | | | 180 | | | | | 185 | | | | | 190 | | |
| Gly | Glu | Gln | Ala | Val | Leu | Cys | Gly | Gly | Thr | Val | Glu | Leu | Val | Lys | Ala |
| | | | 195 | | | | | 200 | | | | | 205 | | |
| Gly | Phe | Glu | Thr | Leu | Val | Glu | Ala | Gly | Tyr | Ala | Pro | Glu | Met | Ala | Tyr |
| | 210 | | | | | 215 | | | | | 220 | | | | |
| Phe | Glu | Cys | Leu | His | Glu | Leu | Lys | Leu | Ile | Val | Asp | Leu | Met | Tyr | Glu |
| 225 | | | | | 230 | | | | | 235 | | | | | 240 |
| Gly | Gly | Ile | Ala | Asn | Met | Asn | Tyr | Ser | Ile | Ser | Asn | Ala | Glu | Tyr |
| | | | | 245 | | | | | 250 | | | | | 255 | |
| Gly | Glu | Tyr | Val | Thr | Gly | Pro | Glu | Val | Ile | Asn | Ala | Glu | Ser | Arg | Gln |
| | | | 260 | | | | | 265 | | | | | 270 | | |
| Ala | Met | Arg | Asn | Ala | Leu | Lys | Arg | Ile | Gln | Asp | Gly | Glu | Tyr | Ala | Lys |
| | | | 275 | | | | | 280 | | | | | 285 | | |
| Met | Phe | Ile | Ser | Glu | Gly | Ala | Thr | Gly | Tyr | Pro | Ser | Met | Thr | Ala | Lys |
| | 290 | | | | | 295 | | | | | 300 | | | | |
| Arg | Arg | Asn | Asn | Ala | Ala | His | Gly | Ile | Glu | Ile | Ile | Gly | Glu | Gln | Leu |
| 305 | | | | | 310 | | | | | 315 | | | | | 320 |
| Arg | Ser | Met | Met | Pro | Trp | Ile | Gly | Ala | Asn | Lys | Ile | Val | Asp | Lys | Ala |
| | | | | 325 | | | | | 330 | | | | | 335 | |
| Lys | Asn | | | | | | | | | | | | | | |

<210> SEQ ID NO 135
<211> LENGTH: 571
<212> TYPE: PRT
<213> ORGANISM: Streptococcus mutans

<400> SEQUENCE: 135

| | | | | | | | | | | | | | | | |
|---|---|---|---|---|---|---|---|---|---|---|---|---|---|---|---|
| Met | Thr | Asp | Lys | Lys | Thr | Leu | Lys | Asp | Leu | Arg | Asn | Arg | Ser | Ser | Val |
| 1 | | | | 5 | | | | 10 | | | | | 15 | | |

-continued

```
Tyr Asp Ser Met Val Lys Ser Pro Asn Arg Ala Met Leu Arg Ala Thr
             20                  25                  30
Gly Met Gln Asp Glu Asp Phe Glu Lys Pro Ile Val Gly Val Ile Ser
             35                  40                  45
Thr Trp Ala Glu Asn Thr Pro Cys Asn Ile His Leu His Asp Phe Gly
 50                  55                  60
Lys Leu Ala Lys Val Gly Val Lys Glu Ala Gly Ala Trp Pro Val Gln
 65                  70                  75                  80
Phe Gly Thr Ile Thr Val Ser Asp Gly Ile Ala Met Gly Thr Gln Gly
                 85                  90                  95
Met Arg Phe Ser Leu Thr Ser Arg Asp Ile Ile Ala Asp Ser Ile Glu
            100                 105                 110
Ala Ala Met Gly Gly His Asn Ala Asp Ala Phe Val Ala Ile Gly Gly
            115                 120                 125
Cys Asp Lys Asn Met Pro Gly Ser Val Ile Ala Met Ala Asn Met Asp
130                 135                 140
Ile Pro Ala Ile Phe Ala Tyr Gly Gly Thr Ile Ala Pro Gly Asn Leu
145                 150                 155                 160
Asp Gly Lys Asp Ile Asp Leu Val Ser Val Phe Glu Gly Val Gly His
                165                 170                 175
Trp Asn His Gly Asp Met Thr Lys Glu Glu Val Lys Ala Leu Glu Cys
            180                 185                 190
Asn Ala Cys Pro Gly Pro Gly Gly Cys Gly Gly Met Tyr Thr Ala Asn
            195                 200                 205
Thr Met Ala Thr Ala Ile Glu Val Leu Gly Leu Ser Leu Pro Gly Ser
210                 215                 220
Ser Ser His Pro Ala Glu Ser Ala Glu Lys Lys Ala Asp Ile Glu Glu
225                 230                 235                 240
Ala Gly Arg Ala Val Val Lys Met Leu Glu Met Gly Leu Lys Pro Ser
                245                 250                 255
Asp Ile Leu Thr Arg Glu Ala Phe Glu Asp Ala Ile Thr Val Thr Met
            260                 265                 270
Ala Leu Gly Gly Ser Thr Asn Ser Thr Leu His Leu Leu Ala Ile Ala
            275                 280                 285
His Ala Ala Asn Val Glu Leu Thr Leu Asp Asp Phe Asn Thr Phe Gln
290                 295                 300
Glu Lys Val Pro His Leu Ala Asp Leu Lys Pro Ser Gly Gln Tyr Val
305                 310                 315                 320
Phe Gln Asp Leu Tyr Lys Val Gly Gly Val Pro Ala Val Met Lys Tyr
                325                 330                 335
Leu Leu Lys Asn Gly Phe Leu His Gly Asp Arg Ile Thr Cys Thr Gly
            340                 345                 350
Lys Thr Val Ala Glu Asn Leu Lys Ala Phe Asp Asp Leu Thr Pro Gly
            355                 360                 365
Gln Lys Val Ile Met Pro Leu Glu Asn Pro Lys Arg Glu Asp Gly Pro
            370                 375                 380
Leu Ile Ile Leu His Gly Asn Leu Ala Pro Asp Gly Ala Val Ala Lys
385                 390                 395                 400
Val Ser Gly Val Lys Val Arg Arg His Val Gly Pro Ala Lys Val Phe
                405                 410                 415
Asn Ser Glu Glu Glu Ala Ile Glu Ala Val Leu Asn Asp Asp Ile Val
            420                 425                 430
```

```
Asp Gly Asp Val Val Val Arg Phe Val Gly Pro Lys Gly Gly Pro
            435                 440                 445

Gly Met Pro Glu Met Leu Ser Leu Ser Ser Met Ile Val Gly Lys Gly
450                 455                 460

Gln Gly Glu Lys Val Ala Leu Leu Thr Asp Gly Arg Phe Ser Gly Gly
465                 470                 475                 480

Thr Tyr Gly Leu Val Val Gly His Ile Ala Pro Glu Ala Gln Asp Gly
                485                 490                 495

Gly Pro Ile Ala Tyr Leu Gln Thr Gly Asp Ile Val Thr Ile Asp Gln
                500                 505                 510

Asp Thr Lys Glu Leu His Phe Asp Ile Ser Asp Glu Leu Lys His
            515                 520                 525

Arg Gln Glu Thr Ile Glu Leu Pro Pro Leu Tyr Ser Arg Gly Ile Leu
            530                 535                 540

Gly Lys Tyr Ala His Ile Val Ser Ser Ala Ser Arg Gly Ala Val Thr
545                 550                 555                 560

Asp Phe Trp Lys Pro Glu Glu Thr Gly Lys Lys
                565                 570

<210> SEQ ID NO 136
<211> LENGTH: 548
<212> TYPE: PRT
<213> ORGANISM: Listeria grayi

<400> SEQUENCE: 136

Met Tyr Thr Val Gly Gln Tyr Leu Val Asp Arg Leu Glu Glu Ile Gly
1               5                   10                  15

Ile Asp Lys Val Phe Gly Val Pro Gly Asp Tyr Asn Leu Thr Phe Leu
                20                  25                  30

Asp Tyr Ile Gln Asn His Glu Gly Leu Ser Trp Gln Gly Asn Thr Asn
            35                  40                  45

Glu Leu Asn Ala Ala Tyr Ala Ala Asp Gly Tyr Ala Arg Glu Arg Gly
        50                  55                  60

Val Ser Ala Leu Val Thr Thr Phe Gly Val Gly Glu Leu Ser Ala Ile
65                  70                  75                  80

Asn Gly Thr Ala Gly Ser Phe Ala Glu Gln Val Pro Val Ile His Ile
                85                  90                  95

Val Gly Ser Pro Thr Met Asn Val Gln Ser Asn Lys Lys Leu Val His
                100                 105                 110

His Ser Leu Gly Met Gly Asn Phe His Asn Phe Ser Glu Met Ala Lys
            115                 120                 125

Glu Val Thr Ala Ala Thr Thr Met Leu Thr Glu Glu Asn Ala Ala Ser
        130                 135                 140

Glu Ile Asp Arg Val Leu Glu Thr Ala Leu Leu Glu Lys Arg Pro Val
145                 150                 155                 160

Tyr Ile Asn Leu Pro Ile Asp Ile Ala His Lys Ala Ile Val Lys Pro
                165                 170                 175

Ala Lys Ala Leu Gln Thr Glu Lys Ser Ser Gly Glu Arg Glu Ala Gln
                180                 185                 190

Leu Ala Glu Ile Ile Leu Ser His Leu Glu Lys Ala Ala Gln Pro Ile
            195                 200                 205

Val Ile Ala Gly His Glu Ile Ala Arg Phe Gln Ile Arg Glu Arg Phe
        210                 215                 220

Glu Asn Trp Ile Asn Gln Thr Lys Leu Pro Val Thr Asn Leu Ala Tyr
225                 230                 235                 240
```

-continued

```
Gly Lys Gly Ser Phe Asn Glu Asn Glu His Phe Ile Gly Thr Tyr
            245                 250                 255
Tyr Pro Ala Phe Ser Asp Lys Asn Val Leu Asp Tyr Val Asp Asn Ser
        260                 265                 270
Asp Phe Val Leu His Phe Gly Lys Ile Ile Asp Asn Ser Thr Ser
    275                 280                 285
Ser Phe Ser Gln Gly Phe Lys Thr Glu Asn Thr Leu Thr Ala Ala Asn
290                 295                 300
Asp Ile Ile Met Leu Pro Asp Gly Ser Thr Tyr Ser Gly Ile Ser Leu
305                 310                 315                 320
Asn Gly Leu Leu Ala Glu Leu Glu Lys Leu Asn Phe Thr Phe Ala Asp
            325                 330                 335
Thr Ala Ala Lys Gln Ala Glu Leu Ala Val Phe Glu Pro Gln Ala Glu
        340                 345                 350
Thr Pro Leu Lys Gln Asp Arg Phe His Gln Ala Val Met Asn Phe Leu
    355                 360                 365
Gln Ala Asp Asp Val Leu Val Thr Glu Gln Gly Thr Ser Ser Phe Gly
370                 375                 380
Leu Met Leu Ala Pro Leu Lys Lys Gly Met Asn Leu Ile Ser Gln Thr
385                 390                 395                 400
Leu Trp Gly Ser Ile Gly Tyr Thr Leu Pro Ala Met Ile Gly Ser Gln
            405                 410                 415
Ile Ala Ala Pro Glu Arg Arg His Ile Leu Ser Ile Gly Asp Gly Ser
        420                 425                 430
Phe Gln Leu Thr Ala Gln Glu Met Ser Thr Ile Phe Arg Glu Lys Leu
    435                 440                 445
Thr Pro Val Ile Phe Ile Ile Asn Asn Asp Gly Tyr Thr Val Glu Arg
450                 455                 460
Ala Ile His Gly Glu Asp Glu Ser Tyr Asn Asp Ile Pro Thr Trp Asn
465                 470                 475                 480
Leu Gln Leu Val Ala Glu Thr Phe Gly Gly Asp Ala Glu Thr Val Asp
            485                 490                 495
Thr His Asn Val Phe Thr Glu Thr Asp Phe Ala Asn Thr Leu Ala Ala
        500                 505                 510
Ile Asp Ala Thr Pro Gln Lys Ala His Val Val Glu Val His Met Glu
    515                 520                 525
Gln Met Asp Met Pro Glu Ser Leu Arg Gln Ile Gly Leu Ala Leu Ser
530                 535                 540
Lys Gln Asn Ser
545

<210> SEQ ID NO 137
<211> LENGTH: 1641
<212> TYPE: DNA
<213> ORGANISM: Macrococcus caseolyticus

<400> SEQUENCE: 137
atgaaacaac gtatcgggca atacttgatc gatgccctac acgttaatgg tgtcgataag    60
atctttggag tcccaggtga tttcacttta gccttttgg acgatatcat aagacatgac    120
aacgtggaat gggtgggaaa tactaatgag ttgaacgccg cttacgccgc tgatggttac    180
gctagagtta atggattagc cgctgtatct accacttttg gggttggcga gttatctgct    240
gtgaatggta ttgctggaag ttacgcagag cgtgttcctg taatcaaaat ctcaggcggt    300
```

```
ccttcatcag ttgctcaaca agagggtaga tatgtccacc attcattggg tgaaggaatc    360
tttgattcat attcaaagat gtacgctcac ataaccgcaa caactacaat cttatccgtt    420
gacaacgcag tcgacgaaat tgatagagtt attcattgtg ctttgaagga aagaggcca     480 gtgcatattc atttgcctat tgacgtagcc ttaactgaga ttgaaatccc tcatgcacca    540
aaagtttaca cacgaatc ccagaacgtc gatgcttaca ttcaagctgt tgagaaaaag     600
ttaatgtctg caaacaacc agtaatcata gcaggtcatg aaatcaattc attcaagttg     660
cacgaacaac tggaacagtt tgtcaatcag acaaacatcc ctgttgcaca actttccttg    720
ggtaagtctg ctttcaatga agagaatgaa cattaccttg gtatctacga tggcaaaatc    780
gcaaaggaaa atgtgagaga gtacgtcgac aatgctgatg tcatattgaa cataggtgcc    840
aaactgactg attctgctac agctggattt tcctacaagt tcgatacaaa caacataatc    900
tacattaacc ataatgactt caaagctgaa gatgtgattt ctgataatgt ttcactgatt    960
gatcttgtga atggcctgaa ttctattgac tatagaaatg aaacacacta cccatcttat   1020
caaagatctg atatgaaata cgaattgaat gacgcaccac ttacacaatc taactatttc   1080
aaaatgatga acgcttttct agaaaaagat gacatcctac tagctgaaca aggtacatcc   1140
tttttcggcg catatgactt atccctatac aagggaaatc agtttatcgg tcagccttta   1200
tgggggtcaa tagggtatac ttttccatct ttactaggaa gtcaactagc agacatgcat   1260
aggagaaaca ttttgcttat aggcgatggt agtttacaac ttactgttca gccctaagt    1320 acaatgatta gaaaggatat caaaccaatc attttcgtta tcaataacga cggttacacc   1380
gtcgaaagac ttatccacgg catggaagag ccatacaatg atatccaaat gtggaactac   1440
aagcaattgc cagaagtatt tggtggaaaa gatactgtaa aagttcatga tgctaaaacc    1500
tccaacgaac tgaaaactgt aatggattct gttaaagcag acaagatca catgcatttc    1560 attgaagtgc atatggcagt agaggacgcc ccaagaagt tgattgatat agctaaagcc    1620
tttagtgatg ctaacaagta a                                             1641
```

<210> SEQ ID NO 138
<211> LENGTH: 347
<212> TYPE: PRT
<213> ORGANISM: Beijerickia indica

<400> SEQUENCE: 138

Met Lys Ala Leu Val Tyr Arg Gly Pro Gly Gln Lys Leu Val Glu Glu
1               5                   10                  15

Arg Gln Lys Pro Glu Leu Lys Glu Pro Gly Asp Ala Ile Val Lys Val
            20                  25                  30

Thr Lys Thr Thr Ile Cys Gly Thr Asp Leu His Ile Leu Lys Gly Asp
        35                  40                  45

Val Ala Thr Cys Lys Pro Gly Arg Val Leu Gly His Glu Gly Val Gly
    50                  55                  60

Val Ile Glu Ser Val Gly Ser Gly Val Thr Ala Phe Gln Pro Gly Asp
65                  70                  75                  80

Arg Val Leu Ile Ser Cys Ile Ser Ser Cys Gly Lys Cys Ser Phe Cys
                85                  90                  95

Arg Arg Gly Met Phe Ser His Cys Thr Thr Gly Gly Trp Ile Leu Gly
            100                 105                 110

Asn Glu Ile Asp Gly Thr Gln Ala Glu Tyr Val Arg Val Pro His Ala
        115                 120                 125

Asp Thr Ser Leu Tyr Arg Ile Pro Ala Gly Ala Asp Glu Glu Ala Leu

```
                    130                 135                 140
Val Met Leu Ser Asp Ile Leu Pro Thr Gly Phe Glu Cys Gly Val Leu
145                 150                 155                 160

Asn Gly Lys Val Ala Pro Gly Ser Ser Val Ala Ile Val Gly Ala Gly
                165                 170                 175

Pro Val Gly Leu Ala Ala Leu Leu Thr Ala Gln Phe Tyr Ser Pro Ala
                180                 185                 190

Glu Ile Ile Met Ile Asp Leu Asp Asn Arg Leu Gly Leu Ala Lys
                195                 200                 205

Gln Phe Gly Ala Thr Arg Thr Val Asn Ser Thr Gly Gly Asn Ala Ala
                210                 215                 220

Ala Glu Val Lys Ala Leu Thr Glu Gly Leu Gly Val Asp Thr Ala Ile
225                 230                 235                 240

Glu Ala Val Gly Ile Pro Ala Thr Phe Glu Leu Cys Gln Asn Ile Val
                245                 250                 255

Ala Pro Gly Gly Thr Ile Ala Asn Val Gly Val His Gly Ser Lys Val
                260                 265                 270

Asp Leu His Leu Glu Ser Leu Trp Ser His Asn Val Thr Ile Thr Thr
                275                 280                 285

Arg Leu Val Asp Thr Ala Thr Thr Pro Met Leu Leu Lys Thr Val Gln
                290                 295                 300

Ser His Lys Leu Asp Pro Ser Arg Leu Ile Thr His Arg Phe Ser Leu
305                 310                 315                 320

Asp Gln Ile Leu Asp Ala Tyr Glu Thr Phe Gly Gln Ala Ala Ser Thr
                325                 330                 335

Gln Ala Leu Lys Val Ile Ile Ser Met Glu Ala
                340                 345

<210> SEQ ID NO 139
<211> LENGTH: 348
<212> TYPE: PRT
<213> ORGANISM: Achromobacter xylosoxidans

<400> SEQUENCE: 139

Met Lys Ala Leu Val Tyr His Gly Asp His Lys Ile Ser Leu Glu Asp
1               5                   10                  15

Lys Pro Lys Pro Thr Leu Gln Lys Pro Thr Asp Val Val Arg Val
                20                  25                  30

Leu Lys Thr Thr Ile Cys Gly Thr Asp Leu Gly Ile Tyr Lys Gly Lys
                35                  40                  45

Asn Pro Glu Val Ala Asp Gly Arg Ile Leu Gly His Glu Gly Val Gly
                50                  55                  60

Val Ile Glu Glu Val Gly Glu Ser Val Thr Gln Phe Lys Lys Gly Asp
65                  70                  75                  80

Lys Val Leu Ile Ser Cys Val Thr Ser Cys Gly Ser Cys Asp Tyr Cys
                85                  90                  95

Lys Lys Gln Leu Tyr Ser His Cys Arg Asp Gly Gly Trp Ile Leu Gly
                100                 105                 110

Tyr Met Ile Asp Gly Val Gln Ala Glu Tyr Val Arg Ile Pro His Ala
                115                 120                 125

Asp Asn Ser Leu Tyr Lys Ile Pro Gln Thr Ile Asp Asp Glu Ile Ala
                130                 135                 140

Val Leu Leu Ser Asp Ile Leu Pro Thr Gly His Glu Ile Gly Val Gln
145                 150                 155                 160
```

Tyr Gly Asn Val Gln Pro Gly Asp Ala Val Ala Ile Val Gly Ala Gly
            165                 170                 175

Pro Val Gly Met Ser Val Leu Leu Thr Ala Gln Phe Tyr Ser Pro Ser
        180                 185                 190

Thr Ile Ile Val Ile Asp Met Asp Glu Asn Arg Leu Gln Leu Ala Lys
        195                 200                 205

Glu Leu Gly Ala Thr His Thr Ile Asn Ser Gly Thr Glu Asn Val Val
        210                 215                 220

Glu Ala Val His Arg Ile Ala Ala Glu Gly Val Asp Val Ala Ile Glu
225                 230                 235                 240

Ala Val Gly Ile Pro Ala Thr Trp Asp Ile Cys Gln Glu Ile Val Lys
                245                 250                 255

Pro Gly Ala His Ile Ala Asn Val Gly Val His Gly Val Lys Val Asp
                260                 265                 270

Phe Glu Ile Gln Lys Leu Trp Ile Lys Asn Leu Thr Ile Thr Thr Gly
        275                 280                 285

Leu Val Asn Thr Asn Thr Thr Pro Met Leu Met Lys Val Ala Ser Thr
        290                 295                 300

Asp Lys Leu Pro Leu Lys Lys Met Ile Thr His Arg Phe Glu Leu Ala
305                 310                 315                 320

Glu Ile Glu His Ala Tyr Gln Val Phe Leu Asn Gly Ala Lys Glu Lys
                325                 330                 335

Ala Met Lys Ile Ile Leu Ser Asn Ala Gly Ala Ala
                340                 345

<210> SEQ ID NO 140

<400> SEQUENCE: 140

000

<210> SEQ ID NO 141
<211> LENGTH: 548
<212> TYPE: PRT
<213> ORGANISM: Lactococcus lactis

<400> SEQUENCE: 141

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val

```
            145                 150                 155                 160
        Tyr Ile Asn Leu Pro Val Asp Val Ala Ala Lys Ala Glu Lys Pro
                        165                 170                 175

Ser Leu Pro Leu Lys Lys Glu Asn Ser Thr Ser Asn Thr Ser Asp Gln
                        180                 185                 190

Glu Ile Leu Asn Lys Ile Gln Glu Ser Leu Lys Asn Ala Lys Lys Pro
                        195                 200                 205

Ile Val Ile Thr Gly His Glu Ile Ile Ser Phe Gly Leu Glu Lys Thr
                        210                 215                 220

Val Thr Gln Phe Ile Ser Lys Thr Lys Leu Pro Ile Thr Thr Leu Asn
        225                 230                 235                 240

Phe Gly Lys Ser Ser Val Asp Glu Ala Leu Pro Ser Phe Leu Gly Ile
                        245                 250                 255

Tyr Asn Gly Thr Leu Ser Glu Pro Asn Leu Lys Glu Phe Val Glu Ser
                        260                 265                 270

Ala Asp Phe Ile Leu Met Leu Gly Val Lys Leu Thr Asp Ser Ser Thr
                        275                 280                 285

Gly Ala Phe Thr His His Leu Asn Glu Asn Lys Met Ile Ser Leu Asn
                        290                 295                 300

Ile Asp Glu Gly Lys Ile Phe Asn Glu Arg Ile Gln Asn Phe Asp Phe
        305                 310                 315                 320

Glu Ser Leu Ile Ser Ser Leu Leu Asp Leu Ser Glu Ile Glu Tyr Lys
                        325                 330                 335

Gly Lys Tyr Ile Asp Lys Lys Gln Glu Asp Phe Val Pro Ser Asn Ala
                        340                 345                 350

Leu Leu Ser Gln Asp Arg Leu Trp Gln Ala Val Glu Asn Leu Thr Gln
                        355                 360                 365

Ser Asn Glu Thr Ile Val Ala Glu Gln Gly Thr Ser Phe Phe Gly Ala
                        370                 375                 380

Ser Ser Ile Phe Leu Lys Ser Lys Ser His Phe Ile Gly Gln Pro Leu
        385                 390                 395                 400

Trp Gly Ser Ile Gly Tyr Thr Phe Pro Ala Ala Leu Gly Ser Gln Ile
                        405                 410                 415

Ala Asp Lys Glu Ser Arg His Leu Leu Phe Ile Gly Asp Gly Ser Leu
                        420                 425                 430

Gln Leu Thr Val Gln Glu Leu Gly Leu Ala Ile Arg Glu Lys Ile Asn
                        435                 440                 445

Pro Ile Cys Phe Ile Ile Asn Asn Asp Gly Tyr Thr Val Glu Arg Glu
        450                 455                 460

Ile His Gly Pro Asn Gln Ser Tyr Asn Asp Ile Pro Met Trp Asn Tyr
        465                 470                 475                 480

Ser Lys Leu Pro Glu Ser Phe Gly Ala Thr Glu Asp Arg Val Val Ser
                        485                 490                 495

Lys Ile Val Arg Thr Glu Asn Glu Phe Val Ser Val Met Lys Glu Ala
                        500                 505                 510

Gln Ala Asp Pro Asn Arg Met Tyr Trp Ile Glu Leu Ile Leu Ala Lys
                        515                 520                 525

Glu Gly Ala Pro Lys Val Leu Lys Lys Met Gly Lys Leu Phe Ala Glu
                        530                 535                 540

Gln Asn Lys Ser
        545

<210> SEQ ID NO 142
```

```
<211> LENGTH: 375
<212> TYPE: PRT
<213> ORGANISM: Equus caballus

<400> SEQUENCE: 142
```

| | | | | | | | | | | | | | | |
|---|---|---|---|---|---|---|---|---|---|---|---|---|---|---|
|Met|Ser|Thr|Ala|Gly|Lys|Val|Ile|Lys|Cys|Lys|Ala|Ala|Val|Leu|Trp|
|1| | | |5| | | | |10| | | | |15|
|Glu|Glu|Lys|Lys|Pro|Phe|Ser|Ile|Glu|Val|Glu|Val|Ala|Pro|Pro|
| | | |20| | | |25| | | |30| | | |
|Lys|Ala|His|Glu|Val|Arg|Ile|Lys|Met|Val|Ala|Thr|Gly|Ile|Cys|Arg|
| | |35| | | |40| | | |45| | | | |
|Ser|Asp|Asp|His|Val|Val|Ser|Gly|Thr|Leu|Val|Thr|Pro|Leu|Pro|Val|
|50| | | | |55| | | | |60| | | | |
|Ile|Ala|Gly|His|Glu|Ala|Ala|Gly|Ile|Val|Glu|Ser|Ile|Gly|Glu|Gly|
|65| | | | |70| | | | |75| | | | |80|
|Val|Thr|Thr|Val|Arg|Pro|Gly|Asp|Lys|Val|Ile|Pro|Leu|Phe|Thr|Pro|
| | | | |85| | | |90| | | | |95| |
|Gln|Cys|Gly|Lys|Cys|Arg|Val|Cys|Lys|His|Pro|Glu|Gly|Asn|Phe|Cys|
| | | |100| | | |105| | | |110| | | |
|Leu|Lys|Asn|Asp|Leu|Ser|Met|Pro|Arg|Gly|Thr|Met|Gln|Asp|Gly|Thr|
| | |115| | | |120| | | |125| | | | |
|Ser|Arg|Phe|Thr|Cys|Arg|Gly|Lys|Pro|Ile|His|His|Phe|Leu|Gly|Thr|
| |130| | | |135| | | |140| | | | | |
|Ser|Thr|Phe|Ser|Gln|Tyr|Thr|Val|Val|Asp|Glu|Ile|Ser|Val|Ala|Lys|
|145| | | |150| | | |155| | | |160| | |
|Ile|Asp|Ala|Ala|Ser|Pro|Leu|Glu|Lys|Val|Cys|Leu|Ile|Gly|Cys|Gly|
| | | |165| | | |170| | | |175| | | |
|Phe|Ser|Thr|Gly|Tyr|Gly|Ser|Ala|Val|Lys|Val|Ala|Lys|Val|Thr|Gln|
| | |180| | | |185| | | |190| | | | |
|Gly|Ser|Thr|Cys|Ala|Val|Phe|Gly|Leu|Gly|Gly|Val|Gly|Leu|Ser|Val|
| |195| | | |200| | | |205| | | | | |
|Ile|Met|Gly|Cys|Lys|Ala|Ala|Gly|Ala|Ala|Arg|Ile|Ile|Gly|Val|Asp|
| |210| | | |215| | | |220| | | | | |
|Ile|Asn|Lys|Asp|Lys|Phe|Ala|Lys|Ala|Lys|Glu|Val|Gly|Ala|Thr|Glu|
|225| | | |230| | | |235| | | |240| | |
|Cys|Val|Asn|Pro|Gln|Asp|Tyr|Lys|Lys|Pro|Ile|Gln|Glu|Val|Leu|Thr|
| | | |245| | | |250| | | |255| | | |
|Glu|Met|Ser|Asn|Gly|Gly|Val|Asp|Phe|Ser|Phe|Glu|Val|Ile|Gly|Arg|
| | |260| | | |265| | | |270| | | | |
|Leu|Asp|Thr|Met|Val|Thr|Ala|Leu|Ser|Cys|Cys|Gln|Glu|Ala|Tyr|Gly|
| |275| | | |280| | | |285| | | | | |
|Val|Ser|Val|Ile|Val|Gly|Val|Pro|Pro|Asp|Ser|Gln|Asn|Leu|Ser|Met|
|290| | | |295| | | |300| | | | | | |
|Asn|Pro|Met|Leu|Leu|Leu|Ser|Gly|Arg|Thr|Trp|Lys|Gly|Ala|Ile|Phe|
|305| | | |310| | | |315| | | |320| | |
|Gly|Gly|Phe|Lys|Ser|Lys|Asp|Ser|Val|Pro|Lys|Leu|Val|Ala|Asp|Phe|
| | | |325| | | |330| | | |335| | | |
|Met|Ala|Lys|Lys|Phe|Ala|Leu|Asp|Pro|Leu|Ile|Thr|His|Val|Leu|Pro|
| | |340| | | |345| | | |350| | | | |
|Phe|Glu|Lys|Ile|Asn|Glu|Gly|Phe|Asp|Leu|Leu|Arg|Ser|Gly|Glu|Ser|
| | |355| | | |360| | | |365| | | | |
|Ile|Arg|Thr|Ile|Leu|Thr|Phe|
| |370| | | |375| |

<210> SEQ ID NO 143
<211> LENGTH: 1206
<212> TYPE: DNA
<213> ORGANISM: Artificial Sequence
<220> FEATURE:
<223> OTHER INFORMATION: Aureobasidin A resistance (AUR1-C)

<400> SEQUENCE: 143

```
atggcaaacc cttttcgag atggtttcta tcagagagac ctccaaactg ccatgtagcc     60
gatttagaaa caagtttaga tccccatcaa acgttgttga aggtgcaaaa atacaaaccc    120
gctttaagcg actgggtgca ttacatcttc ttgggatcca tcatgctgtt tgtgttcatt    180
actaatcccg caccttggat cttcaagatc cttttttatt gtttcttggg cactttattc    240
atcattccag ctacgtcaca gttttcttc aatgccttgc ccatcctaac atgggtggcg     300
ctgtatttca cttcatcgta cttccagat gaccgcaggc ctcctattac tgtcaaagtg     360
ttaccagcgg tggaaacaat tttatacggc gacaatttaa gtgatattct gcaacatcg     420
acgaattcct ttttggacat tttagcatgg ttaccgtacg gactatttca ttatggggcc    480
ccatttgtcg ttgctgccat cttattcgta tttggtccac caactgtttt gcaaggttat    540
gcttttgcat ttggttatat gaacctgttt ggtgttatca tgcaaaatgt ctttccagcc    600
gctcccccat ggtataaaat tctctatgga ttgcaatcag ccaactatga tatgcatggc    660
tcgcctggtg gattagctag aattgataag ctactcggta ttaatatgta tactacatgt    720
ttttcaaatt cctccgtcat tttcggtgct tttccttcac tgcattccgg tgtgctact     780
atggaagccc tgtttttctg ttattgtttt ccaaaattga gcccttgtt tattgcttat     840
gtttgctggt tatggtggtc aactatgtat ctgacacacc attattttgt agaccttatg    900
gcaggttctg tgctgtcata cgttattttc cagtacacaa agtacacaca tttaccaatt    960
gtagatacat ctcttttttg cagatggtca tacacttcaa ttgagaaata cgatatatca   1020
aagagtgatc cattggctgc agattcaaac gatatcgaaa gtgtcccttt gtccaacttg   1080
gaacttgact ttgatcttaa tatgactgat gaacccagtg taagcccttc gttatttgat   1140
ggatctactt ctgtttctcg ttcgtccgcc acgtctataa cgtcactagg tgtaaagagg   1200
gcttaa                                                              1206
```

<210> SEQ ID NO 144
<211> LENGTH: 401
<212> TYPE: PRT
<213> ORGANISM: Artificial Sequence
<220> FEATURE:
<223> OTHER INFORMATION: Aureobasidin A resistance (AUR1-C)

<400> SEQUENCE: 144

```
Met Ala Asn Pro Phe Ser Arg Trp Phe Leu Ser Glu Arg Pro Pro Asn
1               5                   10                  15

Cys His Val Ala Asp Leu Glu Thr Ser Leu Asp Pro His Gln Thr Leu
            20                  25                  30

Leu Lys Val Gln Lys Tyr Lys Pro Ala Leu Ser Asp Trp Val His Tyr
        35                  40                  45

Ile Phe Leu Gly Ser Ile Met Leu Phe Val Phe Ile Thr Asn Pro Ala
    50                  55                  60

Pro Trp Ile Phe Lys Ile Leu Phe Tyr Cys Phe Leu Gly Thr Leu Phe
65                  70                  75                  80

Ile Ile Pro Ala Thr Ser Gln Phe Phe Phe Asn Ala Leu Pro Ile Leu
                85                  90                  95
```

```
Thr Trp Val Ala Leu Tyr Phe Thr Ser Ser Tyr Phe Pro Asp Asp Arg
            100                 105                 110

Arg Pro Pro Ile Thr Val Lys Val Leu Pro Ala Val Glu Thr Ile Leu
        115                 120                 125

Tyr Gly Asp Asn Leu Ser Asp Ile Leu Ala Thr Ser Thr Asn Ser Phe
    130                 135                 140

Leu Asp Ile Leu Ala Trp Leu Pro Tyr Gly Leu Phe His Tyr Gly Ala
145                 150                 155                 160

Pro Phe Val Val Ala Ala Ile Leu Phe Val Phe Gly Pro Pro Thr Val
                165                 170                 175

Leu Gln Gly Tyr Ala Phe Ala Phe Gly Tyr Met Asn Leu Phe Gly Val
            180                 185                 190

Ile Met Gln Asn Val Phe Pro Ala Ala Pro Pro Trp Tyr Lys Ile Leu
        195                 200                 205

Tyr Gly Leu Gln Ser Ala Asn Tyr Asp Met His Gly Ser Pro Gly Gly
    210                 215                 220

Leu Ala Arg Ile Asp Lys Leu Leu Gly Ile Asn Met Tyr Thr Thr Cys
225                 230                 235                 240

Phe Ser Asn Ser Ser Val Ile Phe Gly Ala Phe Pro Ser Leu His Ser
                245                 250                 255

Gly Cys Ala Thr Met Glu Ala Leu Phe Phe Cys Tyr Cys Phe Pro Lys
            260                 265                 270

Leu Lys Pro Leu Phe Ile Ala Tyr Val Cys Trp Leu Trp Ser Thr
        275                 280                 285

Met Tyr Leu Thr His His Tyr Phe Val Asp Leu Met Ala Gly Ser Val
    290                 295                 300

Leu Ser Tyr Val Ile Phe Gln Tyr Thr Lys Tyr Thr His Leu Pro Ile
305                 310                 315                 320

Val Asp Thr Ser Leu Phe Cys Arg Trp Ser Tyr Thr Ser Ile Glu Lys
                325                 330                 335

Tyr Asp Ile Ser Lys Ser Asp Pro Leu Ala Ala Asp Ser Asn Asp Ile
            340                 345                 350

Glu Ser Val Pro Leu Ser Asn Leu Glu Leu Asp Phe Asp Leu Asn Met
        355                 360                 365

Thr Asp Glu Pro Ser Val Ser Pro Ser Leu Phe Asp Gly Ser Thr Ser
    370                 375                 380

Val Ser Arg Ser Ser Ala Thr Ser Ile Thr Ser Leu Gly Val Lys Arg
385                 390                 395                 400

Ala
```

<210> SEQ ID NO 145
<211> LENGTH: 552
<212> TYPE: DNA
<213> ORGANISM: Artificial Sequence
<220> FEATURE:
<223> OTHER INFORMATION: bialiphos resistance protein

<400> SEQUENCE: 145

```
atgagcccag aacgacgccc ggccgacatc cgccgtgcca ccgaggcgga catgccggcg      60
gtctgcacca tcgtcaacca ctacatcgag acaagcacgg tcaacttccg taccgagccg     120
caggaaccgc aggagtggac ggacgacctc gtccgtctgc gggagcgcta tccctggctc     180
gtcgccgagg tggacggcga ggtcgccggc atcgcctacg cgggccctg gaaggcacgc     240 aacgcctacg actggacggc cgagtcgacc gtgtacgtct cccccgcca ccagcggacg     300
```

-continued

```
ggactgggct ccacgctcta cacccacctg ctgaagtccc tggaggcaca gggcttcaag      360
agcgtggtcg ctgtcatcgg gctgcccaac gacccgagcg tgcgcatgca cgaggcgctc      420
ggatatgccc cccgcggcat gctgcgggcg ccggcttca agcacgggaa ctggcatgac       480
gtgggtttct ggcagctgga cttcagcctg ccggtaccgc ccgtccggt cctgcccgtc       540 accgagattt ga                                                          552
```

<210> SEQ ID NO 146
<211> LENGTH: 183
<212> TYPE: PRT
<213> ORGANISM: Artificial Sequence
<220> FEATURE:
<223> OTHER INFORMATION: bialiphos resistance protein

<400> SEQUENCE: 146

```
Met Ser Pro Glu Arg Arg Pro Ala Asp Ile Arg Arg Ala Thr Glu Ala
1               5                   10                  15

Asp Met Pro Ala Val Cys Thr Ile Val Asn His Tyr Ile Glu Thr Ser
                20                  25                  30

Thr Val Asn Phe Arg Thr Glu Pro Gln Glu Pro Gln Glu Trp Thr Asp
            35                  40                  45

Asp Leu Val Arg Leu Arg Glu Arg Tyr Pro Trp Leu Val Ala Glu Val
        50                  55                  60

Asp Gly Glu Val Ala Gly Ile Ala Tyr Ala Gly Pro Trp Lys Ala Arg
65                  70                  75                  80

Asn Ala Tyr Asp Trp Thr Ala Glu Ser Thr Val Tyr Val Ser Pro Arg
                85                  90                  95

His Gln Arg Thr Gly Leu Gly Ser Thr Leu Tyr Thr His Leu Leu Lys
            100                 105                 110

Ser Leu Glu Ala Gln Gly Phe Lys Ser Val Val Ala Val Ile Gly Leu
        115                 120                 125

Pro Asn Asp Pro Ser Val Arg Met His Glu Ala Leu Gly Tyr Ala Pro
    130                 135                 140

Arg Gly Met Leu Arg Ala Ala Gly Phe Lys His Gly Asn Trp His Asp
145                 150                 155                 160

Val Gly Phe Trp Gln Leu Asp Phe Ser Leu Pro Val Pro Pro Arg Pro
                165                 170                 175

Val Leu Pro Val Thr Glu Ile
            180
```

<210> SEQ ID NO 147
<211> LENGTH: 1953
<212> TYPE: DNA
<213> ORGANISM: Artificial Sequence
<220> FEATURE:
<223> OTHER INFORMATION: cerulenin resistance YML007W  Chr 13

<400> SEQUENCE: 147

```
atgagtgtgt ctaccgccaa gaggtcgctg gatgtcgttt ctccgggttc attagcggag      60
tttgagggtt caaaatctcg tcacgatgaa atagaaaatg aacatagacg tactggtaca     120
cgtgatggcg aggatagcga gcaaccgaag aagaagggta gcaaaactag caaaaagcaa     180
gatttggatc ctgaaactaa gcagaagagg actgcccaaa atcgggccgc tcaaagagct     240
tttagggaac gtaaggagag gaagatgaag gaattggaga agaaggtaca agtttagag      300 agtattcagc agcaaaatga agtggaagct acttttttga gggaccagtt aatcactctg     360
gtgaatgagt taaaaaaata tagaccagag acaagaaatg actcaaaagt gctggaatat     420
```

-continued

```
ttagcaaggc gagatcctaa tttgcatttt tcaaaaaata cgttaaccaa cagcaatagc      480
gagccaattg acacacccaa tgatgacata caagaaaatg ttaaacaaaa gatgaatttc      540
acgtttcaat atccgcttga taacgacaac gacaacgaca acagtaaaaa tgtggggaaa      600
caattacctt caccaaatga tccaagtcat tcggctccta tgcctataaa tcagacacaa      660
aagaaattaa gtgacgctac agattcctcc agcgctactt tggattccct ttcaaatagt      720
aacgatgttc ttaataacac accaaactcc tccacttcga tggattggtt agataatgta      780
atatatacta acaggtttgt gtcaggtgat gatggcagca atagtaaaac taagaattta      840
gacagtaata tgttttctaa tgactttaat tttgaaaacc aatttgatga acaagtttcg      900
gagttttgtt cgaaaatgaa ccaggtatgt ggaacaaggc aatgtcccat tcccaagaaa      960
cccatctcgg ctcttgataa agaagttttc gcgtcatctt ctatactaag ttcaaattct     1020
cctgctttaa caaatacttg ggaatcacat tctaatatta cagataatac tcctgctaat     1080
gtcattgcta ctgatgctac taaatatgaa aattccttct ccggttttgg ccgacttggt     1140
ttcgatatga gtgccaatca ttacgtcgtg aatgataata gcactggtag cactgatagc     1200
actggtagca ctggcaataa gaacaaaaag aacaataata atagcgatga tgtactccca     1260
ttcatatccg agtcaccgtt tgatatgaac caagttacta atttttttag tccgggatct     1320
accggcatcg gcaataatgc tgcctctaac accaatccca gcctactgca aagcagcaaa     1380
gaggatatac cttttatcaa cgcaaatctg gctttcccag acgacaattc aactaatatt     1440
caattacaac ctttctctga atctcaatct caaaataagt ttgactacga catgtttttt     1500
agagattcat cgaaggaagg taacaattta tttggagagt ttttagagga tgacgatgat     1560
gacaaaaaag ccgctaatat gtcagacgat gagtcaagtt taatcaagaa ccagttaatt     1620
aacgaagaac cagagcttcc gaaacaatat ctacaatcgg taccaggaaa tgaaagcgaa     1680
atctcacaaa aaaatggcag tagtttacag aatgctgaca aaatcaataa tggcaatgat     1740
aacgataatg ataatgatgt cgttccatct aaggaaggct ctttactaag gtgttcggaa     1800
atttgggata gaataacaac acatccgaaa tactcagata ttgatgtcga tggtttatgt     1860
tccgagctaa tggcaaaggc aaaatgttca gaaagagggg ttgtcatcaa tgcagaagac     1920
gttcaattag ctttgaataa gcatatgaac taa                                  1953
```

<210> SEQ ID NO 148
<211> LENGTH: 650
<212> TYPE: PRT
<213> ORGANISM: Artificial Sequence
<220> FEATURE:
<223> OTHER INFORMATION: cerulenin resistance YML007W Chr 13

<400> SEQUENCE: 148

```
Met Ser Val Ser Thr Ala Lys Arg Ser Leu Asp Val Val Ser Pro Gly
1               5                   10                  15

Ser Leu Ala Glu Phe Glu Gly Ser Lys Ser Arg His Asp Glu Ile Glu
            20                  25                  30

Asn Glu His Arg Arg Thr Gly Thr Arg Asp Gly Glu Asp Ser Glu Gln
        35                  40                  45

Pro Lys Lys Lys Gly Ser Lys Thr Ser Lys Lys Gln Asp Leu Asp Pro
    50                  55                  60

Glu Thr Lys Gln Lys Arg Thr Ala Gln Asn Arg Ala Ala Gln Arg Ala
65                  70                  75                  80

Phe Arg Glu Arg Lys Glu Arg Lys Met Lys Glu Leu Glu Lys Lys Val
```

```
                85                  90                  95
Gln Ser Leu Glu Ser Ile Gln Gln Asn Glu Val Glu Ala Thr Phe
            100                 105                 110
Leu Arg Asp Gln Leu Ile Thr Leu Val Asn Glu Leu Lys Lys Tyr Arg
            115                 120                 125
Pro Glu Thr Arg Asn Asp Ser Lys Val Leu Glu Tyr Leu Ala Arg Arg
            130                 135                 140
Asp Pro Asn Leu His Phe Ser Lys Asn Val Asn His Ser Asn Ser
145                 150                 155                 160
Glu Pro Ile Asp Thr Pro Asn Asp Ile Gln Glu Asn Val Lys Gln
                165                 170                 175
Lys Met Asn Phe Thr Phe Gln Tyr Pro Leu Asp Asn Asp Asn Asp Asn
            180                 185                 190
Asp Asn Ser Lys Asn Val Gly Lys Gln Leu Pro Ser Pro Asn Asp Pro
            195                 200                 205
Ser His Ser Ala Pro Met Pro Ile Asn Gln Thr Gln Lys Lys Leu Ser
            210                 215                 220
Asp Ala Thr Asp Ser Ser Ser Ala Thr Leu Asp Ser Leu Ser Asn Ser
225                 230                 235                 240
Asn Asp Val Leu Asn Asn Thr Pro Asn Ser Ser Thr Ser Met Asp Trp
                245                 250                 255
Leu Asp Asn Val Ile Tyr Thr Asn Arg Phe Val Ser Gly Asp Asp Gly
            260                 265                 270
Ser Asn Ser Lys Thr Lys Asn Leu Asp Ser Asn Met Phe Ser Asn Asp
            275                 280                 285
Phe Asn Phe Glu Asn Gln Phe Asp Glu Gln Val Ser Glu Phe Cys Ser
            290                 295                 300
Lys Met Asn Gln Val Cys Gly Thr Arg Gln Cys Pro Ile Pro Lys Lys
305                 310                 315                 320
Pro Ile Ser Ala Leu Asp Lys Glu Val Phe Ala Ser Ser Ser Ile Leu
            325                 330                 335
Ser Ser Asn Ser Pro Ala Leu Thr Asn Thr Trp Glu Ser His Ser Asn
            340                 345                 350
Ile Thr Asp Asn Thr Pro Ala Asn Val Ile Ala Thr Asp Ala Thr Lys
            355                 360                 365
Tyr Glu Asn Ser Phe Ser Gly Phe Gly Arg Leu Gly Phe Asp Met Ser
            370                 375                 380
Ala Asn His Tyr Val Val Asn Asp Asn Ser Thr Gly Ser Thr Asp Ser
385                 390                 395                 400
Thr Gly Ser Thr Gly Asn Lys Asn Lys Lys Asn Asn Asn Ser Asp
                405                 410                 415
Asp Val Leu Pro Phe Ile Ser Glu Ser Pro Phe Asp Met Asn Gln Val
            420                 425                 430
Thr Asn Phe Phe Ser Pro Gly Ser Thr Gly Ile Gly Asn Asn Ala Ala
            435                 440                 445
Ser Asn Thr Asn Pro Ser Leu Leu Gln Ser Ser Lys Glu Asp Ile Pro
            450                 455                 460
Phe Ile Asn Ala Asn Leu Ala Phe Pro Asp Asn Ser Thr Asn Ile
465                 470                 475                 480
Gln Leu Gln Pro Phe Ser Glu Ser Gln Ser Gln Asn Lys Phe Asp Tyr
            485                 490                 495
Asp Met Phe Phe Arg Asp Ser Ser Lys Glu Gly Asn Asn Leu Phe Gly
            500                 505                 510
```

Glu Phe Leu Glu Asp Asp Asp Asp Lys Lys Ala Ala Asn Met Ser
            515                 520                 525

Asp Asp Glu Ser Ser Leu Ile Lys Asn Gln Leu Ile Asn Glu Glu Pro
        530                 535                 540

Glu Leu Pro Lys Gln Tyr Leu Gln Ser Val Pro Gly Asn Glu Ser Glu
545                 550                 555                 560

Ile Ser Gln Lys Asn Gly Ser Ser Leu Gln Asn Ala Asp Lys Ile Asn
                565                 570                 575

Asn Gly Asn Asp Asn Asp Asn Asp Val Val Pro Ser Lys Glu
            580                 585                 590

Gly Ser Leu Leu Arg Cys Ser Glu Ile Trp Asp Arg Ile Thr Thr His
            595                 600                 605

Pro Lys Tyr Ser Asp Ile Asp Val Asp Gly Leu Cys Ser Glu Leu Met
        610                 615                 620

Ala Lys Ala Lys Cys Ser Glu Arg Gly Val Val Ile Asn Ala Glu Asp
625                 630                 635                 640

Val Gln Leu Ala Leu Asn Lys His Met Asn
                645                 650

<210> SEQ ID NO 149
<211> LENGTH: 810
<212> TYPE: DNA
<213> ORGANISM: Artificial Sequence
<220> FEATURE:
<223> OTHER INFORMATION: Geneticin resistance (kanMX)

<400> SEQUENCE: 149
atgggtaagg aaaagactca cgtttcgagg ccgcgattaa attccaacat ggatgctgat      60
ttatatgggt ataaatgggc tcgcgataat gtcgggcaat caggtgcgac aatctatcga     120
ttgtatggga agcccgatgc gccagagttg tttctgaaac atggcaaagg tagcgttgcc     180
aatgatgtta cagatgagat ggtcagacta aactggctga cggaatttat gcctcttccg     240
accatcaagc attttatccg tactcctgat gatgcatggt tactcaccac tgcgatcccc     300
ggcaaaacag cattccaggt attagaagaa tatcctgatt caggtgaaaa tattgttgat     360
gcgctggcag tgttcctgcg ccggttgcat tcgattcctg tttgtaattg tccttttaac     420
agcgatcgcg tatttcgtct cgctcaggcg caatcacgaa tgaataacgg tttggttgat     480
gcgagtgatt ttgatgacga gcgtaatggc tggcctgttg aacaagtctg gaaagaaatg     540
cataagcttt tgccattctc accggattca gtcgtcactc atggtgattt ctcacttgat     600
aaccttattt ttgacgaggg gaaattaata ggttgtattg atgttggacg agtcggaatc     660
gcagaccgat accaggatct tgccatccta tggaactgcc tcggtgagtt ttctccttca     720
ttacagaaac ggctttttca aaaatatggt attgataatc ctgatatgaa taaattgcag     780
tttcatttga tgctcgatga gttttttctaa                                     810

<210> SEQ ID NO 150
<211> LENGTH: 269
<212> TYPE: PRT
<213> ORGANISM: Artificial Sequence
<220> FEATURE:
<223> OTHER INFORMATION: Geneticin resistance (kanMX)

<400> SEQUENCE: 150

Met Gly Lys Glu Lys Thr His Val Ser Arg Pro Arg Leu Asn Ser Asn
1               5                  10                  15

Met Asp Ala Asp Leu Tyr Gly Tyr Lys Trp Ala Arg Asp Asn Val Gly
                20                  25                  30

Gln Ser Gly Ala Thr Ile Tyr Arg Leu Tyr Gly Lys Pro Asp Ala Pro
            35                  40                  45

Glu Leu Phe Leu Lys His Gly Lys Gly Ser Val Ala Asn Asp Val Thr
50                  55                  60

Asp Glu Met Val Arg Leu Asn Trp Leu Thr Glu Phe Met Pro Leu Pro
65                  70                  75                  80

Thr Ile Lys His Phe Ile Arg Thr Pro Asp Asp Ala Trp Leu Leu Thr
                85                  90                  95

Thr Ala Ile Pro Gly Lys Thr Ala Phe Gln Val Leu Glu Glu Tyr Pro
            100                 105                 110

Asp Ser Gly Glu Asn Ile Val Asp Ala Leu Ala Val Phe Leu Arg Arg
        115                 120                 125

Leu His Ser Ile Pro Val Cys Asn Cys Pro Phe Asn Ser Asp Arg Val
    130                 135                 140

Phe Arg Leu Ala Gln Ala Gln Ser Arg Met Asn Asn Gly Leu Val Asp
145                 150                 155                 160

Ala Ser Asp Phe Asp Asp Glu Arg Asn Gly Trp Pro Val Glu Gln Val
                165                 170                 175

Trp Lys Glu Met His Lys Leu Leu Pro Phe Ser Pro Asp Ser Val Val
            180                 185                 190

Thr His Gly Asp Phe Ser Leu Asp Asn Leu Ile Phe Asp Glu Gly Lys
        195                 200                 205

Leu Ile Gly Cys Ile Asp Val Gly Arg Val Gly Ile Ala Asp Arg Tyr
    210                 215                 220

Gln Asp Leu Ala Ile Leu Trp Asn Cys Leu Gly Glu Phe Ser Pro Ser
225                 230                 235                 240

Leu Gln Lys Arg Leu Phe Gln Lys Tyr Gly Ile Asp Asn Pro Asp Met
                245                 250                 255

Asn Lys Leu Gln Phe His Leu Met Leu Asp Glu Phe Phe
            260                 265

<210> SEQ ID NO 151
<211> LENGTH: 1026
<212> TYPE: DNA
<213> ORGANISM: Artificial Sequence
<220> FEATURE:
<223> OTHER INFORMATION: Hygromycin B resistance (HygR)

<400> SEQUENCE: 151

| | |
|---|---|
| atgaaaaagc ctgaactcac cgcgacgtct gtcgagaagt ttctgatcga aaagttcgac | 60 |
| agcgtctccg acctgatgca gctctcggag ggcgaagaat ctcgtgcttt cagcttcgat | 120 |
| gtaggagggc gtggatatgt cctgcgggta aatagctgcg ccgatggttt ctacaaagat | 180 |
| cgttatgttt atcggcactt tgcatcggcc gcgctcccga ttccggaagt gcttgacatt | 240 |
| ggggagttca gcgagagcct gacctattgc atctcccgcc gtgcacaggg tgtcacgttg | 300 |
| caagacctgc ctgaaaccga actgcccgct gttctccagc cggtcgcgga ggccatggat | 360 |
| gcgatcgctg cggccgatct tagccagacg agcgggttcg gcccattcgg accgcaagga | 420 |
| atcggtcaat acactacatg gcgtgatttc atatgcgcga ttgctgatcc ccatgtgtat | 480 |
| cactggcaaa ctgtgatgga cgacaccgtc agtgcgtccg tcgcgcaggc tctcgatgag | 540 |
| ctgatgcttt gggccgagga ctgccccgaa gtccggcacc tcgtgcatgc ggatttcggc | 600 |
| tccaacaatg tcctgacgga caatggccgc ataacagcgg tcattgactg gagcgaggcg | 660 |

-continued

```
atgttcgggg attcccaata cgaggtcgcc aacatcttct tctggaggcc gtggttggct    720
tgtatggagc agcagacgcg ctacttcgag cggaggcatc cggagcttgc aggatcgccg    780
cgcctccggg cgtatatgct ccgcattggt cttgaccaac tctatcagag cttggttgac    840
ggcaatttcg atgatgcagc ttgggcgcag ggtcgatgcg acgcaatcgt ccgatccgga    900
gccgggactg tcgggcgtac acaaatcgcc cgcagaagcg cggccgtctg gaccgatggc    960
tgtgtagaag tactcgccga tagtggaaac cgacgcccca gcactcgtcc gagggcaaag   1020
gaatag                                                             1026
```

<210> SEQ ID NO 152
<211> LENGTH: 341
<212> TYPE: PRT
<213> ORGANISM: Artificial Sequence
<220> FEATURE:
<223> OTHER INFORMATION: Hygromycin B resistance (HygR)

<400> SEQUENCE: 152

```
Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val Tyr
    50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
    210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
                245                 250                 255

Ala Gly Ser Pro Arg Leu Arg Ala Tyr Met Leu Arg Ile Gly Leu Asp
            260                 265                 270

Gln Leu Tyr Gln Ser Leu Val Asp Gly Asn Phe Asp Asp Ala Ala Trp
        275                 280                 285
```

```
Ala Gln Gly Arg Cys Asp Ala Ile Val Arg Ser Ala Gly Thr Val
    290                 295                 300

Gly Arg Thr Gln Ile Ala Arg Arg Ser Ala Ala Val Trp Thr Asp Gly
305                 310                 315                 320

Cys Val Glu Val Leu Ala Asp Ser Gly Asn Arg Arg Pro Ser Thr Arg
                325                 330                 335

Pro Arg Ala Lys Glu
            340
```

<210> SEQ ID NO 153
<211> LENGTH: 573
<212> TYPE: DNA
<213> ORGANISM: Streptomyces noursei

<400> SEQUENCE: 153

```
atgaccactc ttgacgacac ggcttaccgg taccgcacca gtgtcccggg ggacgccgag    60
gccatcgagg cactggatgg tccttcacc accgacaccg tcttccgcgt caccgccacc   120
ggggacggct tcaccctgcg ggaggtgccg gtggacccgc ccctgaccaa ggtgttcccc   180
gacgacgaat cggacgacga atcggacgac ggggaggacg gcgacccgga ctcccggacg   240
ttcgtcgcgt acgggacga cggcgacctg gcgggcttcg tggtcatctc gtactcggcg   300
tggaaccgcc ggctgaccgt cgaggacatc gaggtcgccc cggagcaccg ggggcacggg   360
gtcgggcgcg cgttgatggg gctcgcgacg gagttcgccg gcgagcgggg cgccgggcac   420
ctctggctgg aggtcaccaa cgtcaacgca ccggcgatcc acgcgtaccg cggatgggg   480 ttcaccctct gcggcctgga caccgccctg tacgacggca ccgcctcgga cggcgagcgg   540
caggcgctct acatgagcat gccctgcccc tag                                 573
```

<210> SEQ ID NO 154
<211> LENGTH: 190
<212> TYPE: PRT
<213> ORGANISM: Streptomyces noursei

<400> SEQUENCE: 154

```
Met Thr Thr Leu Asp Asp Thr Ala Tyr Arg Tyr Arg Thr Ser Val Pro
1               5                   10                  15

Gly Asp Ala Glu Ala Ile Glu Ala Leu Asp Gly Ser Phe Thr Thr Asp
            20                  25                  30

Thr Val Phe Arg Val Thr Ala Thr Gly Asp Gly Phe Thr Leu Arg Glu
        35                  40                  45

Val Pro Val Asp Pro Pro Leu Thr Lys Val Phe Pro Asp Asp Glu Ser
50                  55                  60

Asp Asp Glu Ser Asp Asp Gly Glu Asp Gly Asp Pro Asp Ser Arg Thr
65                  70                  75                  80

Phe Val Ala Tyr Gly Asp Asp Gly Asp Leu Ala Gly Phe Val Val Ile
                85                  90                  95

Ser Tyr Ser Ala Trp Asn Arg Arg Leu Thr Val Glu Asp Ile Glu Val
            100                 105                 110

Ala Pro Glu His Arg Gly His Gly Val Gly Arg Ala Leu Met Gly Leu
        115                 120                 125

Ala Thr Glu Phe Ala Gly Glu Arg Gly Ala Gly His Leu Trp Leu Glu
130                 135                 140

Val Thr Asn Val Asn Ala Pro Ala Ile His Ala Tyr Arg Arg Met Gly
145                 150                 155                 160

Phe Thr Leu Cys Gly Leu Asp Thr Ala Leu Tyr Asp Gly Thr Ala Ser
```

165                 170                 175
Asp Gly Glu Arg Gln Ala Leu Tyr Met Ser Met Pro Cys Pro
        180                 185                 190

<210> SEQ ID NO 155
<211> LENGTH: 375
<212> TYPE: DNA
<213> ORGANISM: Artificial Sequence
<220> FEATURE:
<223> OTHER INFORMATION: Phleomycin zeocin binding protein

<400> SEQUENCE: 155

```
atggccaagt tgaccagtgc cgttccggtg ctcaccgcgc gcgacgtcgc cggagcggtc      60
gagttctgga ccgaccggct cgggttctcc cgggacttcg tggaggacga cttcgccggt     120
gtggtccggg acgacgtgac cctgttcatc agcgcggtcc aggaccaggt ggtgccggac     180
aacaccctgg cctgggtgtg ggtgcgcggc ctggacgagc tgtacgccga gtggtcggag     240
gtcgtgtcca cgaacttccg ggacgcctcc gggccggcca tgaccgagat cggcgagcag     300
ccgtgggggc gggagttcgc cctgcgcgac ccggccggca actgcgtgca cttcgtggcc     360
gaggagcagg actga                                                     375
```

<210> SEQ ID NO 156
<211> LENGTH: 124
<212> TYPE: PRT
<213> ORGANISM: Artificial Sequence
<220> FEATURE:
<223> OTHER INFORMATION: Phleomycin zeocin binding protein

<400> SEQUENCE: 156

Met Ala Lys Leu Thr Ser Ala Val Pro Val Leu Thr Ala Arg Asp Val
1               5                   10                  15

Ala Gly Ala Val Glu Phe Trp Thr Asp Arg Leu Gly Phe Ser Arg Asp
            20                  25                  30

Phe Val Glu Asp Asp Phe Ala Gly Val Val Arg Asp Asp Val Thr Leu
        35                  40                  45

Phe Ile Ser Ala Val Gln Asp Gln Val Val Pro Asp Asn Thr Leu Ala
    50                  55                  60

Trp Val Trp Val Arg Gly Leu Asp Glu Leu Tyr Ala Glu Trp Ser Glu
65                  70                  75                  80

Val Val Ser Thr Asn Phe Arg Asp Ala Ser Gly Pro Ala Met Thr Glu
                85                  90                  95

Ile Gly Glu Gln Pro Trp Gly Arg Glu Phe Ala Leu Arg Asp Pro Ala
            100                 105                 110

Gly Asn Cys Val His Phe Val Ala Glu Glu Gln Asp
        115                 120

<210> SEQ ID NO 157
<211> LENGTH: 1539
<212> TYPE: DNA
<213> ORGANISM: Aspergillus niger

<400> SEQUENCE: 157

```
atggcattac ttgctgtcgc aggcgtctac gctttcgcag cgttgctcgt tgcgatagtc      60
ttaaatgtca cgcgccaatt gctctttcgc aacgagaaag aaccaccgt cgtcttccat     120
tggatcccct tcttgggaag cacaatcagc tatggaatgg accctatac attcttcttc     180
tcctgcagaa aaagtacgg ggacatcttc accttcgtgc ttctgggcca gaagaccact     240
```

| | |
|---|---|
| gtatacttgg gcgttcaagg caacgatttc atcctcaatg gcaaactcaa ggacgtgagc | 300 |
| gcggaagagg tctacagccc cctcaccacc ccggtgttcg ggtccgatgt tgtgtacgac | 360 |
| tgccctaatt ccaagctgat ggagcaaaaa aagttcatca agtttggcct cacgcaagcg | 420 |
| gcgctcgagt cacacgtcca gctgatcgaa aaggaaactc tcgactatct ccgggactct | 480 |
| ccacgcttca acggcgcgag tggagtcatt gatattcctg ctgccatggc tgagattaca | 540 |
| atctatactg ctgcgcgcgc gttgcagggc gaggaggtcc gcaagaagct cacggcagag | 600 |
| ttcgctgaac tgtaccacga tctagacaag ggattcagcc ccattaactt catgctccct | 660 |
| tgggctccat tgccgcacaa ccggaagcgt gatgctgctc atgctcggat gagagaaatc | 720 |
| tacacggaca ttatcaacga acgacgcaag aacccagacg aggagaagtc agacatgatc | 780 |
| tggaatctga tgcattgcac ctacaagagt ggccagccgg tcccggacaa agagattgct | 840 |
| cacatgatga tcactctgtt gatggcaggg caacactcgt cttcttcgat tagttcttgg | 900 |
| atcatgctgc gattggcctc ggagcctcag gtgcttgaag agctctacca gaacagctg | 960 |
| gccagcctta gcaacagaaa tggagtcttc gagccgctgc agtatcagga ccttgacaag | 1020 |
| ctgccattcc tccagagtgt catcaaggag actctacgga tccactcgtc atccactcg | 1080 |
| atcatgcgca aggtgaaaaa cccgctacca gtacctggca cctcctacat tattcccgaa | 1140 |
| gaccatgttc tactcgcctc accaggcgta accgcgctta gtgacgaata ctttcctaac | 1200 |
| gcaaccaggt gggatccgca tcgttgggag aatcagcctg acaagagga ggatggagag | 1260 |
| atggtggact acggatatgg cagcgtgtcg aagggcactg ctagtcccta tctacctttt | 1320 |
| ggcgctggcc gtcaccgctg cattggagag aagttcgcct acgtcaactt gggcgtcatt | 1380 |
| atcgcgacca tagtgcgcca cttgaagcta ttcaatgtgg atggcaggaa aggagtgccc | 1440 |
| ggaaccgatt actcgaccct cttctccggt cccatgaagc ctgctatagt gggttgggag | 1500 |
| cgacgcttcc cggacaacat caaagggtcc atgaactaa | 1539 |

<210> SEQ ID NO 158
<211> LENGTH: 4519
<212> TYPE: DNA
<213> ORGANISM: Artificial Sequence
<220> FEATURE:
<223> OTHER INFORMATION: pLA54

<400> SEQUENCE: 158

| | |
|---|---|
| caccttggct aactcgttgt atcatcactg gataacttcg tataatgtat gctatacgaa | 60 |
| gttatcgaac agagaaacta aatccacatt aattgagagt tctatctatt agaaaatgca | 120 |
| aactccaact aaatgggaaa acagataacc tcttttattt tttttttaatg tttgatattc | 180 |
| gagtcttttt cttttgttag gtttatattc atcatttcaa tgaataaaag aagcttctta | 240 |
| ttttggttgc aaagaatgaa aaaaaggat ttttcatac ttctaaagct tcaattataa | 300 |
| ccaaaaattt tataatgaa gagaaaaaat ctagtagtat caagttaaac ttagaaaaac | 360 |
| tcatcgagca tcaaatgaaa ctgcaattta ttcatatcag gattatcaat accatatttt | 420 |
| tgaaaaagcc gtttctgtaa tgaaggagaa aactcaccga ggcagttcca taggatggca | 480 |
| agatcctggt atcggtctgc gattccgact cgtccaacat caatacaacc tattaatttc | 540 |
| ccctcgtcaa aaataaggtt atcaagtgag aaatcaccat gagtgacgac tgaatccggt | 600 |
| gagaatggca aaagcttatg catttctttc cagacttgtt caacaggcca gccattacgc | 660 |
| tcgtcatcaa aatcactcgc atcaaccaaa ccgttattca ttcgtgattg cgcctgagcg | 720 |
| agacgaaata cgcgatcgct gttaaaagga caattacaaa caggaatcga atgcaaccgg | 780 |

```
cgcaggaaca ctgccagcgc atcaacaata ttttcacctg aatcaggata ttcttctaat    840
acctggaatg ctgttttgcc ggggatcgca gtggtgagta accatgcatc atcaggagta    900
cggataaaat gcttgatggt cggaagaggc ataaattccg tcagccagtt tagtctgacc    960
atctcatctg taacatcatt ggcaacgcta cctttgccat gtttcagaaa caactctggc   1020
gcatcgggct tcccatacaa tcgatagatt gtcgcacctg attgcccgac attatcgcga   1080
gcccatttat acccatataa atcagcatcc atgttgaat ttaatcgcgg cctcgaaacg    1140
tgagtctttt ccttacccat ctcgagtttt aatgttactt ctcttgcagt tagggaacta   1200
taatgtaact caaaataaga ttaaacaaac taaaataaaa agaagttata cagaaaaacc   1260
catataaacc agtactaatc cataataata atacacaaaa aaactatcaa ataaaaccag   1320
aaaacagatt gaatagaaaa attttttcga tctccttta tattcaaaat tcgatatatg    1380
aaaaagggaa ctctcagaaa atcaccaaat caatttaatt agattttct tttccttcta    1440
gcgttggaaa gaaaaatttt tcttttttt tttagaaatg aaaaatttt gccgtaggaa     1500
tcaccgtata aaccctgtat aaacgctact ctgttcacct gtgtaggcta tgattgaccc   1560
agtgttcatt gttattgcga gagagcggga gaaaagaacc gatacaagag atccatgctg   1620
gtatagttgt ctgtccaaca cttgatgaa cttgtaggac gatgatgtgt atttagacga    1680
gtacgtgtgt gactattaag tagttatgat agagaggttt gtacggtgtg ttctgtgtaa   1740
ttcgattgag aaaatggtta tgaatcccta gataacttcg tataatgtat gctatacgaa   1800
gttatctgaa cattagaata cgtaatccgc aatgcgggga tcctctagag tcgacctgca   1860
ggcatgcaag cttggcgtaa tcatggtcat agctgtttcc tgtgtgaaat tgttatccgc   1920
tcacaattcc acacaacata cgagccgaa gcataaagtg taaagcctgg ggtgcctaat    1980
gagtgagcta actcacatta attgcgttgc gctcactgcc cgctttccag tcgggaaacc   2040
tgtcgtgcca gctgcattaa tgaatcggcc aacgcgcggg gagaggcggt ttgcgtattg   2100
ggcgctcttc cgcttcctcg ctcactgact cgctgcgctc ggtcgttcgg ctgcggcgag   2160
cggtatcagc tcactcaaag gcggtaatac ggttatccac agaatcaggg gataacgcag   2220
gaaagaacat gtgagcaaaa ggccagcaaa aggccaggaa ccgtaaaaag gccgcgttgc   2280
tggcgttttt ccataggctc cgcccccctg acgagcatca caaaaatcga cgctcaagtc   2340
agaggtggcg aaacccgaca ggactataaa gataccaggc gtttccccct ggaagctccc   2400
tcgtgcgctc tcctgttccg accctgccgc ttaccggata cctgtccgcc tttctccctt   2460
cgggaagcgt ggcgctttct catagctcac gctgtaggta tctcagttcg gtgtaggtcg   2520
ttcgctccaa gctgggctgt gtgcacgaac cccccgttca gcccgaccgc tgcgccttat   2580
ccggtaacta tcgtcttgag tccaacccgg taagacacga cttatcgcca ctggcagcag   2640
ccactggtaa caggattagc agagcgaggt atgtaggcgg tgctacagag ttcttgaagt   2700
ggtggcctaa ctacggctac actagaagga cagtatttgg tatctgcgct ctgctgaagc   2760
cagttacctt cggaaaaaga gttggtagct cttgatccgg caaacaaacc accgctggta   2820
gcggtggttt ttttgtttgc aagcagcaga ttacgcgcag aaaaaaagga tctcaagaag   2880
atcctttgat cttttctacg gggtctgacg ctcagtggaa cgaaaactca cgttaaggga   2940
ttttggtcat gagattatca aaaggatct tcacctagat cctttaaat taaaatgaa     3000
gttttaaatc aatctaaagt atatatgagt aaacttggtc tgacagttac caatgcttaa   3060
tcagtgaggc acctatctca gcgatctgtc tatttcgttc atccatagtt gcctgactcc   3120
```

-continued

```
ccgtcgtgta gataactacg atacgggagg gcttaccatc tggccccagt gctgcaatga    3180
taccgcgaga cccacgctca ccggctccag atttatcagc aataaaccag ccagccggaa    3240
gggccgagcg cagaagtggt cctgcaactt tatccgcctc catccagtct attaattgtt    3300
gccgggaagc tagagtaagt agttcgccag ttaatagttt gcgcaacgtt gttgccattg    3360
ctacaggcat cgtggtgtca cgctcgtcgt ttggtatggc ttcattcagc tccggttccc    3420
aacgatcaag gcgagttaca tgatccccca tgttgtgcaa aaaagcggtt agctccttcg    3480
gtcctccgat cgttgtcaga agtaagttgg ccgcagtgtt atcactcatg gttatggcag    3540
cactgcataa ttctcttact gtcatgccat ccgtaagatg cttttctgtg actggtgagt    3600
actcaaccaa gtcattctga gaatagtgta tgcggcgacc gagttgctct tgcccggcgt    3660
caatacggga taataccgcg ccacatagca gaactttaaa agtgctcatc attggaaaac    3720
gttcttcggg gcgaaaactc tcaaggatct taccgctgtt gagatccagt tcgatgtaac    3780
ccactcgtgc acccaactga tcttcagcat cttttacttt caccagcgtt tctgggtgag    3840
caaaaacagg aaggcaaaat gccgcaaaaa agggaataag ggcgacacgg aaatgttgaa    3900
tactcatact cttcctttt caatattatt gaagcattta tcagggttat tgtctcatga    3960
gcggatacat atttgaatgt atttagaaaa ataaacaaat aggggttccg cgcacatttc    4020
cccgaaaagt gccacctgac gtctaagaaa ccattattat catgacatta acctataaaa    4080
ataggcgtat cacgaggccc tttcgtctcg cgcgtttcgg tgatgacggt gaaaacctct    4140
gacacatgca gctcccggag acggtcacag cttgtctgta agcggatgcc gggagcagac    4200
aagcccgtca gggcgcgtca gcgggtgttg gcgggtgtcg ggctggctt aactatgcgg    4260
catcagagca gattgtactg agagtgcacc atatgcggtg tgaaataccg cacagatgcg    4320
taaggagaaa ataccgcatc aggcgccatt cgccattcag gctgcgcaac tgttgggaag    4380
ggcgatcggt gcgggcctct tcgctattac gccagctggc gaaaggggga tgtgctgcaa    4440
ggcgattaag ttgggtaacg ccagggtttt cccagtcacg acgttgtaaa acgacggcca    4500
gtgaattcga gctcggtac                                                4519
```

<210> SEQ ID NO 159
<211> LENGTH: 25
<212> TYPE: DNA
<213> ORGANISM: Artificial Sequence
<220> FEATURE:
<223> OTHER INFORMATION: 749

<400> SEQUENCE: 159
caagtctttt gtgccttccc gtcgg                                          25

<210> SEQ ID NO 160
<211> LENGTH: 25
<212> TYPE: DNA
<213> ORGANISM: Artificial Sequence
<220> FEATURE:
<223> OTHER INFORMATION: 413

<400> SEQUENCE: 160
ggacataaaa tacacaccga gattc                                          25

<210> SEQ ID NO 161
<211> LENGTH: 38
<212> TYPE: DNA
<213> ORGANISM: Artificial Sequence
<220> FEATURE:
<223> OTHER INFORMATION: LA468

<400> SEQUENCE: 161

```
gcctcgagtt ttaatgttac ttctcttgca gttaggga                              38
```

<210> SEQ ID NO 162
<211> LENGTH: 10934
<212> TYPE: DNA
<213> ORGANISM: Artificial Sequence
<220> FEATURE:
<223> OTHER INFORMATION: pRS423::TEF(M4)-xpk1+ENO1-eutD

<400> SEQUENCE: 162

```
ggtggagctc cagcttttgt tccctttagt gagggttaat tgcgcgcttg gcgtaatcat      60
ggtcatagct gtttcctgtg tgaaattgtt atccgctcac aattccacac aacataggag    120
ccggaagcat aaagtgtaaa gcctggggtg cctaatgagt gaggtaactc acattaattg    180
cgttgcgctc actgcccgct ttccagtcgg gaaacctgtc gtgccagctg cattaatgaa    240
tcggccaacg cgcggggaga ggcggtttgc gtattgggcg ctcttccgct tcctcgctca    300
ctgactcgct gcgctcggtc gttcggctgc ggcgagcggt atcagctcac tcaaaggcgg    360
taatacggtt atccacagaa tcaggggata acgcaggaaa gaacatgtga gcaaaaggcc    420
agcaaaaggc caggaaccgt aaaaaggccg cgttgctggc gtttttccat aggctccgcc    480
cccctgacga gcatcacaaa aatcgacgct caagtcagag gtggcgaaac ccgacaggac    540
tataaagata ccaggcgttt ccccctggaa gctccctcgt gcgctctcct gttccgaccc    600
tgccgcttac cggatacctg tccgcctttc tcccttcggg aagcgtggcg ctttctcata    660
gctcacgctg taggtatctc agttcggtgt aggtcgttcg ctccaagctg ggctgtgtgc    720
acgaaccccc cgttcagccc gaccgctgcg ccttatccgg taactatcgt cttgagtcca    780
acccggtaag acacgactta tcgccactgg cagcagccac tggtaacagg attagcagag    840
cgaggtatgt aggcggtgct acagagttct tgaagtggtg gcctaactac ggctacacta    900
gaaggacagt atttggtatc tgcgctctgc tgaagccagt taccttcgga aaaagagttg    960
gtagctcttg atccggcaaa caaaccaccg ctggtagcgg tggtttttt gtttgcaagc   1020
agcagattac gcgcagaaaa aaaggatctc aagaagatcc tttgatcttt tctacggggt   1080
ctgacgctca gtggaacgaa aactcacgtt aagggatttt ggtcatgaga ttatcaaaaa   1140
ggatcttcac ctagatcctt ttaaattaaa aatgaagttt aaatcaatc taagtatat   1200
atgagtaaac ttggtctgac agttaccaat gcttaatcag tgaggcacct atctcagcga   1260
tctgtctatt tcgttcatcc atagttgcct gactccccgt cgtgtagata actacgatac   1320
gggagggctt accatctggc cccagtgctg caatgatacc gcgagaccca cgctcaccgg   1380
ctccagattt atcagcaata aaccagccag ccggaagggc cgagcgcaga agtggtcctg   1440
caactttatc cgcctccatc cagtctatta attgttgccg gaagctaga gtaagtagtt   1500
cgccagttaa tagtttgcgc aacgttgttg ccattgctac aggcatcgtg gtgtcacgct   1560
cgtcgtttgg tatggcttca ttcagctccg gttcccaacg atcaaggcga gttacatgat   1620
cccccatgtt gtgcaaaaaa gcggttagct ccttcggtcc tccgatcgtt gtcagaagta   1680
agttggccgc agtgttatca ctcatggtta tggcagcact gcataattct cttactgtca   1740
tgccatccgt aagatgcttt tctgtgactg gtgagtactc aaccaagtca ttctgagaat   1800
agtgtatgcg gcgaccgagt tgctcttgcc cggcgtcaat acgggataat accgcgccac   1860
atagcagaac tttaaaagtg ctcatcattg gaaaacgttc ttcggggcga aaactctcaa   1920
```

```
ggatcttacc gctgttgaga tccagttcga tgtaacccac tcgtgcaccc aactgatctt    1980
cagcatcttt tactttcacc agcgtttctg ggtgagcaaa aacaggaagg caaaatgccg    2040 caaaaaggg  aataagggcg acacggaaat gttgaatact catactcttc cttttcaat    2100 attattgaag catttatcag ggttattgtc tcatgagcgg atacatattt gaatgtattt    2160
agaaaaataa acaaataggg gttccgcgca catttccccg aaaagtgcca cctgaacgaa    2220
gcatctgtgc ttcattttgt agaacaaaaa tgcaacgcga gagcgctaat ttttcaaaca    2280
aagaatctga gctgcatttt tacagaacag aaatgcaacg cgaaagcgct attttaccaa    2340
cgaagaatct gtgcttcatt tttgtaaaac aaaaatgcaa cgcgagagcg ctaattttc    2400 aaacaaagaa tctgagctgc attttacag aacagaaatg caacgcgaga gcgctatttt    2460
accaacaaag aatctatact tctttttgt tctacaaaaa tgcatcccga gagcgctatt    2520
tttctaacaa agcatcttag attactttt ttctcctttg tgcgctctat aatgcagtct    2580
cttgataact ttttgcactg taggtccgtt aaggttagaa gaaggctact ttggtgtcta    2640
ttttctcttc cataaaaaaa gcctgactcc acttcccgcg tttactgatt actagcgaag    2700
ctgcgggtgc attttttcaa gataaaggca tccccgatta tattctatac cgatgtggat    2760
tgcgcatact ttgtgaacag aaagtgatag cgttgatgat tcttcattgg tcagaaaatt    2820
atgaacggtt tcttctattt tgtctctata tactacgtat aggaaatgtt tacattttcg    2880
tattgttttc gattcactct atgaatagtt cttactacaa ttttttgtc taaagagtaa    2940 tactagagat aaacataaaa aatgtagagg tcgagtttag atgcaagttc aaggagcgaa    3000
aggtggatgg gtaggttata tagggatata gcacagagat atatagcaaa gagatacttt    3060
tgagcaatgt ttgtggaagc ggtattcgca atatttttagt agctcgttac agtccggtgc    3120
gtttttggtt ttttgaaagt gcgtcttcag agcgcttttg gttttcaaaa gcgctctgaa    3180
gttcctatac tttctagaga ataggaactt cggaatagga acttcaaagc gtttccgaaa    3240
acgagcgctt ccgaaaatgc aacgcgagct gcgcacatac agctcactgt tcacgtcgca    3300
cctatatctg cgtgttgcct gtatatatat atacatgaga agaacggcat agtgcgtgtt    3360
tatgcttaaa tgcgtactta tatgcgtcta tttatgtagg atgaaaggta gtctagtacc    3420
tcctgtgata ttatcccatt ccatgcgggg tatcgtatgc ttccttcagc actaccctt    3480 agctgttcta tatgctgcca ctcctcaatt ggattagtct catccttcaa tgctatcatt    3540
tcctttgata ttggatcatc taagaaacca ttattatcat gacattaacc tataaaaata    3600
ggcgtatcac gaggcccttt cgtctcgcgc gtttcggtga tgacggtgaa aacctctgac    3660
acatgcagct cccggagacg gtcacagctt gtctgtaagc ggatgccggg agcagacaag    3720
cccgtcaggg cgcgtcagcg ggtgttggcg ggtgtcgggg ctggcttaac tatgcggcat    3780
cagagcagat tgtactgaga gtgcaccata aattcccgtt ttaagagctt ggtgagcgct    3840
aggagtcact gccaggtatc gtttgaacac ggcattagtc agggaagtca taacacagtc    3900
ctttcccgca attttctttt tctattactc ttggcctcct ctagtacact ctatatttt    3960 ttatgcctcg gtaatgattt tcatttttt ttttccccta gcggatgact ctttttttt    4020 cttagcgatt ggcattatca cataatgaat tatacattat ataaagtaat gtgatttctt    4080
cgaagaatat actaaaaaat gagcaggcaa gataaacgaa ggcaaagatg acagagcaga    4140
aagccctagt aaagcgtatt acaaatgaaa ccaagattca gattgcgatc tctttaaagg    4200
gtggtcccct agcgatagag cactcgatct tcccagaaaa agaggcagaa gcagtagcag    4260
aacaggccac acaatcgcaa gtgattaacg tccacacagg tataggggtt ctggaccata    4320
```

```
tgatacatgc tctggccaag cattccggct ggtcgctaat cgttgagtgc attggtgact    4380
tacacataga cgaccatcac accactgaag actgcgggat tgctctcggt caagctttta    4440
aagaggccct actggcgcgt ggagtaaaaa ggtttggatc aggatttgcg cctttggatg    4500
aggcactttc cagagcggtg gtagatcttt cgaacaggcc gtacgcagtt gtcgaacttg    4560
gtttgcaaag ggagaaagta ggagatctct cttgcgagat gatcccgcat tttcttgaaa    4620
gctttgcaga ggctagcaga attaccctcc acgttgattg tctgcgaggc aagaatgatc    4680
atcaccgtag tgagagtgcg ttcaaggctc ttgcggttgc cataagagaa gccacctcgc    4740
ccaatggtac caacgatgtt ccctccacca aaggtgttct tatgtagtga caccgattat    4800
ttaaagctgc agcatacgat atatatacat gtgtatatat gtatacctat gaatgtcagt    4860
aagtatgtat acgaacagta tgatactgaa gatgacaagg taatgcatca ttctatacgt    4920
gtcattctga acgaggcgcg ctttcctttt ttcttttgc ttttcttt tttctctt         4980
gaactcgacg gatctatgcg gtgtgaaata ccgcacagat gcgtaaggag aaaataccgc    5040
atcaggaaat tgtaaacgtt aatattttgt taaaattcgc gttaaatttt tgttaaatca    5100
gctcatttt taaccaatag gccgaaatcg gcaaaatccc ttataaatca aaagaataga    5160
ccgagatagg gttgagtgtt gttccagttt ggaacaagag tccactatta agaacgtgg    5220
actccaacgt caaagggcga aaaccgtct atcagggcga tggcccacta cgtgaaccat    5280
caccctaatc aagttttttg gggtcgaggt gccgtaaagc actaaatcgg aaccctaaag    5340
ggagccccg atttagagct tgacggggaa agccggcgaa cgtggcgaga aggaaggga     5400
agaaagcgaa aggagcgggc gctagggcgc tggcaagtgt agcggtcacg ctgcgcgtaa    5460
ccaccacacc cgccgcgctt aatgcgccgc tacagggcgc gtcgcgccat tcgccattca    5520
ggctgcgcaa ctgttgggaa gggcgatcgg tgcgggcctc ttcgctatta cgccagctgg    5580
cgaaaggggg atgtgctgca aggcgattaa gttgggtaac gccagggttt tcccagtcac    5640
gacgttgtaa aacgacggcc agtgagcgcg cgtaatacga ctcactatag ggcgaattgg    5700
gtaccgggcc ccccctcgag gtcgacggta tcgataagct tgatatcgaa ttcctgcgcc    5760
cgggccacta gtcagatgcc gcgggcactt gagcacctca tgcacagcaa taacacaaca    5820
caatggttag tagcaacctg aattcggtca ttgatgcatg catgtgccgt gaagcgggac    5880
aaccagaaaa gtcgtctata aatgccggca cgtgcgatca tcgtggcggg gttttaagag    5940
tgcatatcac aaattgtcgc attaccgcgg aaccgccaga tattcattac ttgacgcaaa    6000
agcgtttgaa ataatgacga aaagaaggga agaaaaaaaa agaaaaatac cgcttctagg    6060
cgggttatct actgatccga gcttccacta ggatagcacc caaacacctg catatttgga    6120
cgacctttac ttacaccacc aaaaaccact ttcgcctctc ccgcccctga taacgtccac    6180
taattgagcg attacctgag cggtcctctt ttgtttgcag catgagactt gcatactgca    6240
aatcgtaagt agcaacgtct caaggtcaaa actgtatgga aaccttgtca cctcacttaa    6300
ttctagctag cctaccctgc aagtcaagag gtctccgtga ttcctagcca cctcaaggta    6360
tgcctctccc cggaaactgt ggccttttct ggcacacatg atctccacga tttcaacata    6420
taaatagctt ttgataatgg caatattaat caaatttatt ttacttcttt cttgtaacat    6480
ctctcttgta atcccttatt ccttctagct atttttcata aaaaccaag caactgctta     6540
tcaacacaca aacactaaat caaagctgag gatggattta tttgagtcat tagcacaaaa    6600
aattactggt aaagatcaaa caattgtttt ccctgaagga actgaacccc gaattgtcgg    6660
```

```
tgcggcagcg cgattagctg cagacggctt ggttaagccg attgttttag gtgcaacgga    6720
caaagttcag gctgtggcta acgatttgaa tgcggattta acaggcgttc aagtccttga    6780
tcctgcgaca tacccggctg aagataagca agcaatgctt gatgccctcg ttgaacggcg    6840
gaaaggtaag aatacgccag aacaagcggc taaaatgctg gaagatgaaa actactttgg    6900
cacgatgctc gtttatatgg gcaaagcgga tgggatggtt tcaggtgcaa tccatccaac    6960
tggtgatacg gtacggccag cgttacaaat tattaagacc aagcccggtt cacaccgaat    7020
ctcgggtgca tttatcatgc aaaagggtga ggaacgctac gtctttgctg actgtgccat    7080
caatattgat cccgatgccg atacgttagc ggaaattgcc actcagagtg cggctactgc    7140
taaggtcttc gatattgacc cgaaagttgc gatgctcagc ttctcaacta agggttcggc    7200
taagggtgaa atggtcacta agtgcaagaa gcaacggcc aaggcgcaag ctgctgaacc    7260
ggaattggct atcgatggtg aacttcaatt tgacgcggcc ttcgttgaaa agttggtttt    7320
gcaaaaggct cctggttcca agtagctgg tcatgccaat gtctttgtat ttccagagct    7380
tcagtctggt aatattggct ataagattgc gcaacgattt ggtcattttg aagcggtggg    7440
tcctgtcttg caaggcctga acaagccggt ctccgacttg tcacgtggat gcagtgaaga    7500
agacgtttat aaggttgcga ttattacagc agcccaagga ttagcttaat taattaagag    7560
taagcgaatt tcttatgatt tatgattttt attattaaat aagttataaa aaaataagt    7620
gtatacaaat tttaaagtga ctcttaggtt ttaaaacgaa aattcttatt cttgagtaac    7680
tctttcctgt aggtcaggtt gctttctcag gtatagcatg aggtcgctct tattgaccac    7740
acctctaccg gcatgccgag caaatgcctg caaatcgctc cccatttcac ccaattgtag    7800
atatgctaac tccagcaatg agttgatgaa tctcggtgtg tattttatgt cctcagagga    7860
caacacctgt ggtactagtt ctagagcggc cgcccgcaaa ttaaagcctt cgagcgtccc    7920
aaaaccttct caagcaaggt tttcagtata atgttacatg cgtacacgcg tttgtacaga    7980
aaaaaagaa aaatttgaaa tataaataac gttcttaata ctaacataac tattaaaaaa    8040
aataaatagg gacctagact tcaggttgtc taactccttc cttttcggtt agagcggatg    8100
tgggaggagg gcgtgaatgt aagcgtgaca taactaatta catgattaat taattatttt    8160
aaaccctccc attgccaatc attaacttct ggcaagtcag ttccggcatc ccggatatag    8220
gcattgtgtt tagcaagcat attatccatg gattgaacga aggccgcacc agtgttttcc    8280
attgctggtt gcgccgcaat tgccgactta gctaagtcga agcggtccat ctggttcatg    8340
acccgtacgt cgaatggtgt ggtaatatca ccattttcac ggtaaccgtg gacgtataag    8400
ttatggttgt gacgatcaaa gaagatgtca cgaactaagt cttcgtaacc gtggaaagca    8460
aagaccactg gtttgtcctt agtaaagtaa tggtcaaact cagcatctga caagcccgc    8520
ggatcctttt caggactacg taacttcaag atgtcgacca cgttcacgaa acgaatcttc    8580
atctctggga actgtcgtg tagtaattgg atggcagcca acgtttcaag cgttggttcc    8640
gtcccagcag ctgcaaagac aatgtctggt tcgctacctt ggtccgtact tgcccaatca    8700
atgataccaa gaccattgtc aactaattgc ttagcttctt caatgctgaa ccattgttga    8760
cgtgggtgtt ttgacgtaac cacgtagttg atcttttctt ggctccggaa aatgacgtca    8820
ccgacagcta ataacgtgtt ggcatcggct ggtaaatatt cacgaatgta ttctggtttc    8880
ttttcggcca aatgagttaa tgcacctgga tcttggtggg tataaccatt atggtcttgt    8940
tggaatacag ttgaagccgc gataatgtta agtgatgggg actttttacg ccaatcaagt    9000
tcattggctt tacgtaacca cttgaagtgt tgcgtcaaca ttgagtccac aacgcgtagg    9060
```

```
aaggcttcat aactggcaaa taacccatga cgtccagtta agacgtaacc ttctaaccaa      9120
ccttcagctt ggtgttcaga taactgagca tctaagaccc ggccagctgg tgcttcatat      9180
tggtcactat ctggatgaat gtcttccatc cattgacgat tagtggtttc gaagacacca      9240
tataaacggt tagacatggt ttcatcaggt ccgaacaacc ggaagttatc aggatttttc      9300
ttgatgacat cccgcaaata gtctgaccaa acgatcatat cttgcttaac attcgcgcct      9360
tctttggacg tatcgaccgc ataatcacgg aagtttggta agttcaaggc tttcggatcg      9420
accccaccat tggtgattgg gttagcagcc atccgactgt ccccagtagg aataatttct      9480
ttaatatcat ccttcaaaga gccatcttca ttgaagagtt cttttggttg atatgattcg      9540
agccaatcaa ctaaagcatc cgcatgttcc atgtcatttt gatcaacagg aatcggaatt      9600
tgatgagcac ggaatgaacc ttcgatctta tcaccgtccc atgacttcgg accagtccag      9660
cccttaggtg cgcggaagac gatcattggc catactggca atgttgcatc gttattttcg      9720
cgagcatgct tctggattgc cttgatcttt tcaacggctt catccatggc cttagctaag      9780
gctgggtgaa ccttttcagg atcgtcacct tcaacgaaga ttggttccca attcatgctt      9840
tcgaagtatt ccttaatctt agcatcagaa gtccgaccaa aaatcgttgg attagaaatc      9900
ttaaaaccat ttaagttcaa gattggtaaa acagcccgt cgttgattgg gttaatgaac       9960
ttcgttgatt gccatgaagt tgctaatgga cccgtttcgg attccccatc accaacaaca     10020
accgcggcga tttcgtcagg attgtcaaga attgccccaa ccccgtgtga aattgagtaa     10080
ccaagttcgc caccttcgtg gattgaaccg ggtgtttcag gtgccgcatg ggaagcaacc     10140
ccacctggga atgagaattg cttgaagagc ttttgcatcc cttcaacatc ctgcgtaatt     10200
tctggataaa tatcggtgta agtaccgtca aggtaagagt ttgaaaccat cacttgacca     10260
ccatgacctg gaccttcaac gtagaacatc ttcaaaccgt acttgttgat gacccggtta     10320
agatgagcat agataaagtt ttgaccggca atcgtccccc agtgaccaat tggatgaacc     10380
ttaacgtcac tggccttcaa tggccgttgt aatagtggat tatcttttaa ataaagttga     10440
ccaactgata agtagttggc agcacgccag tacttatcaa cttttgcaa atatgctggt      10500 gatgagtaat ctgttgtcat cctcagctgg aacttagatt agattgctat gctttctctc     10560
taacgagcaa gaagtaaaaa agttgtaat agaacaagaa aaatgaaact gaagcttgag       10620
aaattgaaga ccgtttatta gcttaaatat caatgggagg tcatcgaaag agaaaaaat      10680 caagaaagaa actctcaaga aaagaaacg tgataaaaat ttttattgcc tctctcgacg      10740
aagagaaaga aacgaggcgg tccctttttt cttttccaaa cctttagtac gggtaattag     10800
cgacacccta gaggaagaaa gaggggaaat ttagtatgct gtgcttgggt gtcttgaagt     10860
ggtacggcga tgcgcggagt ccgagaaaat ctggaagagt aaaaggggg tagaagcgtt      10920 ttgaagctat ccgc                                                       10934
```

<210> SEQ ID NO 163
<211> LENGTH: 80
<212> TYPE: DNA
<213> ORGANISM: Artificial Sequence
<220> FEATURE:
<223> OTHER INFORMATION: N1341

<400> SEQUENCE: 163

```
gttgcaagaa atgcattatg caattttttg attatgacaa tctctcgaaa atagcttcaa        60
aacgcttcta cccccttttt                                                    80
```

<210> SEQ ID NO 164
<211> LENGTH: 80
<212> TYPE: DNA
<213> ORGANISM: Artificial Sequence
<220> FEATURE:
<223> OTHER INFORMATION: N1338

<400> SEQUENCE: 164
catacattat acgaacggta ctgaacatta gaatacgtaa tccgcaatgc ccgcaaatta    60
aagccttcga gcgtcccaaa                                                80

<210> SEQ ID NO 165
<211> LENGTH: 30
<212> TYPE: DNA
<213> ORGANISM: Artificial Sequence
<220> FEATURE:
<223> OTHER INFORMATION: N1033c

<400> SEQUENCE: 165
gcattgcgga ttacgtattc taatgttcag                                     30

<210> SEQ ID NO 166
<211> LENGTH: 81
<212> TYPE: DNA
<213> ORGANISM: Artificial Sequence
<220> FEATURE:
<223> OTHER INFORMATION: N1342

<400> SEQUENCE: 166
acatatgtga aaaaaaatag ttgatatttt aaaccaaatc agaaatttat caccttggct    60
aactcgttgt atcatcactg g                                              81

<210> SEQ ID NO 167
<211> LENGTH: 30
<212> TYPE: DNA
<213> ORGANISM: Artificial Sequence
<220> FEATURE:
<223> OTHER INFORMATION: N1364

<400> SEQUENCE: 167
atgacaacag attactcatc accagcatat                                     30

<210> SEQ ID NO 168
<211> LENGTH: 604
<212> TYPE: DNA
<213> ORGANISM: Artificial Sequence
<220> FEATURE:
<223> OTHER INFORMATION: L8

<400> SEQUENCE: 168
gcctacttgg cttcacatac gttgcatacg acgatataga aaataatgat aatgacagca    60
ggattatcgt ataacgtaat agtcgaaaaa tctcaaaaat ctgtgggtca ttacgtaaat   120
aatgatagga atgtgattct tctatttttc cttttttccat tctggcagcc gtcgggaaaa   180
cgtggcttcc tctctttcgg gctctattgg agtaacgctg ccgtgagctt cctctctttc   240
catatctaac aactgagcac gtaaccaatg gtaaagcatg agcttagcgt tgctccaaag   300
aagtattgga aggttaatac catgtgtctg ttctcttctg actttgactc ctcaaataaa   360
aaaaaattct acaatcaaca gatcgcttca attacgctct cacaaaaact ttttccttc    420 ttcttcgccc acgttaaatt ttaaccctca tgctgtctaa cggatttctg cacttaattt   480
attataaaac gacaaagaca taatacttct ctatcaattt cagttattgt tcttcattgc   540

```
attactcttc tgttcttctt tttcatttgt catatacaac cataaccaaa taatacatat    600
tcaa                                                                604

<210> SEQ ID NO 169
<211> LENGTH: 80
<212> TYPE: DNA
<213> ORGANISM: Artificial Sequence
<220> FEATURE:
<223> OTHER INFORMATION: N1366

<400> SEQUENCE: 169
gttgcaagaa atgcattatg caatttttg attatgacaa tctctcgaaa gcctacttgg    60
cttcacatac gttgcatacg                                               80

<210> SEQ ID NO 170
<211> LENGTH: 65
<212> TYPE: DNA
<213> ORGANISM: Artificial Sequence
<220> FEATURE:
<223> OTHER INFORMATION: N1368

<400> SEQUENCE: 170
atatgctggt gatgagtaat ctgttgtcat tttgaatatg tattatttgg ttatggttgt    60
atatg                                                               65

<210> SEQ ID NO 171
<211> LENGTH: 80
<212> TYPE: DNA
<213> ORGANISM: Artificial Sequence
<220> FEATURE:
<223> OTHER INFORMATION: N1371

<400> SEQUENCE: 171
aaaaactaat acgtaaacct gcattaaggt aagattatat cagaaaatgt gttgcaagaa    60
atgcattatg caatttttg                                                80

<210> SEQ ID NO 172
<211> LENGTH: 85
<212> TYPE: DNA
<213> ORGANISM: Artificial Sequence
<220> FEATURE:
<223> OTHER INFORMATION: N1372

<400> SEQUENCE: 172
tagaagctaa tctttaacct ggaagacagg acagaaaagt aattacaaga acatatgtga    60
aaaaaaatag ttgatatttt aaacc                                         85

<210> SEQ ID NO 173
<211> LENGTH: 25
<212> TYPE: DNA
<213> ORGANISM: Artificial Sequence
<220> FEATURE:
<223> OTHER INFORMATION: BK93

<400> SEQUENCE: 173
aaaaattgat tctcatcgta aatgc                                         25

<210> SEQ ID NO 174
<211> LENGTH: 30
<212> TYPE: DNA
<213> ORGANISM: Artificial Sequence
<220> FEATURE:
```

<223> OTHER INFORMATION: N1114

<400> SEQUENCE: 174

| | |
|---|---|
| atatgctggt gatgagtaat ctgttgtcat | 30 |

<210> SEQ ID NO 175
<211> LENGTH: 6728
<212> TYPE: DNA
<213> ORGANISM: Artificial Sequence
<220> FEATURE:
<223> OTHER INFORMATION: pJT254

<400> SEQUENCE: 175

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcaggcgcg tcagcgcgtg | 120 |
| ttggcgggtg tcgggctgg cttaactatg cggcatcaga gcagattgta ctgagagtgc | 180 |
| accataaatt cccgttttaa gagcttggtg agcgctagga gtcactgcca ggtatcgttt | 240 |
| gaacacggca ttagtcaggg aagtcataac acagtccttt cccgcaattt tctttttcta | 300 |
| ttactcttgg cctcctctag tacactctat attttttat gcctcggtaa tgattttcat | 360 |
| ttttttttt cccctagcgg atgactcttt ttttttctta gcgattggca ttatcacata | 420 |
| atgaattata cattatataa agtaatgtga tttcttcgaa gaatatacta aaaaatgagc | 480 |
| aggcaagata aacgaaggca aagatgacag agcagaaagc cctagtaaag cgtattacaa | 540 |
| atgaaaccaa gattcagatt gcgatctctt taaagggtgg tcccctagcg atagagcact | 600 |
| cgatcttccc agaaaagag gcagaagcag tagcagaaca ggccacacaa tcgcaagtga | 660 |
| ttaacgtcca cacaggtata gggtttctgg accatatgat acatgctctg gccaagcatt | 720 |
| ccggctggtc gctaatcgtt gagtgcattg gtgacttaca catagacgac catcacacca | 780 |
| ctgaagactg cgggattgct ctcggtcaag ctttttaaga ggccctactg gcgcgtggag | 840 |
| taaaaaggtt tggatcagga tttgcgcctt tggatgaggc actttccaga gcggtggtag | 900 |
| atctttcgaa caggccgtac gcagttgtcg aacttggttt gcaaagggag aaagtaggag | 960 |
| atctctcttg cgagatgatc ccgcattttc ttgaaagctt tgcagaggct agcagaatta | 1020 |
| ccctccacgt tgattgtctg cgaggcaaga atgatcatca ccgtagtgag agtgcgttca | 1080 |
| aggctcttgc ggttgccata agagaagcca cctcgcccaa tggtaccaac gatgttccct | 1140 |
| ccaccaaagg tgttcttatg tagtgacacc gattatttaa agctgcagca tacgatatat | 1200 |
| atacatgtgt atatatgtat acctatgaat gtcagtaagt atgtatacga acagtatgat | 1260 |
| actgaagatg acaaggtaat gcatcattct atacgtgtca ttctgaacga ggcgcgcttt | 1320 |
| ccttttttct ttttgctttt tctttttttt tctcttgaac tcgacggatc tatgcggtgt | 1380 |
| gaaataccgc acagatgcgt aaggagaaaa taccgcatca ggaaattgta aacgttaata | 1440 |
| ttttgttaaa attcgcgtta aattttttgtt aaatcagctc attttttaac caataggccg | 1500 |
| aaatcggcaa aatcccttat aaatcaaaag aatagaccga gatagggttg agtgttgttc | 1560 |
| cagtttggaa caagagtcca ctattaaaga acgtggactc caacgtcaaa gggcgaaaaa | 1620 |
| ccgtctatca gggcgatggc ccactacgtg aaccatcacc ctaatcaagt tttttgggt | 1680 |
| cgaggtgccg taaagcacta atcggaacc ctaaagggag cccccgattt agagcttgac | 1740 |
| ggggaaagcc ggcgaacgtg gcgagaaagg aagggaagaa agcgaaagga gcgggcgcta | 1800 |
| gggcgctggc aagtgtagcg gtcacgctgc gcgtaaccac cacacccgcc gcgcttaatg | 1860 |
| cgccgctaca gggcgcgtcg cgccattcgc cattcaggct gcgcaactgt tgggaagggc | 1920 |

```
gatcggtgcg ggcctcttcg ctattacgcc agctggcgaa aggggatgt gctgcaaggc    1980
gattaagttg ggtaacgcca gggttttccc agtcacgacg ttgtaaaacg acggccagtg   2040
agcgcgcgta atacgactca ctatagggcg aattgggtac cgggccccc ctcgaggtcg    2100
acggtatcga taagcttgat tagaagccgc cgagcgggcg acagccctcc gacggaagac   2160
tctcctccgt gcgtcctcgt cttccggt cgcgttcctg aaacgcagat gtgcctcgcg    2220
ccgcactgct ccgaacaata aagattctac aatactagct tttatggtta tgaagaggaa   2280
aaattggcag taacctggcc ccacaaacct tcaaattaac gaatcaaatt aacaaccata   2340
ggatgataat gcgattagtt ttttagcctt atttctgggg taattaatca gcgaagcgat   2400
gattttgat ctattaacag atatataaat ggaaaagctg cataaccact ttaactaata   2460
ctttcaacat tttcagtttg tattacttct tattcaaatg tcataaagt atcaacaaa    2520
aattgttaat atacctctat actttaacgt caaggagaaa aatgtccaat ttactgcccg   2580
tacaccaaaa tttgcctgca ttaccggtcg atgcaacgag tgatgaggtt cgcaagaacc   2640
tgatggacat gttcagggat cgccaggcgt tttctgagca tacctggaaa atgcttctgt   2700
ccgtttgccg gtcgtgggcg gcatggtgca agttgaataa ccggaaatgg tttcccgcag   2760
aacctgaaga tgttcgcgat tatcttctat atcttcaggc gcgcggtctg gcagtaaaaa   2820
ctatccagca acatttgggc cagctaaaca tgcttcatcg tcggtccggg ctgccacgac   2880
caagtgacag caatgctgtt tcactggtta tgcggcggat ccgaaaagaa aacgttgatg   2940
ccggtgaacg tgcaaaacag gctctagcgt tcgaacgcac tgatttcgac caggttcgtt   3000
cactcatgga aaatagcgat cgctgccagg atatacgtaa tctggcattt ctggggattg   3060
cttataacac cctgttacgt atagccgaaa ttgccaggat cagggttaaa gatatctcac   3120
gtactgacgg tgggagaatg ttaatccata ttggcagaac gaaaacgctg gttagcaccg   3180
caggtgtaga gaaggcactt agcctggggg taactaaact ggtcgagcga tggatttccg   3240
tctctggtgt agctgatgat ccgaataact acctgttttg ccgggtcaga aaaaatggtg   3300
ttgccgcgcc atctgccacc agccagctat caactcgcgc cctggaaggg attttttgaag  3360
caactcatcg attgatttac ggcgctaagg atgactctgg tcagagatac ctggcctggt   3420
ctggacacag tgcccgtgtc ggagccgcgc gagatatggc ccgcgctgga gtttcaatac   3480
cggagatcat gcaagctggt ggctggacca atgtaaatat tgtcatgaac tatatccgta   3540
acctggatag tgaaacaggg gcaatggtgc gcctgctgga agatggcgat taggagtaag   3600
cgaatttctt atgatttatg attttttatta ttaaataagt tataaaaaaa ataagtgtat   3660
acaaatttta aagtgactct taggttttaa aacgaaaatt cttattcttg agtaactctt   3720
tcctgtaggt caggttgctt tctcaggtat agcatgaggt cgctcttatt gaccacacct   3780
ctaccggcat gccgagcaaa tgcctgcaaa tcgctcccca tttcacccaa ttgtagatat   3840
gctaactcca gcaatgagtt gatgaatctc ggtgtgtatt ttatgtcctc agaggacaac   3900
acctgtggtg ttctagagcg gccgccaccg cggtggagct ccagcttttg ttccctttag   3960
tgagggttaa ttgcgcgctt ggcgtaatca tggtcatagc tgtttcctgt gtgaaattgt   4020
tatccgctca caattccaca caacatagga gccggaagca taaagtgtaa agcctggggt   4080
gcctaatgag tgaggtaact cacattaatt gcgttgcgct cactgcccgc tttccagtcg   4140
ggaaacctgt cgtgccagct gcattaatga atcggccaac gcgcggggag aggcggtttg   4200
cgtattgggc gctcttccgc ttcctcgctc actgactcgc tgcgctcggt cgttcggctg   4260
```

```
cggcgagcgg tatcagctca ctcaaaggcg gtaatacggt tatccacaga atcaggggat    4320
aacgcaggaa agaacatgtg agcaaaaggc cagcaaaagg ccaggaaccg taaaaaggcc    4380
gcgttgctgg cgttttttcca taggctccgc cccctgacg agcatcacaa aaatcgacgc    4440
tcaagtcaga ggtggcgaaa cccgacagga ctataaagat accaggcgtt tcccctggga    4500
agctccctcg tgcgctctcc tgttccgacc ctgccgctta ccggatacct gtccgccttt    4560
ctcccttcgg gaagcgtggc gctttctcat agctcacgct gtaggtatct cagttcggtg    4620
taggtcgttc gctccaagct gggctgtgtg cacgaacccc ccgttcagcc cgaccgctgc    4680
gccttatccg gtaactatcg tcttgagtcc aacccggtaa gacacgactt atcgccactg    4740
gcagcagcca ctggtaacag gattagcaga gcgaggtatg taggcggtgc tacagagttc    4800
ttgaagtggt ggcctaacta cggctacact agaaggacag tatttggtat ctgcgctctg    4860
ctgaagccag ttaccttcgg aaaaagagtt ggtagctctt gatccggcaa acaaaccacc    4920
gctggtagcg gtggtttttt tgtttgcaag cagcagatta cgcgcagaaa aaaggatct    4980 caagaagatc ctttgatctt ttctacgggg tctgacgctc agtggaacga aaactcacgt    5040
taagggattt tggtcatgag attatcaaaa aggatcttca cctagatcct tttaaattaa    5100
aaatgaagtt ttaaatcaat ctaaagtata tatgagtaaa cttggtctga cagttaccaa    5160
tgcttaatca gtgaggcacc tatctcagcg atctgtctat ttcgttcatc catagttgcc    5220
tgactccccg tcgtgtagat aactacgata cgggagggct taccatctgg ccccagtgct    5280
gcaatgatac cgcgagaccc acgctcaccg gctccagatt tatcagcaat aaaccagcca    5340
gccggaaggg ccgagcgcag aagtggtcct gcaactttat ccgcctccat ccagtctatt    5400
aattgttgcc gggaagctag agtaagtagt tcgccagtta atagtttgcg caacgttgtt    5460
gccattgcta caggcatcgt ggtgtcacgc tcgtcgtttg gtatggcttc attcagctcc    5520
ggttcccaac gatcaaggcg agttacatga tcccccatgt tgtgcaaaaa agcggttagc    5580
tccttcggtc ctccgatcgt tgtcagaagt aagttggccg cagtgttatc actcatggtt    5640
atggcagcac tgcataattc tcttactgtc atgccatccg taagatgctt ttctgtgact    5700
ggtgagtact caaccaagtc attctgagaa tagtgtatgc ggcgaccgag ttgctcttgc    5760
ccggcgtcaa tacgggataa taccgcgcca catagcagaa ctttaaaagt gctcatcatt    5820
ggaaaacgtt cttcggggcg aaaactctca aggatcttac cgctgttgag atccagttcg    5880
atgtaaccca ctcgtgcacc caactgatct tcagcatctt ttactttcac cagcgtttct    5940
gggtgagcaa aaacaggaag gcaaaatgcc gcaaaaaagg gaataagggc gacacggaaa    6000
tgttgaatac tcatactctt cctttttcaa tattattgaa gcatttatca gggttattgt    6060
ctcatgagcg gatacatatt tgaatgtatt tagaaaaata aacaaatagg ggttccgcgc    6120
acatttcccc gaaaagtgcc acctgggtcc ttttcatcac gtgctataaa aataattata    6180
atttaaattt tttaatataa atatataaat taaaaataga aagtaaaaaa agaaattaaa    6240
gaaaaaatag ttttgttttt ccgaagatgt aaaagactct aggggatcg ccaacaaata    6300 ctaccttta tcttgctctt cctgctctca ggtattaatg ccgaattgtt tcatcttgtc    6360
tgtgtagaag accacacacg aaaatcctgt gatttttacat tttacttatc gttaatcgaa    6420
tgtatatcta tttaatctgc ttttcttgtc taataaatat atatgtaaag tacgcttttt    6480
gttgaaattt tttaaacctt tgtttatttt ttttcttca ttccgtaact cttctacctt    6540
ctttatttac tttctaaaat ccaaatacaa aacataaaaa taaataaaca cagagtaaat    6600
tcccaaatta ttccatcatt aaaagatacg aggcgcgtgt aagttacagg caagcgatcc    6660
```

```
gtcctaagaa accattatta tcatgacatt aacctataaa aataggcgta tcacgaggcc    6720
ctttcgtc                                                            6728

<210> SEQ ID NO 176
<211> LENGTH: 22
<212> TYPE: DNA
<213> ORGANISM: Artificial Sequence
<220> FEATURE:
<223> OTHER INFORMATION: N160SeqF5

<400> SEQUENCE: 176
cctgaagtct aggtccctat tt                                              22

<210> SEQ ID NO 177
<211> LENGTH: 1650
<212> TYPE: DNA
<213> ORGANISM: Artificial Sequence
<220> FEATURE:
<223> OTHER INFORMATION: AMN1

<400> SEQUENCE: 177
atgaagctgg agcgcgtgag ttctaacggg agctttaagc gtggccgtga catccaaagt      60
ttggagagtc cgtgtacccg cccattaaag aaaatgtcgc catcaccttc atttacgagc     120
ctgaagatga aaaaccgtt taaggacatt gttcgaaaat acggggtca cctgcaccag       180 tcctcgtata acccaggttc ttcaaaagtt gaactcgtgc gtccggacct gagcttgaaa     240
acggaccaat cattttttgca gagcagcgtg cagacaaccc cgaacaaaaa gagttgtaac     300
gagtatctgt ccacacccga agccactccc cttaagaaca cggccaccga aatgcgtgg      360 gctacgtcaa gggtggtgag cgcatcaagc ctgtcaatcg tcacgccgac cgaaatcaaa    420
aatatactgg ttgacgagtt tagtgaacta aaacttggtc agcccttaac agcccagcac    480
caacggagcc atgcagtttt cgagataccct gagatcgtag agaacataat caagatgatc   540
gtttccctcg agagcgccaa tattccgaaa gaacgtccgt gcctgcgtcg caacccgcag    600
agttatgagc attcccttct gatgtataaa gacgaggaac gcgcgaagaa agcatggtcc    660
gcggctcaac aactgcgcga tccgccgctg gtgggtcata aggaaaaaaa acagggcgct    720
ctgtttagct gcatgatggt caaccgcctg tggttgaatg tcacgcgtcc gttcttatt    780 aagtctctgc atttcaaatc agtgcacaac ttcaaagaat ttctgcgcac aagtcaggaa    840
accacgcaag tgatgaggcc atcgcacttt atcctgcata aattgcacca ggtaacgcag    900
ccggatattg agagactgtc tagaatggaa tgccagaacc tcaagtggtt ggaattttat   960
gtatgtcccc gtattacacc tccactgtct tggttcgaca atttgcataa gttagaaaaa   1020
ttaatcatcc ccgaaacaa gaatatcgac gataatttcc tcttacggct gtctcagagt    1080
attcctaacc tgaaacacct cgtgcttcgt gcttgcgaca atgtttccga tagtggtgta   1140
gtttgtatcg ccctgaactg ccctaagctg aagacgttca acatcggacg tcatcgccgc   1200
ggcaatctga ttacatcagt tagcttggtt gccctgggta agtatacgca agttgagacc    1260
gttggttttg caggctgcga tgtggacgac gcaggcatat gggagttcgc gcgtttaaac   1320
gggaaaaacg tcgagcgcct gtcactcaac agttgccggc ttttaaccga ctatagcttg   1380
ccaatcctgt ttgcccttaa tagtttcccg aaccttgcgg tgttggaaat cgaaacctc   1440 gataaaatta cagatgtccg ccattttgtg aaatataatc tgtggaagaa atcactggat    1500
gctcctatcc tgattgaggc gtgcgaacgc ataacaaagc tgattgatca ggaagagaac    1560
```

```
cgggtcaaac gcataaatag cctggtcgct ttaaaggata tgaccgcgtg ggtgaacgct    1620
gacgatgaaa ttgaaaacaa cgtcgattga                                     1650
```

<210> SEQ ID NO 178
<211> LENGTH: 549
<212> TYPE: PRT
<213> ORGANISM: Artificial Sequence
<220> FEATURE:
<223> OTHER INFORMATION: AMN1

<400> SEQUENCE: 178

```
Met Lys Leu Glu Arg Val Ser Ser Asn Gly Ser Phe Lys Arg Gly Arg
1               5                   10                  15

Asp Ile Gln Ser Leu Glu Ser Pro Cys Thr Arg Pro Leu Lys Lys Met
            20                  25                  30

Ser Pro Ser Pro Ser Phe Thr Ser Leu Lys Met Glu Lys Pro Phe Lys
        35                  40                  45

Asp Ile Val Arg Lys Tyr Gly Gly His Leu His Gln Ser Ser Tyr Asn
    50                  55                  60

Pro Gly Ser Ser Lys Val Glu Leu Val Arg Pro Asp Leu Ser Leu Lys
65                  70                  75                  80

Thr Asp Gln Ser Phe Leu Gln Ser Ser Val Gln Thr Thr Pro Asn Lys
                85                  90                  95

Lys Ser Cys Asn Glu Tyr Leu Ser Thr Pro Glu Ala Thr Pro Leu Lys
            100                 105                 110

Asn Thr Ala Thr Glu Asn Ala Trp Ala Thr Ser Arg Val Val Ser Ala
        115                 120                 125

Ser Ser Leu Ser Ile Val Thr Pro Thr Glu Ile Lys Asn Ile Leu Val
    130                 135                 140

Asp Glu Phe Ser Glu Leu Lys Leu Gly Gln Pro Leu Thr Ala Gln His
145                 150                 155                 160

Gln Arg Ser His Ala Val Phe Glu Ile Pro Glu Ile Val Glu Asn Ile
                165                 170                 175

Ile Lys Met Ile Val Ser Leu Glu Ser Ala Asn Ile Pro Lys Glu Arg
            180                 185                 190

Pro Cys Leu Arg Arg Asn Pro Gln Ser Tyr Glu His Ser Leu Leu Met
        195                 200                 205

Tyr Lys Asp Glu Glu Arg Ala Lys Lys Ala Trp Ser Ala Ala Gln Gln
    210                 215                 220

Leu Arg Asp Pro Pro Leu Val Gly His Lys Glu Lys Gln Gly Ala
225                 230                 235                 240

Leu Phe Ser Cys Met Met Val Asn Arg Leu Trp Leu Asn Val Thr Arg
                245                 250                 255

Pro Phe Leu Phe Lys Ser Leu His Phe Lys Ser Val His Asn Phe Lys
            260                 265                 270

Glu Phe Leu Arg Thr Ser Gln Glu Thr Thr Gln Val Met Arg Pro Ser
        275                 280                 285

His Phe Ile Leu His Lys Leu His Gln Val Thr Gln Pro Asp Ile Glu
    290                 295                 300

Arg Leu Ser Arg Met Glu Cys Gln Asn Leu Lys Trp Leu Glu Phe Tyr
305                 310                 315                 320

Val Cys Pro Arg Ile Thr Pro Pro Leu Ser Trp Phe Asp Asn Leu His
                325                 330                 335

Lys Leu Glu Lys Leu Ile Ile Pro Gly Asn Lys Asn Ile Asp Asp Asn
            340                 345                 350
```

```
Phe Leu Leu Arg Leu Ser Gln Ser Ile Pro Asn Leu Lys His Leu Val
            355                 360                 365
Leu Arg Ala Cys Asp Asn Val Ser Asp Ser Gly Val Val Cys Ile Ala
    370                 375                 380
Leu Asn Cys Pro Lys Leu Lys Thr Phe Asn Ile Gly Arg His Arg Arg
385                 390                 395                 400
Gly Asn Leu Ile Thr Ser Val Ser Leu Val Ala Leu Gly Lys Tyr Thr
                405                 410                 415
Gln Val Glu Thr Val Gly Phe Ala Gly Cys Asp Val Asp Asp Ala Gly
            420                 425                 430
Ile Trp Glu Phe Ala Arg Leu Asn Gly Lys Asn Val Glu Arg Leu Ser
        435                 440                 445
Leu Asn Ser Cys Arg Leu Leu Thr Asp Tyr Ser Leu Pro Ile Leu Phe
    450                 455                 460
Ala Leu Asn Ser Phe Pro Asn Leu Ala Val Leu Glu Ile Arg Asn Leu
465                 470                 475                 480
Asp Lys Ile Thr Asp Val Arg His Phe Val Lys Tyr Asn Leu Trp Lys
                485                 490                 495
Lys Ser Leu Asp Ala Pro Ile Leu Ile Glu Ala Cys Glu Arg Ile Thr
            500                 505                 510
Lys Leu Ile Asp Gln Glu Glu Asn Arg Val Lys Arg Ile Asn Ser Leu
        515                 520                 525
Val Ala Leu Lys Asp Met Thr Ala Trp Val Asn Ala Asp Asp Glu Ile
    530                 535                 540
Glu Asn Asn Val Asp
545

<210> SEQ ID NO 179
<211> LENGTH: 6638
<212> TYPE: DNA
<213> ORGANISM: Artificial Sequence
<220> FEATURE:
<223> OTHER INFORMATION: pLA67

<400> SEQUENCE: 179
aaacgccagc aacgcggcct ttttacggtt cctggccttt tgctggcctt ttgctcacat      60
gttctttcct gcgttatccc ctgattctgt ggataaccgt attaccgcct ttgagtgagc     120
tgataccgct cgccgcagcc gaacgaccga gcgcagcgag tcagtgagcg aggaagcgga     180
agagcgccca tacgcaaac cgcctctccc gcgcgttgg ccgattcatt aatgcagctg      240
gcacgacagg tttcccgact ggaaagcggg cagtgagcgc aacgcaatta atgtgagtta     300
gctcactcat taggcacccc aggctttaca ctttatgctt ccggctcgta tgttgtgtgg     360
aattgtgagc ggataacaat ttcacacagg aaacagctat gaccatgatt acgccaagct     420
tgcatgcctg caggtcgact ctagaggatc cgcattgcgg attacgtatt ctaatgttca     480
gtaccgttcg tataatgtat gctatacgaa gttatgcaga ttgtactgag agtgcaccat     540
accacagctt tcaattcaa ttcatcattt tttttttatt cttttttttg atttcggttt      600
ctttgaaatt ttttttgattc ggtaatctcc gaacagaagg aagaacgaag gaaggagcac     660
agacttagat tggtatatat acgcatatgt agtgttgaag aaacatgaaa ttgcccagta     720
ttcttaaccc aactgcacag aacaaaaacc tgcaggaaac gaagataaat catgtcgaaa     780
gctacatata aggaacgtgc tgctactcat cctagtcctg ttgctgccaa gctatttaat     840
atcatgcacg aaaagcaaac aaacttgtgt gcttcattgg atgttcgtac caccaaggaa     900
```

```
ttactggagt tagttgaagc attaggtccc aaaatttgtt tactaaaaac acatgtggat    960
atcttgactg atttttccat ggagggcaca gttaagccgc taaaggcatt atccgccaag   1020
tacaatttt tactcttcga agacagaaaa tttgctgaca ttggtaatac agtcaaattg    1080
cagtactctg cgggtgtata cagaatagca gaatgggcag acattacgaa tgcacacggt   1140
gtggtgggcc caggtattgt tagcggtttg aagcaggcgg cagaagaagt aacaaaggaa   1200
cctagaggcc ttttgatgtt agcagaattg tcatgcaagg ctccctatc tactggagaa    1260
tatactaagg gtactgttga cattgcgaag agcgacaaag attttgttat cggctttatt   1320
gctcaaagag acatgggtgg aagagatgaa ggttacgatt ggttgattat gacacccggt   1380
gtgggtttag atgacaaggg agacgcattg ggtcaacagt atagaaccgt ggatgatgtg   1440
gtctctacag gatctgacat tattattgtt ggaagaggac tatttgcaaa gggaagggat   1500
gctaaggtag agggtgaacg ttacagaaaa gcaggctggg aagcatattt gagaagatgc   1560
ggccagcaaa actaaaaaac tgtattataa gtaaatgcat gtatactaaa ctcacaaatt   1620
agagcttcaa tttaattata tcagttatta ccctatgcgg tgtgaaatac cgcacagatg   1680
cgtaaggaga aaataccgca tcaggaaatt gtaaacgtta atattttgtt aaaattcgcg   1740
ttaaatttt gttaaatcag ctcatttttt aaccaatagg ccgaaatcgg caaaatccct    1800
tataaatcaa agaatagac cgagataggg ttgagtgttg ttccagtttg gaacaagagt    1860
ccactattaa agaacgtgga ctccaacgtc aaagggcgaa aaaccgtcta tcagggcgat   1920
ggcccactac gtgaaccatc accctaatca agataacttc gtataatgta tgctatacga   1980
acggtaccag tgatgataca acgagttagc caaggtgaat tcgacttagg atgtctcatc   2040
aatcatctta ttcctgctgg tgttttttgt atcgccttgc cttggagtgt ttatgcttgt   2100
cctttgttca gtaaccattc ttcaagtttg tttcaagtag taggatacct tcagatatac   2160
gaaagaaagg gagtatagtt gtggatatat atatatatag caaccttct ttataagggt    2220
cctatagact atactcttca cactttaaag tacggaatta aggcccaagg gaactaacaa   2280
aaacgttcaa aaagttttaa aactatatgt gttaactgta caaaaataac ttatttatca   2340
tatcatttt ttctctgttt atttcttcta gaacttatac ctgtcttttc cttttattct    2400
ttgaatttgk tttaatatcc cttttttgktt taatatccat ccattccttt cacttagaac   2460
taataattcc cttcgtttga taatttatca ttttcctttt ctgttagtaa agtacccatt   2520
aaatgaagct ggagcgcgtg agttctaacg ggagctttaa gcgtggccgt gacatccaaa   2580
gtttggagag tccgtgtacc cgcccattaa agaaaatgtc gccatcacct tcatttacga   2640
gcctgaagat ggaaaaaccg tttaaggaca ttgttcgaaa atacggggt cacctgcacc    2700
agtcctcgta taacccaggt tcttcaaaag ttgaactcgt gcgtccggac ctgagcttga   2760
aaacggacca atcatttttg cagagcagcg tgcagacaac cccgaacaaa agagttgta    2820
acgagtatct gtccacaccc gaagccactc cccttaagaa cacggccacc gagaatgcgt   2880
gggctacgtc aagggtggtg agcgcatcaa gcctgtcaat cgtcacgccg accgaaatca   2940
aaaatatact ggttgacgag tttagtgaac taaaacttgg tcagccctta acagcccagc   3000
accaacggag ccatgcagtt ttcgagatac ctgagatcgt agagaacata atcaagatga   3060
tcgtttccct cgagagcgcc aatattccga agaacgtcc gtgcctgcgt cgcaacccgc    3120
agagttatga gcattccctt ctgatgtata agacgagga acgcgcgaag aaagcatggt   3180
ccgcggctca acaactgcgc gatccgccgc tggtgggtca taaggaaaaa aaacagggcg   3240
```

```
ctctgtttag ctgcatgatg gtcaaccgcc tgtggttgaa tgtcacgcgt ccgttcttat    3300
ttaagtctct gcatttcaaa tcagtgcaca acttcaaaga atttctgcgc acaagtcagg    3360
aaaccacgca agtgatgagg ccatcgcact ttatcctgca taaattgcac caggtaacgc    3420
agccggatat tgagagactg tctagaatgg aatgccagaa cctcaagtgg ttggaatttt    3480
atgtatgtcc ccgtattaca cctccactgt cttggttcga caatttgcat aagttagaaa    3540
aattaatcat ccccggaaac aagaatatcg acgataattt cctcttacgg ctgtctcaga    3600
gtattcctaa cctgaaacac ctcgtgcttc gtgcttgcga caatgttttcc gatagtggtg    3660 tagtttgtat cgccctgaac tgccctaagc tgaagacgtt caacatcgga cgtcatcgcc    3720
gcggcaatct gattacatca gttagcttgg ttgccctggg taagtatacg caagttgaga    3780
ccgttggttt tgcaggctgc gatgtggacg acgcaggcat atgggagttc gcgcgtttaa    3840
acgggaaaaa cgtcgagcgc ctgtcactca acagttgccg gcttttaacc gactatagct    3900
tgccaatcct gtttgccctt aatagtttcc cgaaccttgc ggtgttggaa attcgaaacc    3960
tcgataaaat tacagatgtc cgccatttttg tgaaatataa tctgtggaag aaatcactgg    4020
atgctcctat cctgattgag gcgtgcgaac gcataacaaa gctgattgat caggaagaga    4080
accgggtcaa acgcataaat agcctggtcg ctttaaagga tatgaccgcg tgggtgaacg    4140
ctgacgatga aattgaaaac aacgtcgatt gagacgatga aattgaaaac aacgtcgatt    4200
gaggtaccat ggttttgtg actttaccta taaatagtac acaacagacc accagtaatt    4260
ctacacactt cttaactgat aatattatta taattgtaac ttttttagcag cactaaattt    4320 aatgaataca tagatttta actagcattt tactattctg tacttttac ttgaaattcc    4380 agaagggccg aagaaccag aattccttca cagaaaacga attcactggc cgtcgtttta    4440
caacgtcgtg actgggaaaa ccctggcgtt acccaactta atcgccttgc agcacatccc    4500
cctttcgcca gctggcgtaa tagcgaagag gcccgcaccg atcgcccttc ccaacagttg    4560
cgcagcctga atggcgaatg gcgcctgatg cggtattttc tccttacgca tctgtgcggt    4620
atttcacacc gcatatggtg cactctcagt acaatctgct ctgatgccgc atagttaagc    4680
cagccccgac acccgccaac acccgctgac gcgccctgac gggcttgtct gctcccggca    4740
tccgcttaca gacaagctgt gaccgtctcc gggagctgca tgtgtcagag gttttcaccg    4800
tcatcaccga aacgcgcgag acgaaagggc ctcgtgatac gcctattttt ataggttaat    4860
gtcatgataa taatggtttc ttagacgtca ggtggcactt ttcggggaaa tgtgcgcgga    4920
acccctattt gtttatttt ctaaatacat tcaaatatgt atccgctcat gagacaataa    4980
ccctgataaa tgcttcaata atattgaaaa aggaagagta tgagtattca acatttccgt    5040
gtcgccctta ttcccttttt tgcggcattt tgccttcctg ttttttgctca cccagaaacg    5100 ctggtgaaag taaaagatgc tgaagatcag ttgggtgcac gagtgggtta catcgaactg    5160
gatctcaaca gcggtaagat ccttgagagt tttcgccccg aagaacgttt tccaatgatg    5220 agcacttta aagttctgct atgtggcgcg gtattatccc gtattgacgc cgggcaagag    5280
caactcggtc gccgcataca ctattctcag aatgacttgg ttgagtactc accagtcaca    5340
gaaaagcatc ttacgatgg catgacagta agagaattat gcagtgctgc cataaccatg    5400
agtgataaca ctgcggccaa cttacttctg acaacgatcg gaggaccgaa ggagctaacc    5460
gcttttttgc acaacatggg ggatcatgta actcgccttg atcgttggga accggagctg    5520
aatgaagcca taccaaacga cgagcgtgac accacgatgc ctgtagcaat ggcaacaacg    5580
ttgcgcaaac tattaactgg cgaactactt actctagctt cccggcaaca attaatagac    5640
```

```
tggatggagg cggataaagt tgcaggacca cttctgcgct cggcccttcc ggctggctgg    5700
tttattgctg ataaatctgg agccggtgag cgtgggtctc gcggtatcat tgcagcactg    5760
gggccagatg gtaagccctc ccgtatcgta gttatctaca cgacggggag tcaggcaact    5820
atggatgaac gaaatagaca gatcgctgag ataggtgcct cactgattaa gcattggtaa    5880
ctgtcagacc aagtttactc atatatactt tagattgatt taaaacttca ttttttaattt   5940 aaaaggatct aggtgaagat cctttttgat aatctcatga ccaaaatccc ttaacgtgag    6000
ttttcgttcc actgagcgtc agaccccgta gaaaagatca aggatcttc ttgagatcct     6060 ttttttctgc gcgtaatctg ctgcttgcaa acaaaaaaac caccgctacc agcggtggtt    6120
tgtttgccgg atcaagagct accaactctt tttccgaagg taactggctt cagcagagcg    6180
cagataccaa atactgtcct tctagtgtag ccgtagttag gccaccactt caagaactct    6240
gtagcaccgc ctacatacct cgctctgcta atcctgttac cagtggctgc tgccagtggc    6300
gataagtcgt gtcttaccgg gttggactca agacgatagt taccggataa ggcgcagcgg    6360
tcgggctgaa cggggggttc gtgcacacag cccagcttgg agcgaacgac ctacaccgaa    6420
ctgagatacc tacagcgtga gctatgagaa agcgccacgc ttcccgaagg gagaaaggcg    6480
gacaggtatc cggtaagcgg cagggtcgga acaggagagc gcacgaggga gcttccaggg    6540
ggaaacgcct ggtatcttta tagtcctgtc gggtttcgcc acctctgact tgagcgtcga    6600 ttttttgtgat gctcgtcagg gggcggagc ctatggaa                            6638

<210> SEQ ID NO 180
<211> LENGTH: 100
<212> TYPE: DNA
<213> ORGANISM: Artificial Sequence
<220> FEATURE:
<223> OTHER INFORMATION: LA712

<400> SEQUENCE: 180
cttaattgaa agaaagaatt tccttcaact tcggtttcct ggttccgcta tttctcgctt     60
gtttcttcta gcattgcgga ttacgtattc taatgttcag                          100

<210> SEQ ID NO 181
<211> LENGTH: 30
<212> TYPE: DNA
<213> ORGANISM: Artificial Sequence
<220> FEATURE:
<223> OTHER INFORMATION: LA746

<400> SEQUENCE: 181
gttttctgtg aaggaattct ggtttcttcg                                      30

<210> SEQ ID NO 182
<211> LENGTH: 343
<212> TYPE: PRT
<213> ORGANISM: Artificial Sequence
<220> FEATURE:
<223> OTHER INFORMATION: Anaerostipes caccae KARI variant K9JB4P

<400> SEQUENCE: 182

Met Glu Glu Cys Lys Met Ala Lys Ile Tyr Tyr Gln Glu Asp Cys Asn
1               5                   10                  15

Leu Ser Leu Leu Asp Gly Lys Thr Ile Ala Val Ile Gly Tyr Gly Ser
            20                  25                  30

Gln Gly His Ala His Ala Leu Asn Ala Lys Glu Ser Gly Cys Asn Val
        35                  40                  45
```

-continued

```
Ile Ile Gly Leu Tyr Glu Gly Ala Glu Glu Trp Lys Arg Ala Glu Glu
 50                  55                  60

Gln Gly Phe Glu Val Tyr Thr Ala Ala Glu Ala Ala Lys Lys Ala Asp
 65                  70                  75                  80

Ile Ile Met Ile Leu Ile Pro Asp Glu Lys Gln Ala Thr Met Tyr Lys
                 85                  90                  95

Asn Asp Ile Glu Pro Asn Leu Glu Ala Gly Asn Met Leu Met Phe Ala
            100                 105                 110

His Gly Phe Asn Ile His Phe Gly Cys Ile Val Pro Pro Lys Asp Val
        115                 120                 125

Asp Val Thr Met Ile Ala Pro Lys Gly Pro Gly His Thr Val Arg Ser
130                 135                 140

Glu Tyr Glu Glu Gly Lys Gly Val Pro Cys Leu Val Ala Val Glu Gln
145                 150                 155                 160

Asp Ala Thr Gly Lys Ala Leu Asp Met Ala Leu Ala Tyr Ala Leu Ala
                165                 170                 175

Ile Gly Gly Ala Arg Ala Gly Val Leu Glu Thr Thr Phe Arg Thr Glu
            180                 185                 190

Thr Glu Thr Asp Leu Phe Gly Glu Gln Ala Val Leu Cys Gly Gly Val
        195                 200                 205

Cys Ala Leu Met Gln Ala Gly Phe Glu Thr Leu Val Glu Ala Gly Tyr
210                 215                 220

Asp Pro Arg Asn Ala Tyr Phe Glu Cys Ile His Glu Met Lys Leu Ile
225                 230                 235                 240

Val Asp Leu Ile Tyr Gln Ser Gly Phe Ser Gly Met Arg Tyr Ser Ile
                245                 250                 255

Ser Asn Thr Ala Glu Tyr Gly Asp Tyr Ile Thr Gly Pro Lys Ile Ile
            260                 265                 270

Thr Glu Asp Thr Lys Lys Ala Met Lys Lys Ile Leu Ser Asp Ile Gln
        275                 280                 285

Asp Gly Thr Phe Ala Lys Asp Phe Leu Val Asp Met Ser Asp Ala Gly
290                 295                 300

Ser Gln Val His Phe Lys Ala Met Arg Lys Leu Ala Ser Glu His Pro
305                 310                 315                 320

Ala Glu Val Val Gly Glu Glu Ile Arg Ser Leu Tyr Ser Trp Ser Asp
                325                 330                 335

Glu Asp Lys Leu Ile Asn Asn
            340
```

<210> SEQ ID NO 183
<211> LENGTH: 571
<212> TYPE: PRT
<213> ORGANISM: Artificial Sequence
<220> FEATURE:
<223> OTHER INFORMATION: Streptococcus mutans DHAD variant L2V4

<400> SEQUENCE: 183

```
Met Thr Asp Lys Lys Thr Leu Lys Asp Leu Arg Asn Arg Ser Ser Val
 1               5                  10                  15

Tyr Asp Ser Met Val Lys Ser Pro Asn Arg Ala Met Leu Arg Ala Thr
                20                  25                  30

Gly Met Gln Asp Glu Asp Phe Glu Lys Pro Ile Val Gly Val Ile Ser
            35                  40                  45

Thr Trp Ala Glu Asn Thr Pro Cys Asn Ile His Leu His Asp Phe Gly
 50                  55                  60
```

```
Lys Leu Ala Lys Val Gly Val Lys Glu Ala Gly Ala Trp Pro Val Gln
 65                  70                  75                  80

Phe Gly Thr Ile Thr Val Ser Asp Gly Ile Ala Met Gly Thr Gln Gly
                 85                  90                  95

Met Arg Phe Ser Leu Thr Ser Arg Asp Ile Ile Ala Asp Ser Ile Glu
            100                 105                 110

Ala Ala Met Gly Gly His Asn Ala Asp Ala Phe Val Ala Ile Gly Gly
            115                 120                 125

Cys Asp Lys Asn Met Pro Gly Ser Val Ile Ala Met Ala Asn Met Asp
            130                 135                 140

Ile Pro Ala Ile Phe Ala Tyr Gly Gly Thr Ile Ala Pro Gly Asn Leu
145                 150                 155                 160

Asp Gly Lys Asp Ile Asp Leu Val Ser Val Phe Glu Gly Val Gly His
                165                 170                 175

Trp Asn His Gly Asp Met Thr Lys Glu Glu Val Lys Ala Leu Glu Cys
            180                 185                 190

Asn Ala Cys Pro Gly Pro Gly Gly Cys Gly Gly Met Tyr Thr Ala Asn
            195                 200                 205

Thr Met Ala Thr Ala Ile Glu Val Leu Gly Leu Ser Leu Pro Gly Ser
210                 215                 220

Ser Ser His Pro Ala Glu Ser Ala Glu Lys Lys Ala Asp Ile Glu Glu
225                 230                 235                 240

Ala Gly Arg Ala Val Val Lys Met Leu Glu Met Gly Leu Lys Pro Ser
                245                 250                 255

Asp Ile Leu Thr Arg Glu Ala Phe Glu Asp Ala Ile Thr Val Thr Met
                260                 265                 270

Ala Leu Gly Gly Ser Thr Asn Ser Thr Leu His Leu Leu Ala Ile Ala
            275                 280                 285

His Ala Ala Asn Val Glu Leu Thr Leu Asp Asp Phe Asn Thr Phe Gln
290                 295                 300

Glu Lys Val Pro His Leu Ala Asp Leu Lys Pro Ser Gly Gln Tyr Val
305                 310                 315                 320

Phe Gln Asp Leu Tyr Lys Val Gly Gly Val Pro Ala Val Met Lys Tyr
                325                 330                 335

Leu Leu Lys Asn Gly Phe Leu His Gly Asp Arg Ile Thr Cys Thr Gly
            340                 345                 350

Lys Thr Val Ala Glu Asn Leu Lys Ala Phe Asp Asp Leu Thr Pro Gly
            355                 360                 365

Gln Lys Val Ile Met Pro Leu Glu Asn Pro Lys Arg Glu Asp Gly Pro
            370                 375                 380

Val Ile Ile Leu His Gly Asn Leu Ala Pro Asp Gly Ala Val Ala Lys
385                 390                 395                 400

Val Ser Gly Val Lys Val Arg Arg His Val Gly Pro Ala Lys Val Phe
                405                 410                 415

Asn Ser Glu Glu Glu Ala Ile Glu Ala Val Leu Asn Asp Asp Ile Val
            420                 425                 430

Asp Gly Asp Val Val Val Arg Phe Val Gly Pro Lys Gly Gly Pro
            435                 440                 445

Gly Met Pro Glu Met Leu Ser Leu Ser Ser Met Ile Val Gly Lys Gly
            450                 455                 460

Gln Gly Glu Lys Val Ala Leu Leu Thr Asp Gly Arg Phe Ser Gly Gly
465                 470                 475                 480
```

```
Thr Tyr Gly Leu Val Val Gly His Ile Ala Pro Glu Ala Gln Asp Gly
                485                 490                 495

Gly Pro Ile Ala Tyr Leu Gln Thr Gly Asp Ile Val Thr Ile Asp Gln
            500                 505                 510

Asp Thr Lys Glu Leu His Phe Asp Ile Ser Asp Glu Glu Leu Lys His
        515                 520                 525

Arg Gln Glu Thr Ile Glu Leu Pro Pro Leu Tyr Ser Arg Gly Ile Leu
    530                 535                 540

Gly Lys Tyr Ala His Ile Val Ser Ser Ala Ser Arg Gly Ala Val Thr
545                 550                 555                 560

Asp Phe Trp Lys Pro Glu Glu Thr Gly Lys Lys
            565                 570

<210> SEQ ID NO 184
<211> LENGTH: 7523
<212> TYPE: DNA
<213> ORGANISM: Artificial Sequence
<220> FEATURE:
<223> OTHER INFORMATION: pLA34

<400> SEQUENCE: 184
```

| | | | | | |
|---|---|---|---|---|---|
| ccagcttttg | ttcccttttag | tgagggttaa | ttgcgcgctt | ggcgtaatca | tggtcatagc | 60 |
| tgtttcctgt | gtgaaattgt | tatccgctca | caattccaca | caacatagga | gccggaagca | 120 |
| taaagtgtaa | agcctggggt | gcctaatgag | tgaggtaact | cacattaatt | gcgttgcgct | 180 |
| cactgcccgc | tttccagtcg | ggaaacctgt | cgtgccagct | gcattaatga | atcggccaac | 240 |
| gcgcggggag | aggcggtttg | cgtattgggc | gctcttccgc | ttcctcgctc | actgactcgc | 300 |
| tgcgctcggt | cgttcggctg | cggcgagcgg | tatcagctca | ctcaaaggcg | gtaatacggt | 360 |
| tatccacaga | atcaggggat | aacgcaggaa | agaacatgtg | agcaaaaggc | cagcaaaagg | 420 |
| ccaggaaccg | taaaaaggcc | gcgttgctgg | cgtttttcca | taggctccgc | ccccctgacg | 480 |
| agcatcacaa | aaatcgacgc | tcaagtcaga | ggtggcgaaa | cccgacagga | ctataaagat | 540 |
| accaggcgtt | tccccctgga | agctccctcg | tgcgctctcc | tgttccgacc | ctgccgctta | 600 |
| ccggatacct | gtccgccttt | ctcccttcgg | gaagcgtggc | gctttctcat | agctcacgct | 660 |
| gtaggtatct | cagttcggtg | taggtcgttc | gctccaagct | gggctgtgtg | cacgaacccc | 720 |
| ccgttcagcc | cgaccgctgc | gccttatccg | gtaactatcg | tcttgagtcc | aacccggtaa | 780 |
| gacacgactt | atcgccactg | gcagcagcca | ctggtaacag | gattagcaga | gcgaggtatg | 840 |
| taggcggtgc | tacagagttc | ttgaagtggt | ggcctaacta | cggctacact | agaaggacag | 900 |
| tatttggtat | ctgcgctctg | ctgaagccag | ttaccttcgg | aaaaagagtt | ggtagctctt | 960 |
| gatccggcaa | acaaaccacc | gctggtagcg | gtggtttttt | tgtttgcaag | cagcagatta | 1020 |
| cgcgcagaaa | aaaaggatct | caagaagatc | ctttgatctt | ttctacgggg | tctgacgctc | 1080 |
| agtggaacga | aaactcacgt | taagggattt | tggtcatgag | attatcaaaa | aggatcttca | 1140 |
| cctagatcct | tttaaattaa | aaatgaagtt | ttaaatcaat | ctaaagtata | tatgagtaaa | 1200 |
| cttggtctga | cagttaccaa | tgcttaatca | gtgaggcacc | tatctcagcg | atctgtctat | 1260 |
| ttcgttcatc | catagttgcc | tgactccccg | tcgtgtagat | aactacgata | cgggagggct | 1320 |
| taccatctgg | ccccagtgct | gcaatgatac | cgcgagaccc | acgctcaccg | gctccagatt | 1380 |
| tatcagcaat | aaaccagcca | gccggaaggg | ccgagcgcag | aagtggtcct | gcaactttat | 1440 |
| ccgcctccat | ccagtctatt | aattgttgcc | gggaagctag | agtaagtagt | tcgccagtta | 1500 |
| atagtttgcg | caacgttgtt | gccattgcta | caggcatcgt | ggtgtcacgc | tcgtcgtttg | 1560 |

```
gtatggcttc attcagctcc ggttcccaac gatcaaggcg agttacatga tcccccatgt    1620
tgtgcaaaaa agcggttagc tccttcggtc ctccgatcgt tgtcagaagt aagttggccg    1680
cagtgttatc actcatggtt atggcagcac tgcataattc tcttactgtc atgccatccg    1740
taagatgctt ttctgtgact ggtgagtact caaccaagtc attctgagaa tagtgtatgc    1800
ggcgaccgag ttgctcttgc ccggcgtcaa tacgggataa taccgcgcca catagcagaa    1860 cttttaaaagt gctcatcatt ggaaaacgtt cttcggggcg aaaactctca aggatcttac    1920
cgctgttgag atccagttcg atgtaaccca ctcgtgcacc caactgatct tcagcatctt    1980
ttactttcac cagcgtttct gggtgagcaa aaacaggaag gcaaaatgcc gcaaaaaagg    2040
gaataagggc gacacggaaa tgttgaatac tcatactctt cctttttcaa tattattgaa    2100
gcatttatca gggttattgt ctcatgagcg gatacatatt tgaatgtatt tagaaaaata    2160
aacaaatagg ggttccgcgc acatttcccc gaaaagtgcc acctgaacga agcatctgtg    2220
cttcattttg tagaacaaaa atgcaacgcg agagcgctaa ttttcaaac aaagaatctg    2280 agctgcattt ttacagaaca gaaatgcaac gcgaaagcgc tattttacca acgaagaatc    2340
tgtgcttcat ttttgtaaaa caaaaatgca acgcgagagc gctaattttt caaacaaaga    2400
atctgagctg cattttttaca gaacagaaat gcaacgcgag agcgctattt taccaacaaa    2460
gaatctatac ttcttttttg ttctacaaaa atgcatcccg agagcgctat ttttctaaca    2520
aagcatctta gattactttt tttctccttt gtgcgctcta atgcagtc tcttgataac      2580 tttttgcact gtaggtccgt taaggttaga agaaggctac tttggtgtct attttctctt    2640
ccataaaaaa agcctgactc cacttcccgc gtttactgat tactagcgaa gctgcgggtg    2700
cattttttca agataaaggc atccccgatt atattctata ccgatgtgga ttgcgcatac    2760
tttgtgaaca gaaagtgata gcgttgatga ttcttcattg gtcagaaaat tatgaacggt    2820
ttcttctatt ttgtctctat atactacgta taggaaatgt ttacattttc gtattgtttt    2880
cgattcactc tatgaatagt tcttactaca attttttttgt ctaaagagta atactagaga    2940
taaacataaa aaatgtagag gtcgagttta gatgcaagtt caaggagcga aggtggatg     3000 ggtaggttat atagggatat agcacagaga tatatagcaa agagatactt ttgagcaatg    3060
tttgtggaag cggtattcgc aatattttag tagctcgtta cagtccggtg cgttttggt     3120 tttttgaaag tgcgtcttca gagcgctttt ggttttcaaa agcgctctga gttcctata     3180 ctttctagag aataggaact tcggaatagg aacttcaaag cgtttccgaa acgagcgct     3240 tccgaaaatg caacgcgagc tgcgcacata cagctcactt tcacgtcgc acctatatct     3300 gcgtgttgcc tgtatatata tacatgag aagaacggca tagtgcgtgt ttatgcttaa      3360
atgcgtactt atatgcgtct atttatgtag gatgaaaggt agtctagtac ctcctgtgat    3420
attatcccat tccatgcggg gtatcgtatg cttccttcag cactacccct tagctgttct    3480
atatgctgcc actcctcaat tggattagtc tcatccttca atgctatcat ttccttggat    3540
attggatcat ctaagaaacc attattatca tgacattaac ctataaaaat aggcgtatca    3600
cgaggccctt tcgtctcgcg cgtttcggtg atgacggtga aaacctctga cacatgcagc    3660
tcccggagac ggtcacagct tgtctgtaag cggatgccgg gagcagacaa gcccgtcagg    3720
gcgcgtcagc gggtgttggc gggtgtcggg gctggcttaa ctatgcggca tcagagcaga    3780
ttgtactgag agtgcaccat aaaattcccgt tttaagagct tggtgagcgc taggagtcac    3840
tgccaggtat cgtttgaaca cggcattagt cagggaagtc ataacacagt cctttcccgc    3900
```

```
aattttctttt ttctattact cttggcctcc tctagtacac tctatatttt tttatgcctc    3960
ggtaatgatt ttcattttt ttttccccct agcggatgac tcttttttt tcttagcgat       4020 tggcattatc acataatgaa ttatacatta tataaagtaa tgtgatttct tcgaagaata    4080
tactaaaaaa tgagcaggca agataaacga aggcaaagat gacagagcag aaagccctag    4140
taaagcgtat tacaaatgaa accaagattc agattgcgat ctctttaaag ggtggtcccc    4200
tagcgataga gcactcgatc ttcccagaaa aagaggcaga agcagtagca gaacaggcca    4260
cacaatcgca agtgattaac gtccacacag gtataggggtt tctggaccat atgatacatg    4320
ctctggccaa gcattccggc tggtcgctaa tcgttgagtg cattggtgac ttacacatag    4380
acgaccatca caccactgaa gactgcggga ttgctctcgg tcaagctttt aaagaggccc    4440
tactggcgcg tggagtaaaa aggtttggat caggatttgc gcctttggat gaggcacttt    4500
ccagagcggt ggtagatctt tcgaacaggc cgtacgcagt tgtcgaactt ggtttgcaaa    4560
gggagaaagt aggagatctc tcttgcgaga tgatcccgca ttttcttgaa agctttgcag    4620
aggctagcag aattaccctc cacgttgatt gtctgcgagg caagaatgat catcaccgta    4680
gtgagagtgc gttcaaggct cttgcggttg ccataagaga agccacctcg cccaatggta    4740
ccaacgatgt tccctccacc aaaggtgttc ttatgtagtg acaccgatta tttaaagctg    4800
cagcatacga tatatataca tgtgtatata tgtataccta tgaatgtcag taagtatgta    4860
tacgaacagt atgatactga agatgacaag gtaatgcatc attctatacg tgtcattctg    4920
aacgaggcgc gctttccttt tttcttttg cttttctttt ttttttctct tgaactcgac     4980
ggatctatgc ggtgtgaaat accgcacaga tgcgtaagga aaaataccg catcaggaaa     5040 ttgtaaacgt taatatttg ttaaaattcg cgttaaattt ttgttaaatc agctcatttt    5100
ttaaccaata ggccgaaatc ggcaaaatcc cttataaatc aaaagaatag accgagatag    5160
ggttgagtgt tgttccagtt tggaacaaga gtccactatt aaagaacgtg gactccaacg    5220
tcaaagggcg aaaaaccgtc tatcagggcg atggcccact acgtgaacca tcaccctaat    5280
caagtttttt ggggtcgagg tgccgtaaag cactaaatcg gaaccctaaa gggagccccc    5340
gatttagagc ttgacgggga aagccggcga acgtggcgag aaaggaaggg aagaaagcga    5400
aaggagcggg cgctagggcg ctggcaagtg tagcggtcac gctgcgcgta accaccacac    5460
ccgccgcgct taatgcgccg ctacaggggcg cgtcgcgcca ttcgccattc aggctgcgca    5520
actgttggga aggggcgatcg gtgcgggcct cttcgctatt acgccagctg gcgaaagggg    5580
gatgtgctgc aaggcgatta agttgggtaa cgccagggtt ttcccagtca cgacgttgta    5640
aaacgacggc cagtgagcgc gcgtaatacg actcactata gggcgaattg ggtaccgggc    5700 ccccctcga ggtattagaa gccgccgagc gggcgacagc cctccgacgg aagactctcc     5760
tccgtgcgtc ctcgtcttca ccggtcgcgt tcctgaaacg cagatgtgcc tcgcgccgca    5820
ctgctccgaa cataaagat tctacaatac tagcttttat ggttatgaag aggaaaaatt     5880
ggcagtaacc tggcccccaca aaccttcaaa ttaacgaatc aaattaacaa ccataggatg    5940
ataatgcgat tagttttta gccttatttc tggggtaatt aatcagcgaa gcgatgattt    6000
ttgatctatt aacagatata taatggaaa agctgcataa ccactttaac taatactttc     6060
aacattttca gtttgtatta cttcttattc aaatgtcata aaagtatcaa caaaaaattg    6120
ttaatatacc tctatacttt aacgtcaagg agaaaaatgt ccaatttact gcccgtacac    6180
caaaatttgc ctgcattacc ggtcgatgca acgagtgatg aggttcgcaa gaacctgatg    6240
gacatgttca gggatcgcca ggcgttttct gagcatacct ggaaaatgct tctgtccgtt    6300
```

-continued

```
tgccggtcgt gggcggcatg gtgcaagttg aataaccgga aatggtttcc cgcagaacct    6360
gaagatgttc gcgattatct tctatatctt caggcgcgcg gtctggcagt aaaaactatc    6420
cagcaacatt tgggccagct aaacatgctt catcgtcggt ccgggctgcc acgaccaagt    6480
gacagcaatg ctgtttcact ggttatgcgg cggatccgaa agaaaaacgt tgatgccggt    6540
gaacgtgcaa aacaggctct agcgttcgaa cgcactgatt tcgaccaggt tcgttcactc    6600
atggaaaata gcgatcgctg ccaggatata cgtaatctgg catttctggg gattgcttat    6660
aacaccctgt tacgtatagc cgaaattgcc aggatcaggg ttaaagatat ctcacgtact    6720
gacggtggga gaatgttaat ccatattggc agaacgaaaa cgctggttag caccgcaggt    6780
gtagagaagg cacttagcct gggggtaact aaactggtcg agcgatggat ttccgtctct    6840
ggtgtagctg atgatccgaa taactacctg ttttgccggg tcagaaaaaa tggtgttgcc    6900
gcgccatctg ccaccagcca gctatcaact cgcgccctgg aagggatttt tgaagcaact    6960
catcgattga tttacggcgc taaggatgac tctggtcaga gatacctggc ctggtctgga    7020
cacagtgccc gtgtcggagc cgcgcgagat atggcccgcg ctggagtttc aataccggag    7080
atcatgcaag ctggtggctg gaccaatgta aatattgtca tgaactatat ccgtaacctg    7140
gatagtgaaa caggggcaat ggtgcgcctg ctggaagatg gcgattagga gtaagcgaat    7200
ttcttatgat ttatgatttt tattattaaa taagttataa aaaaaataag tgtatacaaa    7260
ttttaaagtg actcttaggt tttaaaacga aaattcttat tcttgagtaa ctctttcctg    7320
taggtcaggt tgctttctca ggtatagcat gaggtcgctc ttattgacca cacctctacc    7380
ggcatgccga gcaaatgcct gcaaatcgct ccccatttca cccaattgta gatatgctaa    7440
ctccagcaat gagttgatga atctcggtgt gtattttatg tcctcagagg acaacacctg    7500
tggtccgcca ccgcggtgga gct                                           7523
```

<210> SEQ ID NO 185
<211> LENGTH: 96
<212> TYPE: DNA
<213> ORGANISM: Artificial Sequence
<220> FEATURE:
<223> OTHER INFORMATION: LA722

<400> SEQUENCE: 185

```
tgccaattat ttacctaaac atctataacc ttcaaaagta aaaaaataca caaacgttga    60
atcatcacct tggctaactc gttgtatcat cactgg                              96
```

<210> SEQ ID NO 186
<211> LENGTH: 80
<212> TYPE: DNA
<213> ORGANISM: Artificial Sequence
<220> FEATURE:
<223> OTHER INFORMATION: LA733

<400> SEQUENCE: 186

```
cataatcaat ctcaaagaga acaacacaat acaataacaa gaagaacaaa gcattgcgga    60
ttacgtattc taatgttcag                                                80
```

<210> SEQ ID NO 187
<211> LENGTH: 30
<212> TYPE: DNA
<213> ORGANISM: Artificial Sequence
<220> FEATURE:
<223> OTHER INFORMATION: LA453

```
<400> SEQUENCE: 187
caccgaagaa gaatgcaaaa atttcagctc                                30

<210> SEQ ID NO 188
<211> LENGTH: 25
<212> TYPE: DNA
<213> ORGANISM: Artificial Sequence
<220> FEATURE:
<223> OTHER INFORMATION: LA694

<400> SEQUENCE: 188
gctgaagttg ttagaactgt tgttg                                     25

<210> SEQ ID NO 189
<211> LENGTH: 21
<212> TYPE: DNA
<213> ORGANISM: Artificial Sequence
<220> FEATURE:
<223> OTHER INFORMATION: LA695

<400> SEQUENCE: 189
tgttagctgg agtagacttg g                                         21

<210> SEQ ID NO 190
<211> LENGTH: 22
<212> TYPE: DNA
<213> ORGANISM: Artificial Sequence
<220> FEATURE:
<223> OTHER INFORMATION: oBP594

<400> SEQUENCE: 190
agctgtctcg tgttgtgggt tt                                        22

<210> SEQ ID NO 191
<211> LENGTH: 49
<212> TYPE: DNA
<213> ORGANISM: Artificial Sequence
<220> FEATURE:
<223> OTHER INFORMATION: oBP595

<400> SEQUENCE: 191
cttaataata gaacaatatc atcctttacg ggcatcttat agtgtcgtt           49

<210> SEQ ID NO 192
<211> LENGTH: 49
<212> TYPE: DNA
<213> ORGANISM: Artificial Sequence
<220> FEATURE:
<223> OTHER INFORMATION: oBP596

<400> SEQUENCE: 192
gcgccaacga cactataaga tgcccgtaaa ggatgatatt gttctatta           49

<210> SEQ ID NO 193
<211> LENGTH: 49
<212> TYPE: DNA
<213> ORGANISM: Artificial Sequence
<220> FEATURE:
<223> OTHER INFORMATION: oBP597

<400> SEQUENCE: 193
tatggaccct gaaaccacag ccacattgca acgacgacaa tgccaaacc           49

<210> SEQ ID NO 194
<211> LENGTH: 49
```

```
<212> TYPE: DNA
<213> ORGANISM: Artificial Sequence
<220> FEATURE:
<223> OTHER INFORMATION: oBP598

<400> SEQUENCE: 194
tccttggttt ggcattgtcg tcgttgcaat gtggctgtgg tttcagggt                49

<210> SEQ ID NO 195
<211> LENGTH: 49
<212> TYPE: DNA
<213> ORGANISM: Artificial Sequence
<220> FEATURE:
<223> OTHER INFORMATION: oBP599

<400> SEQUENCE: 195
atcctctcgc ggagtccctg ttcagtaaag gccatgaagc ttttctttt                49

<210> SEQ ID NO 196
<211> LENGTH: 49
<212> TYPE: DNA
<213> ORGANISM: Artificial Sequence
<220> FEATURE:
<223> OTHER INFORMATION: oBP600

<400> SEQUENCE: 196
attggaaaga aaagcttca tggcctttac tgaacaggga ctccgcgag                 49

<210> SEQ ID NO 197
<211> LENGTH: 22
<212> TYPE: DNA
<213> ORGANISM: Artificial Sequence
<220> FEATURE:
<223> OTHER INFORMATION: oBP601

<400> SEQUENCE: 197
tcataccaca atcttagacc at                                             22

<210> SEQ ID NO 198
<211> LENGTH: 21
<212> TYPE: DNA
<213> ORGANISM: Artificial Sequence
<220> FEATURE:
<223> OTHER INFORMATION: oBP602

<400> SEQUENCE: 198
tgttcaaacc cctaaccaac c                                              21

<210> SEQ ID NO 199
<211> LENGTH: 22
<212> TYPE: DNA
<213> ORGANISM: Artificial Sequence
<220> FEATURE:
<223> OTHER INFORMATION: oBP603

<400> SEQUENCE: 199
tgttcccaca atctattacc ta                                             22

<210> SEQ ID NO 200
<211> LENGTH: 31
<212> TYPE: DNA
<213> ORGANISM: Artificial Sequence
<220> FEATURE:
<223> OTHER INFORMATION: LA811

<400> SEQUENCE: 200
```
aacgaagcat ctgtgcttca ttttgtagaa c                                    31

<210> SEQ ID NO 201
<211> LENGTH: 59
<212> TYPE: DNA
<213> ORGANISM: Artificial Sequence
<220> FEATURE:
<223> OTHER INFORMATION: LA817

<400> SEQUENCE: 201
cgatccactt gtatatttgg atgaattttt gaggaattct gaaccagtcc taaaacgag      59

<210> SEQ ID NO 202
<211> LENGTH: 31
<212> TYPE: DNA
<213> ORGANISM: Artificial Sequence
<220> FEATURE:
<223> OTHER INFORMATION: LA812

<400> SEQUENCE: 202
aacaaagata tgctattgaa gtgcaagatg g                                    31

<210> SEQ ID NO 203
<211> LENGTH: 33
<212> TYPE: DNA
<213> ORGANISM: Artificial Sequence
<220> FEATURE:
<223> OTHER INFORMATION: LA818

<400> SEQUENCE: 203
ctcaaaaatt catccaaata tacaagtgga tcg                                  33

<210> SEQ ID NO 204
<211> LENGTH: 90
<212> TYPE: DNA
<213> ORGANISM: Artificial Sequence
<220> FEATURE:
<223> OTHER INFORMATION: LA512

<400> SEQUENCE: 204
gtattttggt agattcaatt ctctttccct ttccttttcc ttcgctcccc ttccttatca     60
gcattgcgga ttacgtattc taatgttcag                                      90

<210> SEQ ID NO 205
<211> LENGTH: 90
<212> TYPE: DNA
<213> ORGANISM: Artificial Sequence
<220> FEATURE:
<223> OTHER INFORMATION: LA513

<400> SEQUENCE: 205
ttggttgggg gaaaagagg caacaggaaa gatcagaggg ggaggggggg ggagagtgtc      60
accttggcta actcgttgta tcatcactgg                                      90

<210> SEQ ID NO 206
<211> LENGTH: 29
<212> TYPE: DNA
<213> ORGANISM: Artificial Sequence
<220> FEATURE:
<223> OTHER INFORMATION: LA516

<400> SEQUENCE: 206
ctcgaaacaa taagacgacg atggctctg                                       29

```
<210> SEQ ID NO 207
<211> LENGTH: 30
<212> TYPE: DNA
<213> ORGANISM: Artificial Sequence
<220> FEATURE:
<223> OTHER INFORMATION: LA514

<400> SEQUENCE: 207
cactatctgg tgcaaacttg gcaccggaag                                      30

<210> SEQ ID NO 208
<211> LENGTH: 29
<212> TYPE: DNA
<213> ORGANISM: Artificial Sequence
<220> FEATURE:
<223> OTHER INFORMATION: LA515

<400> SEQUENCE: 208
tgtttgtagc cactcgtgaa cttctctgc                                       29

<210> SEQ ID NO 209
<211> LENGTH: 6903
<212> TYPE: DNA
<213> ORGANISM: Artificial Sequence
<220> FEATURE:
<223> OTHER INFORMATION: pLA71

<400> SEQUENCE: 209
aaacgccagc aacgcggcct ttttacggtt cctggccttt tgctggcctt ttgctcacat     60
gttctttcct gcgttatccc ctgattctgt ggataaccgt attaccgcct ttgagtgagc    120
tgataccgct cgccgcagcc gaacgaccga gcgcagcgag tcagtgagcg aggaagcgga    180
agagcgccca atacgcaaac cgcctctccc cgcgcgttgg ccgattcatt aatgcagctg    240
gcacgacagg tttcccgact ggaaagcggg cagtgagcgc aacgcaatta atgtgagtta    300
gctcactcat taggcacccc aggctttaca ctttatgctt ccggctcgta tgttgtgtgg    360
aattgtgagc ggataacaat ttcacacagg aaacagctat gaccatgatt acgccaagct    420
tgcatgcgat ctgaaatgaa taacaatact gacagtagat ctgaaatgaa taacaatact    480
gacagtacta ataattgcc tacttggctt cacatacgtt gcatacgtcg atatagataa     540
taatgataat gacagcagga ttatcgtaat acgtaatagt tgaaaatctc aaaaatgtgt    600
gggtcattac gtaaataatg ataggaatgg gattcttcta ttttttccttt ttccattcta   660 gcagccgtcg ggaaaacgtg gcatcctctc tttcgggctc aattggagtc acgctgccgt    720
gagcatcctc tctttccata tctaacaact gagcacgtaa ccaatggaaa agcatgagct    780
tagcgttgct ccaaaaaagt attggatggt taataccatt tgtctgttct cttctgactt    840
tgactcctca aaaaaaaaaa atctacaatc aacagatcgc ttcaattacg ccctcacaaa    900
aacttttttc cttcttcttc gcccacgtta aattttatcc ctcatgttgt ctaacggatt    960
tctgcacttg attattata aaagacaaa gacataatac ttctctatca atttcagtta    1020
ttgttcttcc ttgcgttatt cttctgttct tcttttctt ttgtcatata taaccataac    1080
caagtaatac atattcaaat ctagagctga ggatgttgac aaaagcaaca aaagaacaaa    1140
aatcccttgt gaaaaacaga ggggcggagc ttgttgttga ttgcttagtg gagcaaggtg    1200
tcacacatgt atttggcatt ccaggtgcaa aaattgatgc ggtatttgac gctttacaag    1260
ataaaggacc tgaaattatc gttgcccggc acgaacaaaa cgcagcattc atggcccaag    1320
cagtcggccg tttaactgga aaaccggag tcgtgttagt cacatcagga ccgggtgcct    1380
```

```
ctaacttggc aacaggcctg ctgacagcga acactgaagg agaccctgtc gttgcgcttg    1440
ctggaaacgt gatccgtgca gatcgtttaa aacggacaca tcaatctttg gataatgcgg    1500
cgctattcca gccgattaca aaatacagtg tagaagttca agatgtaaaa aatataccgg    1560
aagctgttac aaatgcattt aggatagcgt cagcagggca ggctggggcc gcttttgtga    1620
gctttccgca agatgttgtg aatgaagtca caaatacgaa aaacgtgcgt gctgttgcag    1680
cgccaaaact cggtcctgca gcagatgatg caatcagtgc ggccatagca aaaatccaaa    1740
cagcaaaact tcctgtcgtt ttggtcggca tgaaaggcgg aagaccggaa gcaattaaag    1800
cggttcgcaa gcttttgaaa aaggttcagc ttccatttgt tgaaacatat caagctgccg    1860 gtacccttc tagagattta gaggatcaat attttggccg tatcggtttg ttccgcaacc    1920
agcctggcga tttactgcta gagcaggcag atgttgttct gacgatcggc tatgacccga    1980
ttgaatatga tccgaaattc tggaatatca atggagaccg gacaattatc catttagacg    2040
agattatcgc tgacattgat catgcttacc agcctgatct tgaattgatc ggtgacattc    2100
cgtccacgat caatcatatc gaacacgatg ctgtgaaagt ggaatttgca gagcgtgagc    2160
agaaaatcct ttctgattta aaacaatata tgcatgaagg tgagcaggtg cctgcagatt    2220
ggaaatcaga cagagcgcac cctcttgaaa tcgttaaaga gttgcgtaat gcagtcgatg    2280
atcatgttac agtaacttgc gatatcggtt cgcacgccat ttggatgtca cgttatttcc    2340
gcagctacga gccgttaaca ttaatgatca gtaacgtat gcaaacactc ggcgttgcgc    2400
ttccttgggc aatcggcgct tcattggtga accgggaga aaaagtggtt tctgtctctg    2460
gtgacggcgg tttcttattc tcagcaatgg aattagagac agcagttcga ctaaaagcac    2520
caattgtaca cattgtatgg aacgacagca catatgacat ggttgcattc cagcaattga    2580
aaaaatataa ccgtacatct gcggtcgatt tcggaaatat cgatatcgtg aaatatgcgg    2640
aaagcttcgg agcaactggc ttgcgcgtag aatcaccaga ccagctggca gatgttctgc    2700
gtcaaggcat gaacgctgaa ggtcctgtca tcatcgatgt cccggttgac tacagtgata    2760
acattaattt agcaagtgac aagcttccga aagaattcgg ggaactcatg aaaacgaaag    2820
ctctctagtt aattaatcat gtaattagtt atgtcacgct tacattcacg ccctcccccc    2880
acatccgctc taaccgaaaa ggaaggagtt agacaacctg aagtctaggt ccctatttat    2940
ttttttatag ttatgttagt attaagaacg ttatttatat tcaaattttt tcttttttt    3000 ctgtacagac gcgtgtacgc atgtaacatt atactgaaaa ccttgcttga aaggttttg    3060 ggacgctcga aggctttaat ttaggttttg ggacgctcga aggctttaat ttggatccgc    3120
attgcggatt acgtattcta atgttcagta ccgttcgtat aatgtatgct atacgaagtt    3180
atgcagattg tactgagagt gcaccatacc acagcttttc aattcaattc atcatttttt    3240
ttttattctt ttttttgatt tcggtttctt tgaaatttt ttgattcggt aatctccgaa    3300
cagaaggaag aacgaaggaa ggagcacaga cttagattgg tatatatacg catatgtagt    3360
gttgaagaaa catgaaattg cccagtattc ttaacccaac tgcacagaac aaaaacctgc    3420
aggaaacgaa gataaatcat gtcgaaagct acatataagg aacgtgctgc tactcatcct    3480
agtcctgttg ctgccaagct atttaatatc atgcacgaaa agcaaacaaa cttgtgtgct    3540
tcattggatg ttcgtaccac caaggaatta ctggagttag ttgaagcatt aggtcccaaa    3600
atttgtttac taaaaacaca tgtggatatc ttgactgatt tttccatgga gggcacagtt    3660
aagccgctaa aggcattatc cgccaagtac aatttttac tcttcgaaga cagaaaattt    3720
gctgacattg gtaatacagt caaattgcag tactctgcgg gtgtatacag aatagcagaa    3780
```

```
tgggcagaca ttacgaatgc acacggtgtg gtgggcccag gtattgttag cggtttgaag    3840
caggcggcag aagaagtaac aaaggaacct agaggccttt tgatgttagc agaattgtca    3900
tgcaagggct ccctatctac tggagaatat actaagggta ctgttgacat tgcgaagagc    3960
gacaaagatt ttgttatcgg ctttattgct caaagagaca tgggtggaag agatgaaggt    4020
tacgattggt tgattatgac acccggtgtg ggtttagatg acaagggaga cgcattgggt    4080
caacagtata gaaccgtgga tgatgtggtc tctacaggat ctgacattat tattgttgga    4140
agaggactat ttgcaaaggg aagggatgct aaggtagagg gtgaacgtta cagaaaagca    4200
ggctgggaag catatttgag aagatgcggc cagcaaaact aaaaaactgt attataagta    4260
aatgcatgta tactaaactc acaaattaga gcttcaattt aattatatca gttattaccc    4320
tatgcggtgt gaaataccgc acagatgcgt aaggagaaaa taccgcatca ggaaattgta    4380
aacgttaata ttttgttaaa attcgcgtta aattttgtt aaatcagctc attttttaac    4440
caataggccg aaatcggcaa atcccttat aaatcaaaag aatagaccga gatagggttg    4500
agtgttgttc cagtttggaa caagagtcca ctattaaaga acgtggactc caacgtcaaa    4560
gggcgaaaaa ccgtctatca gggcgatggc ccactacgtg aaccatcacc ctaatcaaga    4620
taacttcgta taatgtatgc tatacgaacg gtaccagtga tgatacaacg agttagccaa    4680
ggtgaattca ctggccgtcg ttttacaacg tcgtgactgg gaaaaccctg gcgttaccca    4740
acttaatcgc cttgcagcac atccccttt cgccagctgg cgtaatagcg aagaggcccg    4800
caccgatcgc ccttcccaac agttgcgcag cctgaatggc gaatggcgcc tgatgcggta    4860
ttttctcctt acgcatctgt gcggtatttc acaccgcata tggtgcactc tcagtacaat    4920
ctgctctgat gccgcatagt taagccagcc ccgacacccg ccaacacccg ctgacgcgcc    4980
ctgacgggct tgtctgctcc cggcatccgc ttacagacaa gctgtgaccg tctccgggag    5040
ctgcatgtgt cagaggtttt caccgtcatc accgaaacgc gcgagacgaa agggcctcgt    5100
gatacgccta tttttatagg ttaatgtcat gataataatg gtttcttaga cgtcaggtgg    5160
cacttttcgg ggaaatgtgc gcggaacccc tatttgttta ttttctaaaa tacattcaaa    5220
tatgtatccg ctcatgagac aataaccctg ataaatgctt caataatatt gaaaaaggaa    5280
gagtatgagt attcaacatt tccgtgtcgc ccttattccc ttttttgcgg cattttgcct    5340
tcctgttttt gctcacccag aaacgctggt gaaagtaaaa gatgctgaag atcagttggg    5400
tgcacgagtg ggttacatcg aactggatct caacagcggt aagatccttg agagttttcg    5460
ccccgaagaa cgttttccaa tgatgagcac ttttaaagtt ctgctatgtg gcgcggtatt    5520
atcccgtatt gacgccgggc aagagcaact cggtcgccgc atacactatt ctcagaatga    5580
cttggttgag tactcaccag tcacagaaaa gcatcttacg gatggcatga cagtaagaga    5640
attatgcagt gctgccataa ccatgagtga taacactgcg gccaacttac ttctgacaac    5700
gatcggagga ccgaaggagc taaccgcttt tttgcacaac atgggggatc atgtaactcg    5760
ccttgatcgt tgggaaccgg agctgaatga agccataccaa aacgacgagc gtgacaccac    5820
gatgcctgta gcaatggcaa caacgttgcg caaactatta actggcgaac tacttactct    5880
agcttcccgg caacaattaa tagactggat ggaggcggat aaagttgcag gaccacttct    5940
gcgctcggcc cttccggctg gctggtttat tgctgataaa tctggagccg gtgagcgtgg    6000 gtctcgcgg atcattgcag cactggggcc agatggtaag ccctcccgta tcgtagttat    6060
ctacacgacg gggagtcagg caactatgga tgaacgaaat agacagatcg ctgagatagg    6120
```

```
tgcctcactg attaagcatt ggtaactgtc agaccaagtt tactcatata actttagat    6180 tgatttaaaa cttcattttt aatttaaaag gatctaggtg aagatccttt ttgataatct    6240
catgaccaaa atcccttaac gtgagttttc gttccactga gcgtcagacc ccgtagaaaa    6300
gatcaaagga tcttcttgag atccttttt tctgcgcgta atctgctgct tgcaaacaaa    6360
aaaaccaccg ctaccagcgg tggtttgttt gccggatcaa gagctaccaa ctcttttcc    6420 gaaggtaact ggcttcagca gagcgcagat accaaatact gtccttctag tgtagccgta    6480
gttaggccac cacttcaaga actctgtagc accgcctaca tacctcgctc tgctaatcct    6540
gttaccagtg gctgctgcca gtggcgataa gtcgtgtctt accgggttgg actcaagacg    6600
atagttaccg gataaggcgc agcggtcggg ctgaacgggg ggttcgtgca cacagcccag    6660
cttggagcga acgacctaca ccgaactgag atacctacag cgtgagctat gagaaagcgc    6720
cacgcttccc gaagggagaa aggcggacag gtatccggta agcggcaggg tcggaacagg    6780
agagcgcacg agggagcttc caggggggaaa cgcctggtat ctttatagtc ctgtcgggtt    6840
tcgccacctc tgacttgagc gtcgatttt gtgatgctcg tcaggggggc ggagcctatg    6900
gaa                                                                  6903

<210> SEQ ID NO 210
<211> LENGTH: 6924
<212> TYPE: DNA
<213> ORGANISM: Artificial Sequence
<220> FEATURE:
<223> OTHER INFORMATION: pLA78

<400> SEQUENCE: 210
gatccgcatt gcggattacg tattctaatg ttcagtaccg ttcgtataat gtatgctata      60
cgaagttatg cagattgtac tgagagtgca ccataccacc ttttcaattc atcatttttt     120
ttttattctt ttttttgatt tcggtttcct tgaaattttt ttgattcggt aatctccgaa     180
cagaaggaag aacagaggaa ggagcacaga cttagattgg tatatatacg catatgtagt     240
gttgaagaaa catgaaattg cccagtattc ttaacccaac tgcacagaac aaaaacctgc     300
aggaaacgaa gataaatcat gtcgaaagct acatataagg aacgtgctgc tactcatcct     360
agtcctgttg ctgccaagct atttaatatc atgcacgaaa agcaaacaaa cttgtgtgct     420
tcattggatg ttcgtaccac caaggaatta ctggagttag ttgaagcatt aggtcccaaa     480
atttgtttac taaaaacaca tgtggatatc ttgactgatt tttccatgga gggcacagtt     540
aagccgctaa aggcattatc cgccaagtac aattttttac tcttcgaaga cagaaaattt     600
gctgacattg gtaatacagt caaattgcag tactctgcgg gtgtatacag aatagcagaa     660
tgggcagaca ttacgaatgc acacggtgtg gtgggcccag gtattgttag cggttttgaag    720 caggcggcag aagaagtaac aaaggaacct agaggccttt tgatgttagc agaattgtca    780
tgcaagggct ccctatctac tggagaatat actaagggta ctgttgacat tgcgaagagc    840
gacaaagatt ttgttatcgg ctttattgct caaagagaca tgggtggaag agatgaaggt    900
tacgattggt tgattatgac acccggtgtg ggtttagatg acaagggaga cgcattgggt    960
caacagtata gaaccgtgga tgatgtggtc tctacaggat ctgacattat tattgttgga   1020
agaggactat ttgcaaaggg aagggatgct aaggtagagg gtgaacgtta cagaaaagca   1080
ggctgggaag catatttgag aagatgcggc cagcaaaact aaaaaactgt attataagta   1140
aatgcatgta tactaaactc acaaattaga gcttcaattt aattatatca gttattaccc   1200
tatgcggtgt gaaataccgc acagatgcgt aaggagaaaa taccgcatca ggaaattgta   1260
```

```
aacgttaata ttttgttaaa attcgcgtta aattttttgtt aaatcagctc attttttaac   1320
caataggccg aaatcggcaa aatccctat  aaatcaaaag aatagaccga gatagggttg   1380
agtgttgttc cagtttggaa caagagtcca ctattaaaga acgtggactc caacgtcaaa   1440
gggcgaaaaa ccgtctatca gggcgatggc ccactacgtg aaccatcacc ctaatcaaga   1500
taacttcgta taatgtatgc tatacgaacg gtaccagtga tgatacaacg agttagccaa   1560
ggtgaattca ctggccgtcg ttttacaacg tcgtgactgg gaaaaccctg gcgttaccca   1620
acttaatcgc cttgcagcac atccccctttt cgccagctgg cgtaatagcg aagaggcccg   1680
caccgatcgc ccttcccaac agttgcgcag cctgaatggc gaatgcgcc  tgatgcggta   1740 ttttctcctt acgcatctgt gcggtatttc acaccgcata tggtgcactc tcagtacaat   1800
ctgctctgat gccgcatagt taagccagcc ccgacacccg ccaacacccg ctgacgcgcc   1860
ctgacgggct tgtctgctcc cggcatccgc ttacagacaa gctgtgaccg tctccgggag   1920
ctgcatgtgt cagaggtttt caccgtcatc accgaaacgc gcgagacgaa agggcctcgt   1980
gatacgccta ttttttatagg ttaatgtcat gataataatg gtttcttaga cgtcaggtgg   2040
cacttttcgg ggaaatgtgc gcggaacccc tatttgttta ttttttctaaa tacattcaaa   2100 tatgtatccg ctcatgagac aataaccctg ataaatgctt caataatatt gaaaaaggaa   2160
gagtatgagt attcaacatt tccgtgtcgc ccttattccc ttttttgcgg cattttgcct   2220
tcctgttttt gctcacccag aaacgctggt gaaagtaaaa gatgctgaag atcagttggg   2280
tgcacgagtg ggttacatcg aactggatct caacagcggt aagatccttg agagttttcg   2340
ccccgaagaa cgttttccaa tgatgagcac ttttaaagtt ctgctatgtg gcgcggtatt   2400
atcccgtatt gacgccgggc aagagcaact cggtcgccgc atacactatt ctcagaatga   2460
cttggttgag tactcaccag tcacagaaaa gcatcttacg gatggcatga cagtaagaga   2520
attatgcagt gctgccataa ccatgagtga taacactgcg gccaacttac ttctgacaac   2580
gatcggagga ccgaaggagc taaccgcttt tttgcacaac atgggggatc atgtaactcg   2640
ccttgatcgt tgggaaccgg agctgaatga agccatacca aacgacgagc gtgacaccac   2700
gatgcctgta gcaatggcaa caacgttgcg caaactatta actggcgaac tacttactct   2760
agcttcccgg caacaattaa tagactggat ggaggcggat aaagttgcag gaccacttct   2820
gcgctcggcc cttccggctg gctggtttat tgctgataaa tctggagccg gtgagcgtgg   2880
gtctcgcggt atcattgcag cactggggcc agatggtaag ccctcccgta tcgtagttat   2940
ctacacgacg gggagtcagg caactatgga tgaacgaaat agacagatcg ctgagatagg   3000
tgcctcactg attaagcatt ggtaactgtc agaccaagtt tactcatata ctttagat    3060 tgatttaaaa cttcattttt aatttaaaag gatctaggtg aagatccttt ttgataatct   3120
catgaccaaa atcccttaac gtgagttttc gttccactga gcgtcagacc ccgtagaaaa   3180
gatcaaagga tcttcttgag atcctttttt tctgcgcgta atctgctgct tgcaaacaaa   3240
aaaaccaccg ctaccagcgg tggtttgttt gccggatcaa gagctaccaa ctctttttcc   3300
gaaggtaact ggcttcagca gagcgcagat accaaatact gtccttctag tgtagccgta   3360
gttaggccac cacttcaaga actctgtagc accgcctaca tacctcgctc tgctaatcct   3420
gttaccagtg gctgctgcca gtggcgataa gtcgtgtctt accgggttgg actcaagacg   3480
atagttaccg gataaggcgc agcggtcggg ctgaacgggg ggttcgtgca cacagcccag   3540
cttggagcga acgacctaca ccgaactgag atacctacag cgtgagctat gagaaagcgc   3600
```

```
cacgcttccc gaagggagaa aggcggacag gtatccggta agcggcaggg tcggaacagg    3660
agagcgcacg agggagcttc caggggaaa cgcctggtat ctttatagtc ctgtcgggtt     3720
tcgccacctc tgacttgagc gtcgatttt gtgatgctcg tcagggggc ggagcctatg      3780
gaaaaacgcc agcaacgcgg ccttttacg gttcctggcc ttttgctggc cttttgctca    3840
catgttcttt cctgcgttat cccctgattc tgtggataac cgtattaccg cctttgagtg   3900
agctgatacc gctcgccgca gccgaacgac cgagcgcagc gagtcagtga gcgaggaagc   3960
ggaagagcgc ccaatacgca aaccgcctct ccccgcgcgt tggccgattc attaatgcag   4020
ctggcacgac aggtttcccg actggaaagc gggcagtgag cgcaacgcaa ttaatgtgag   4080
ttagctcact cattaggcac cccaggcttt acactttatg cttccggctc gtatgttgtg   4140
tggaattgtg agcggataac aatttcacac aggaaacagc tatgaccatg attacgccaa   4200
gcttccaatt accgtcgctc gtgatttgtt tgcaaaaaga acaaaactga aaaacccag    4260
acacgctcga cttcctgtct tcctattgat tgcagcttcc aatttcgtca cacaacaagg   4320
tcctgtcgac gcctacttgg cttcacatac gttgcatacg tcgatataga taataatgat   4380
aatgacagca ggattatcgt aatacgtaat agttgaaaat ctcaaaaatg tgtgggtcat   4440
tacgtaaata atgataggaa tgggattctt ctattttttcc ttttttccatt ctagcagccg  4500
tcgggaaaac gtggcatcct ctctttcggg ctcaattgga gtcacgctgc cgtgagcatc   4560
ctctctttcc atatctaaca actgagcacg taaccaatgg aaaagcatga gcttagcgtt   4620
gctccaaaaa agtattggat ggttaatacc atttgtctgt tctcttctga ctttgactcc   4680
tcaaaaaaaa aaaatctaca atcaacagat cgcttcaatt acgccctcac aaaaactttt   4740
ttccttcttc ttcgcccacg ttaaatttta tccctcatgt tgtctaacgg atttctgcac   4800
ttgatttatt ataaaaagac aaagacataa tacttctcta tcaatttcag ttattgttct   4860
tccttgcgtt attcttctgt tcttcttttt cttttgtcat atataaccat aaccaagtaa   4920
tacatattca agtttaaaca tgtataccgt aggacagtac ttggtagata gactagaaga   4980
gattggtatc gataaggttt tcggtgtgcc aggggattac aatttgactt tctagatta   5040
cattcaaaat cacgaaggac tttcctggca agggaatact aatgaactaa acgcagcata   5100
tgcagcagat ggctacgccc gtgaaagagg cgtatcagct cttgttacta cattcggagt   5160
gggtgaactg tcagccatta acggaacagc tggtagtttt gcagaacaag tccctgtcat   5220
ccacatcgtg ggttctccaa ctatgaatgt gcaatccaac aaaaagctgg ttcatcattc   5280
cttaggaatg ggtaactttc ataactttag tgaaatggct aaggaagtca ctgccgctac   5340
aaccatgctt actgaagaga atgcagcttc agagatcgac agagtattag aaacagcctt   5400
gttggaaaag aggccagtat acatcaatct tccaattgat atagctcata agcaatagt    5460
taaacctgca aaagcactac aaacagagaa atcatctggt gagagagagg cacaacttgc   5520
agaaatcata ctatcacact tagaaaaggc cgctcaacct atcgtaatcg ccggtcatga   5580
gatcgcccgt ttccagataa gagaaagatt tgaaaactgg ataaaccaaa caagttgcc    5640
agtaaccaat ttggcatatg gcaaaggctc tttcaatgaa gagaacgaac atttcattgg   5700
tacctattac ccagcttttt ctgacaaaaa cgttctggat tacgttgaca atagtgactt   5760
cgttttacat tttggtggga aaatcattga caattctacc tcctcatttt ctcaaggctt   5820
taagactgaa aacactttaa ccgctgcaaa tgacatcatt atgctgccag atgggtctac   5880
ttactctggg atttctctta acggtctttt ggcagagctg gaaaaactaa actttactt    5940
tgctgatact gctgctaaac aagctgaatt agctgttttc gaaccacagg ccgaaacacc   6000
```

```
actaaagcaa gacagatttc accaagctgt tatgaacttt ttgcaagctg atgatgtgtt    6060
ggtcactgag caggggacat catctttcgg tttgatgttg gcacctctga aaagggtat    6120
gaatttgatc agtcaaacat tatggggctc cataggatac acattacctg ctatgattgg    6180
ttcacaaatt gctgcccccag aaaggagaca cattctatcc atcggtgatg gatcttttca    6240
actgacagca caggaaatgt ccaccatctt cagagagaaa ttgacaccag tgatattcat    6300
tatcaataac gatggctata cagtcgaaag agccatccat ggagaggatg agagttacaa    6360
tgatatacca acttggaact tgcaattagt tgctgaaaca tttggtggtg atgccgaaac    6420
tgtcgacact cacaacgttt tcacagaaac agacttcgct aatactttag ctgctatcga    6480
tgctactcct caaaaagcac atgtcgttga agttcatatg gaacaaatgg atatgccaga    6540
atcattgaga cagattggct tagccttatc taagcaaaac tcttaagttt aaactaagcg    6600
aatttcttat gatttatgat ttttattatt aaataagtta taaaaaaaat aagtgtatac    6660
aaattttaaa gtgactctta ggttttaaaa cgaaaattct tattcttgag taactctttc    6720
ctgtaggtca ggttgctttc tcaggtatag catgaggtcg ctcttattga ccacacctct    6780
accggcatgc cgagcaaatg cctgcaaatc gctccccatt tcacccaatt gtagatatgc    6840
taactccagc aatgagttga tgaatctcgg tgtgtatttt atgtcctcag aggacaacac    6900
ctgttgtaat cgttcttcca cacg                                           6924
```

<210> SEQ ID NO 211
<211> LENGTH: 6761
<212> TYPE: DNA
<213> ORGANISM: Artificial Sequence
<220> FEATURE:
<223> OTHER INFORMATION: pLA65

<400> SEQUENCE: 211

```
gatccgcatt gcggattacg tattctaatg ttcagtaccg ttcgtataat gtatgctata      60
cgaagttatg cagattgtac tgagagtgca ccataccacc ttttcaattc atcattttt     120
ttttattctt ttttttgatt tcggtttcct tgaaattttt ttgattcggt aatctccgaa     180
cagaaggaag aacgaaggaa ggagcacaga cttagattgg tatatatacg catatgtagt     240
gttgaagaaa catgaaattg cccagtattc ttaacccaac tgcacagaac aaaaacctgc     300
aggaaacgaa gataaatcat gtcgaaagct acatataagg aacgtgctgc tactcatcct     360
agtcctgttg ctgccaagct atttaatatc atgcacgaaa agcaaacaaa cttgtgtgct     420
tcattggatg ttcgtaccac caaggaatta ctggagttag ttgaagcatt aggtcccaaa     480
atttgtttac taaaaacaca tgtggatatc ttgactgatt tttccatgga gggcacagtt     540
aagccgctaa aggcattatc cgccaagtac aatttttac tcttcgaaga cagaaaattt     600
gctgacattg gtaatacagt caaattgcag tactctgcgg gtgtatacag aatagcagaa     660
tgggcagaca ttacgaatgc acacggtgtg gtgggcccag gtattgttag cggtttgaag     720
caggcggcag aagaagtaac aaaggaacct agaggccttt tgatgttagc agaattgtca     780
tgcaagggct ccctatctac tggagaatat actaagggta ctgttgacat tgcgaagagc     840
gacaaagatt ttgttatcgg ctttattgct caaagagaca tgggtggaag atgaaaggt     900
tacgattggt tgattatgac acccggtgtg ggtttagatg acaagggaga cgcattgggt     960
caacagtata gaaccgtgga tgatgtggtc tctacaggat ctgacattat tattgttgga    1020
agaggactat ttgcaaaggg aagggatgct aaggtagagg gtgaacgtta cagaaaagca    1080
```

```
ggctgggaag catatttgag aagatgcggc cagcaaaact aaaaaactgt attataagta    1140
aatgcatgta tactaaactc acaaattaga gcttcaattt aattatatca gttattaccc    1200
tatgcggtgt gaaataccgc acagatgcgt aaggagaaaa taccgcatca ggaaattgta    1260
aacgttaata ttttgttaaa attcgcgtta aattttttgtt aaatcagctc attttttaac    1320
caataggccg aaatcggcaa atcccttat aaatcaaaag aatagaccga gatagggttg     1380
agtgttgttc cagtttggaa caagagtcca ctattaaaga acgtggactc caacgtcaaa    1440
gggcgaaaaa ccgtctatca gggcgatggc ccactacgtg aaccatcacc ctaatcaaga    1500
taacttcgta taatgtatgc tatacgaacg gtaccagtga tgatacaacg agttagccaa    1560
ggtgaattca ctggccgtcg ttttacaacg tcgtgactgg gaaaaccctg gcgttaccca    1620
acttaatcgc cttgcagcac atccccctttt cgccagctgg cgtaatagcg aagaggcccg    1680
caccgatcgc ccttcccaac agttgcgcag cctgaatggc gaatggcgcc tgatgcggta    1740
ttttctcctt acgcatctgt gcggtatttc acaccgcata tggtgcactc tcagtacaat    1800
ctgctctgat gccgcatagt taagccagcc ccgacacccg ccaacacccg ctgacgcgcc    1860
ctgacgggct tgtctgctcc cggcatccgc ttacagacaa gctgtgaccg tctccgggag    1920
ctgcatgtgt cagaggtttt caccgtcatc accgaaacgc gcgagacgaa agggcctcgt    1980
gatacgccta tttttatagg ttaatgtcat gataataatg gtttcttaga cgtcaggtgg    2040
cacttttcgg ggaaatgtgc gcggaacccc tatttgttta ttttttctaaa tacattcaaa    2100
tatgtatccg ctcatgagac aataaccctg ataaatgctt caataatatt gaaaaaggaa    2160
gagtatgagt attcaacatt tccgtgtcgc ccttattccc ttttttgcgg cattttgcct    2220
tcctgttttt gctcacccag aaacgctggt gaaagtaaaa gatgctgaag atcagttggg    2280
tgcacgagtg ggttacatcg aactggatct caacagcggt aagatccttg agagttttcg    2340
ccccgaagaa cgttttccaa tgatgagcac ttttaaagtt ctgctatgtg gcgcggtatt    2400
atcccgtatt gacgccgggc aagagcaact cggtcgccgc atacactatt ctcagaatga    2460
cttggttgag tactcaccag tcacagaaaa gcatcttacg gatggcatga cagtaagaga    2520
attatgcagt gctgccataa ccatgagtga taacactgcg gccaacttac ttctgacaac    2580
gatcggagga ccgaaggagc taaccgcttt tttgcacaac atgggggatc atgtaactcg    2640
ccttgatcgt tgggaaccgg agctgaatga agccatacca aacgacgagc gtgacaccac    2700
gatgcctgta gcaatggcaa caacgttgcg caaactatta actggcgaac tacttactct    2760
agcttcccgg caacaattaa tagactggat ggaggcggat aaagttgcag gaccacttct    2820
gcgctcggcc cttccggctg gctggtttat tgctgataaa tctggagccg gtgagcgtgg    2880
gtctcgcggt atcattgcag cactggggcc agatggtaag ccctcccgta tcgtagttat    2940
ctacacgacg gggagtcagg caactatgga tgaacgaaat agacagatcg ctgagatagg    3000
tgcctcactg attaagcatt ggtaactgtc agaccaagtt tactcatata ctttagat     3060
tgatttaaaa cttcattttt aatttaaaag gatctaggtg aagatccttt ttgataatct    3120
catgaccaaa atcccttaac gtgagttttc gttccactga gcgtcagacc ccgtagaaaa    3180
gatcaaagga tcttcttgag atcctttttt tctgcgcgta atctgctgct tgcaaacaaa    3240
aaaaccaccg ctaccagcgg tggtttgttt gccggatcaa gagctaccaa ctctttttcc    3300
gaaggtaact ggcttcagca gagcgcagat accaaatact gtccttctag tgtagccgta    3360
gttaggccac cacttcaaga actctgtagc accgcctaca tacctcgctc tgctaatcct    3420
gttaccagtg gctgctgcca gtggcgataa gtcgtgtctt accgggttgg actcaagacg    3480
```

```
atagttaccg gataaggcgc agcggtcggg ctgaacgggg ggttcgtgca cacagcccag    3540
cttggagcga acgacctaca ccgaactgag atacctacag cgtgagctat gagaaagcgc    3600
cacgcttccc gaagggagaa aggcggacag gtatccggta agcggcaggg tcggaacagg    3660
agagcgcacg agggagcttc cagggggaaa cgcctggtat ctttatagtc ctgtcgggtt    3720
tcgccacctc tgacttgagc gtcgattttt gtgatgctcg tcagggggc ggagcctatg    3780 gaaaaacgcc agcaacgcgg cctttttacg gttcctggcc ttttgctggc cttttgctca    3840
catgttcttt cctgcgttat cccctgattc tgtggataac cgtattaccg cctttgagtg    3900
agctgatacc gctcgccgca gccgaacgac cgagcgcagc gagtcagtga gcgaggaagc    3960
ggaagagcgc ccaatacgca aaccgcctct ccccgcgcgt tggccgattc attaatgcag    4020
ctggcacgac aggtttcccg actggaaagc gggcagtgag cgcaacgcaa ttaatgtgag    4080
ttagctcact cattaggcac cccaggcttt acactttatg cttccggctc gtatgttgtg    4140
tggaattgtg agcggataac aatttcacac aggaaacagc tatgaccatg attacgccaa    4200
gcttacctgg taaaacctct agtggagtag tagatgtaat caatgaagcg gaagccaaaa    4260
gaccagagta gaggcctata gaagaaactg cgatacctt tgtgatggct aaacaaacag    4320
acatcttttt atatgttttt acttctgtat atcgtgaagt agtaagtgat aagcgaattt    4380
ggctaagaac gttgtaagtg aacaagggac ctcttttgcc tttcaaaaaa ggattaaatg    4440
gagttaatca ttgagattta gttttcgtta gattctgtat ccctaaataa ctcccttacc    4500
cgacgggaag gcacaaaaga cttgaataat agcaaacggc cagtagccaa gaccaaataa    4560
tactagagtt aactgatggt cttaaacagg cattacgtgg tgaactccaa gaccaatata    4620
caaaatatcg ataagttatt cttgcccacc aatttaagga gcctacatca ggacagtagt    4680
accattcctc agagaagagg tatacataac aagaaaatcg cgtgaacacc ttatataact    4740
tagcccgtta ttgagctaaa aaaccttgca aaatttccta tgaataagaa tacttcagac    4800
gtgataaaaa tttacttct aactcttctc acgctgcccc tatctgttct tccgctctac    4860
cgtgagaaat aaagcatcga gtacggcagt tcgctgtcac tgaactaaaa caataaggct    4920
agttcgaatg atgaacttgc ttgctgtcaa acttctgagt tgccgctgat gtgacactgt    4980
gacaataaat tcaaaccggt tatagcggtc tcctccggta ccggttctgc cacctccaat    5040
agagctcagt aggagtcaga acctctgcgg tggctgtcag tgactcatcc gcgtttcgta    5100
agttgtgcgc gtgcacattt cgcccgttcc cgctcatctt gcagcaggcg gaaattttca    5160
tcacgctgta ggacgcaaaa aaaaataat taatcgtaca agaatcttgg aaaaaaaatt    5220
gaaaaatttt gtataaaagg gatgacctaa cttgactcaa tggcttttac acccagtatt    5280 ttcccttttcc ttgtttgtta caattataga agcaagacaa aaacatatag caacctatt    5340 cctaggagtt atattttttt accctaccag caatataagt aaaaaactgt ttatgaaagc    5400
attagtgtat aggggcccag gccagaagtt ggtggaagag agacagaagc cagagcttaa    5460
ggaacctggt gacgctatag tgaaggtaac aaagactaca atttgcggaa ccgatctaca    5520
cattcttaaa ggtgacgttg cgacttgtaa acccggtcgt gtattagggc atgaaggagt    5580
gggggttatt gaatcagtcg gatctggggt tactgctttc caaccaggcg atagagtttt    5640
gatatcatgt atatcgagtt gcggaaagtg ctcattttgt agaagaggaa tgttcagtca    5700
ctgtacgacc gggggttgga ttctgggcaa cgaaattgat ggtacccaag cagagtacgt    5760
aagagtacca catgctgaca catcccttta tcgtattccg gcaggtgcgg atgaagaggc    5820
```

| | |
|---|---|
| cttagtcatg ttatcagata ttctaccaac gggttttgag tgcggagtcc taaacggcaa | 5880 |
| agtcgcacct ggttcttcgg tggctatagt aggtgctggt cccgttggtt tggccgcctt | 5940 |
| actgacagca caattctact ccccagctga aatcataatg atcgatcttg atgataacag | 6000 |
| gctgggatta gccaaacaat ttggtgccac cagaacagta aactccacgg gtggtaacgc | 6060 |
| cgcagccgaa gtgaaagctc ttactgaagg cttaggtgtt gatactgcga ttgaagcagt | 6120 |
| tgggatacct gctacatttg aattgtgtca gaatatcgta gctcccggtg aactatcgc | 6180 |
| taatgtcggc gttcacggta gcaaagttga tttgcatctt gaaagtttat ggtcccataa | 6240 |
| tgtcacgatt actacaaggt tggttgacac ggctaccacc ccgatgttac tgaaaactgt | 6300 |
| tcaaagtcac aagctagatc catctagatt gataacacat agattcagcc tggaccagat | 6360 |
| cttggacgca tatgaaactt ttggccaagc tgcgtctact caagcactaa aagtcatcat | 6420 |
| ttcgatggag gcttgattaa ttaagagtaa gcgaatttct tatgatttat gattttatt | 6480 |
| attaaataag ttataaaaaa aataagtgta tacaattttt aaagtgactc ttaggtttta | 6540 |
| aaacgaaaat tcttattctt gagtaactct ttcctgtagg tcaggttgct ttctcaggta | 6600 |
| tagcatgagg tcgctcttat tgaccacacc tctaccggca tgccgagcaa atgcctgcaa | 6660 |
| atcgctcccc atttcaccca attgtagata tgctaactcc agcaatgagt tgatgaatct | 6720 |
| cggtgtgtat tttatgtcct cagaggacaa cacctgtggt g | 6761 |

<210> SEQ ID NO 212
<211> LENGTH: 90
<212> TYPE: DNA
<213> ORGANISM: Artificial Sequence
<220> FEATURE:
<223> OTHER INFORMATION: 895

<400> SEQUENCE: 212

| | |
|---|---|
| tctcaattat tattttctac tcataacctc acgcaaaata acacagtcaa atcaatcaaa | 60 |
| atgttgacaa aagcaacaaa agaacaaaaa | 90 |

<210> SEQ ID NO 213
<211> LENGTH: 81
<212> TYPE: DNA
<213> ORGANISM: Artificial Sequence
<220> FEATURE:
<223> OTHER INFORMATION: 679

<400> SEQUENCE: 213

| | |
|---|---|
| gtggagcatc gaagactggc aacatgattt caatcattct gatcttagag caccttggct | 60 |
| aactcgttgt atcatcactg g | 81 |

<210> SEQ ID NO 214
<211> LENGTH: 20
<212> TYPE: DNA
<213> ORGANISM: Artificial Sequence
<220> FEATURE:
<223> OTHER INFORMATION: 681

<400> SEQUENCE: 214

| | |
|---|---|
| ttattgctta gcgttggtag | 20 |

<210> SEQ ID NO 215
<211> LENGTH: 22
<212> TYPE: DNA
<213> ORGANISM: Artificial Sequence
<220> FEATURE:
<223> OTHER INFORMATION: 92

<400> SEQUENCE: 215
gagaagatgc ggccagcaaa ac                                          22

<210> SEQ ID NO 216
<211> LENGTH: 25
<212> TYPE: DNA
<213> ORGANISM: Artificial Sequence
<220> FEATURE:
<223> OTHER INFORMATION: N245

<400> SEQUENCE: 216
agggtagcct ccccataaca taaac                                       25

<210> SEQ ID NO 217
<211> LENGTH: 25
<212> TYPE: DNA
<213> ORGANISM: Artificial Sequence
<220> FEATURE:
<223> OTHER INFORMATION: N246

<400> SEQUENCE: 217
tctccaaata tacctctt gtgtg                                         25

<210> SEQ ID NO 218
<211> LENGTH: 90
<212> TYPE: DNA
<213> ORGANISM: Artificial Sequence
<220> FEATURE:
<223> OTHER INFORMATION: 896

<400> SEQUENCE: 218
ttttatatac agtataaata aaaacccac gtaatatagc aaaaacatat tgccaacaaa   60
aattaccgtc gctcgtgatt tgtttgcaaa                                  90

<210> SEQ ID NO 219
<211> LENGTH: 90
<212> TYPE: DNA
<213> ORGANISM: Artificial Sequence
<220> FEATURE:
<223> OTHER INFORMATION: 897

<400> SEQUENCE: 219
caaactgtgt aagtttattt atttgcaaca ataattcgtt tgagtacact actaatggcc   60
accttggcta actcgttgta tcatcactgg                                  90

<210> SEQ ID NO 220
<211> LENGTH: 28
<212> TYPE: DNA
<213> ORGANISM: Artificial Sequence
<220> FEATURE:
<223> OTHER INFORMATION: 365

<400> SEQUENCE: 220
ctctatctcc gctcaggcta agcaattg                                    28

<210> SEQ ID NO 221
<211> LENGTH: 26
<212> TYPE: DNA
<213> ORGANISM: Artificial Sequence
<220> FEATURE:
<223> OTHER INFORMATION: 366

<400> SEQUENCE: 221
cagccgactc aacggcctgt ttcacg                                    26

<210> SEQ ID NO 222
<211> LENGTH: 28
<212> TYPE: DNA
<213> ORGANISM: Artificial Sequence
<220> FEATURE:
<223> OTHER INFORMATION: N638

<400> SEQUENCE: 222
aaaagatagt gtagtagtga taaactgg                                  28

<210> SEQ ID NO 223
<211> LENGTH: 22
<212> TYPE: DNA
<213> ORGANISM: Artificial Sequence
<220> FEATURE:
<223> OTHER INFORMATION: 740

<400> SEQUENCE: 223
cgataatcct gctgtcatta tc                                        22

<210> SEQ ID NO 224
<211> LENGTH: 83
<212> TYPE: DNA
<213> ORGANISM: Artificial Sequence
<220> FEATURE:
<223> OTHER INFORMATION: 856

<400> SEQUENCE: 224
gcttatttag aagtgtcaac aacgtatcta ccaacgattt gaccctttc cacaccttgg    60 ctaactcgtt gtatcatcac tgg                                       83

<210> SEQ ID NO 225
<211> LENGTH: 80
<212> TYPE: DNA
<213> ORGANISM: Artificial Sequence
<220> FEATURE:
<223> OTHER INFORMATION: 857

<400> SEQUENCE: 225
gcacaatatt tcaagctata ccaagcatac aatcaactat ctcatataca atgaaagcat    60
tagtgtatag gggcccaggc                                           80

<210> SEQ ID NO 226
<211> LENGTH: 25
<212> TYPE: DNA
<213> ORGANISM: Artificial Sequence
<220> FEATURE:
<223> OTHER INFORMATION: BK415

<400> SEQUENCE: 226
gcctcattga tggtggtaca taacg                                     25

<210> SEQ ID NO 227
<211> LENGTH: 26
<212> TYPE: DNA
<213> ORGANISM: Artificial Sequence
<220> FEATURE:
<223> OTHER INFORMATION: N1092

<400> SEQUENCE: 227
agagttttga tatcatgtat atcgag                                    26

```
<210> SEQ ID NO 228
<211> LENGTH: 92
<212> TYPE: DNA
<213> ORGANISM: Artificial Sequence
<220> FEATURE:
<223> OTHER INFORMATION: 906

<400> SEQUENCE: 228
atgacaggtg aaagaattga aaaggtgaaa ataaatgacg aatttgcaaa atcacatttc      60
acctggtaaa acctctagtg gagtagtaga tg                                    92

<210> SEQ ID NO 229
<211> LENGTH: 87
<212> TYPE: DNA
<213> ORGANISM: Artificial Sequence
<220> FEATURE:
<223> OTHER INFORMATION: 907

<400> SEQUENCE: 229
aaaaagattc aatgccgtct cctttcgaaa cttaataata gaacaatatc atccttcacc      60
ttggctaact cgttgtatca tcactgg                                          87

<210> SEQ ID NO 230
<211> LENGTH: 70
<212> TYPE: DNA
<213> ORGANISM: Artificial Sequence
<220> FEATURE:
<223> OTHER INFORMATION: 667

<400> SEQUENCE: 230
tctcctttcg aaacttaata atagaacaat atcatccttt tgtaaaacga cggccagtga      60
attcaccttg                                                             70
```